US010064904B2

(12) United States Patent
Schneider et al.

(10) Patent No.: US 10,064,904 B2
(45) Date of Patent: Sep. 4, 2018

(54) **TREATMENT OF *CLOSTRIDIUM DIFFICILE* INFECTION**

(71) Applicant: Vedanta Biosciences, Inc., Cambridge, MA (US)

(72) Inventors: Jessica Schneider, Cambridge, MA (US); Yun-Gi Kim, Watertown, MA (US); Bernat Olle, Cambridge, MA (US); Shilpa Reddy, Watertown, MA (US); Jason Norman, North Weymouth, MA (US); Juan Patarroyo, Lexington, MA (US)

(73) Assignee: Vedanta Biosciences, Inc., Cambridge, MA (US)

( * ) Notice: Subject to any disclaimer, the term of this patent is extended or adjusted under 35 U.S.C. 154(b) by 0 days.

(21) Appl. No.: 15/884,029

(22) Filed: Jan. 30, 2018

(65) Prior Publication Data

US 2018/0169157 A1 Jun. 21, 2018

Related U.S. Application Data

(63) Continuation of application No. 15/630,088, filed on Jun. 22, 2017, now Pat. No. 9,999,641, which is a continuation of application No. PCT/US2017/037498, filed on Jun. 14, 2017.

(60) Provisional application No. 62/349,914, filed on Jun. 14, 2016.

(51) Int. Cl.

| | |
|---|---|
| ***A61K 9/48*** | (2006.01) |
| ***A61K 35/747*** | (2015.01) |
| ***A61K 9/00*** | (2006.01) |
| ***A61K 35/742*** | (2015.01) |
| ***A61K 35/74*** | (2015.01) |
| ***A23L 5/00*** | (2016.01) |
| ***A23L 33/135*** | (2016.01) |
| *A23K 10/18* | (2016.01) |
| *A23K 50/30* | (2016.01) |

(52) U.S. Cl.

CPC .............. *A61K 35/747* (2013.01); *A23L 5/00* (2016.08); *A23L 33/135* (2016.08); *A61K 9/0053* (2013.01); *A61K 9/48* (2013.01); *A61K 35/74* (2013.01); *A61K 35/742* (2013.01); *A23K 10/18* (2016.05); *A23K 50/30* (2016.05)

(58) Field of Classification Search

None

See application file for complete search history.

(56) References Cited

U.S. PATENT DOCUMENTS

| | | | |
|---|---|---|---|
| 6,635,260 | B1 | 10/2003 | Gerding |
| 8,460,648 | B2 | 6/2013 | Borody |
| 9,386,793 | B2 | 7/2016 | Blaser et al. |
| 2010/0074872 | A1 | 3/2010 | Blaser et al. |
| 2014/0199281 | A1 | 7/2014 | Henn et al. |
| 2014/0328803 | A1 | 11/2014 | McKenzie et al. |
| 2014/0341921 | A1 | 11/2014 | Honda et al. |
| 2015/0037476 | A1 | 2/2015 | Dhingra et al. |
| 2015/0079209 | A1 | 3/2015 | Kameyama et al. |
| 2016/0022745 | A1 | 1/2016 | Wang |
| 2016/0022746 | A1 | 1/2016 | Lawley et al. |
| 2016/0040215 | A1 | 2/2016 | Henn et al. |
| 2016/0113971 | A1 | 4/2016 | Kaplan et al. |
| 2016/0228476 | A1 | 8/2016 | Cutcliffe et al. |
| 2017/0143772 | A1 | 5/2017 | Mulder et al. |
| 2017/0354697 | A1 | 12/2017 | Schneider et al. |

FOREIGN PATENT DOCUMENTS

| | | | |
|---|---|---|---|
| WO | WO 2002/007741 | A1 | 1/2002 |
| WO | WO 2006/050479 | A1 | 5/2006 |
| WO | WO 2011/152566 | A1 | 12/2011 |
| WO | WO 2013/037067 | A1 | 3/2013 |
| WO | WO 2013/037068 | A1 | 3/2013 |
| WO | WO 2013/080561 | A1 | 6/2013 |
| WO | WO 2013/182038 | A1 | 12/2013 |
| WO | WO 2014/082050 | A1 | 5/2014 |
| WO | WO 2014/121298 | A1 | 8/2014 |
| WO | WO 2014/121301 | A1 | 8/2014 |
| WO | WO 2014/121302 | A1 | 8/2014 |
| WO | WO 2014/145958 | A2 | 9/2014 |
| WO | WO 2014/153194 | A2 | 9/2014 |
| WO | WO 2015/006355 | A2 | 1/2015 |
| WO | WO 2015/051323 | A1 | 4/2015 |
| WO | WO 2015/077794 | A1 | 5/2015 |
| WO | WO 2015/095241 | A2 | 6/2015 |
| WO | WO 2015/156419 | A1 | 10/2015 |
| WO | WO 2015/164555 | A1 | 10/2015 |
| WO | WO 2015/179437 | A1 | 11/2015 |
| WO | WO 2016/086161 | A1 | 6/2016 |
| WO | WO 2016/086205 | A2 | 6/2016 |
| WO | WO 2016/086206 | A1 | 6/2016 |
| WO | WO 2016/086208 | A1 | 6/2016 |
| WO | WO 2016/086209 | A1 | 6/2016 |
| WO | WO 2016/086210 | A1 | 6/2016 |

(Continued)

OTHER PUBLICATIONS

Alang et al., Weight gain after fecal microbiota transplantation. Open Forum Infect Dis. Feb. 4, 2015;2(1):ofv004. doi: 10.1093/ofid/ofv004. eCollection Jan. 2015.

Blaser, The microbiome revolution. J Clin Invest. Oct. 2014;124(10):4162-5. doi: 10.1172/JCI78366. Epub Oct. 1, 2014.

Borody et al., Therapeutic faecal microbiota transplantation: current status and future developments. Curr Opin Gastroenterol.Jan. 2014;30(1):97-105. doi: 10.1097/MOG.0000000000000027.

(Continued)

*Primary Examiner* — Mary Maille Lyons

(74) *Attorney, Agent, or Firm* — Wolf, Greenfield & Sacks, P.C.

(57) ABSTRACT

Provided herein are compositions and methods for the treatment or prevention of pathogenic infections.

12 Claims, 41 Drawing Sheets

Specification includes a Sequence Listing.

(56) References Cited

FOREIGN PATENT DOCUMENTS

| | | | |
|---|---|---|---|
| WO | WO 2016/185469 | A1 | 11/2016 |
| WO | WO 2016/201053 | A1 | 12/2016 |
| WO | WO 2016/203217 | A1 | 12/2016 |
| WO | WO 2016/203218 | A1 | 12/2016 |
| WO | WO 2016/203220 | A1 | 12/2016 |
| WO | WO 2016/203221 | A1 | 12/2016 |
| WO | WO 2016/203223 | A1 | 12/2016 |
| WO | WO 2016/209806 | A1 | 12/2016 |
| WO | WO 2017/008026 | A1 | 1/2017 |
| WO | WO 2017/035188 | A1 | 3/2017 |
| WO | WO 2017/075098 | A1 | 5/2017 |
| WO | WO 2017/085518 | A1 | 5/2017 |
| WO | WO 2017/085520 | A1 | 5/2017 |
| WO | WO 2017/089794 | A1 | 6/2017 |
| WO | WO 2017/089795 | A1 | 6/2017 |
| WO | WO 2017/091783 | A2 | 6/2017 |
| WO | WO 2017/148596 | A1 | 9/2017 |

OTHER PUBLICATIONS

Buffie et al., Precision microbiome reconstitution restores bile acid mediated resistance to Clostridium difficile. Nature. Jan. 8, 2015;517(7533):205-8. doi: 10.1038/nature13828. Epub Oct. 22, 2014.

Burns et al., Donor Recruitment and Eligibility for Fecal Microbiota Transplantation: Results From an International Public Stool Bank. Gastro. Apr. 2015;148(4):S96-S97.

Calfee, Clostridium difficile: a reemerging pathogen. Geriatrics. Sep. 1, 2008;63(9):10-21.

Cammarota et al., Randomised clinical trial: faecal microbiota transplantation by colonoscopy vs. vancomycin for the treatment of recurrent Clostridium difficile infection. Aliment Pharmacol Ther. May 2015;41(9):835-43. doi: 10.1111/apt.13144. Epub Mar. 1, 2015.

Drancourt et al., 16S ribosomal DNA sequence analysis of a large collection of environmental and clinical unidentifiable bacterial isolates. J Clin Microbiol. Oct. 2000;38(10):3623-30.

Eyre et al., Whole-genome sequencing demonstrates that fidaxomicin is superior to vancomycin for preventing reinfection and relapse of infection with Clostridium difficile. J Infect Dis. May 1, 2014;209(9):1446-51. doi:10.1093/infdis/jit598. Epub Nov. 11, 2013.

Genbank Accession No. NR 104687.1. NCBI. Sakamoto. Feb. 3, 2015.

Hooper et al., Interactions between the microbiota and the immune system. Science. Jun. 8, 2012;336(6086):1268-73. doi:10.1126/science.1223490. Epub Jun. 6, 2012.

Hughes et al., Immune activation in irritable bowel syndrome: can neuroimmune interactions explain symptoms? AM J Gastroenterol. Jul. 2013;108(7):1066-74. doi: 10.1038/ajg.2013.120. Epub May 7, 2013.

Kassam et al., Fecal microbiota transplantation for Clostridium difficile infection: systematic review and meta-analysis. Am J Gastroenterol. Apr. 2013;108(4):500-8. doi: 10.1038/ajg.2013.59. Epub Mar. 19, 2013.

Khoruts et al., Emergence of fecal microbiota transplantation as an approach to repair disrupted microbial gut ecology. Immunol Lett. Dec. 2014;162(2 Pt A):77-81. doi: 10.1016/j.imlet.2014.07.016. Epub Aug. 10, 2014.

Leblanc et al., Bacteria as vitamin suppliers to their host: a gut microbiota perspective. Curr Opin Biotechnol. Apr. 2013;24(2):160-8. doi: 10.1016/j.copbio.2012.08.005. Epub Aug. 30, 2012.

Lessa et al., Burden of Clostridium difficile infection in the United States. N Engl J Med. Feb. 26, 2015;372(9):825-34. doi:10.1056/NEJMoa1408913.

Louie et al., Fidaxomicin preserves the intestinal microbiome during and after treatment of Clostridium difficile infection (CDI) and reduces both toxin reexpression and recurrence of CDI. Clin Infect Dis. Aug. 2012;55 Suppl 2:S132-42. doi: 10.1093/cid/cis338.

Marvola et al., Enteric polymers as binders and coating materials in multiple-unit site-specific drug delivery systems. Eur J Pharm Sci. Feb. 1999;7(3):259-67.

Miller, Fidaxomicin (OPT-80) for the treatment of Clostridium difficile infection. Expert Opin Pharmacother. Jun. 2010;11(9):1569-78. doi:10.1517/14656566.2010.485614.

Mullane, Fidaxomicin in Clostridium difficile infection: latest evidence and clinical guidance. Ther Adv Chronic Dis. Mar. 2014;5(2):69-84. doi:10.1177/2040622313511285.

Narushima et al., Characterization of the 17 strains of regulatory T cell-inducing human-derived Clostridia. Gut Microbes. May-Jun. 2014;5(3):333-9. doi: 10.4161/gmic.28572. Epub Mar. 18, 2014.

Paramsothy et al., Donor Recruitment for Fecal Microbiota Transplantation. Inflamm Bowel Dis. Jul. 2015;21(7):1600-6. doi: 10.1097/MIB.0000000000000405.

Rossi-Tamisier et al., Cautionary tale of using 16S rRNA gene sequence similarity values in identification of human-associated bacterial species. Int J Syst Evol Microbiol. Jun. 2015;65(Pt 6):1929-34. doi:10.1099/ijs.0.000161. Epub Mar. 3, 2015.

Shannon-Lowe et al., Prevention and medical management of Clostridium difficile infection. BMJ. Mar. 12, 2010;340:c1296. doi:10.1136/bmj.c1296.

Surawicz, Fecal microbiota transplantation: what we know and what we need to know. Ann Intern Med. May 5, 2015;162(9):662-3. doi: 10.7326/M15-0609.

Tannock et al., A new macrocyclic antibiotic, fidaxomicin (OPT-80), causes less alteration to the bowel microbiota of Clostridium difficile-infected patients than does vancomycin. Microbiology. Nov. 2010;156(Pt 11):3354-9. doi: 10.1099/mic.0.042010-0. Epub Aug. 19, 2010.

Van Nood et al., Duodenal infusion of donor feces for recurrent Clostridium difficile. N Engl J Med. Jan. 31, 2013;368(5):407-15. doi: 10.1056/NEJMoa1205037. Epub Jan. 16, 2013.

Youngster et al., Fecal microbiota transplant for relapsing Clostridium difficile infection using a frozen inoculum from unrelated donors: a randomized, open-label, controlled pilot study. Clin Infect Dis. Jun. 2014;58(11):1515-22. doi: 10.1093/cid/ciu135. Epub Apr. 23, 2014.

Figure 1

| Composition A | Composition B | Composition C | Composition D |
|---|---|---|---|
| SEQ_03 - 5 - Clostridium_hathewayi (XIVa)* | **SEQ_10 - 211 - Flavonifractor_plautii (IV)** | SEQ_12 - VE202-26 - Clostridium_scindens (XIVa)* | SEQ_12 - VE202-26 - Clostridium_scindens (XIVa)* |
| SEQ_04 - 7 - Blautia_hansenii (XIVa)* | **SEQ_14 - VE202-13 - Anaerotruncus_colihominis (IV)** | SEQ_03 - 5 - Clostridium_hathewayi (XIVa)* | SEQ_03 - 5 - Clostridium_hathewayi (XIVa)* |
| SEQ_05 - 10 - Blautia_hansenii (XIVa)* | SEQ_15 - VE202-14 - Eubacterium_fissicatena (XIVa) | SEQ_05 - 10 - Blautia_hansenii (XIVa)* | SEQ_05 - 10 - Blautia_hansenii (XIVa)* |
| SEQ_07 - 59 - Blautia_producta / Blautia_coccoides (XIVa) | SEQ_16 - VE202-16 - Clostridium_symbiosum (XIVa) | SEQ_01 - 71 - Blautia_wexlerae (XIVa)* | SEQ_01 - 71 - Blautia_wexlerae (XIVa)* |
| SEQ_08 - 79 - Blautia_hansenii (XIVa)* | SEQ_17 - VE202-7 - Clostridium_bolteae (XIVa) | SEQ_07 - 59 - Blautia_producta/Blautia_coccoides (XIVa)* | **SEQ_14 - VE202-13 - Anaerotruncus_colihominis (IV)** |
| SEQ_09 - VE202-21 - Eubacterium_contortum / Eubacterium_fissicatena (XIVa)* | SEQ_20 – 170 – Dorea longicatena (XIVa) | SEQ_18 - 148 - Dorea_longicatena (XIVa) | SEQ_18 - 148 - Dorea_longicatena (XIVa) |
| SEQ_11 - VE202-9 - Anaerostipes_caccae (XIVa)* | SEQ_19 - 16 - Blautia_producta (XIVa) | **SEQ_21 - 189 - Clostridium_innocuum (XVII)** | **SEQ_21 - 189 - Clostridium_innocuum (XVII)** |
| SEQ_12 - VE202-26 - Clostridium_scindens (XIVa)* | **SEQ_21 - 189 - Clostridium_innocuum (XVII)** | **SEQ_10 - 211 - Flavonifractor_plautii (IV) /** | **SEQ_10 - 211 - Flavonifractor_plautii (IV) /** |
| SEQ_13 - 136 - Marvinbryantia_formatexigens (XIVa)* | | **SEQ_14 - VE202-13 - Anaerotruncus_colihominis (IV)** | **SEQ_02 - 102 - Turicibacter_sanguinis (non-Clostridium)** |
| SEQ_23 - VE202-29 - Eisenbergiella_tayi (XIVa)* | | SEQ_16 - VE202-16 - Clostridium_symbiosum (XIVa) | **SEQ_06 - 40 - Lactobacillus_mucosae (non-Clostridium)** |

*= $BaiCD^+$

*bolding indicates strains other than Clostridium cluster XIVa*

Clostridium difficile Infection Mouse Models
Day −10
−3
−1 0 1 2 3 4
C. difficile
Clindamycin IP
Antibiotic cocktail in drinking water
Switch to regular water
Abx Cocktail
Day −6
−1 0 1 2 3 4
C. difficile
Clindamycin IP
Clindamycin
Day −12
−2 -1 0 1 2 3 4
C. difficile
LBP, 10⁸ CFUs
Cefoperazone in drinking water
Switch to regular water
Cefoperazon
LBP, live biotherapeutic product

Figure 3

| Groups | # of animals | Abx | *C. difficile* Spores |
|---|---|---|---|
| (1) Control | 5 | - | $10^1$ |
| (2) Control | 5 | - | $10^4$ |
| (3) Abx cocktail | 5 | + | $10^1$ |
| (4) Abx cocktail | 5 | + | $10^4$ |
| (5) Clindamycin | 5 | + | $10^1$ |
| (6) Clindamycin | 5 | + | $10^4$ |
| (7) Cefoperazone | 5 | + | $10^1$ |
| (8) Cefoperazone | 5 | + | $10^4$ |

No Abx
10 spores
10000 spores
Survival (%)
100
80
60
40
20
0
0 1 2 3 4 5 6 7
Days after infection Abx Cocktail
Days after infection Clindamycin
Days after infection Cefoperazone
Days after infection

Figure 5

| Groups | # of animals | Abx | CFUs (Spores) |
|---|---|---|---|
| (1) Control- | 5 | - | $10^4$ |
| (2) Control+ | 5 | + | $10^4$ |
| (3) Van | 5 | + | $10^4$ |
| (4) Composition E | 5 | + | $10^4$ |
| (5) Composition I | 5 | + | $10^4$ |
| (6) Composition A | 5 | + | $10^4$ |
| (7) Composition B | 5 | + | $10^4$ |
| (8) Composition C | 5 | + | $10^4$ |
| (9) Composition D | 5 | + | $10^4$ |

Figure 9

| Groups | # of animals | Abx | *C. difficile* spore | CFUs LBPs |
|---|---|---|---|---|
| (1) Control | 7 | + | $10^4$ | - |
| (2) Composition B | 8 | + | $10^4$ | $10^8$/mouse |

Figure 13

Composition F

| SEQ_NO | StrainID | Genus_species | SEQ_NO | StrainID | Genus_species |
|---|---|---|---|---|---|
| SEQ_24 | YK96 | Dorea_longicatena | SEQ_52 | YK51 | Eubacterium_rectale |
| SEQ_25 | YK101 | Ruminococcus_obeum | SEQ_53 | YK52 | Eubacterium_rectale |
| SEQ_26 | YK110 | Megasphaera_elsdenii | SEQ_54 | YK54 | Anaerostipes_hadrus |
| SEQ_27 | YK149 | Acidaminococcus_fermentans / Acidaminococcus_intestini | SEQ_55 | YK56 | Ruminococcus_faecis |
| SEQ_28 | YK154 | Megasphaera_elsdenii | SEQ_56 | YK57 | Ruminococcus_faecis |
| SEQ_29 | YK36 | Ruminococcus_faecis | SEQ_57 | YK58 | Dorea_longicatena |
| SEQ_30 | YK95 | Bacteroides_cellulosilyticus | SEQ_58 | YK65 | Roseburia_faecis |
| SEQ_31 | YK32 | Anaerostipes_hadrus | SEQ_59 | YK67 | Blautia_luti |
| SEQ_32 | YK64 | Ruminococcus_obeum | SEQ_60 | YK69 | Fusicatenibacter_saccharivorans |
| SEQ_33 | YK73 | Flavonifractor_plautii | SEQ_61 | YK70 | Fusicatenibacter_saccharivorans |
| SEQ_34 | YK87 | Eubacterium_rectale | SEQ_62 | YK71 | Roseburia_faecis |
| SEQ_35 | YK105 | Flavonifractor_plautii | SEQ_63 | YK74 | Megasphaera_elsdenii |
| SEQ_36 | YK153 | Megasphaera_elsdenii | SEQ_64 | YK88 | Eubacterium_rectale |
| SEQ_37 | YK163 | Eubacterium_rectale | SEQ_65 | YK89 | Eubacterium_rectale |
| SEQ_38 | YK191 | Ruminococcus_champanellensis / Ruminococcus_albus | SEQ_66 | YK97 | Roseburia_faecis |
| SEQ_39 | YK99 | Ruminococcus_champanellensis | SEQ_67 | YK98 | Blautia_faecis |
| SEQ_40 | YK55 | Ruminococcus_faecis | SEQ_68 | YK139 | Fusicatenibacter_saccharivorans |
| SEQ_41 | YK75 | Bifidobacterium_bifidum | SEQ_69 | YK141 | Dorea_formicigenerans |
| SEQ_42 | YK90 | Anaerostipes_hadrus | SEQ_70 | YK142 | Ruminococcus_faecis |
| SEQ_43 | YK30 | Anaerostipes_hadrus | SEQ_71 | YK152 | Blautia_hansenii |
| SEQ_44 | YK31 | Anaerostipes_hadrus | SEQ_72 | YK155 | Blautia_hansenii |
| SEQ_45 | YK12 | Eubacterium_rectale | SEQ_73 | YK157 | Eubacterium_rectale |
| SEQ_46 | YK27 | Ruminococcus_faecis | SEQ_74 | YK160 | Roseburia_faecis |
| SEQ_47 | YK28 | Blautia_luti | SEQ_75 | YK166 | Eubacterium_rectale |
| SEQ_48 | YK29 | Ruminococcus_faecis | SEQ_76 | YK168 | Eubacterium_rectale |
| SEQ_49 | YK33 | Anaerostipes_hadrus | SEQ_77 | YK169 | Eubacterium_rectale |
| SEQ_50 | YK34 | Anaerostipes_hadrus | SEQ_78 | YK171 | Eubacterium_rectale |
| SEQ_51 | YK35 | Ruminococcus_faecis | SEQ_79 | YK192 | Roseburia_faecis |

Figure 14

| Cluster | Composition F | SCFAs |
|---|---|---|
| XIVa | *Eubacterium rectale* 12 | A, B, L |
| | *Ruminococcus faecis* 8 | A, L |
| | *Ruminococcus obeum* 2 | A, L |
| | *Blautia faecis* 1 | A, L |
| | *Blautia hansenii* 2 | A, L |
| | *Blautia luti* 2 | A, L |
| | *Anaerostipes hadrus* 7 | B |
| | *Roseburia faecis* 5 | A, B |
| | *Fusicatenibacter saccharivorans* 3 | A, L |
| | *Dorea formicigenerans* 1 | A |
| | *Dorea longicatena* 2 | A |
| IV | *Flavonifractor_plautii* 2 | A, B |
| | *Ruminococcus champanellensis* 2 | A |
| IX | *Acidaminococcus fermentans* 1 | A, B, P |
| | *Megasphaera elsdeni* 4 | P |
| other | *Bacteroides cellulosilyticus* 1 | A, S |
| | Bifiidobacterium Bifidum | L, A |

A, acetate;
B, Butyrate;
L, lactate;
P, propionate;
S, succinate

Figure 15

| Groups | # of animals | Abx | *C. difficile* spore | CFUs LBPs |
|---|---|---|---|---|
| (1) Control | 10 | + | $10^4$ | - |
| (2) Composition B dosed at day -1 | 10 | + | $10^4$ | $10^8$/mouse |
| (3) Composition B dosed at day -2 and -1 | 10 | + | $10^4$ | $10^8$/mouse |
| (4) Composition B dosed at day -2, -1, 1, 2, and 3 | 10 | + | $10^4$ | $10^8$/mouse |
| (5) Composition F dosed at day -1 | 5 | + | $10^4$ | OD Normalized |
| (6) Composition F dosed at day -2, -1, 1, 2, and 3 | 5 | + | $10^4$ | OD Normalized |
| (7) FMT mouse | 5 | + | $10^4$ | 200ul of 10% fecal samples/mouse |
| (8) FMT human | 5 | + | $10^4$ | 200ul of 10% fecal samples/mouse |

Figure 19

Composition G

| | | |
|---|---|---|
| SEQ_27 | YK149 | Acidaminococcus_fermentans/Acidaminococcus_intesti |
| SEQ_43 | YK90 | Anaerostipes_hadrus |
| SEQ_44 | YK30 | Anaerostipes_hadrus |
| SEQ_51 | YK34 | Anaerostipes_hadrus |
| SEQ_55 | YK54 | Anaerostipes_hadrus |
| SEQ_68 | YK98 | Blautia_faecis |
| SEQ_72 | YK152 | Blautia_hansenii |
| SEQ_70 | YK141 | Dorea_formicigenerans |
| SEQ_24 | YK96 | Dorea_longicatena |
| SEQ_34 | YK87 | Eubacterium_rectale |
| SEQ_37 | YK163 | Eubacterium_rectale |
| SEQ_46 | YK12 | Eubacterium_rectale |
| SEQ_76 | YK166 | Eubacterium_rectale |
| SEQ_77 | YK168 | Eubacterium_rectale |
| SEQ_35 | YK105 | Flavonifractor_plautii |
| SEQ_62 | YK70 | Fusicatenibacter_saccharivorans |
| SEQ_26 | YK110 | Megasphaera_elsdenii |
| SEQ_63 | YK71 | Roseburia_faecis |
| SEQ_67 | YK97 | Roseburia_faecis |
| SEQ_40 | YK99 | Ruminococcus_champanellensis |
| SEQ_38 | YK191 | Ruminococcus_champanellensis/Ruminococcus_albus |
| SEQ_47 | YK27 | Ruminococcus_faecis |
| SEQ_56 | YK56 | Ruminococcus_faecis |
| SEQ_25 | YK101 | Ruminococcus_obeum |
| SEQ_32 | YK64 | Ruminococcus_obeum |

Figure 20

| Groups | N | Abx | CFUs *C. difficile* | CFUs LBPs |
|---|---|---|---|---|
| **(1) Vehicle** | 7 | + | $10^4$ | 200ul of PBS |
| **(2) Composition B** | 8 | + | $10^4$ | $10^8$/mouse |
| **(3) Composition B1** | 8 | + | $10^4$ | $10^8$/mouse |
| **(4) Composition B2** | 8 | + | $10^4$ | $10^8$/mouse |
| **(5) Composition F** | 7 | + | $10^4$ | OD Normalized |
| **(6) Composition G** | 7 | + | $10^4$ | OD Normalized |
| **(7) EtOH treated Human fecal samples** | 5 | + | $10^4$ | 200ul of 10% fecal samples/mouse |
| **(8) EtOH treated Composition B** | 5 | + | $10^4$ | $10^8$/mouse |
| **(9) Frozen Composition B** | 5 | + | $10^4$ | $10^8$/mouse |
| **(10) EtOH treated Composition J** | 5 | + | $10^4$ | colony scrapes |

Figure 25

| Groups | N | Abx | CFUs *C. difficile* | CFUs LBPs |
|---|---|---|---|---|
| **(1) Vehicle** | 10 | + | $10^4$ | 200ul of PBS |
| **(2) human FMT** | 10 | + | $10^4$ | 200ul of 10% fecal samples/mouse |
| **(3) Composition B** | 10 | + | $10^4$ | $10^8$/mouse |
| **(4) Composition B + 4 spores*** | 10 | + | $10^4$ | $10^8$ live bacteria+spores/mouse |
| **(5) Composition H**** | 10 | + | $10^4$ | $10^8$/mouse |

*Composition B + 4 spores = The strains of Composition B plus the following four strains in spore form: *Clostrodium bolteae*, *Anaerotruncus colihominis*, *Clostridium symbiosum*, and *Clostridium innocuum*

**Composition H contains the following six strains in spore form: *Clostrodium bolteae*, *Anaerotruncus colihominis*, *Clostridium symbiosum*, *Clostridium innocuum*, *Clostridium disporicum*, and *Erysipelatoclostridium ramosum*

Figure 26

Composition H

**Composition H = The following six strains in spore form *Clostrodium bolteae, Anaerotruncus colihominis, Clostridium symbiosum, Clostridium innocuum, Clostridium disporicum and Erysipelatoclostridium ramosum*

Composition H sequence info:

| | |
|---|---|
| SEQ ID NO: 14 - VE202-13 – *Anaerotruncus colihominis* | **Cluster IV** |
| SEQ ID NO: 16 - VE202-16 – *Clostridium symbiosum* | **Cluster XIVa** |
| SEQ ID NO: 21 - 189 – *Clostridium innocuum* | **Cluster XVII** |
| SEQ ID NO: 82 - PE9 – *Clostridium disporicum* | **Cluster I** |
| SEQ ID NO: 81 – PE5 – *Clostridium bolteae* | **Cluster XIVa** |
| SEQ ID NO: 80 – VE202-18 – *Erysipelatoclostridium ramosum* | **Cluster XVIII** |

TREATMENT OF *CLOSTRIDIUM DIFFICILE* INFECTION

RELATED APPLICATIONS

This application is a continuation of U.S. application Ser. No. 15/630,088, filed Jun. 22, 2017, which is a continuation of international application number PCT/US2017/037498, filed Jun. 14, 2017, which claims the benefit under 35 U.S.C. § 119(e) of U.S. provisional application No. 62/349,914, filed Jun. 14, 2016, each of which is incorporated by reference herein in its entirety.

FIELD OF INVENTION

The disclosure relates to compositions of purified bacterial strains, and methods for treating pathogenic infections, such as *Clostridium difficile* infections, by administering the compositions to a subject having a pathogenic infection.

BACKGROUND OF THE INVENTION

The collection of bacterial, viral, and fungal commensal microorganisms that reside within and on the human body are collectively known as the human microbiome. The bacterial subset of the human microbiome plays an important role in host nutrient acquisition, development, immunological homeostasis, neurological health, and protection against pathogens (LeBlanc et al. *Curr. Opin. Biotechnol.* (2013) 24(2): 160-168; Hooper et al. *Science* (2012) 336 (6086): 1268-1273; Hughes et al. *Am. J. Gastroenterol.* (2013) 108(7): 1066-1074). As the largest reservoir of mammalian commensals, bacteria residing in the gastrointestinal (GI) tract influence nearly all of these aspects of human biology (Blaser *J. Clin. Invest.* (2014) 124(10): 4162-4165). Consequently, perturbation of the normal bacterial populations within the GI niche, a state known as dysbiosis, can predispose humans to a variety of diseases.

*Clostridium difficile* infection (CDI) arises after intestinal colonization by the anaerobic spore-forming Gram-positive pathogen *Clostridium difficile*. Upon colonization of the GI tract, *C. difficile* produces toxins which causes diarrhea and may ultimately lead to death. This illness is the most common identifiable cause of nosocomial diarrhea and is thought to arise as a direct result of dysbiosis (Calfee *Geriatrics* (2008) 63: 10-21; Shannon-Lowe et al *BMJ* (2010) 340: c1296). Not surprisingly, usage of nearly all classes of antibiotics has been associated with CDI, presumably by inducing dysbiosis in the GI tract and thereby enabling *C. difficile* outgrowth. The Center for Disease Control currently classifies CDI as a public health threat requiring immediate and aggressive action because of its natural resistance to many drugs and the emergence of a fluoroquinolone-resistant strain that is now prevalent throughout North America and Europe. *C. difficile* was responsible for almost half a million infections and was associated with approximately 29,000 deaths in 2011 (Lessa et al. *NEJM* 2015, 372: 825-834).

The antibiotics metronidazole, *vancomycin, and fidaxomicin* are the current therapeutic options for treatment of CDI. However, metronidazole is inadequate because of decreased response rates and neither metronidazole nor vancomycin prevent disease recurrence, with up to 30% of patients initially responding experiencing a clinical recurrence after antibiotic cessation (Miller *Expert Opin. Pharmacother.* (2010) 11: 1569-1578). Fidaxomicin has been shown to be superior to *vancomycin* in preventing recurrent CDI (Mullane *Ther. Adv. Chronic Dis.* (2014) 5(2): 69-84). Because of its narrow spectrum of activity, fidaxomicin is thought to enable normal microbiome repopulation of the gut following dysbiosis and CDI, thereby lowering the likelihood of recurrent disease (Tannock et al. *Microbiology* (2010) 156 (Pt 11): 3354-3359; Louie et al. *Clin. Infect. Dis.* (2012) 55 Suppl. 2: S132-142). Nonetheless, 14% of fidaxomicin-treated patients experience CDI relapse and mutations conferring reduced sensitivity have already been reported (Eyre et al. *J. Infect. Dis.* (2014) 209(9): 1446-1451).

Because the risk of recurrent CDI is heightened by antibiotic use and *C. difficile* spores are inherently recalcitrant to the available chemotherapeutic arsenal, alternative therapeutic modalities are being pursued for the treatment of CDI. Fecal microbiota transplantation (FMT) is one such modality that has shown efficacy against CDI (Khoruts et al. *Immunol. Lett.* (2014) 162(2): 77-81; van Nood et al. *N. Engl. J. Med.* (2013) 368(5): 407-415). To date, results of FMT studies for the treatment of CDI, have reported cure rates up to 90% in three randomized controlled studies (Cammarota et al. *Alimen. Pharmacol. Therap.* (2015) 41(9): 835-843; Kassam et al. *Am. J. Gastroenterol.* (2013) 108(4): 500-508; van Nood et al. *N. Engl. J. Med.* (2013) 368(5): 407-415; Youngster et al. *Infec. Dis. Soc. Am.* (2014) 58(11): 1515-1522).

Despite the success of FMT, this therapeutic approach is not without risks and logistical concerns. Selection of FMT donors is critical and challenging. When FMT donor recruitment is performed with stringent screening and standardization protocols, most prospective donors fail this process. Only 6-10% of prospective FMT donors qualify, with the majority of failures arising from asymptomatic carriage of GI pathogens (Paramsothy et al. *Inflamm. Bowel Dis.* (2015) 21(7): 1600-1606; Borody et al. *Curr. Opin. Gastroenterol.* (2014) 30(10): 97-105; Burns et al. *Gastroenterology* (2015) 148: S96-S97; Surawicz *Ann. Intern. Med.* (2015) 162(9): 662-663). Furthermore, variation between donors may lead to variation in FMT efficacy. In addition, the risk of transmission of even non-infectious illnesses may be heightened by FMT. Indeed, significant weight gain has been reported in a patient who received an FMT from an overweight stool donor (Alang et al. *Open Forum Infect. Dis.* (Winter 2015) 2(1)).

SUMMARY OF THE INVENTION

Provided herein are compositions and methods for the treatment or prevention of pathogenic infections including *C. difficile*.

In one aspect, the disclosure provides compositions comprising two or more purified bacterial strains of species selected from the group consisting of: *Clostridium hathewayi, Blautia hansenii, Blautia producta, Blautia producta* ATCC 27340, *Clostridium bacterium* UC5.1-1D4, *Blautia coccoides, Eubacterium contortum, Eubacterium fissicatena, Sellimonas intestinalis, Dracourtella massiliensis, Dracourtella massilinesis* GD1, *Ruminococcus torques, Anaerostipes caccae, Clostridium scindens, Marvinbryanta formatexigens, Eisenbergiella tayi, Flavinofractor plautii, Clostridium orbiscindens* 1_3_50AFAA, *Lachnospiraceae bacterium* 7_1_58FAA, *Subdoligranulum, Anaerotruncus colihominis, Anaerotruncus colihominis* DSM 17241, *Clostridium symbiosum, Clostridium symbiosum* WAL-14163, *Clostridium bolteae, Clostridium bolteae* 90A9, *Dorea longicatena, Dorea longicatena* CAG:42, *Clostridium innocuum, Erysipelotrichaceae_bacterium_21-*

3, *Blautia wexlerae, Clostridium disporicum, Erysipelatoclostridium ramosum, Pseudoflavinofractor capillosus, Turicibacter sanguinis, Lactobacillus mucosae, Ruminococcus obeum, Megasphaera elsdenii, Acidaminococcus fermentans, Acidaminococcus intestine, Ruminococcus faecis, Bacteroides cellulosilyticus, Anaerostipes hadrus, Eubacterium rectale, Ruminococcus champanellnsis, Ruminococcus albus, Bifidobacterium bifidum, Blautia luti, Roseburia faecis, Fusicatenibacter saccharivorans, Roseburia faecis, Blautia faecis, Dorea formicigenerans* and *Bacteroides ovatus.*

In some embodiments of the compositions provided herein, the composition comprises two or more purified bacterial strains of species selected from the group consisting of: *Clostridium hathewayi, Blautia hansenii, Blautia producta, Blautia producta* ATCC 27340, *Clostridium bacterium* UC5.1-1D4, *Blautia coccoides, Eubacterium contortum, Eubacterium fissicatena, Sellimonas intestinalis, Dracourtella massiliensis, Dracourtella massilinesis* GD1, *Ruminococcus torques, Anaerostipes caccae, Clostridium scindens, Marvinbryanta formatexigens, Eisenbergiella tayi, Flavinofractor plautii, Clostridium orbiscindens* 1_3_50AFAA, *Lachnospiraceae bacterium* 7_1_58FAA, *Subdoligranulum, Anaerotruncus colihominis, Anaerotruncus colihominis* DSM 17241, *Clostridium symbiosum, Clostridium symbiosum* WAL-14163, *Clostridium bolteae, Clostridium bolteae* 90A9, *Dorea longicatena, Dorea longicatena* CAG:42, *Clostridium* innocuum, Erysipelotrichaceae_*bacterium*_21-3, *Blautia wexlerae, Turicibacter sanguinis, Lactobacillus mucosae*, and *Bacteroides ovatus.*

In some embodiments of the compositions provided herein, the composition comprises two or more purified bacterial strains of species selected from the group consisting of: *Clostridium hathewayi, Blautia hansenii, Blautia producta, Blautia coccoides, Eubacterium contortum, Eubacterium fissicatena, Anaerostipes caccae, Clostridium scindens, Marvinbryanta formatexigens*, and *Eisenbergiella tayi.*

In some embodiments of the compositions provided herein, the composition comprises two or more purified bacterial strains of species selected from the group consisting of: *Flavinofractor plautii, Clostridium orbiscindens* 1_3_50AFAA, *Lachnospiraceae bacterium* 7_1_58FAA, *Subdoligranulum, Anaerotruncus colihominis, Anaerotruncus colihominis* DSM 17241, *Eubacterium fissicatena, Sellimonas intestinalis, Dracourtella massiliensis, Dracourtella massilinesis* GD1, *Ruminococcus torques, Clostridium symbiosum, Clostridium symbiosum* WAL-14163, *Clostridium bolteae, Clostridium bolteae* 90A9, *Dorea longicatena, Dorea longicatena* CAG:42, *Blautia producta, Blautia producta* ATCC 27340, *Clostridium bacterium* UC5.1-1D4, *Clostridium innocuum*, and *Erysipelotrichaceae_bacterium*_21-3.

In some embodiments of the compositions provided herein, the composition comprises two or more purified bacterial strains of species selected from the group consisting of: *Clostridium* orbiscindens 1_3_50AFAA, *Anaerotruncus colihominis* DSM 17241, *Dracourtella massilinesis* GD1, *Clostridium symbiosum* WAL-14163, *Clostridium bolteae* 90A9, *Dorea longicatena* CAG:42, *Clostridium bacterium* UC5.1-1D4, and *Erysipelotrichaceae_bacterium*_21-3.

In some embodiments of the compositions provided herein, the composition comprises two or more purified bacterial strains of species selected from the group consisting of: *Clostridium orbiscindens* 1_3_50AFAA, *Anaerotruncus colihominis* DSM 17241, *Sellimonas intestinalis, Clostridium symbiosum* WAL-14163, *Clostridium bolteae* 90A9, *Dorea longicatena* CAG:42, *Clostridium bacterium* UC5.1-1D4, and *Erysipelotrichaceae_bacterium*_21_3.

In some embodiments of the compositions provided herein, the composition comprises purified bacterial strains *Clostridium* orbiscindens 1_3_50AFAA, *Anaerotruncus colihominis* DSM 17241, *Dracourtella massilinesis* GD1, *Clostridium symbiosum* WAL-14163, *Clostridium bolteae* 90A9, *Dorea longicatena* CAG:42, *Clostridium bacterium* UC5.1-1D4, and *Erysipelotrichaceae_bacterium*_21-3.

In some embodiments of the compositions provided herein, the composition comprises purified bacterial strains *Clostridium orbiscindens* 1_3_50AFAA, *Anaerotruncus colihominis* DSM 17241, *Sellimonas intestinalis* GD1, *Clostridium symbiosum* WAL-14163, *Clostridium bolteae* 90A9, *Dorea longicatena* CAG:42, *Clostridium bacterium* UC5.1-1D4, and *Erysipelotrichaceae_bacterium*_21_3.

In some embodiments of the compositions provided herein, the composition comprises two or more purified bacterial strains of species selected from the group consisting of: *Flavinofractor plautii, Anaerotruncus colihominis, Dracourtella massiliensis, Clostridium symbiosum, Clostridium bolteae, Dorea longicatena, Blautia producta*, and *Clostridium innocuum.*

In some embodiments of the compositions provided herein, the composition comprises purified bacterial strains *Flavinofractor plautii, Anaerotruncus colihominis, Dracourtella massiliensis, Clostridium symbiosum, Clostridium bolteae, Dorea longicatena, Blautia producta*, and *Clostridium innocuum.*

In some embodiments of the compositions provided herein, the composition comprises two or more purified bacterial strains of species selected from the group consisting of: *Flavinofractor plautii, Anaerotruncus colihominis, Eubacterium fissicatena, Clostridium symbiosum, Clostridium bolteae, Dorea longicatena, Blautia producta*, and *Clostridium innocuum.*

In some embodiments of the compositions provided herein, the composition comprises purified bacterial strains *Flavinofractor plautii, Anaerotruncus colihominis, Eubacterium fissicatena, Clostridium symbiosum, Clostridium bolteae, Dorea longicatena, Blautia producta*, and *Clostridium innocuum.*

In some embodiments of the compositions provided herein, the composition comprises two or more purified bacterial strains of species selected from the group consisting of: *Flavinofractor plautii, Lachnospiraceae bacterium* 7_1_58FAA, *Subdoligranulum, Anaerotruncus colihominis, Eubacterium fissicatena, Ruminococcus torques, Clostridium symbiosum, Clostridium bolteae, Dorea longicatena, Blautia producta, Clostridium innocuum, Erysipelotrichaceae_bacterium*_21-3, and *Bacteroides ovatus.*

In some embodiments of the compositions provided herein, the composition comprises two or more purified bacterial strains of species selected from the group consisting of: *Clostridium orbiscindens* 1_3_50AFAA, *Anaerotruncus colihominis* DSM 17241, *Dracourtella massiliensis* GD1, *Clostridium symbiosum* WAL-14163, *Clostridium bolteae* 90A9, *Dorea longicatena* CAG:42, *Clostridium bacterium* UC5.1-1D4, *Erysipelotrichaceae_ bacterium*_21-3, and *Bacteroides ovatus.*

In some embodiments of the compositions provided herein, the composition comprises two or more purified bacterial strains of species selected from the group consisting of: *Clostridium orbiscindens* 1_3_50AFAA, *Anaerotruncus colihominis* DSM 17241, *Sellimonas intes-*

*tinalis, Clostridium symbiosum* WAL-14163, *Clostridium bolteae* 90A9, *Dorea longicatena* CAG:42, *Clostridium bacterium* UC5.1-1D4, *Erysipelotrichaceae_bacterium*_21-3, and *Bacteroides ovatus*.

In some embodiments of the compositions provided herein, the composition does not include a bacterial strain of the species *Flavinofractor plautii, Subdoligranulum*, or *Lachnospiraceae bacterium* 7_1_58FAA. In some embodiments of the compositions provided herein, the composition does not include a bacterial strain of the species *Bacteroides ovatus*. The composition of any one of claims 4-12, wherein the composition does not include a bacterial strain of the species *Flavinofractor plautii, Subdoligranulum, Clostridium orbiscindens* 1_3_50AFAA, or *Lachnospiraceae bacterium* 7-¬_1_58FAA.

In some embodiments of the compositions provided herein, the composition comprises two or more purified bacterial strains of species selected from the group consisting of: *Clostridium scindens, Clostridium hathewayi, Blautia hansenii, Blautia wexlerae, Blautia producta, Blautia coccoides, Dorea longicatena, Clostridium innocuum, Erysipelotrichaceae_bacterium*_21-3, *Flavinofractor plautii, Lachnospiraceae bacterium* 7-_1_58FAA, *Subdoligranulum, Anaerotruncus colihominis*, and *Clostridium symbiosum*. In some embodiments of the compositions provided herein, the composition does not include a bacterial strain of the species *Flavinofractor plautii, Subdoligranulum*, or *Lachnospiraceae bacterium* 7_1_58FAA.

In some embodiments of the compositions provided herein, the composition comprises two or more purified bacterial strains of species selected from the group consisting of: *Clostridium scindens, Clostridium hathewayi, Blautia hansenii, Blautia wexlerae, Anaerotruncus colihominis, Dorea longicatena, Clostridium innocuum, Erysipelotrichaceae_bacterium*_21-3, *Flavinofractor plautii, Lachnospiraceae bacterium* 7-_1_58FAA, *Subdoligranulum, Turicibacter sanguinis*, and *Lactobacillus mucosae*. In some embodiments of the compositions provided herein, the composition does not include a bacterial strain of the species *Flavinofractor plautii, Subdoligranulum* or *Lachnospiraceae bacterium* 7_1_58FAA.

In some embodiments of the compositions provided herein, the composition comprises two or more purified bacterial strains of species selected from the group consisting of: *Dorea longicatena, Ruminococcus obeum, Megasphaera elsdenii, Acidaminococcus fermentans, Acidaminococcus intestine, Ruminococcus faecis, Bacteroides cellulosilyticus, Anaerostipes hadrus, Flavinofractor plautii, Eubacterium rectale, Ruminococcus champanellensis, Ruminococcus albus, Bifidobacterium bifidum, Ruminococcus faecis, Blautia luti, Roseburia faecis, Fusicatenibacter saccharivorans, Blautia faecis, Dorea formicigenerans*, and *Blautia hansenii*.

In some embodiments of the compositions provided herein, the composition comprises two or more purified bacterial strains of species selected from the group consisting of: *Acidaminococcus fermentans, Acidaminococcus intestine, Anaerostipes hadrus, Blautia faecis, Blautia hansenii, Dorea formicigenerans, Dorea longicatena, Eubacterium rectale, Flavinofractor plautii, Fusicatenibacter saccharivorans, Megasphaera elsdenii, Roseburia faecis, Ruminococcus champanellensis, Ruminococcus albus, Ruminococcus faecis*, and *Ruminococcus obeum*.

In one aspect the disclosure provides compositions comprising two or more purified bacterial strains, wherein the two or more purified bacterial strains comprise 16S rDNA sequences having at least 97% homology with nucleic acid sequences selected from the group consisting of SEQ ID NOs:1-83 and 124-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs:1-23, SEQ ID NO:83, SEQ ID NOs: 124-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21. In some embodiments of the compositions provided herein, the composition comprises purified bacterial strains that comprise 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs: 124-159. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO: 124, SEQ ID NO: 129, SEQ ID NO: 132, SEQ ID NO: 137, SEQ ID NO: 141, SEQ ID NO: 146, SEQ ID NO: 152, and SEQ ID NO: 157. In some embodiments of the compositions provided herein, the composition comprises purified bacterial strains that comprise 16S rDNA sequences having at least 97% homology with nucleic acid sequences selected from the group consisting of SEQ ID NO: 124, SEQ ID NO: 129, SEQ ID NO: 132, SEQ ID NO: 137, SEQ ID NO: 141, SEQ ID NO: 146, SEQ ID NO: 152, and SEQ ID NO: 157.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:20 and SEQ ID NO:21, and wherein the composition does not include a bacterial strain comprising a 16S rDNA sequence having at least 97% homology with a nucleic acid sequence of SEQ ID NO:10. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs:124-156, and wherein the composition does not include a bacterial strain comprising a 16S rDNA sequence having at least 97% homology with a nucleic acid sequence selected from the group consisting of SEQ ID NOs:157-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21 and SEQ ID NO:22. In some embodiments of the compositions provided herein, the composition comprises two or more purified bacterial strains, wherein the two or more purified bacterial strains comprise 16S rDNA sequences having at least 97% homology with nucleic acid sequence selected from the group consisting of SEQ ID NO: 124-145, SEQ ID NO: 152-159, SEQ ID NO: 18, and SEQ ID NO: 22.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:21 and SEQ ID NO:22, and wherein the composition does not include a bacterial strain comprising a 16S rDNA sequence having at least 97% homology with a nucleic acid sequence of SEQ ID NO:10. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO: 124-145 and SEQ ID NO: 152-156, and wherein the composition does not include a bacterial strain comprising a 16S rDNA sequence having at least 97% homology with a nucleic acid sequence selected from the group consisting of SEQ ID NOs:157-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:10 and SEQ ID NOs:14-22. In some embodiments of the compositions provided herein, the composition comprises two or more purified bacterial strains, wherein the two or more purified bacterial strains comprise 16S rDNA sequences having at least 97% homology with nucleic acid sequence selected from the group consisting of SEQ ID NOs: 124-159, SEQ ID NO: 18, and SEQ ID NO: 22.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs:14-22 and wherein the composition does not include a bacterial strain comprising a 16S rDNA sequence having at least 97% homology with a nucleic acid sequence of SEQ ID NO:10. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs: 129-156, SEQ ID NO: 18, SEQ ID NO: 22, and wherein the composition does not include a bacterial strain comprising a 16S rDNA sequence having at least 97% homology with a nucleic acid sequence selected from the group consisting of SEQ ID NOs:157-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21 and SEQ ID NO:83. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID Nos: 124-159 and SEQ ID NO: 83.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:20, SEQ ID NO:21 and SEQ ID NO:83, and wherein the composition does not include a bacterial strain comprising a 16S rDNA sequence having at least 97% homology with a nucleic acid sequence of SEQ ID NO:10. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs: 124-156 and SEQ ID NO: 83, and wherein composition does not include a bacterial strain comprising a 16S rDNA sequence having at least 97% homology with a nucleic acid sequence selected from the group consisting of SEQ ID NOs:157-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22 and SEQ ID NO:83. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs: 124-159, SEQ ID NO: 22, and SEQ ID NO: 83, In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:21, SEQ ID NO:22 and SEQ ID NO:83, and wherein the composition does not include a bacterial strain comprising a 16S rDNA sequence having at least 97% homology with a nucleic acid sequence of SEQ ID NO:10. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs: 124-145, SEQ ID NOs: 152-156, SEQ ID NO: 22, and SEQ ID NO: 83, wherein composition does not include a bacterial strain comprising a 16S rDNA sequence having at least 97% homology with a nucleic acid sequence selected from the group consisting of SEQ ID NOs:157-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:10, SEQ ID NOs:14-22, and SEQ ID NO:83. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs: 124-159, SEQ ID NO: 18, SEQ ID NO:22, and SEQ ID NO: 83.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs:14-22 and SEQ ID NO:83, and wherein the composition does not include a bacterial strain comprising a 16S rDNA sequence having at least 97% homology with a nucleic acid sequence of SEQ ID NO:10. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO: 124-15, SEQ ID NO: 18, SEQ ID NO:22, and SEQ ID NO: 83, wherein composition does not include a bacterial strain comprising a 16S rDNA sequence having at least 97% homology with a nucleic acid sequence selected from the group consisting of SEQ ID NOs:157-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:1, SEQ ID NO:3, SEQ ID NO:5, SEQ ID NO:7, SEQ ID NO:10, SEQ ID NO:12, SEQ ID NO:14, SEQ ID NO:16, SEQ ID NO:18, and SEQ ID NO:21.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:1, SEQ ID NO:2, SEQ ID NO:3, SEQ ID NO:5, SEQ ID NO:6, SEQ ID NO:10, SEQ ID NO:12, SEQ ID NO:14, SEQ ID NO:18, and SEQ ID NO:21.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs:24-79.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs:24-27, SEQ ID NO:32, SEQ ID NO:34, SEQ ID NO:35, SEQ ID NO:37, SEQ ID NO:38, SEQ ID NO:40, SEQ ID NO:43, SEQ ID NO:44, SEQ ID NO:46, SEQ ID NO:47, SEQ ID NO:51, SEQ ID NO:55, SEQ ID NO:56, SEQ ID NO:62, SEQ ID NO:63, SEQ ID NO:67, SEQ ID NO:68, SEQ ID NO:70, SEQ ID NO:72, SEQ ID NO:76 and SEQ ID NO:77.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:14, SEQ ID NO:16, SEQ ID NO:21, and SEQ ID NOs:80-82.

In one aspect the disclosure provides compositions comprising two or more purified bacterial strains, wherein the two or more purified bacterial strains comprise 16S rDNA sequences having at least 97% homology with nucleic acid sequences selected from the group consisting of SEQ ID NOs:84-123.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:87, SEQ ID NO:88, SEQ ID NO:89, SEQ ID NO:90, SEQ ID NO:91, SEQ ID NO:93, SEQ ID NO:94, SEQ ID NO:95, SEQ ID NO:97, SEQ ID NO:98, SEQ ID NO:99, SEQ ID NO:101, SEQ ID NO:102, SEQ ID NO:103, SEQ ID NO:105, SEQ ID NO:106, SEQ ID NO:108, SEQ ID NO:109, SEQ ID NO:110, SEQ ID NO:121, and SEQ ID NO:122.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:87, SEQ ID NO:88, SEQ ID NO:89, SEQ ID NO:99, SEQ ID NO:103, SEQ ID NO:105, SEQ ID NO:106, SEQ ID NO:108, SEQ ID NO:109, and SEQ ID NO:121.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:93, SEQ ID NO:95, SEQ ID NO:97, SEQ ID NO:98, SEQ ID NO:102, SEQ ID NO:106, SEQ ID NO:110, and SEQ ID NO:122.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:95, SEQ ID NO:97, SEQ ID NO:98, SEQ ID NO:102, SEQ ID NO:106, SEQ ID NO:110, and SEQ ID NO:122, and wherein the composition does not include a bacterial strain comprising a 16S rDNA sequence having at least 97% homology with a nucleic acid sequence of SEQ ID NO:93.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:93, SEQ ID NO:95, SEQ ID NO:97, SEQ ID NO:98, SEQ ID NO:101, SEQ ID NO:102, SEQ ID NO:106, SEQ ID NO:110, and SEQ ID NO:122.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:95, SEQ ID NO:97, SEQ ID NO:98, SEQ ID NO:101, SEQ ID NO:102, SEQ ID NO:106, SEQ ID NO:110, and SEQ ID NO:122, and wherein the composition does not include a bacterial strain comprising a 16S rDNA sequence having at least 97% homology with a nucleic acid sequence of SEQ ID NO:93.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:87, SEQ ID NO:93, SEQ ID NO:94, SEQ ID NO:95, SEQ ID NO:97, SEQ ID NO:98, SEQ ID NO:99, SEQ ID NO:103, SEQ ID NO:105, SEQ ID NO:106, and SEQ ID NO:122.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:87, SEQ ID NO:90, SEQ ID NO:91, SEQ ID NO:93, SEQ ID NO:94, SEQ ID NO:95, SEQ ID NO:97, SEQ ID NO:98, SEQ ID NO:99, and SEQ ID NO:105.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:84, SEQ ID NO:85, SEQ ID NO:92, SEQ ID NO:93, SEQ ID NO:96, SEQ ID NO:97, SEQ ID NO:99, SEQ ID NO:100, SEQ ID NO:104, SEQ ID NO:107, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, and SEQ ID NO:120.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:84, SEQ ID NO:85, SEQ ID NO:92, SEQ ID NO:93, SEQ ID NO:96, SEQ ID NO:97, SEQ ID NO:99, SEQ ID NO:104, SEQ ID NO:107, SEQ ID NO:111, SEQ ID NO:112, SEQ ID NO:113, SEQ ID NO:114, SEQ ID NO:115, SEQ ID NO:116, SEQ ID NO:117, and SEQ ID NO:119.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:86, SEQ ID NO:95, SEQ ID NO:98, SEQ ID NO:110, SEQ ID NO:122, and SEQ ID NO:123.

In some embodiments of the compositions provided herein, the composition comprises at least one bacterial strain from *Clostridium* cluster XIVa and at least one bacterial strain from *Clostridium* cluster XVII. In some embodiments of the compositions provided herein, the composition comprises at least one bacterial strain from *Clostridium* cluster IV and at least one bacterial strain from *Clostridium* cluster XVII. In some embodiments of the compositions provided herein, the composition comprises at least one bacterial strain from *Clostridium* cluster XIVa, at least one strain from *Clostridium* cluster IV and at least one bacterial strain from *Clostridium* cluster XVII.

In some embodiments of the compositions provided herein, the composition comprises at least one *Bacteroides* strain. In some embodiments of the compositions provided herein, the composition does not include *Clostridium* scindens.

In some embodiments of the compositions provided herein, the composition comprises at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 purified bacterial strains.

In some embodiments of the compositions provided herein, one or more of the bacterial strains are spore formers. In some embodiments of the compositions provided herein, one or more of the bacterial strains are in spore form. In some embodiments of the compositions provided herein, each of the bacterial strains is in spore form.

In some embodiments of the compositions provided herein, one or more of the bacterial strains is in vegetative form. In some embodiments of the compositions provided herein, each of the bacterial strains is in vegetative form.

In some embodiments of the compositions provided herein, the composition comprises only obligate anaerobic bacterial strains. In some embodiments of the compositions provided herein, the composition comprises bacterial strains that originate from more than one human donor.

In some embodiments of the compositions provided herein, one or more of the bacterial strains are baiCD−. In some embodiments of the compositions provided herein, each of the bacterial strains is baiCD−. In some embodiments of the compositions provided herein, the composition does not mediate bile acid 7-alpha-dehydroxylation. In some embodiments of the compositions provided herein, the composition inhibits *C. difficile* toxin production. In some embodiments of the compositions provided herein, the composition inhibits *C. difficile* replication and/or survival.

In some embodiments of the compositions provided herein, the bacterial strains are lyophilized.

In some embodiments of the compositions provided herein, the composition induces the proliferation and/or accumulation of regulatory T cells (Tregs).

In one aspect, the disclosure provides compositions comprising two or more purified bacterial strains, wherein the composition comprises at least one bacterial strain from *Clostridium* cluster XIVa and at least one bacterial strain from *Clostridium* cluster XVII. In one aspect, the disclosure provides compositions comprising two or more purified bacterial strains, wherein the composition comprises at least one bacterial strain from *Clostridium* cluster IV and at least one bacterial strain from *Clostridium* cluster XVII. In one aspect, the disclosure provides compositions comprising two or more purified bacterial strains, wherein the composition comprises at least one bacterial strain from *Clostridium* cluster IV, at least one bacterial strain from *Clostridium* cluster XIVa and at least one bacterial strain from *Clostridium* cluster XVII.

In some embodiments of the compositions provided herein, the composition comprises at least one *Bacteroides* strain. In some embodiments of the compositions provided herein, the composition does not include *Clostridium scindens*.

In some embodiments of the compositions provided herein, the composition comprises at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 purified bacterial strains.

In some embodiments of the compositions provided herein, one or more of the bacterial strains are spore formers. In some embodiments of the compositions provided herein, one or more of the bacterial strains are in spore form. In some embodiments of the compositions provided herein, each of the bacterial strains is in spore form.

In some embodiments of the compositions provided herein, one or more of the bacterial strains is in vegetative form. In some embodiments of the compositions provided herein, each of the bacterial strains is in vegetative form.

In some embodiments of the compositions provided herein, the composition comprises only obligate anaerobic bacterial strains.

In some embodiments of the compositions provided herein, the composition comprises bacterial strains that originate from more than one human donor.

In some embodiments of the compositions provided herein, one or more of the bacterial strains are baiCD−. In some embodiments of the compositions provided herein, each of the bacterial strains is baiCD−. In some embodiments of the compositions provided herein, the composition does not mediate bile acid 7-alpha-dehydroxylation. In some embodiments of the compositions provided herein, the composition inhibits *C. difficile* toxin production. In some embodiments of the compositions provided herein, the composition inhibits *C. difficile* replication and/or survival.

In some embodiments of the compositions provided herein, the bacterial strains are lyophilized.

In some embodiments of the compositions provided herein, the composition induces the proliferation and/or accumulation of regulatory T cells (Tregs).

In one aspect, the disclosure provides a pharmaceutical composition comprising any of the compositions provided herein further comprising a pharmaceutically acceptable excipient. In some embodiments of the pharmaceutical compositions provided herein, the pharmaceutical composition is formulated for oral delivery. In some embodiments of the pharmaceutical compositions provided herein, the pharmaceutical composition is formulated for rectal delivery. In some embodiments of the pharmaceutical compositions provided herein, the pharmaceutical composition is formulated for delivery to the intestine. In some embodiments of the pharmaceutical compositions provided herein, the pharmaceutical composition is formulated for delivery to the colon.

In one aspect, the disclosure provides a food product comprising any of the compositions provided herein further comprising a nutrient.

In one aspect, the disclosure provides a method of treating a pathogenic infection in a subject, comprising administering to the subject a therapeutically effective amount of any of the compositions or food products provided herein to treat the pathogenic infection.

In some embodiments of the methods provided herein, the pathogenic infection is *C. difficile, Vancomycin* Resistant *Enterococci* (VRE), Carbapenem Resistant *Enterobacteriaceae* (CRE), *Neisseria gonorrheae*, Multidrug Resistant *Acinetobacter, Campylobacter*, Extended spectrum beta-lactamese (ESBL) producing *Enterobacteriaceae*, Multidrug Resistant *Pseudomonas aeruginosa, Salmonella*, Drug resistant non-typhoid *Salmonella*, Drug resistant *Salmonella Typhi*, Drug resistant *Shigella, Methicillin* Resistant *Staphylococcus aureus*, Drug resistant *Streptococcus pneumoniae*, Drug resistant Tuberculosis, *Vancomycin resistant Staphylococcus aureus*, Erythromycin Resistant Group A *Streptococcus*, Clindamycin resistant Group B *Streptococcus*, and combinations thereof. In some embodiments of the methods provided herein, the pathogenic infection is *C. difficile*. In some embodiments of the methods provided herein, the pathogenic infection is *Vancomycin*-Resistant *Enterococci*.

In some embodiments of the methods provided herein, the subject is human. In some embodiments of the methods provided herein, the subject is an asymptotic carrier.

In some embodiments of the methods provided herein, the subject is administered a dose of an antibiotic prior to administration of the composition. In some embodiments of the methods provided herein, the subject is administered more than one dose of the antibiotic prior to administration of the composition. In some embodiments of the methods provided herein, the subject has not been administered an antibiotic prior to administration of the composition.

In some embodiments of the methods provided herein, the composition is administered to the subject by oral administration. In some embodiments of the methods provided herein, the composition is administered to the subject by rectal administration.

In some embodiments of the methods provided herein, the administering results in proliferation and/or accumulation of regulatory T cells (Tregs).

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF THE DRAWINGS

The accompanying drawings are not intended to be drawn to scale. The figures are illustrative only and are not required for enablement of the disclosure. For purposes of clarity, not every component may be labeled in every drawing. In the drawings:

FIG. 1 shows the strains of Compositions A-D. Each entry includes the SEQ ID NO of the 16S rDNA sequence of the strain, a strain identifier, and the species with the closest known homology (can be more than one species). The bracketed roman numeral indicates the *Clostridium* cluster classification of each strain based on the closest species homology. Strains that are not classified in Cluster XIVa are highlighted in bold. The two non-clostridial strains (SEQ ID NO:2, closest known species *Turicibacter sanguinis*, and SEQ ID NO:6, closest known species *Lactobacillus mucosae*) do not belong to the *Clostridium* genus.

FIG. 3 shows the experimental conditions described in Example 1. The groups of mice were divided based on the antibiotic regimen received prior to administration of the indicated amount of *C. difficile* spores. "Abx" refers to treatment with any of the antibiotic regimens.

FIGS. 4A-4D show survival of mice that received no treatment (FIG. 4A), antibiotic cocktail (FIG. 4B), clindamycin (FIG. 4C), or cefoperazone (FIG. 4D) prior to *C. difficile* infection. FIGS. 4E-4H show body weight of mice that received no treatment (FIG. 4E), antibiotic cocktail (FIG. 4F), clindamycin (FIG. 4G), or cefoperazone (FIG. 4H) prior to *C. difficile* infection. FIGS. 4I-4L show *C. difficile* burden (CFU) per gram of feces from mice that received no treatment (FIG. 4I), antibiotic cocktail (FIG. 4J), clindamycin (FIG. 4K), or cefoperazone (FIG. 4L) prior to *C. difficile* infection. Open circles indicate infection with 10 *C. difficile* spores; closed squares indicate infection with 10,000 *C. difficile* spores. Black triangles in FIG. 4J indicate an additional experimental arm in which mice were treated with *vancomycin following C. difficile* infection.

FIG. 5 shows experimental conditions evaluated in Example 2, the results for which are presented in FIGS. 7-9. Composition E corresponds to a mixture of 17 bacterial strains (See e.g., Narushima et al., Gut Microbes 5: 3, 333-339). Composition I corresponds to a mixture of *Clostridium scindens, Pseudoflavonifractor capillosus*, and *Blautia hansenii*. "Abx" refers to treatment with any of the antibiotic regimens.

FIG. 7A shows weight of the mice that received no antibiotic treatment. FIG. 7B shows weight of the mice that received cefoperazone treatment. FIG. 7C shows weight of the mice that received cefoperazone treatment followed by *vancomycin*. FIG. 7D shows weight of the mice that received cefoperazone treatment followed by Composition I. FIG. 7E shows weight of the mice that received cefoperazone treatment followed by Composition E. FIG. 7F shows weight of the mice that received cefoperazone treatment followed by composition A. FIG. 7G shows weight of the mice that received cefoperazone treatment followed by composition B. FIG. 7H shows weight of the mice that received cefoperazone treatment followed by composition C. FIG. 7I shows weight of the mice that received cefoperazone treatment followed by composition D.

FIG. 8A shows *C. difficile* CFU/g feces one-day post infection. FIG. 8B shows *C. difficile* CFU/g feces 3 days post infection. FIG. 8C shows *C. difficile* CFU/g feces 8 days post infection.

FIG. 9 shows experimental conditions evaluated in Example 3, the results for which are presented in FIGS. 10-12.

FIG. 13 shows the strains of Composition F. The genus-species notation indicates the closest species based on the sequence of the isolated strain.

FIG. 14 shows the classification by *Clostridium* cluster of the strains in Composition F and their short-chain fatty acid producing abilities.

FIG. 15 shows experimental conditions evaluated in Example 4, the results for which are presented in FIGS. 16-18. The dosing days are relative to *C. difficile* infection. FMT refers to Fecal Matter Transplant with fecal matter isolated from mice or from humans.

FIG. 17A shows weight of the mice that received cefoperazone treatment. FIG. 17B shows weight of the mice that received cefoperazone treatment followed by FMT with fecal matter from a human. FIG. 17C shows weight of the mice that received cefoperazone treatment followed by FMT with fecal matter from a mouse. FIG. 17D shows weight of the mice that received cefoperazone treatment followed by Composition B on day −1. FIG. 17E shows weight of the mice that received cefoperazone treatment followed by Composition B on days −2 and −1. FIG. 17F shows weight of the mice that received cefoperazone treatment followed by Composition B on days −2, −1, 1, 2, and 3. FIG. 17G shows weight of the mice that received cefoperazone treatment followed by Composition F on day −1. FIG. 17H shows weight of the mice that received cefoperazone treatment followed by Composition F on days −2, −1, 1, 2, and 3.

FIG. 18A shows *C. difficile* CFU/g feces 8 days post infection. FIG. 18B shows *C. difficile* CFU/g feces 17 days post infection.

FIG. 19 shows the strains of Composition G. The genus-species notation indicates the closest species based on the sequence of the isolated strain.

FIG. 20 shows experimental conditions evaluated in Example 5, the results for which are presented in FIGS. 21-23. Composition B1=Composition B with *Bacteroides*; Composition B2=Composition B with *Bacteroides* but without *Flavonifractor plautii*.

FIG. 22A shows weight of the mice that received vehicle control. FIG. 22B shows weight of the mice that received Composition F. FIG. 22C shows weight of the mice that received Composition G. FIG. 22D shows weight of the mice that received cefoperazone treatment followed by Composition B. FIG. 22E shows weight of the mice that received cefoperazone treatment followed by Composition B2 (=Composition B without *Flavonifractor plautii* and with added *Bacteroides*). FIG. 22F shows weight of the mice that received cefoperazone treatment followed by Composition B1 (=Composition B with *Bacteroides* added). FIG. 22G shows weight of the mice that received cefoperazone treatment followed by frozen Composition B. FIG. 22H shows weight of the mice that received cefoperazone treatment followed by ethanol treated human fecal samples. FIG. 22I shows weight of the mice that received cefoperazone treatment followed by ethanol treated Composition B. FIG. 22J shows weight of the mice that received cefoperazone treatment followed by Composition J.

FIG. 25 shows experimental conditions evaluated in Example 6, the results of which are presented in FIGS. 27-29.

FIG. 26 shows the strains in Composition H (SEQ ID NO:14-VE202-13-*Anaerotruncus colihominis* (Cluster IV); SEQ ID NO:16-VE202-16-*Clostridium symbiosum* (Cluster XIVa); SEQ ID NO:21-189-*Clostridium innocuum* (Cluster XVII); SEQ ID NO:82-PE9-*Clostridium disporicum* (Cluster I); SEQ ID NO:81-PE5-*Clostridium bolteae* (Cluster XIVa); SEQ ID NO:80-VE202-18-*Erysipelatoclostridium ramosum* (Cluster XVIII).

FIG. 28A shows survival/mortality of mice that received the indicated treatment prior to *C. difficile* infection. FIG. 28B shows the weight over time of mice that received the indicated treatment prior to *C. difficile* infection.

FIGS. 29A and 29B show the *C. difficile* burden in CFU/gram feces collected from mice that received the indicated treatment prior to *C. difficile*. FIG. 29A shows *C. difficile* burden at one-day post *C. difficile* infection. FIG. 29B shows *C. difficile* burden at 4 days post *C. difficile* infection.

DETAILED DESCRIPTION OF THE INVENTION

Figure 2:
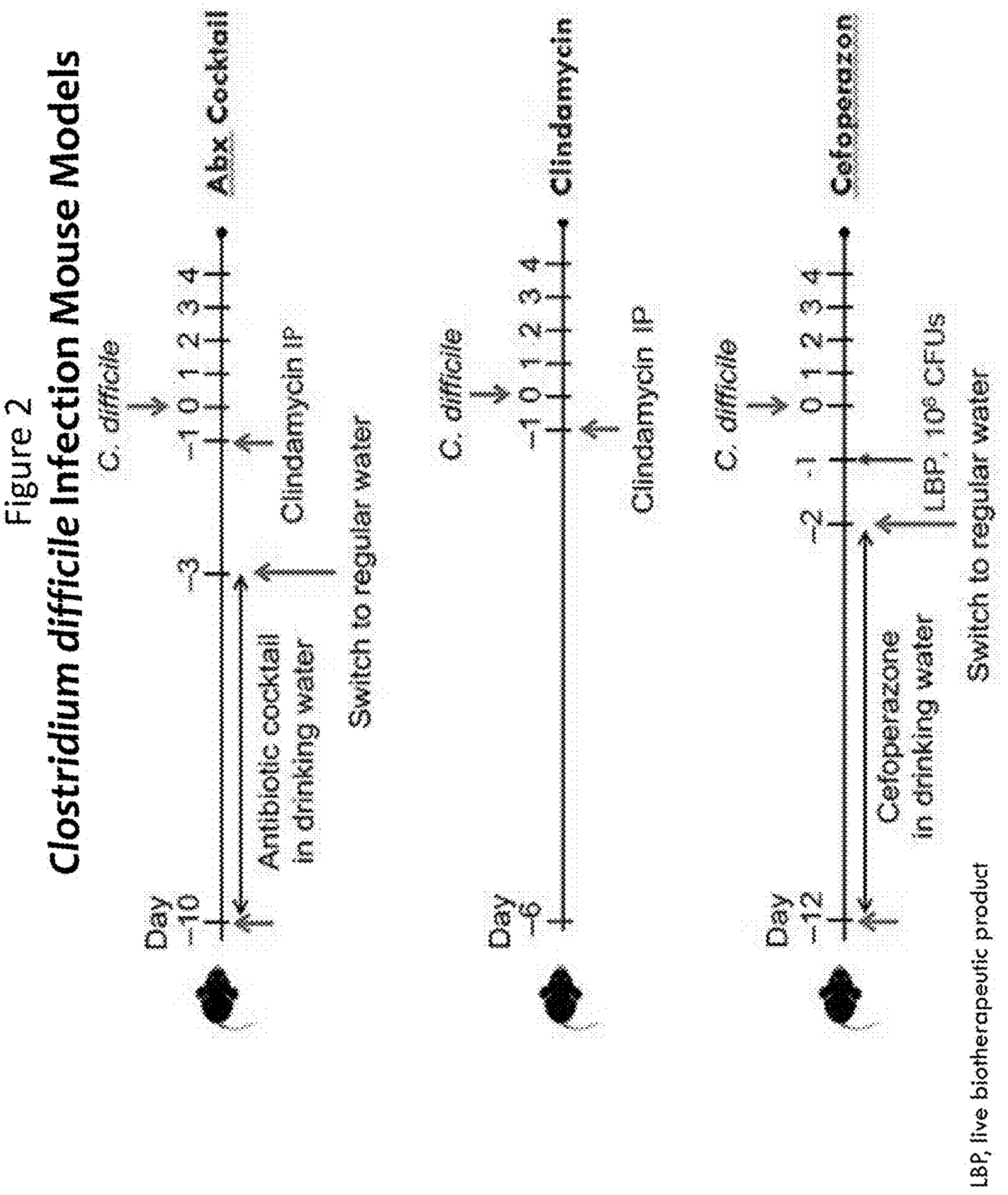
FIG. 2 shows various *Clostridium difficile* infection models. Timelines indicate antibiotic type, duration of treatment, as well as exposure to *C. difficile* spores. The top panel shows an antibiotic cocktail treatment model in which the antibiotic cocktail is provided in the drinking water from day −10 to day −3 followed by intraperitoneal clindamycin on day −1. The middle panel shows a clindamycin IP injection model, in which clindamycin is administered by intraperitoneal injection on day −1. The bottom panel shows the cefoperazone treatment model, in which cefoperazone is provided in the drinking water from day −12 to day −2, followed by administration of a live biotherapeutic product (LBP) on day −1.

Disclosed herein are compositions comprising purified bacterial strains and pharmaceutical compositions and food products containing such compositions and bacterial strains. Also disclosed are methods of treating a pathogenic infection, such as *Clostridium difficile* (*C. difficile*) infection, in a subject by administering said compositions to the subject.

Various factors including antibiotic usage can induce dysbiosis of the gastrointestinal tract, which may allow for colonization by pathogenic microorganisms, such as *C. difficile*. Such colonization or pathogenic infection can lead to a variety of adverse effects in the subject including diarrhea, which is one of the primary symptoms characteristic of *C. difficile* infection (CDI). In the case of CDI, diarrhea is thought to be a result of *C. difficile* production of Toxin B (also referred to as cytotoxin TcdB), which results in opening of the tight junctions between intestinal epithelial cells, increasing vascular permeability, hemorrhage, and inflammation.

The compositions described herein are effective in the treatment of *C. difficile* infection. As shown herein, the disclosed compositions are effective in suppressing the pathogenic effects of *C. difficile* infection. The compositions provided herein reduce the amount of *C. difficile* after infection and thereby provide an effective method for eliminating *C. difficile* from the body (e.g., the gut). The compositions provided herein induce the proliferation and/or accumulation of regulatory T cells (Tregs), for example when administered to a subject. Remarkably, the compositions disclosed herein have been found to reduce or inhibit production or activity of *C. difficile* Toxin B and thereby represent effective compositions for the treatment or prevention of CDI. The compositions disclosed herein have also been found to inhibit the growth and/or survival of *C. difficile*.

The present disclosure provides compositions comprising purified bacterial strains that can be administered to subjects experiencing or having experienced a pathogenic infection to treat the infection. In some embodiments, the compositions may be administered to subjects who may be at risk for a pathogenic infection. Such subjects include subjects who previously had pathogenic infections, subjects who have been treated with antibiotics and subjects who will undergo a procedure that will put them at an increased risk for a pathogenic infection (e.g., surgery and/or hospitalization). In some embodiments, the pathogenic infection, is infection by a pathogen that is present predominantly in the gut or the intestine. In some embodiments, the pathogen that is present predominantly in the gut or the intestine is *Clostridium difficile*.

In some embodiments, the one or more of the bacterial strains of the compositions provided herein colonize or recolonize the intestinal tract or parts of the intestinal tract (e.g., the colon or the cecum) of the subject. Such colonization or recolonization may also be referred to as grafting. In some embodiments, the one or more of the bacterial strains of the compositions recolonize the intestinal tract (e.g., the colon or the cecum) of the subject after the naturally present microbiome has been partially or completely removed, e.g., because of administration of antibiotics. In some embodiments, the one or more of the bacterial strains of the compositions colonize a dysbiotic gastrointestinal tract.

In some embodiments, the one or more of the bacterial strains of the compositions can "outgrow" a pathogen, such as *C. difficile*. Thus, in some embodiments, if a pathogen (e.g., *C. difficile*) and one or more bacteria of compositions provided herein are both present in the intestinal tract (e.g., the colon or the cecum), the one or more bacteria of compositions provided herein grow faster (e.g., have a shorter doubling time) than the pathogen, thereby preventing the pathogen from accumulating in the intestinal tract (e.g., the colon or the cecum). In some embodiments, the faster growth results because the one or more bacteria of the compositions provided herein are better at grafting in the intestinal tract (e.g., the colon or the cecum). In some embodiments, the faster growth results because the one or more bacteria of the compositions provided herein are better at metabolizing nutrients present in the intestinal tract (e.g., the colon or the cecum). In some embodiments, the compositions of bacterial strains provided herein prevent or inhibit production of bacterial toxins by the pathogenic infection, or prevent or inhibit the cytopathic or cytotoxic effects of such bacterial toxins. In some embodiments, the bacterial strains of the compositions provided herein can treat pathogenic infections, because of the synergy between the bacterial strains. Thus, without being limiting, in some embodiments, the combination of the bacterial strains of the compositions provided herein act synergistically because the combination of the strains is particularly well-suited to use nutrients in the intestinal tract (e.g., the colon or the cecum), or instance through metabolic interactions, and/or because the combination is superior in grafting (e.g., by providing a favorable microenvironment).

In some embodiments, a pathogenic infection such as *C. difficile* is treated because the combination of bacterial strains of the compositions provided herein is superior in the use of nutrients when compared to the pathogen such as *C. difficile*, thereby suppressing the growth of the pathogen such as *C. difficile*. In some embodiments, a pathogenic infection such as *C. difficile* is treated because the combination of bacterial strains of the compositions provided herein is superior in grafting when compared to the pathogen such as *C. difficile*, thereby suppressing the growth of the pathogen such as *C. difficile*. In some embodiments, a pathogenic infection such as *C. difficile* is treated because the combination of bacterial strains of the compositions provided herein is superior in the use of nutrients and in grafting when compared to the pathogen such as *C. difficile*, thereby suppressing the growth of the pathogen such as *C. difficile*. In some embodiments, a pathogenic infection such as *C. difficile* is treated because the combination of bacterial strains of the compositions provided herein inhibits the growth and/or survival of the pathogen such as *C. difficile*. In some embodiments, a pathogenic infection such as *C. difficile* is treated because the combination of bacterial strains of the compositions provided herein induces regulatory T cells (Tregs) in the subject that results in reduction or elimination of the pathogen such as *C. difficile*. In some embodiments, a pathogenic infection such as *C. difficile* is treated because the combination of bacterial strains of the compositions provided herein inhibits the growth and/or survival of the pathogen and induces regulatory T cells (Tregs) in the subject that results in reduction or elimination of the pathogen such as *C. difficile*.

In some embodiments, the synergistic effect is provided by the capacity of the combination to colonize specific niches in the intestinal tract (e.g., the colon or the cecum). In some embodiments, the synergistic effect is provided by the capacity of the combination to metabolize specific nutrients. In some embodiments, the synergistic effect is provided by the capacity of the combination to provide specific metabolites to the environment. Such specific metabolites may suppress growth of the pathogen and/or stimulate growth of non-pathogens. In some embodiments, the synergistic effect is provided by the capacity of the combination to provide short-chain fatty acids to the environment. In some embodiments, the synergistic effect is provided by the capacity of the combination to provide specific short-chain fatty acids to the environment. In some embodiments, the synergistic effect is provided by the capacity of the combination to produce butyrate. In some embodiments, the synergistic effect is provided by the capacity of the combination to produce acetate. In some embodiments, the synergistic effect is provided by the capacity of the combination to produce lactate. In some embodiments, the synergistic effect is provided by the capacity of the combination to produce propionate. In some embodiments, the synergistic effect is provided by the capacity of the combination to produce succinate. In some embodiments, the synergistic effect is provided by the capacity of the combination to produce multiple metabolites. In some embodiments, the synergistic effect is provided by the capacity of the combination to produce multiple short-chain fatty acids. In some embodiments, the synergistic effect is provided by the capacity of the combination to produce both butyrate and acetate. In some embodiments, the synergistic effect is provided by the capacity of the combination to produce both butyrate and lactate. In some embodiments, the synergistic effect is provided by the capacity of the combination to produce both butyrate and propionate. In some embodiments, the synergistic effect is provided by the capacity of the combination to produce both butyrate and succinate. In some embodiments, the synergistic effect is provided by the capacity of the combination to produce butyrate, acetate and additional short-chain fatty acids.

The bacterial strains used in the compositions provided herein generally are isolated from the microbiome of healthy individuals. In some embodiments, the compositions include strains originating from a single individual. In some embodiments, the compositions include strains originating from multiple individuals. In some embodiments, the bacterial strains are obtained from multiple individuals, isolated and grown up individually. The bacterial compositions that are grown up individually may subsequently be combined to provide the compositions of the disclosure. It should be appreciated that the origin of the bacterial strains of the compositions provided herein is not limited to the human microbiome from a healthy individual. In some embodiments, the bacterial strains originate from a human with a microbiome in dysbiosis. In some embodiments, the bacterial strains originate from non-human animals or the environment (e.g., soil or surface water). In some embodiments, the combinations of bacterial strains provided herein originate from multiple sources (e.g., human and non-human animals).

In some embodiments, the bacteria of the compositions provided herein are anaerobic bacteria. In some embodiments, the bacteria of the compositions provided herein are obligate anaerobic bacteria. In some embodiments, the bacteria of the compositions provided herein are *clostridia*. *Clostridia* may be classified into phylogenetic clusters with other closely related strains and species. (See e.g., Rajilic-Stojanovic, M., and de Vos, W. M. *FEMS Microbiol Rev* 38, (2014) 996-1047). In general, *clostridia* are classified as belonging to a specific cluster based on their 16S rRNA (or 16S rDNA) nucleic acid sequence. Methods for determining the identity of specific bacterial species based on their 16S rRNA (or 16S rDNA) nucleic acid sequence are well known in the art (See e.g., *Jumpstart Consortium Human Microbiome Project Data Generation Working*, G. PLoS One (2012) 7, e39315).

Provided herein are compositions comprising bacterial strains belonging to specific *Clostridium* clusters that have been found to be effective in treating and/or preventing pathogenic infection (e.g., *C. difficile* infection). In some embodiments, at least one of the bacterial strains of the composition belongs to *Clostridium* cluster IV. In some embodiments, at least one of the bacterial strains of the composition belongs to *Clostridium* cluster XIVa. In some embodiments, at least one of the bacterial strains of the composition belongs to *Clostridium* cluster XVII. In some embodiments, at least one of the bacterial strains of the composition belongs to *Clostridium* cluster I. In some embodiments, at least one of the bacterial strains of the composition belongs to *Clostridium* cluster IX. In some embodiments, at least one of the bacterial strains of the composition belongs to *Clostridium* cluster XIVa and at least one of the bacterial strains belongs to *Clostridium* cluster XVII. In some embodiments, at least one of the bacterial strains of the composition belongs to *Clostridium* cluster IV and at least one of the bacterial strains belongs to *Clostridium* cluster XVII. In some embodiments, at least one of the bacterial strains of the composition belongs to *Clostridium* cluster IV, at least one of the bacterial strains belongs to *Clostridium* cluster XIVa, and at least one of the bacterial strains belongs to *Clostridium* cluster XVII.

In some embodiments, the composition has at least twice as many bacterial strains that belong to *Clostridium* cluster XIVa when compared to the bacterial strains that belong to *Clostridium* cluster IV. In some embodiments, at least two of the bacterial strains of the composition belong to *Clostridium* cluster IV and at least five of the bacterial strains belong to *Clostridium* cluster XIVa. In some embodiments, the composition has at least twice as many bacterial strains that belong to *Clostridium* cluster XIVa when compared to the bacterial strains that belong to *Clostridium* cluster IV, and the composition has at least one strain that belongs to *Clostridium* cluster XVII. In some embodiments, at least two of the bacterial strains of the composition belong to *Clostridium* cluster IV, at least five of the bacterial strains belongs to *Clostridium* cluster XIVa, and at least one of the bacterial strains belongs to *Clostridium* cluster XVII.

In some embodiments, the compositions provided herein do not include bacterial strains belonging to *Clostridium* cluster XVIII. In some embodiments, the compositions provided herein do not include bacterial strains belonging to *Clostridium* cluster XVI. In some embodiments, the compositions provided herein do not include bacterial strains belonging to *Clostridium* cluster XI. In some embodiments, the compositions provided herein do not include bacterial strains belonging to *Clostridium* cluster I.

In one aspect, the disclosure provides bacterial strains comprising a 16S rDNA sequence with a nucleic acid sequence selected from the group consisting of SEQ ID NOs: 1-83 and 124-159. It should be appreciated that SEQ ID NOs: 1-83 and 124-159 may include both full length and partial 16S rDNA sequences.

In one aspect, the disclosure provides compositions comprising a bacterial strain comprising a 16S rDNA sequence with a nucleic acid sequence selected from the group consisting of SEQ ID NOs: 1-83 and 124-159. In one aspect, the disclosure provides compositions comprising as an active ingredient a bacterial strain comprising a 16S rDNA sequence with a nucleic acid sequence selected from the group consisting of SEQ ID NOs: 1-83 and 124-159. It should be appreciated that for all compositions provided herein, in some embodiments, the bacterial strain or the bacterial strains are the active ingredient of the composition.

It should be appreciated that for all compositions provided herein, in some embodiments, the bacterial strains are purified. Thus, for example the disclosure provides purified bacterial strains comprising a 16S rDNA sequence with a nucleic acid sequence selected from the group consisting of SEQ ID NOs: 1-83 and 124-159. In addition, for example, the disclosure provides compositions comprising purified bacterial strains comprising a 16S rDNA sequence with a nucleic acid sequence selected from the group consisting of SEQ ID NOs: 1-83 and 124-159. The bacterial strains disclosed herein originally may have been obtained and purified from the microbiota of one or more human individuals or obtained from sources other than the human microbiota, including soil and non-human microbiota. As provided herein, in some embodiments, bacteria isolated from the human microbiota, non-human microbiota, soil, or any alternative source are purified prior to use in the compositions and methods provided herein.

In one aspect, the disclosure provides compositions comprising one or more bacterial strains, wherein the one or more bacterial strains comprise a 16S rDNA sequence with a nucleic acid sequence selected from the group consisting of SEQ ID NOs:1-83 and 124-159. In one aspect, the disclosure provides compositions comprising one or more bacterial strains wherein the one or more bacterial strains comprise 16S rDNA sequences having at least 97% homology with nucleic acid sequences selected from the group consisting of SEQ ID NOs:1-83 and 124-159. As discussed previously, in some embodiments, the bacterial strains are purified. Thus, in one aspect, the disclosure provides compositions comprising one or more purified bacterial strains wherein the one or more purified bacterial strains comprise 16S rDNA sequences having at least 97% homology with nucleic acid sequences selected from the group consisting of SEQ ID NOs:1-83 and 124-159.

In one aspect, the disclosure provides compositions comprising two or more purified bacterial strains wherein the two or more purified bacterial strains comprise 16S rDNA sequences having at least 97% homology with nucleic acid sequences selected from the group consisting of SEQ ID NOs:1-83 and 124-159. As discussed above, in some embodiments, the bacterial strains are the active ingredient of the composition. Thus, in some embodiments, the disclosure provides compositions comprising as an active ingredient two or more purified bacterial strains wherein the two or more purified bacterial strains comprise 16S rDNA sequences having at least 97% homology with nucleic acid sequences selected from the group consisting of SEQ ID NOs:1-83 and 124-159.

In one aspect, the disclosure provides bacterial strains and combinations of bacterial strains that are homologous or have a high percent of homology with bacterial strains comprising 16S rDNA sequences selected from the group consisting of SEQ ID NOs:1-83 and 124-159. As discussed previously, in some embodiments, the bacterial strains are purified. The bacterial strains disclosed herein that have a 16S rDNA sequence with a nucleic acid sequence selected from the group consisting of SEQ ID NOs:1-83 and 124-159 have a high percent of homology (e.g., greater than 90%) with 16S rDNA sequences of bacterial strains that have been described in various databases (See e.g., the National Center for Biotechnology Information). Table 1 and Table 3 provides the closest known species by homology when the 16S rDNA sequences comprising SEQ ID NOs:1-83 and 124-159 are compared to 16S rDNA sequences of bacterial species available in public databases. By way of example, the bacterial strain comprising a 16S rDNA sequence with SEQ ID NO:1 (also referred to herein as "Strain 71") disclosed herein has the highest homology with a bacterial strain of the species *Blautia wexlerae* as defined by Accession # NR_044054 (having 16S rDNA sequence SEQ ID NO:94). While the bacterial strain with SEQ ID NO:1 has homology with other published bacterial strains as well, the highest homology is with a bacterial strain of the species *Blautia wexlerae* as defined by Accession # NR_044054. In this particular example the homology of SEQ ID NO:1 is 96.6% with SEQ ID NO:94 (corresponding to *Blautia wexlerae*). It should be appreciated that multiple bacterial strains disclosed herein may have the highest homology with the same species. (e.g., both SEQ ID NO:4 and SEQ ID NO:5 have the highest homology with a 16S rDNA sequence of a strain of the species *Blautia hansenii*).

It should further be appreciated that the bacterial strains disclosed herein that have a 16S rDNA sequence with a nucleic acid sequence selected from the group consisting of SEQ ID NOs:1-83 and 124-159, are also homologous to other strains based on their whole genome sequence, or subset of their whole genome sequence. Homologies based on whole genome analysis are provided in Table 2 and Table 3.

In one aspect, the disclosure provides compositions comprising one or more bacterial strains wherein the one or more bacterial strains are of species selected from the group consisting of *Clostridium hathewayi, Blautia hansenii, Blautia producta, Blautia producta* ATCC 27340, *Clostridium bacterium UC*5.1-1D4, *Blautia coccoides, Eubacterium contortum, Eubacterium fissicatena, Sellimona intestinalis, Dracourtella massiliensis, Dracourtella massiliensis* GD1, *Ruminococcus torques, Anaerostipes caccae, Clostridium scindens, Marvinbryanta formatexigens, Eisenbergiella tayi, Flavinofractor plautii, Clostridium orbiscindens* 1_3_50AFAA, *Lachnospiraceae bacterium* 7_1_58FAA, *Subdoligranulum, Anaerotruncus colihominis, Anaerotruncus colihominis* DSM 17241, *Clostridium symbiosum, Clostridium symbiosum* WAL-14163, *Clostridium bolteae, Clostrdium bolteae* 90A9, *Dorea longicatena, Dorea longicatena* CAG:42, *Clostridium innocuum, Erysipelotrichaceae_bacterium*_21-3, *Blautia wexlerae, Clostridium disporicum, Erysipelatoclostridium ramosum, Pseudoflavinofractor capillosus, Turicibacter sanguinis, Lactobacillus mucosae, Ruminococcus obeum, Megasphaera elsdenii, Acidaminococcus fermentans, Acidaminococcus intestine, Ruminococcus faecis, Bacteroides cellulosilyticus, Anaerostipes hadrus, Eubacterium rectale, Ruminococcus champanellensis, Ruminococcus albus, Bifidobacterium bifidum, Blautia luti, Roseburia faecis, Fusicatenibacter saccharivorans, Roseburia faecis, Blautia faecis, Dorea formicigenerans* and *Bacteroides ovatus.*

In some embodiments, the disclosure provides compositions comprising two or more bacterial strains, wherein the two or more bacterial strains are of species selected from the group consisting of *Clostridium hathewayi, Blautia hansenii, Blautia producta, Blautia producta* ATCC 27340, *Clostridium bacterium* UC5.1-1D4, *Blautia coccoides, Eubacterium contortum, Eubacterium fissicatena, Sellimona intestinalis, Dracourtella massiliensis, Dracourtella massiliensis* GD1, *Ruminococcus torques, Anaerostipes caccae, Clostridium scindens, Marvinbryanta formatexigens, Eisenbergiella tayi, Flavinofractor plautii, Clostridium orbiscindens* 1_3_50AFAA, *Lachnospiraceae bacterium* 7_1_58FAA, *Subdoligranulum, Anaerotruncus colihominis, Anaerotruncus colihominis* DSM 17241, *Clostridium symbiosum, Clostridium symbiosum* WAL-14163, *Clostridium bolteae, Clostrdium bolteae* 90A9, *Dorea longicatena, Dorea longicatena* CAG:42, *Clostridium innocuum, Erysipelotrichaceae_bacterium*_21-3, *Blautia wexlerae, Clostridium disporicum, Erysipelatoclostridium ramosum, Pseudoflavinofractor capillosus, Turicibacter sanguinis, Lactobacillus mucosae, Ruminococcus obeum, Megasphaera elsdenii, Acidaminococcus fermentans, Acidaminococcus intestine, Ruminococcus faecis, Bacteroides cellulosilyticus, Anaerostipes hadrus, Eubacterium rectale, Ruminococcus champanellensis, Ruminococcus albus, Bifidobacterium bifidum, Blautia luti, Roseburia faecis, Fusicatenibacter saccharivorans, Roseburia faecis, Blautia faecis, Dorea formicigenerans* and *Bacteroides ovatus.*

It should be appreciated that the compositions may include multiple strains of a particular species. Thus, for illustration, a non-limiting example of the compositions disclosed herein, comprises one strain of *Clostridium hathewayi* and two strains of *Blautia hansenii.*

The invention also encompasses compositions comprising bacterial strains that are close in homology to and/or fall within the species *Clostridium hathewayi, Blautia hansenii, Blautia producta, Blautia producta* ATCC 27340, *Clostridia bacteria* UC5.1-1D4, *Blautia coccoides, Eubacterium contortum, Eubacterium fissicatena, Sellimona intestinalis, Dracourtella massiliensis, Dracourtella massiliensis* GD1, *Ruminococcus torques, Anaerostipes caccae, Clostridium scindens, Marvinbryanta formatexigens, Eisenbergiella tayi, Flavinofractor plautii, Clostridium orbiscindens* 1_3_50AFAA, *Lachnospiraceae bacterium* 7_1_58FAA, *Subdoligranulum, Anaerotruncus colihominis, Anaerotruncus colihominis* DSM 17241, *Clostridium symbiosum, Clostridium symbiosum* WAL-14163, *Clostridium bolteae, Clostrdium bolteae* 90A9, *Dorea longicatena, Dorea longicatena* CAG:42, *Clostridium innocuum, Erysipelotrichaceae_bacterium*_21-3, *Blautia wexlerae, Clostridium disporicum, Erysipelatoclostridium ramosum, Pseudoflavinofractor capillosus, Turicibacter sanguinis, Lactobacillus mucosae, Ruminococcus obeum, Megasphaera elsdenii, Acidaminococcus fermentans, Acidaminococcus intestine, Ruminococcus faecis, Bacteroides cellulosilyticus, Anaerostipes hadrus, Eubacterium rectale, Ruminococcus champanellensis, Ruminococcus albus, Bifi-

*dobacterium bifidum, Blautia luti, Roseburia faecis, Fusicatenibacter saccharivorans, Roseburia faecis, Blautia faecis, Dorea formicigenerans* and *Bacteroides ovatus*. Thus, in one embodiment, the compositions of the disclosure include one or more bacterial strains comprising 16S rDNA sequences having at least 97% homology with nucleic acid sequences selected from the group consisting of SEQ ID NOs: 84-123. In some embodiments, the compositions of the disclosure include two or more bacterial strains comprising 16S rDNA sequences having at least 97% homology with nucleic acid sequences selected from the group consisting of SEQ ID NOs:84-123.

In one aspect, the compositions of the disclosure include two or more purified bacterial strains comprising 16S rDNA sequences having at least 97% homology with nucleic acid sequences selected from the group consisting of SEQ ID NOs:1-23 and 124-159. In some embodiments, the compositions of the disclosure include two or more bacterial strains of species selected from the group consisting of *Clostridium hathewayi, Blautia hansenii, Blautia producta, Blautia producta* ATCC 27340, *Clostridia bacteria* UC5.1-1D4, *Blautia coccoides, Eubacterium contortum, Eubacterium fissicatena, Sellimona intestinalis, Dracourtella massiliensis, Dracourtella massiliensis* GD1, *Ruminococcus torques, Anaerostipes caccae, Clostridium scindens, Marvinbryanta formatexigens, Eisenbergiella tayi, Flavinofractor plautii, Clostridium orbiscindens* 1_3_50AFAA, *Lachnospiraceae bacterium* 7_1_58FAA, *Subdoligranulum, Anaerotruncus colihominis, Anaerotruncus colihominis* DSM 17241, *Clostridium symbiosum, Clostridium symbiosum* WAL-14163, *Clostridium bolteae, Clostrdium bolteae* 90A9, *Dorea longicatena, Dorea longicatena* CAG:42, *Clostridium innocuum, Erysipelotrichaceae_bacterium_*21-3, *Blautia wexlerae, Turicibacter sanguinis, Lactobacillus mucosae*, and *Bacteroides ovatus*. In some embodiments, the compositions of the disclosure include two or more purified bacterial strains comprising 16S rDNA sequences having at least 97% homology with nucleic acid sequences selected from the group consisting of SEQ ID NO:87, SEQ ID NO:88, SEQ ID NO:89, SEQ ID NO:90, SEQ ID NO:91, SEQ ID NO:93, SEQ ID NO:94, SEQ ID NO:95, SEQ ID NO:97, SEQ ID NO:98, SEQ ID NO:99, SEQ ID NO:102, SEQ ID NO:103, SEQ ID NO:105, SEQ ID NO:106, SEQ ID NO:108, SEQ ID NO:109, SEQ ID NO:110, SEQ ID NO:121, and SEQ ID NO:122.

In one aspect, the disclosure provides Composition A (See e.g., FIG. 1, Table A). As shown in FIG. 1, Composition A contains bacterial strains that comprise 16S rDNA sequences with nucleic acid sequences: SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23. In some embodiments, the disclosure provides compositions with two or more purified bacterial strains that comprise 16S rDNA sequences with nucleic acid sequences selected from the group consisting of SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23. In some embodiments, the disclosure provides compositions with five or more purified bacterial strains that comprise 16S rDNA sequences with nucleic acid sequences selected from the group consisting of SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23. In some embodiments, the disclosure provides compositions with at least ten purified bacterial strains, wherein the bacterial strains comprise 16S rDNA sequences with nucleic acid sequences SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23, respectively. In some embodiments, the disclosure provides a composition consisting of ten purified bacterial strains, wherein the bacterial strains comprise 16S rDNA sequences with nucleic acid sequences SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23, respectively. In some embodiments, the disclosure provides a composition essentially consisting of ten purified bacterial strains, wherein the bacterial strains comprise 16S rDNA sequences with nucleic acid sequences SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23, respectively. As used herein, essentially consisting of refers to a composition that includes no additional bacterial strains.

In some embodiments, the disclosure provides compositions with bacterial strains that comprise 16S rDNA sequences having at least 97% homology with nucleic acid sequences selected from the group consisting of: SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23. In some embodiments, the disclosure provides compositions with two or more purified bacterial strains that comprise 16S rDNA sequences having at least 97% homology with nucleic acid sequences selected from the group consisting of SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23. In some embodiments, the disclosure provides compositions with five or more purified bacterial strains that comprise 16S rDNA having at least 97% homology with nucleic acid sequences selected from the group consisting of SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23. In some embodiments, the disclosure provides compositions with at least ten purified bacterial strains, wherein the bacterial strains comprise 16S rDNA sequences having at least 97% homology with nucleic acid sequences SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23, respectively. In some embodiments, the disclosure provides a composition consisting of ten purified bacterial strains, wherein the bacterial strains comprise 16S rDNA sequences having at least 97% homology with nucleic acid sequences SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23, respectively. In some embodiments, the disclosure provides a composition essentially consisting of ten purified bacterial strains, wherein the bacterial strains comprise 16S rDNA sequences having at least 97% homology with nucleic acid sequences SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23, respectively.

The bacterial strains in Composition A are related to the following bacterial species: *Clostridium hathewayi, Blautia hansenii, Blautia producta, Blautia coccoides, Eubacterium contortum, Eubacterium fissicatena, Anaerostipes caccae, Clostridium scindens, Marvinbryanta formatexigens*, and *Eisenbergiella tayi* (See e.g., Table 1). It should be appreciated that multiple bacterial strains of the compositions disclosed herein can have the same related bacterial species.

For instance, the bacterial strains having 16S rDNA sequences with nucleic acid sequences SEQ ID NO:4, SEQ ID NO:5 and SEQ ID NO:7 all have *Blautia hansenii* as related species. In some embodiments, the disclosure provides compositions with two or more bacteria of species selected from the group consisting of *Clostridium hathewayi, Blautia hansenii, Blautia producta, Blautia coccoides, Eubacterium contortum, Eubacterium fissicatena, Anaerostipes caccae, Clostridium scindens, Marvinbryanta formatexigens*, and *Eisenbergiella tayi*. In some embodiments, the disclosure provides compositions with two or more purified bacterial strains comprising 16S rDNA sequences having at least 97% homology with nucleic acid sequences selected from the group consisting of SEQ ID NO:87, SEQ ID NO:88, SEQ ID NO:89, SEQ ID NO:99, SEQ ID NO:103, SEQ ID NO:105, SEQ ID NO:106, SEQ ID NO:108, SEQ ID NO:109, and SEQ ID NO:121.

In some embodiments, the composition comprises two or more purified bacterial strains comprising 16S rDNA sequences having at least 97% homology with nucleic acid sequences selected from the group consisting of SEQ ID NO:3, SEQ ID NO:4, SEQ ID NO:7, SEQ ID NO:8, SEQ ID NO:9, SEQ ID NO:11, SEQ ID NO:12, SEQ ID NO:13, and SEQ ID NO:23. In some embodiments, the composition comprises two or more purified bacterial strains comprising 16S rDNA sequences having at least 97% homology with nucleic acid sequences selected from the group consisting of SEQ ID NO:3, SEQ ID NO:5, SEQ ID NO:7, SEQ ID NO:8, SEQ ID NO:9, SEQ ID NO:11, SEQ ID NO:12, SEQ ID NO:13, and SEQ ID NO:23. In some embodiments, the composition comprises two or more purified bacterial strains comprising 16S rDNA sequences having at least 97% homology with nucleic acid sequences selected from the group consisting of SEQ ID NO:3, SEQ ID NO:4, SEQ ID NO:5, SEQ ID NO:7, SEQ ID NO:9, SEQ ID NO:11, SEQ ID NO:12, SEQ ID NO:13, and SEQ ID NO:23. In some embodiments, the composition comprises two or more purified bacterial strains comprising 16S rDNA sequences having at least 97% homology with nucleic acid sequences selected from the group consisting of SEQ ID NO:3, SEQ ID NO:4, SEQ ID NO:7, SEQ ID NO:9, SEQ ID NO:11, SEQ ID NO:12, SEQ ID NO:13, and SEQ ID NO:23. In some embodiments, the composition comprises two or more purified bacterial strains comprising 16S rDNA sequences having at least 97% homology with nucleic acid sequences selected from the group consisting of SEQ ID NO:3, SEQ ID NO:5, SEQ ID NO:7, SEQ ID NO:9, SEQ ID NO:11, SEQ ID NO:12, SEQ ID NO:13, and SEQ ID NO:23. In some embodiments, the composition comprises two or more purified bacterial strains comprising 16S rDNA sequences having at least 97% homology with nucleic acid sequences selected from the group consisting of SEQ ID NO:3, SEQ ID NO:7, SEQ ID NO:8, SEQ ID NO:9, SEQ ID NO:11, SEQ ID NO:12, SEQ ID NO:13, and SEQ ID NO:23. In some embodiments, the composition comprises two or more purified bacterial strains comprising 16S rDNA sequences having at least 97% homology with nucleic acid sequences selected from the group consisting of SEQ ID NO:3, SEQ ID NO:4, SEQ ID NO:5; SEQ ID NO:7, SEQ ID NO:8, and SEQ ID NO:13.

Each of the bacterial strains of Composition A are BaiCD+, meaning that the bacterial strains encode, or are predicted to encode, the bile inducible operon gene BaiCD and/or a protein with stereospecific NAD(H)-dependent 3-oxo-$\Delta^4$-cholenoic acid oxidoreductase activity. The BaiCD status of a bacterial strain can be determined for instance by PCR (See e.g., Wells et al. *Clin Chim Acta* (2003) May; 331(1-2):127-34). Furthermore, each of the strains of Composition A are classified as belonging to *Clostridium* cluster XIVa. In some embodiments, the disclosure provides compositions comprising two or more bacterial strains, wherein the bacterial strains are BaiCD+ strains. In some embodiments, the disclosure provides compositions comprising two or more bacterial strains, wherein the bacterial strains are BaiCD+ and belong to *Clostridium* cluster XIVa. In some embodiments of the compositions comprising two or more bacterial strains that are BaiCD+ strains and that belong to *Clostridium* cluster XIVa, the compositions do not include bacterial strains that belong to *Clostridium* cluster IV.

In some embodiments, the disclosure provides compositions with two or more purified bacterial strains that comprise 16S rDNA sequences having at least 97% homology with nucleic acid sequences selected from the group consisting of SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23, wherein all the bacterial strains belong to *Clostridium* cluster XIVa.

TABLE A

| Composition A |
|---|
| SEQ_03 - 5 - *Clostridium_hathewayi* (XIVa)* |
| SEQ_04 - 7 - *Blautia_hansenii* (XIVa)* |
| SEQ_05 - 10 - *Blautia_hansenii* (XIVa)* |
| SEQ_07 - 59 - *Blautia_producta/Blautia_coccoides* (XIVa) |
| SEQ_08 - 79 - *Blautia_hansenii* (XIVa)* |
| SEQ_09 - VE202-21 - *Eubacterium_contortum/ Eubacterium_fissicatena* (XIVa)* |
| SEQ_11 - VE202-9 - *Anaerostipes_caccae* (XIVa)* |
| SEQ_12 - VE202-26 - *Clostridium_scindens* (XIVa)* |
| SEQ_13 - 136 - *Marvinbryantia_formatexigens* (XIVa)* |
| SEQ_23 - VE202-29 - *Eisenbergiella_tayi* (XIVa)* |

*= $BaiCD^+$

In one aspect, the disclosure provides Composition B (See e.g., FIG. 1, Table B). As shown in FIG. 1, Composition B contains bacterial strains that comprise 16S rDNA sequences with nucleic acid sequences: SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159. In some embodiments, the compositions include two or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159. In some embodiments, the compositions include two or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some embodiments, the compositions include two or more purified bacterial strains comprising 16S rDNA sequences with nucleic acid sequences selected from the group consisting of SEQ ID NOs: 124-159. In some embodiments, the compositions include two or more purified bacterial strains comprising 16S rDNA sequences with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include five or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159. In some embodiments, the compositions include five or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some embodiments, the compositions include five or more purified bacterial strains comprising 16S rDNA sequences with nucleic acid sequences selected from the group consisting of SEQ ID NOs: 124-159. In some embodiments, the compositions include five or more purified bacterial strains comprising 16S rDNA sequences with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159, respectively. In some embodiments, the compositions include at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the compositions include at least eight purified bacterial strains comprising 16S rDNA sequences with nucleic acid sequences selected from the group consisting of SEQ ID NOs: 124-159, respectively. In some embodiments, the compositions include at least eight purified bacterial strains comprising 16S rDNA sequences with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition consists of at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159, respectively. In some embodiments, the composition consists of at least eight purified bacterial strains comprising 16S rDNA sequences with nucleic acid sequences SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the composition consists of eight purified bacterial strains comprising 16S rDNA sequences with nucleic acid sequences selected from the group consisting of SEQ ID NOs:124-159, respectively. In some embodiments, the compositions consists of at least eight purified bacterial strains comprising 16S rDNA sequences with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition essentially consists of at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159, respectively. In some embodiments, the composition essentially consists of at least eight purified bacterial strains comprising 16S rDNA sequences with nucleic acid sequences SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the composition essentially consists of at least eight purified bacterial strains comprising 16S rDNA sequences with nucleic acid sequences selected from the group consisting of SEQ ID NOs:124-159, respectively. In some embodiments, the composition essentially consists of at least eight purified bacterial strains comprising 16S rDNA sequences with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159, respectively. In some embodiments, the compositions include eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the compositions include eight purified bacterial strains comprising 16S rDNA sequences with nucleic acid sequences selected from the group consisting of SEQ ID NOs: 124-159, respectively. In some embodiments, the compositions include eight purified bacterial strains comprising 16S rDNA sequences with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition consists of eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159, respectively. In some embodiments, the composition consists of eight purified bacterial strains comprising 16S rDNA sequences with nucleic acid sequences SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the composition consists of eight purified bacterial strains comprising 16S rDNA sequences with nucleic acid sequences selected from the group consisting of SEQ ID NOs:124-159, respectively. In some embodiments, the compositions consists of eight purified bacterial strains comprising 16S rDNA sequences with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition essentially consists of eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159, respectively. In some embodiments, the composition essentially consists of eight purified bacterial strains comprising 16S rDNA sequences with nucleic acid sequences SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the composition essentially consists of eight purified bacterial strains comprising 16S rDNA sequences with nucleic acid sequences selected from the group consisting of SEQ ID NOs:124-159, respectively. In some embodiments, the composition essentially consists of eight purified bacterial strains comprising 16S rDNA sequences with nucleic acid sequences SEQ ID NO: 124, SEQ ID NO:129, SEQ ID NO:132, SEQ ID NO:137, SEQ ID NO:141, SEQ ID NO:146, SEQ ID NO:152, and SEQ ID NO:157.

In one aspect, the disclosure provides a composition that contains bacterial strains that comprise 16S rDNA sequences with nucleic acid sequences: SEQ ID NO:10, SEQ ID NO:14, SEQ ID NO:15, SEQ ID NO:16, SEQ ID NO:17, SEQ ID NO:19, SEQ ID NO:21, SEQ ID NO:22, and SEQ ID NOs: 124-159. In one aspect, the disclosure provides a composition that contains bacterial strains that comprise 16S rDNA sequences with nucleic acid sequences: SEQ ID NO:10, SEQ ID NO:14, SEQ ID NO:15, SEQ ID NO:16, SEQ ID NO:17, SEQ ID NO:19, SEQ ID NO:21, and SEQ ID NO:22. In one aspect, the disclosure provides a composition that contains bacterial strains that comprise 16S rDNA sequences with nucleic acid sequences: SEQ ID NOs: 124-159. In one aspect, the disclosure provides a composition that contains bacterial strains that comprise 16S rDNA sequences with nucleic acid sequences: SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include two or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NOs: 124-145, and SEQ ID NOs: 152-159. In some embodiments, the compositions include two or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, and SEQ ID NO:22. In some embodiments, the compositions include two or more purified bacterial strains comprising 16S rDNA sequences with nucleic acid sequences selected from the group consisting of SEQ ID NO:22, SEQ ID NOs: 124-145, and SEQ ID NOs: 152-159. In some embodiments, the compositions include two or more purified bacterial strains comprising 16S rDNA sequences with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152, and SEQ ID NO:157.

In some embodiments, the compositions include five or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, and SEQ ID NOs: 124-145, and SEQ ID NOs: 152-159. In some embodiments, the compositions include five or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, and SEQ ID NO:22. In some embodiments, the compositions include five or more purified bacterial strains comprising 16S rDNA sequences with nucleic acid sequences selected from the group consisting of SEQ ID NO: 22, SEQ ID NOs: 124-145, and SEQ ID NOs: 152-159. In some embodiments, the compositions include five or more purified bacterial strains comprising 16S rDNA sequences with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NOs: 124-145, and SEQ ID NOs: 152-159, respectively. In some embodiments, the compositions include at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, and SEQ ID NO:22, respectively. In some embodiments, the compositions include at least eight purified bacterial strains comprising 16S rDNA sequences with nucleic acid sequences selected from the group consisting of SEQ ID NO:22, SEQ ID NOs: 124-145, and SEQ ID NOs: 152-159. In some embodiments, the compositions include five or more purified bacterial strains comprising 16S rDNA sequences with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition consists of at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NOs: 124-145, and SEQ ID NOs: 152-159, respectively. In some embodiments, the composition consists of at least eight purified bacterial strains comprising 16S rDNA sequences with nucleic acid sequences SEQ ID NO:10, SEQ ID NO:14, SEQ ID NO:15, SEQ ID NO:16, SEQ ID NO:17, SEQ ID NO:19, SEQ ID NO:21, and SEQ ID NO:22, respectively. In some embodiments, the composition consists of at least eight purified bacterial strains comprising 16S rDNA sequences with nucleic acid sequences selected from the group consisting of SEQ ID NO: 22, SEQ ID NOs: 124-145, and SEQ ID NOs: 152-159. In some embodiments, the composition consists of at least eight purified bacterial strains comprising 16S rDNA sequences with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition essentially consists of at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NOs: 124-145, and SEQ ID NOs: 152-159, respectively. In some embodiments, the composition essentially consists of at least eight purified bacterial strains comprising 16S rDNA sequences with nucleic acid sequences SEQ ID NO:10, SEQ ID NO:14, SEQ ID NO:15, SEQ ID NO:16, SEQ ID NO:17, SEQ ID NO:19, SEQ ID NO:21, and SEQ ID NO:22, respectively. In some embodiments, the composition essentially consists of at least eight purified bacterial strains comprising 16S rDNA sequences with nucleic acid sequences selected from the group consisting of SEQ ID NO: 22, SEQ ID NOs: 124-145, and SEQ ID NOs: 152-159. In some embodiments, the composition essentially consists of at least eight purified bacterial strains comprising 16S rDNA sequences with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In one aspect, the disclosure provides compositions that contain bacterial strains that comprise 16S rDNA sequences having at least 97% homology with nucleic acid sequences selected from the group consisting of: SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NO: 124-159. In one aspect, the disclosure provides compositions that contain bacterial strains that comprise 16S rDNA sequences having at least 97% homology with nucleic acid sequences: SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In one aspect, the disclosure provides compositions that contain bacterial strains that comprise 16S rDNA sequences having at least 97% homology with nucleic acid sequences selected from the group consisting of: SEQ ID NOs: 124-159. In one aspect, the disclosure provides compositions that contain bacterial strains that comprise 16S rDNA sequences having at least 97% homology with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159. In some embodiments, the compositions include two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some embodiments, the compositions include two or more purified bacterial strains comprising 16S rDNA sequences having at least 97% homology with nucleic acid sequences selected from the group consisting of SEQ ID NOs: 124-159. In some embodiments, the compositions include two or more purified bacterial strains comprising 16S rDNA sequences having at least 97% homology with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include five or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159. In some embodiments, the compositions include five or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some embodiments, the compositions include five or more purified bacterial strains comprising 16S rDNA sequences having at least 97% homology with nucleic acid sequences selected from the group consisting of SEQ ID NOs: 124-159. In some embodiments, the compositions include five or more purified bacterial strains comprising 16S rDNA sequences having at least 97% homology with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include at least eight purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NO: 124-159, respectively. In some embodiments, the compositions include at least eight purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the compositions include at least eight purified bacterial strains comprising 16S rDNA sequences having at least 97% homology with nucleic acid sequences selected from the group consisting of SEQ ID NOs: 124-159. In some embodiments, the compositions include at least eight purified bacterial strains comprising 16S rDNA sequences having at least 97% homology with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition consists of at least eight purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159, respectively. In some embodiments, the composition consists of at least eight purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the composition consists of at least eight purified bacterial strains comprising 16S rDNA sequences having at least 97% homology with nucleic acid sequences selected from the group consisting of SEQ ID NOs:124-159, respectively. In some embodiments, the composition consists of at least eight purified bacterial strains comprising 16S rDNA sequences having at least 97% homology with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition essentially consists of at least eight purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NO: 124-159, respectively. In some embodiments, the composition essentially consists of at least eight purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the composition essentially consists of at least eight purified bacterial strains comprising 16S rDNA sequences having at least 97% homology with nucleic acid sequences selected from the group consisting of SEQ ID NOs: 124-159, respectively. In some embodiments, the composition essentially consists of at least eight purified bacterial strains comprising 16S rDNA sequences having at least 97% homology with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In one aspect, the disclosure provides a composition that contains bacterial strains that comprise 16S rDNA sequences having at least 97% homology with nucleic acid sequences: SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NO: 124-145, and SEQ ID NOs: 152-159. In one aspect, the disclosure provides a composition that contains bacterial strains that comprise 16S rDNA sequences having at least 97% homology with nucleic acid sequences: SEQ ID NO:10, SEQ ID NO:14, SEQ ID NO:15, SEQ ID NO:16, SEQ ID NO:17, SEQ ID NO:19, SEQ ID NO:21, and SEQ ID NO:22. In one aspect, the disclosure provides a composition that contains bacterial strains that comprise 16S rDNA sequences having at least 97% homology with nucleic acid sequences: SEQ ID NO:22, SEQ ID NO: 124-145, and SEQ ID NOs: 152-159.

In some embodiments, the compositions include two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, and SEQ ID NO: 124-145, and SEQ ID NOs: 152-159. In some embodiments, the compositions include two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, and SEQ ID NO:22. In some embodiments, the compositions include two or more purified bacterial strains comprising 16S rDNA sequences having at least 97% homology with nucleic acid sequences selected from the group consisting of SEQ ID NO: 22, SEQ ID NO: 124-145, and SEQ ID NOs: 152-159.

In some embodiments, the compositions include five or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NO: 124-145, and SEQ ID NOs: 152-159. In some embodiments, the compositions include five or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, and SEQ ID NO:22. In some embodiments, the compositions include five or more purified bacterial strains comprising 16S rDNA sequences having at least 97% homology with nucleic acid sequences selected from the group consisting of SEQ ID NO: 20, SEQ ID NO: 124-145, and SEQ ID NOs: 152-159.

In some embodiments, the compositions include at least eight purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NO: 124-145, and SEQ ID NOs: 152-159, respectively. In some embodiments, the compositions include at least eight purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, and SEQ ID NO:22, respectively. In some embodiments, the compositions include at least eight purified bacterial strains comprising 16S rDNA sequences having at least 97% homology with nucleic acid sequences selected from the group consisting of SEQ ID NO: 22, SEQ ID NO: 124-145, and SEQ ID NOs: 152-159.

In some embodiments, the composition consists of at least eight purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NO: 124-145, and SEQ ID NOs: 152-159, respectively. In some embodiments, the composition consists of at least eight purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:19, SEQ ID NO:21, and SEQ ID NO:22, respectively. In some embodiments, the composition consists of at least eight purified bacterial strains comprising 16S rDNA sequences having at least 97% homology with nucleic acid sequences SEQ ID NO: 22, SEQ ID NO: 124-145, and SEQ ID NOs: 152-159.

In some embodiments, the composition essentially consists of at least eight purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NO: 124-145, and SEQ ID NOs: 152-159, respectively. In some embodiments, the composition essentially consists of at least eight purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:19, SEQ ID NO:21, and SEQ ID NO:22, respectively. In some embodiments, the composition essentially consists of at least eight purified bacterial strains comprising 16S rDNA sequences having at least 97% homology with nucleic acid sequences SEQ ID NO: 22, SEQ ID NO: 124-145, and SEQ ID NOs: 152-159.

In one aspect, the disclosure provides a composition that contains bacterial strains that comprise 16S rDNA sequences with nucleic acid sequences: SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NO: 124-159. In one aspect, the disclosure provides a composition that contains bacterial strains that comprise 16S rDNA sequences with nucleic acid sequences: SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22. In one aspect, the disclosure provides a composition that contains bacterial strains that comprise 16S rDNA sequences with nucleic acid sequences: SEQ ID NO:18, SEQ ID NO:22, and SEQ ID NO: 124-159.

In some embodiments, the compositions include two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NO: 124-159. In some embodiments, the compositions include two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22. In some embodiments, the compositions include two or more purified bacterial strains comprising 16S rDNA sequences having at least 97% homology with nucleic acid sequences selected from the group consisting of SEQ ID NO:18, SEQ ID NO:22, and SEQ ID NO: 124-159.

In some embodiments, the compositions include five or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NOs: 124-159. In some embodiments, the compositions include five or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22. In some embodiments, the compositions include five or more purified bacterial strains comprising 16S rDNA sequences having at least 97% homology with nucleic acid sequences selected from the group consisting of SEQ ID NO:18, SEQ ID NO:22, and SEQ ID NOs: 124-159.

In some embodiments, the compositions include at least ten purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NOs: 124-159, respectively. In some embodiments, the compositions include at least ten purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, respectively. In some embodiments, the compositions include at least ten purified bacterial strains comprising 16S rDNA sequences having at least 97% homology with nucleic acid sequences selected from the group consisting of SEQ ID NO: 18, SEQ ID NO: 22, and SEQ ID NOs: 124-159.

In some embodiments, the composition consists of ten purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NO: 124-159, respectively. In some embodiments, the composition consists of ten purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, respectively. In some embodiments, the composition consists of ten purified bacterial strains comprising 16S rDNA sequences having at least 97% homology with nucleic acid sequences selected from the group consisting of SEQ ID NO:18, SEQ ID NO:22, SEQ ID NOs: 124-159, respectively.

In some embodiments, the composition essentially consists of ten purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NO: 124-159, respectively. In some embodiments, the composition essentially consists of ten purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, respectively. In some embodiments, the composition essentially consists of ten purified bacterial strains comprising 16S rDNA sequences having at least 97% homology with nucleic acid sequences selected from the group consisting of SEQ ID NO:18, SEQ ID NO:22, and SEQ ID NO: 124-159, respectively.

The bacterial strains in Composition B are related to the following bacterial species: *Flavinofractor plautii, Lachnospiraceae, bacterium* 7_1_58FAA, *Subdoligranulum Anaerotruncus colihominis, Eubacterium fissicatena, Ruminococcus torques Clostridium symbiosum, Clostridium bolteae, Dorea longicatena, Blautia producta, Clostridium innocuum*, and *Erysipelotrichaceae_bacterium*_21-3 (See e.g., Table 2).

Selected strains were subjected to whole genome sequencing using a PacBio Biosciences platform (Menlo Park, Calif.) and sequences were assembled into whole genomes (Table 3). The 16S rDNA sequences were identified using Prokka and Barrnap. It was found that several strains contained more than one 16S sequence. All identified 16S rRNA gene nucleotide sequences for each strain were then clustered at 97% identity using the usearch (v 5.2.236) algorithm and the cluster seed sequence was selected as the representative sequence for each Composition B strain (The Consensus 16S sequence: column labeled "*Consensus SEQ ID # of 16S region as determined by WGS" in Table 3). Table 3 provides identification of the indicated strains included in Composition B based on Sanger sequencing of the 16S region as well as on whole genome sequencing (WGS). The closest species of the bacterial strains were identified both by comparison to a 16S database (column labeled: "Closest species based on Consensus SEQ ID # of 16S region as compared with 16S database") and to whole genome databases (column labeled: "Closest species based on WGS compared versus WG databases).

Based on identification of 16S sequences through whole genome sequencing, and by comparing these sequences with 16S databases, the bacterial strains in Composition B are related to the following bacterial species: *Clostridium bolteae, Anaerotruncus colihominis, Dracourtella massiliensis, Clostridium symbiosum Blautia producta, Dorea longicatena Clostridium innocuum* and *Flavinofractor plautii* (see, e.g., Table 3).

Based on whole genome sequencing and comparing of the whole genome to whole genome databases, the bacterial strains in Composition B are most closely related to the following bacterial species: *Clostridium bolteae* 90A9, *Anaerotruncus colihominis* DSM 17241, *Dracourtella massiliensis* GD1, *Clostridium symbiosum* WAL-14163, *Clostridium bacterium* UC5.1-1D4, *Dorea longicatena* CAG:42, *Erysipelotrichaceae bacterium* 21_3, and *Clostridium orbiscindens* 1_3_50AFAA (see, e.g., Table 3).

It should be appreciated that multiple strains of the compositions disclosed herein can have the same related bacterial species. For instance, the bacterial strains comprising 16S rDNA sequences with nucleic acid sequences SEQ ID NO 18, SEQ ID NO:20 and SEQ ID NO:22 all have *Dorea longicatena* as related bacterial species. In some embodiments, the disclosure provides compositions with two or more bacteria selected from the group consisting of *Flavinofractor plautii, Lachnospiraceae, bacterium* 7_1_58FAA, *Subdoligranulum Anaerotruncus colihominis, Eubacterium fissicatena, Ruminococcus torques Clostridium symbiosum, Clostridium bolteae, Dorea longicatena, Blautia producta, Clostridium innocuum* and *Erysipelotrichaceae_bacterium*_21-3. In some embodiments, the disclosure provides compositions with two or more bacteria selected from the group consisting of *Flavinofractor plautii, Anaerotruncus colihominis, Eubacterium fissicatena, Clostridium symbiosum, Clostridium bolteae, Dorea longicatena, Blautia producta*, and *Clostridium innocuum*. In some embodiments, the disclosure provides compositions that include two or more purified bacterial strains comprising 16S rDNA sequences having at least 97% homology with nucleic acid sequences selected from the group consisting of SEQ ID NO:93, SEQ ID NO:95, SEQ ID NO:97, SEQ ID NO:98, SEQ ID NO:102, SEQ ID NO:106, SEQ ID NO:110, and SEQ ID NO:122.

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, SEQ ID NO:22, and SEQ ID NOs: 124-159. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NO:22. In some embodiments, the composition comprises two or more purified bacterial strains comprising 16S rDNA sequences having at least 97% homology with nucleic acid sequences selected from the group consisting of SEQ ID NOs: 124-159. In some embodiments, the composition comprises two or more purified bacterial strains comprising 16S rDNA sequences having at least 97% homology with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:21, SEQ ID NO:22, and SEQ ID NO: 124-159. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:21, and SEQ ID NO:22. In some embodiments, the composition comprises two or more purified bacterial strains comprising 16S rDNA sequences having at least 97% homology with nucleic acid sequences selected from the group consisting of SEQ ID NO:18, SEQ ID NO:22, and SEQ ID NO: 124-159. In some embodiments, the composition comprises two or more purified bacterial strains comprising 16S rDNA sequences having at least 97% homology with nucleic acid sequences selected from the group consisting of SEQ ID NO:18, SEQ ID NO:22, SEQ ID NO: 124, SEQ ID NO:129, SEQ ID NO:132, SEQ ID NO:137, SEQ ID NO:141, SEQ ID NO:146, SEQ ID NO:152, and SEQ ID NO:157.

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO: 124-159. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, and SEQ ID NO:21. In some embodiments, the composition comprises two or more purified bacterial strains comprising 16S rDNA sequences having at least 97% homology with nucleic acid sequences selected from the group consisting of SEQ ID NO:18 and SEQ ID NO: 124-159. In some embodiments, the composition comprises two or more purified bacterial strains comprising 16S rDNA sequences having at least 97% homology with nucleic acid sequences selected from the group consisting of SEQ ID NO:18, SEQ ID NO: 124, SEQ ID NO:129, SEQ ID NO:132, SEQ ID NO:137, SEQ ID NO:141, SEQ ID NO:146, SEQ ID NO:152, and SEQ ID NO:157

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, and SEQ ID NO: 124-145, and SEQ ID NO: 151-159. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, and SEQ ID NO:22. In some embodiments, the composition comprises two or more purified bacterial strains comprising 16S rDNA sequences having at least 97% homology with nucleic acid sequences selected from the group consisting of SEQ ID NO:22, SEQ ID NO: 124-145, and SEQ ID NO: 151-159. In some embodiments, the composition comprises two or more purified bacterial strains comprising 16S rDNA sequences having at least 97% homology with nucleic acid sequences selected from the group consisting of SEQ ID NO: 124, SEQ ID NO:129, SEQ ID NO:132, SEQ ID NO:137, SEQ ID NO:141, SEQ ID NO:152, and SEQ ID NO:157

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NO: 124-159. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some embodiments, the composition comprises two or more purified bacterial strains comprising 16S rDNA sequences having at least 97% homology with nucleic acid sequences selected from the group consisting of SEQ ID NOs: 124-159.

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:21, SEQ ID NOs: 124-145, and SEQ ID NOs: 152-159. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, and SEQ ID NO:21. In some embodiments, the composition comprises two or more purified bacterial strains comprising 16S rDNA sequences having at least 97% homology with nucleic acid sequences selected from the group consisting of SEQ ID NO: 18, SEQ ID NOs: 124-145, and SEQ ID NOs: 152-159.

In some embodiments, the composition comprises two or more purified bacterial strains comprising 16S rDNA sequences having at least 97% homology with nucleic acid sequences selected from the group consisting of SEQ ID NO:10, SEQ ID NO:18, SEQ ID NO:19, SEQ ID NO:20, SEQ ID NO:21, SEQ ID NO:22, SEQ ID NOs: 157-159, and SEQ ID NOs:141-156. In some embodiments, the composition comprises two or more purified bacterial strains comprising 16S rDNA sequences having at least 97% homology with nucleic acid sequences selected from the group consisting of SEQ ID NO:10, SEQ ID NO:18, SEQ ID NO:19, SEQ ID NO:20, SEQ ID NO:21, and SEQ ID NO:22. In some embodiments, the composition comprises two or more purified bacterial strains comprising 16S rDNA sequences having at least 97% homology with nucleic acid sequences selected from the group consisting of SEQ ID NO:18, SEQ ID NO:22, SEQ ID NOs: 157-159, and SEQ ID NO:141-156.

Each of the bacteria of Composition B are BaiCD− strains, meaning that the strains do not encode and/or are not predicted to encode the bile inducible operon gene baiCD and/or a protein with stereospecific NAD(H)-dependent 3-oxo-$\Delta^4$-cholenoic acid oxidoreductase activity. In some embodiments, the disclosure provides compositions comprising two or more bacteria, wherein the bacteria are BaiCD− strains. The strains of Composition B are classified as belonging to *Clostridium* clusters IV, XIVa, and XVII. In some embodiments, the disclosure provides two or more bacterial strains, wherein the bacteria are BaiCD− strains and belong to *Clostridium* clusters IV, XIVa, or XVII. In some embodiments, the disclosure provides two or more bacterial strains, wherein the bacteria are BaiCD− strains and belong to *Clostridium* clusters IV or XVII. In some embodiments, the disclosure provides two or more bacterial strains, wherein the bacteria are BaiCD− strains and belong to *Clostridium* clusters XIVa or XVII. In some embodiments, the disclosure provides two or more bacterial strains, wherein the bacteria are BaiCD− strains and belong to *Clostridium* clusters IV or XIVa. In some embodiments, the disclosure provides two or more bacterial strains, wherein the bacteria are BaiCD− strains and belong to *Clostridium* cluster IV. In some embodiments, the disclosure provides two or more bacterial strains, wherein the bacteria are BaiCD− strains and belong to *Clostridium* cluster XIVa. In some embodiments, the disclosure provides two or more bacterial strains, wherein the bacteria are BaiCD− strains and belong to *Clostridium* clusters XVII. In some embodiments, the disclosure provides two or more bacterial strains, wherein the bacteria are BaiCD− strains and belong to *Clostridium* clusters IV, XIVa, and XVII and do not belong to *Clostridium* clusters XVI or XVIII.

In some embodiments, the disclosure provides two or more bacterial strains wherein the bacterial strains are spore forming bacterial strains. In some embodiments, the disclosure provides two or more bacterial strains wherein the bacteria are spore formers and wherein the bacterial strains comprise 16S rDNA sequences having at least 97% homology with nucleic acid sequences selected from the group consisting of SEQ ID NO:14, SEQ ID NO:16, SEQ ID NO:17, SEQ ID NO:21, SEQ ID NOs 124-140, and SEQ ID NO: 152-156. In some embodiments, the disclosure provides two or more bacterial strains wherein the bacteria are spore formers and wherein the bacterial strains comprise 16S rDNA sequences having at least 97% homology with nucleic acid sequences selected from the group consisting of SEQ ID NO:14, SEQ ID NO:16, SEQ ID NO:17, and SEQ ID NO:21. In some embodiments, the disclosure provides two or more bacterial strains wherein the bacteria are spore formers and wherein the bacterial strains comprise 16S rDNA sequences having at least 97% homology with nucleic acid sequences selected from the group consisting of SEQ ID NOs: 124-140, and SEQ ID NOs: 152-156.

In some embodiments, the disclosure provides two or more bacterial strains wherein the bacteria include both spore formers and non-spore formers. In some embodiments, the disclosure provides two or more bacterial strains wherein the bacteria include both spore formers and non-spore formers, and wherein the spore forming bacterial strains comprise two or more purified bacterial strains comprising 16S rDNA sequences having at least 97% homology with nucleic acid sequences selected from the group consisting of SEQ ID NO:14, SEQ ID NO:16, SEQ ID NO:17, SEQ ID NO:21, SEQ ID NOs: 124-140, and SEQ ID NOs: 152-156. In some embodiments, the disclosure provides two or more bacterial strains wherein the bacteria include both spore formers and non-spore formers, and wherein the spore forming bacterial strains comprise two or more purified bacterial strains comprising 16S rDNA sequences having at least 97% homology with nucleic acid sequences selected from the group consisting of SEQ ID NO:14, SEQ ID NO:16, SEQ ID NO:17, and SEQ ID NO:21. In some embodiments, the disclosure provides two or more bacterial strains wherein the bacteria include both spore formers and non-spore formers, and wherein the spore forming bacterial strains comprise two or more purified bacterial strains comprising 16S rDNA sequences having at least 97% homology with nucleic acid sequences selected from the group consisting of SEQ ID NOs: 124-140 and SEQ ID NO: 152-156.

TABLE B

| Composition B |
|---|
| SEQ_10 - 211 - *Flavonifractor_plautii* (IV) |
| SEQ_14 - VE202-13 - *Anaerotruncus_colihominis* (IV) |
| SEQ_15 - VE202-14 - *Eubacterium_fissicatena* (XIVa) |
| SEQ_16 - VE202-16 - *Clostridium_symbiosum* (XIVa) |
| SEQ_17 - VE202-7 - *Clostridium_bolteae* (XIVa) |
| SEQ_19 - 16 - *Blautia_producta* (XIVa) |
| SEQ_20 - 170 - *Dorea_longicatena* (XIVa) |
| SEQ_21 - 189 - *Clostridium_innocuum* (XVII) |

In some embodiments, the compositions include one or more bacterial species from the *Bacteroides* genus. In some embodiments, the compositions include one or more bacterial species selected from the group consisting of *B. acidifaciens, B. caccae, B. coprocola, B. coprosuis, B. eggerthii, B. finegoldii, B. fragilis, B. helcogenes, B. intestinalis, B. massiliensis, B. nordii, B. ovatus, B. thetaiotaomicron, B. vulgatus, B. plebeius, B. uniformis B. salyersai, B. pyogenes, B. goldsteinii, B. dorei*, and *B. johnsonii*. In some embodiments, the compositions include *Bacteroides ovatus*. In some embodiments, the *Bacteroides ovatus* has a 16S rDNA sequence comprising SEQ ID NO:83. In some embodiments, the *Bacteroides ovatus* has a 16S rDNA sequence having at least 97% homology with a nucleic acid sequence comprising SEQ ID NO:83. In some embodiments, the *Bacteroides ovatus* has a 16S rDNA sequence having at least 97% homology with a nucleic acid sequence comprising SEQ ID NO:101.

While not being limited to a specific mechanism it is thought that the inclusion of a *Bacteroides* species in the bacterial compositions disclosed herein increases the ability to sense and adapt to nutrient availability or influence the host immune system so that it becomes more effective in fighting pathogens (e.g., *C. difficile*). In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, SEQ ID NO: 124-159, and SEQ ID NO:83. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NO:83. (Composition B1, See e.g., Table B1). In some embodiments, the composition comprises two or more purified bacterial strains comprising 16S rDNA sequences having at least 97% homology with nucleic acid sequences selected from the group consisting of SEQ ID NOs: 124-159, and SEQ ID NO: 83.

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NO: 124-145, SEQ ID NO: 152-159, and SEQ ID NO:83. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, and SEQ ID NO:83. In some embodiments, the composition comprises two or more purified bacterial strains comprising 16S rDNA sequences having at least 97% homology with nucleic acid sequences selected from the group consisting of SEQ ID NOs: 124-145, SEQ ID NO: 152-159, and SEQ ID NO: 83.

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO: 124-159, and SEQ ID NO:83. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:83. In some embodiments, the composition comprises two or more purified bacterial strains comprising 16S rDNA sequences having at least 97% homology with nucleic acid sequences selected from the group consisting of SEQ ID NOs: 124-159, SEQ ID NO: 18, SEQ ID NO: 22, and SEQ ID NO: 83.

In some embodiments, the composition comprises two or more purified bacterial strains comprising 16s rDNA sequences having at least 97% homology with nucleic acid sequences selected from the group consisting of SEQ ID NO:93, SEQ ID NO:95, SEQ ID NO:97, SEQ ID NO:98, SEQ ID NO:101, SEQ ID NO:102, SEQ ID NO:106, SEQ ID NO:110, and SEQ ID NO:122. It should also be appreciated that in some embodiments, the compositions disclosed herein do not include bacterial species from the *Bacteroides* genus.

TABLE B1

| Composition B1 |
|---|
| SEQ_10 - 211 - *Flavonifractor_plautii* (IV) |
| SEQ_14 - VE202-13 - *Anaerotruncus_colihominis* (IV) |
| SEQ_15 - VE202-14 - *Eubacterium_fissicatena* (XIVa) |
| SEQ_16 - VE202-16 - *Clostridium_symbiosum* (XIVa) |
| SEQ_17 - VE202-7 - *Clostridium_bolteae* (XIVa) |
| SEQ_20 - 170 - *Dorea_longicatena* (XIVa) |
| SEQ_19 - 16 - *Blautia_producta* (XIVa) |
| SEQ_21 - 189 - *Clostridium_innocuum* (XVII) |
| SEQ_83 *Bacteroides ovatus* |

In some embodiments, the compositions disclosed herein do not include *Clostridium orbiscindens* 1_3_50AFAA, *Flavinofractor plautii, Subdoligranulum* or *Lachnospiraceae bacterium* 7_1_58FAA. In some embodiments, the compositions disclosed herein do not include *Clostridium orbiscindens* 1_3_50AFAA. In some embodiments, the compositions disclosed herein do not include *Flavinofractor plautii. In some embodiments, the composi-*

*tions disclosed herein do not include Subdoligranulum*. In some embodiments, the compositions disclosed herein do not include *Lachnospiraceae bacterium* 7_1_58FAA.

In some embodiments, the composition comprises two or more purified bacterial strains comprising 16S rDNA sequences having at least 97% homology with nucleic acid sequences selected from the group consisting of SEQ ID NO:14, SEQ ID NO: 15, SEQ ID NO:16, SEQ ID NO:17, SEQ ID NO:19, SEQ ID NO:20, SEQ ID NO:21, and SEQ ID NO: 124-156, wherein the composition does not include a bacterial strain comprising a 16s rDNA sequence having at least 97% homology with a nucleic acid sequence of SEQ ID NO:10 and SEQ ID NOs: 157-159. In some embodiments, the composition comprises two or more purified bacterial strains comprising 16S rDNA sequences having at least 97% homology with nucleic acid sequences selected from the group consisting of SEQ ID NO:14, SEQ ID NO: 15, SEQ ID NO:16, SEQ ID NO:17, SEQ ID NO:19, SEQ ID NO:20, and SEQ ID NO:21, wherein the composition does not include a bacterial strain comprising a 16s rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NOs: 124-156, wherein the composition does not include a bacterial strain comprising a 16S rDNA sequence having at least 97% homology with a nucleic acid sequence of SEQ ID NOs:157-159.

In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:21, SEQ ID NO:22, and SEQ ID NOs: 124-146 and SEQ ID NO: 152-156, wherein the composition does not include a bacterial strain comprising a 16S rDNA sequence having at least 97% homology with a nucleic acid sequence of SEQ ID NO:10 and SEQ ID NOs: 157-159. In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:21, and SEQ ID NO:22, wherein the composition does not include a bacterial strain comprising a 16S rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NO:22, SEQ ID NOs: 124-146, and SEQ ID NOs: 152-156, wherein the composition does not include a bacterial strain comprising a 16S rDNA sequence having at least 97% homology with a nucleic acid sequence of SEQ ID NOs: 157-159.

In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NOs: 124-156, wherein the composition does not include a bacterial strain comprising a 16S rDNA sequence having at least 97% homology with a nucleic acid sequence of SEQ ID NO:10 and SEQ ID NOs: 157-159. In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, wherein the composition does not include a bacterial strain comprising a 16S rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NO:18, SEQ ID NO:22, and SEQ ID NOs: 124-159, wherein the composition does not include a bacterial strain comprising a 16S rDNA sequence having at least 97% homology with a nucleic acid sequence of SEQ ID NOs: 157-159.

In some embodiments, the composition comprises two or more purified bacterial strains comprising 16S rDNA sequences having at least 97% homology with nucleic acid sequences selected from the group consisting of SEQ ID NO:95, SEQ ID NO:97, SEQ ID NO:98, SEQ ID NO:102, SEQ ID NO:106, SEQ ID NO:110, and SEQ ID NO:122, wherein the composition does not include a bacterial strain comprising a 16S rDNA sequence having at least 97% homology with a nucleic acid sequence of SEQ ID NO:93.

In some embodiments, the compositions include one or more bacterial species from the *Bacteroides* genus and do not include *Clostridium orbiscindens* 1_3_50AFAA, *Flavinofractor plautii, Subdoligranulum* or *Lachnospiraceae bacterium* 7_1_58FAA. (Composition B2, See e.g., Table B2). In some embodiments, the compositions include *Bacteroides ovatus* and do not include *Clostridium orbiscindens* 1_3_50AFAA, *Flavinofractor plautii, Subdoligranulum* or *Lachnospiraceae bacterium* 7_1_58FAA.

In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:20, SEQ ID NO:21 SEQ ID NO:83, and SEQ ID NOs: 124-156, wherein the composition does not include a bacterial strain comprising a 16S rDNA sequence having at least 97% homology with a nucleic acid sequence of SEQ ID NO:10 and SEQ ID NOs: 157-159. In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:20, SEQ ID NO:21 and SEQ ID NO:83, wherein the composition does not include a bacterial strain comprising a 16S rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NO:83 and SEQ ID NOs: 124-156, wherein the composition does not include a bacterial strain comprising a 16S rDNA sequence having at least 97% homology with a nucleic acid sequence of SEQ ID NOs: 157-159.

In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:21, SEQ ID NO:22, SEQ ID NO:83, SEQ ID NOs: 124-145, and SEQ ID NOs: 152-156, wherein the composition does not include a bacterial strain comprising a 16S rDNA sequence having at least 97% homology with a nucleic acid sequence of SEQ ID NO:10 and SEQ ID NOs: 157-159. In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:21, SEQ ID NO:22 and SEQ ID NO:83, wherein the composition does not include a bacterial strain comprising a 16S rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NO:22 SEQ ID NO:83, SEQ ID NOs: 124-145, and SEQ ID NOs: 152-156, wherein the composition does not include a bacterial strain comprising a 16S rDNA sequence having at least 97% homology with a nucleic acid sequence of SEQ ID NOs: 157-159.

In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:83, and SEQ ID NO: 124-156, wherein the composition does not include a bacterial strain comprising a 16S rDNA sequence having at least 97% homology with a nucleic acid sequence of SEQ ID NO:10 and SEQ ID NOs: 157-159. In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:83, wherein the composition does not include a bacterial strain comprising a 16S rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NO:22, SEQ ID NO:83, and SEQ ID NO: 124-156, wherein the composition does not include a bacterial strain comprising a 16S rDNA sequence having at least 97% homology with a nucleic acid sequence of SEQ ID NOs: 157-159.

In some embodiments, the composition comprises two or more purified bacterial strains comprising 16S rDNA sequences having at least 97% homology with nucleic acid sequences selected from the group consisting of SEQ ID NO:95, SEQ ID NO:97, SEQ ID NO:98, SEQ ID NO:101, SEQ ID NO:102, SEQ ID NO:106, SEQ ID NO:110, and SEQ ID NO:122, wherein the composition does not include a bacterial strain comprising a 16S rDNA sequence having at least 97% homology with a nucleic acid sequence of SEQ ID NO:93.

TABLE B2

| Composition B2 |
|---|
| SEQ_14 - VE202-13 - *Anaerotruncus_colihominis* (IV) |
| SEQ_15 - VE202-14 - *Eubacterium_fissicatena* (XIVa) |
| SEQ_16 - VE202-16 - *Clostridium_symbiosum* (XIVa) |
| SEQ_17 - VE202-7 - *Clostridium_bolteae* (XIVa) |
| SEQ_20 - 170 - *Dorea_longicatena* (XIVa) |
| SEQ_19 - 16 - *Blautia_producta* (XIVa) |
| SEQ_21 - 189 - *Clostridium_innocuum* (XVII) |
| SEQ_83 *Bacteroides ovatus* |

In one aspect, the disclosure provides Composition C (See e.g., FIG. 1, Table C). As shown in FIG. 1, Composition C contains bacteria that have the following 16S rDNA sequences: SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16. In some embodiments, the disclosure provides compositions with two or more purified bacterial strains that have 16S rDNA sequences selected from the group consisting of SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16. In some embodiments, the compositions include four or more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16. In some embodiments, the compositions include at least ten purified bacterial strains comprising 16S rDNA sequences with nucleic acid sequences selected from the group consisting of SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16. In some embodiments, the composition consists of ten purified bacterial strains comprising 16S rDNA sequences with nucleic acid sequences SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16, respectively. In some embodiments, the composition consists essentially of ten purified bacterial strains comprising 16S rDNA sequences with nucleic acid sequences SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16, respectively.

In some embodiments, the compositions include two or more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16. In some embodiments, the compositions include four or more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16. In some embodiments, the compositions include at least ten purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16. In some embodiments, the composition consists of ten purified bacterial strains comprising 16S rDNA sequences having at least 97% homology with nucleic acid sequences SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16, respectively. In some embodiments, the composition essentially consists of ten purified bacterial strains comprising 16S rDNA sequences having at least 97% homology with nucleic acid sequences SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16, respectively.

The bacterial strains in Composition C are related to the following species: *Clostridium scindens, Clostridium hathewayi, Blautia hansenii, Blautia wexlerae, Blautia producta, Blautia coccoides, Dorea longicatena, Clostridium innocuum, Flavonifractor plautii, Lachnospiraceae bacterium* 7_1_58FAA, *Subdoligranulum, Anaerotruncus colihominis*, and *Clostridium symbiosum*. In some embodiments, the disclosure provides compositions with two or more bacterial strains of species selected from the group consisting of *Clostridium scindens, Clostridium hathewayi, Blautia hansenii, Blautia wexlerae, Blautia* product, *Blautia coccoides, Dorea longicatena, Clostridium innocuum, Flavonifractor plautii, Lachnospiraceae bacterium* 7_1_58FAA, *Subdoligranulum, Anaerotruncus colihominis*, and *Clostridium symbiosum*. In some embodiments, the disclosure provides compositions that include two or more purified bacterial strains comprising 16S rDNA sequences having at least 97% homology with nucleic acid sequences selected from the group consisting of SEQ ID NO:87, SEQ ID NO:93, SEQ ID NO:94, SEQ ID NO:95, SEQ ID NO:97, SEQ ID NO:98, SEQ ID NO:99, SEQ ID NO:103, SEQ ID NO:105, SEQ ID NO:106, and SEQ ID NO:122.

In some embodiments, the compositions disclosed herein do not include *Flavinofractor plautii, Subdoligranulum* or *Lachnospiraceae bacterium* 7_1_58FAA. In some embodiments, the composition comprises two or more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:7, SEQ ID NO:18, SEQ ID NO:21, SEQ ID NO:14, and SEQ ID NO:16, wherein the composition does not include a bacterial strain comprising a 16S rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NO:87, SEQ ID NO:94, SEQ ID NO:95, SEQ ID NO:97, SEQ ID NO:98, SEQ ID NO:99, SEQ ID NO:103, SEQ ID NO:105, SEQ ID NO:106, and SEQ ID NO:122, wherein the composition does not include a bacterial strain comprising a 16S rDNA sequence having at least 97% homology with a nucleic acid sequence of SEQ ID NO:93.

The strains of Composition C include both $BaiCD^{+}$ strains and Bai CD− strains. In some embodiments, the disclosure provides compositions comprising two or more bacteria, wherein one or more bacteria are BaiCD+ strains and one or more bacteria are BaiCD− strains. In some embodiments of the one or more bacteria that are BaiCD+ strains are selected from bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, and SEQ ID NO:7. In some embodiments the one or more bacteria that are BaiCD− strains are selected from bacterial strains comprising 16S rDNA sequences having at least 97% homology with nucleic acid sequences selected from the group consisting of SEQ ID NO:18, SEQ ID NO:21, SEQ ID NO:10, SEQ ID NO:14, and SEQ ID NO:16. In some embodiments of the one or more bacteria that are BaiCD+ strains are selected from the bacterial species *Clostridium scindens, Clostridium hathewayi, Blautia hansenii, Blautia wexlerae, Blautia* product, and *Blautia coccoides*. In some embodiments of the one or more bacteria that are BaiCD− strains are selected from the bacterial species *Dorea longicatena, Clostridium innocuum, Flavonifractor plautii*, or *Lachnospiraceae bacterium* 7_1_58FAA, *Anaerotruncus colihominis*, and *Clostridium symbiosum*. The clostridial strains of Composition C are classified as belonging to *Clostridium* clusters IV, XIVa, and XVII. In some embodiments, the disclosure provides two or more bacterial strains, wherein the bacteria are BaiCD− strains and BaiCD+ strains and belong to *Clostridium* clusters IV, XIVa, or XVII. In some embodiments, the disclosure provides two or more bacterial strains, wherein the bacteria are BaiCD− strains and BaiCD+ strains and belong to *Clostridium* clusters XIVa or XVII. In some embodiments, the disclosure provides two or more bacterial strains, wherein the bacteria are BaiCD− strains and BaiCD+ strains and belong to *Clostridium* clusters IV or XIVa.

TABLE C

| Composition C |
|---|
| SEQ_12 - VE202-26 - *Clostridium_scindens* (XIVa)* |
| SEQ_03 - 5 - *Clostridium_hathewayi* (XIVa)* |
| SEQ_05 - 10 - *Blautia_hansenii* (XIVa)* |
| SEQ_01 - 71 - *Blautia_wexlerae* (XIVa)* |
| SEQ_07 - 59 - *Blautia_producta/Blautia_coccoides* (XIVa)* |
| SEQ_18 - 148 - *Dorea_longicatena* (XIVa) |
| SEQ_21 - 189 - *Clostridium_innocuum* (XVII) |
| SEQ_10 - 211 - *Flavonifractor_plautii* (IV) |
| SEQ_14 - VE202-13 - *Anaerotruncus_colihominis* (IV) |
| SEQ_16 - VE202-16 - *Clostridium_symbiosum*) (XIVa) |

*= BaiCD+

In one aspect, the disclosure provides Composition D (See e.g., FIG. 1, Table D). As shown in FIG. 1, Composition D contains bacteria that have the following 16S rDNA sequences: SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6. In some embodiments, the disclosure provides compositions with two or more purified bacterial strains that have 16S rDNA sequences selected from the group consisting of SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6. In some embodiments, the disclosure provides compositions that include three or more purified bacterial strains comprising 16S rDNA sequences with nucleic acid sequences selected from the group consisting of SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6. In some embodiments, the disclosure provides compositions that include at least ten purified bacterial strains comprising 16S rDNA sequences with nucleic acid sequences selected from the group consisting of SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6. In some embodiments, the disclosure provides a composition that consists of ten purified bacterial strains comprising 16S rDNA sequences with nucleic acid sequences SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6, respectively. In some embodiments, the disclosure provides a composition that consists essentially of ten purified bacterial strains comprising 16S rDNA sequences with nucleic acid sequences SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6, respectively In some embodiments, the disclosure provides compositions that include two or more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6. In some embodiments, the disclosure provides compositions that include three or more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6. In some embodiments, the disclosure provides compositions that include at least ten more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6. In some embodiments, the disclosure provides a composition that consists of ten purified bacterial strains comprising 16S rDNA sequences having at least 97% homology with nucleic acid sequences SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6, respectively. In some embodiments, the disclosure provides a composition that consists essentially of ten purified bacterial strains comprising 16S rDNA sequences having at least 97% homology with nucleic acid sequences SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6, respectively.

The bacterial strains in Composition D are related to the following bacteria: *Clostridium scindens, Clostridium hathewayi, Blautia hansenii, Blautia wexlerae, Anaerotruncus colihominis, Dorea longicatena, Clostridium innocuum, Flavonifractor plautii, Lachnospiraceae bacterium* 7_1_58FAA, *Subdoligranulum, Turicibacter sanguinis*, and *Lactobacillus mucosae*. In some embodiments, the disclosure provides compositions with two or more bacterial strains of species selected from the group consisting of *Clostridium scindens, Clostridium hathewayi, Blautia hansenii, Blautia wexlerae, Anaerotruncus colihominis, Dorea longicatena, Clostridium innocuum, Erysipelotrichaceae_ bacterium_*21-3, *Flavonifractor plautii, Lachnospiraceae bacterium* 7_1_58FAA, *Turicibacter sanguinis*, and *Lactobacillus mucosae*. In some embodiments, the disclosure provides compositions that include two or more purified bacterial strains comprise 16S rDNA sequences having at least 97% homology with nucleic acid sequences selected from the group consisting of SEQ ID NO:87, SEQ ID NO:90, SEQ ID NO:91, SEQ ID NO:93, SEQ ID NO:94, SEQ ID NO:95, SEQ ID NO:97, SEQ ID NO:98, SEQ ID NO:99, and SEQ ID NO:105.

In some embodiments, the compositions disclosed herein do not include *Flavinofractor plautii, Subdoligranulum* or *Lachnospiraceae bacterium* 7_1_58FAA. In some embodiments, the composition comprises two or more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:14, SEQ ID NO:18, SEQ ID NO:21, SEQ ID NO:2, and SEQ ID NO:6, wherein the composition does not include a bacterial strain comprising a 16S rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NO:87, SEQ ID NO:90, SEQ ID NO:91, SEQ ID NO:94, SEQ ID NO:95, SEQ ID NO:97, SEQ ID NO:98, SEQ ID NO:99, and SEQ ID NO:105, wherein the composition does not include a bacterial strain comprising a 16S rDNA sequence having at least 97% homology with a nucleic acid sequence of SEQ ID NO:93.

The strains of Composition D include both $BaiCD_+$ strains and Bai CD− strains. In some embodiments, the disclosure provides compositions comprising two or more bacteria, wherein one or more bacteria are BaiCD+ strains and one or more bacteria are BaiCD− strains. In some embodiments of the one or more bacteria that are BaiCD+ strains are selected from bacterial strains comprising 16S rDNA sequences having at least 97% homology with nucleic acid sequences selected from the group consisting of SEQ ID NO:12, SEQ ID NO:3, SEQ ID NO:5, and SEQ ID NO:1. In some embodiments the one or more bacteria that are BaiCD− strains are selected from bacterial strains comprising 16S rDNA sequences having at least 97% homology with nucleic acid sequences selected from the group consisting of SEQ ID NO:18, SEQ ID NO:21, SEQ ID NO:10, and SEQ ID NO:14. In some embodiments of the one or more bacteria that are BaiCD+ strains are selected from the bacterial species *Clostridium scindens, Clostridium hathewayi, Blautia hansenii*, and *Blautia wexlerae*. In some embodiments of the one or more bacteria that are BaiCD− strains are selected from the bacterial species *Dorea longicatena, Clostridium innocuum, Flavonifractor plautii*, and *Anaerotruncus colihominis*. The Clostridial strains of Composition D are classified as belonging to *Clostridium* clusters IV, XIVa, and XVII. In some embodiments, the disclosure provides two or more bacterial strains, wherein the bacteria are BaiCD− strains and BaiCD+ strains and belong to *Clostridium* clusters IV, XIVa, or XVII. In some embodiments, the disclosure provides two or more bacterial strains, wherein the bacteria are BaiCD− strains and BaiCD+ strains and belong to *Clostridium* clusters XIVa or XVII. In some embodiments, the disclosure provides two or more bacterial strains, wherein the bacteria are BaiCD− strains and BaiCD+ strains and belong to *Clostridium* clusters IV or XIVa.

Composition D includes the non-*Clostridium* strains *Turicibacter sanguinis* and *Lactobacillus mucosae*. In some embodiments, the disclosure provides compositions comprising two or more bacteria, wherein the composition includes both *Clostridium* strains and non-*Clostridium* strains. In some embodiments, the non-*clostridium strains are the members of the genus Lactobacillus*. Members of the genus *Lactobacillus* include, without limitation *L. acetotolerans, L. acidifarinae, L. acidipiscis, L. acidophilus, L.*

*agilis*, *L. algidus*, *L. alimentarius*, *L. amylolyticus*, *L. amylophilus*, *L. amylotrophicus*, *L. amylovorus*, *L. animalis*, *L. antri*, *L. apodemi*, *L. aviarius*, *L. bifermentans*, *L. brevis*, *L. buchneri*, *L. camelliae*, *L. casei*, *L. catenaformis*, *L. ceti*, *L. coleohominis*, *L. collinoides*, *L. composti*, *L. concavus*, *L. coryniformis*, *L. crispatus*, *L. crustorum*, *L. curvatus*, *L. delbrueckii* subsp. *bulgaricus*, *L. delbrueckii* subsp. *delbrueckii*, *L. delbrueckii* subsp. lactis, *L. dextrinicus*, *L. diolivorans*, *L. equi*, *L. equigenerosi*, *L. farraginis*, *L. farciminis*, *L. fermentum*, *L. fornicalis*, *L. fructivorans*, *L. frumenti*, *L. fuchuensis*, *L. gallinarum*, *L. gasseri*, *L. gastricus*, *L. ghanensis*, *L. graminis*, *L. hammesii*, *L. hamsteri*, *L. harbinensis*, *L. hayakitensis*, *L. helveticus*, *L. hilgardii*, *L. homohiochii*, *L. iners*, *L. ingluviei*, *L. intestinalis*, *L. jensenii*, *L. johnsonii*, *L. kalixensis*, *L. kefiranofaciens*, *L. kefiri*, *L. kimchii*, *L. kitasatonis*, *L. kunkeei*, *L. leichmannii*, *L. lindneri*, *L. malefermentans*, *L. mali*, *L. manihotivorans*, *L. mindensis*, *L. mucosae*, *L. murinus*, *L. nagelii*, *L. namurensis*, *L. nantensis*, *L. oligofermentans*, *L. oris*, *L. panis*, *L. pantheris*, *L. parabrevis*, *L. parabuchneri*, *L. paracasei*, *L. paracollinoides*, *L. parafarraginis*, *L. parakefiri*, *L. paralimentarius*, *L. paraplantarum*, *L. pentosus*, *L. perolens*, *L. plantarum*, *L. pontis*, *L. protectus*, *L. psittaci*, *L. rennini*, *L. reuteri*, *L. rhamnosus*, *L. rimae*, *L. rogosae*, *L. rossiae*, *L. ruminis*, *L. saerimneri*, *L. sakei*, *L. salivarius*, *L. sanfranciscensis*, *L. satsumensis*, *L. secaliphilus*, *L. sharpeae*, *L. siliginis*, *L. spicheri*, *L. suebicus*, *L. thailandensis*, *L. ultunensis*, *L. vaccinostercus*, *L. vaginalis*, *L. versmoldensis*, *L. vini*, *L. vitulinus*, *L. zeae*, and *L. zymae*. In some embodiments, the non-*clostridium strain is Lactobacillus mucosae*. In some embodiments, the non-*clostridium strain is Lactobacillus mucosae*. In some embodiments, the *Lactobacillus mucosae* has a 16S rDNA sequence comprising SEQ ID NO:2. In some embodiments, the *Lactobacillus mucosae* has a 16S rDNA sequence having at least 97% homology with a nucleic acid comprising SEQ ID NO:2. In some embodiments, the *Lactobacillus mucosae* has a 16S rDNA sequence having at least 97% homology with a nucleic acid comprising SEQ ID NO:91.

In some embodiments, the disclosure provides compositions comprising two or more bacteria, wherein the composition includes both *Clostridium* strains and non-*Clostridium* strains. In some embodiments, the non-*clostridium strains are members of the genus Turicibacter*. In some embodiments, the non-*clostridium strain is Turicibacter sanguinis*. In some embodiments, the *Turicibacter sanguinis* has a 16S rDNA sequence comprising SEQ ID NO:6. In some embodiments, the *Turicibacter sanguinis* has a 16S rDNA sequence having at least 97% homology with a nucleic acid comprising SEQ ID NO:6. In some embodiments, the *Turicibacter sanguinis* has a 16S rDNA sequence having at least 97% homology with a nucleic acid comprising SEQ ID NO:90.

In some embodiments, the disclosure provides compositions comprising two or more bacteria, wherein the composition includes both *Clostridium* strains and non-*Clostridium* strains. In some embodiments, the non-*Clostridium* strains are *Lactobacillus mucosae* and *Turicibacter sanguinis*.

In some embodiments, the disclosure provides compositions comprising two or more bacteria, wherein the composition does not include *Lactobacillus*. In some embodiments, the disclosure provides compositions comprising two or more bacteria, wherein the composition does not include *Turicibacter*. In some embodiments, the disclosure provides compositions comprising two or more bacteria, wherein the composition does not include *Lactobacillus* or *Turicibacter*. In some embodiments, the disclosure provides compositions comprising two or more bacteria, wherein the composition only includes *clostridia* strains. In some embodiments, the disclosure provides compositions comprising two or more bacteria, wherein the composition only includes *clostridia* strains belonging to *Clostridium* cluster IV, XIVa or XVII strains. In some embodiments, the disclosure provides compositions comprising two or more bacteria, wherein the composition does not include *Clostridium* cluster XI strains.

In some embodiments, the disclosure provides compositions comprising two or more purified bacterial strains selected from the group consisting of: *Clostridium scindens*, *Pseudoflavonifractor capillosus*, and *Blautia hansenii*. In some embodiments, the compositions disclosed herein do not include *Clostridium scindens*, *Pseudoflavonifractor capillosus*, or *Blautia hansenii*.

TABLE D

| Composition D |
|---|
| SEQ_12 - VE202-26 - *Clostridium_scindens* (XIVa)* |
| SEQ_03 - 5 - *Clostridium_hathewayi* (XIVa)* |
| SEQ_05 - 10 - *Blautia_hansenii* (XIVa)* |
| SEQ_01 - 71 - *Blautia_wexlerae* (XIVa)* |
| SEQ_14 - VE202-13 - *Anaerotruncus_colihominis* (IV) |
| SEQ_18 - 148 - *Dorea_longicatena* (XIVa) |
| SEQ_21 - 189 - *Clostridium_innocuum* (XVII) |
| SEQ_10 - 211 - *Flavonifractor_plautii* (IV |
| SEQ_02 - 102 - *Turicibacter_sanguinis* (non-Clostridium) |
| SEQ_06 - 40 - *Lactobacillus_mucosae* (non-Clostridium) |

*= BaiCD+

In one aspect, the disclosure provides Composition F (See e.g., FIGS. 13 and 14, and Tables F1 and F2). As shown in FIG. 13, Composition F contains bacteria that have the following 16S rDNA sequences: SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, and SEQ ID NO:79.

In some embodiments, the disclosure provides compositions with two or more purified bacterial strains that have 16S rDNA sequences selected from the group consisting of SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, and SEQ ID NO:79.

In some embodiments, the compositions include two or more purified bacterial strains comprising 16S rDNA sequences having at least 97% homology with nucleic acid sequences selected from the group consisting of SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, and SEQ ID NO:79.

The bacterial strains in Composition F are related to the following bacteria: *Dorea longicatena, Ruminococcus obeum, Megasphaera elsdenii, Acidaminococcus fermentans, Acidaminococcus intestine, Megasphaera elsdenii, Ruminococcus faecis, Bacteroides cellulosilyticus, Anaerostipes hadrus, Ruminococcus obeum, Flavonifractor plautii, Eubacterium rectale, Flavonifractor plautii, Megasphaera elsdenii, Eubacterium rectale, Ruminococcus champanellensis, Ruminococcus albus, Ruminococcus champanellensis, Ruminococcus faecis, Bifidobacterium bifidum, Anaerostipes hadrus, Anaerostipes hadrus, Anaerostipes hadrus, Eubacterium rectale, Ruminococcus faecis, Blautia luti, Ruminococcus faecis, Anaerostipes hadrus, Anaerostipes hadrus, Ruminococcus faecis, Eubacterium rectale, Eubacterium rectale, Anaerostipes hadrus, Ruminococcus faecis, Ruminococcus faecis, Dorea longicatena, Roseburia faecis, Blautia luti, Fusicatenibacter saccharivorans, Fusicatenibacter saccharivorans, Roseburia faecis, Megasphaera elsdenii, Eubacterium rectale, Eubacterium rectale, Roseburia faecis, Blautia faecis, Fusicatenibacter saccharivorans*, and *Dorea formicigenerans.*

In some embodiments, the disclosure provides compositions with two or more bacterial strains of species selected from the group consisting of *Dorea longicatena, Ruminococcus obeum, Megasphaera elsdenii, Acidaminococcus fermentans, Acidaminococcus intestine, Megasphaera elsdenii, Ruminococcus faecis, Bacteroides cellulosilyticus, Anaerostipes hadrus, Ruminococcus obeum, Flavonifractor plautii, Eubacterium rectale, Flavonifractor plautii, Megasphaera elsdenii, Eubacterium rectale, Ruminococcus champanellensis, Ruminococcus albus, Ruminococcus champanellensis, Ruminococcus faecis, Bifidobacterium bifidum, Anaerostipes hadrus, Anaerostipes hadrus, Anaerostipes hadrus, Eubacterium rectale, Ruminococcus faecis, Blautia luti, Ruminococcus faecis, Anaerostipes hadrus, Anaerostipes hadrus, Ruminococcus faecis, Eubacterium rectale, Eubacterium rectale, Anaerostipes hadrus, Ruminococcus faecis, Ruminococcus faecis, Dorea longicatena, Roseburia faecis, Blautia luti, Fusicatenibacter saccharivorans, Fusicatenibacter saccharivorans, Roseburia faecis, Megasphaera elsdenii, Eubacterium rectale, Eubacterium rectale, Roseburia faecis, Blautia faecis, Fusicatenibacter saccharivorans*, and *Dorea formicigenerans.*

In some embodiments, the disclosure provides compositions that include two or more purified bacterial strains comprise 16S rDNA sequences having at least 97% homology with nucleic acid sequences selected from the group consisting of SEQ ID NO:84, SEQ ID NO:85, SEQ ID NO:92, SEQ ID NO:93, SEQ ID NO:96, SEQ ID NO:97, SEQ ID NO:99, SEQ ID NO:100, SEQ ID NO:104, SEQ ID NO:107, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, and SEQ ID NO:120. It should be appreciated that multiple strains of the compositions disclosed herein can have the same related bacterial species. For instance, Composition F includes 12 strains that have *Eubacterium rectale* as the closest related species.

In some embodiments, at least one of the bacterial strains of the composition belongs to *Clostridium* cluster IV. In some embodiments, at least one of the bacterial strains of the composition belongs to *Clostridium* cluster XIVa. In some embodiments, at least one of the bacterial strains of the composition belongs to *Clostridium* cluster IX. In some embodiments, at least one of the bacterial strains of the composition belongs to *Clostridium* cluster IV. In some embodiments, at least one of the bacterial strains of the composition belongs to *Clostridium* cluster XIVa and at least one of the bacterial strains belongs to *Clostridium* cluster IX. In some embodiments, at least one of the bacterial strains of the composition belongs to *Clostridium* cluster IV and at least one of the bacterial strains belongs to *Clostridium* cluster IX. In some embodiments, at least one of the bacterial strains of the composition belongs to *Clostridium* cluster IV, at least one of the bacterial strains belongs to *Clostridium* cluster XIVa, and at least one of the bacterial strains belongs to *Clostridium* cluster IX. In some embodiments, the compositions provided herein do not include bacterial strains belonging to *Clostridium* cluster XVIII. In some embodiments, the compositions provided herein do not include bacterial strains belonging to *Clostridium* cluster XVI or XVIII.

Composition F includes non-*clostridium bacterial strains. In some embodiments, the disclosure provides compositions comprising two or more bacteria, wherein the composition includes both Clostridium* strains and non-*clostridium* strains. In some embodiments, the non-*clostridium strains are the members of the genus Bacteroides*. In some embodiments, the non-*clostridium strain is Bacteroides cellulosilyticus*. In some embodiments, the non-*clostridium strains are the members of the genus Bifidobacterium*. In some embodiments, the non-*clostridium strain is Bifidobacterium bifidum*. In some embodiments, the disclosure provides compositions comprising two or more bacteria, wherein the composition includes both *Clostridium* strains and non-*Clostridium* strains, and wherein the non-*Clostridium* strains are *Bacteroides cellulosilyticus* and *Bifidobacterium bifidum.*

In some embodiments, the disclosure provides compositions comprising two or more bacteria, wherein the composition does not include *Bacteroides*. In some embodiments, the disclosure provides compositions comprising two or more bacteria, wherein the composition does not include *Bifidobacterium*. In some embodiments, the disclosure provides compositions comprising two or more bacteria, wherein the composition does not include *Bacteroides* and does not include *Bifidobacterium*. In some embodiments, the disclosure provides compositions comprising two or more bacteria, wherein the composition does not include non-*Clostridium* strains. In some embodiments, the disclosure provides compositions comprising two or more bacteria, wherein the composition only includes *clostridia strains belonging to Clostridium* cluster IV, XIVa or XVII strains. In some embodiments, the disclosure provides compositions comprising two or more bacteria, wherein the composition does not include *Clostridium* cluster XI strains.

TABLE F1

| Composition F | | |
|---|---|---|
| SEQ_NO | StrainID | Genus_species |
| SEQ_24 | YK96 | *Dorea_longicatena* |
| SEQ_25 | YK101 | *Ruminococcus_obeum* |
| SEQ_26 | YK110 | *Megasphaera_elsdenii* |
| SEQ_27 | YK149 | *Acidaminococcus_fermentans/ Acidaminococcus_intestini* |
| SEQ_28 | YK154 | *Megasphaera_elsdenii* |
| SEQ_29 | YK36 | *Ruminococcus_faecis* |
| SEQ_30 | YK95 | *Bacteroides_cellulosilyticus* |
| SEQ_31 | YK32 | *Anaerostipes_hadrus* |
| SEQ_32 | YK64 | *Ruminococcus_obeum* |
| SEQ_33 | YK73 | *Flavonifractor_plautii* |
| SEQ_34 | YK87 | *Eubacterium_rectale* |
| SEQ_35 | YK105 | *Flavonifractor_plautii* |
| SEQ_36 | YK153 | *Megasphaera_elsdenii* |
| SEQ_37 | YK163 | *Eubacterium_rectale* |
| SEQ_38 | YK191 | *Ruminococcus_champanellensis/ Ruminococcus_albus* |
| SEQ_39 | YK99 | *Ruminococcus_champanellensis* |
| SEQ_40 | YK55 | *Ruminococcus_faecis* |
| SEQ_41 | YK75 | *Bifidobacterium_bifidum* |
| SEQ_42 | YK90 | *Anaerostipes_hadrus* |
| SEQ_43 | YK30 | *Anaerostipes_hadrus* |
| SEQ_44 | YK31 | *Anaerostipes_hadrus* |
| SEQ_45 | YK12 | *Eubacterium_rectale* |
| SEQ_46 | YK27 | *Ruminococcus_faecis* |
| SEQ_47 | YK28 | *Blautia_luti* |
| SEQ_48 | YK29 | *Ruminococcus_faecis* |
| SEQ_49 | YK33 | *Anaerostipes_hadrus* |
| SEQ_50 | YK34 | *Anaerostipes_hadrus* |
| SEQ_51 | YK35 | *Ruminococcus_faecis* |
| SEQ_52 | YK51 | *Eubacterium_rectale* |
| SEQ_53 | YK52 | *Eubacterium_rectale* |
| SEQ_54 | YK54 | *Anaerostipes_hadrus* |
| SEQ_55 | YK56 | *Ruminococcus_faecis* |
| SEQ_56 | YK57 | *Ruminococcus_faecis* |
| SEQ_57 | YK58 | *Dorea_longicatena* |
| SEQ_58 | YK65 | *Roseburia_faecis* |
| SEQ_59 | YK67 | *Blautia_luti* |
| SEQ_60 | YK69 | *Fusicatenibacter_saccharivorans* |
| SEQ_61 | YK70 | *Fusicatenibacter_saccharivorans* |
| SEQ_62 | YK71 | *Roseburia_faecis* |
| SEQ_63 | YK74 | *Megasphaera_elsdenii* |
| SEQ_64 | YK88 | *Eubacterium_rectale* |
| SEQ_65 | YK89 | *Eubacterium_rectale* |
| SEQ_66 | YK97 | *Roseburia_faecis* |
| SEQ_67 | YK98 | *Blautia_faecis* |
| SEQ_68 | YK139 | *Fusicatenibacter_saccharivorans* |
| SEQ_69 | YK141 | *Dorea_formicigenerans* |
| SEQ_70 | YK142 | *Ruminococcus_faecis* |
| SEQ_71 | YK152 | *Blautia_hansenii* |
| SEQ_72 | YK155 | *Blautia_hansenii* |
| SEQ_73 | YK157 | *Eubacterium_rectale* |
| SEQ_74 | YK160 | *Roseburia_faecis* |
| SEQ_75 | YK166 | *Eubacterium_rectale* |
| SEQ_76 | YK168 | *Eubacterium_rectale* |
| SEQ_77 | YK169 | *Eubacterium_rectale* |
| SEQ_78 | YK171 | *Eubacterium_rectale* |
| SEQ_79 | YK192 | *Roseburia_faecis* |

TABLE F2

| Composition F, strain groupings | | |
|---|---|---|
| Cluster | Composition F | *SCFAs |
| XIVa | *Eubacterium rectale* 12 | A, B, L |
| | *Ruminococcus faecis* 8 | A, L |
| | *Ruminococcus obeum* 2 | A, L |
| | *Blautia faecis* 1 | A, L |
| | *Blautia hansenii* 2 | A, L |
| | *Blautia luti* 2 | A, L |
| | *Anaerostipes hadrus* 7 | B |
| | *Roseburia faecis* 5 | A, B |
| | *Fusicatenibacter saccharivorans* 3 | A, L |
| | *Dorea formicigenerans* 1 | A |
| | *Dorea longicatena* 2 | A |
| IV | *Flavomfractor_plautii* 2 | A, B |
| | *Ruminococcus champanellensis* 2 | A |
| IX | *Acidaminococcus fermentans* 1 | A, B, P |
| | *Megasphaera elsdeni* 4 | P |
| other | *Bacteroides cellulosilyticus* 1 | A, S |
| | *Bifiidobacterium Bifidum* | L, A |

*Short chain fatty acid legend:
A, acetate;
B, Butyrate;
L, lactate;
P, propionate;
S, succinate In one aspect, the disclosure provides Composition G (See e.g., FIG. 19; Table G). As shown in FIG. 19, Composition G contains bacteria that have the following 16S rDNA sequences: SEQ ID NO:27, SEQ ID NO:43, SEQ ID NO:44, SEQ ID NO:51, SEQ ID NO:55, SEQ ID NO:68, SEQ ID NO:72, SEQ ID NO:70, SEQ ID NO:24, SEQ ID NO:34, SEQ ID NO:37, SEQ ID NO:46, SEQ ID NO:76, SEQ ID NO:77, SEQ ID NO:35, SEQ ID NO:62, SEQ ID NO:26, SEQ ID NO:63, SEQ ID NO:67, SEQ ID NO:40, SEQ ID NO:38, SEQ ID NO:47, SEQ ID NO:56, SEQ ID NO:25, and SEQ ID NO: 32.

In some embodiments, the disclosure provides compositions with two or more purified bacterial strains that have 16S rDNA sequences selected from the group consisting of SEQ ID NO:27, SEQ ID NO:43, SEQ ID NO:44, SEQ ID NO:51, SEQ ID NO:55, SEQ ID NO:68, SEQ ID NO:72, SEQ ID NO:70, SEQ ID NO:24, SEQ ID NO:34, SEQ ID NO:37, SEQ ID NO:46, SEQ ID NO:76, SEQ ID NO:77, SEQ ID NO:35, SEQ ID NO:62, SEQ ID NO:26, SEQ ID NO:63, SEQ ID NO:67, SEQ ID NO:40, SEQ ID NO:38, SEQ ID NO:47, SEQ ID NO:56, SEQ ID NO:25, and SEQ ID NO: 32.

In some embodiments, the compositions include two or more purified bacterial strains comprising 16S rDNA sequences having at least 97% homology with nucleic acid sequences selected from the group consisting of SEQ ID NO:27, SEQ ID NO:43, SEQ ID NO:44, SEQ ID NO:51, SEQ ID NO:55, SEQ ID NO:68, SEQ ID NO:72, SEQ ID NO:70, SEQ ID NO:24, SEQ ID NO:34, SEQ ID NO:37, SEQ ID NO:46, SEQ ID NO:76, SEQ ID NO:77, SEQ ID NO:35, SEQ ID NO:62, SEQ ID NO:26, SEQ ID NO:63, SEQ ID NO:67, SEQ ID NO:40, SEQ ID NO:38, SEQ ID NO:47, SEQ ID NO:56, SEQ ID NO:25, and SEQ ID NO: 32.

The bacterial strains in Composition G are related to the following bacteria: *Acidaminococcus fermentans, Acidaminococcus intestine, Anaerostipes hadrus, Blautia faecis, Blautia hansenii, Dorea formicigenerans, Dorea longicatena, Eubacterium rectale, Flavonifractor plautii, Fusicatenibacter saccharivorans, Megasphaera elsdenii, Rose-*

*buria faecis, Ruminococcus champanellensis, Ruminococcus albus, Ruminococcus faecis*, and *Ruminococcus obeum.*

In some embodiments, the disclosure provides compositions with two or more bacterial strains of species selected from the group consisting of *Acidaminococcus fermentans, Acidaminococcus intestine, Anaerostipes hadrus, Blautia faecis, Blautia hansenii, Dorea formicigenerans, Dorea longicatena, Eubacterium rectale, Flavonifractor plautii, Fusicatenibacter saccharivorans, Megasphaera elsdenii, Roseburia faecis, Ruminococcus champanellensis, Ruminococcus albus, Ruminococcus faecis*, and *Ruminococcus obeum.*

In some embodiments, the disclosure provides compositions that include two or more purified bacterial strains comprise 16S rDNA sequences having at least 97% homology with nucleic acid sequences selected from the group consisting of SEQ ID NO:84, SEQ ID NO:85, SEQ ID NO:92, SEQ ID NO:93, SEQ ID NO:96, SEQ ID NO:97, SEQ ID NO:99, SEQ ID NO:104, SEQ ID NO:107, SEQ ID NO:111, SEQ ID NO:112, SEQ ID NO:113, SEQ ID NO:114, SEQ ID NO:115, SEQ ID NO:116, SEQ ID NO:117, and SEQ ID NO:119.

TABLE G

| Composition G | | |
|---|---|---|
| SEQ_27 | YK149 | *Acidaminococcus_fermentans/ Acidaminococcus_intesti* |
| SEQ_43 | YK90 | *Anaerostipes_hadrus* |
| SEQ_44 | YK30 | *Anaerostipes_hadrus* |
| SEQ_51 | YK34 | *Anaerostipes_hadrus* |
| SEQ_55 | YK54 | *Anaerostipes_hadrus* |
| SEQ_68 | YK98 | *Blautia_faecis* |
| SEQ_72 | YK152 | *Blautia_hansenii* |
| SEQ_70 | YK141 | *Dorea_formicigenerans* |
| SEQ_24 | YK96 | *Dorea_longicatena* |
| SEQ_34 | YK87 | *Eubacterium_rectale* |
| SEQ_37 | YK163 | *Eubacterium_rectale* |
| SEQ_46 | YK12 | *Eubacterium_rectale* |
| SEQ_76 | YK166 | *Eubacterium_rectale* |
| SEQ_77 | YK168 | *Eubacterium_rectale* |
| SEQ_35 | YK105 | *Flavonifractor_plautii* |
| SEQ_62 | YK70 | *Fusicatenibacter_saccharivorans* |
| SEQ_26 | YK110 | *Megasphaera_elsdenii* |
| SEQ_63 | YK71 | *Roseburia_faecis* |
| SEQ_67 | YK97 | *Roseburia_faecis* |
| SEQ_40 | YK99 | *Ruminococcus_champanellensis* |
| SEQ_38 | YK191 | *Ruminococcus_champanellensis/ Ruminococcus_albus* |
| SEQ_47 | YK27 | *Ruminococcus_faecis* |
| SEQ_56 | YK56 | *Ruminococcus_faecis* |
| SEQ_25 | YK101 | *Ruminococcus_obeum* |
| SEQ_32 | YK64 | *Ruminococcus_obeum* |

In one aspect, the disclosure provides Composition H (See e.g., FIG. 26, Table H). As shown in FIG. 26, Composition H contains bacteria that have the following 16S rDNA sequences: SEQ ID NO:14, SEQ ID NO:16, SEQ ID NO:21, SEQ ID NO:82, SEQ ID NO:81, and SEQ ID NO:80. In some embodiments, the disclosure provides compositions with two or more purified bacterial strains that have 16S rDNA sequences selected from the group consisting of SEQ ID NO:14, SEQ ID NO:16, SEQ ID NO:21, SEQ ID NO:82, SEQ ID NO:81, and SEQ ID NO:80.

In some embodiments, the compositions include two or more purified bacterial strains comprising 16S rDNA sequences having at least 97% homology with nucleic acid sequences selected from the group consisting of SEQ ID NO:14, SEQ ID NO:16, SEQ ID NO:21, SEQ ID NO:82, SEQ ID NO:81, and SEQ ID NO:80. In some embodiments, the compositions include four or more purified bacterial strains comprising 16S rDNA sequences having at least 97% homology with nucleic acid sequences selected from the group consisting of SEQ ID NO:14, SEQ ID NO:16, SEQ ID NO:21, SEQ ID NO:82, SEQ ID NO:81, and SEQ ID NO:80.

The bacterial strains in Composition H are related to the following bacteria: *Anaerotruncus colihominis, Clostridium symbiosum, Clostridium innocuum, Erysipelotrichaceae_bacterium_*21-3, *Clostridium disporicum, Clostridium bolteae*, and *Erysipelatoclostridium ramosum*. In some embodiments, the disclosure provides compositions with two or more bacterial strains selected from the group consisting of *Anaerotruncus colihominis, Clostridium symbiosum, Clostridium innocuum, Erysipelotrichaceae_bacterium_*21-3, *Clostridium disporicum, Clostridium bolteae*, and *Erysipelatoclostridium ramosum.*

In some embodiments, the disclosure provides compositions that include two or more purified bacterial strains comprise 16S rDNA sequences having at least 97% homology with nucleic acid sequences selected from the group consisting of SEQ ID NO:86, SEQ ID NO:95, SEQ ID NO:98, SEQ ID NO:110, SEQ ID NO:122, and SEQ ID NO:123.

Composition H includes bacteria from *Clostridium* cluster I, IV, XIVa, XVII and XVIII. In some embodiments, the disclosure provides compositions that include two or more purified bacterial strains from *Clostridium* cluster I, IV, XIVa, XVII and XVIII. In some embodiments, at least one of the bacterial strains of the composition belongs to *Clostridium* cluster IV. In some embodiments, at least one of the bacterial strains of the composition belongs to *Clostridium* cluster XIVa. In some embodiments, at least one of the bacterial strains of the composition belongs to *Clostridium* cluster XVII. In some embodiments, at least one of the bacterial strains of the composition belongs to *Clostridium* cluster I. In some embodiments, at least one of the bacterial strains of the composition belongs to *Clostridium* cluster XVIII. In some embodiments, at least one of the bacterial strains of the composition belongs to *Clostridium* cluster XIVa and at least one of the bacterial strains belongs to *Clostridium* cluster IV. In some embodiments, at least one of the bacterial strains of the composition belongs to *Clostridium* cluster XIVa and at least one of the bacterial strains belongs to *Clostridium* cluster XVII.

TABLE H

| Composition H | | | |
|---|---|---|---|
| SEQ ID NO | Strain | Closest species | Cluster |
| SEQ ID NO: 14 | VE202-13 | *Anaerotruncus colihominis* | Cluster IV |
| SEQ ID NO: 16 | VE202-16 | *Clostridium symbiosum* WAL-14163 | Cluster XIVa |
| SEQ ID NO: 21 | 189 | *Clostridium innocuum* | Cluster XVII |
| SEQ ID NO: 82 | PE9 | *Clostridium disporicum* | Cluster I |
| SEQ ID NO: 81 | PE5 | *Clostridium bolteae* | Cluster XIVa |
| SEQ ID NO: 80 | VE202-18 | *Erysipelatoclostridium ramosum* | Cluster XVIII |

In some embodiments, the disclosure provides compositions comprising two or more bacteria, wherein the composition does not include bacteria from *Clostridium* cluster I. In some embodiments, the disclosure provides compositions comprising two or more bacteria, wherein the composition does not include bacteria from *Clostridium* cluster XVIII. In some embodiments, the disclosure provides compositions comprising two or more bacteria, wherein the composition does not include bacteria from *Clostridium* cluster I and does not include bacteria from *Clostridium* cluster XVIII.

In some embodiments, the disclosure provides compositions comprising two or more bacteria, wherein all the bacteria are anaerobic bacteria. In some embodiments, the disclosure provides compositions comprising two or more bacteria, wherein all the bacteria are obligate anaerobic bacteria.

In some embodiments, the disclosure provides compositions comprising two or more bacteria (e.g., purified bacterial strains), wherein the composition does not include *Clostridium scindens*. In some embodiments, the disclosure provides compositions comprising two or more bacteria, wherein the composition does not include *Flavonifractor plautii*. In some embodiments, the disclosure provides compositions comprising two or more bacteria, wherein the composition does not include *Parabacteroides*. In some embodiments, the disclosure provides compositions comprising two or more bacteria, wherein the composition does not include *Lactobacillus*. In some embodiments, the disclosure provides compositions comprising two or more bacteria, wherein the composition does not include *Colinsella*. In some embodiments, the disclosure provides compositions comprising two or more bacteria, wherein the composition does not include *Dialister*. In some embodiments, the disclosure provides compositions comprising two or more bacteria, wherein the composition does not include *Raoultella*. In some embodiments, the disclosure provides compositions comprising two or more bacteria, wherein the composition does not include *Streptococcus*. In some embodiments, the disclosure provides compositions comprising two or more bacteria, wherein the composition does not include *Staphylococcus*. In some embodiments, the disclosure provides compositions comprising two or more bacteria, wherein the composition does not include *Microbacterium*. In some embodiments, the disclosure provides compositions comprising two or more bacteria, wherein the composition does not include *Proteobacteria*. In some embodiments, the disclosure provides compositions comprising two or more bacteria, wherein the composition does not include *Peptostreptococcaceae*. In some embodiments, the disclosure provides compositions comprising two or more bacteria, wherein the composition does not include *Oscillospiraceae*.

In one aspect, the disclosure provides bacterial strains with 16S rDNA sequences that have homology to a nucleic acid sequence of any one of the sequences of the bacterial strains or species described herein. In some embodiments, the bacterial strain has at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8% or 99.9% homology relative to any of the strains or bacterial species described herein over a specified region or over the entire sequence. It would be appreciated by one of skill in the art that the term "homology" or "percent homology," in the context of two or more nucleic acid sequences or amino acid sequences, refers to a measure of similarity between two or more sequences or portion(s) thereof. The homology may exist over a region of a sequence that is at least about 50 nucleotides in length, or more preferably over a region that is 100 to 500 or 1000 or more nucleotides in length. In some embodiments, the homology exists over the length the 16S rRNA or 16S rDNA sequence, or a portion thereof.

Additionally, or alternatively, two or more sequences may be assessed for the identity between the sequences. The terms "identical" or percent "identity" in the context of two or more nucleic acids or amino acid sequences, refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides in length, or more preferably over a region that is 100 to 500 or 1000 or more nucleotides in length. In some embodiments, the identity exists over the length the 16S rRNA or 16S rDNA sequence.

Additionally, or alternatively, two or more sequences may be assessed for the alignment between the sequences. The terms "alignment" or percent "alignment" in the context of two or more nucleic acids or amino acid sequences, refer to two or more sequences or subsequences that are the same. Two sequences are "substantially aligned" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the following sequence comparison algorithms or by manual alignment and visual inspection. Optionally, the alignment exists over a region that is at least about 50 nucleotides in length, or more preferably over a region that is 100 to 500 or 1000 or more nucleotides in length. In some embodiments, the identity exists over the length the 16S rRNA or 16S rDNA sequence.

For sequence comparison, typically one sequence acts as a reference sequence, to which test sequences are compared. Methods of alignment of sequences for comparison are well known in the art. See, e.g., by the local homology algorithm of Smith and Waterman (1970) *Adv. Appl. Math.* 2:482c, by the homology alignment algorithm of Needleman and Wunsch, *J. Mol. Biol.* (1970) 48:443, by the search for similarity method of Pearson and Lipman. *Proc. Natl. Acad. Sci. USA* (1998) 85:2444, by computerized implementations of these algorithms (GAP, BESTFIT, FASTA, and TFASTA in the Wisconsin Genetics Software Package, Genetics Computer Group. Madison. Wis.), or by manual alignment and visual inspection (see. e.g., Brent et al., Current Protocols in Molecular Biology, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., *Nuc. Acids Res.* (1977) 25:3389-3402, and Altschul et al., *J. Mol. Biol.* (1990) 215:403-410, respectively.

In one aspect, the disclosure provides compositions comprising multiple purified bacterial strains (e.g., Compositions A-J). For instance, FIGS. 1, 13, 19, and 26 present several example compositions comprising multiple bacterial strains. In one aspect, the 16S rDNA sequences of purified bacterial strains of the compositions were compared to 16S rDNA sequences of known bacterial species/strains in a bacterial genome database to identify the closest known related bacterial species to the bacterial strains disclosed herein (See e.g., Table 1). It should be appreciated that multiple bacterial strains of the compositions disclosed herein may have the same closest related bacterial species. In one aspect, the disclosure provides compositions comprising one or more bacterial strains or species with 16S rDNA sequences that have homology to a nucleic acid sequence of any one of the sequences provided by SEQ ID NOs:1-83 and 124-159. In some embodiments, the species with 16S rDNA sequences with homology to a nucleic acid sequence of any one of the closest related species to any of the strains described herein, correspond to bacterial strains with 16S rDNA sequences provided by SEQ ID NOs:84-123.

In some embodiments, the compositions disclosed herein provide at least one of the bacterial strains (e.g., purified bacterial strains) described herein. In some embodiments, the compositions that comprise at least one bacterial strain, comprise at least one bacterial strain with a 16S rDNA sequence selected from any one of SEQ ID NOs:1-122 and 124-159. In some embodiments, the compositions that comprise at least one bacterial strain, comprise at least one bacterial strain with a 97% homology to 16S rDNA sequence selected from any one of SEQ ID NOs:1-122 and 124-159.

In some embodiments, the compositions disclosed herein comprise two or more bacterial strains. In some embodiments, the compositions described herein comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 or more bacterial strains (e.g., purified bacterial strains).

It should be appreciated the compositions and methods provided herein can be distinguished from compositions and methods associated with the treatment of *C. difficile* infection that are available. For instance, it has been proposed that non-toxigenic *C. difficile* strains, i.e., strains that do not produce *C. difficile* toxins, may be used to treat *C. difficile* infection (See, e.g., U.S. Pat. No. 6,635,260). The compositions disclosed herein can be distinguished at least because the compositions described herein do not comprise non-toxigenic strains of *C. difficile*. Thus, in some embodiments, the compositions herein do not include comprise non-toxigenic strains of *C. difficile*. *C. difficile* belongs to *Clostridium* cluster XI. In some embodiments, the compositions herein do not include bacterial strains belonging to *Clostridium* cluster XI.

It is also considered in the art that bacterial strains expressing a bile inducible 7α/β-dehydroxylation operon can be used in the treatment of *C. difficile* (see, e.g., Buffie et al. *Nature* (2015) 517:205-208). The catalysis of bile acid 7a dihydroxylation is mediated by a stereo-specific NAD (H)-dependent 3-oxo-$\Delta^4$-cholenoic acid oxidoreductase encoded by the gene baiCD. In some embodiments, the compositions provided herein do not mediate bile acid 7-alpha-dehydroxylation.

In contrast to the findings in the art, in some embodiments, as shown herein, combinations of bacterial strains that do not encode baiCD (or a homolog thereof), or encode a baiCD that comprises one or more mutations that result in a non-functional BaiCD protein ("baiCD−"), are more effective at treating *C. difficile* infection and/or reducing or inhibiting production of Toxin B by *C. difficile* than combinations of bacterial strains that have a functional BaiCD protein ("baiCD+"). Thus, in some embodiments, the compositions of bacterial strains provided herein are baiCD− (i.e., the combination of the bacteria has no effective baiCD+ function). In some embodiments, all of bacterial strains in the compositions provided herein are baiCD−. In some embodiments, the majority (i.e., 50% or greater) of the bacterial strains in the compositions are baiCD−. In some embodiments, the majority (i.e., 50% or greater) of the bacterial strains in the compositions are baiCD- and the composition has no effective BaiCD function. In some embodiments, the minority (i.e., 50% or less) of the bacterial strains in the compositions are baiCD- and the composition has no effective BaiCD function. In some embodiments, bacterial strains for the compositions are selected based on the absence (or presence) of a baiCD gene or a predicted baiCD gene. In some embodiments, bacterial strains may be modified (e.g., genetically engineered) to prevent or reduce expression of a baiCD gene and/or to reduce or eliminate NAD(H)-dependent 3-oxo-$\Delta^4$-cholenoic acid oxidoreductase activity of BaiCD protein. The NAD(H)-dependent 3-oxo-$\Delta^4$-cholenoic acid oxidoreductase activity of a bacterial strain may be assessed by methods such as measuring the amount of 7α-dehydroxylated bile acid. In some embodiments, the compositions described herein comprise bacterial strains without the baiCD operon (baiCD$^-$) or baiCD function.

In some embodiments, the compositions described herein do not include *Clostridium scindens*. In some embodiments, the compositions described herein do not include *Barnesiella intestihominis*. In some embodiments, the compositions described herein do not include *Blautia hansenii*. In some embodiments, the compositions described herein do not include *Pseudoflavinofractor capillosus*. In some embodiments, the compositions described herein do not include *Clostridium scindens. Barnesiella intestihominis, Blautia hansenii* or *Pseudoflavinofractor capillosus*.

In some embodiments, the compositions provided herein do not include *Colinsella aerofaciens*. In some embodiments, the compositions provided herein do not include *Acetovibrio ethanolgignens*. In some embodiments, the compositions provided herein do not bacterial strains belonging to *Clostridum* cluster I. In some embodiments, the compositions provided herein do not include *Clostridium butyricum*. In some embodiments, the compositions provided herein do not include *Clostridium disporicum*. In some embodiments, the compositions provided herein do not include strains belonging to *Clostridum* cluster XI. In some embodiments, the compositions provided herein do not include *Clostridium* glycolicum. In some embodiments, the compositions provided herein do not include *Faecalibacterium prausnitzii*. In some embodiments, the compositions provided herein do not include *Turicibacter sanguinis*. In some embodiments, the compositions provided herein do not include *Eubacterium rectale*. In some embodiments, the compositions provided herein do not include *Eubacterium ventriosum*. In some embodiments, the compositions provided herein do not include *Ruminococcus obeum*. In some embodiments, the compositions provided herein do not include *Pseudobutyrivibrio*. In some embodiments, the compositions provided herein do not include *Christensenellaceae*. In some embodiments, the compositions do not comprise gram-negative bacteria. In some embodiments, the compositions do not comprise *E. coli*. In some embodiments, the compositions do not comprise fungi, such as *Monilla* species.

In some embodiments of the compositions provided herein, the compositions do not include bacterial strains that are resistant to one or more antibiotics. It should be appreciated that it may be desirable to have a mechanism to remove the bacterial compositions provided herein from the body of the subject after administration. One such mechanism is to remove the bacterial compositions by antibiotic treatment. Thus, in some embodiments, the compositions do not include bacterial strains that are resistant to one or more antibiotics. In some embodiments, the compositions do not include bacterial strains that are resistant to one or more antibiotics selected from the group consisting of penicillin, benzylpenicillin, ampicillin, sulbactam, amoxicillin, clavulanate, tazobactam, piperacillin, cefmetazole, *vancomycin, imipenem, meropenem, metronidazole* and *clindamycin*. In some embodiments, the compositions do not include bacterial strains that are resistant to vancomycin.

In some embodiments, the compositions include bacterial strains that are susceptible to at least four antibiotics that are efficacious in humans. In some embodiments, the compositions include bacterial strains that are susceptible to at least three antibiotics that are efficacious in humans. In some embodiments, the compositions include bacterial strains that are susceptible to at least two antibiotics that are efficacious in humans. In some embodiments, the compositions include bacterial strains that are susceptible to at least one antibiotic that is efficacious in humans. In some embodiments, the compositions include only bacterial strains that are susceptible to at least four antibiotics that are efficacious in humans. In some embodiments, the compositions include only bacterial strains that are susceptible to at least three antibiotics that are efficacious in humans. In some embodiments, the compositions include only bacterial strains that are susceptible to at least two antibiotics that are efficacious in humans. In some embodiments, the compositions include bacterial strains that are susceptible to at least one antibiotic that is efficacious in humans. As used herein, an "antibiotic that is efficacious in a human" refers to an antibiotic that has been used to successfully treat bacterial infections in a human.

In some embodiments, the compositions described herein comprise spore forming and non-spore forming bacterial strains. In some embodiments, the compositions described herein comprise spore forming bacterial strains. In some embodiments, the compositions described herein comprise only spore forming bacterial strains. In some embodiments, the compositions described herein comprise only non-spore forming bacterial strains. The spore-forming bacteria can be in spore form (i.e., as spores) or in vegetative form (i.e., as vegetative cells). In spore form, bacteria are generally more resistant to environmental conditions, such as heat, acid, radiation, oxygen, chemicals, and antibiotics. In contrast, in the vegetative state or actively growing state, bacteria are more susceptible to such environmental conditions, compared to in the spore form. In general, bacterial spores are able to germinate from the spore form into a vegetative/actively growing state, under appropriate conditions. For instance, bacteria in spore format may germinate when they are introduced in the intestine.

In some embodiments, at least one (e.g., 1, 2, 3, 4, 5, or more) of the bacterial strains in the composition is a spore former. In some embodiments, at least one (e.g., 1, 2, 3, 4, 5, or more) of the bacterial strains in the composition is in spore form. In some embodiments, at least one (e.g., 1, 2, 3, 4, 5, or more) of the bacterial strains in the composition is a non-spore former. In some embodiments, at least one (e.g., 1, 2, 3, 4, 5, or more) of the bacterial strains in the composition is in vegetative form (As discussed above, spore forming bacteria can also be in vegetative form). In some embodiments, at least one (e.g., 1, 2, 3, 4, 5, or more) of the bacterial strains in the composition is in spore form and at least one (e.g., 1, 2, 3, 4, 5, or more) of the bacterial strains in the composition is in vegetative form. In some embodiments, at least one bacterial strain that is considered able to form spores (i.e., a spore-former) but is present in the composition in vegetative form. In some embodiments, at least one bacterial strain that is considered able to form spores is present in the composition both in spore form and in vegetative form.

In some embodiments, the disclosure provides compositions wherein the compositions comprise bacterial strains that are spore forming bacterial strains. In some embodiments, the disclosure provides compositions wherein the compositions comprise bacterial strains that are non-spore forming bacterial strains. In some embodiments, the disclosure provides compositions wherein the compositions comprise bacterial strains that are spore forming bacterial strains and bacterial strains that are non-spore forming bacterial strains. In some embodiments, the disclosure provides compositions, wherein the compositions comprise a mixture of bacterial strains wherein at least 10% of the bacterial strains are spore forming bacterial strains, at least 20% of the bacterial strains are spore forming bacterial strains, at least 30% of the bacterial strains are spore forming bacterial strains, at least 40% of the bacterial strains are spore forming bacterial strains, at least 50% of the bacterial strains are spore forming bacterial strains, at least 60% of the bacterial strains are spore forming bacterial strains, at least 70% of the bacterial strains are spore forming bacterial strains, at least 80% of the bacterial strains are spore forming bacterial strains, at least 90% of the bacterial strains are spore forming bacterial strains bacteria up to 100% spore forming bacterial strains. Whether a bacterial strain is a spore forming strain can be determined for instance by evaluating the genome of the bacterial strain for the presence of sporulation genes. However, it should be appreciated that not all bacteria that are predicted to encode spore forming genes can be made to sporulate. In addition, whether a bacterial strain is a spore forming strain can be determined by exposing the bacterial strain to stress conditions, e.g., heat or exposure to chemicals (e.g., ethanol or chloroform), that are known to induce sporulation.

It should be appreciated that spore forming bacteria can be in spore form or in vegetative form. In some embodiments of the compositions provided herein, the spore forming bacteria are in spore form. In some embodiments of the compositions provided herein, the spore forming bacteria are in vegetative form. In some embodiments of the compositions provided herein, the spore forming bacteria are both present in spore form and in vegetative form. In some embodiments, the disclosure provides compositions, wherein the compositions comprise spore forming bacteria at least 10% of the spore forming bacteria are in spore format, at least 20% of the spore forming bacteria are in spore format, at least 30% of the spore forming bacteria are in spore format, at least 40% of the spore forming bacteria are in spore format, at least 50% of the spore forming bacteria are in spore format, at least 60% of the spore forming bacteria are in spore format, at least 70% of the spore forming bacteria are in spore format, at least 80% of the spore forming bacteria are in spore format, at least 90% of the spore forming bacteria are in spore format, up to 100% in spore format.

It is envisioned that the bacterial strains of the compositions provided herein are alive and will be alive when they reach the target area (e.g., the intestines). Bacterial spores are considered to be alive in this regards. In some embodiments, bacteria that are administered as spores may germinate in the target area (e.g., the intestines). It should further be appreciated that not all of the bacteria are alive and the compositions can include a percentage (e.g., by weight) that is not alive. In addition, in some embodiments, the compositions include bacterial strains that are not alive when administered or at the time when the composition reaches the target area (e.g., the intestines). It is envisioned that non-living bacteria may still be useful by providing some nutrients and metabolites for the other bacterial strains in the composition.

Methods of inducing sporulation of spore-forming bacterial strains are well known in the art (See e.g., Paredes-Sabja et al., *Trends Microbial*. (2011) 19(2):85-94). Generally, bacterial strains that are spore-formers can be made to go into spore form by stressing the bacterial strains. Non-limiting examples of stresses that can induce sporulation are an increase in temperature, change in the nutrients available and/or exposure to chemicals (e.g., ethanol or chloroform). It should be noted that bacteria that are non-spore formers, for instance because they are missing sporulation genes, cannot be made to sporulate by stress. To prepare compositions in which all the bacterial strains are in the spore form, the composition or bacterial cultures used to prepare the composition may be subjected to treatment to kill any bacteria not in spore form (e.g., in vegetative form), for example by exposing the composition to heat and are chemically breaking down the non-spore bacteria. The bacteria in spore format can subsequently be separated from the non-spore bacteria for instance by filtration.

The amount of spores can be quantified using techniques know in the art. These techniques include phase contrast microscopy for enumerating spores using a hemocytometer. In addition, the viability of spores can be determined by plating the spores and growing the spores. For instance, spores can be plated in appropriate media and incubated in the anaerobic chamber for a period of time (e.g., 48-96 hrs.). Viability can subsequently be determined by quantifying the colony forming units which correspond to spores that germinated. For instance, spores can be plated on TCCFA plates (Taurocholate, cycloserine, cefoxintin, fructose agar plates), in which taurocholate helps the spores to germinate. In addition, spores can be quantified using the dipicolinic assay (DPA assay). DPA is an agent that allows for spore selection and is a clear indicator of endospores. When complexed with terbium, bright green luminescence is observed.

In any of the compositions provided herein, in some embodiments, the bacterial strains are purified. In any of the compositions provided herein, in some embodiments, the bacterial strains are isolated. Any of the bacterial strains described herein may be isolated and/or purified, for example, from a source such as a culture or a microbiota sample (e.g., fecal matter). The bacterial strains used in the compositions provided herein generally are isolated from the microbiome of healthy individuals. However, bacterial strains can also be isolated from individuals that are considered not to be healthy. In some embodiments, the compositions include strains originating from multiple individuals.

As used herein, the term "isolated" bacteria that have been separated from one or more undesired component, such as another bacterium or bacterial strain, one or more component of a growth medium, and/or one or more component of a sample, such as a fecal sample. In some embodiments, the bacteria are substantially isolated from a source such that other components of the source are not detected.

As also used herein, the term "purified" refers to a bacterial strain or composition comprising such that has been separated from one or more components, such as contaminants. In some embodiments, the bacterial strain is substantially free of contaminants. In some embodiments, one or more bacterial strains of a composition may be independently purified from one or more other bacteria produced and/or present in a culture or a sample containing the bacterial strain. In some embodiments, a bacterial strain is isolated or purified from a sample and then cultured under the appropriate conditions for bacterial replication, e.g., under anaerobic culture conditions. The bacteria that is grown under appropriate conditions for bacterial replication can subsequently be isolated/purified from the culture in which it is grown.

In some embodiments, the bacterial strains of the compositions provided herein are obligate anaerobes. In some embodiments, the bacterial strains of the compositions provided herein are facultative anaerobes.

Aspects of the present disclosure are related to methods for treating a pathogenic infection in a subject by administering a therapeutically effective amount of any of the compositions described herein. In some embodiments, the subject is a mammalian subject, such as a human, non-human primate, rodent, rabbit, sheep, pig, dog, cat, horse, or cow. In some embodiments, the subject is a human subject. In some embodiments, the subject is a pig.

In some embodiments, the subject is a carrier of a pathogenic organism and is suffering from the effects of the infection (e.g., diarrhea caused by *C. difficile* toxins). In some embodiments the subject is an asymptomatic carrier of a pathogen. In some embodiments, the subject is a carrier of *C. difficile*. In some embodiments the subject is an asymptomatic *C. difficile* carrier. In some embodiments, the subject has experienced recurrent or chronic pathogenic infections. In some embodiments, the subject is suffering from a first occurrence of a particular pathogenic infection. In some embodiments, the subject has been treated with antibiotics which resulted in the recurrence of the pathogenic infection. In some embodiments, the subject has been treated with antibiotics which resulted in a first occurrence of a pathogenic infection. In some embodiments, the subject is to undergo a procedure that puts the subject at a higher risk of infection. In some embodiments, the compositions provided herein are administered to a subject to lower the risk of becoming infected by a pathogen.

In some embodiments, the compositions provided herein are administered to a subject if the subject has a dysbiosis (e.g., has as microbiome associated with a disease state). In some embodiments, treatment with the compositions provided herein results in the change in the microbiome of the subject. In some embodiments, treatment with the compositions provided herein removes the dysbiosis in the subject resulting in a healthy microbiome. In some embodiments, treatment with the compositions provided herein removes the dysbiosis in the subject resulting in microbiome refractory or less susceptible to infection by a pathogen.

As used herein, the term "pathogen" in regard to a pathogenic infection refers to a microorganism (e.g., a bacterium) that causes a disease or a disease state in a subject. In some embodiments, the disease or disease state of the subject may include symptoms such as colitis, diarrhea, watery diarrhea, abdominal cramping, fever, blood or pus in the stool, nausea, dehydration, loss of appetite, chills, weight loss, and/or kidney failure. In some embodiments, the pathogenic infection may be diagnosed, for example, by detecting a pathogen (or protein or nucleic acid associated with a pathogen) in a fecal sample collected from the subject. In some embodiments, the pathogenic infection may be diagnosed, for example, by comparing the microbiota of a fecal sample of the subject with the microbiota in a fecal sample of a healthy subject.

In some embodiments, the pathogenic infection is *C. difficile; Clostridium perfringens; Clostridium botulinum;*

*Clostridium tributrycum; Clostridium sporogenes; Escherichia coli; Pseudomonas aeruginosa*, such as Multidrug Resistant *Pseudomonas aeruginosa; Vancomycin Resistant Enterococci* (VRE); Carbapenem Resistant *Enterobacteriaceae* (CRE); *Neisseria gonorrheae; Acinetobacter*; Multidrug Resistant *Acinetobacter; Campylobacter*; Multi-drug resistant *Campylobacter; Candida*; Fluconazole-resistant *Candida*; Extended spectrum beta-lactamese (ESBL) producing *Enterobacteriaceae; Salmonella, Salmonella Typhimurium*, Drug resistant non-typhoid *Salmonella* spp.; Drug resistant *Salmonella Typhi*; Drug resistant *Shigella; Staphylococcus aureus*, such as *Methicillin* Resistant *S. aureus* or *vancomycin* resistant *S. aureus*; Drug resistant *Streptococcus pneumoniae*; Drug resistant Tuberculosis; Erythromycin Resistant Group A *Streptococcus*; Clindamycin resistant Group B *Streptococcus*, and any combinations thereof. In some embodiments, the pathogenic infection is *C. difficile*. In some embodiments, the *C. difficile* is an antibiotic-resistant *C. difficile*, e.g., fluoroquinolone resistant *C. difficile*. In some embodiments, the pathogenic infection is *vancomycin*-resistant *Enterococci*.

Additional non-limiting examples of pathogens responsible for pathogenic infection that can be treated according to the methods provided herein are *Leishmania, Staphylococcus epidermis, Staphylococcus saprophyticus, Streptococcus pyogenes, Streptococcus pneumoniae, Streptococcus agalactiae, Enterococcus faecalis, Corynebacterium diptheriae, Bacillus anthracis, Listeria monocytogenes, Clostridium perfringens, Clostridium tetanus, Clostridium botulinum, Clostridium difficile, Neisseria meningitidis, Neisseria gonorrhoeae, Escherichia coli, Salmonella typhimurium, Salmonella cholerasuis, Salmonella enterica, Salmonella enteriditis, Yersinia pestis, Yersinia pseudotuberculosis, Yersinia enterocolitica, Vibrio cholerae, Campylobacter jejuni, Campylobacter fetus, Helicobacter pylori, Pseudomonas aeruginosa, Pseudomonas mallei, Haemophilus influenzae, Bordetella pertussis, Mycoplasma pneumoniae, Ureaplasma urealyticum, Legionella pneumophila, Treponema pallidum, Leptospira interrogans, Borrelia burgdorferi, Mycobacterium tuberculosis, Mycobacterium leprae, Chlamydia psittaci, Chlamydia trachomatis, Chlamydia pneumoniae, Rickettsia ricketsii, Rickettsia akari, Rickettsia prowazekii, Brucella abortus, Brucella melitens, Brucella suis*, and *Francisella tularensis*. In general, any bacterium that is capable of inducing a disease in a subject and/or that is not present in healthy individual is considered a pathogen herein. It should be appreciated that a subject may carry multiple pathogens and/or have multiple pathogenic infections.

Any of the compositions described herein may be administered to a subject in a therapeutically effective amount or a dose of a therapeutically effective amount to treat or prevent a pathogenic infection (e.g., one or more pathogenic infections). The terms "treat" or "treatment" refer to reducing or alleviating one or more of the symptoms associated with a pathogenic infection, reducing the amount of bacterial toxin produced by the pathogenic infection, and/or reducing the bacterial load of the pathogenic infection. The terms "prevent" or "prevention" encompass prophylactic administration and may reduce the incidence or likelihood of pathogenic infection or a recurrent or chronic pathogenic infection. For instance, in some embodiments, administration of the compositions provided herein result in a healthy microbiome that is refractory to pathogenic infection, thereby preventing the pathogenic infection.

As used herein, a "therapeutically effective amount" of composition, such as a pharmaceutical composition, is any amount that results in a desired response or outcome in a subject, such as those described herein, including but not limited to prevention of infection, an immune response or an enhanced immune response to the pathogenic infection, prevention or reduction of symptoms associated with pathogenic infection, and/or a reduction or inhibition of toxin production by the pathogenic infection. It should be appreciated that the term effective amount may be expressed in number of bacteria or bacterial spores to be administered. It should further be appreciated that the bacteria can multiply once administered. Thus, administration of even a relatively small amount of bacteria may have therapeutic effects.

In some embodiments, the therapeutically effective amount of any of the compositions described herein is an amount sufficient to enhance survival of the subject, reduce the bacterial burden of the pathogenic infection in the subject, and/or reduce or inhibit toxin production by the pathogenic infection. In some embodiments, the therapeutically effective amount is an amount sufficient to reduce the bacterial burden of the pathogenic infection in a fecal sample from the subject by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the bacterial burden in a subject with a pathogenic infection that has not received any of the compositions described herein, or as compared to a fecal sample from the same subject that was collected prior to administration of any of the compositions.

In some embodiments, the compositions provided herein inhibit the production of a bacterial toxin, e.g., *C. difficile* Toxin B. In some embodiments, the therapeutically effective amount is an amount sufficient to reduce or inhibit the amount of bacterial toxin (e.g., *C. difficile* Toxin B) produced by pathogenic infection in a fecal sample from the subject by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 150-fold, 200-fold, 500-fold or more, as compared to the amount of the bacterial toxin in a subject with a pathogenic infection that has not received any of the compositions described herein or as compared to a fecal sample from the same subject that was collected prior to administration of any of the compositions.

In some embodiments, the compositions provided herein induce the proliferation and/or accumulation of regulatory T cells in the subject. As will be evident to one of ordinary skill in the art, regulatory T cells, also referred to as "Tregs," are a subset of T lymphocytes that are generally thought to suppress an abnormal or excessive immune response and play a role in immune tolerance. Regulatory T cells may be identified based expression of the markers Foxp3 and CD4 (Foxp3+ CD4+). The term regulatory T cells may also include Foxp3-negative regulatory T cells that are IL-10-producing CD4-positive T cells.

In some embodiments, the therapeutically effective amount is an amount sufficient to induce the proliferation and/or accumulation of Tregs in the subject (or in a sample obtained from a subject) by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 150-fold, 200-fold, 500-fold or more, as compared to the amount of Tregs in a subject (e.g., a subject with a pathogenic infection) that has not received any of the compositions described herein or as compared to a fecal sample from the same subject that was collected prior to administration of any of the compositions.

As used herein, the phrase "induces proliferation and/or accumulation of regulatory T cells" refers to an effect of inducing the differentiation of immature T cells into regulatory T cells, which differentiation leads to the proliferation and/or the accumulation of regulatory T cells. Further, the meaning of "induces proliferation and/or accumulation of regulatory T cells" includes in vivo effects, in vitro effects, and ex vivo effects. In some embodiments, the proliferation and/or accumulation of regulatory T cells may be assessed by detecting and/or quantifying the number of cells that express markers of regulatory T cells (e.g., Foxp3 and CD4), for example by flow cytometry. In some embodiments, the proliferation and/or accumulation of regulatory T cells may be assessed by determining the activity of the regulatory T cells, such as the production of cytokines (e.g., IL-10).

In some embodiments, the therapeutically effective amount is an amount sufficient to recolonize or repopulate the gastrointestinal tract of the subject with non-pathogenic bacteria. In some embodiments, the therapeutically effective amount is an amount sufficient to graft one or more of the bacterial strains of the composition in the gastrointestinal tract of the subject. In some embodiments, a fecal sample is obtained from the subject to assess the bacterial burden of the pathogenic infection and/or evaluate the efficacy of administration of the bacterial compositions described herein. In some embodiments, the microbiota of the subject (e.g., the identity and abundance of strains and/or species of the microbiota) may be assessed to determine a disease state of the subject and/or assess progress of the treatment. In some embodiments, the microbiota of the subject having a pathogenic infection is compared to the microbiota of a healthy subject, such as a subject that is not experiencing or has not experienced the pathogenic infection. In some embodiments, the microbiota of the subject having a pathogenic infection is compared to the microbiota of the same subject from a fecal sample obtained from the subject prior to the pathogenic infection.

Any of the compositions described herein, including the pharmaceutical compositions and food products comprising the compositions, may contain bacterial strains in any form, for example in an aqueous form, such as a solution or a suspension, embedded in a semi-solid form, in a powdered form or freeze dried form. In some embodiments, the composition or the bacterial strains of the composition are lyophilized. In some embodiments, a subset of the bacterial strains in a composition is lyophilized. Methods of lyophilizing compositions, specifically compositions comprising bacteria, are well known in the art. See, e.g., U.S. Pat. Nos. 3,261,761; 4,205,132; PCT Publications WO 2014/029578 and WO 2012/098358, herein incorporated by reference in their entirety. The bacteria may be lyophilized as a combination and/or the bacteria may be lyophilized separately and combined prior to administration. A bacterial strain may be combined with a pharmaceutical excipient prior to combining it with the other bacterial strain or multiple lyophilized bacteria may be combined while in lyophilized form and the mixture of bacteria, once combined may be subsequently be combined with a pharmaceutical excipient. In some embodiments, the bacterial strain is a lyophilized cake. In some embodiments, the compositions comprising the one or more bacterial strains are a lyophilized cake.

The bacterial strains of the composition can be manufactured using fermentation techniques well known in the art. In some embodiments, the active ingredients are manufactured using anaerobic fermenters, which can support the rapid growth of anaerobic bacterial species. The anaerobic fermenters may be, for example, stirred tank reactors or disposable wave bioreactors. Culture media such as BL media and EG media, or similar versions of these media devoid of animal components, can be used to support the growth of the bacterial species. The bacterial product can be purified and concentrated from the fermentation broth by traditional techniques, such as centrifugation and filtration, and can optionally be dried and lyophilized by techniques well known in the art.

In some embodiments, the composition of bacterial strains may be formulated for administration as a pharmaceutical composition. The term "pharmaceutical composition" as used herein means a product that results from the mixing or combining of at least one active ingredient, such as any two or more purified bacterial strains described herein, and one or more inactive ingredients, which may include one or more pharmaceutically acceptable excipient.

An "acceptable" excipient refers to an excipient that must be compatible with the active ingredient and not deleterious to the subject to which it is administered. In some embodiments, the pharmaceutically acceptable excipient is selected based on the intended route of administration of the composition, for example a composition for oral or nasal administration may comprise a different pharmaceutically acceptable excipient than a composition for rectal administration. Examples of excipients include sterile water, physiological saline, solvent, a base material, an emulsifier, a suspending agent, a surfactant, a stabilizer, a flavoring agent, an aromatic, an excipient, a vehicle, a preservative, a binder, a diluent, a tonicity adjusting agent, a soothing agent, a bulking agent, a disintegrating agent, a buffer agent, a coating agent, a lubricant, a colorant, a sweetener, a thickening agent, and a solubilizer.

Pharmaceutical compositions of the invention can be prepared in accordance with methods well known and routinely practiced in the art (see e.g., Remington: The Science and Practice of Pharmacy, Mack Publishing Co. 20th ed. 2000). The pharmaceutical compositions described herein may further comprise any carriers or stabilizers in the form of a lyophilized formulation or an aqueous solution. Acceptable excipients, carriers, or stabilizers may include, for example, buffers, antioxidants, preservatives, polymers, chelating reagents, and/or surfactants. Pharmaceutical compositions are preferably manufactured under GMP conditions. The pharmaceutical compositions can be used orally, nasally or parenterally, for instance, in the form of capsules, tablets, pills, sachets, liquids, powders, granules, fine granules, film-coated preparations, pellets, troches, sublingual preparations, chewables, buccal preparations, pastes, syrups, suspensions, elixirs, emulsions, liniments, ointments, plasters, cataplasms, transdermal absorption systems, lotions, inhalations, aerosols, injections, suppositories, and the like.

In some embodiments, the bacteria are formulated for delivery to the intestines (e.g., the small intestine and/or the colon). In some embodiments, the bacteria are formulated with an enteric coating that increases the survival of the bacteria through the harsh environment in the stomach. The enteric coating is one which resists the action of gastric juices in the stomach so that the bacteria which are incorporated therein will pass through the stomach and into the intestines. The enteric coating may readily dissolve when in contact with intestinal fluids, so that the bacteria enclosed in the coating will be released in the intestinal tract. Enteric coatings may consist of polymer and copolymers well known in the art, such as commercially available EUDRAGIT (Evonik Industries). (See e.g., Zhang, *AAPS PharmSciTech*, (2016) 17 (1), 56-67).

The bacteria may also be formulated for rectal delivery to the intestine (e.g., the colon). Thus, in some embodiments, the bacterial compositions may be formulated for delivery by suppository, colonoscopy, endoscopy, sigmoidoscopy or enema. A pharmaceutical preparation or formulation and particularly a pharmaceutical preparation for oral administration, may include an additional component that enables efficient delivery of the compositions of the disclosure to the intestine (e.g., the colon). A variety of pharmaceutical preparations that allow for the delivery of the compositions to the intestine (e.g., the colon) can be used. Examples thereof include pH sensitive compositions, more specifically, buffered sachet formulations or enteric polymers that release their contents when the pH becomes alkaline after the enteric polymers pass through the stomach. When a pH sensitive composition is used for formulating the pharmaceutical preparation, the pH sensitive composition is preferably a polymer whose pH threshold of the decomposition of the composition is between about 6.8 and about 7.5. Such a numeric value range is a range in which the pH shifts toward the alkaline side at a distal portion of the stomach, and hence is a suitable range for use in the delivery to the colon. It should further be appreciated that each part of the intestine (e.g., the duodenum, jejunum, ileum, cecum, colon and rectum), has different biochemical and chemical environment. For instance, parts of the intestines have different pHs, allowing for targeted delivery by compositions that have a specific pH sensitivity. Thus, the compositions provided herein may be formulated for delivery to the intestine or specific parts of the intestine (e.g., the duodenum, jejunum, ileum, cecum, colon and rectum) by providing formulations with the appropriate pH sensitivity. (See e.g., Villena et al., *Int J Pharm* 2015, 487 (1-2): 314-9).

Another embodiment of a pharmaceutical preparation useful for delivery of the compositions to the intestine (e.g., the colon) is one that ensures the delivery to the colon by delaying the release of the contents (e.g., the bacterial strains) by approximately 3 to 5 hours, which corresponds to the small intestinal transit time. In one embodiment of a pharmaceutical preparation for delayed release, a hydrogel is used as a shell. The hydrogel is hydrated and swells upon contact with gastrointestinal fluid, with the result that the contents are effectively released (released predominantly in the colon). Delayed release dosage units include drug-containing compositions having a material which coats or selectively coats a drug or active ingredient to be administered. Examples of such a selective coating material include in vivo degradable polymers, gradually hydrolyzable polymers, gradually water-soluble polymers, and/or enzyme degradable polymers. A wide variety of coating materials for efficiently delaying the release is available and includes, for example, cellulose-based polymers such as hydroxypropyl cellulose, acrylic acid polymers and copolymers such as methacrylic acid polymers and copolymers, and vinyl polymers and copolymers such as polyvinylpyrrolidone.

Additional examples of pharmaceutical compositions that allow for the delivery to the intestine (e.g., the colon) include bioadhesive compositions which specifically adhere to the colonic mucosal membrane (for example, a polymer described in the specification of U.S. Pat. No. 6,368,586) and compositions into which a protease inhibitor is incorporated for protecting particularly a biopharmaceutical preparation in the gastrointestinal tracts from decomposition due to an activity of a protease.

Another example of a system enabling the delivery to the intestine (e.g., the colon) is a system of delivering a composition to the colon by pressure change in such a way that the contents are released by utilizing pressure change caused by generation of gas in bacterial fermentation at a distal portion of the stomach. Such a system is not particularly limited, and a more specific example thereof is a capsule which has contents dispersed in a suppository base and which is coated with a hydrophobic polymer (for example, ethyl cellulose).

A further example of a system enabling the delivery of a composition to the intestine (e.g., the colon), is a composition that includes a coating that can be removed by an enzyme present in the gut (e.g., the colon), such as, for example, a carbohydrate hydrolase or a carbohydrate reductase. Such a system is not particularly limited, and more specific examples thereof include systems which use food components such as non-starch polysaccharides, amylose, xanthan gum, and azopolymers.

The compositions provided herein can also be delivered to specific target areas, such as the intestine, by delivery through an orifice (e.g., a nasal tube) or through surgery. In addition, the compositions provided herein that are formulated for delivery to a specific area (e.g., the cecum or the colon), may be administered by a tube (e.g., directly into the small intestine). Combining mechanical delivery methods such as tubes with chemical delivery methods such as pH specific coatings, allow for the delivery of the compositions provided herein to a desired target area (e.g., the cecum or the colon).

The compositions comprising bacterial strains are formulated into pharmaceutically acceptable dosage forms by conventional methods known to those of skill in the art. Dosage regimens are adjusted to provide the optimum desired response (e.g., the prophylactic or therapeutic effect). In some embodiments, the dosage form of the composition is a tablet, pill, capsule, powder, granules, solution, or suppository. In some embodiments, the pharmaceutical composition is formulated for oral administration. In some embodiments, the pharmaceutical composition is formulated such that the bacteria of the composition, or a portion thereof, remain viable after passage through the stomach of the subject. In some embodiments, the pharmaceutical composition is formulated for rectal administration, e.g. as a suppository. In some embodiments, the pharmaceutical composition is formulated for delivery to the intestine or a specific area of the intestine (e.g., the colon) by providing an appropriate coating (e.g., a pH specific coating, a coating that can be degraded by target area specific enzymes, or a coating that can bind to receptors that are present in a target area).

Dosages of the active ingredients in the pharmaceutical compositions of the present invention can be varied so as to obtain an amount of the active ingredient which is effective to achieve the desired pharmaceutical response for a particular subject, composition, and mode of administration, without being toxic or having an adverse effect on the subject. The selected dosage level depends upon a variety of factors including the activity of the particular compositions of the present invention employed, the route of administration, the time of administration, the duration of the treatment, other drugs, compounds and/or materials used in combination with the particular compositions employed, the age, sex, weight, condition, general health and prior medical history of the subject being treated, and like factors.

A physician, veterinarian or other trained practitioner, can start doses of the pharmaceutical composition at levels lower than that required to achieve the desired therapeutic effect and gradually increase the dosage until the desired effect (e.g., treatment of a pathogenic infection, reduction of bacterial burden of pathogenic infection, reduction or inhibition of toxin production) is achieved. In general, effective doses of the compositions of the present invention, for the prophylactic treatment of groups of people as described herein vary depending upon many different factors, including routes of administration, physiological state of the subject, whether the subject is human or an animal, other medications administered, and the therapeutic effect desired. Dosages need to be titrated to optimize safety and efficacy. In some embodiments, the dosing regimen entails oral administration of a dose of any of the compositions described herein. In some embodiments, the dosing regimen entails oral administration of multiple doses of any of the compositions described herein. In some embodiments, the composition is administered orally the subject once, twice, 3 times, 4 times, 5 times, 6 times, 7 times, 8 times, 9 times, or at least 10 times.

The compositions, including the pharmaceutical compositions disclosed herein, include compositions with a range of active ingredients (e.g., live bacteria, bacteria in spore format). The amount of bacteria in the compositions may be expressed in weight, number of bacteria and/or CFUs (colony forming units). In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more of each of the bacteria of the composition per dosage amount. In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more total bacteria per dosage amount. It should further be appreciated that the bacteria of the compositions may be present in different amounts. Thus, for instance, as a non-limiting example, a composition may include $10^3$ of bacteria A, $10^4$ of bacteria B and $10^6$ of bacteria C. In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs of each of the bacteria in the composition per dosage amount. In some embodiments, the pharmaceutical compositions disclosed herein contain about $10^1$, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs in total for all of the bacteria combined per dosage amount. As discussed above, bacteria of the compositions may be present in different amounts. In some embodiments, the pharmaceutical compositions disclosed herein contain about $10^{-7}$, about $10^{-6}$, about $10^{-5}$, about $10^{-4}$, about $10^{-3}$, about $10^{-2}$, about $10^{-1}$ or more grams of each of the bacteria in the composition per dosage amount. In some embodiments, the pharmaceutical compositions disclosed herein contain about $10^{-7}$, about $10^{-6}$, about $10^{-5}$, about $10^{-4}$, about $10^{-3}$, about $10^{-2}$, about $10^{-1}$ or more grams in total for all of the bacteria combined per dosage amount. In some embodiment, the dosage amount is one administration device (e.g., one table, pill or capsule). In some embodiment, the dosage amount is the amount that is administered in a particular period (e.g., one day or one week).

In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ of each of the bacteria of the composition per dosage amount. In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ total bacteria per dosage amount.

In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ CFUs of each of the bacteria of the composition per dosage amount. In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$, and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ total CFUs per dosage amount.

In some embodiments, the pharmaceutical compositions disclosed herein contain between $10^{-7}$ and $10^{-1}$, between $10^{-6}$ and $10^{-1}$, between $10^{-5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^{-4}$ and $10^{-2}$, between $10^{-3}$ and $10^{-2}$, between $10^{-7}$ and $10^{-3}$, between $10^{-6}$ and $10^{-3}$, between $10^{-5}$ and $10^{-3}$, between $10^{-4}$ and $10^{-3}$, between $10^{-7}$ and $10^{-4}$, between $10^{-6}$ and $10^{-4}$, between $10^{-5}$ and $10^{-4}$, between $10^{-7}$ and $10^{-5}$, between $10^{-6}$ and $10^{-5}$, or between $10^{-7}$ and $10^{-6}$ grams of each of the bacteria in the composition per dosage amount. In some embodiments, the pharmaceutical compositions disclosed herein contain between $10^{-7}$ and $10^{-1}$, between $10^{-6}$ and $10^{-1}$, between $10^{-5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^{-4}$ and $10^{-2}$, between $10^{-3}$ and $10^{-2}$, between $10^{-7}$ and $10^{-3}$, between $10^{-6}$ and $10^{-3}$, between $10^{-5}$ and $10^{-3}$, between $10^{-4}$ and $10^{-3}$, between $10^{-7}$ and $10^{-4}$, between $10^{-6}$ and $10^{-4}$, between $10^{-5}$ and $10^{-4}$, between $10^{-7}$ and $10^{-5}$, between $10^{-6}$ and $10^{-5}$, or between $10^{-7}$ and $10^{-6}$ grams of all of the bacteria combined per dosage amount.

Also with the scope of the present disclosure are food products comprising any of the bacterial strains described herein and a nutrient. Food products are, in general, intended for the consumption of a human or an animal. Any of the bacterial strains described herein may be formulated as a food product. In some embodiments, the bacterial strains are formulated as a food product in spore form. In some embodiments, the bacterial strains are formulated as a food product in vegetative form. In some embodiments, the food product comprises both vegetative bacteria and bacteria in spore form. The compositions disclosed herein can be used in a food or beverage, such as a health food or beverage, a food or beverage for infants, a food or beverage for pregnant women, athletes, senior citizens or other specified group, a functional food, a beverage, a food or beverage for specified health use, a dietary supplement, a food or beverage for patients, or an animal feed. Non-limiting examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, soups; dairy products such as milk, dairy beverages, ice creams, cheeses, and yogurts; fermented products such as fermented soybean pastes, yogurts, fermented beverages, and pickles; bean products; various confectionery products such as Western confectionery products including biscuits, cookies, and the like, Japanese confectionery products including steamed bean-jam buns, soft adzuki-bean jellies, and the like, candies, chewing gums, gummies, cold desserts including jellies, cream caramels, and frozen desserts; instant foods such as instant soups and instant soy-bean soups; microwavable foods; and the like. Further, the examples also include health foods and beverages prepared in the forms of powders, granules, tablets, capsules, liquids, pastes, and jellies.

Food products containing bacterial strains described herein may be produced using methods known in the art and may contain the same amount of bacteria (e.g., by weight, amount or CFU) as the pharmaceutical compositions provided herein. Selection of an appropriate amount of bacteria in the food product may depend on various factors, including for example, the serving size of the food product, the frequency of consumption of the food product, the specific bacterial strains contained in the food product, the amount of water in the food product, and/or additional conditions for survival of the bacteria in the food product.

Examples of food products which may be formulated to contain any of the bacterial strains described herein include, without limitation, a beverage, a drink, a bar, a snack, a dairy product, a confectionery product, a cereal product, a ready-to-eat product, a nutritional formula, such as a nutritional supplementary formulation, a food or beverage additive.

In some embodiments, the subject has not received a dose of an antibiotic prior to administration of the bacterial composition. In some embodiments, the subject has not been administered an antibiotic at least 1, at least 2, at least 3, at least 5, at least 10, at least 15, at least 20, at least 25, at least 30, at least 60, at least 90, at least 120, at least 180 or at least 360 days prior to administration of the compositions provided herein. In some embodiments, the person has not been administered and antibiotic to treat the pathogenic infection. In some embodiments, the compositions provided herein comprise the first treatment of the pathogenic infection.

In some embodiments, the subject may be administered one or more doses of an antibiotic prior to or concurrently with a bacterial composition. Generally, the first line of defense in the treatment of a pathogenic infection is the administration of an antibiotic. In some embodiments, the subject is administered a single dose of an antibiotic prior to the bacterial composition. In some embodiments, the subject is administered multiple doses of an antibiotic prior to the bacterial composition. In some embodiments, the subject is administered at least 2, 3, 4, 5 or more doses of an antibiotic prior to the bacterial composition. In some embodiments, the subject is administered a dose of an antibiotic at substantially the same time as the bacterial composition. Examples of antibiotics that can be administered include, without limitation, kanamycin, gentamicin, colistin, metronidazole, *vancomycin, clindamycin, fidaxomicin, and cefoperazone.*

Table 1 below provides sequence identifier numbers (SEQ ID NOs) used in the compositions of the experiments disclosed herein, along with the accompanying strain identification number (Strain ID). The closest bacterial species to the indicated strain is presented by genus-species. The 16S rDNA sequence associated with each genus species identified as the closest related genus species is also provided. The percent alignment presents the percent identity between the sequence of the indicated strain with the sequence from the closest genus species and the length of the alignment. The GenBank Accession Number of the closest related species is provided in the last column.

TABLE 1

Closest bacterial species to the strains described herein

| SEQ ID | Strain ID | Closest Genus_species | SEQ ID NO. of closest species | Percent alignment | Alignment length | Accession # of closest species |
|---|---|---|---|---|---|---|
| SEQ ID NO: 01 | 71 | *Blautia wexlerae* | SEQ_94 | 96.62 | 207 | NR_044054 |
| SEQ ID NO: 02 | 102 | *Turicibacter_sanguinis* | SEQ_91 | 97.81 | 183 | NR_028816 |
| SEQ ID NO: 03 | 5 | *Clostridium_hathewayi* | SEQ_105 | 92.42 | 198 | NR_036928 |
| SEQ ID NO: 04 | 7 | *Blautia_hansenii* | SEQ_99 | 96.62 | 207 | NR_104687 |
| SEQ ID NO: 05 | 10 | *Blautia_hansenii* | SEQ_99 | 98.06 | 206 | NR_104687 |
| SEQ ID NO: 06 | 40 | *Lactobacillus_mucosae* | SEQ_90 | 87.57 | 185 | NR_024994 |
| SEQ ID NO: 07 | 59 | *Blautia_producta* | SEQ_106 | 98.54 | 206 | NR_113270 |
| SEQ ID NO: 07 | 59 | *Blautia_coccoides* | SEQ_103 | 98.54 | 206 | NR_104700 |
| SEQ ID NO: 08 | 79 | *Blautia_hansenii* | SEQ_99 | 100 | 194 | NR_104687 |
| SEQ ID NO: 09 | VE202-21 | *Eubacterium_contortum* | SEQ_109 | 94.59 | 296 | NR_117147 |
| SEQ ID NO: 09 | VE202-21 | *Eubacterium_fissicatena* | SEQ_108 | 94.59 | 296 | NR_117142 |
| SEQ ID NO: 10 | 211 | *Flavonifractor_plautii* | SEQ_93 | 98.49 | 199 | NR_043142 |
| SEQ ID NO: 11 | VE202-9 | *Anaerostipes_caccae* | SEQ_88 | 99.5 | 399 | NR_028915 |
| SEQ ID NO: 12 | VE202-26 | *Clostridium_scindens* | SEQ_87 | 95.76 | 354 | NR_028785 |
| SEQ ID NO: 13 | 136 | *Marvinbryantia_formatexigens* | SEQ_89 | 94.66 | 131 | NR_042152 |
| SEQ ID NO: 14 | VE202-13 | *Anaerotruncus_colihominis* | SEQ_95 | 99.34 | 1365 | NR_027558 |
| SEQ ID NO: 15 | VE202-14 | *Eubacterium_fissicatena* | SEQ_102 | 93.33 | 1530 | NR_117563 |
| SEQ ID NO: 16 | VE202-16 | *Clostridium_symbiosum* | SEQ_122 | 98.43 | 1469 | NR_118730 |
| SEQ ID NO: 17 | VE202-7 | *Clostridium_bolteae* | SEQ_110 | 99.86 | 1390 | NR_113410 |
| SEQ ID NO: 18 | 148 | *Dorea_longicatena* | SEQ_97 | 99.7 | 1318 | NR_028883 |
| SEQ ID NO: 19 | 16 | *Blautia_producta* | SEQ_106 | 98.33 | 1493 | NR_113270 |
| SEQ ID NO: 20 | 170 | *Dorea_longicatena* | SEQ_97 | 99.7 | 1318 | NR_028883 |
| SEQ ID NO: 21 | 189 | *Clostridium_innocuum* | SEQ_98 | 98.64 | 1476 | NR_029164 |
| SEQ ID NO: 22 | 169 | *Dorea_longicatena* | SEQ_97 | 99.58 | 475 | NR_028883 |
| SEQ ID NO: 23 | VE202-29 | *Eisenbergiella_tayi* | SEQ_121 | 100 | 354 | NR_118643 |

TABLE 1-continued

Closest bacterial species to the strains described herein

| SEQ ID | Strain ID | Closest Genus_species | SEQ ID NO. of closest species | Percent alignment | Alignment length | Accession # of closest species |
|---|---|---|---|---|---|---|
| SEQ ID NO: 24 | YK96 | *Dorea_longicatena* | SEQ_97 | 99.48 | 191 | NR_028883 |
| SEQ ID NO: 25 | YK101 | *Ruminococcus_obeum* | SEQ_85 | 96.81 | 188 | NR_118692 |
| SEQ ID NO: 26 | YK110 | *Megasphaera_elsdenii* | SEQ_119 | 96.62 | 207 | NR_102980 |
| SEQ ID NO: 27 | YK149 | *Acidaminococcus_fermentans* | SEQ_115 | 99.48 | 192 | NR_074928 |
| SEQ ID NO: 27 | YK149 | *Acidaminococcus_intestini* | SEQ_112 | 99.48 | 192 | NR_074306 |
| SEQ ID NO: 28 | YK154 | *Megasphaera_elsdenii* | SEQ_119 | 96.12 | 206 | NR_102980 |
| SEQ ID NO: 29 | YK36 | *Ruminococcus_faecis* | SEQ_96 | 99.29 | 425 | NR_116747 |
| SEQ ID NO: 30 | YK95 | *Bacteroides_cellulosilyticus* | SEQ_100 | 99.54 | 437 | NR_112933 |
| SEQ ID NO: 31 | YK32 | *Anaerostipes_hadrus* | SEQ_107 | 98.8 | 415 | NR_104799 |
| SEQ ID NO: 32 | YK64 | *Ruminococcus_obeum* | SEQ_84 | 99.04 | 415 | NR_119185 |
| SEQ ID NO: 33 | YK73 | *Flavonifractor_plautii* | SEQ_93 | 98.56 | 418 | NR_043142 |
| SEQ ID NO: 34 | YK87 | *Eubacterium_rectale* | SEQ_114 | 99.52 | 416 | NR_074634 |
| SEQ ID NO: 35 | YK105 | *Flavonifractor_plautii* | SEQ_93 | 99.26 | 407 | NR_043142 |
| SEQ ID NO: 36 | YK153 | *Megasphaera_elsdenii* | SEQ_119 | 96.04 | 429 | NR_102980 |
| SEQ ID NO: 37 | YK163 | *Eubacterium_rectale* | SEQ_114 | 99.76 | 415 | NR_074634 |
| SEQ ID NO: 38 | YK191 | *Ruminococcus_champanellensis* | SEQ_117 | 94.47 | 416 | NR_102884 |
| SEQ ID NO: 38 | YK191 | *Ruminococcus_albus* | SEQ_113 | 94.47 | 416 | NR_074399 |
| SEQ ID NO: 39 | YK99 | *Ruminococcus_champanellensis* | SEQ_117 | 97.28 | 184 | NR_102884 |
| SEQ ID NO: 40 | YK55 | *Ruminococcus_faecis* | SEQ_96 | 99.02 | 408 | NR_116747 |
| SEQ ID NO: 41 | YK75 | *Bifidobacterium_bifidum* | SEQ_118 | 99.45 | 183 | NR_102971 |
| SEQ ID NO: 42 | YK90 | *Anaerostipes_hadrus* | SEQ_107 | 98.97 | 194 | NR_104799 |
| SEQ ID NO: 43 | YK30 | *Anaerostipes_hadrus* | SEQ_107 | 99.48 | 191 | NR_104799 |
| SEQ ID NO: 44 | YK31 | *Anaerostipes_hadrus* | SEQ_107 | 98.97 | 194 | NR_104799 |
| SEQ ID NO: 45 | YK12 | *Eubacterium_rectale* | SEQ_114 | 99.27 | 412 | NR_074634 |
| SEQ ID NO: 46 | YK27 | *Ruminococcus_faecis* | SEQ_96 | 99.51 | 412 | NR_116747 |
| SEQ ID NO: 47 | YK28 | *Blautia_luti* | SEQ_111 | 99.5 | 400 | NR_041960 |
| SEQ ID NO: 48 | YK29 | *Ruminococcus_faecis* | SEQ_96 | 99.03 | 413 | NR_116747 |
| SEQ ID NO: 49 | YK33 | *Anaerostipes_hadrus* | SEQ_107 | 99.27 | 413 | NR_104799 |
| SEQ ID NO: 50 | YK34 | *Anaerostipes_hadrus* | SEQ_107 | 99.51 | 410 | NR_104799 |
| SEQ ID NO: 51 | YK35 | *Ruminococcus_faecis* | SEQ_96 | 99.51 | 409 | NR_116747 |
| SEQ ID NO: 52 | YK51 | *Eubacterium_rectale* | SEQ_114 | 99.27 | 413 | NR_074634 |
| SEQ ID NO: 53 | YK52 | *Eubacterium_rectale* | SEQ_114 | 99.03 | 413 | NR_074634 |
| SEQ ID NO: 54 | YK54 | *Anaerostipes_hadrus* | SEQ_107 | 85.82 | 409 | NR_104799 |
| SEQ ID NO: 55 | YK56 | *Ruminococcus_faecis* | SEQ_96 | 99.03 | 413 | NR_116747 |
| SEQ ID NO: 56 | YK57 | *Ruminococcus_faecis* | SEQ_96 | 98.79 | 413 | NR_116747 |
| SEQ ID NO: 57 | YK58 | *Dorea_longicatena* | SEQ_97 | 98.8 | 417 | NR_028883 |
| SEQ ID NO: 58 | YK65 | *Roseburia_faecis* | SEQ_92 | 99.27 | 413 | NR_042832 |

TABLE 1-continued

Closest bacterial species to the strains described herein

| SEQ ID | Strain ID | Closest Genus_species | SEQ ID NO. of closest species | Percent alignment | Alignment length | Accession # of closest species |
|---|---|---|---|---|---|---|
| SEQ ID NO: 59 | YK67 | *Blautia_luti* | SEQ_111 | 98.57 | 419 | NR_041960 |
| SEQ ID NO: 60 | YK69 | *Fusicatenibacter_saccharivorans* | SEQ_116 | 99.27 | 413 | NR_114326 |
| SEQ ID NO: 61 | YK70 | *Fusicatenibacter_saccharivorans* | SEQ_116 | 98.79 | 414 | NR_114326 |
| SEQ ID NO: 62 | YK71 | *Roseburia_faecis* | SEQ_92 | 99.28 | 414 | NR_042832 |
| SEQ ID NO: 63 | YK74 | *Megasphaera_elsdenii* | SEQ_119 | 96.06 | 431 | NR_102980 |
| SEQ ID NO: 64 | YK88 | *Eubacterium_rectale* | SEQ_114 | 99.28 | 415 | NR_074634 |
| SEQ ID NO: 65 | YK89 | *Eubacterium_rectale* | SEQ_114 | 99.27 | 413 | NR_074634 |
| SEQ ID NO: 66 | YK97 | *Roseburia_faecis* | SEQ_92 | 99.28 | 414 | NR_042832 |
| SEQ ID NO: 67 | YK98 | *Blautia_faecis* | SEQ_104 | 98.02 | 405 | NR_109014 |
| SEQ ID NO: 68 | YK139 | *Fusicatenibacter_saccharivorans* | SEQ_116 | 99.03 | 412 | NR_114326 |
| SEQ ID NO: 69 | YK141 | *Dorea_formicigenerans* | SEQ_120 | 98.51 | 402 | NR_044645 |
| SEQ ID NO: 70 | YK142 | *Ruminococcus_faecis* | SEQ_96 | 98.79 | 413 | NR_116747 |
| SEQ ID NO: 71 | YK152 | *Blautia_hansenii* | SEQ_99 | 99.5 | 401 | NR_104687 |
| SEQ ID NO: 72 | YK155 | *Blautia_hansenii* | SEQ_99 | 98.79 | 413 | NR_104687 |
| SEQ ID NO: 73 | YK157 | *Eubacterium_rectale* | SEQ_114 | 99.27 | 413 | NR_074634 |
| SEQ ID NO: 74 | YK160 | *Roseburia_faecis* | SEQ_92 | 99.03 | 414 | NR_042832 |
| SEQ ID NO: 75 | YK166 | *Eubacterium_rectale* | SEQ_114 | 99.27 | 409 | NR_074634 |
| SEQ ID NO: 76 | YK168 | *Eubacterium_rectale* | SEQ_114 | 99.27 | 413 | NR_074634 |
| SEQ ID NO: 77 | YK169 | *Eubacterium_rectale* | SEQ_114 | 99.28 | 416 | NR_074634 |
| SEQ ID NO: 78 | YK171 | *Eubacterium_rectale* | SEQ_114 | 97.87 | 188 | NR_074634 |
| SEQ ID NO: 79 | YK192 | *Roseburia_faecis* | SEQ_92 | 99.03 | 414 | NR_042832 |
| SEQ ID NO: 80 | VE202-18 | *Erysipelatoclostridium_ramosum* | SEQ_123 | 100 | 1485 | NR_113243 |
| SEQ ID NO: 81 | PE5 | *Clostridium_bolteae* | SEQ_110 | 100 | 1385 | NR_113410 |
| SEQ ID NO: 82 | PE9 | *Clostridium_disporicum* | SEQ_86 | 99.21 | 382 | NR_026491 |
| SEQ ID NO: 83 | 211-B | *Bacteroides_ovatus* | SEQ_101 | 95.64 | 436 | NR_112940 |

TABLE 2

Bacterial species with a high degree of homology based on whole genome analysis:

| Strain | Whole genome homology |
|---|---|
| SEQ_10 - 211 | *Lachnospiraceae bacterium* 7_1_58FAA<br>*Subdoligranulum*<br>*Flavinofractor plautii* |
| SEQ_14 - VE202-13 | *Anaerotruncus_colihominis* |
| SEQ_15 - VE202-14 | *Eubacterium_fissicatena*<br>*Ruminococcus torques* |
| SEQ_16 - VE202-16 | *Clostridium_symbiosum* |
| SEQ_17 - VE202-7 | *Clostridium_bolteae* |

TABLE 2-continued

Bacterial species with a high degree of homology based on whole genome analysis:

| Strain | Whole genome homology |
|---|---|
| SEQ_22 - 169/SEQ_20—170 | *Dorea_longicatena* |
| SEQ_19 - 16 | *Blautia_producta* |
| SEQ_21 - 189 | *Clostridium_innocuum*<br>*Erysipelotrichaceae_bacterium_21_3* |

TABLE 3

Bacterial species with highest degree of homology based on whole genome analysis

| Composition B strain number | Strain identifier | SEQ ID # of 16S region as determined by Sanger sequencing | Closest species based on Sanger sequencing of 16S region | SEQ ID # of 16S regions as determined by WGS^ | *Consensus SEQ ID # of 16S region as determined by WGS | Closest species based on Concensus SEQ ID # of 16S region as compared with 16S database | Closest species based on WGS compared versus WG databases | Additional closely related sequences | *Clostridium* cluster |
|---|---|---|---|---|---|---|---|---|---|
| 1 | VE202-7 | 17 | *Clostridium bolteae* | 124, 125, 126, 127, 128 | 124 | *Clostridium bolteae* | *Clostridium bolteae* 90A9 | | XIVa |
| 2 | VE202-13 | 14 | *Anaerotruncus colihominis* | 129,130, 131 | 129 | *Anaerotruncus colihominis* | *Anaerotruncus colihominis* DSM 17241 | | IV |
| 3 | VE202-14 | 15 | *Eubacterium fissicatena* | 132, 133, 134, 135, 136 | 132 | *Dracourtella massiliensis* | *Dracourtella massiliensis* GD1 | *Ruminococcus torques*; *Sellimonas intestinalis* | XIVa |
| 4 | VE202-16 | 16 | *Clostridium symbiosum* | 137, 138, 139, 140 | 137 | *Clostridium symbiosum* | *Clostridium symbiosum* WAL-14163 | | XIVa |
| 5 | strain #16 | 19 | *Blautia producta* | 141, 142, 143, 144, 145 | 141 | *Blautia producta* | *Clostridium* bacterium UC5.1-1D4 | *Blautia* product ATCC 27340 | XIVa |
| 6 | strain #170 | 20 | *Dorea longicatena* | 146, 147, 148, 149, 150, 151 | 146 | *Dorea longicatena* | *Dorea longicatena* CAG:42 | | XIVa |
| 7 | strain #189 | 21 | *Clostridium innocuum* | 152, 153, 154, 155, 156 | 152 | *Clostridium innocuum* | Erysipelotrichaceae bacterium 21_3 | | XVII |
| 8 | strain #211 | 10 | *Flavinofractor plautii* | 157, 158, 159 | 157 | *Flavinofractor plautii* | *Clostridium orbiscindens* 1_3_50AFAA | *Subdolinogranulum* | IV |

^WGS refers to Whole Genome Sequencing performed on a PacBio Biosciences platform (Menlo Park, CA).
*Consensus sequence is defined as the 16S sequence that has the most overlap with all other identified 16S sequences.

In some embodiments, in any of the compositions described herein, *Clostridium bolteae* can be replaced with *Clostridium bolteae* 90A9. In some embodiments, in any of the compositions described herein, *Anaerotruncus colihominis* can be replaced with *Anaerotruncus colihominis* DSM 17241. In some embodiments, in any of the compositions described herein, *Eubacterium fissicatena* can be replaced with *Sellimonas instestinalis, Drancourtella massiliensis* or *Drancourtella massiliensis*GP1. In some embodiments, in any of the compositions described herein, *Clostridium symbiosum* can be replaced with *Clostridium symbiosum* WAL-14163. In some embodiments, in any of the compositions described herein, *Blautia* producta can be replaced with *Clostridium bacterium* CD5.1-1D4 or *Blautia* product ATCC27340. In some embodiments, in any of the compositions described herein, *Dorea longicatena* can be replaced with *Dorea longicatena* CAG:42. In some embodiments, in any of the compositions described herein, *Clostridium innocuum* can be replaced with *Erysipelotrichaceae bacterium* 21_3. In some embodiments, in any of the compositions described herein, *Flavonifractor plautii* can be replaced with *Clostridium orbiscindens* 1_3_50AFAA.

Aspects described herein provide pharmaceutical composition comprising a purified bacterial mixture consisting of bacterial strains comprising 16S rDNA sequences of at least 95% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some aspects, the bacterial strains have at least 97% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some aspects, the bacterial strains have at least 98% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some aspects, the bacterial strains have at least 99% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21.

In some aspects, at least a portion of the bacteria of the pharmaceutical composition are in spore-form. In some aspects, the pharmaceutical composition further comprises a pharmaceutically acceptable excipient.

In some aspects, the pharmaceutical composition is formulated for oral administration. In some aspects, the pharmaceutical composition is in the form of a capsule. In some aspects, the pharmaceutical composition is formulated for delivery to the colon. In some aspects, the pharmaceutical composition further comprises a pH sensitive composition comprising one or more enteric polymers.

Aspects described herein provide pharmaceutical compositions comprising a purified bacterial mixture consisting of bacterial strains comprising 16S rDNA sequences of at least 95% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157. In some aspects, the bacterial strains have at least 97% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157. In some aspects, the bacterial strains have at least 98% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157. In some aspects, the bacterial strains have at least 99% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157.

In some aspects, at least a portion of the bacterial strains are in spore-form. In some aspects, the pharmaceutical composition further comprises a pharmaceutically acceptable excipient.

In some aspects, the pharmaceutical composition is formulated for oral administration. In some aspects, the pharmaceutical composition is in the form of a capsule. In some aspects, the pharmaceutical composition is formulated for delivery to the colon. In some aspects, the pharmaceutical composition further comprises a pH sensitive composition comprising one or more enteric polymers.

Aspects described herein provide pharmaceutical compositions comprising a purified bacterial mixture comprising bacterial strains comprising 16S rDNA sequences of at least 95% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some aspects, the bacterial strains have at least 97% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some aspects, the bacterial strains have at least 98% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some aspects, the bacterial strains have at least 99% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21.

In some aspects, at least a portion of the bacterial strains are in spore-form. In some aspects, the pharmaceutical composition further comprises a pharmaceutically acceptable excipient.

In some aspects, the pharmaceutical composition is formulated for oral administration. In some aspects, the pharmaceutical composition is in the form of a capsule. In some aspects, the pharmaceutical composition is formulated for delivery to the colon. In some aspects, the pharmaceutical composition further comprises a pH sensitive composition comprising one or more enteric polymers.

Aspects described herein provide pharmaceutical compositions comprising a purified bacterial mixture comprising bacterial strains comprising 16S rDNA sequences of at least 95% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157. In some aspects, the bacterial strains have at least 97% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157. In some aspects, the bacterial strains have at least 98% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157. In some aspects, the bacterial strains have at least 99% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157. In some aspects, at least a portion of the bacterial strains are in spore-form. In some aspects, the pharmaceutical composition further comprises a pharmaceutically acceptable excipient.

In some aspects, the pharmaceutical composition is formulated for oral administration. In some aspects, the pharmaceutical composition is in the form of a capsule. In some aspects, the pharmaceutical composition is formulated for delivery to the colon. In some aspects, the pharmaceutical composition further comprises a pH sensitive composition comprising one or more enteric polymers.

Aspects described herein provide pharmaceutical compositions comprising a purified bacterial mixture consisting of the following bacterial strains: *Clostridium bolteae, Anaerostruncus colihominis, Sellimonas intestinalis, Clostridium symbiosum, Blautia* producta, *Dorea Longicatena, Erysipelotrichaceae bacterium*, and *Clostridium orbiscindens.*

In some aspects, at least a portion of the bacterial strains are in spore-form. In some aspects, the pharmaceutical composition further comprises a pharmaceutically acceptable excipient.

In some aspects, the pharmaceutical composition is formulated for oral administration. In some aspects, the pharmaceutical composition is in the form of a capsule. In some aspects, the pharmaceutical composition is formulated for delivery to the colon. In some aspects, the pharmaceutical composition further comprises a pH sensitive composition comprising one or more enteric polymers.

Aspects described herein provide pharmaceutical compositions comprising a purified bacterial mixture comprising the following bacterial strains: *Clostridium bolteae, Anaerostruncus colihominis, Sellimonas intestinalis, Clostridium symbiosum, Blautia* producta, *Dorea Longicatena, Erysipelotrichaceae bacterium*, and *Clostridium orbiscindens.*

In some aspects, at least a portion of the bacterial strains are in spore-form. In some aspects, the pharmaceutical composition further comprises a pharmaceutically acceptable excipient.

In some aspects, the pharmaceutical composition is formulated for oral administration. In some aspects, the pharmaceutical composition is in the form of a capsule. In some aspects, the pharmaceutical composition is formulated for delivery to the colon. In some aspects, the pharmaceutical composition further comprises a pH sensitive composition comprising one or more enteric polymers.

Aspects described herein provide methods of treating an infectious disease in a subject, the method comprising administering the pharmaceutical composition of any of the aspects described herein to the subject in an amount sufficient to treat the infectious disease. In some aspects, the infectious disease is *Clostridium difficile* infection. The nucleic acid sequences of the 16S rDNA, or portion thereof, for the bacterial strains described herein are provided below:

```
>SEQ ID NO: 01|71|
GCCCGGAGCAGTTGATGTGAAGGATGGGTCACCTGTGGACTGCATTGGAACTGTCATACTTGAGTGCCGGAGGGTAA

GCGGAATTCCTAGTGTAGCGGTGAAATGCGTAGATATTAGGAGGAACACCAGTGGCGAAGGCGGCTTACTGGACGGT

AACTGACGTTGAGGCTCGAAAGCGTGGGGAGCAAACAGGATTAGATACCCTGGTAA
```

-continued

>SEQ ID NO: 02|102|
CTAACCGTGGAGGTCATTGGAAACTGGTCAACTTGAGTGCAGAAGAGGGAAGTGGAATTCCATGTGTAGCGGTGAAA

TGCGTAGAGATATGGAGGAACACCAGTGGCGAAGGCGGCTTCCTGGTCTGTAACTGACACTGAGGCGCGAAAGCGTG

GGGGGCAAACAGGATTAGATCCCCCGGTAA

>SEQ ID NO: 03|5|
ATGAAAGCCGGGGCTCAACCCCGGTACTGCTTTGGAAACTGTTTGACTTGAGTGCTTGAGAGGTAAGTGGAATTCCT

AGTGTAGCGGGAAATGTTTAGATATTAGGAGGACACCAGTGGCGAAGGCGGCTTACTGGACTGTAACTGACGTTGTG

GCTCGATTTGTGGGGAGCAAACAGGATTATATCCCCTGGTAA

>SEQ ID NO: 04|7|
CGGAAGGTCTGATGTGAAGGTTGGGGCTTACCCCGGACTGCATTGGAAACTGTTTTTCTAGAGTGCCCGAGAGGTAA

GCGGAATTCCTAGTGTAGCGGTGAAATGCTTTAGATATTAGGAGGAACACCAGTGGCGAAGGCGGCTTACTGGACGG

TAACTGACGTTGAGGCTCGAAAGCGTGGGGAGCAAACAGGATTAGATACCCTGGTAA

>SEQ ID NO: 05|10|
CGATGTCTGAGTGAAGGCTGGGGCTTACCCCAGGACTGCATTGGAACTGTTTTTCTAGAGTGCCGGAGAGGTAAGCG

GAATTCCTAGTGTAGCGGTGAAATGCGTAGATATTAGGAGGAACACCAGTGGCGAAGGCGGCTTACTGGACGGTAAC

TGACGTTGAGGCTCGAAAGCGTGGGGAGCAAACAGGATTAGATACCCTGGTAA

>SEQ ID NO: 06|40|
TTAACCAAGAAGTGCATTGGAACTGTCAGACTTGGGGGAAAAAAAGACAGTGCAACTCCATGTGTAGCGGTGGAATG

CTCCATATATATGGAAGAACACCAGTGGCGAAGGCGGCTGTCTGGTCTGCAACTGACGCTGAGGCTCGAATTCATGG

GTAAGAAAGTATTAGTCCCTTGTAA

>SEQ ID NO: 07|59|
ACCCGCTTGGTCTGAGGTGAGGCTGGGGCTTAACCCCAGGACTGCATTGGAAACTGTTGTTCTAGAGTGCCGGAGAG

GTAAGCGGAATTCCTAGTGTAGCGGTGAAATGCGTAGATATTAGGAGGAACACCAGTGGCGAAGGCGGCTTACTGGA

CGGTAACTGACGTTGAGGCTCGAAAGCGTGGGGAGCAAACAGGATTAGATACCCTGGTAA

>SEQ ID NO: 08|79|
TAGGCTGGGGCTTAACCCCAGGACTGCATTGGAAACTGTTTTTCTAGAGTGCCGGAGAGGTAAGCGGAATTCCTAGT

GTAGCGGTGAAATGCGTAGATATTAGGAGGAACACCAGTGGCGAAGGCGGCTTACTGGACGGTAACTGACGTTGAGG

CTCGAAAGCGTGGGGAGCAAACAGGATTAGATACCCTGGTAA

>SEQ ID NO: 09|VE202-21|
TTGCATTGGACACTATGTCAGCTGAGTGTCGGAGAGGTAAGTGGAATTCCTAGTGTAGCGGTGAAATGCGTAGATAT

TAGGAGGAACACCAGTGGCGAAGGCGGCTTACTGCACGTTTTCTGACGTTGAGGCTCGAAATCGTGGGGAGCAAACA

AAAATAGATACCCTGGTAGTCCACGCCGTAAACGATGCATACTAGGTGTCGGGTGGCAAAGCCATTCGGTGCCGCAG

CAAACGCAATAAGTATGCCACCTGGGGAGTACGTTCGCAAGAATGAAACTCAAATAAATTGACGGA

>SEQ ID NO: 10|211|
CCCGTCGTAGATGTGAACTGGGGGCTCACCTCCAGCCTGCATTTGAAACTGTAGTTCTTGAGTGCTGGAGAGGCAAT

CGGAATTCCGTGTGTAGCGGTGAAATGCGTAGATATACGGAGGAACACCAGTGGCGAAGGCGGATTGCTGGACAGTA

ACTGACGCTGAGGCGCGAAAGCGTGGGGAGCAAACAGGATTAGATACCCTCATAA

>SEQ ID NO: 11|VE202-9|
ACCTGATGCAGCGACGCCGCGTGAGTGAAGAAGTATTTCGGTATGTAAAGCTCTATCAGCAGGGAAGAAAAAAGACG

GTACCTGACTAAGAAGCCCCGGCTAACTACGTGCCAGCAGCCGCGGTAATACGTAGGGGGCAAGCGTTATCCGGAAT

TACTGGGTGTAAAGGGTGCGTAGGTGGCATGGTAAGTCAGAAGTGAAAGCCCGGGGCTTAACCCCGGGACTGCTTTT

GAAACTGTCATGCTGGAGTGCAGGAGAGGTAAGCGGAATTCCTAGTGTAGCGGTGAAATGCGTAGATATTAGGAGGA

ACACCAGTGGCGAAGGCGGCTTACTGGACTGTCACTGACACTGATGCACGAAAGCGTGGGGAGCAAACAGGATTAGA

TACCCTGGAAGTCCAT

-continued

>SEQ ID NO: 12|VE202-26|
ATGGGAGCGTAGATGGCGACTGGGCCATATGTGACAGCCCTGGTCTCAACCCCTTAACTGCATTTGGAACTGAGTGG
CTGGAGTGTCGGAGAGGCAGGCGGAATTCCTAGTGTAGCGGTGAAATGCGTAGATATTAGGAGGAACACCAGTGGCG
AAGGCGGCCTGCTGGACGATGACTGACGTTGAGGCTCGAAAGCGTGGGGAGCAAACAGGATTAGATACCCTGGTAGT
CCACGCCGTAAACGATGACTACTAGGTGTCGGGTGGCAAGGACATTCGGTGCCGCAGCAAACGCAATAAGTAGTCCA
CCTGGGGAGTACGTTCGCAAGAATGAAACTCAAAGGAAATTGACGGA

>SEQ ID NO: 13|136|
CGCAGCGGAGTGTATCCTAGGCTCACCTGGCTGCTTTCGAACTGGTTTTCTAGATCGTGTAGAGGGGGAGATTCCTG
GTGTAGCGTGAAATGCGTAGATATCTGGAGGAACACCAGTGGCGAAGGCGGCCTCCTGGACGGCAACTGACGTTGAG
GCTCGAAAGTGTGGGGAGCAAACAGGATTAGATACCCTGGTAA

>SEQ ID NO: 14|VE202-13|
TCAAAGAGTTTGATCCTGGCTCAGGACGAACGCTGGCGGCGCGCCTAACACATGCAAGTCGAACGGAGCTTACGTTT
TGAAGTTTTCGGATGGACGAATGTAAGCTTAGTGGCGGACGGGTGAGTAACACGTGAGCAACCTGCCTTTCAGAGGG
GGATAACAGCCGGAAACGGCTGCTAATACCGCATGATGTTGCGGGGGCACATGCCCCTGCAACCAAAGGAGCAATCC
GCTGAAAGATGGGCTCGCGTCCGATTAGCCAGTTGGCGGGGTAACGGCCCACCAAAGCGACGATCGGTAGCCGGACT
GAGAGGTTGAACGGCCACATTGGGACTGAGACACGGCCCAGACTCCTACGGGAGGCAGCAGTGGGGGATATTGCACA
ATGGGCGAAAGCCTGATGCAGCGACGCCGCGTGAGGGAAGACGGTCTTCGGATTGTAAACCTCTGTCTTTGGGGAAG
AAAATGACGGTACCCAAAGAGGAAGCTCCGGCTAACTACGTGCCAGCAGCCGCGGTAATACGTAGGGAGCAAGCGTT
GTCCGGAATTACTGGGTGTAAAGGGAGCGTAGGCGGGATGGCAAGTAGAATGTTAAATCCATCGGCTCAACCGGTGG
CTGCGTTCTAAACTGCCGTTCTTGAGTGAAGTAGAGGCAGGCGGAATTCCTAGTGTAGCGGTGAAATGCGTAGATAT
TAGGAGGAACACCAGTGGCGAAGGCGGCCTGCTGGGCTTTAACTGACGCTGAGGCTCGAAAGCGTGGGGAGCAAACA
GGATTAGATACCCTGGTAGTCCACGCCGTAAACGATGATTACTAGGTGTGGGGGGACTGACCCCTTCCGTGCCGCAG
TTAACACAATAAGTAATCCACCTGGGGAGTACGGCCGCAAGGTTGAAACTCAAAGGAATTGACGGGGGCCCGCACAA
GCAGTGGAGTATGTGGTTTAATTCGAAGCAACGCGAAGAACCTTACCAGGTCTTGACATCGGATGCATAGCCTAGAG
ATAGGTGAAGCCCTTCGGGGCATCCAGACAGGTGGTGCATGGTTGTCGTCAGCTCGTGTCGTGAGATGTTGGGTTAA
GTCCCGCAACGAGCGCAACCCTTATTATTAGTTGCTACGCAAGAGCACTCTAATGAGACTGCCGTTGACAAAACGGA
GGAAGGTGGGGATGACGTCAAATCATCATGCCCCTTATGACCTGGGCTACACACGTACTACAATGGCACTAAAACAG
AGGGCGGCGACACCGCGAGGTGAAGCGAATCCCGAAAAAGTGTCTCAGTTCAGATTGCAGGCTGCAACCCGCCTGCA
TGAAGTCGGAATTGCTAGTAATCGCGGATCAGCATGCCGCGGTGAATACGTTCCCGGGCCTTGTACACACCGCCCGT
CACACCATGGGAGTCGGTAACACCCGAAGCCAGTAGCCTAACCGCAAGGGGGGCGCTGTCGAAGGTGGGATTGATGA
CTGGGGTGAAGTCGTAACAAGGTAGCCGTATCGGAAGGTGCGGCTGGATCACCTCCTTT

>SEQ ID NO: 15|VE202-14|
TACGAGAGTTTGATCCTGGCTCAGGATGAACGCTGGCGGCGTGCCTAACACATGCAAGTCGAGCGAAGCGCTGTTTT
CAGAATCTTCGGAGGAAGAGGACAGTGACTGAGCGGCGGACGGGTGAGTAACGCGTGGGCAACCTGCCTCATACAGG
GGGATAACAGTTAGAAATGACTGCTAATACCGCATAAGCGCACAGGACCGCATGGTGTAGTGTGAAAAACTCCGGTG
GTATGAGATGGACCCGCGTCTGATTAGGTAGTTGGTGGGGTAAAGGCCTACCAAGCCGACGATCAGTAGCCGACCTG
AGAGGGTGACCGGCCACATTGGGACTGAGACACGGCCCAAACTCCTACGGGAGGCAGCAGTGGGGAATATTGCACAA
TGGGGGAAACCCTGATGCAGCGACGCCGCGTGAAGGAAGAAGTATTTCGGTATGTAAACTTCTATCAGCAGGGAAGA
AGATGACGGTACCTGAGTAAGAAGCACCGGCTAAATACGTGCCAGCAGCCGCGGTAATACGTATGGTGCAAGCGTTA
TCCGGATTTACTGGGTGTAAAGGGAGCGTAGACGGATAGGCAAGTCTGGAGTGAAAACCCAGGGCTCAACCCTGGGA
CTGCTTTGGAAACTGCAGATCTGGAGTGCCGGAGAGGTAAGCGGAATTCCTAGTGTAGCGGTGAAATGCGTAGATAT
TAGGAGGAACACCAGTGGCGAAGGCGGCTTACTGGACGGTGACTGACGTTGAGGCTCGAAAGCGTGGGGAGCAAACA

-continued

GGATTAGATACCCTGGTAGTCCACGCCGTAAACGATGACTACTAGGTGTCGGTGTGCAAAGCACATCGGTGCCGCAG

CAAACGCAATAAGTAGTCCACCTGGGGAGTACGTTCGCAAGAATGAAACTCAAAGGAATTGACGGGGACCCGCACAA

GCGGTGGAGCATGTGGTTTAATTCGAAGCAACGCGAAGAACCTTACCTGGTCTTGACATCCGGATGACGGGCGAGTA

ATGTCGCCGTCCCTTCGGGGCATCCGAGACAGGTGGTGCATGGTTGTCGTCAGCTCGTGTCGTGAGATGTTGGGTTA

AGTCCCGCAACGAGCGCAACCCTTATCTTCAGTAGCCAGCATATAAGGTGGGCACTCTGGAGAGACTGCCAGGGAGA

ACCTGGAGGAAGGTGGGGATGACGTCAAATCATCATGCCCCTTATGGCCAGGGCTACACACGTGCTACAATGGCGTA

AACAAAGGGAAGCGAGAGGGTGACCTGGAGCGAATCCCAAAAATAACGTCTCAGTTCGGATTGTAGTCTGCAACTCG

ACTACATGAAGCTGGAATCGCTAGTAATCGCGGATCAGCATGCCGCGGTGAATACGTTCCCGGGTCTTGTACACACC

GCCCGTCACACCATGGGAGTCAGTAACGCCCGAAGCCAGTGACCCAACCTTAGAGGAGGGAGCTGTCGAAGGCGGGA

CGGATAACTGGGGTGAAGTCGTAACAAGGTAGCCGTATCGGAAGGTGCGGCTGGATCACCTCCTTT

>SEQ ID NO: 16|VE202-16|
ATGAGAGTTTGATCCTGGCTCAGGATGAACGCTGGCGGCGTGCCTAACACATGCAAGTCGAACGAAGCGATTTAACG

GAAGTTTTCGGATGGAAGTTGAATTGACTGAGTGGCGGACGGGTGAGTAACGCGTGGGTAACCTGCCTTGTACTGGG

GGACAACAGTTAGAAATGACTGCTAATACCGCATAAGCGCACAGTATCGCATGATACAGTGTGAAAAACTCCGGTGG

TACAAGATGGACCCGCGTCTGATTAGCTAGTTGGTAAGGTAACGGCTTACCAAGGCGACGATCAGTAGCCGACCTGA

GAGGGTGACCGGCCACATTGGGACTGAGACACGGCCCAAACTCCTACGGGAGGCAGCAGTGGGGAATATTGCACAAT

GGGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGTAAAGCAAGTCTGAAGTGAAAGCCCGCGGCTCAACTGCGGGAC

TGCTTTGGAAACTGTTTAACTGGAGTGTCGGAGAGGTAAGTGGAATTCCTAGTGTAGCGGTGAAATGCGTAGATATT

AGGAGGAACACCAGTGGCGAAGGCGACTTACTGGACGATAACTGACGTTGAGGCTCGAAAGCGTGGGGAGCAAACAG

GATTAGATACCCTGGTAGTCCACGCCGTAAACGATGAATACTAGGTGTTGGGGAGCAAAGCTCTTCGGTGCCGTCGC

AAACGCAGTAAGTATTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCAGGTCTTGACATCGATCCGACGGGGGAGTAA

CGTCCCCTTCCCTTCGGGGCGGAGAAGACAGGTGGTGCATGGTTGTCGTCAGCTCGTGTCGTGAGATGTTGGGTTAA

GTCCCGCAACGAGCGCAACCCTTATTCTAAGTAGCCAGCGGTTCGGCCGGGAACTCTTGGGAGACTGCCAGGGATAA

CCTGGAGGAAGGTGGGGATGACGTCAAATCATCATGCCCCTTATGATCTGGGCTACACACGTGCTACAATGGCGTAA

ACAAAGAGAAGCAAGACCGCGAGGTGGAGCAAATCTCAAAAATAACGTCTCAGTTCGGACTGCAGGCTGCAACTCGC

CTGCACGAAGCTGGAATCGCTAGTAATCGCGAATCAGAATGTCGCGGTGAATACGTTCCCGGGTCTTGTACACACCG

CCCGTCACACCATGGGAGTCAGTAACGCCCGAAGTCAGTGACCCAACCGCAAGGAGGGAGCTGCCGAAGGCGGGACC

GATAACTGGGGTGAAGTCGTAACAAGGTAGCCGTATCGGAAGGTGCGGCTGGATCACCTCCTTT

>SEQ ID NO: 17|VE202-7|
ATGAGAGTTTGATCCTGGCTCAGGATGAACGCTGGCGGCGTGCCTAACACATGCAAGTCGAACGAAGCAATTAAAAT

GAAGTTTTCGGATGGATTTTTGATTGACTGAGTGGCGGACGGGTGAGTAACGCGTGGATAACCTGCCTCACACTGGG

GGATAACAGTTAGAAATGACTGCTAATACCGCATAAGCGCACAGTACCGCATGGTACGGTGTGAAAAACTCCGGTGG

TGTGAGATGGATCCGCGTCTGATTAGCCAGTTGGCGGGGTAACGGCCCACCAAAGCGACGATCAGTAGCCGACCTGA

GAGGGTGACCGGCCACATTGGGACTGAGACACGGCCCAAACTCCTACGGGAGGCAGCAGTGGGGAATATTGCACAAT

GGGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGCGAAGCAAGTCTGAAGTGAAAACCCAGGGCTCAACCCTGGGAC

TGCTTTGGAAACTGTTTTGCTAGAGTGTCGGAGAGGTAAGTGGAATTCCTAGTGTAGCGGTGAAATGCGTAGATATT

AGGAGGAACACCAGTGGCGAAGGCGGCTTACTGGACGATAACTGACGTTGAGGCTCGAAAGCGTGGGGAGCAAACAG

-continued

GATTAGATACCCTGGTAGTCCACGCCGTAAACGATGAATGCTAGGTGTTGGGGGGCAAAGCCCTTCGGTGCCGTCGC

AAACGCAGTAAGCATTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCAAGTCTTGACATCCTCTTGACCGGCGTGTAA

CGGCGCCTTCCCTTCGGGGCAAGAGAGACAGGTGGTGCATGGTTGTCGTCAGCTCGTGTCGTGAGATGTTGGGTTAA

GTCCCGCAACGAGCGCAACCCTTATCCTTAGTAGCCAGCAGGTAAAGCTGGGCACTCTAGGGAGACTGCCAGGGATA

ACCTGGAGGAAGGTGGGGATGACGTCAAATCATCATGCCCCTTATGATTTGGGCTACACACGTGCTACAATGGCGTA

AACAAAGGGAAGCAAGACAGTGATGTGGAGCAAATCCCAAAAATAACGTCCCAGTTCGGACTGTAGTCTGCAACCCG

ACTACACGAAGCTGGAATCGCTAGTAATCGCGAATCAGAATGTCGCGGTGAATACGTTCCCGGGTCTTGTACACACC

GCCCGTCACACCATGGGAGTCAGCAACGCCCGAAGTCAGTGACCCAACTCGCAAGAGAGGGAGCTGCCGAAGGCGGG

GCAGGTAACTGGGGTGAAGTCGTAACAAGGTAGCCGTATCGGAAGGTGCGGCTGGATCACCTCCTTT

>SEQ ID NO: 18|148|
AACGAGAGTTTGATCCTGGCTCAGGATGAACGCTGGCGGCGTGCTTAACACATGCAAGTCGAGCGAAGCACTTTGGA

AGATTCTTCGGATGAAGACTTTTGTGACTGAGCGGCGGACGGGTGAGTAACGCGTGGGTAACCTGCCTCATACAGGG

GGATAACAGTTAGAAATGACTGCTAATACCGCATAAGACCACGGTACCGCATGGTACAGTGGTAAAAACTCCGGTGG

TATGAGATGGACCCGCGTCTGATTAGGTAGTTGGTGGGGTAACGGCCTACCAAGCCGACGATCAGTAGCCGACCTGA

GAGGGTGACCGGCCACATTGGGACTGAGACACGGCCCAGACTCCTACGGGAGGCAGCAGTGGGGAATATTGCACAAT

GGAGGAAACTCTGATGCAGCGACGCCGCGTGAAGGATGAAGTATTTCGGTATGTAAACTTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGCACGGCAAGCCAGATGTGAAAGCCCGGGGCTCAACCCCGGGAC

TGCATTTGGAACTGCTGAGCTAGAGTGTCGGAGAGGCAAGTGGAATTCCTAGTGTAGCGGTGAAATGCGTAGATATT

AGGAGGAACACCAGTGGCGAAGGCGGCTTGCTGGACGATGACTGACGTTGAGGCTCGAAAGCGTGGGGAGCAAACAG

GATTAGATACCCTGGTAGTCCACGCCGTAAACGATGACTGCTAGGTGTCGGGTGGCAAAGCCATTCGGTGCCGCAGC

TAACGCAATAAGCAGTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCTGATCTTGACATCCCGATGACCGCTTCGTAA

TGGAAGCTTTTCTTCGGAACATCGGTGACAGGTGGTGCATGGTTGTCGTCAGCTCGTGTCGTGAGATGTTGGGTTAA

GTCCCGCAACGAGCGCAACCCCTATCTTCAGTAGCCAGCAGGTTAAGCTGGGCACTCTGGAGAGACTGCCAGGGATA

ACCTGGAGGAAGGTGGGGATGACGTCAAATCATCATGCCCCTTATGACCAGGGCTACACACGTGCTACAATGGCGTA

AACAAAGAGAAGCGAACTCGCGAGGGTAAGCAAATCTCAAAAATAACGTCTCAGTTCGGATTGTAGTCTGCAACTCG

ACTACATGAAGCTGGAATCGCTAGTAATCGCAGATCAGAATGCTGCGGTGAATACGTTCCCGGGTCTTGTACACACC

GCCCGTCACACCATGGGAGTCAGTAACGCCCGAAGTCAGTGACCCAACCGTAAGGAGGGAGCTGCCGAAGGTGGGAC

CGATAACTGGGGTGAAGTCGTAACAAGGTAGCCGTATCGGAAGGTGCGGCTGGATCACCTCCTTT

>SEQ ID NO: 19|16|
ATCAGAGAGTTTGATCCTGGCTCAGGATGAACGCTGGCGGCGTGCTTAACACATGCAAGTCGAGCGAAGCACTTAAG

TGGATCTCTTCGGATTGAAACTTATTTGACTGAGCGGCGGACGGGTGAGTAACGCGTGGGTAACCTGCCTCATACAG

GGGGATAACAGTTAGAAATGGCTGCTAATACCGCATAAGCGCACAGGACCGCATGGTCTGGTGTGAAAAACTCCGGT

GGTATGAGATGGACCCGCGTCTGATTAGCTAGTTGGAGGGGTAACGGCCCACCAAGGCGACGATCAGTAGCCGGCCT

GAGAGGGTGAACGGCCACATTGGGACTGAGACACGGCCCAGACTCCTACGGGAGGCAGCAGTGGGGAATATTGCACA

ATGGGGGAAACCCTGATGCAGCGACGCCGCGTGAAGGAAGAAGTATCTCGGTATGTAAACTTCTATCAGCAGGGAAG

AAAATGACGGTACCTGACTAAGAAGCCCCGGCTAACTACGTGCCAGCAGCCGCGGTAATACGTAGGGGGCAAGCGTT

ATCCGGATTTACTGGGTGTAAAGGGAGCGTAGACGGAAGAGCAAGTCTGATGTGAAAGGCTGGGGCTTAACCCCAGG

ACTGCATTGGAAACTGTTTTTCTAGAGTGCCGGAGAGGTAAGCGGAATTCCTAGTGTAGCGGTGAAATGCGTAGATA

-continued

TTAGGAGGAACACCAGTGGCGAAGGCGGCTTACTGGACGGTAACTGACGTTGAGGCTCGAAAGCGTGGGGAGCAAAC

AGGATTAGATACCCTGGTAGTCCACGCCGTAAACGATGAATACTAGGTGTCGGGTGGCAAAGCCATTCGGTGCCGCA

GCAAACGCAATAAGTATTCCACCTGGGGAGTACGTTCGCAAGAATGAAACTCAAAGGAATTGACGGGGACCCGCACA

AGCGGTGGAGCATGTGGTTTAATTCGAAGCAACGCGAAGAACCTTACCAAGTCTTGACATCCCTCTGACCGGCCCGT

AACGGGGCCTTCCCTTCGGGGCAGAGGAGACAGGTGGTGCATGGTTGTCGTCAGCTCGTGTCGTGAGATGTTGGGTT

AAGTCCCGCAACGAGCGCAACCCCTATCCTTAGTAGCCAGCAGGTGAAGCTGGGCACTCTAGGGAGACTGCCGGGGA

TAACCCGGAGGAAGGCGGGGACGACGTCAAATCATCATGCCCCTTATGATTTGGGCTACACACGTGCTACAATGGCG

TAAACAAAGGGAAGCGAGACAGCGATGTTGAGCAAATCCCAAAAATAACGTCCCAGTTCGGACTGCAGTCTGCAACT

CGACTGCACGAAGCTGGAATCGCTAGTAATCGCGAATCAGAATGTCGCGGTGAATACGTTCCCGGGTCTTGTACACA

CCGCCCGTCACACCATGGGAGTCAGTAACGCCCGAAGTCAGTGACCCAACCTTACAGGAGGGAGCTGCCGAAGGCGG

GACCGATAACTGGGGTGAAGTCGTAACAAGGTAGCCGTATCGGAAGGTGCGGCTGGATCACCTCCTTT

>SEQ ID NO: 20|170|
AACGAGAGTTTGATCCTGGCTCAGGATGAACGCTGGCGGCGTGCTTAACACATGCAAGTCGAGCGAAGCACTTTGGA

AGATTCTTCGGATGATTTCCTTTGTGACTGAGCGGCGGACGGGTGAGTAACGCGTGGGTAACCTGCCTCATACAGGG

GGATAACAGTTAGAAATGACTGCTAATACCGCATAAGACCACGGTACCGCATGGTACAGTGGTAAAAACTCCGGTGG

TATGAGATGGACCCGCGTCTGATTAGGTAGTTGGTGGGGTAACGGCCTACCAAGCCGACGATCAGTAGCCGACCTGA

GAGGGTGACCGGCCACATTGGGACTGAGACACGGCCCAGACTCCTACGGGAGGCAGCAGTGGGGAATATTGCACAAT

GGAGGAAACTCTGATGCAGCGACGCCGCGTGAAGGATGAAGTATTTCGGTATGTAAACTTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGCACGGCAAGCCAGATGTGAAAGCCCGGGGCTCAACCCCGGGAC

TGCATTTGGAACTGCTGAGCTAGAGTGTCGGAGAGGCAAGTGGAATTCCTAGTGTAGCGGTGAAATGCGTAGATATT

AGGAGGAACACCAGTGGCGAAGGCGGCTTGCTGGACGATGACTGACGTTGAGGCTCGAAAGCGTGGGGAGCAAACAG

GATTAGATACCCTGGTAGTCCACGCCGTAAACGATGACTGCTAGGTGTCGGGTGGCAAAGCCATTCGGTGCCGCAGC

TAACGCAATAAGCAGTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCTGATCTTGACATCCCGATGACCGCTTCGTAA

TGGAAGCTTTTCTTCGGAACATCGGTGACAGGTGGTGCATGGTTGTCGTCAGCTCGTGTCGTGAGATGTTGGGTTAA

GTCCCGCAACGAGCGCAACCCCTATCTTCAGTAGCCAGCAGGTTAAGCTGGGCACTCTGGAGAGACTGCCAGGGATA

ACCTGGAGGAAGGTGGGGATGACGTCAAATCATCATGCCCCTTATGACCAGGGCTACACACGTGCTACAATGGCGTA

AACAAAGAGAAGCGAACTCGCGAGGGTAAGCAAATCTCAAAAATAACGTCTCAGTTCGGATTGTAGTCTGCAACTCG

ACTACATGAAGCTGGAATCGCTAGTAATCGCAGATCAGAATGCTGCGGTGAATACGTTCCCGGGTCTTGTACACACC

GCCCGTCACACCATGGGAGTCAGTAACGCCCGAAGTCAGTGACCCAACCGTAAGGAGGGAGCTGCCGAAGGTGGGAC

CGATAACTGGGGTGAAGTCGTAACAAGGTAGCCGTATCGGAAGGTGCGGCTGGATCACCTCCTTT

>SEQ ID NO: 21|189|
ATGGAGAGTTTGATCCTGGCTCAGGATGAACGCTGGCGGCATGCCTAATACATGCAAGTCGAACGAAGTTTCGAGGA

AGCTTGCTTCCAAAGAGACTTAGTGGCGAACGGGTGAGTAACACGTAGGTAACCTGCCCATGTGTCCGGGATAACTG

CTGGAAACGGTAGCTAAAACCGGATAGGTATACAGAGCGCATGCTCAGTATATTAAAGCGCCCATCAAGGCGTGAAC

ATGGATGGACCTGCGGCGCATTAGCTAGTTGGTGAGGTAACGGCCCACCAAGGCGATGATGCGTAGCCGGCCTGAGA

GGGTAAACGGCCACATTGGGACTGAGACACGGCCCAAACTCCTACGGGAGGCAGCAGTAGGGAATTTTCGTCAATGG

GGGAAACCCTGAACGAGCAATGCCGCGTGAGTGAAGAAGGTCTTCGGATCGTAAAGCTCTGTTGTAAGTGAAGAACG

GCTCATAGAGGAAATGCTATGGGAGTGACGGTAGCTTACCAGAAAGCCACGGCTAACTACGTGCCAGCAGCCGCGGT

AATACGTAGGTGGCAAGCGTTATCCGGAATCATTGGGCGTAAAGGGTGCGTAGGTGGCGTACTAAGTCTGTAGTAAA

AGGCAATGGCTCAACCATTGTAAGCTATGGAAACTGGTATGCTGGAGTGCAGAAGAGGGCGATGGAATTCCATGTGT

-continued

AGCGGTAAAATGCGTAGATATATGGAGGAACACCAGTGGCGAAGGCGGTCGCCTGGTCTGTAACTGACACTGAGGCA

CGAAAGCGTGGGGAGCAAATAGGATTAGATACCCTAGTAGTCCACGCCGTAAACGATGAGAACTAAGTGTTGGAGGA

ATTCAGTGCTGCAGTTAACGCAATAAGTTCTCCGCCTGGGGAGTATGCACGCAAGTGTGAAACTCAAAGGAATTGAC

GGGGGCCCGCACAAGCGGTGGAGTATGTGGTTTAATTCGAAGCAACGCGAAGAACCTTACCAGGCCTTGACATGGAA

ACAAATACCCTAGAGATAGGGGGATAATTATGGATCACACAGGTGGTGCATGGTTGTCGTCAGCTCGTGTCGTGAGA

TGTTGGGTTAAGTCCCGCAACGAGCGCAACCCTTGTCGCATGTTACCAGCATCAAGTTGGGGACTCATGCGAGACTG

CCGGTGACAAACCGGAGGAAGGTGGGGATGACGTCAAATCATCATGCCCCTTATGGCCTGGGCTACACACGTACTAC

AATGGCGGCCACAAAGAGCAGCGACACAGTGATGTGAAGCGAATCTCATAAAGGTCGTCTCAGTTCGGATTGAAGTC

TGCAACTCGACTTCATGAAGTCGGAATCGCTAGTAATCGCAGATCAGCATGCTGCGGTGAATACGTTCTCGGGCCTT

GTACACACCGCCCGTCAAACCATGGGAGTCAGTAATACCCGAAGCCGGTGGCATAACCGTAAGGAGTGAGCCGTCGA

AGGTAGGACCGATGACTGGGGTTAAGTCGTAACAAGGTATCCCTACGGGAACGTGGGGATGGATCACCTCCTTT

>SEQ ID NO: 22|169|
AGTAACGCGTGGGTAACCTGCCTCATACAGGGGGATAACAGTTAGAAATGACTGCTAATACCGCATAAGACCACGGT

ACCGCATGGTACAGTGGTAAAAACTCCGGTGGTATGAGATGGACCCGCGTCTGATTAGGTAGTTGGTGGGGTAACGG

CCTACCAAGCCGACGATCAGTAGCCGACCTGAGAGGGTGACCGGCCACATTGGGACTGAGACACGGCCCAGACTCCT

ACGGGAGGCAGCAGTGGGGAATATTGCACAATGGAGGAAACTCTGATGCAGCGACGCCGCGTGAAGGATGAAGTATT

TCGGTATGTAAACTTCTATCAGCAGGGAAGAAAATGACGGTACCTGACTAAGAAGCCCCGGCTAACTACGTGCCAGC

AGCCGCGGTAATACGTAGGGGGCAAGCGTTATCCGGATTTACTGGGTGTAAAGGGAGCGTAGACGGCACGGCAAGCC

AGATGTGAAAGCCC

>SEQ ID NO: 23|VE202-29|
CAGGCTGGAGTGCAGGAGAGGTAAGCGGAATTCCTAGTGTAGCGGTGAAATGCGTAGATATTAGGAGGAACACCAGT

GGCGAAGGCGGCTTACTGGACTGTAACTGACGTTGAGGCTCGAAAGCGTGGGGAGCAAACAGGATTAGATACCCTGG

TAGTCCACGCGGTAAACGATGATTGCTAGGTGTAGGTGGGTATGGACCCATCGGTGCCGCAGCTAACGCAATAAGCA

ATCCACCTGGGGAGTACGTTCGCAAGAATGAAACTCAAAGGAATTGACGGGGACCCGCACAAGCGGTGGAGCATGTG

GTTTAATTCGAAGCAACGCGAAGAACCTTACCAAGTCTTGACATCC

>SEQ ID NO: 24|YK96|
CCGGGGCTCACCCCGGGACTGCATTTGGAACTGCTGAGCTAGAGTGTCGGAGAGGCAAGTGGAATTCCTAGTGTAGC

GGTGAAATGCGTAGATATTAGGAGGAACACCAGTGGCGAAGGCGGCTTGCTGGACGATGACTGACGTTGAGGCTCGA

AAGCGTGGGGAGCAAACAGGATTAGATACCCTGGTA

>SEQ ID NO: 25|YK101|
AGGGTCAACCCCTGGACTGCATTGGAAACTGTCAGGCTGGAGTGCCGGAGAGGTAAGCGGAATTCCTAGTGTAGCGG

TGAAATGCGTAGATATTAGGAGGAACACCAGTGGCGAAGGCGGCTTACTGGACGGTAACTGACGTTGATGCTCGAAA

GCGTGGGGAGCAAACAGGATTAGATAACCTGGTAAA

>SEQ ID NO: 26|YK110|
GGGAAGTCGGTCTTAAGTGCGGGGCTTAACCCCGTGAGGGGACCGAAACTGTGAAGCTCGAGTGTCGGAGAGGAAAG

CGGAATTCCTAGTGTAGCGGTGAAATGCGTAGATATTAGGAGGAACACCAGTGGCGAAAGCGGCTTTCTGGACGACA

ACTGACGCTGAGGCGCGAAAGCCAGGGGAGCAAACGGGATTAGATACCCCAGTAA

>SEQ ID NO: 27|YK149|
TAGTCTGAGTGATGCGGGGCTTAACCCCGTATGGCGTTGGATACTGGAAGTCTTGAGTGCAGGAGAGGAAAGGGGAA

TTCCCAGTGTAGCGGTGAAATGCGTAGATATTGGGAGGAACACCAGTGGCGAAGGCGCCTTTCTGGACTGTGTCTGA

CGCTGAGATGCGAAAGCCAGGGTAGCAAACGGGATTAGATACCACGGTA

-continued

>SEQ ID NO: 28|YK154|
GATAGTCGGTCTTAAGTGCGGGGCTTACCCCGTGAGGGGACCGAAACTGTGAAGCTCGAGTGTCGGAGAGGAAAGCG

GAATTCCTAGTGTAGCGGTGAAATGCGTAGATATTAGGAGGAACACCAGTGGCGAAAGCGGCTTTCTGGACGACAAC

TGACGCTGAGGCGCGAAAGCCAGGGGAGCAAACGGGATTAGATACCACGGTAA

>SEQ ID NO: 29|YK36|
CGTTTGCTCCACGCTTTCGAGCCTCACGTCAGTTACCGTCCAGTAAGCCGCCTTCGCCACTGGTGTTCCTCCTAATA

TCTACGCATTTCACCGCTACACTAGGAATTCCGCTTACCTCTCCGGTACTCTAGATTGACAGTTTCCAATGCAGTCC

CGGGGTTGAGCCCCGGGTTTTCACATCAGACTTGCCACTCCGTCTACGCTCCCTTTACACCCAGTAAATCCGGATAA

CGCTTGCACCATACGTATTACCGCGGCTGCTGGCACGTATTTAGCCGGTGCTTCTTAGTCAGGTACCGTCATTTTCT

TCCCTGCTGATAGAGCTTTACATACCGAAATACTTCATCGCTCACGCGGCGTCGCTGCATCAGGGTTTCCCCCATTG

TGCAATATTCCCCACTGCTGCCTCCCGTAGGAGTTTGGA

>SEQ ID NO: 30|YK95|
TGTCACACTTTCGAGCATCAGCGTCAGTTACAGTCCAGTAAGCTGCCTTCGCAATCGGAGTTCTTCGTGATATCTAA

GCATTTCACCGCTACACCACGAATTCCGCCTACCTCTACTGCACTCAAGACGACCAGTATCAACTGCAATTTTACGG

TTGAGCCGCAAACTTTCACAGCTGACTTAATAGTCCGCCTACGCTCCCTTTAAACCCAATAAATCCGGATAACGCTT

GGATCCTCCGTATTACCGCGGCTGCTGGCACGGAGTTAGCCGATCCTTATTCGTATGGTACATACAAAAAGCCACAC

GTGGCTCACTTTATTCCCATATAAAAGAAGTTTACAACCCATAGGGCAGTCATCCTTCACGCTACTTGGCTGGTTCA

GACTCTCGTCCATTGACCAATATTCCTCACTGCTGCCTCCCGTAGGTAGTTTGGAA

>SEQ ID NO: 31|YK32|
CCGTTGTCACGCTTTCGTGCTCAGTGTCAGTTTCAGTCCAGTAAGCCGCCTTCGCCACTGATGTTCCTCCTAATATC

TACGCATTTCACCGCTACACTAGGAATTCCGCTTACCTCTCCTGCACTCCAGTCTGACAGTTTCAAAAGCAGTCCCA

GAGTTAAGCCCTGGGTTTTCACTTCTGACTTGCCATACCACCTACGCACCCTTTACACCCAGTAATTCCGGATAACG

CTTGCCCCCTACGTATTACCGCGGCTGCTGGCACGTAGTTAGCCGGGGCTTCTTAGTCAGGTACCGTCATTTTCTTC

CCTGCTGATAGAGCTTTACATACCGAAATACTTCTTCACTCACGCGGCGTCGCTGCATCAGGGTTCCCCCCATTGTG

CAATATTCCCCACTGCTGCCTCCCGTGGAAGTTTGGA

>SEQ ID NO: 32|YK64|
GCGAATGTCACGCATTCGAGCCTCACGTCAGTTACCGTCCAGTAAGCCGCCTTCGCCACTGGTGTTCCTCCTAATAT

CTACGCATTTCACCGCTACACTAGGAATTCCGCTTACCTCTCCGGCACTCAAGACTAACAGTTTCCAATGCAGTCCA

GGGGTTGAGCCCCCGCCTTTCACATCAGACTTGCCAGTCCGTCTACGCTCCCTTTACACCCAGTAAATCCGGATAAC

GCTTGCCCCCTACGTATTACCGCGGCTGCTGGCACGTAGTTAGCCGGGGCTTCTTAGTCAGGTACCGTCACTATCTT

CCCTGCTGATAGAAGTTTACATACCGAGATACTTCTTCCTTCACGCGGCGTCGCTGCATCAGGGTTTCCCCCATTGT

GCAATATTCCCCACTGCTGCCTCCCGTGGGAGTTTGGAA

>SEQ ID NO: 33|YK73|
TGCTCACGCTTTCGCGCTCAGCGTCAGTTACTGTCCAGCAATCCGCCTTCGCCACTGGTGTTCCTCCGTATATCTAC

GCATTTCACCGCTACACACGGAATTCCGATTGCCTCTCCAGCACTCAAGAACTACAGTTTCAAATGCAGGCTGGAGG

TTGAGCCCCCAGTTTTCACATCTGACTTGCAATCCCGCCTACACGCCCTTTACACCCAGTAAATCCGGATAACGCTT

GCCACCTACGTATTACCGCGGCTGCTGGCACGTAGTTAGCCGTGGCTTATTCGTCAGGTACCGTCATTTGTTTCGTC

CCTGACAAAAGAAGTTTACAACCCGAAAGCCTTCTTCCTTCACGCGGCGTTGCTGGGTCAGGCTTGCGCCCATTGCC

CAATATTCCCCACTGCTGCCTCCCGTGGTAGTTTGGA

>SEQ ID NO: 34|YK87|
TGTCCACGCTTTCGAGCTCAGCGTCAGTTATCGTCCAGTAAGCCGCCTTCGCCACTGGTGTTCCTCCTAATATCTAC

GCATTTCACCGCTACACTAGGAATTCCGCTTACCCCTCCGACACTCTAGTACGACAGTTTCCAATGCAGTACCGGGG

TTGAGCCCCGGGCTTTCACATCAGACTTGCCGCACCGCCTGCGCTCCCTTTACACCCAGTAAATCCGGATAACGCTT

GCACCATACGTATTACCGCGGCTGCTGGCACGTATTTAGCCGGTGCTTCTTAGTCAGGTACCGTCATTATCTTCCCT

-continued

GCTGATAGAGCTTTACATACCGAAATACTTCTTCGCTCACGCGGCGTCGCTGCATCAGGCTTTCGCCCATTGTGCAA

TATTCCCCACTGCTGACTCCCGTAGGAGTTTGGA

>SEQ ID NO: 35|YK105|
CGTTTCTCCACGCTTCGCGCTCAGCGTCAGTTACTGTCCAGCAATCCGCCTTCGCCACTGGTGTTCCTCCGTATATC

TACGCATTTCACCGCTACACACGGAATTCCGATTGCCTCTCCAGCACTCAAGAACTACAGTTTCAAATGCAGGCTGG

AGGTTGAGCCCCCAGTTTTCACATCTGACTTGCAATCCCGCCTACACGCCCTTTACACCCAGTAAATCCGGATAACG

CTTGCCACCTACGTATTACCGCGGCTGCTGGCACGTAGTTAGCCGTGGCTTATTCGTCAGGTACCGTCATTTGTTTC

GTCCCCGACAAAAGAAGTTTACAACCCGAAAGCCTTCTTCCTTCACGCGGCGTTGCTGGGTCAGGCTTGCGCCCATT

GCCCAATATTCCCCACTGCTGCCTCCCTGGGAAGTTTGG

>SEQ ID NO: 36|YK153|
ATGTCCTGACTTCGCGCCTCAGCGTCAGTTGTCGTCCAGAAAGCCGCTTTCGCCACTGGTGTTCCTCCTAATATCTA

CGCATTTCACCGCTACACTAGGAATTCCGCTTTCCTCTCCGACACTCGAGCTTCACAGTTTCGGTCCCCTCACGGGG

TTAAGCCCCGCACTTTTAAGACCGACTTGCGATGCCGCCTGCGCGCCCTTTACGCCCAATAATTCCGGACAACGCTT

GCCACCTACGTATTACCGCGGCTGCTGGCACGTAGTTAGCCGTGGCTTTCTCTTACGGTACCGTCAGGGATAACGGG

TATTGACCGCTATCCTGTTCGTCCCATATAACAGAACTTTACAACCCGAAGGCCGTCATCGTTCACGCGGCGTTGCT

CCGTCAGACTTTCGTCCATTGCGGAAGATTCCCCACTGCTGCCTCCCTGGGAAGTTTGGA

>SEQ ID NO: 37|YK163|
GTTTGCTCACGCTTTCGAGCTCAGCGTCAGTTATCGTCCAGTAAGCCGCCTTCGCCACTGGTGTTCCTCCTAATATC

TACGCATTTCACCGCTACACTAGGAATTCCGCTTACCCCTCCGACACTCTAGTACGACAGTTTCCAATGCAGTACCG

GGGTTGAGCCCCGGGCTTTCACATCAGACTTGCCGCACCGCCTGCGCTCCCTTTACACCCAGTAAATCCGGATAACG

CTTGCACCATACGTATTACCGCGGCTGCTGGCACGTATTTAGCCGGTGCTTCTTAGTCAGGTACCGTCATTATCTTC

CCTGCTGATAGAGCTTTACATACCGAAATACTTCTTCGCTCACGCGGCGTCGCTGCATCAGGCTTTCGCCCATTGTG

CAATATTCCCCACTGCTGCCTCCCGTAGGAGTTTGG

>SEQ ID NO: 38|YK191|
CGTTGCTCACGCATTCGAGCCTCAGCGTCAGTTAAGCCCAGTAAGCCGCCTTCGCCACTGATGTTCCTCCTAATATC

TACGCATTTCACCGCTACACTAGGAATTCCGCTTACCTCTACTTCACTCAAGAACCACAGTTTCAAATGCAGTTTAT

GGGTTAAGCCCATAGTTTTCACATCTGACTTGCGATCCCGCCTACGCTCCCTTTACACCCAGTAATTCCGGACAACG

CTCGCTCCCTACGTATTACCGCGGCTGCTGGCACGTAGTTAGCCGGAGCTTCCTCCTCAGGTACCGTCTTTTTTCGT

CCCTGAAGACAGAGGTTTACAATCCTAAAACCTTCTTCCCTCACGCGGCATCGCTGCATCAGAGTTTCCTCCATTGT

GCAATATTCCCCACTGCTGCCTCCCGTAGGAGTTTGGAA

>SEQ ID NO: 39|YK99|
TGGGCTTACCCATAAACTGCATTTGAAACTGTGGTTCTTGAGTGAAGTAGAGGTAAGCGGAATTCCTAGTGTAGCGG

TGAAATGCGTAGATATTAGGAGGAACATCAGTGGCGAAGGCGGCTTACTGGGCTTTAACTGACGCTGAGGCTCGAAA

GCGTGGGGAGCAAACAGGATTAGATACCCAAGTAA

>SEQ ID NO: 40|YK55|
GTCAGCATCGAGCTCACGTCAGTTACCGTCCAGTAAGCCGCCTTCGCCACTGGTGTTCCTCCTAATATCTACGCATT

TCACCGCTACACTAGGAATTCCGCTTACCTCTCCGGTACTCTAGATTGACAGTTTCCAATGCAGTCCCGGGGTTGAG

CCCCGGGTTTTCACATCAGACTTGCCACTCCGTCTACGCTCCCTTTACACCCAGTAAATCCGGATAACGCTTGCACC

ATACGTATTACCGCGGCTGCTGGCACGTATTTAGCCGGTGCTTCTTAGTCAGGTACCGTCATTTTCTTCCCTGCTGA

TAGAGCTTTACATACCGAAATACTTCATCGCTCACGCGGCGTCGCTGCATCAGGGTTTCCCCCATTGTGCAATATTC

CCCACTGCTGCCTCCCGAGGGAGTTTGGA

-continued

>SEQ ID NO: 41|YK75|
TCATCGCTTACGGTGGATCTGCGCCGGGTACGGGCGGGCTGGAGTGCGGTAGGGGAGACTGGAATTCCCGGTGTAAC

GGTGGAATGTGTAGATATCGGGAAGAACACCGATGGCGAAGGCAGGTCTCTGGGCCGTCACTGACGCTGAGGAGCGA

AAGCGTGGGGAGCGAACAGGATTAGATACAACGGTAA

>SEQ ID NO: 42|YK90|
TGAACCCAGGGCTTAACTCTGGGACTGCTTTTGAACTGTCAGACTGGAGTGCAGGAGAGGTAAGCGGAATTCCTAGT

GTAGCGGTGAAATGCGTAGATATTAGGAGGAACATCAGTGGCGAAGGCGGCTTACTGGACTGAAACTGACACTGAGG

CACGAAAGCGTGGGGAGCAAACAGGATTAGATACCATGGTAA

>SEQ ID NO: 43|YK30|
ACCAGGGCTTAACTCTGGGACTGCTTTTGAACTGTCAGACTGGAGTGCAGGAGAGGTAAGCGGAATTCCTAGTGTAG

CGGTGAAATGCGTAGATATTAGGAGGAACATCAGTGGCGAAGGCGGCTTACTGGACTGAAACTGACACTGAGGCACG

AAAGCGTGGGGAGCAAACAGGATTAGATACCCTGGTAA

>SEQ ID NO: 44|YK31|
GAACCCAGGGCTTAACTCTGGGACTGCTTTTGAACTGTCAGACTGGAGTGCAGGAGAGGTAAGCGGAATTCCTAGTG

TAGCGGTGAAATGCGTAGATATTAGGAGGAACATCAGTGGCGAAGGCGGCTTACTGGACTGAAACTGACACTGAGGC

ACGAAAGCGTGGGGAGCAAACAGGATTAGATACCCCGGTAA

>SEQ ID NO: 45|YK12|
GAGTCAGCTTTCGAGCTCAGCGTCAGTTATCGTCCAGTAAGCCGCCTTCGCCACTGGTGTTCCTCCTAATATCTACG

CATTTCACCGCTACACTAGGAATTCCGCTTACCCCTCCGACACTCTAGTACGACAGTTTCCAATGCAGTACCGGGGT

TGAGCCCCGGGCTTTCACATCAGACTTGCCGCACCGCCTGCGCTCCCTTTACACCCAGTAAATCCGGATAACGCTTG

CACCATACGTATTACCGCGGCTGCTGGCACGTATTTAGCCGGTGCTTCTTAGTCAGGTACCGTCATTATCTTCCCTG

CTGATAGAGCTTTACATACCGAAATACTTCTTCGCTCACGCGGCGTCGCTGCATCAGGCTTTCGCCCATTGTGCAAT

ATTCCCCACTGCTGCCTCCCGAGGGAGTTTGGA

>SEQ ID NO: 46|YK27|
TGTCAGCTTTCGAGCTCACGTCAGTTACCGTCCAGTAAGCCGCCTTCGCCACTGGTGTTCCTCCTAATATCTACGCA

TTTCACCGCTACACTAGGAATTCCGCTTACCTCTCCGGTACTCTAGATTGACAGTTTCCAATGCAGTCCCGGGGTTG

AGCCCCGGGTTTTCACATCAGACTTGCCACTCCGTCTACGCTCCCTTTACACCCAGTAAATCCGGATAACGCTTGCA

CCATACGTATTACCGCGGCTGCTGGCACGTATTTAGCCGGTGCTTCTTAGTCAGGTACCGTCATTTTCTTCCCTGCT

GATAGAGCTTTACATACCGAAATACTTCATCGCTCACGCGGCGTCGCTGCATCAGGGTTTCCCCCATTGTGCAATAT

TCCCCACTGCTGCCTCCCGTAGGAGTTTGGA

>SEQ ID NO: 47|YK28|
CACGTCAGTTACCGTCCAGTAAGCCGCCTTCGCCACTGGTGTTCCTCCTAATATCTACGCATTTCACCGCTACACTA

GGAATTCCGCTTACCTCTCCGGCACTCAAGACGGGCAGTTTCCAATGCAGTCCCGGGGTTGAGCCCCAGCCTTTCAC

ATCAGACTTGTCCATCCGTCTACGCTCCCTTTACACCCAGTAAATCCGGATAACGCTTGCCCCCTACGTATTACCGC

GGCTGCTGGCACGTAGTTAGCCGGGGCTTCTTAGTCAGGTACCGTCATTTTCTTCCCTGCTGATAGAAGTTTACATA

CCGAGATACTTCTTCCTTCACGCGGCGTCGCTGCATCAGGGTTTCCCCCATTGTGCAATATTCCCCACTGCTGCCTC

CCGTAGGAGTTTGGG

>SEQ ID NO: 48|YK29|
GTCAGCTTTCGAGCTCACGTCAGTTACCGTCCAGTAAGCCGCCTTCGCCACTGGTGTTCCTCCTAATATCTACGCAT

TTCACCGCTACACTAGGAATTCCGCTTACCTCTCCGGTACTCTAGATTGACAGTTTCCAATGCAGTCCCGGGGTTGA

GCCCCGGGTTTTCACATCAGACTTGCCACTCCGTCTACGCTCCCTTTACACCCAGTAAATCCGGATAACGCTTGCAC

CATACGTATTACCGCGGCTGCTGGCACGTATTTAGCCGGTGCTTCTTAGTCAGGTACCGTCATTTTCTTCCCTGCTG

ATAGAGCTTTACATACCGAAATACTTCATCGCTCACGCGGCGTCGCTGCATCAGGGTTTCCCCCATTGTGCAATATT

CCCCACTGCTGCCTCCCGTGGGGAGTTTGGA

-continued

>SEQ ID NO: 49|YK33|
GATGCTCAGCTTTCGTGCTCAGTGTCAGTTTCAGTCCAGTAAGCCGCCTTCGCCACTGATGTTCCTCCTAATATCTA

CGCATTTCACCGCTACACTAGGAATTCCGCTTACCTCTCCTGCACTCCAGTCTGACAGTTTCAAAAGCAGTCCCAGA

GTTAAGCCCTGGGTTTTCACTTCTGACTTGCCATACCACCTACGCACCCTTTACACCCAGTAATTCCGGATAACGCT

TGCCCCCTACGTATTACCGCGGCTGCTGGCACGTAGTTAGCCGGGGCTTCTTAGTCAGGTACCGTCATTTTCTTCCC

TGCTGATAGAGCTTTACATACCGAGATACTTCTTCACTCACGCGGCGTCGCTGCATCAGGGTTTCCCCCATTGTGCA

ATATTCCCCACTGCTGCCTCCCGAAGGAAGTTTGGA

>SEQ ID NO: 50|YK34|70A_009_YK34_A1_A02
GTGTCAGCTTCGTGCTCAGTGTCAGTTTCAGTCCAGTAAGCCGCCTTCGCCACTGATGTTCCTCCTAATATCTACGC

ATTTCACCGCTACACTAGGAATTCCGCTTACCTCTCCTGCACTCCAGTCTGACAGTTTCAAAAGCAGTCCCAGAGTT

AAGCCCTGGGTTTTCACTTCTGACTTGCCATACCACCTACGCACCCTTTACACCCAGTAATTCCGGATAACGCTTGC

CCCCTACGTATTACCGCGGCTGCTGGCACGTAGTTAGCCGGGGCTTCTTAGTCAGGTACCGTCATTTTCTTCCCTGC

TGATAGAGCTTTACATACCGAGATACTTCTTCACTCACGCGGCGTCGCTGCATCAGGGTTTCCCCCATTGTGCAATA

TTCCCCACTGCTGCCTCCCGTAGGGAGTTTGGA

>SEQ ID NO: 51|YK35|
GTCAGCTTCGAGCCTCACGTCAGTTACCGTCCAGTAAGCCGCCTTCGCCACTGGTGTTCCTCCTAATATCTACGCAT

TTCACCGCTACACTAGGAATTCCGCTTACCTCTCCGGTACTCTAGATTGACAGTTTCCAATGCAGTCCCGGGGTTGA

GCCCCGGGTTTTCACATCAGACTTGCCACTCCGTCTACGCTCCCTTTACACCCAGTAAATCCGGATAACGCTTGCAC

CATACGTATTACCGCGGCTGCTGGCACGTATTTAGCCGGTGCTTCTTAGTCAGGTACCGTCATTTTCTTCCCTGCTG

ATAGAGCTTTACATACCGAAATACTTCATCGCTCACGCGGCGTCGCTGCATCAGGGTTTCCCCCATTGTGCAATATT

CCCCACTGCTGCCTCGCGTAGGAGTTTGGA

>SEQ ID NO: 52|YK51|
TGTCAGCTTTCGAGCTCAGCGTCAGTTATCGTCCAGTAAGCCGCCTTCGCCACTGGTGTTCCTCCTAATATCTACGC

ATTTCACCGCTACACTAGGAATTCCGCTTACCCCTCCGACACTCTAGTACGACAGTTTCCAATGCAGTACCGGGGTT

GAGCCCCGGGCTTTCACATCAGACTTGCCGCACCGCCTGCGCTCCCTTTACACCCAGTAAATCCGGATAACGCTTGC

ACCATACGTATTACCGCGGCTGCTGGCACGTATTTAGCCGGTGCTTCTTAGTCAGGTACCGTCATTATCTTCCCTGC

TGATAGAGCTTTACATACCGAAATACTTCTTCGCTCACGCGGCGTCGCTGCATCAGGCTTTCGCCCATTGTGCAATA

TTCCCCACTGCTGCCTCCCGAAGGGAGTTTGGA

>SEQ ID NO: 53|YK52|
TTCAGCTTTCGAGCTCAGCGTCAGTTATCGTCCAGTAAGCCGCCTTCGCCACTGGTGTTCCTCCTAATATCTACGCA

TTTCACCGCTACACTAGGAATTCCGCTTACCCCTCCGACACTCTAGTACGACAGTTTCCAATGCAGTACCGGGGTTG

AGCCCCGGGCTTTCACATCAGACTTGCCGCACCGCCTGCGCTCCCTTTACACCCAGTAAATCCGGATAACGCTTGCA

CCATACGTATTACCGCGGCTGCTGGCACGTATTTAGCCGGTGCTTCTTAGTCAGGTACCGTCATTATCTTCCCTGCT

GATAGAGCTTTACATACCGAAATACTTCTTCGCTCACGCGGCGTCGCTGCATCAGGCTTTCGCCCATTGTGCAATAT

TCCCCACTGCTGCCTCCCGAGGGGAGTTTGG

>SEQ ID NO: 54|YK54|
TTCGGTCTGCTTTCCCCTTCTCGCGCCTCAGTGTCAGTTTCTGTCTAGTAAGCCGCCTTCGCCACTGATGTTCCTCC

TAATATCTACGCACTTCACCGCTCCACAATGAATTCCGCTTACCCCTCCCGCGCTCTAGTCTGACAGTTTTAAAAAA

ACTCCCCGAGAGAAACCCTGGGTTTTTTCTTCTGACATGCGATATCCCACCCCCACCCTTTATACACCCAAAAATCG

GATAAAAGGTGCGACCTACGTATTATACCGGCTGCTGGGGCGTAGATAGCCGGGGGTTCTTATACAGGGACCGTCAT

TTTCTTTCCCGCTGATACAGCTTTACATACCGAAATACTTCTTTCTCACGCGGCGTCGCTGCATCAGGGTTTCCCCC

ATTGTGCAATATTCCCCACTGCTGCCTCCCGAAGGGGAAGTTGGGGGAAA

-continued

>SEQ ID NO: 55|YK56|
GTTCAGCTTTCGAGCCTCACGTCAGTTACCGTCCAGTAAGCCGCCTTCGCCACTGGTGTTCCTCCTAATATCTACGC

ATTTCACCGCTACACTAGGAATTCCGCTTACCTCTCCGGTACTCTAGATTGACAGTTTCCAATGCAGTCCCGGGGTT

GAGCCCCGGGTTTTCACATCAGACTTGCCACTCCGTCTACGCTCCCTTTACACCCAGTAAATCCGGATAACGCTTGC

ACCATACGTATTACCGCGGCTGCTGGCACGTATTTAGCCGGTGCTTCTTAGTCAGGTACCGTCATTTTCTTCCCTGC

TGATAGAGCTTTACATACCGAAATACTTCATCGCTCACGCGGCGTCGCTGCATCAGGGTTTCCCCCATTGTGCAATA

TTCCCCACTGCTGCCTCCCGAGGGGAGTTTGGA

>SEQ ID NO: 56|YK57|
GTCAGCTTTCGAGCTCACGTCAGTTACCGTCCAGTAAGCCGCCTTCGCCACTGGTGTTCCTCCTAATATCTACGCAT

TTCACCGCTACACTAGGAATTCCGCTTACCTCTCCGGTACTCTAGATTGACAGTTTCCAATGCAGTCCCGGGGTTGA

GCCCCGGGTTTTCACATCAGACTTGCCACTCCGTCTACGCTCCCTTTACACCCAGTAAATCCGGATAACGCTTGCAC

CATACGTATTACCGCGGCTGCTGGCACGTATTTAGCCGGTGCTTCTTAGTCAGGTACCGTCATTTTCTTCCCTGCTG

ATAGAGCTTTACATACCGAAATACTTCATCGCTCACGCGGCGTCGCTGCATCAGGGTTTCCCCCATTGTGCAATATT

CCCCACTGCTGCCTCCCGAGGGGAGTTTGGA

>SEQ ID NO: 57|YK58|
TCTCACGCTTTCGAGCTCACGTCAGTCATCGTCCAGCAAGCCGCCTTCGCCACTGGTGTTCCTCCTAATATCTACGC

ATTTCACCGCTACACTAGGAATTCCACTTGCCTCTCCGACACTCTAGCTCAGCAGTTCCAAATGCAGTCCCGGGGTT

GAGCCCCGGGCTTTCACATCTGGCTTGCCGTGCCGTCTACGCTCCCTTTACACCCAGTAAATCCGGATAACGCTTGC

CCCCTACGTATTACCGCGGCTGCTGGCACGTAGTTAGCCGGGGCTTCTTAGTCAGGTACCGTCATTTTCTTCCCTGC

TGATAGAAGTTTACATACCGAAATACTTCATCCTTCACGCGGCGTCGCTGCATCAGAGTTTCCTCCATTGTGCAATA

TTCCCCACTGCTGCCTCCCGTAGGGAGTTTGG

>SEQ ID NO: 58|YK65|
GTCAGCTTTCGAGCTCAGCGTCAGTTATCGTCCAGTAAGCCGCCTTCGCCACTGGTGTTCCTCCTAATATCTACGCA

TTTCACCGCTACACTAGGAATTCCACTTACCCCTCCGACACTCTAGTACGACAGTTTCCAATGCAGTACCGGGGTTG

AGCCCCGGGCTTTCACATCAGACTTGCCGCACCGCCTGCGCTCCCTTTACACCCAGTAAATCCGGATAACGCTTGCA

CCATACGTATTACCGCGGCTGCTGGCACGTATTTAGCCGGTGCTTCTTAGTCAGGTACCGTCATTCTTCTTCCCTGC

TGATAGAGCTTTACATACCGAAATACTTCTTCGCTCACGCGGCGTCGCTGCATCAGGGTTTCCCCCATTGTGCAATA

TTCCCCACTGCTGCCTCCCGAGGGAGTTTGGA

>SEQ ID NO: 59|YK67|
AGCCCCGCTTTCGAGCCTCACGTCAGTTACCGTCCAGTAAGCCGCCTTCGCCACTGGTGTTCCTCCTAATATCTACG

CATTTCACCGCTACACTAGGAATTCCGCTTACCTCTCCGGCACTCAAGACGGGCAGTTTCCAATGCAGTCCCGGGGT

TGAGCCCCAGCCTTTCACATCAGACTTGTCCATCCGTCTACGCTCCCTTTACACCCAGTAAATCCGGATAACGCTTG

CCCCCTACGTATTACCGCGGCTGCTGGCACGTAGTTAGCCGGGGCTTCTTAGTCAGGTACCGTCATTTTCTTCCCTG

CTGATAGAAGTTTACATACCGAGATACTTCTTCCTTCACGCGGCGTCGCTGCATCAGGGTTTCCCCCATTGTGCAAT

ATTCCCCACTGCTGCCTCCCGAAGGAAGTTTGGA

>SEQ ID NO: 60|YK69|
TGCTCAGCTTTCGAGCCTCACGTCAGTTACCGTCCAGTAAGCCGCCTTCGCCACTGGTGTTCTTCCTAATATCTACG

CATTTCACCGCTACACTAGGAATTCCGCTTACCTCTCCGGCACTCGAGCCAGACAGTTTCCAATGCAGTCCCAGGGT

TAAGCCCTGGGTTTTCACATCAGACTTGCCTTGCCGTCTACGCTCCCTTTACACCCAGTAAATCCGGATAACGCTTG

CCCCCTACGTATTACCGCGGCTGCTGGCACGTAGTTAGCCGGGGCTTCTTAGTCAGGTACCGTCATTATCTTCCCTG

CTGATAGAGCTTTACATACCGAAATACTTCTTCGCTCACGCGGCGTCGCTGCATCAGGGTTTCCCCCATTGTGCAAT

ATTCCCCACTGCTGCCTCCCGAAGGGAGTTTGGA

-continued

>SEQ ID NO: 61|YK70|
GTTGCTCAGCTTTCGAGCTCACGTCAGTTACCGTCCAGTAAGCCGCCTTCGCCACTGGTGTTCTTCCTAATATCTAC

GCATTTCACCGCTACACTAGGAATTCCGCTTACCTCTCCGGCACTCGAGCCAGACAGTTTCCAATGCAGTCCCAGGG

TTAAGCCCTGGGTTTTCACATCAGACTTGCCTTGCCGTCTACGCTCCCTTTACACCCAGTAAATCCGGATAACGCTT

GCCCCCTACGTATTACCGCGGCTGCTGGCACGTAGTTAGCCGGGGCTTCTTAGTCAGGTACCGTCATTATCTTCCCT

GCTGATAGAGCTTTACATACCGAAATACTTCTTCGCTCACGCGGCGTCGCTGCATCAGGGTTTCCCCCATTGTGCAA

TATTCCCCACTGCTGCCTCCCGAAGGAAAGTTTGGA

>SEQ ID NO: 62|YK71|
TGCTCAGCTTTCGAGCTCAGCGTCAGTTATCGTCCAGTAAGCCGCCTTCGCCACTGGTGTTCCTCCTAATATCTACG

CATTTCACCGCTACACTAGGAATTCCACTTACCCCTCCGACACTCTAGTACGACAGTTTCCAATGCAGTACCGGGGT

TGAGCCCCGGGCTTTCACATCAGACTTGCCGCACCGCCTGCGCTCCCTTTACACCCAGTAAATCCGGATAACGCTTG

CACCATACGTATTACCGCGGCTGCTGGCACGTATTTAGCCGGTGCTTCTTAGTCAGGTACCGTCATTCTTCTTCCCT

GCTGATAGAGCTTTACATACCGAAATACTTCTTCGCTCACGCGGCGTCGCTGCATCAGGGTTTCCCCCATTGTGCAA

TATTCCCCACTGCTGCCTCCCGAAGGGAGTTTGGA

>SEQ ID NO: 63|YK74|
GATGCCCTGGCTTCGCGCTCAGCGTCAGTTGTCGTCCAGAAAGCCGCTTTCGCCACTGGTGTTCCTCCTAATATCTA

CGCATTTCACCGCTACACTAGGAATTCCGCTTTCCTCTCCGACACTCGAGCTTCACAGTTTCGGTCCCCTCACGGGG

TTAAGCCCCGCACTTTTAAGACCGACTTGCGATGCCGCCTGCGCGCCCTTTACGCCCAATAATTCCGGACAACGCTT

GCCACCTACGTATTACCGCGGCTGCTGGCACGTAGTTAGCCGTGGCTTTCTCTTACGGTACCGTCAGGGATAACGGG

TATTGACCGCTATCCTGTTCGTCCCATATAACAGAACTTTACAACCCGAAGGCCGTCATCGTTCACGCGGCGTTGCT

CCGTCAGACTTTCGTCCATTGCGGAAGATTCCCCACTGCTGCCTCCCGGGGGGAGTTTGGA

>SEQ ID NO: 64|YK88|
GTCCCGCTTTCGAGCCTCAGCGTCAGTTATCGTCCAGTAAGCCGCCTTCGCCACTGGTGTTCCTCCTAATATCTACG

CATTTCACCGCTACACTAGGAATTCCGCTTACCCCTCCGACACTCTAGTACGACAGTTTCCAATGCAGTACCGGGGT

TGAGCCCCGGGCTTTCACATCAGACTTGCCGCACCGCCTGCGCTCCCTTTACACCCAGTAAATCCGGATAACGCTTG

CACCATACGTATTACCGCGGCTGCTGGCACGTATTTAGCCGGTGCTTCTTAGTCAGGTACCGTCATTATCTTCCCTG

CTGATAGAGCTTTACATACCGAAATACTTCTTCGCTCACGCGGCGTCGCTGCATCAGGCTTTCGCCCATTGTGCAAT

ATTCCCCACTGCTGCCTCCCGAAGGGAAGTTTGG

>SEQ ID NO: 65|YK89|
TGTCAGCTTTCGAGCTCAGCGTCAGTTATCGTCCAGTAAGCCGCCTTCGCCACTGGTGTTCCTCCTAATATCTACGC

ATTTCACCGCTACACTAGGAATTCCGCTTACCCCTCCGACACTCTAGTACGACAGTTTCCAATGCAGTACCGGGGTT

GAGCCCCGGGCTTTCACATCAGACTTGCCGCACCGCCTGCGCTCCCTTTACACCCAGTAAATCCGGATAACGCTTGC

ACCATACGTATTACCGCGGCTGCTGGCACGTATTTAGCCGGTGCTTCTTAGTCAGGTACCGTCATTATCTTCCCTGC

TGATAGAGCTTTACATACCGAAATACTTCTTCGCTCACGCGGCGTCGCTGCATCAGGCTTTCGCCCATTGTGCAATA

TTCCCCACTGCTGCCTCCCGAAGGGAGTTTGGA

>SEQ ID NO: 66|YK97|
TGCTCAGCTTTCGAGCTCAGCGTCAGTTATCGTCCAGTAAGCCGCCTTCGCCACTGGTGTTCCTCCTAATATCTACG

CATTTCACCGCTACACTAGGAATTCCACTTACCCCTCCGACACTCTAGTACGACAGTTTCCAATGCAGTACCGGGGT

TGAGCCCCGGGCTTTCACATCAGACTTGCCGCACCGCCTGCGCTCCCTTTACACCCAGTAAATCCGGATAACGCTTG

CACCATACGTATTACCGCGGCTGCTGGCACGTATTTAGCCGGTGCTTCTTAGTCAGGTACCGTCATTCTTCTTCCCT

GCTGATAGAGCTTTACATACCGAAATACTTCTTCGCTCACGCGGCGTCGCTGCATCAGGGTTTCCCCCATTGTGCAA

TATTCCCCACTGCTGCCTCCCGAAGGGAGTTTGGA

-continued

>SEQ ID NO: 67|YK98|
ATTCAGCTTTCGAGCTCACGTCAGTTACCGTCCAGTAAGCCGCCTTCGCCACTGGTGTTCCTCCTAATATCTACGCA

TTTCACCGCTACACTAGGAATTCCGCTTACCCCTCCGGCACTCAAGCATACCAGTTTCCAATGCAGTCCAGGGGTTA

AGCCCCTGCCTTTCACATCAGACTTGATACGCCGTCTACGCTCCCTTTACACCCAGTAAATCCGGATAACGCTCGCC

CCCTACGTATTACCGCGGCTGCTGGCACGTAGTTAGCCGGGGCTTCTTAGTCAGGTACCGTCATTATCTTCCCTGCT

GATAGAAGTTTACATACCGAGATACTTCTTCCTTCACGCGGCGTCGCTGCATCAGGGTTTCCCCCATTGTGCAATAT

TCCCCACTGCTGCCTCCCGAGGGAAGTTTGGA

>SEQ ID NO: 68|YK139|
GTGTCAGCTTTCGAGCTCACGTCAGTTACCGTCCAGTAAGCCGCCTTCGCCACTGGTGTTCTTCCTAATATCTACGC

ATTTCACCGCTACACTAGGAATTCCGCTTACCTCTCCGGCACTCGAGCCAGACAGTTTCCAATGCAGTCCCAGGGTT

AAGCCCTGGGTTTTCACATCAGACTTGCCTTGCCGTCTACGCTCCCTTTACACCCAGTAAATCCGGATAACGCTTGC

CCCCTACGTATTACCGCGGCTGCTGGCACGTAGTTAGCCGGGGCTTCTTAGTCAGGTACCGTCATTATCTTCCCTGC

TGATAGAGCTTTACATACCGAAATACTTCTTCGCTCACGCGGCGTCGCTGCATCAGGGTTTCCCCCATTGTGCAATA

TTCCCCACTGCTGCCTCCCGAGGGAGTTTGG

>SEQ ID NO: 69|YK141|
GCCAGCTTCGAGCCTCACGTCAGTCATCGTCCAGTAAGCCGCCTTCGCCACTGGTGTTCCTCCTAATATCTACGCAT

TTCACCGCTACACTAGGAATTCCACTTACCTCTCCGACACTCTAGCTGCACAGTTTCCAAAGCAGTCCACAGGTTGA

GCCCATGCCTTTCACTTCAGACTTGCACAGCCGTCTACGCTCCCTTTACACCCAGTAAATCCGGATAACGCTTGCCC

CCTACGTATTACCGCGGCTGCTGGCACGTAGTTAGCCGGGGCTTCTTAGTCAGGTACCGTCATTTTCTTCCCTGCTG

ATAGAAGTTTACATACCGAAATACTTCATCCTTCACGCGGCGTCGCTGCATCAGGCTTTCGCCCATTGTGCAATATT

CCCCACTGCTGCCTCCCGAGGGAAGTTTGGA

>SEQ ID NO: 70|YK142|
TGATCAGCTTTCGAGCTCACGTCAGTTACCGTCCAGTAAGCCGCCTTCGCCACTGGTGTTCCTCCTAATATCTACGC

ATTTCACCGCTACACTAGGAATTCCGCTTACCTCTCCGGTACTCTAGATTGACAGTTTCCAATGCAGTCCCGGGGTT

GAGCCCCGGGTTTTCACATCAGACTTGCCACTCCGTCTACGCTCCCTTTACACCCAGTAAATCCGGATAACGCTTGC

ACCATACGTATTACCGCGGCTGCTGGCACGTATTTAGCCGGTGCTTCTTAGTCAGGTACCGTCATTTTCTTCCCTGC

TGATAGAGCTTTACATACCGAAATACTTCATCGCTCACGCGGCGTCGCTGCATCAGGGTTTCCCCCATTGTGCAATA

TTCCCCACTGCTGCCTCCCGGGGGGAGTTTGGA

>SEQ ID NO: 71|YK152|
GATGATCAGCTTTCGAGCTCACGTCAGTTACCGTCCAGTAAGCCGCCTTCGCCACTGGTGTTCCTCCTAATATCTAC

GCATTTCACCGCTACACTAGGAATTCCGCTTACCTCTCCGGCACTCTAGAAAAACAGTTTCCAATGCAGTCCTGGGG

TTAAGCCCCAGCCTTTCACATCAGACTTGCTCTTCCGTCTACGCTCCCTTTACACCCAGTAAATCCGGATAACGCTT

GCCCCCTACGTATTACCGCGGCTGCTGGCACGTAGTTAGCCGGGGCTTCTTAGTCAGGTACCGTCATTTTCTTCCCT

GCTGATAGAAGTTTACATACCGAGATACTTCTTCCTTCACGCGGCGTCGCTGCATCAGGGTTTCCCCCATTGTGCAA

TATTCCCCACTGCTGCCTCCCGGGGGAAGTTTGGA

>SEQ ID NO: 72|YK155|
TTGATCAGCTTTCGAGCTCACGTCAGTTACCGTCCAGTAAGCCGCCTTCGCCACTGGTGTTCCTCCTAATATCTACG

CATTTCACCGCTACACTAGGAATTCCGCTTACCTCTCCGGCACTCTAGAAAAACAGTTTCCAATGCAGTCCTGGGGT

TAAGCCCCAGCCTTTCACATCAGACTTGCTCTTCCGTCTACGCTCCCTTTACACCCAGTAAATCCGGATAACGCTTG

CCCCCTACGTATTACCGCGGCTGCTGGCACGTAGTTAGCCGGGGCTTCTTAGTCAGGTACCGTCATTTTCTTCCCTG

CTGATAGAAGTTTACATACCGAGATACTTCTTCCTTCACGCGGCGTCGCTGCATCAGGGTTTCCCCCATTGTGCAAT

ATTCCCCACTGCTGCCTCCCGAAGGGAGTTTGG

-continued

>SEQ ID NO: 73|YK157|
GTATTTCAGCTTTCGAGCTCAGCGTCAGTTATCGTCCAGTAAGCCGCCTTCGCCACTGGTGTTCCTCCTAATATCTA

CGCATTTCACCGCTACACTAGGAATTCCGCTTACCCCTCCGACACTCTAGTACGACAGTTTCCAATGCAGTACCGGG

GTTGAGCCCCGGGCTTTCACATCAGACTTGCCGCACCGCCTGCGCTCCCTTTACACCCAGTAAATCCGGATAACGCT

TGCACCATACGTATTACCGCGGCTGCTGGCACGTATTTAGCCGGTGCTTCTTAGTCAGGTACCGTCATTATCTTCCC

TGCTGATAGAGCTTTACATACCGAAATACTTCTTCGCTCACGCGGCGTCGCTGCATCAGGCTTTCGCCCATTGTGCA

ATATTCCCCACTGCTGCCTCCCGAAGGGAGTTTGGA

>SEQ ID NO: 74|YK160|
GCTCAGCTTTCGAGCTCAGCGTCAGTTATCGTCCAGTAAGCCGCCTTCGCCACTGGTGTTCCTCCTAATATCTACGC

ATTTCACCGCTACACTAGGAATTCCACTTACCCCTCCGACACTCTAGTACGACAGTTTCCAATGCAGTACCGGGGTT

GAGCCCCGGGCTTTCACATCAGACTTGCCGCACCGCCTGCGCTCCCTTTACACCCAGTAAATCCGGATAACGCTTGC

ACCATACGTATTACCGCGGCTGCTGGCACGTATTTAGCCGGTGCTTCTTAGTCAGGTACCGTCATTCTTCTTCCCTG

CTGATAGAGCTTTACATACCGAAATACTTCTTCGCTCACGCGGCGTCGCTGCATCAGGGTTTCCCCCATTGTGCAAT

ATTCCCCACTGCTGCCTCCCGAGGGGAGTTTGGA

>SEQ ID NO: 75|YK166|
TTTCAGCTTCGAGCCTCAGCGTCAGTTATCGTCCAGTAAGCCGCCTTCGCCACTGGTGTTCCTCCTAATATCTACGC

ATTTCACCGCTACACTAGGAATTCCGCTTACCCCTCCGACACTCTAGTACGACAGTTTCCAATGCAGTACCGGGGTT

GAGCCCCGGGCTTTCACATCAGACTTGCCGCACCGCCTGCGCTCCCTTTACACCCAGTAAATCCGGATAACGCTTGC

ACCATACGTATTACCGCGGCTGCTGGCACGTATTTAGCCGGTGCTTCTTAGTCAGGTACCGTCATTATCTTCCCTGC

TGATAGAGCTTTACATACCGAAATACTTCTTCGCTCACGCGGCGTCGCTGCATCAGGCTTTCGCCCATTGTGCAATA

TTCCCCACTGCTAGCTCCCGAAGGAGTTTGGA

>SEQ ID NO: 76|YK168|
AGCTCAGCTTTCGAGCTCAGCGTCAGTTATCGTCCAGTAAGCCGCCTTCGCCACTGGTGTTCCTCCTAATATCTACG

CATTTCACCGCTACACTAGGAATTCCGCTTACCCCTCCGACACTCTAGTACGACAGTTTCCAATGCAGTACCGGGGT

TGAGCCCCGGGCTTTCACATCAGACTTGCCGCACCGCCTGCGCTCCCTTTACACCCAGTAAATCCGGATAACGCTTG

CACCATACGTATTACCGCGGCTGCTGGCACGTATTTAGCCGGTGCTTCTTAGTCAGGTACCGTCATTATCTTCCCTG

CTGATAGAGCTTTACATACCGAAATACTTCTTCGCTCACGCGGCGTCGCTGCATCAGGCTTTCGCCCATTGTGCAAT

ATTCCCCACTGCTGCCTCCCGAAGGGAGTTTGGA

>SEQ ID NO: 77|YK169|
GTCCAGCTTTCGAGCCTCAGCGTCAGTTATCGTCCAGTAAGCCGCCTTCGCCACTGGTGTTCCTCCTAATATCTACG

CATTTCACCGCTACACTAGGAATTCCGCTTACCCCTCCGACACTCTAGTACGACAGTTTCCAATGCAGTACCGGGGT

TGAGCCCCGGGCTTTCACATCAGACTTGCCGCACCGCCTGCGCTCCCTTTACACCCAGTAAATCCGGATAACGCTTG

CACCATACGTATTACCGCGGCTGCTGGCACGTATTTAGCCGGTGCTTCTTAGTCAGGTACCGTCATTATCTTCCCTG

CTGATAGAGCTTTACATACCGAAATACTTCTTCGCTCACGCGGCGTCGCTGCATCAGGCTTTCGCCCATTGTGCAAT

ATTCCCCACTGCTGCCTCCCGAGGGAGTTTGGA

>SEQ ID NO: 78|YK171|
TGAGCCGGGCTCACCCCGGTACTGCATTGGAACTGTCGTACTAGAGTGTCGGAGGGGTAAGCGGAATTCCTAGTGTA

GCGGTGAAATGCGTAGATATTAGGAGGAACACCAGTGGCGAAGGCGGCTTACTGGACGATAACTGACGCTGAGGCTC

GAAAGCGTGGGGAGCAAACAGGATTAGATACACCGGTAA

>SEQ ID NO: 79|YK192|
CACGATGTCAGCTTTCGAGCTCAGCGTCAGTTATCGTCCAGTAAGCCGCCTTCGCCACTGGTGTTCCTCCTAATATC

TACGCATTTCACCGCTACACTAGGAATTCCACTTACCCCTCCGACACTCTAGTACGACAGTTTCCAATGCAGTACCG

GGGTTGAGCCCCGGGCTTTCACATCAGACTTGCCGCACCGCCTGCGCTCCCTTTACACCCAGTAAATCCGGATAACG

CTTGCACCATACGTATTACCGCGGCTGCTGGCACGTATTTAGCCGGTGCTTCTTAGTCAGGTACCGTCATTCTTCTT

-continued

CCCTGCTGATAGAGCTTTACATACCGAAATACTTCTTCGCTCACGCGGCGTCGCTGCATCAGGGTTTCCCCCATTGT

GCAATATTCCCCACTGCTGCCTCCCGAGGGGAGTTTGGA

>SEQ ID NO: 80|VE202-18|
ATGGAGAGTTTGATCCTGGCTCAGGATGAACGCTGGCGGCGTGCCTAATACATGCAAGTCGAACGCGAGCACTTGTG

CTCGAGTGGCGAACGGGTGAGTAATACATAAGTAACCTGCCCTAGACAGGGGGATAACTATTGGAAACGATAGCTAA

GACCGCATAGGTACGGACACTGCATGGTGACCGTATTAAAAGTGCCTCAAAGCACTGGTAGAGGATGGACTTATGG

CGCATTAGCTGGTTGGCGGGGTAACGGCCCACCAAGGCGACGATGCGTAGCCGACCTGAGAGGGTGACCGGCCACAC

TGGGACTGAGACACGGCCCAGACTCCTACGGGAGGCAGCAGTAGGGAATTTTCGGCAATGGGGGAAACCCTGACCGA

GCAACGCCGCGTGAAGGAAGAAGGTTTTCGGATTGTAAACTTCTGTTATAAAGGAAGAACGGCGGCTACAGGAAAT

GGTAGCCGAGTGACGGTACTTTATTAGAAAGCCACGGCTAACTACGTGCCAGCAGCCGCGGTAATACGTAGGTGGCA

AGCGTTATCCGGAATTATTGGGCGTAAAGAGGGAGCAGGCGGCAGCAAGGGTCTGTGGTGAAAGCCTGAAGCTTAAC

TTCAGTAAGCCATAGAAACCAGGCAGCTAGAGTGCAGGAGAGGATCGTGGAATTCCATGTGTAGCGGTGAAATGCG

TAGATATATGGAGGAACACCAGTGGCGAAGGCGACGATCTGGCCTGCAACTGACGCTCAGTCCCGAAAGCGTGGGGA

GCAAATAGGATTAGATACCCTAGTAGTCCACGCCGTAAACGATGAGTACTAAGTGTTGGATGTCAAAGTTCAGTGCT

GCAGTTAACGCAATAAGTACTCCGCCTGAGTAGTACGTTCGCAAGAATGAAACTCAAAGGAATTGACGGGGGCCCG

CACAAGCGGTGGAGCATGTGGTTTAATTCGAAGCAACGCGAAGAACCTTACCAGGTCTTGACATACTCATAAAGGCT

CCAGAGATGGAGAGATAGCTATATGAGATACAGGTGGTGCATGGTTGTCGTCAGCTCGTGTCGTGAGATGTTGGGTT

AAGTCCCGCAACGAGCGCAACCCTTATCGTTAGTTACCATCATTAAGTTGGGGACTCTAGCGAGACTGCCAGTGAC

AAGCTGGAGGAAGGCGGGGATGACGTCAAATCATCATGCCCCTTATGACCTGGGCTACACACGTGCTACAATGGATG

GTGCAGAGGGAAGCGAAGCCGCGAGGTGAAGCAAAACCCATAAAACCATTCTCAGTTCGGATTGTAGTCTGCAACTC

GACTACATGAAGTTGGAATCGCTAGTAATCGCGAATCAGCATGTCGCGGTGAATACGTTCTCGGGCCTTGTACACA

CCGCCCGTCACACCACGAGAGTTGATAACACCCGAAGCCGGTGGCCTAACCGCAAGGAAGGAGCTGTCTAAGGTGGG

ATTGATGATTGGGGTGAAGTCGTAACAAGGTATCCCTACGGGAACGTGGGGATGGATCACCTCCTTT

>SEQ ID NO: 81|PE5|
ATGAGAGTTTGATCCTGGCTCAGGATGAACGCTGGCGGCGTGCCTAACACATGCAAGTCGAACGAAGCAATTGAAGG

AAGTTTTCGGATGGAATTCGATTGACTGAGTGGCGGACGGGTGAGTAACGCGTGGATAACCTGCCTCACACTGGGGG

ATAACAGTTAGAAATGACTGCTAATACCGCATAAGCGCACAGTACCGCATGGTACAGTGTGAAAAACTCCGGTGGT

GTGAGATGGATCCGCGTCTGATTAGCCAGTTGGCGGGGTAACGGCCCACCAAAGCGACGATCAGTAGCCGACCTGAG

AGGGTGACCGGCCACATTGGGACTGAGACACGGCCCAAACTCCTACGGGAGGCAGCAGTGGGGAATATTGCACAATG

GGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGCGAAGCAAGTCTGAAGTGAAAACCCAGGGCTCAACCCTGGGAC

TGCTTTGGAAACTGTTTTGCTAGAGTGTCGGAGAGGTAAGTGGAATTCCTAGTGTAGCGGTGAAATGCGTAGATAT

TAGGAGGAACACCAGTGGCGAAGGCGGCTTACTGGACGATAACTGACGTTGAGGCTCGAAAGCGTGGGGAGCAAACA

GGATTAGATACCCTGGTAGTCCACGCCGTAAACGATGAATGCTAGGTGTTGGGGGGCAAAGCCCTTCGGTGCCGTCG

CAAACGCAGTAAGCATTCCACCTGGGGAGTACGTTCGCAAGAATGAAACTCAAAGGAATTGACGGGGACCCGCACA

AGCGGTGGAGCATGTGGTTTAATTCGAAGCAACGCGAAGAACCTTACCAAGTCTTGACATCCTCTTGACCGGCGTGT

AACGGCGCCTTCCCTTCGGGGCAAGAGAGACAGGTGGTGCATGGTTGTCGTCAGCTCGTGTCGTGAGATGTTGGGTT

AAGTCCCGCAACGAGCGCAACCCTTATCCTTAGTAGCCAGCAGGTAAAGCTGGGCACTCTAGGGAGACTGCCAGGG

ATAACCTGGAGGAAGGTGGGGATGACGTCAAATCATCATGCCCCTTATGATTTGGGCTACACACGTGCTACAATGGC

GTAAACAAAGGGAAGCAAGACAGTGATGTGGAGCAAATCCCAAAAATAACGTCCCAGTTCGGACTGTAGTCTGCAAC

-continued

CCGACTACACGAAGCTGGAATCGCTAGTAATCGCGAATCAGAATGTCGCGGTGAATACGTTCCCGGGTCTTGTACA

CACCGCCCGTCACACCATGGGAGTCAGCAACGCCCGAAGTCAGTGACCCAACTCGCAAGAGAGGGAGCTGCCGAAGG

CGGGGCAGGTAACTGGGGTGAAGTCGTAACAAGGTAGCCGTATCGGAAGGTGCGGCTGGATCACCTCCTTT

>SEQ ID NO: 82|PE9|
AATTCGACGTTGTCCGGATTACTGGGCGTAAAGGGAGCGTAGGCGGACTTTTAAGTGAGATGTGAAATACCCGGGCT

CAACTTGGGTGCTGCATTTCAAACTGGAAGTCTAGAGTGCAGGAGAGGAGAATGGAATTCCTAGTGTAGCGGTGAAA

TGCGTAGAGATTAGGAAGAACACCAGTGGCGAAGGCGATTCTCTGGACTGTAACTGACGCTGAGGCTCGAAAGCGTG

GGGAGCAAACAGGATTAGATACCCTGGTAGTCCACGCCGTAAACGATGAATACTAGGTGTAGGGGTTGTCATGACCT

CTGTGCCGCCGCTAACGCATTAAGTATTCCGCCTGGGGAGTACGGTCGCAAGATTAAAACTCAAAGAAATTGACGGA

>SEQ ID NO: 83|211-B|
ACGAGCGTATCGGATTATTGGGTTTAAGGGAGCGTAGGTGGATTGTTAAGTCAGTTGTGAAAGTTTGCGGCTCAACC

GTAAAATTGCAGTTGAAACTGGCAGTCTTGAGTACAGTAGAGGTGGGCGGAATTCGTGGTGTAGCGGTGAAATGCTT

AGATATCACGAAGAACTCCGATTGCGAAGGCAGCTCACTAGACTGTCACTGACACTGATGCTCGAAAGTGTGGGTAT

CAAACAGGATTAGATACCCTGGTAGTCCACACAGTAAACGATGAATACTCGCTGTTTGCGATATACAGTAAGCGGCC

AAGCGAAAGCATTAAGTATTCCACCTGGGGAGTACGCCGGCAACGGTGAAACTCAAAGAAATTGACGGAAGCCCGCC

CAGGGGGGAAAAACATGGGGTTTAGTTGGATGATACGGGGAGGAACCTC

>SEQ ID NO: 84|NR_119185.1|*Ruminococcus obeum* 16S ribosomal RNA gene,
complete sequence
GGCGGCGTGCTTAACACATGCAAGTCGAACGGGAAACCTTTCATTGAAGCTTCGGCAGATTTGGNNTGTTTCTAGTG

GCGGACGGGTGAGTAACGCGTGGGTAACCTGCCTTATACAGGGGGATAACAACCAGAAATGGTTGCTAATACCGCAT

AAGCGCACAGGACCGCATGGTCTGGTGTGAAAAACTCCGGTGGTATAAGATGGACCCGCGTTGGATTAGCTAGTTGG

CAGGGTAACGGCCTACCAAGGCGACGATCCATAGCCGGCCTGAGAGGGTGAACGGCCACATTGGGACTGAGACACGG

CCCAGACTCCTACGGGAGGCAGCAGTGGGGAATATTGCACAATGGGGGAAACCCTGATGCAGCGACGCCGCGTGAAG

GAAGAAGTATCTCGGTATGTAAACTTCTATCAGCAGGGAAGATAGTGACGGTACCTGACTAAGAAGCCCCGGCTAAC

TACGTGCCAGCAGCCGCGGTAATACGTAGGGGGCAAGCGTTATCCGGATTTACTGGGTGTAAAGGGAGCGTAGACGG

ACTGGCAAGTCTGATGTGAAAGGCGGGGGCTCAACCCCTGGACTGCATTGGAAACTGTTAGTCTTGAGTGCCGGAGA

GGTAAGCGGAATTCCTAGTGTAGCGGTGAAATGCGTAGATATTAGGAGGAACACCAGTGGCGAAGGCGGCTTACTGG

ACGGTAACTGACGTTGAGGCTCGAAAGCGTGGGGAGCAAACAGGATTAGATACCCTGGTAGTCCACGCCGTAAACGA

TGATTACTAGGTGTTGGGGAGCAAAGCTCTTCGGTGCCGCCGCAAACGCATTAAGTATTCCACCTGGGGAGTACGTT

CGCAAGAATGAAACTCAAAGGAATTGACGGGGACCCGCACAAGCGGTGGAGCATGTGGTTTAATTCGAAGCAACGCG

AAGAACCTTACCAAGTCTTGACATCCCTCTGACCGNCCCTTAACCGGATCTTTCCTTCGGGACAGGGGAGACAGGTG

GTGCATGGTTGTCGTCAGCTCGTGTCGTGAGATGTTGGGTTAAGTCCCGCAACGAGCGCAACCCCTATCCCCAGTAG

CCAGCAGTCCGGCTGGGCACTCTGAGGAGACTGCCAGGGATAACCTGGAGGAAGGCGGGGATGACGTCAAATCATCA

TGCCCCTTATGATTTGGGCTACACACGTGCTACAATGGCGTAAACAAAGGGAAGCAAGCCTGCGAAGGTAAGCAAAT

CCCAAAAATAACGTCCCAGTTCGGACTGCAGTCTGCAACTCGACTGCACGAAGCTGGAATCGCTAGTAATCGCGGAT

CAGAATGCCGCGGTGAATACGTTCCCGGGTCTTGTACACACCGCCCGTCACACCATGGGAGTCAGTAACGCCCGAAG

TCAGTGACCTAACTGCAAAGAAGGAGCTGCCGAAGGCGGGACCGATGACTGGGGTGAAGTCGTAACAAGGT

>SEQ ID NO: 85|NR_118692.1|*Ruminococcus obeum* strain ATCC 29174 16S ribosomal
RNA gene, complete sequence
GGCGTGCTTAACACATGCAAGTCGAACGGGAAACTTTTCATTGAAGCTTCGGCAGATTTGGTCTGTTTCTAGTGGCG

GACGGGTGAGTAACGCGTGGGTAACCTGCCTTATACAGGGGGATAACAACCAGAAATGGTTGCTAATACCGCATAAG

CGCACAGGACCGCATGGTCTGGTGTGAAAAACTCCGGTGGTATAAGATGGACCCGCGTTGGATTAGCTAGTTGGCAG

GGTAACGGCCTACCAAGGCGACGATCCATAGCCGGCCTGAGAGGGTGAACGGCCACATTGGGACTGAGACACGCCCC

AGACTCCTCGGGAGGCAGCAGTGGGGAATATTGCACAATGGGGGAAACCCTGATGCAGCGACGCCGCGTGAAGGAAG

-continued

AAGTATCTCGGTATGTAAACTTCTATCAGCAGGGAAGATAGTGACGGTACCTGACTAAGAAGCCCCGKCTAACTACG

TGCCAGCAGCCGCGGTAATACGTAGGGGGCAAGCGTTATCCGGATTTACTGGGTGTAAAGGGAGCGTAGACGGACTG

GCAAGTCTGATGTGAAAGGCGGGGGCTCAACCCCTGGACTGCATTGGAAACTGTTAGTCTTGAGTGCCGGAGAGGTA

AGCGGAATTCCTAGTGTAGCGGTGAAATGCGTAGATATTAGGAGGAACACCAGTGGCGAAGGCGGCTTACTGGACGG

TAACTGACGTTGAGGCTCGAAAGCGTGGGGAGCAAACAGGATTAGATACCCTGGTAGTCCACGCCGCAAACGATGAA

TACTAGGTGTTGGGGAGCAAAGCTCTTCGGTGCCGCCGCAAACGCATTAAGTATTCCACCTGGGGAGTACGTTCGCA

AGAATGAAACTCAAAGGAATTGACGGGGACCCGCACAAGCGGTGGAGCATGTGGTTTAATTCGAAGCAACGCGAAGA

ACCTTACCAAGTCTTGACATCCCTCTGACCGTCCCTTAACCGGATCTTTCCTTCGGGACAGGGGAGACAGGTGGTGC

ATGGTTGTCGTCAGCTCGTGTCGTGAGATGTTGGGTTAAGTCCCGCAACGAGCGCAACCCCTATCCCCAGTAGCCAG

CAGTNCGGCTGGGCACTCTGAGGAGACTGCCAGGGATAACCTGGAGGAAGGCGGGGATGACGTCAAATCATCATGCC

CCTTATGATTTGGGCTACACACGTGCTACAATGGCGTAAACAAAGGGAAGCNAGCCTKCGRAGGTAAGCAAATCCCA

NAAATAACGTCCCAGTTCGGACTGCAGTCTGCAACTCGACTGCACGAAGCTGGAATCGCTAGTAATCGCGGATCAGA

ATGCCGCGGTGAATACGTTCCCGGGTCTTGTACACACCGCCCGTCACACCATGGGAGTCAGTAACGCCCGAAGTCAG

TGACCTAACTGC

>SEQ ID NO: 86|NR_026491.1|*Clostridium disporicum* strain DS1 16S ribosomal RNA gene, partial sequence

GCTCAGGACGAACGCTGGCGGCGTGCCTAACACATGCAAGTCGAGCGAGTTGATTCTCTTCGGAGATGAAGCTAGCG

GCGGACGGGTGAGTAACACGTGGGCAACCTGCCTCATAGAGGGGAATAGCCTCCCGAAAGGGAGATTAATACCGCAT

AAGATTGTAGCTTCGCATGAAGTAGCAATTAAAGGAGCAATCCGCTATGAGATGGGCCCGCGGCGCATTAGCTAGTT

GGTGAGGTAACGGCTCACCAAGGCGACGATGCGTAGCCGACCTGAGAGGGTGATCGGCCACATTGGGACTGAGACAC

GGCCCAGACTCCTACGGGAGGCAGCAGTGGGGAATATTGCACAATGGGGGAAACCCTGATGCAGCAACGCCGCGTGA

GTGATGACGGCCTTCGGGTTGTAAAGCTCTGTCTTCAGGGACGATAATGACGGTACCTGAGGAGGAAGCCACGGCTA

ACTACGTGCCAGCAGCCGCGGTAATACGTAGGTGGCGAGCGTTGTCCGGATTTACTGGGCGTAAAGGGAGCGTAGGC

GGACTTTTAAGTGAGATGTGAAATACCCGGGCTCAACTTGGGTGCTGCATTTCAAACTGGAAGTCTAGAGTGCAGGA

GAGGAGAATGGAATTCCTAGTGTAGCGGTGAAATGCGTAGAGATTAGGAAGAACACCAGTGGCGAAGGCGATTCTCT

GGACTGTAACTGACGCTGAGGCTCGAAAGCGTGGGGAGCAAACAGGATTAGATACCCTGGTAGTCCACGCCGTAAAC

GATGAATACTAGGTGTAGGGGTTGTCATGACCTCTGTGCCGCCGCTAACGCATTAAGTATTCCGCCTGGGGAGTACG

GTCGCAAGATTAAAACTCAAAGGAATTGACGGGGGCCCGCACAAGCAGCGGAGCATGTGGTTTAATTCGAAGCAACG

CGAAGAACCTTACCTAGACTTGACATCTCCTGAATTACCCGTAACTGGGGAAGCCACTTCGGTGGCAGGAAGACAGG

TGGTGCATGGTTGTCGTCAGCTCGTGTCGTGAGATGTTGGGTTAAGTCCCGCAACGAGCGCAACCCTTATTGTTAGT

TGCTACCATTTAGTTGAGCACTCTAGCGAGACTGCCCGGGTTAACCGGGAGGAAGGTGGGGATGACGTCAAATCATC

ATGCCCCTTATGTCTAGGGCTACACACGTGCTACAATGGCAAGTACAAAGAGAAGCAAGACCGCGAGGTGGAGCAAA

ACTCAAAAACTTGTCTCAGTTCGGATTGTAGGCTGAAACTCGCCTACATGAAGCTGGAGTTGCTAGTAATCGCGAAT

CAGCATGTCGCGGTGAATACGTTCCCGGGCCTTGTACACACCGCCCGTCACACCATGAGAGTTGGCAATACCCAACG

TACGTGATCTAACCCGCAAGGGAGGAAGCGTCCTAAGGTAGGGTCAGCGATTGGGGTGAAGTCGTAACAAGGTAGCC

GTAGGAGAA

>SEQ ID NO: 87|NR_028785.1|*Clostridium scindens* strain ATCC 35704 16S ribosomal RNA gene, complete sequence

GAGAGTTTGATCCTGGCTCAGGATGAACGCTGGCGGCGTGCCTAACACATGCAAGTCGAACGAAGCGCCTGGCCCCG

ACTTCTTCGGAACGAGGAGCCTTGCGACTGAGTGGCGGACGGGTGAGTAACGCGTGGGCAACCTGCCTTGCACTGGG

GGATAACAGCCAGAAATGGCTGCTAATACCGCATAAGACCGAAGCGCCGCATGGCGCGGCGGCCAAAGCCCCGGCGG

TGCAAGATGGGCCCGCGTCTGATTAGGTAGTTGGCGGGGTAACGGCCCACCAAGCCGACGATCAGTAGCCGACCTGA

-continued

GAGGGTGACCGGCCACATTGGGACTGAGACACGGCCCAGACTCCTACGGGAGGCAGCAGTGGGGAATATTGCACAAT

GGGGGAAACCCTGATGCAGCGACGCCGCGTGAAGGATGAAGTATTTCGGTATGTAAACTTCTATCAGCAGGGAAGAA

GATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGCGATGCAAGCCAGATGTGAAAGCCCGGGGCTCAACCCCGGGAC

TGCATTTGGAACTGCGTGGCTGGAGTGTCGGAGAGGCAGGCGGAATTCCTAGTGTAGCGGTGAAATGCGTAGATATT

AGGAGGAACACCAGTGGCGAAGGCGGCCTGCTGGACGATGACTGACGTTGAGGCTCGAAAGCGTGGGGAGCAAACAG

GATTAGATACCCTGGTAGTCCACGCCGTAAACGATGACTACTAGGTGTCGGGTGGCAAGGCCATTCGGTGCCGCAGC

AAACGCAATAAGTAGTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCTGATCTTGACATCCCGATGCCAAAGCGCGTA

ACGCGCTCTTTCTTCGGAACATCGGTGACAGGTGGTGCATGGTTGTCGTCAGCTCGTGTCGTGAGATGTTGGGTTAA

GTCCCGCAACGAGCGCAACCCCTATCTTCAGTAGCCAGCATTTTGGATGGGCACTCTGGAGAGACTGCCAGGGAGAA

CCTGGAGGAAGGTGGGGATGACGTCAAATCATCATGCCCCTTATGACCAGGGCTACACACGTGCTACAATGGCGTAA

ACAAAGGGAGGCGAACCCGCGAGGGTGGGCAAATCCCAAAAATAACGTCTCAGTTCGGATTGTAGTCTGCAACTCGA

CTACATGAAGTTGGAATCGCTAGTAATCGCGAATCAGAATGTCGCGGTGAATACGTTCCCGGGTCTTGTACACACCG

CCCGTCACACCATGGGAGTCAGTAACGCCCGAAGCCGGTGACCCAACCCGTAAGGGAGGGAGCCGTCGAAGGTGGGA

CCGATAACTGGGGTGAAGTCGTAACAAGGTAGCCGTATCGGAAGGTGCGGCTGGATCACCTCCTTC

>SEQ ID NO: 88|NR_028915.1|*Anaerostipes caccae* strain L1-92 16S ribosomal RNA gene, partial sequence
GCGCTTAATACATGTCAAGTCGAACGAAGCATTTAGGATTGAAGTTTTCGGATGGATTTCCTATATGACTGAGTGGC

GGACGGGTGAGTAACGCGTGGGGAACCTGCCCTATACAGGGGGATAACAGCTGGAAACGGCTGCTAATACCGCATAA

GCGCACAGAATCGCATGATTCAGTGTGAAAAGCCCTGGCAGTATAGGATGGTCCCGCGTCTGATTAGCTGGTTGGTG

AGGTAACGGCTCACCAAGGCGACGATCAGTAGCCGGCTTGAGAGAGTGAACGGCCACATTGGGACTGAGACACGGCC

CAAACTCCTACGGGAGGCAGCAGTGGGGAATATTGCACAATGGGGGTAAACCCTGATGCAGCGACGCCGCGTGAGTG

AAGAAGTATTTCGGTATGTAAAGCTCTATCAGCAGGGAAGAAAACAGACGGTACCTGACTAAGAAGCCCCGGCTAAC

TACGTGCCAGCAGCCGCGGTAATACGTAGGGGGCAAGCGTTATCCGGAATTACTGGGTGTAAAGGGTGCGTAGGTGG

CATGGTAAGTCAGAAGTGAAAGCCCGGGGCTTAACCCCGGGACTGCTTTTGAAACTGTCATGCTGGAGTGCAGGAGA

GGTAAGCGGAATTCCTAGTGTAGCGGTGAAATGCGTAGATATTAGGAGGAACACCAGTGGCGAAGGCGGCTTACTGG

ACTGTCACTGACACTGATGCACGAAAGCGTGGGGAGCAAACAGGATTAGATACCCTGGTAGTCCACGCCGTAAACGA

TGAATACTAGGTGTCGGGGCCGTAGAGGCTTCGGTGCCGCAGCAAACGCAGTAAGTATTCCACCTGGGGAGTACGTT

CGCAAGAATGAAACTCAAAGGAATTGACGGGGACCCGCACAAGCGGTGGAGCATGTGGTTTAATTCGAAGCAACGCG

AAGAACCTTACCTGGTCTTGACATCCCAATGACCGAACCTTAACCGGTTTTTTCTTTCGAGACATTGGAGACAGGTG

GTGCATGGTTGTCGTCAGCTCGTGTCGTGAGATGTTGGGTTAAGTCCCGCAACGAGCGCAACCCCTATCTTTAGTAG

CCAGCATTTAAGGTGGGCACTCTAGAGAGACTGCCAGGGATAACCTGGAGGAAGGTGGGGACGACGTCAAATCATCA

TGCCCCTTATGGCCAGGGCTACACACGTGCTACAATGGCGTAAACAAAGGGAAGCGAAGTCGTGAGGCGAAGCAAAT

CCCAGAAATAACGTCTCAGTTCGGATTGTAGTCTGCAACTCGACTACATGAAGCTGGAATCGCTAGTAATCGTGAAT

CAGAATGTCACGGTGAATACGTTCCCGGGTCTTGTACACACCGCCCGTCACACCATGGGAGTCAGTAACGCCCGAAG

TCAGTGACCCAACCGCAAGGAGGGAGCTGCCGAAGGTGGGACCGATAACTGGGGTGAAGTCGTAACAAGG

>SEQ ID NO: 89|NR_042152.1|*Marvinbryantia formatexigens* strain I-52 16S ribosomal RNA gene, partial sequence >gi|636558750|ref|NR_114807.1| *Marvinbryantia formatexigens* strain I-52 16S ribosomal RNA gene, complete sequence
TGGCGGCGTGCTTAACACATGCAAGTCGAGCGAAGCATTTTAAATGAAGTTTTCGGACGGAATTTAAAATGACTGAG

CGGCGGACGGGTGAGTAACGCGTGGATAACCTGCCTTATACAGGGGGATAACAGCCAGAAATGGCTGCTAATACCGC

ATAAGCGCACGGTACCGCATGGTACAGTGTGAAAAACTCCGGTGGTATAAGATGGGTCCGCGTTGGATTAGGCAGTT

-continued

GGCGGGGTAAAGGCCCACCAAACCGACGATCCATAGCCGGCCTGAGAGGGTGGACGGCCACATTGGGACTGAGACAC

GGCCCAGACTCCTACGGGAGGCAGCAGTGGGGAATATTGCACAATGGGGGAAACCCTGATGCAGCGACGCCGCGTGG

GTGAAGAAGTATTTCGGTATGTAAAGCCCTATCAGCAGGGAAGAAAATGACGGTACCTGACCAAGAAGCCCCGGCTA

ACTACGTGCCAGCAGCCGCGGTAATACGTAGGGGGCAAGCGTTATCCGGATTTACTGGGTGTAAAGGGAGCGTAGAC

GGCCATGCAAGTCTGGTGTGAAAGGCGGGGGCTCAACCCCCGGACTGCATTGGAAACTGTATGGCTTGAGTGCCGGA

GAGGTAAGCGGAATTCCTGGTGTAGCGGTGAAATGCGTAGATATCAGGAGGAACACCAGTGGCGAAGGCGGCTTACT

GGACGGTAACTGACGTTGAGGCTCGAAAGCGTGGGGAGCAAACAGGATTAGATACCCTGGTAGTCCACGCCGTAAAC

GATGAATACCAGGTGTCGGGGGACACGGTCCTTCGGTGCCGCAGCAAACGCACTAAGTATTCCACCTGGGGAGTACG

TTCGCAAGAATGAAACTCAAAGGAATTGACGGGGACCCGCACAAGCGGTGGAGCATGTGGTTTAATTCGAAGCAACG

CGAAGAACCTTACCAGGTCTTGACATCCGGACGACCGGACAGTAACGTGTCCTTCCCTTCGGGGCGTCCGAGACAGG

TGGTGCATGGTTGTCGTCAGCTCGTGTCGTGAGATGTTGGGTTAAGTCCCGCAACGAGCGCAACCCCTGTTCCCAGT

AGCCAGCATTCAGGATGGGCACTCTGGGGAGACTGCCAGGGATAACCTGGAGGAAGGCGGGGATGACGTCAAATCAT

CATGCCCCTTATGATCTGGGCTACACACGTGCTACAATGGCGTGAACAGAGGGAAGCGAACCCGCGAGGGGGAGCAA

ATCCCAGAAATAACGTCCCAGTTCGGATTGTAGTCTGCAACCCGGCTACATGAAGCTGGAATCGCTAGTAATCGCGG

ATCAGCATGCCGCGGTGAATACGTTCCCGGGTCTTGTACACACCGCCCGTCACACCATGGGAGTCGGAAATGCCCGA

AGTCAGTGACCCAACCGGAAGGAGGGAGCTGCCGAAGGCGGGGCCGGTAACTGGGGTGAAGTCGTAACAA

>SEQ ID NO: 90|NR_024994.1|*Lactobacillus mucosae* strain S32 16S ribosomal RNA gene, complete sequence

AGAGTTTGATCCTGGCTCAGGATGAACGCCGGCGGTGTGCCTAATACATGCAAGTCGAACGCGTTGGCCCAACTGAT

TGAACGTGCTTGCACGGACTTGACGTTGGTTTACCAGCGAGTGGCGGACGGGTGAGTAACACGTAGGTAACCTGCCC

CAAAGCGGGGGATAACATTTGGAAACAGATGCTAATACCGCATAACAATTTGAATCGCATGATTCAAATTTAAAAGA

TGGCTTCGGCTATCACTTTGGGATGGACCTGCGGCGCATTAGCTTGTTGGTAGGGTAACGGCCTACCAAGGCTGTGA

TGCGTAGCCGAGTTGAGAGACTGATCGGCCACAATGGAACTGAGACACGGTCCATACTCCTACGGGAGGCAGCAGTA

GGGAATCTTCCACAATGGGCGCAAGCCTGATGGAGCAACACCGCGTGAGTGAAGAAGGGTTTCGGCTCGTAAAGCTC

TGTTGTTAGAGAAGAACGTGCGTGAGAGCAACTGTTCACGCAGTGACGGTATCTAACCAGAAAGTCACGGCTAACTA

CGTGCCAGCAGCCGCGGTAATACGTAGGTGGCAAGCGTTATCCGGATTTATTGGGCGTAAAGCGAGCGCAGGCGGTT

TGATAAGTCTGATGTGAAAGCCTTTGGCTTAACCAAAGAAGTGCATCGGAAACTGTCAGACTTGAGTGCAGAAGAGG

ACAGTGGAACTCCATGTGTAGCGGTGGAATGCGTAGATATATGGAAGAACACCAGTGGCGAAGGCGGCTGTCTGGTC

TGCAACTGACGCTGAGGCTCGAAAGCATGGGTAGCGAACAGGATTAGATACCCTGGTAGTCCATGCCGTAAACGATG

AGTGCTAGGTGTTGGAGGGTTTCCGCCCTTCAGTGCCGCAGCTAACGCATTAAGCACTCCGCCTGGGGAGTACGACC

GCAAGGTTGAAACTCAAAGGAATTGACGGGGGCCCGCACAAGCGGTGGAGCATGTGGTTTAATTCGAAGCTACGCGA

AGAACCTTACCAGGTCTTGACATCTTGCGCCAACCCTAGAGATAGGGCGTTTCCTTCGGGAACGCAATGACAGGTGG

TGCATGGTCGTCGTCAGCTCGTGTCGTGAGATGTTGGGTTAAGTCCCGCAACGAGCGCAACCCTTGTTACTAGTTGC

CAGCATTCAGTTGGGCACTCTAGTGAGACTGCCGGTGACAAACCGGAGGAAGGTGGGGACGACGTCAGATCATCATG

CCCCTTATGACCTGGGCTACACACGTGCTACAATGGACGGTACAACGAGTCGCGAACTCGCGAGGGCAAGCTAATCT

CTTAAAACCGTTCTCAGTTCGGACTGCAGGCTGCAACTCGCCTGCACGAAGTCGGAATCGCTAGTAATCGCGGATCA

GCATGCCGCGGTGAATACGTTCCCGGGCCTTGTACACACCGCCCGTCACACCATGAGAGTTTGCAACACCCAAAGTC

GGTGGGGTAACCCTTCGGGGAGCTAGCCGCCTAAGGTGGGGCAGATGATTAGGGTGAAGTCGTAACAAGGTAGCCGT

AGGAGAACCTGCGGCTGGATCACCTCCT

-continued

>SEQ ID NO: 91|NR_028816.1|*Turicibacter sanguinis* strain MOL361 16S ribosomal RNA gene, complete sequence

AGAGTTTGATCATGGCTCAGGATGAACGCTGGCGGCGTGCCTAATACATGCAAGTCGAGCGAACCACTTCGGTGGTG

AGCGGCGAACGGGTGAGTAACACGTAGGTTATCTGCCCATCAGACGGGGACAACGATTGGAAACGATCGCTAATACC

GGATAGGACGAAAGTTTAAAGGTGCTTCGGCACCACTGATGGATGAGCCTGCGGCGCATTAGCTAGTTGGTAGGGTA

AAGGCCTACCAAGGCGACGATGCGTAGCCGACCTGAGAGGGTGAACGGCCACACTGGGACTGAGACACGGCCCAGAC

TCCTACGGGAGGCAGCAGTAGGGAATCTTCGGCAATGGGCGAAAGCCTGACCGAGCAACGCCGCGTGAATGATGAAG

GCCTTCGGGTTGTAAAATTCTGTTATAAGGGAAGAATGGCTCTAGTAGGAAATGGCTAGAGTGTGACGGTACCTTAT

GAGAAAGCCACGGCTAACTACGTGCCAGCAGCCGCGGTAATACGTAGGTGGCGAGCGTTATCCGGAATTATTGGGCG

TAAAGAGCGCGCAGGTGGTTGATTAAGTCTGATGTGAAAGCCCACGGCTTAACCGTGGAGGGTCATTGGAAACTGGT

CAACTTGAGTGCAGAAGAGGGAAGTGGAATTCCATGTGTAGCGGTGAAATGCGTAGAGATATGGAGGAACACCAGTG

GCGAAGGCGGCTTCCTGGTCTGTAACTGACACTGAGGCGCGAAAGCGTGGGGAGCAAACAGGATTAGATACCCTGGT

AGTCCACGCCGTAAACGATGAGTGCTAAGTGTTGGGGGTCGAACCTCAGTGCTGAAGTTAACGCATTAAGCACTCCG

CCTGGGGAGTACGGTCGCAAGACTGAAACTCAAAGGAATTGACGGGGACCCGCACAAGCGGTGGAGCATGTGGTTTA

ATTCGAAGCAACGCGAAGAACCTTACCAGGTCTTGACATACCAGTGACCGTCCTAGAGATAGGATTTTCCCTTCGGG

GACAATGGATACAGGTGGTGCATGGTTGTCGTCAGCTCGTGTCGTGAGATGTTGGGTTAAGTCCCGCAACGAGCGCA

ACCCCTGTCGTTAGTTGCCAGCATTCAGTTGGGGACTCTAACGAGACTGCCAGTGACAAACTGGAGGAAGGTGGGGA

TGACGTCAAATCATCATGCCCCTTATGACCTGGGCTACACACGTGCTACAATGGTTGGTACAAAGAGAAGCGAAGCG

GTGACGTGGAGCAAACCTCATAAAGCCAATCTCAGTTCGGATTGTAGGCTGCAACTCGCCTACATGAAGTTGGAATC

GCTAGTAATCGCGAATCAGCATGTCGCGGTGAATACGTTCCCGGGTCTTGTACACACCGCCCGTCACACCACGAGAG

TTTACAACACCCGAAGTCAGTGGCCTAACCGCAAGGAGGGAGCTGCCTAAGGTGGGGTAGATGATTGGGGTGAAGTC

GTAACAAGGTATCCCTACCGGAAGGTGGGGTTGGATCACCTCCTT

>SEQ ID NO: 92|NR_042832.1|*Roseburia faecis* strain M72/1 16S ribosomal RNA gene, partial sequence

GATGAACGCTGGCGGCGTGCTTAACACATGCAAGTCGAACGAAGCACTCTATTTGATTTTCTTCGGAAATGAAGATT

TTGTGACTGAGTGGCGGACGGGTGAGTAACGCGTGGGTAACCTGCCTCATACAGGGGGATAACAGTTGGAAACGACT

GCTAATACCGCATAAGCGCACAGGATCGCATGATCCGGTGTGAAAAACTCCGGTGGTATGAGATGGACCCGCGTCTG

ATTAGCCAGTTGGCAGGGTAACGGCCTACCAAAGCGACGATCAGTAGCCGACCTGAGAGGGTGACCGGCCACATTGG

GACTGAGACACGGCCCAAACTCCTACGGGAGGCAGCAGTGGGGAATATTGCACAATGGGGGAAACCCTGATGCAGCG

ACGCCGCGTGAGCGAAGAAGTATTTCGGTATGTAAAGCTCTATCAGCAGGGAAGAAGAATGACGGTACCTGACTAAG

AAGCACCGGCTAAATACGTGCCAGCAGCCGCGGTAATACGTATGGTGCAAGCGTTATCCGGATTTACTGGGTGTAAA

GGGAGCGCAGGCGGTGCGGCAAGTCTGATGTGAAAGCCCGGGGCTCAACCCCGGTACTGCATTGGAAACTGTCGTAC

TAGAGTGTCGGAGGGGTAAGTGGAATTCCTAGTGTAGCGGTGAAATGCGTAGATATTAGGAGGAACACCAGTGGCGA

AGGCGGCTTACTGGACGATAACTGACGCTGAGGCTCGAAAGCGTGGGGAGCAAACAGGATTAGATACCCTGGTAGTC

CACGCCGTAAACGATGAATACTAGGTGTCGGGGAGCATTGCTCTTCGGTGCCGCAGCAAACGCAATAAGTATTCCAC

CTGGGGAGTACGTTCGCAAGAATGAAACTCAAAGGAATTGACGGGGACCCGCACAAGCGGTGGAGCATGTGGTTTAA

TTCGAAGCAACGCGAAGAACCTTACCAAGTCTTGACATCCCGATGACAGAGTATGTAATGTACYTTCTCTTCGGAGC

ATCGGTGACAGGTGGTGCATGGTTGTCGTCAGCTCGTGTCGTGAGATGTTGGGTTAAGTCCCGCAACGAGCGCAACC

CCTGTCCTTAGTAGCCAGCGGTTCGGCCGGGCACTCTAGGGAGACTGCCAGGGATAACCTGGAGGAAGGCGGGGATG

ACGTCAAATCATCATGCCCCTTATGACTTGGGCTACACACGTGCTACAATGGCGTAAACAAAGGGAAGCGGAGCCGT

GAGGCCGAGCAAATCTCAAAAATAACGTCTCAGTTCGGACTGTAGTCTGCAACCCGACTACACGAAGCTGGAATCGC

-continued

TAGTAATCGCAGATCAGAATGCTGCGGTGAATACGTTCCCGGGTCTTGTACACACCGCCCGTCACACCATGGGAGTT

GGAAATGCCCGAAGTCAGTGACCCAACCGCAAGGAGGGAGCTGCCGAAGGCAGGTTCGATAACTGGGGTG

>SEQ ID NO: 93|NR_043142.1|*Flavonifractor plautii* strain Prevot S1 16S ribosomal RNA gene, partial sequence

CGCTGGCGGCGTGCTTAACACATGCAAGTCGAACGGGGTGCTCATGACGGAGGATTCGTCCAATGGATTGAGTTACC

TAGTGGCGGACGGGTGAGTAACGCGTGAGGAACCTGCCTTGGAGAGGGGAATAACACTCCGAAAGGAGTGCTAATAC

CGCATGAAGCAGTTGGGTCGCATGGCTCTGACTGCCAAAGATTTATCGCTCTGAGATGGCCTCGCGTCTGATTAGCT

AGTAGGCGGGGTAACGGCCCACCTAGGCGACGATCAGTAGCCGGACTGAGAGGTTGACCGGCCACATTGGGACTGAG

ACACGGCCCAGACTCCTACGGGAGGCAGCAGTGGGGAATATTGGGCAATGGGCGCAAGCCTGACCCAGCAACGCCGC

GTGAAGGAAGAAGGCTTTCGGGTTGTAAACTTCTTTTGTCGGGGACGAAACAAATGACGGTACCCGACGAATAAGCC

ACGGCTAACTACGTGCCAGCAGCCGCGGTAATACGTAGGTGGCAAGCGTTATCCGGATTTACTGGGTGTAAAGGGCG

TGTAGGCGGGATTGCAAGTCAGATGTGAAAACTGGGGGCTCAACCTCCAGCCTGCATTTGAAACTGTAGTTCTTGAG

TGCTGGAGAGGCAATCGGAATTCCGTGTGTAGCGGTGAAATGCGTAGATATACGGAGGAACACCAGTGGCGAAGGCG

GATTGCTGGACAGTAACTGACGCTGAGGCGCGAAAGCGTGGGGAGCAAACAGGATTAGATACCCTGGTAGTCCACGC

CGTAAACGATGGATACTAGGTGTGGGGGGTCTGACCCCCTCCGTGCCGCAGTTAACACAATAAGTATCCCACCTGGG

GAGTACGATCGCAAGGTTGAAACTCAAAGGAATTGACGGGGGCCCGCACAAGCGGTGGAGTATGTGGTTTAATTCGA

AGCAACGCGAAGAACCTTACCAGGGCTTGACATCCCACTAACGAGGCAGAGATGCGTTAGGTGCCCTTCGGGGAAAG

TGGAGACAGGTGGTGCATGGTTGTCGTCAGCTCGTGTCGTGAGATGTTGGGTTAAGTCCCGCAACGAGCGCAACCCT

TATTGTTAGTTGCTACGCAAGAGCACTCTAGCGAGACTGCCGTTGACAAAACGGAGGAAGGTGGGGACGACGTCAAA

TCATCATGCCCCTTATGTCCTGGGCCACACACGTACTACAATGGTGGTTAACAGAGGGAGGCAATACCGCGAGGTGG

AGCAAATCCCTAAAAGCCATCCCAGTTCGGATTGCAGGCTGAAACCCGCCTGTATGAAGTTGGAATCGCTAGTAATC

GCGGATCAGCATGCCGCGGTGAATACGTTCCCGGGCCTTGTACACACCGCCCGTCACACCATGAGAGTCGGGAACAC

CCGAAGTCCGTAGCCTAACCGCAAGGAGGGCGCGGCCGAAGGTGGGTTCGATAATTGGGGTGAAGTCGTAACAAGGT

AG

>SEQ ID NO: 94|NR_044054.1|*Blautia wexlerae* strain DSM 19850 16S ribosomal RNA gene, partial sequence

CAAGTCGAACGGGAATTANTTTATTGAAACTTCGGTCGATTTAATTTAATTCTAGTGGCGGACGGGTGAGTAACGCG

TGGGTAACCTGCCTTATACAGGGGGATAACAGTCAGAAATGGCTGCTAATACCGCATAAGCGCACAGAGCTGCATGG

CTCAGTGTGAAAAACTCCGGTGGTATAAGATGGACCCGCGTTGGATTAGCTTGTTGGTGGGGTAACGGCCCACCAAG

GCGACGATCCATAGCCGGCCTGAGAGGGTGAACGGCCACATTGGGACTGAGACACGGCCCAGACTCCTACGGGAGGC

AGCAGTGGGGAATATTGCACAATGGGGGAAACCCTGATGCAGCGACGCCGCGTGAAGGAAGAAGTATCTCGGTATGT

AAACTTCTATCAGCAGGGAAGATAGTGACGGTACCTGACTAAGAAGCCCCGGCTAACTACGTGCCAGCAGCCGCGGT

AATACGTAGGGGGCAAGCGTTATCCGGATTTACTGGGTGTAAAGGGAGCGTAGACGGTGTGGCAAGTCTGATGTGAA

AGGCATGGGCTCAACCTGTGGACTGCATTGGAAACTGTCATACTTGAGTGCCGGAGGGGTAAGCGGAATTCCTAGTG

TAGCGGTGAAATGCGTAGATATTAGGAGGAACACCAGTGGCGAAGGCGGCTTACTGGACGGTAACTGACGTTGAGGC

TCGAAAGCGTGGGGAGCAAACAGGATTAGATACCCTGGTAGTCCACGCCGTAAACGATGAATAACTAGGTGTCGGGT

GGCAAAGCCATTCGGTGCCGTCGCAAACGCAGTAAGTATTCCACCTGGGGAGTACGTTCGCAAGAATGAAACTCAAA

GGAATTGACGGGGACCCGCACAAGCGGTGGAGCATGTGGTTTAATTCGAAGCAACGCGAAGAACCTTACCAAGTCTT

GACATCCGCCTGACCGATCCTTAACCGGATCTTTCCTTCGGGACAGGCGAGACAGGTGGTGCATGGTTGTCGTCAGC

TCGTGTCGTGAGATGTTGGGTTAAGTCCCGCAACGAGCGCAACCCCTATCCTCAGTAGCCAGCATTTAAGGTGGGCA

CTCTGGGGAGACTGCCAGGGATAACCTGGAGGAAGGCGGGGATGACGTCAAATCATCATGCCCCTTATGATTTGGGC

TACACACGTGCTACAATGGCGTAAACAAAGGGAAGCGAGATTGTGAGATGGAGCAAATCCCAAAAATAACGTCCCAG

-continued

TTCGGACTGTAGTCTGCAACCCGACTACACGAAGCTGGAATCGCTAGTAATCGCGGATCAGAATGCCGCGGTGAATA

CGTTCCCGGGTCTTGTACACACCGCCCGTCACACCATGGGAGTCAGTAACGCCCGAAGTCAGTGACCTAACTGCAAA

GAAGGAGCTGCCGAAGGCGGGACCGATGACTGGGGTGAAGTCGTAACAAGGT

>SEQ ID NO: 95|NR_027558.1|*Anaerotruncus colihominis* strain WAL 14565 16S ribosomal RNA gene, partial sequence

AACGGAGCTTACGTTTTGAAGTTTTCGGATGGATGAATGTAAGCTTAGTGGCGGACGGGTGAGTAACACGTGAGCAA

CCTGCCTTTCAGAGGGGGATAACAGCCGGAAACGGCTGCTAATACCGCATGATGTTGCGGGGGCACATGCCCCTGCA

ACCAAAGGAGCAATCCGCTGAAAGATGGGCTCGCGTCCGATTAGCCAGTTGGCGGGGTAACGGCCCACCAAAGCGAC

GATCGGTAGCCGGACTGAGAGGTTGAACGGCCACATTGGGACTGAGACACGGCCCAGACTCCTACGGGAGGCAGCAG

TGGGGGATATTGCACAATGGGCGAAAGCCTGATGCAGCGACGCCGCGTGAGGGAAGACGGTCTTCGGATTGTAAACC

TCTGTCTTTGGGGAAGAAAATGACGGTACCCAAAGAGGAAGCTCCGGCTAACTACGTGCCAGCAGCCGCGGTAATAC

GTAGGGAGCAAGCGTTGTCCGGAATTACTGGGTGTAAAGGGAGCGTAGGCGGGATGGCAAGTAGAATGTTAAATCCA

TCGGCTCAACCGGTGGCTGCGTTCTAAACTGCCGTTCTTGAGTGAAGTAGAGGCAGGCGGAATTCCTAGTGTAGCGG

TGAAATGCGTAGATATTAGGAGGAACACCAGTGGCGAAGGCGGCCTGCTGGGCTTTAACTGACGCTGAGGCTCGAAA

GCGTGGGGAGCAAACAGGATTAGATACCCTGGTAGTCCACGCCGTAAACGATGATTACTAGGTGTGGGGGGACTGAC

CCCTTCCGTGCCGCAGTTAACACAATAAGTAATCCACCTGGGGAGTACGGCCGCAAGGTTGAAACTCAAAGGAATTG

ACGGGGGCCCGCACAAGCAGTGGAGTATGTGGTTTAATTCGAAGCAACGCGAAGAACCTTACCAGGTCTTGACATCG

GCGTAATAGCCTAGAGAGTAGGTGAAGCCCTTCGGGGCATCCAGACAGGTGGTGCATGGTTGTCGTCAGCTCGTGTC

GTGAGATGTTGGGTTAAGTCCCGCAACGAGCGCAACCCTTATTATTAGTTGCTACGCAAGAGCACTCTAATGAGACT

GCCGTTGACAAAACGGAGGAAGGTGGGGATGACGTCAAATCATCATGCCCCTTATGACCTGGGCTACACACGTACTA

CAATGGCACTAAAACAGAGGGCGGCGACACCGCGAGGTGAAGCGAATCCCAGAAAAAGTGTCTCAGTTCAGATTGCA

GGCTGCAACCCGCCTGCATGAAGTCGGAATTGCTAGTAATCGCGGATCAGCATGCCGCGGTGAATACGTTCCCGGGC

CTTGTACACACCGCCCGTCACACCATGGGAGTCCGGGTAACACCCGAAGCCAGTAG

>SEQ ID NO: 96|NR_116747.1|*Ruminococcus faecis* strain Eg2 16S ribosomal RNA gene, partial sequence

ATGCAAGTCGAACGAAGCACCTTGATTTGATTCTTCGGATGAAGATCTTGGTGACTGAGTGGCGGACGGGTGAGTAA

CGCGTGGGTAACCTGCCTCATACAGGGGGATAACAGTTAGAAATGACTGCTAATACCGCATAAGACCACAGCACCGC

ATGGTGCAGGGGTAAAAACTCCGGTGGTATGAGATGGACCCGCGTCTGATTAGGTAGTTGGTGGGGTAACGGCCTAC

CAAGCCGACGATCAGTAGCCGACCTGAGAGGGTGACCGGCCACATTGGGACTGAGACACGGCCCAAACTCCTACGGG

AGGCAGCAGTGGGGAATATTGCACAATGGGGGAAACCCTGATGCAGCGACGCCGCGTGAGCGATGAAGTATTTCGGT

ATGTAAAGCTCTATCAGCAGGGAAGAAAATGACGGTACCTGACTAAGAAGCACCGGCTAAATACGTGCCAGCAGCCG

CGGTAATACGTATGGTGCAAGCGTTATCCGGATTTACTGGGTGTAAAGGGAGCGTAGACGGAGTGGCAAGTCTGATG

TGAAAACCCGGGGCTCAACCCCGGGACTGCATTGGAAACTGTCAATCTAGAGTACCGGAGAGGTAAGCGGAATTCCT

AGTGTAGCGGTGAAATGCGTAGATATTAGGAGGAACACCAGTGGCGAAGGCGGCTTACTGGACGGTAACTGACGTTG

AGGCTCGAAAGCGTGGGGAGCAAACAGGATTAGATACCCTGGTAGTCCACGCCGTAAACGATGACTACTAGGTGTCG

GGCAGCAAAGCTGTTCGGTGCCGCAGCAAACGCAATAAGTAGTCCACCTGGGGAGTACGTTCGCAAGAATGAAACTC

AAAGGAATTGACGGGGACCCGCACAAGCGGTGGAGCATGTGGTTTAATTCGAAGCAACGCGAAGAACCTTACCTGCT

CTTGACATCTCCCTGACCGGCAAGTAATGTTGCCTTTCCTTCGGGACAGGGATGACAGGTGGTGCATGGTTGTCGTC

AGCTCGTGTCGTGAGATGTTGGGTTAAGTCCCGCAACGAGCGCAACCCCTATCTTTAGTAGCCAGCGGTTTGGCCGG

GCACTCTAGAGAGACTGCCAGGGATAACCTGGAGGAAGGTGGGGATGACGTCAAATCATCATGCCCCTTATGAGCAG

GGCTACACACGTGCTACAATGGCGTAAACAAAGGGAGGCAGAACCGCGAGGTCGAGCAAATCCCAAAAATAACGTCT

CAGTTCGGATTGTAGTCTGCAACTCGACTACATGAAGCTGGAATCGCTAGTAATCGCGAATCAGAATGTCGCGGTGA

-continued

ATACGTTCCCGGGTCTTGTACACACCGCCCGTCACACCATGGGAGTCAGTAACGCCCGAAGTCAGTGACCCAACCGT

AAGGAGGAGCTGCCGAAG

>SEQ ID NO: 97|NR_028883.1|*Dorea longicatena* strain 111-35 16S ribosomal RNA gene, partial sequence
TAACGCGTGGGTAACCTGCCTCATACAGGGGGATAACAGTTAGAAATGACTGCTAATACCGCATAAGACCACGTACC

GCATGGTACAGTGGTAAAAACTCCGGTGGTATGAGATGGACCCGCGTCTGATTAGGTAGTTGGTGGGGTAACGGCCT

ACCAAGCCGACGATCAGTAGCCGACCTGAGAGGGTGACCGGCCACATTGGGACTGAGACACGGCCCAGACTCCTACG

GGAGGCAGCAGTGGGGAATATTGCACAATGGAGGAAACTCTGATGCAGCGACGCCGCGTGAAGGATGAAGTATTTCG

GTATGTAAACTTCTATCAGCAGGGAAGAAAATGACGGTACCTGACTAAGAAGCCCCGGCTAACTACGTGCCAGCAGC

CGCGGTAATACGTAGGGGGCAAGCGTTATCCGGATTTACTGGGTGTAAAGGGAGCGTAGACGGCACGGCAAGCCAGA

TGTGAAAAGCCCGGGGCTCAACCCCGGGACTGCATTTGGAACTGCTGAGCTAGAGTGTCGGAGAGGCAAGTGGAATT

CCTAGTGTAGCGGTGAAATGCGTAGATATTAGGAGGAACACCAGTGGCGAAGGCGGCTTGCTGGACGATGACTGACG

TTGAGGCTCGAAAGCGTGGGGAGCAAACAGGATTAGATACCCTGGTAGTCCACGCCGTAAACGATGACTGCTAGGTG

TCGGGTGGCAAAGCCATTCGGTGCCGCAGCTAACGCAATAAGCAGTCCACCTGGGGAGTACGTTCGCAAGAATGAAA

CTCAAAGGAATTGACGGGGACCCGCACAAGCGGTGGAGCATGTGGTTTAATTCGAAGCAACGCGAAGAACCTTACCT

GATCTTGACATCCCGATGACCGCTTCGTAATGGAAGTTTTTCTTCGGAACATCGGTGACAGGTGGTGCATGGTTGTC

GTCAGCTCGTGTCGTGAGATGTTGGGTTAAGTCCCGCAACGAGCGCAACCCCTATCTTCAGTAGCCAGCAGGTTAAG

CTGGGCACTCTGGAGAGACTGCCAGGGATAACCTGGAGGAAGGTGGGGATGACGTCAAATCATCATGCCCCTTATGA

CCAGGGCTACACACGTGCTACAATGGCGTAAACAAAGAGAAGCGAACTCGCGAGGGTAAGCAAATCTCAAAAATAAC

GTCTCAGTTCGGATTGTAGTCTGCAACTCGACTACATGAAGCTGGAATCGCTAGTAATCGCAGATCAGAATGCTGCG

GTGAATACGTTCCCGGGTCTTGTACACACCGCCCGTCACACCATGGGAGTCATAACGCCCGAAGTCAGTGACCCAAC

CGTAAGG

>SEQ ID NO: 98|NR_029164.1|*Clostridium innocuum* strain B-3 16S ribosomal RNA gene, partial sequence
ATGGAGAGTTTGATCCTGGCTCAGGATGAACGCTGGCGGCATGCCTAATACATGCAAGTCGAACGAAGTCTTCAGGA

AGCTTGCTTCCAAAAAGACTTAGTGGCGAACGGGTGAGTAACACGTAGGTAACCTGCCCATGTGTCCGGGATAACTG

CTGGAAACGGTAGCTAAAACCGGATAGGTATACGGAGCGCATGCTCTGTATATTAAAGCGCCCTTCAAGGCGTGAAC

ATGGATGGACCTGCGACGCATTAGCTAGTTGGTGAGGTAACGGCCCACCAAGGCGATGATGCGTAGCCGGCCTGAGA

GGGTAAACGGCCACATTGGGACTGAGACACGGCCCAAACTCCTACGGGAGGCAGCAGTAGGGAATTTTCGTCAATGG

GGGAAACCCTGAACGAGCAATGCCGCGTGAGTGAAGAAGGTCTTCGGATCGTAAAGCTCTGTTGTAAGTGAAGAACG

GCTCATAGAGGAAATGCTATGGGAGTGACGGTAGCTTACCAGAAAGCCACGGCTAACTACGTGCCAGYAGCCGCGGT

AATACGTAGGTGGCAAGCGTTATCCGGAATCATTGGGCGTAAAGGGTGCGTAGGTGGCGTACTAAGTCTGTAGTAAA

AGGCAATGGCTCAACCATTGTAAGCTATGGAAACTGGTATGCTGGAGTGCAGAAGAGGGCGATGGAATTCCATGTGT

AGCGGTAAAATGCGTAGATATATGGAGGAACACCAGTGGCGAAGGCGGTCGCCTGGTCTGTAACTGACACTGAGGCA

CGAAAGCGTGGGGAGCAAATAGGATTAGATACCCTAGTAGTCCACGCCGTAAACGATGAGAACTAAGTGTTGGAGAA

ATTCAGTGCTGCAGTTAACGCAATAAGTTCTCCGCCTGGGGAGTATGCACGCAAGTTNGAAACTCAAAGGAATTGAC

GGGGGCCCGCACAAGCGNTGGAGTATGTGGTTTAATTCGAAGCAACGCGAAGAACCTTACCAGGCCTTGACATGGAA

ACAAATACCCTAGAGATAGGGGGATAATTATGGATCACACAGGTGGTGCATGGTTGTCGTCAGCTCGTGTCGTGAGA

TGTTGGGTTAAGTCCCGCAACGAGCGCAACCCTTGTCGCATGTTACCAGCATCAAGTTGGGGACTCATGCGAGACTG

CCGGTGACAAACCGGAGGAAGGTGGGGATGACGTCAAATCATCATGCCCCTTATGGCCTGGGCTACACACGTACTAC

AATGGCGACCACAAAGAGCAGCGACTTGGTGACAAGAAGCGAATCTCATAAAGATCGTCTCAGTTCGGATTGAAGTC

TGCAACTCGACTTCATGAAGTCGGAATCGCTAGTAATCGCAGATCAGCATGCTGCGGTGAATACGTTCTCGGGCCTT

-continued

GTACACACCGCCCGTCAAACCATGGGAGTCAGTAATACCCGAAGCCGGTGGCATAACCGTAAGGAGTGAGCCGTCGA

AGGTAGGACCGA

>SEQ ID NO: 99|NR_104687.1|*Blautia hansenii* strain JCM 14655 16S ribosomal RNA gene, partial sequence

AGAGTTTGATCCTGGCTCAGGATGAACGCTGGCGGCGTGCTTAACACATGCAAGTCGAGCGAAGCACTTATCATTGA

CTCTTCGGAAGATTTGATATTTGACTGAGCGGCGGACGGGTGAGTAACGCGTGGGTAACCTGCCTCATACAGGGGAA

TAACAGTTAGAAATGGCTGCTAATGCCGCATAAGCGCACAGGACCGCATGGTCTGGTGTGAAAAACTGAGGTGGTAT

GAGATGGACCCGCGTCTGATTAGGTAGTTGGTGGGGTAACGGCCTACCAAGCCGACGATCAGTAGCCGGCCTGAGAG

GGTGAACGGCCACATTGGGACTGAGACACGGCCCAGACTCCTACGGGAGGCAGCAGTGGGGAATATTGCACAATGGG

GGAAACCCTGATGCAGCGACGCCGCGTGAAGGAAGAAGTATCTCGGTATGTAAACTTCTATCAGCAGGGAAGAAAAT

GACGGTACCTGACTAAGAAGCCCCGGCTAACTACGTGCCAGCAGCCGCGGTAATACGTAGGGGGCAAGCGTTATCCG

GATTTACTGGGTGTAAAGGGAGCGTAGACGGAAGAGCAAGTCTGATGTGAAAGGCTGGGGCTTAACCCCAGGACTGC

ATTGGAAACTGTTTTTCTAGAGTGCCGGAGAGGTAAGCGGAATTCCTAGTGTAGCGGTGAAATGCGTAGATATTAGG

AGGAACACCAGTGGCGAAGGCGGCTTACTGGACGGTAACTGACGTTGAGGCTCGAAAGCGTGGGGAGCAAACAGGAT

TAGATACCCTGGTAGTCCACGCCGTAAACGATGAATACTAGGTGTCGGGGTGCAAAGCAGTTCGGTGCCGCAGCAAA

CGCAATAAGTATTCCACCTGGGGAGTACGTTCGCAAGAATGAAACTCAAAGGAATTGACGGGGACCCGCACAAGCGG

TGGAGCATGTGGTTTAATTCGAAGCAACGCGAAGAACCTTACCAAGTCTTGACATCTGCCTGACCGTTCCTTAACCG

GAGCTTTCCTTCGGGACAGGCAAGACAGGTGGTGCATGGTTGTCGTCAGCTCGTGTCGTGAGATGTTGGGTTAAGTC

CCGCAACGAGCGCAACCCCTATCCTTAGTAGCCAGCAGTCCGGCTGGGCACTCTAGGGAGACTGCCGGGGATAACCC

GGAGGAAGGCGGGGACGACGTCAAATCATCATGCCCCTTATGATTTGGGCTACACACGTGCTACAATGGCGTAAACA

AAGGGAAGCGAAGCGGTGACGCTTAGCAAATCTCAAAAATAACGTCCCAGTTCGGACTGCAGTCTGCAACTCGACTG

CACGAAGCTGGAATCGCTAGTAATCGCGAATCAGAATGTCGCGGTGAATACGTTCCCGGGTCTTGTACACACCGCCC

GTCACACCATGGGAGTCAGTAACGCCCGAAGTCAGTGACCCAACCTTATGGAGGGAGCTGCCGAAGGCGGGACCGAT

AACTGGGGTGAAGTCGTAACAAGGTAACC

>SEQ ID NO: 100|NR_112933.1|*Bacteroides cellulosilyticus* strain JCM 15632 16S ribosomal RNA gene, partial sequence

AGAGTTTGATCCTGGCTCAGGATGAACGCTAGCTACAGGCTTAACACATGCAAGTCGAGGGGCAGCATGACCTAGCA

ATAGGTTGATGGCGACCGGCGCACGGGTGAGTAACACGTATCCAACCTACCGGTTATTCCGGGATAGCCTTTCGAAA

GAAAGATTAATACCGGATAGTATAACGAGAAGGCATCTTTTTGTTATTAAAGAATTTCGATAACCGATGGGGATGCG

TTCCATTAGTTTGTTGGCGGGGTAACGGCCCACCAAGACATCGATGGATAGGGGTTCTGAGAGGAAGGTCCCCCACA

TTGGAACTGAGACACGGTCCAAACTCCTACGGGAGGCAGCAGTGAGGAATATTGGTCAATGGACGAGAGTCTGAACC

AGCCAAGTAGCGTGAAGGATGACTGCCCTATGGGTTGTAAACTTCTTTTATATGGGAATAAAGTGAGCCACGTGTGG

CTTTTTGTATGTACCATACGAATAAGGATCGGCTAACTCCGTGCCAGCAGCCGCGGTAATACGGAGGATCCGAGCGT

TATCCGGATTTATTGGGTTTAAAGGGAGCGTAGGCGGACTATTAAGTCAGCTGTGAAAGTTTGCGGCTCAACCGTAA

AATTGCAGTTGATACTGGTCGTCTTGAGTGCAGTAGAGGTAGGCGGAATTCGTGGTGTAGCGGTGAAATGCTTAGAT

ATCACGAAGAACTCCGATTGCGAAGGCAGCTTACTGGACTGTAACTGACGCTGATGCTCGAAAGTGTGGGTATCAAA

CAGGATTAGATACCCTGGTAGTCCACACAGTAAACGATGAATACTCGCTGTTTGCGATATACAGCAAGCGGCCAAGC

GAAAGCATTAAGTATTCCACCTGGGGAGTACGCCGGCAACGGTGAAACTCAAAGGAATTGACGGGGGCCCGCACAAG

CGGAGGAACATGTGGTTTAATTCGATGATACGCGAGGAACCTTACCCGGGCTTAAATTGCATCTGAATAATTTGGAA

ACAGATTAGCCGCAAGGCAGATGTGAAGGTGCTGCATGGTTGTCGTCAGCTCGTGCCGTGAGGTGTCGGCTTAAGTG

CCATAACGAGCGCAACCCTTATCTTTAGTTACTAACAGGTCATGCTGAGGACTCTAGAGAGACTGCCGTCGTAAGAT

GTGAGGAAGGTGGGGATGACGTCAAATCAGCACGGCCCTTACGTCCGGGGCTACACACGTGTTACAATGGGGGGTAC

AGAAGGCAGCTACACAGCGATGTGATGCTAATCCCAAAAGCCTCTCTCAGTTCGGATTGGAGTCTGCAACCCGACTC

-continued

CATGAAGCTGGATTCGCTAGTAATCGCGCATCAGCCACGGCGCGGTGAATACGTTCCCGGGCCTTGTACACACCGCC

CGTCAAGCCATGAAAGCCGGGGGTACCTGAAGTCCGTAACCGCAAGGAGCGGCCTAGGGTAAAACTGGTAATTGGGG

CTAAGTCGTA

>SEQ ID NO: 101|NR_112940.1|*Bacteroides ovatus* strain JCM 5824 16S ribosomal RNA gene, partial sequence

GGCTCAGGATGAACGCTAGCTACAGGCTTAACACATGCAAGTCGAGGGGCAGCATTTTAGTTTGCTTGCAAACTGAA

GATGGCGACCGGCGCACGGGTGAGTAACACGTATCCAACCTGCCGATAACTCCGGAATAGCCTTTCGAAAGAAAGAT

TAATACCGGATAGCATACGAATATCGCATGATATTTTTATTAAAGAATTTCGGTTATCGATGGGGATGCGTTCCATT

AGTTTGTTGGCGGGGTAACGGCCCACCAAGACTACGATGGATAGGGGTTCTGAGAGGAAGGTCCCCCACATTGGAAC

TGAGACACGGTCCAAACTCCTACGGGAGGCAGCAGTGAGGAATATTGGTCAATGGGCGAGAGCCTGAACCAGCCAAG

TAGCGTGAAGGATGAAGGCTCTATGGGTCGTAAACTTCTTTTATATGGGAATAAAGTTTTCCACGTGTGGAATTTTG

TATGTACCATATGAATAAGGATCGGCTAACTCCGTGCCAGCAGCCGCGGTAATACGGAGGATCCGAGCGTTATCCGG

ATTTATTGGGTTTAAAGGGAGCGTAGGTGGATTGTTAAGTCAGTTGTGAAAGTTTGCGGCTCAACCGTAAAATTGCA

GTTGAAACTGGCAGTCTTGAGTACAGTAGAGGTGGGCGGAATTCGTGGTGTAGCGGTGAAATGCTTAGATATCACGA

AGAACTCCGATTGCGAAGGCAGCTCACTAGACTGTTACTGACACTGATGCTCGAAAGTGTGGGTATCAAACAGGATT

AGATACCCTGGTAGTCCACACAGTAAACGATGAATACTCGCTGTTTGCGATATACAGTAAGCGGCCAAGCGAAAGCA

TTAAGTATTCCACCTGGGGAGTACGCCGGCAACGGTGAAACTCAAAGGAATTGACGGGGGCCCGCACAAGCGGAGGA

ACATGTGGTTTAATTCGATGATACGCGAGGAACCTTACCCGGGCTTAAATTGCAACAGAATATATTGGAAACAGTAT

AGCCGTAAGGCTGTTGTGAAGGTGCTGCATGGTTGTCGTCAGCTCGTGCCGTGAGGTGTCGGCTTAAGTGCCATAAC

GAGCGCAACCCTTATCTTTAGTTACTAACAGGTTATGCTGAGGACTCTAGAGAGACTGCCGTCGTAAGATGTGAGGA

AGGTGGGGATGACGTCAAATCAGCACGGCCCTTACGTCCGGGGCTACACACGTGTTACAATGGGGGGTACAGAAGGC

AGCTACCTGGCGACAGGATGCTAATCCCAAAAACCTCTCTCAGTTCGGATCGAAGTCTGCAACCCGACTTCGTGAAG

CTGGATTCGCTAGTAATCGCGCATCAGCCATGGCGCGGTGAATACGTTCCCGGGCCTTGTACACACCGCCCGTCAAG

CCATGAAAGCCGGGGGTACCTGAAGTACGTAACCGCAAGGAGCGTCCTAGGGTAAAACTGGTAATTGGGGCTA

>SEQ ID NO: 102|NR_117563.1|*Eubacterium fissicatena* 16S ribosomal RNA gene, partial sequence

TAGAGTTTGATCCTGGCTCAGGATGAACGCTGGCGGCGTGCTTAACACATGCAAGTCGAGCGAAGCGCTTTACTTAG

ATTTCTTCGGATTGAAGAGTTTTGCGACTGAGCGGCGGACGGGTGAGTAACGCGTGGGTAACCTGCCTCATACAGGG

GGATAACAGTTAGAAATGACTGCTAATACCGCATAAGACCACAGTACCGCATGGTACAGTGGGAAAAACTCCGGTGG

TATGAGATGGACCCGCGTCTGATTAGCTAGTTGGTAAGGTAACGGCTTACCAAGGCGACGATCAGTAGCCGACCTGA

GAGGGTGACCGGCCACATTGGGACTGAGACACGGCCCAAACTCCTACGGGAGGCAGCAGTGGGGAATATTGCACAAT

GGGGGAAACCCTGATGCAGCGACGCCGCGTGAAGGATGAAGTATTTCGGTATGTAAACTTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGTTATGTAAGTCTGATGTGAAAACCCGGGGCTCAACCCCGGGAC

TGCATTGGAAACTATGTAACTAGAGTGTCGGAGAGGTAAGTGGAATTCCTAGTGTAGCGGTGAAATGCGTAGATATT

AGGAGGAACACCAGTGGCGAAGGCGGCTTACTGGACGATCACTGACGTTGAGGCTCGAAAGCGTGGGGAGCAAACAG

GATTAGATACCCTGGTAGTCCACGCCGTAAACGATGAATACTAGGTGTCGGGTGGCAAAGCCATTCGGTGCCGCAGC

AAACGCAATAAGTATTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCTGCTCTTGACATCCCACTGACCGGCGTGTAA

TGGCGCCTTCCCTTCGGGGCAGTGGAGACAGGTGGTGCATGGTTGTCGTCAGCTCGTGTCGTGAGATGTTGGGTTAA

GTCCCGCAACGAGCGCAACCCTTATCTTTAGTAGCCAGCGGTTTGGCCGGGCACTCTAGAGAGACTGCCAGGGATAA

CCTGGAGGAAGGTGGGGATGACGTCAAATCATCATGCCCCTTATGAGCAGGGCTACACACGTGCTACAATGGCGTAA

-continued

ACAAAGGGAGGCAATACCGCGAGGTTGAGCAAATCCCAAAAATAACGTCTCAGTTCGGATTGTAGTCTGCAACTCGA

CTACATGAAGCTGGAATCGCTAGTAATCGCGAATCAGAATGTCGCGGTGAATACGTTCCCGGGTCTTGTACACACCG

CCCGTCACACCATGGGAGTTGGTAACGCCCGAAGTCAGTGACCCAACCGTAAGGAGGGAGCTGCCGAAGGCGGGATC

GATAACTGGGGTGAAGTCGTAACAAGGTAGCCGTATCGGAAGGTGCGGCTGGATCACCTCCTT

>SEQ ID NO: 103|NR_104700.1|*Blautia coccoides* strain JCM 1395 16S ribosomal RNA gene, partial sequence

AGAGTTTGATCCTGGCTCAGGATGAACGCTGGCGGCGTGCTTAACACATGCAAGTCGAGCGAAGCGCTAAGACAGAT

TTCTTCGGATTGAAGTCTTTGTGACTGAGCGGCGGACGGGTGAGTAACGCGTGGGTAACCTGCCTCATACAGGGGGA

TAACAGTTAGAAATGACTGCTAATACCGCATAAGCGCACAGGACCGCATGGTCTGGTGTGAAAAACTCCGGTGGTAT

GAGATGGACCCGCGTCTGATTAGCTAGTTGGAGGGGTAACGGCCCACCAAGGCGACGATCAGTAGCCGGCCTGAGAG

GGTGAACGGCCACATTGGGACTGAGACACGGCCCAGACTCCTACGGGAGGCAGCAGTGGGGAATATTGCACAATGGG

GGAAACCCTGATGCAGCGACGCCGCGTGAAGGAAGAAGTATCTCGGTATGTAAACTTCTATCAGCAGGGAAGAAAAT

GACGGTACCTGACTAAGAAGCCCCGGCTAACTACGTGCCAGCAGCCGCGGTAATACGTAGGGGGCAAGCGTTATCCG

GATTTACTGGGTGTAAAGGGAGCGTAGACGGAAGAGCAAGTCTGATGTGAAAGGCTGGGGCTTAACCCCAGGACTGC

ATTGGAAACTGTTGTTCTAGAGTGCCGGAGAGGTAAGCGGAATTCCTAGTGTAGCGGTGAAATGCGTAGATATTAGG

AGGAACACCAGTGGCGAAGGCGGCTTACTGGACGGTAACTGACGTTGAGGCTCGAAAGCGTGGGGAGCAAACAGGAT

TAGATACCCTGGTAGTCCACGCCGTAAACGATGAATACTAGGTGTCGGGTGGCAAAGCCATTCGGTGCCGCAGCAAA

CGCAATAAGTATTCCACCTGGGGAGTACGTTCGCAAGAATGAAACTCAAAGGAATTGACGGGGACCCGCACAAGCGG

TGGAGCATGTGGTTTAATTCGAAGCAACGCGAAGAACCTTACCAAGTCTTGACATCCCTCTGACCGTCCCGTAACGG

GGGCTTCCCTTCGGGGCAGAGGAGACAGGTGGTGCATGGTTGTCGTCAGCTCGTGTCGTGAGATGTTGGGTTAAGTC

CCGCAACGAGCGCAACCCTTATCCTTAGTAGCCAGCACATGATGGTGGGCACTCTAGGGAGACTGCCGGGGATAACC

CGGAGGAAGGCGGGGACGACGTCAAATCATCATGCCCCTTATGATTTGGGCTACACACGTGCTACAATGGCGTAAAC

AAAGGGAAGCGAGACAGCGATGTTGAGCGAATCCCAAAAATAACGTCCCAGTTCGGACTGCAGTCTGCAACTCGACT

GCACGAAGCTGGAATCGCTAGTAATCGCGGATCAGAATGCCGCGGTGAATACGTTCCCGGGTCTTGTACACACCGCC

CGTCACACCATGGGAGTCAGTAACGCCCGAAGTCAGTGACCTAACCGAAAGGAAGGAGCTGCCGAAGGCGGGACCGA

TAACTGGGGTGAAGTCGTAACAAGGTAACC

>SEQ ID NO: 104|NR_109014.1|*Blautia faecis* strain M25 16S ribosomal RNA gene, partial sequence

ATAACAGCCAGAAATGACTGCTAATACCGCATAAGCGCACAGAACCGCATGGTTCGGTGTGAAAAACTCCGGTGGTA

TAAGATGGACCCGCGTTGGATTAGCTAGTTGGCAGGGCAGCGGCCTACCAAGGCGACGATCCATAGCCGGCCTGAGA

GGGTGAACGGCCACATTGGGACTGAGACACGGCCCAGACTCCTACGGGAGGCAGCAGTGGGGAATATTGCACAATGG

GGGAAACCCTGATGCAGCGACGCCGCGTGAAGGAAGAAGTATCTCGGTATGTAAACTTCTATCAGCAGGGAAGATAA

TGACGGTACCTGACTAAGAAGCCCCGGCTAACTACGTGCCAGCAGCCGCGGTAATACGTAGGGGGCAAGCGTTATCC

GGATTTACTGGGTGTAAAGGGAGCGTAGACGGCGCAGCAAGTCTGATGTGAAAGGCAGGGGCTTAACCCCTGGACTG

CATTGGAAACTGCTGTGCTTGAGTGCCGGAGGGGTAAGCGGAATTCCTAGTGTAGCGGTGAAATGCGTAGATATTAG

GAGGAACACCAGTGGCGAAGGCGGCTTACTGGACGGTAACTGACGTTGAGGCTCGAAAGCGTGGGGAGCAAACAGGA

TTAGATACCCTGGTAGTCCACGCCGTAAACGATGAATACTAGGTGTCAGGGAGCACAGCTCTTTGGTGCCGCCGCAA

ACGCATTAAGTATTCCACCTGGGGAGTACGTTCGCAAGAATGAAACTCAAAGGAATTGACGGGGACCCGCACAAGCG

GTGGAGCATGTGGTTTAATTCGAAGCAACGCGAAGAACCTTACCAAATCTTGACATCCCTCTGACCGGGACTTAACC

GTCCCTTTCCTTCGGGACAGGGGAGACAGGTGGTGCATGGTTGTCGTCAGCTCGTGTCGTGAGATGTTGGGTTAAGT

CCCGCAACGAGCGCAACCCCTATCCTTAGTAGCCAGCACGCARTGGTGGGCACTCTGAGGAGACTGCCAGGGATAAC

CTGGAGGAAGGCGGGGATGACGTCAAATCATCATGCCCCTTATGATTTGGGCTACACACGTGCTACAATGGCGTAAA

CAAAGGGAAGCGAACCCGCGAGGGTGGGCAAATCTCAAAAATAACGTCCCAGTTCGGACTGCAGTCTGCAACTCGAC

-continued

TGCACGAAGCTGGAATCGCTAGTAATCGCGGATCAGAATGCCGCGGTGAATACGTTCCCGGGTCTTGTACACACCGC

CCGTCACACCATGGGAGTCAGTAACGCCCG

>SEQ ID NO: 105|NR_036928.1|*Clostridium hathewayi* strain 1313 16S ribosomal RNA gene, partial sequence
CTCAGGATGAACGCTGGCGGCGTGCTTAACACATGCAAGTCGAGCGAAGCGGTTTCAATGAAGTTTTCGGATGGATT

TGAAATTGACTTAGCGGCGGACGGGTGAGTAACGCGTGGGTAACCTGCCTTACACTGGGGGATAACAGTTAGAAATG

ACTGCTAATACCGCATAAGCGCACAGGGCCGCATGGNCTGGTGTGAAAAACTCCGGNGGTGTAAGATGGACCCGCGT

CTGATTAGGTAGTTGGNGGGGTAACGGCCCACCAAGCCGACGATCAGTAGCCGACCTGAGAGGGTGACCGGCCACAT

TGGGACTGAGACACGGCCCAAACTCCTACGGGAGGCAGCAGTGGGGAATATTGGACAATGGGCGAAAGCCTGATCCA

GCGACGCCGCGTGAGTGAAGAAGTATTTCGGTATGTAAAGCTCTATCAGCAGGGAAGAAAATGACGGTACCTGACTA

AGAAGCCCCGGCTAACTACGTGCCAGCAGCCGCGGTAATACGTAGGGGGCAAGCGTTATCCGGATTTACTGGGTGTA

AAGGGAGCGTAGACGGTTTAGCAAGTCTGAAGTGAAAGCCCGGGGCTCAACCCCGGTACTGCTTTGGAAACTGTTAG

ACTTGAGTGCAGGAGAGGTAAGTGGAATTCCTAGTGTAGCGGTGAAATGCGTAGATATTAGGAGGAACACCAGTGGC

GAAGGCGGCTTACTGGACTGTAACTGACGTTGAGGCTCGAAAGCGTGGGGAGCAAACAGGATTAGATACCCTGGTAG

TCCACGCCGTAAACGATGAATACTAGGTGTCGGGGGGCAAAGCCCTTCGGTGCCGCCGCAAACGCAATAAGTATTCC

ACCTGGGGAGTACGTTCGCAAGAATGAAACTCAAAGGAATTGACGGGGACCCGCACAAGCGGTGGAGCATGTGGTTT

AATTCGAAGCAACGCGAAGAACCTTACCAAGTCTTGACATCCCACTGAAAACACNTTAACCGTGATCCCTCTTCGGA

GCAGTGGAGACAGGTGGTGCATGGTTGTCGTCAGCTCGTGTCGTGAGATGTTGGGTTAAGTCCCGCAACGAGCGCAA

CCCTTATCCTTAGTAGCCAGCGAGTAGAGTCGGGCACTCTGGGGAGACTGCCAGGGATAACCTGGAGGAAGGTGGGG

ATGACGTCAAATCATCATGCCCCTTATGATTTGGGCTACACACGTGCTACAATGGCGTAAACAAAGGGAGGCAAAGG

AGCGATCTGGAGCAAACCCCAAAAATAACGTCTCAGTTCGGATTGCAGGCTGCAACTCGCCTGCATGAAGCTGGAAT

CGCTAGTAATCGCGAATCAGAATGTCGCGGTGAATACGTTCCCGGGTCTTGTACACACCGCCCGTCACACCATGGGA

GTTGGTAACGCCCGAAGTCAGTGACCCAACCGAAAGGAGGGAGCT

>SEQ ID NO: 106|NR_113270.1|B*lautia producta* strain JCM 1471 16S ribosomal RNA gene, partial sequence
AGAGTTTGATCCTGGCTCAGGATGAACGCTGGCGGCGTGCTTAACACATGCAAGTCGAGCGAAGCACTAAGACGGAT

TTCTTCGGATTGAAGTCTTTGTGACTGAGCGGCGGACGGGTGAGTAACGCGTGGGTAACCTGCCTCATACAGGGGGA

TAACAGTTAGAAATGACTGCTAATACCGCATAAGCGCACAGGACCGCATGGTCTGGTGTGAAAAACTCCGGTGGTAT

GAGATGGACCCGCGTCTGATTAGCTAGTTGGAGGGGTAACGGCCCACCAAGGCGACGATCAGTAGCCGGCCTGAGAG

GGTGAACGGCCACATTGGGACTGAGACACGGCCCAGACTCCTACGGGAGGCAGCAGTGGGGAATATTGCACAATGGG

GGAAACCCTGATGCAGCGACGCCGCGTGAAGGAAGAAGTATCTCGGTATGTAAACTTCTATCAGCAGGGAAGAAAAT

GACGGTACCTGACTAAGAAGCCCCGGCTAACTACGTGCCAGCAGCCGCGGTAATACGTAGGGGGCAAGCGTTATCCG

GATTTACTGGGTGTAAAGGGAGCGTAGACGGAAGAGCAAGTCTGATGTGAAAGGCTGGGGCTTAACCCCAGGACTGC

ATTGGAAACTGTTGTTCTAGAGTGCCGGAGAGGTAAGCGGAATTCCTAGTGTAGCGGTGAAATGCGTAGATATTAGG

AGGAACACCAGTGGCGAAGGCGGCTTACTGGACGGTAACTGACGTTGAGGCTCGAAAGCGTGGGGAGCAAACAGGAT

TAGATACCCTGGTAGTCCACGCCGTAAACGATGAATACTAGGTGTCGGGTGGCAAAGCCATTCGGTGCCGCAGCAAA

CGCAATAAGTATTCCACCTGGGGAGTACGTTCGCAAGAATGAAACTCAAAGGAATTGACGGGGACCCGCACAAGCGG

TGGAGCATGTGGTTTAATTCGAAGCAACGCGAAGAACCTTACCAAGTCTTGACATCCCTCTGACCGTCCCGTAACGG

GGACTTCCCTTCGGGGCAGAGGAGACAGGTGGTGCATGGTTGTCGTCAGCTCGTGTCGTGAGATGTTGGGTTAAGTC

CCGCAACGAGCGCAACCCTTATCCTTAGTAGCCAGCACATGATGGTGGGCACTCTAGGGAGACTGCCGGGGATAACC

CGGAGGAAGGCGGGGACGACGTCAAATCATCATGCCCCTTATGATTTGGGCTACACACGTGCTACAATGGCGTAAAC

AAAGGGAAGCGAGACAGCGATGTTGAGCGAATCCCAAAAATAACGTCCCAGTTCGGACTGCAGTCTGCAACTCGACT

-continued

GCACGAAGCTGGAATCGCTAGTAATCGCGGATCAGAATGCCGCGGTGAATACGTTCCCGGGTCTTGTACACACCGCC

CGTCACACCATGGGAGTCAGTAACGCCCGAAGTCAGTGACCTAACCGAAAGGAAGGAGCTGCCGAAGGCGGGACCGA

TAACTGGGGTGAAGTCGTAACAAGGTAACC

>SEQ ID NO: 107|NR_104799.1|*Anaerostipes hadrus* strain DSM 3319 16S ribosomal RNA gene, partial sequence

TGGCTCAGGATGAACGCTGGCGGCGTGCTTAACACATGCAAGTCGAACGAAGCTGCTTAACTGATCTTCTTCGGAAT

TGACGTTTTGTAGACTGAGTGGCGGACGGGTGAGTAACGCGTGGGCAACCTGCCCTGTACAGGGGGATAACAGTCAG

AAATGACTGCTAATACCGCATAAGACCACAGCACCGCATGGTGCAGGGGTAAAAACTCCGGTGGTACAGGATGGACC

CGCGTCTGATTAGCTGGTTGGTGAGGTAACGGCTCACCAAGGCGACGATCAGTAGCCGGCTTGAGAGAGTGAACGGC

CACATTGGGACTGAGACACGGCCCAAACTCCTACGGGAGGCAGCAGTGGGGAATATTGCACAATGGGGGAAACCCTG

ATGCAGCGACGCCGCGTGAGTGAAGAAGTATCTCGGTATGTAAAGCTCTATCAGCAGGGAAGAAAATGACGGTACCT

GACTAAGAAGCCCCGGCTAACTACGTGCCAGCAGCCGCGGTAATACGTAGGGGGCAAGCGTTATCCGGAATTACTGG

GTGTAAAGGGTGCGTAGGTGGTATGGCAAGTCAGAAGTGAAAACCCAGGGCTTAACTCTGGGACTGCTTTTGAAACT

GTCAGACTGGAGTGCAGGAGAGGTAAGCGGAATTCCTAGTGTAGCGGTGAAATGCGTAGATATTAGGAGGAACATCA

GTGGCGAAGGCGGCTTACTGGACTGAAACTGACACTGAGGCACGAAAGCGTGGGGAGCAAACAGGATTAGATACCCT

GGTAGTCCACGCCGTAAACGATGAATACTAGGTGTCGGGGCCGTAGAGGCTTCGGTGCCGCAGCCAACGCAGTAAGT

ATTCCACCTGGGGAGTACGTTCGCAAGAATGAAACTCAAAGGAATTGACGGGGACCCGCACAAGCGGTGGAGCATGT

GGTTTAATTCGAAGCAACGCGAAGAACCTTACCTGGTCTTGACATCCTTCTGACCGGTCCTTAACCGGACCTTTCCT

TCGGGACAGGAGAGACAGGTGGTGCATGGTTGTCGTCAGCTCGTGTCGTGAGATGTTGGGTTAAGTCCCGCAACGAG

CGCAACCCCTATCTTTAGTAGCCAGCATTTCAGGTGGGCACTCTAGAGAGACTGCCAGGGATAACCTGGAGGAAGGT

GGGGACGACGTCAAATCATCATGCCCCTTATGACCAGGGCTACACACGTGCTACAATGGCGTAAACAGAGGGAAGCA

GCCTCGTGAGAGTGAGCAAATCCCAAAAATAACGTCTCAGTTCGGATTGTAGTCTGCAACTCGACTACATGAAGCTG

GAATCGCTAGTAATCGCGAATCAGAATGTCGCGGTGAATACGTTCCCGGGTCTTGTACACACCGCCCGTCACACCAT

GGGAGTCAGTAACGCCCGAAGTCAGTGACCCAACCGTAAGGAGGGAGCTGCCGAAGGCGGGACCGATAACTGGGGTG

AAGTCGTAACAAGGTAGCCGTATCGGAAGGTGCGGCTGGATCACCTCCTTTC

>SEQ ID NO: 108|NR_117142.1|*Eubacterium fissicatena* strain DSM 3598 16S ribosomal RNA gene, partial sequence

GTTTGATCCTGGCTCAGGATGAACGCTGGCGGCGTGCTTAACACATGCAAGTCGAGCGAAGCGCTTTACTTAGATTT

CTTCGGATTGAAGAGTTTTGCGACTGAGCGGCGGACGGGTGAGTAACGCGTGGGTAACCTGCCTCATACAGGGGGAT

AACAGTTAGAAATGACTGCTAATACCGCATAAGACCACAGTACCGCATGGTACAGTGGGAAAAACTCCGGTGGTATG

AGATGGACCCGCGTCTGATTAGCTAGTTGGTAAGGTAACGGCTTACCAAGGCAACGATCAGTAGCCGACCTGAGAGG

GTGACCGGCCACATTGGGACTGAGACACGGCCCAAACTCCTACGGGAGGCAGCAGTGGGGAATATTGCACAATGGGG

GAAACCCTGATGCAGCGACGCCGCGTGAAGGATGAAGTATTTCGGTATGTAAACTTCTATCAGCAGGGAAGAAAATG

ACGGTACCTGACTAAGAAGCCCCGGCTAACTACGTGCCAGCAGCCGCGGTAATACGTAGGGGGCAAGCGTTATCCGG

ATTTACTGGGTGTAAAGGGAGCGTAGACGGTTATGTAAGTCTGATGTGAAAACCCGGGGCTCAACCCCGGGACTGCA

TTGGAAACTATGTAACTAGAGTGTCGGAGAGGTAAGTGGAATTCCTAGTGTAGCGGTGAAATGCGTAGATATTAGGA

GGAACACCAGTGGCGAAGGCGGCTTACTGGACGATCACTGACGTTGAGGCTCGAAAGCGTGGGGAGCAAACAGGATT

AGATACCCTGGTAGTCCACGCCGTAAACGATGAATACTAGGTGTCGGGTGGCAAAGCCATTCGGTGCCGCAGCAAAC

GCAATAAGTATTCCACCTGGGGAGTACGTTCGCAAGAATGAAACTCAAAGGAATTGACGGGGACCCGCACAAGCGGT

GGAGCATGTGGTTTAATTCGAAGCAACGCGAAGAACCTTACCTGCTCTTGACATCCCACTGACCGGCGTGTAATGGC

GCCTTCCCTTCGGGGCAGTGGAGACAGGTGGTGCATGGTTGTCGTCAGCTCGTGTCGTGAGATGTTGGGTTAAGTCC

CGCAACGAGCGCAACCCTTATCTTTAGTAGCCAGCGGTTTGGCCGGGCACTCTAGAGAGACTGCCAGGGATAACCTG

GAGGAAGGTGGGGATGACGTCAAATCATCATGCCCCTTATGAGCAGGGCTACACACGTGCTACAATGGCGTAAACAA

-continued

AGGGAGGCAATACCGCGAGGTTGAGCAAATCCCAAAAATAACGTCTCAGTTCGGATTGTAGTCTGCAACTCGACTAC

ATGAAGCTGGAATCGCTAGTAATCGCGAATCAGAATGTCGCGGTGAATACGTTCCCGGGTCTTGTACACACCGCCCG

TCACACCATGGGAGTTGGTAACGCCCGAAGTCAGTGACCCAACCGTAAGGAGGGAGCTGCCGAAGGCGGGATCGATA

ACTGGGGTGAAGTCGTAACAAGGTAGCCGTATCGGAAGGTGCGGCTGGATCACCTCCTTT

>SEQ ID NO: 109|NR_117147.1|*Eubacterium contortum* strain DSM 3982 16S
ribosomal RNA gene, partial sequence
TTTGATCCTGGCTCAGGATGAACGCTGGCGACGTGCTTAACACATGCAAGTCGAGCGAAGCACTTTACTTTGATTTC

TTCGGAATGAAAGGTTTTGTGACTGAGCGGCGGACGGGTGAGTAACGCGTGGGTAACCTGCCTCATACAGGGGGATA

ACAGTTAGAAATGACTGCTAATACCGCATAAGACCACAGTACCGCATGGTACAGTGGGAAAAACTCCGGTGGTATGA

GATGGACCCGCGTCTGATTAGCTAGTTGGTAAGGTAACGGCTTACCAAGGCGACGATCAGTAGCCGACCTGAGAGGG

TGACCGGCCACATTGGGACTGAGACACGGCCCAAACTCCTACGGGAGGCAGCAGTGGGGAATATTGCACAATGGGGG

AAACCCTGATGCAGCGACGCCGCGTGAAGGATGAAGTATTTCGGTATGTAAACTTCTATCAGCAGGGAAGAAAATGA

CGGTACCTGACTAAGAAGCCCCGGCTAACTACGTGCCAGCAGCCGCGGTAATACGTAGGGGGCAAGCGTTATCCGGA

TTTACTGGGTGTAAAGGGAGCGTAGACGGTTATGTAAGTCTGATGTGAAAACCCGGGGCTCAACCCCGGGACTGCAT

TGGAAACTATGTAACTAGAGTGTCGGAGAGGTAAGTGGAATTCCTAGTGTAGCGGTGAAATGCGTAGATATTAGGAG

GAACACCAGTGGCGAAGGCGGCTTACTGGACGATGACTGACGTTGAGGCTCGAAAGCGTGGGGAGCAAACAGGATTA

GATACCCTGGTAGTCCACGCCGTAAACGATGAATACTAGGTGTCGGGTGGCAAAGCCATTCGGTGCCGCAGCAAACG

CAATAAGTATTCCACCTGGGGAGTACGTTCGCAAGAATGAAACTCAAAGGAATTGACGGGGACCCGCACAAGCGGTG

GAGCATGTGGTTTAATTCGAAGCAACGCGAAGAACCTTACCTGCTCTTGACATCCCCCTGACCGGCGTGTAATGGTG

CCTTTCCTTCGGGACAGGGGAGACAGGTGGTGCATGGTTGTCGTCAGCTCGTGTCGTGAGATGTTGGGTTAAGTCCC

GCAACGAGCGCAACCCTTATCTTTAGTAGCCAGCGGTTTGGCCGGGCACTCTAGAGAGACTGCCAGGGATAACCTGG

AGGAAGGTGGGGATGACGTCAAATCATCATGCCCCTTATGAGCAGGGCTACACACGTGCTACAATGGCGTAAACAAA

GGGAGGCGAAGCCGTGAGGTGGAGCAAATCCCAAAAATAACGTCTCAGTTCGGATTGTAGTCTGCAACTCGACTACA

TGAAGCTGGAATCGCTAGTAATCGCGAATCAGAATGTCGCGGTGAATACGTTCCCGGGTCTTGTACACACCGCCCGT

CACACCATGGGAGTTGGTAACGCCCGAAGTCAGTGACCCAACCGCAAGGAGGGAGCTGCCGAGGGTGGGACCGATAA

CTGGGGTGAAGTCGTAACAAGGTAGCCGTATCGGAAGGTGCGGCTGGATCACCTCCTTTCT

>SEQ ID NO: 110|NR_113410.1|*Clostridium bolteae* strain JCM 12243 16S
ribosomal RNA gene, partial sequence
TTTTAATTGACTGAGTGGCGGACGGGTGAGTAACGCGTGGATAACCTGCCTCACACTGGGGGATAACAGTTAGAAAT

GACTGCTAATACCGCATAAGCGCACAGTACCGCATGGTACAGTGTGAAAAACTCCGGTGGTGTGAGATGGATCCGCG

TCTGATTAGCCAGTTGGCGGGGTAACGGCCCACCAAAGCGACGATCAGTAGCCGACCTGAGAGGGTGACCGGCCACA

TTGGGACTGAGACACGGCCCAAACTCCTACGGGAGGCAGCAGTGGGGAATATTGCACAATGGGCGAAAGCCTGATGC

AGCGACGCCGCGTGAGTGAAGAAGTATTTCGGTATGTAAAGCTCTATCAGCAGGGAAGAAAATGACGGTACCTGACT

AAGAAGCCCCGGCTAACTACGTGCCAGCAGCCGCGGTAATACGTAGGGGGCAAGCGTTATCCGGATTTACTGGGTGT

AAAGGGAGCGTAGACGGCGAAGCAAGTCTGAAGTGAAAACCCAGGGCTCAACCCTGGGACTGCTTTGGAAACTGTTT

TGCTAGAGTGTCGGAGAGGTAAGTGGAATTCCTAGTGTAGCGGTGAAATGCGTAGATATTAGGAGGAACACCAGTGG

CGAAGGCGGCTTACTGGACGATAACTGACGTTGAGGCTCGAAAGCGTGGGGAGCAAACAGGATTAGATACCCTGGTA

GTCCACGCCGTAAACGATGAATGCTAGGTGTTGGGGGGCAAAGCCCTTCGGTGCCGTCGCAAACGCAGTAAGCATTC

CACCTGGGGAGTACGTTCGCAAGAATGAAACTCAAAGGAATTGACGGGGACCCGCACAAGCGGTGGAGCATGTGGTT

TAATTCGAAGCAACGCGAAGAACCTTACCAAGTCTTGACATCCTCTTGACCGGCGTGTAACGGCGCCTTCCCTTCGG

GGCAAGAGAGACAGGTGGTGCATGGTTGTCGTCAGCTCGTGTCGTGAGATGTTGGGTTAAGTCCCGCAACGAGCGCA

ACCCTTATCCTTAGTAGCCAGCAGGTAAAGCTGGGCACTCTAGGGAGACTGCCAGGGATAACCTGGAGGAAGGTGGG

-continued
GATGACGTCAAATCATCATGCCCCTTATGATTTGGGCTACACACGTGCTACAATGGCGTAAACAAAGGGAAGCAAGA

CAGTGATGTGGAGCAAATCCCAAAAATAACGTCCCAGTTCGGACTGTAGTCTGCAACCCGACTACACGAAGCTGGAA

TCGCTAGTAATCGCGAATCAGAATGTCGCGGTGAATACGTTCCCGGGTCTTGTACACACCGCCCGTCACACCATGGG

AGTCAGCAACGCCCGAAGTCAGTGACCCAACTCGCAAGAGAGGGAGCTGCCGAAGGCGGGGCAGGTAACTGGGGTGA

AGTC

>SEQ ID NO: 111|NR_041960.1|*Blautia luti* strain BInIX 16S ribosomal RNA gene, complete sequence
GTGGGTAACCTGCCTTATACAGGGGGATAACAGTCAGAAATGACTGCTAATACCGCATAAGCGCACAGAGCTGCATG

GCTCCGGTGTGAAAAACTCCGGTGGTATAAGATGGACCCGCGTTGGATTAGCTAGTTGGTGAGGTAACGGCCCACCA

AGGCGACGATCCATAGCCGGCCTGAGAGGGTGAACGGCCACATTGGGACTGAGACACGGCCCAGACTCCTACGGGAG

GCAGCAGTGGGGAATATTGCACAATGGGGGAAACCCTGATGCAGCGACGCCGCGTGAAGGAAGAAGTATCTCGGTAT

GTAAACTTCTATCAGCAGGGAAGAAAATGACGGTACCTGACTAAGAAGCCCCGGCTAACTACGTGCCAGCAGCCGCG

GTAATACGTAGGGGGCAAGCGTTATCCGGATTTACTGGGTGTAAAGGGAGCGTAGACGGCATGGACAAGTCTGATGT

GAAAGGCTGGGGCTCAACCCCGGGACTGCATTGGAAACTGCCCGTCTTGAGTGCCGGAGAGGTAAGCGGAATTCCTA

GTGTAGCGGTGAAATGCGTAGATATTAGGAGGAACACCAGTGGCGAAGGCGGCTTACTGGACGGTAACTGACGTTGA

GGCTCGAAAGCGTGGGGAGCAAACAGGATTAGATACCCTGGTAGTCCACGCGGTAAACGATGAATCCTAGGTGTCGG

GGAGCAAANNNNTTCGGTGCCGCCGCAAACGCATTAAGCATTCCACCTGGGGAGTACGTTCGCAAGAATGAAACTCA

AAGGAATTGACGGGGACCCGCACAAGCGGTGGAGCATGTGGTTTAATTCGAAGCAACGCGAAGAACCTTACCAAGTC

TTGACATCCCTCTGACCGAGTATGTATGGTACTTTTCCTTCGGGAGAGAGAGGAGACAGGTGGTGCATGGTTGTCGT

CAGCTCGTGTCGTGAGATGTTGGGTTAAGTCCCGCAACGAGCGCAACCCCTATCCCCAGTAGCCAGCGGTTCGGCCG

GGCACTCTGAGGAGACTGCCAGGGATAACCTGGAGGAAGGCGGGGATGACGTCAAATCATCATGCCCCTTATGATTT

GGGCTACACACGTGCTACAATGGCGTAAACAAAGGGAAGCAAGCCTGCGAGGGTGGGCAAATCCCAAAAATAACGTC

CCAGTTCGGACTGTAGTCTGCAACCCGACTACACGAAGCTGGAATCGCTAGTAATCGCGGATCAGAATGCCGCGGTG

AATACGTTCCCGGGTCTTGTACACACCGCCCGTCACACCATGGGAGTCAGTAACGCCCGAAGTCAGTGACCTAACT

>SEQ ID NO: 112|NR_074306.1|*Acidaminococcus intestini* RyC-MR95 strain RyC-MR95 16S ribosomal RNA, complete sequence
CTGGCGGCGTGCTTAACACATGCAAGTCGAACGGAGAACTTATTTCGGTAAGTTCTTAGTGGCGAACGGGTGAGTAA

CGCGTGGGCAACCTGCCCTCCAGTTGGGGACAACATTCCGAAAGGGATGCTAATACCGAATGTCCTCCCTCCTCCGC

ATGGAGGAGGGAGGAAAGATGGCCTCTGCTTGCAAGCTATCGCTGGAAGATGGGCCCGCGTCTGATTAGCTAGTTGG

TGGGGTAACGGCTCACCAAGGCGATGATCAGTAGCCGGTCTGAGAGGATGAACGGCCACATTGGGACTGAGACACGG

CCCAAACTCCTACGGGAGGCAGCAGTGGGGAATCTTCCGCAATGGACGAAAGTCTGACGGAGCAACGCCGCGTGAGT

GATGAAGGTCTTCGGATTGTAAAACTCTGTTGTTAGGGACGAAAGCACCGTGTTCGAACAGGTCATGGTGTTGACGG

TACCTAACGAGGAAGCCACGGCTAACTACGTGCCAGCAGCCGCGGTAATACGTAGGTGGCAAGCGTTGTCCGGAATT

ATTGGGCGTAAAGAGCATGTAGGCGGGCTTTTAAGTCTGACGTGAAAATGCGGGGCTTAACCCCGTATGGCGTTGGA

TACTGGAAGTCTTGAGTGCAGGAGAGGAAAGGGGAATTCCCAGTGTAGCGGTGAAATGCGTAGATATTGGGAGGAAC

ACCAGTGGCGAAGGCGCCTTTCTGGACTGTGTCTGACGCTGAGATGCGAAAGCCAGGGTAGCAAACGGGATTAGATA

CCCCGGTAGTCCTGGCCGTAAACGATGGATACTAGGTGTAGGAGGTATCGACCCCTTCTGTGCCGGAGTTAACGCAA

TAAGTATCCCGCCTGGGGACTACGATCGCAAGATTGAAACTCAAAGGAATTGACGGGGGCCCGCACAAGCGGTGGAG

TATGTGGTTTAATTCGACGCAACGCGAAGAACCTTACCAAGGCTTGACATTGAGTGAAAGACCTAGAGATAGGTCCC

TCCCTTCGGGGACACGAAAACAGGTGGTGCATGGCTGTCGTCAGCTCGTGTCGTGAGATGTTGGGTTAAGTCCCGCA

ACGAGCGCAACCCCTATCCTATGTTACCAGCGCGTAAAGGCGGGGACTCATAGGAGACTGCCAGGGATAACTTGGAG

GAAGGCGGGGATGACGTCAAGTCATCATGCCCCTTATGTCTTGGGCTACACACGTACTACAATGGTCGGCAACAAAG

GGCAGCGAAACCGCGAGGTGGAGCAAATCCCAGAAACCCGACCCCAGTTCGGATCGTAGGCTGCAACCCGCCTACGT

-continued

GAAGTTGGAATCGCTAGTAATCGCAGGTCAGCATACTGCGGTGAATACGTTCCCGGGCCTTGTACACACCGCCCGTC

ACACCACGAAAGTTGGTAACACCCGAAGCCGGTGAGATAACCTTTTAGGAGTCAGCTGTCTAAGGTGGGGCCGATGA

TTGGGGTGAAGTCGTAACAAGGTAGC

>SEQ ID NO: 113|NR_074399.1|*Ruminococcus albus* strain 7 16S ribosomal RNA gene, complete sequence
AGAGTTTGATCCTGGCTCAGGACGAACGCTGGCGGCACGCTTAACACATGCAAGTCGAACGAGCGAAAGAGTGCTTG

CACTCTCTAGCTAGTGGCGGACGGGTGAGTAACACGTGAGCAATCTGCCTTTCGGAGAGGGATACCAATTGGAAACG

ATTGTTAATACCTCATAACATAACGAAGCCGCATGACTTTGTTATCAAATGAATTTCGCCGAAAGATGAGCTCGCGT

CTGATTAGGTAGTTGGTGAGGTAACGGCCCACCAAGCCGACGATCAGTAGCCGGACTGAGAGGTTGAACGGCCACAT

TGGGACTGAGACACGGCCCAGACTCCTACGGGAGGCAGCAGTGGGGAATATTGCACAATGGGCGAAAGCCTGATGCA

GCGATGCCGCGTGAGGGAAGAAGGTTTTAGGATTGTAAACCTCTGTCTTTGGGGACGATAATGACGGTACCCAAGGA

GGAAGCTCCGGCTAACTACGTGCCAGCAGCCGCGGTAATACGTAGGGAGCGAGCGTTGTCCGGAATTACTGGGTGTA

AAGGGAGCGTAGGCGGGATTGCAAGTCAGGTGTGAAATTTAGGGGCTTAACCCCTGAACTGCACTTGAAACTGTAGT

TCTTGAGTGAAGTAGAGGTAAGCGGAATTCCTAGTGTAGCGGTGAAATGCGTAGATATTAGGAGGAACATCAGTGGC

GAAGGCGGCTTACTGGGCTTTAACTGACGCTGAGGCTCGAAAGCGTGGGGAGCAAACAGGATTAGATACCCTGGTAG

TCCACGCCGTAAACGATGATTACTAGGTGTGGGGGGACTGACCCCTTCCGTGCCGCAGTTAACACAATAAGTAATCC

ACCTGGGGAGTACGGCCGCAAGGCTGAAACTCAAAGGAATTGACGGGGACCCGCACAAGCAGTGGAGTATGTGGTTT

AATTCGAAGCAACGCGAAGAACCTTACCAGGTCTTGACATCGTACGCATAGCATAGAGATATGTGAAATCCCTTCGG

GGACGTATAGACAGGTGGTGCATGGTTGTCGTCAGCTCGTGTCGTGAGATGTTGGGGTTAAGTCCCGCAACGAGCGC

AACCCTTACTGTTAGTTGCTACGCAAGAGCACTCTAGCAGGACTGCCGTTGACAAAACGGAGGAAGGTGGGGATGAC

GTCAAATCATCATGCCCCTTATGACCTGGGCTACACACGTACTACAATGGCTGTTAACAGAGGGAAGCAAAACAGTG

ATGTGGAGCAAAACCCTAAAAGCAGTCTTAGTTCGGATTGTAGGCTGCAACCCGCCTACATGAAGTCGGAATTGCTA

GTAATCGCGGATCAGCATGCCGCGGTGAATACGTTCCCGGGCCTTGTACACACCGCCCGTCACGCCATGGGAGTCGG

TAACACCCGAAGCCTGTGTTCTAACCGCAAGGAGGAAGCAGTCGAAGGTGGGATTGATGACTGGGGTGAAGTCGTAA

CAAGGTAGCCGTATCGGAAGGTGCGGCTGGATCACCT

>SEQ ID NO: 114|NR_074634.1|*Eubacterium rectale* strain ATCC 33656 16S ribosomal RNA gene, complete sequence
AGAGTTTGATCCTGGCTCAGGATGAACGCTGGCGGCGTGCTTAACACATGCAAGTCGAACGAAGCACTTTATTTGAT

TTCCTTCGGGACTGATTATTTTGTGACTGAGTGGCGGACGGGTGAGTAACGCGTGGGTAACCTGCCTTGTACAGGGG

GATAACAGTTGGAAACGGCTGCTAATACCGCATAAGCGCACGGCATCGCATGATGCAGTGTGAAAAACTCCGGTGGT

ATAAGATGGACCCGCGTTGGATTAGCTAGTTGGTGAGGTAACGGCCCACCAAGGCGACGATCCATAGCCGACCTGAG

AGGGTGACCGGCCACATTGGGACTGAGACACGGCCCAAACTCCTACGGGAGGCAGCAGTGGGGAATATTGCACAATG

GGCGAAAGCCTGATGCAGCGACGCCGCGTGAGCGAAGAAGTATTTCGGTATGTAAAGCTCTATCAGCAGGGAAGATA

ATGACGGTACCTGACTAAGAAGCACCGGCTAAATACGTGCCAGCAGCCGCGGTAATACGTATGGTGCAAGCGTTATC

CGGATTTACTGGGTGTAAAGGGAGCGCAGGCGGTGCGGCAAGTCTGATGTGAAAGCCCGGGGCTCAACCCCGGTACT

GCATTGGAAACTGTCGTACTAGAGTGTCGGAGGGGTAAGCGGAATTCCTAGTGTAGCGGTGAAATGCGTAGATATTA

GGAGGAACACCAGTGGCGAAGGCGGCTTACTGGACGATAACTGACGCTGAGGCTCGAAAGCGTGGGGAGCAAACAGG

ATTAGATACCCTGGTAGTCCACGCCGTAAACGATGAATACTAGGTGTTGGGAAGCATTGCTTCTCGGTGCCGTCGCA

AACGCAGTAAGTATTCCACCTGGGGAGTACGTTCGCAAGAATGAAACTCAAAGGAATTGACGGGGACCCGCACAAGC

GGTGGAGCATGTGGTTTAATTCGAAGCAACGCGAAGAACCTTACCAAGTCTTGACATCCTTCTGACCGGTACTTAAC

CGTACCTTCTCTTCGGAGCAGGAGTGACAGGTGGTGCATGGTTGTCGTCAGCTCGTGTCGTGAGATGTTGGGTTAAG

TCCCGCAACGAGCGCAACCCTTATCTTTAGTAGCCAGCGGTTCGGCCGGGCACTCTAGAGAGACTGCCAGGGATAAC

-continued

CTGGAGGAAGGCGGGGATGACGTCAAATCATCATGCCCCTTATGACTTGGGCTACACACGTGCTACAATGGCGTAAA

CAAAGGGAAGCAAAGCTGTGAAGCCGAGCAAATCTCAAAAATAACGTCTCAGTTCGGACTGTAGTCTGCAACCCGAC

TACACGAAGCTGGAATCGCTAGTAATCGCAGATCAGAATGCTGCGGTGAATACGTTCCCGGGTCTTGTACACACCGC

CCGTCACACCATGGGAGTTGGGAATGCCCGAAGCCAGTGACCTAACCGAAAGGAAGGAGCTGTCGAAGGCAGGCTCG

ATAACTGGGGTGAAGTCGTAACAAGGTAGCCGTATCGGAAGGTGCGGCTGGATCACCT

>SEQ ID NO: 115|NR_074928.1|*Acidaminococcus fermentans* strain DSM 20731 16S ribosomal RNA gene, complete sequence

AGAGTTTGATCCTGGCTCAGGACGAACGCTGGCGGCGTGCTTAACACATGCAAGTCGAACGGAGAACTTTCTTCGGA

ATGTTCTTAGTGGCGAACGGGTGAGTAACGCGTAGGCAACCTGCCCTCTGGTTGGGGACAACATTCCGAAAGGGATG

CTAATACCGAATGAGATCCTCTTTCCGCATGGAGAGAGGATGAAAGATGGCCTCTACTTGTAAGCTATCGCCAGAAG

ATGGGCCTGCGTCTGATTAGCTAGTAGGTGAGGTAACGGCTCACCTAGGCGATGATCAGTAGCCGGTCTGAGAGGAT

GAACGGCCACATTGGGACTGAGACACGGCCCAAACTCCTACGGGAGGCAGCAGTGGGGAATCTTCCGCAATGGACGA

AAGTCTGACGGAGCAACGCCGCGTGAGTGATGAAGGCCTTCGGGTTGTAAAACTCTGTTGTCAGGGACGAAAGCACC

GATCTATAATACATTTTGGTGTTGACGGTACCTGACGAGGAAGCCACGGCTAACTACGTGCCAGCAGCCGCGGTAAT

ACGTAGGTGGCAAGCGTTGTCCGGAATTATTGGGCGTAAAGAGCATGTAGGCGGGCTTTTAAGTCCGACGTGAAAAT

GCGGGGCTTAACCCCGTATGGCGTTGGATACTGGAAGTCTTGAGTGCAGGAGAGGAAAGGGGAATTCCCAGTGTAGC

GGTGAAATGCGTAGATATTGGGAGGAACACCAGTGGCGAAGGCGCCTTTCTGGACTGTGTCTGACGCTGAGATGCGA

AAGCCAGGGTAGCAAACGGGATTAGATACCCCGGTAGTCCTGGCCGTAAACGATGGGTACTAGGTGTAGGAGGTATC

GACCCCTTCTGTGCCGGAGTTAACGCAATAAGTACCCCGCCTGGGGACTACGATCGCAAGATTGAAACTCAAAGGAA

TTGACGGGGGCCCGCACAAGCGGTGGAGTATGTGGTTTAATTCGACGCAACGCGAAGAACCTTACCAAGGCTTGACA

TTGAGTGAAAGACCCAGAGATGGGTCCCCTTCTTCGGAAGCACGAAAACAGGTGGTGCATGGCTGTCGTCAGCTCGT

GTCGTGAGATGTTGGGTTAAGTCCCGCAACGAGCGCAACCCTTATCCTATGTTACCAGCACGTAATGGTGGGGACTC

ATAGGAGACTGCCAGGGATAACCTGGAGGAAGGCGGGGATGACGTCAAGTCATCATGCCCCTTATGTCTTGGGCTAC

ACACGTACTACAATGGTCGGCAACAAAGGGCAGCGAAGCCGCGAGGCGGAGCCAATCCCAGAAACCCGACCCCAGTT

CGGATCGCAGGCTGCAACCCGCCTGCGTGAAGTTGGAATCGCTAGTAATCGCAGGTCAGCATACTGCGGTGAATACG

TTCCCGGGCCTTGTACACACCGCCCGTCACACCACGAAAGTTGGTAACACCCGAAGCCGGTGAGATAACCTTTTAGG

AGTCAGCTGTCTAAGGTGGGGCCGATGATTGGGGTGAAGTCGTAACAAGGTAGCCGTTCGAGAACGAGCGGCTGGAT

CACCT

>SEQ ID NO: 116|NR_114326.1|*Fusicatenibacter saccharivorans* strain HT03-11 16*S* ribosomal RNA gene, partial sequence

TGGCTCAGGATGAACGCTGGCGGCGTGCTTAACACATGCAAGTCGAGCGAAGCAGTTAAGAAGATTYTTCGGATGAT

TCTTGACTGACTGAGCGGCGGACGGGTGAGTAACGCGTGGGTGACCTGCCCCATACCGGGGGATAACAGCTGGAAAC

GGCTGCTAATACCGCATAAGCGCACAGAGCTGCATGGCTCGGTGTGAAAAACTCCGGTGGTATGGGATGGGCCCGCG

TCTGATTAGGCAGTTGGCGGGGTAACGGCCCACCAAACCGACGATCAGTAGCCGGCCTGAGAGGGCGACCGGCCACA

TTGGGACTGAGACACGGCCCAAACTCCTACGGGAGGCAGCAGTGGGGAATATTGCACAATGGGGGAAACCCTGATGC

AGCGACGCCGCGTGAGCGAAGAAGTATTTCGGTATGTAAAGCTCTATCAGCAGGGAAGATAATGACGGTACCTGACT

AAGAAGCCCCGGCTAACTACGTGCCAGCAGCCGCGGTAATACGTAGGGGGCAAGCGTTATCCGGATTTACTGGGTGT

AAAGGGAGCGTAGACGGCAAGGCAAGTCTGATGTGAAAACCCAGGGCTTAACCCTGGGACTGCATTGGAAACTGTCT

GGCTCGAGTGCCGGAGAGGTAAGCGGAATTCCTAGTGTAGCGGTGAAATGCGTAGATATTAGGAAGAACACCAGTGG

CGAAGGCGGCTTACTGGACGGTAACTGACGTTGAGGCTCGAAAGCGTGGGGAGCAAACAGGATTAGATACCCTGGTA

GTCCACGCCGTAAACGATGAATGCTAGGTGTTGGGGAGCAAAGCTCTTCGGTGCCGCCGCAAACGCATTAAGCATTC

CACCTGGGGAGTACGTTCGCAAGAATGAAACTCAAAGGAATTGACGGGGACCCGCACAAGCGGTGGAGCATGTGGTT

TAATTCGAAGCAACGCGAAGAACCTTACCAGGTCTTGACATCCCGATGACCGGCCCGTAACGGGGCCTTCTCTTCGG

-continued

AGCATTGGAGACAGGTGGTGCATGGTTGTCGTCAGCTCGTGTCGTGAGATGTTGGGTTAAGTCCCGCAACGAGCGCA

ACCCTTATCCTCAGTAGCCAGCAGGTAAAGCTGGGCACTCTGTGGAGACTGCCAGGGATAACCTGGAGGAAGGTGGG

GATGACGTCAAATCATCATGCCCCTTATGATCTGGGCTACACACGTGCTACAATGGCGTAAACAAAGGGAGGCAAAG

CCGCGAGGTGGAGCAAATCCCAAAAATAACGTCTCAGTTCGGACTGCAGTCTGCAACTCGACTGCACGAAGCTGGAA

TCGCTAGTAATCGCGAATCAGAATGTCGCGGTGAATACGTTCCCGGGTCTTGTACACACCGCCCGTCACACCATGGG

AGTTGGTAACGCCCGAAGTCAGTGACCCAACCTTTTA

>SEQ ID NO: 117|NR_102884.1|*Ruminococcus champanellensis* strain 18P13 16S ribosomal RNA gene, complete sequence

AGAGTTTGATCCTGGCTCAGGACGAACGCTGGCGGCACGCCTAACACATGCAAGTCGAACGGAGATAAAGACTTCGG

TTTTTATCTTAGTGGCGGACGGGTGAGTAACACGTGAGCAACCTGCCTCTGAGAGAGGGATAGCTTCTGGAAACGGA

TGGTAATACCTCATAACATAGCGGTACCGCATGATACTGCTATCAAAGATTTATCGCTCAGAGATGGGCTCGCGTCT

GATTAGCTAGATGGTGAGGTAACGGCTCACCATGGCGACGATCAGTAGCCGGACTGAGAGGTTGAACGGCCACATTG

GGACTGAGACACGGCCCAGACTCCTACGGGAGGCAGCAGTGGGGAATATTGCACAATGGGCGCAAGCCTGATGCAGC

GATGCCGCGTGGAGGAAGAAGGTTTTCGGATTGTAAACTCCTGTCTTAAGGGACGATAATGACGGTACCTTAGGAGG

AAGCTCCGGCTAACTACGTGCCAGCAGCCGCGGTAATACGTAGGGAGCGAGCGTTGTCCGGAATTACTGGGTGTAAA

GGGAGCGTAGGCGGGATTGCAAGTCAGATGTGAAAACTATGGGCTTAACCCATAGACTGCATTTGAAACTGTAGTTC

TTGAGTGAAGTAGAGGTAAGCGGAATTCCTAGTGTAGCGGTGAAATGCGTAGATATTAGGAGGAACATCGGTGGCGA

AGGCGGCTTACTGGGCTTTTACTGACGCTGAGGCTCGAAAGCGTGGGGAGCAAACAGGATTAGATACCCTGGTAGTC

CACGCTGTAAACGATGATTACTAGGTGTGGGGGGACTGACCCCTTCCGTGCCGCAGTTAACACAATAAGTAATCCAC

CTGGGGAGTACGGCCGCAAGGTTGAAACTCAAAGGAATTGACGGGGGCCCGCACAAGCAGTGGAGTATGTGGTTTAA

TTCGAAGCAACGCGAAAAACCTTACCAGGTCTTGACATCGAGTGAATGATCTAGAGATAGATCAGTCCTTCGGGACA

CAAAGACAGGTGGTGCATGGTTGTCGTCAGCTCGTGTCGTGAGATGTTGGGTTAAGTCCCGCAACGAGCGCAACCCT

TACCTTTAGTTGCTACGCAAGAGCACTCTAGAGGGACTGCCGTTGACAAAACGGAGGAAGGTGGGGATGACGTCAAA

TCATCATGCCCCTTATGACCTGGGCTACACACGTACTACAATGGCAATGAACAGAGGGAAGCAATACAGTGATGTGG

AGCAAATCCCCAAAAATTGTCCCAGTTCAGATTGTAGGCTGCAACTCGCCTACATGAAGTCGGAATTGCTAGTAATC

GCAGATCAGCATGCTGCGGTGAATACGTTCCCGGGCCTTGTACACACCGCCCGTCACACCATGGGAGTCGGTAACAC

CCGAAGCCAGTAGCCTAACCGCAAGGAGGGCGCTGTCGAAGGTGGGATTGATGACTGGGGTGAAGTCGTAACAAGGT

AGCCGTATCGGAAGGTGCGGCTGGATCACCT

>SEQ ID NO: 118|NR_102971.1|*Bifidobacterium bifidum* S17 strain S17 16S ribosomal RNA, complete sequence

TTTTTGTGGAGGGTTCGATTCTGGCTCAGGATGAACGCTGGCGGCGTGCTTAACACATGCAAGTCGAACGGGATCCA

TCGGGCTTTGCTTGGTGGTGAGAGTGGCGAACGGGTGAGTAATGCGTGACCGACCTGCCCCATGCTCCGGAATAGCT

CCTGGAAACGGGTGGTAATGCCGGATGTTCCACATGATCGCATGTGATTGTGGGAAAGATTCTATCGGCGTGGGATG

GGGTCGCGTCCTATCAGCTTGTTGGTGAGGTAACGGCTCACCAAGGCTTCGACGGGTAGCCGGCCTGAGAGGGCGAC

CGGCCACATTGGGACTGAGATACGGCCCAGACTCCTACGGGAGGCAGCAGTGGGGAATATTGCACAATGGGCGCAAG

CCTGATGCAGCGACGCCGCGTGAGGGATGGAGGCCTTCGGGTTGTAAACCTCTTTTGTTTGGGAGCAAGCCTTCGGG

TGAGTGTACCTTTCGAATAAGCGCCGGCTAACTACGTGCCAGCAGCCGCGGTAATACGTAGGGCGCAAGCGTTATCC

GGATTTATTGGGCGTAAAGGGCTCGTAGGCGGCTCGTCGCGTCCGGTGTGAAAGTCCATCGCTTAACGGTGGATCTG

CGCCGGGTACGGGCGGGCTGGAGTGCGGTAGGGGAGACTGGAATTCCCGGTGTAACGGTGGAATGTGTAGATATCGG

GAAGAACACCGATGGCGAAGGCAGGTCTCTGGGCCGTCACTGACGCTGAGGAGCGAAAGCGTGGGGAGCGAACAGGA

TTAGATACCCTGGTAGTCCACGCCGTAAACGGTGGACGCTGGATGTGGGGCACGTTCCACGTGTTCCGTGTCGGAGC

TAACGCGTTAAGCGTCCCGCCTGGGGAGTACGGCCGCAAGGCTAAAACTCAAAGAAATTGACGGGGGCCCGCACAAG

-continued

CGGCGGAGCATGCGGATTAATTCGATGCAACGCGAAGAACCTTACCTGGGCTTGACATGTTCCCGACGACGCCAGAG

ATGGCGTTTCCCTTCGGGGCGGGTTCACAGGTGGTGCATGGTCGTCGTCAGCTCGTGTCGTGAGATGTTGGGTTAAG

TCCCGCAACGAGCGCAACCCTCGCCCCGTGTTGCCAGCACGTTATGGTGGGAACTCACGGGGGACCGCCGGGGTTAA

CTCGGAGGAAGGTGGGGATGACGTCAGATCATCATGCCCCTTACGTCCAGGGCTTCACGCATGCTACAATGGCCGGT

ACAGCGGGATGCGACATGGCGACATGGAGCGGATCCCTGAAAACCGGTCTCAGTTCGGATCGGAGCCTGCAACCCGG

CTCCGTGAAGGCGGAGTCGCTAGTAATCGCGGATCAGCAACGCCGCGGTGAATGCGTTCCCGGGCCTTGTACACACC

GCCCGTCAAGTCATGAAAGTGGGCAGCACCCGAAGCCGGTGGCCTAACCCCTTGTGGGATGGAGCCGTCTAAGGTGA

GGCTCGTGATTGGGACTAAGTCGTAACAAGGTAGCCGTACCGGAAGGTGCGGCTGGATCACCTCCTTTCT

>SEQ ID NO: 119|NR_102980.1|*Megasphaera elsdenii* strain DSM 20460 16S ribosomal RNA gene, complete sequence

AGAGTTTGATCCTGGCTCAGGACGAACGCTGGCGGCGTGCTTAACACATGCAAGTCGAACGAGAAGAGATGAGAAGC

TTGCTTCTTATCAATTCGAGTGGCAAACGGGTGAGTAACGCGTAAGCAACCTGCCCTTCAGATGGGGACAACAGCTG

GAAACGGCTGCTAATACCGAATACGTTCTTTTTGTCGCATGGCAGAGGGAAGAAAGGGAGGCTCTTCGGAGCTTTCG

CTGAAGGAGGGGCTTGCGTCTGATTAGCTAGTTGGAGGGGTAACGGCCCACCAAGGCGACGATCAGTAGCCGGTCTG

AGAGGATGAACGGCCACATTGGGACTGAGACACGGCCCAGACTCCTACGGGAGGCAGCAGTGGGGAATCTTCCGCAA

TGGACGAAAGTCTGACGGAGCAACGCCGCGTGAACGATGACGGCCTTCGGGTTGTAAAGTTCTGTTATACGGGACGA

ATGGCGTAGCGGTCAATACCCGTTACGAGTGACGGTACCGTAAGAGAAAGCCACGGCTAACTACGTGCCAGCAGCCG

CGGTAATACGTAGGTGGCAAGCGTTGTCCGGAATTATTGGGCGTAAAGGGCGCGCAGGCGGCGTCGTAAGTCGGTCT

TAAAAGTGCGGGGCTTAACCCCGTGAGGGGACCGAAACTGCGATGCTAGAGTATCGGAGAGGAAAGCGGAATTCCTA

GTGTAGCGGTGAAATGCGTAGATATTAGGAGGAACACCAGTGGCGAAAGCGGCTTTCTGGACGACAACTGACGCTGA

GGCGCGAAAGCCAGGGGAGCAAACGGGATTAGATACCCCGGTAGTCCTGGCCGTAAACGATGGATACTAGGTGTAGG

AGGTATCGACCCCTTCTGTGCCGGAGTTAACGCAATAAGTATCCCGCCTGGGGAGTACGGCCGCAAGGCTGAAACTC

AAAGGAATTGACGGGGGCCCGCACAAGCGGTGGAGTATGTGGTTTAATTCGACGCAACGCGAAGAACCTTACCAAGC

CTTGACATTGATTGCTATGGATAGAGATATCCAGTTCCTCTTCGGAGGACAAGAAAACAGGTGGTGCACGGCTGTCG

TCAGCTCGTGTCGTGAGATGTTGGGTTAAGTCCCGCAACGAGCGCAACCCCTATCTTCTGTTACCAGCGGTTCGGCC

GGGGACTCAGGAGAGACTGCCGCAGACAATGCGGAGGAAGGCGGGGATGACGTCAAGTCATCATGCCCCTTATGGCT

TGGGCTACACACGTACTACAATGGCTCTTAATAGAGGGAAGCGAAGGAGCGATCCGGAGCAAACCCCAAAAACAGAG

TCCCAGTTCGGATTGCAGGCTGCAACTCGCCTGCATGAAGCAGGAATCGCTAGTAATCGCAGGTCAGCATACTGCGG

TGAATACGTTCCCGGGCCTTGTACACACCGCCCGTCACACCACGAAAGTCATTCACACCCGAAGCCGGTGAGGTAAC

CTTTTGGAGCCAGCCGTCGAAGGTGGGGCGATGATTGGGGTGAAGTCGTAACAAGGTAGCCGTATCGGAAGGTGCG

GCTGGATCACCT

>SEQ ID NO: 120|NR_044645.2|*Dorea formicigenerans* strain ATCC 27755 16S ribosomal RNA gene, complete sequence

TTAAACGAGAGTTTGATCCTGGCTCAGGATGAACGCTGGCGGCGTGCTTAACACATGCAAGTCGAGCGAAGCACATA

AGTTTGATTCTTCGGATGAAGACTTTTGTGACTGAGCGGCGGACGNNNGAGTAACGCGTGGGTAACCTGCCTCATAC

AGGGGGATAACAGYTAGAAATGGCTGCTAATACCGCATAAGACCACAGTACTGCATGGTACAGTGNNNAAAACTCCG

GTGGTATGAGATGGACCCGCGTCTGATTAGGTAGTTGGTGAGGTAACGGCCCACCNAGCCGACGATCAGTAGCCGAC

CTGAGAGGGTGACCGGCCACATTGGGACTGAGACACGGCCNNGACTCCTACGGGAGGCAGCAGTGGGGAATATTGCA

CAATGGGCGAAAGCCTGATGCAGCGACGCCGCGTGAAGGATGAAGTATTTCGGTATGTAAACTTCTATCAGCAGGGA

AGAAAATGACGGTACCTGACTAAGAAGCCCCGGCTAACTACGTGCCAGCAGCCGNGGTAATACGTAGGGGGNNAGCG

TTATCCGGATTTACTGGGTGTAAAGGGAGCGTAGACGGCTGTGCAAGTCTGAAGTGAAAGGCATGGGCTCAACCTGT

GGACTGCTTTGGAAACTGTGCAGCTAGAGTGTCGGAGAGGTAAGTGGAATTCCTAGTGTAGCGGTGAAATGCGTAGA

TATTAGGAGGAACACCAGTGGCGAAGGCGGCNTACTGGACGATGACTGACGTTGAGGCTCGAAAGCGTGGGGAGCAA

-continued

ACAGGATTAGATACCCTGGTAGTCCACGCCGTAAACGATGACTGCTAGGTGTCGGGTAGCAAAGCTATTCGGTGCCG

CAGCTAACGCAATAAGCAGTCCACCTGGGGAGTACGTTCGCAAGAATGAAACTCAAAGGAATTGACGGGGNCCNGCA

CAAGCGGTGGAGCATGTGGTTTAATTCGAANNAACGCGAAGAACCTTACCTGATCTTGACATCCCGATGACCGCTTC

GTAATGGAAGYTTTTCTTCGGAACATCGGTGACAGGTGGTGCATGGTTGTCGTCAGCTCGTGTCGTGAGATGTTGGG

TTAAGTCCCGCAACGAGCGCAACCCTTATCTTCAGTAGCCAGCATTTAGGATGGGCACTCTGGAGAGACTGCCAGGG

ATAACCTGGAGGAAGGTGGGGATGACGTNNAATCATCATGCCCCTTATGACCAGGGCTACACACGTGCTACAATGGC

GTAAACAGAGGGAGGCAGAGCCGCGAGGCCGAGCAAATCTCAAAAATAACGTCTCAGTTCGGATTGTAGTCTGCAAC

TCGACTACATGAAGCTGGAATCGCTAGTAATCGCAGATCAGAATGCTGCGGTGAATACGTTCCCGGGTCTTGTACAC

ACCGCCCGTCACACCATGGGAGTCAGTAACGCCCGAAGTCAGTGACCCAACCGAAAGGAGGGAGCTGCCGAAGGTGG

GACCGATAACTGGGGT

>SEQ ID NO: 121|NR_118643.1|*Eisenbergiella tayi* strain B086562 16S ribosomal RNA gene, partial sequence

GGTATAACTTAGTGGCGGACGGGTGAGTAACGCGTGGGAAACCTGCCCTGTACCGGGGGATAACACTTAGAAATAGG

TGCTAATACCGCATAAGCGCACGGAACCGCATGGTTCCGTGTGAAAAACTCCGGTGGTACAGGATGGTCCCGCGTCT

GATTAGCCAGTTGGCAGGGTAACGGCCTACCAAAGCGACGATCAGTAGCCGGCCTGAGAGGGTGAACGGCCACATTG

GGACTGAGACACGGCCCAAACTCCTACGGGAGGCAGCAGTGGGGAATATTGCACAATGGGGGAAACCCTGATGCAGC

GACGCCGCGTGAGTGAAGAAGTATTTCGGTATGTAAAGCTCTATCAGCAGGGAAGAAAATGACGGTACCTGACTAAG

AAGCCCCGGCTAACTACGTGCCAGCAGCCGCGGTAATACGTAGGGGGCAAGCGTTATCCGGATTTACTGGGTGTAAA

GGGAGCGTAGACGGCATGGCAAGCCAGATGTGAAAACCCAGGGCTCAACCTTGGGATTGCATTTGGAACTGCCAGGC

TGGAGTGCAGGAGAGGTAAGCGGAATTCCTAGTGTAGCGGTGAAATGCGTAGATATTAGGAGGAACACCAGTGGCGA

AGGCGGCTTACTGGACTGTAACTGACGTTGAGGCTCGAAAGCGTGGGGAGCAAACAGGATTAGATACCCTGGTAGTC

CACGCGGTAAACGATGATTGCTAGGTGTAGGTGGGTATGGACCCATCGGTGCCGCAGCTAACGCAATAAGCAATCCA

CCTGGGGAGTACGTTCGCAAGAATGAAACTCAAAGGAATTGACGGGGACCCGCACAAGCGGTGGAGCATGTGGTTTA

ATTCGAAGCAACGCGAAGAACCTTACCAAGTCTTGACATCCCAATGACGCACCTGTAAAGAGGTGTTCCCTTCGGGG

CATTGGAGACAGGTGGTGCATGGTTGTCGTCAGCTCGTGTCGTGAGATGTTGGGTTAAGTCCCGCAACGAGCGCAAC

CCTTATTCTTAGTAGCCAGCAGGTAAAGCTGGGCACTCTAAGGAGACTGCCGGGGATAACCCGGAGGAAGGCGGGGA

TGACGTCAAATCATCATGCCCCTTATGATTTGGGCTACACACGTGCTACAATGGCGTAAACAAAGGGAAGCGAGACA

GTGATGTGGAGCAAATCYCAGAAATAACGTCTCAGTTCGGATTGTAGTCTGCAACTCGACTACATGAAGCTGGAATC

GCTAGTAATCGCGAATCAGCATGTCGCGGTGAATACGTTCCCGGGTCTTGTACACACCGCCCGTCACACCATGGGAG

TTGGAAATGCCCGAAGTCTGTGACCTAACCGAAAGGGAGGAGCAGCCGAAGGCAGGTCTGATAACTGGGGTGAAGTC

GTAA

>SEQ ID NO: 122|NR_118730.1|*Clostridium symbiosum* strain ATCC 14940 16S ribosomal RNA gene, partial sequence

AAACATGAGAGTTTGATCCTGGCTCAGGATGAACGCTGGCGGCGTGCCTAACACATGCAAGTCGAACGAAGCGATTT

AACGGAAGTTTTCGGATGGAAGTTGAATTGACTGAGTGGCGGACGGGTGAGTAACGCGTGGGTAACCTGCCTTGTAC

TGGGGGACAACAGTTAGAAATGACTGCTAATACCGCATAAGCGCACAGTATTGCATGATACAGTGTGAAAAACTCCG

GTGGTACAAGATGGACCCGCGTCTGATTAGCTAGTTGGTAAGGTAACGGCTTACCAAGGCGACGATCAGTAGCCGAC

CTGAGAGGGTGACCGGCCACATTGGGACTGAGACACGGCCNNAACTCCTACGGGAGGCAGCAGTGGGGAATATTGCA

CAATGGGCGAAAGCCTGATGCAGCGACGCCGCGTGAGTGAAGAAGTATTTCGGTATGTAAAGCTCTATCAGCAGGGA

AGAAAATGACGGTACCTGACTAAGAAGCCCCGGCTAACTACGTGCCAGCAGCCGCGGTAATACGTAGGGGGNNAGCG

TTATCCGGATTTACTGGGTGTAAAGGGAGCGTAGACGGTAAAGCAAGTCTGAAGTGAAAGCCCGCGNCTCAACTGCG

GNNCTGCTTTGGAAACTGTTTAACTGGAGTGTCGGAGAGGTAAGTGGAATTCCTAGTGTAGCGGTGAAATGCGTAGA

-continued

TATTAGGAGGAACACNAGTGGCGAAGGCGACTTACTGGACGATAACTGACGTTGAGGCTCGAAAGCGTGGGGAGCAA

ACAGGATTAGATACCCTGGTAGTCCACGCCGTAAACGATGAATACTAGGTGTTGGGGAGCAAAGCTCTTCGGTGCCG

TCGCAAACGCAGTAAGTATTCCACCTGGGGAGTACGTTCGCAAGAATGAAACTCAAAGGAATTGACGGGGACCNGCA

CAAGCGGTGGAGCATGTGGTTTAATTCGAANNAACGCGAAGAACCTTACCAGGTCTTGACATCGACTCGACGGGGGA

GTAACGTCCCNNTNCCTTCGGGGCGGAGAAGACAGGTGGTGCATGGTTGTCGTCAGCTCGTGTCGTGAGATGTTGGG

TTNAGTCCCGCAACGAGCGCAACCCTTATTCTAAGTAGCCAGCGGTTCGGCCGGGAACTCTTGGGAGACTGCCAGGG

ATAACCTGGAGGAAGGTGGGGATGACGTCNAATCATCATGCCCCTTATGATCTGGGCTACACACGTGCTACAATGGC

GTAAACANAGAGAAGCAAGACCGCGAGGTGGAGCAAATCTCAAAAATAACGTCTCAGTTCGGACTGCAGGCTGCAAC

TCGCCTGCACGAAGCTGGAATCGCTAGTAATCGCGAATCAGAATGTCGCGGTGAATACGTTCCCGGGTCTTGTACAC

ACCGNNCGTCACACCATGGGAGTCAGTAACGCCCGAAGTCAGTGACCCAACCGCAAGGAGGGAGCTGCCGAAGGCGG

GACCGANAAACNNGGG

>SEQ ID NO: 123|NR_113243.1|*Erysipelatoclostridium ramosum* strain JCM 1298
16S ribosomal RNA gene, partial sequence

AGAGTTTGATCCTGGCTCAGGATGAACGCTGGCGGCGTGCCTAATACATGCAAGTCGAACGCGAGCACTTGTGCTCG

AGTGGCGAACGGGTGAGTAATACATAAGTAACCTGCCCTAGACAGGGGGATAACTATTGGAAACGATAGCTAAGACC

GCATAGGTACGGACACTGCATGGTGACCGTATTAAAAGTGCCTCAAAGCACTGGTAGAGGATGGACTTATGGCGCAT

TAGCTGGTTGGCGGGGTAACGGCCCACCAAGGCGACGATGCGTAGCCGACCTGAGAGGGTGACCGGCCACACTGGGA

CTGAGACACGGCCCAGACTCCTACGGGAGGCAGCAGTAGGGAATTTTCGGCAATGGGGGAAACCCTGACCGAGCAAC

GCCGCGTGAAGGAAGAAGGTTTTCGGATTGTAAACTTCTGTTATAAAGGAAGAACGGCGGCTACAGGAAATGGTAGC

CGAGTGACGGTACTTTATTAGAAAGCCACGGCTAACTACGTGCCAGCAGCCGCGGTAATACGTAGGTGGCAAGCGTT

ATCCGGAATTATTGGGCGTAAAGAGGGAGCAGGCGGCAGCAAGGGTCTGTGGTGAAAGCCTGAAGCTTAACTTCAGT

AAGCCATAGAAACCAGGCAGCTAGAGTGCAGGAGAGGATCGTGGAATTCCATGTGTAGCGGTGAAATGCGTAGATAT

ATGGAGGAACACCAGTGGCGAAGGCGACGATCTGGCCTGCAACTGACGCTCAGTCCCGAAAGCGTGGGGAGCAAATA

GGATTAGATACCCTAGTAGTCCACGCCGTAAACGATGAGTACTAAGTGTTGGATGTCAAAGTTCAGTGCTGCAGTTA

ACGCAATAAGTACTCCGCCTGAGTAGTACGTTCGCAAGAATGAAACTCAAAGGAATTGACGGGGGCCCGCACAAGCG

GTGGAGCATGTGGTTTAATTCGAAGCAACGCGAAGAACCTTACCAGGTCTTGACATACTCATAAAGGCTCCAGAGAT

GGAGAGATAGCTATATGAGATACAGGTGGTGCATGGTTGTCGTCAGCTCGTGTCGTGAGATGTTGGGTTAAGTCCCG

CAACGAGCGCAACCCTTATCGTTAGTTACCATCATTAAGTTGGGGACTCTAGCGAGACTGCCAGTGACAAGCTGGAG

GAAGGCGGGGATGACGTCAAATCATCATGCCCCTTATGACCTGGGCTACACACGTGCTACAATGGATGGTGCAGAGG

GAAGCGAAGCCGCGAGGTGAAGCAAAACCCATAAAACCATTCTCAGTTCGGATTGTAGTCTGCAACTCGACTACATG

AAGTTGGAATCGCTAGTAATCGCGAATCAGCATGTCGCGGTGAATACGTTCTCGGGCCTTGTACACACCGCCCGTCA

CACCACGAGAGTTGATAACACCCGAAGCCGGTGGCCTAACCGCAAGGAAGGAGCTGTCTAAGGTGGGATTGATGATT

GGGGTGAAGTCGTAACAAGGTAACC

>SEQ ID NO: 124 |PROKKA_00507 16S ribosomal RNA gene | VE202-7

ATGAGAGTTTGATCCTGGCTCAGGATGAACGCTGGCGGCGTGCCTAACACATGCAAGTCGAACGAAGCAATTAAAGG

AAGTTTTCGGATGGAATTTGATTGACTGAGTGGCGGACGGGTGAGTAACGCGTGGATAACCTGCCTCACACTGGGGG

ATAACAGTTAGAAATGACTGCTAATACCGCATAAGCGCACAGTACCGCATGGTACGGTGTGAAAAACTCCGGTGGTG

TGAGATGGATCCGCGTCTGATTAGCCAGTTGGCGGGGTAACGGCCCACCAAAGCGACGATCAGTAGCCGACCTGAGA

GGGTGACCGGCCACATTGGGACTGAGACACGGCCCAAACTCCTACGGGAGGCAGCAGTGGGGAATATTGCACAATGG

GCGAAAGCCTGATGCAGCGACGCCGCGTGAGTGAAGAAGTATTTCGGTATGTAAAGCTCTATCAGCAGGGAAGAAAA

TGACGGTACCTGACTAAGAAGCCCCGGCTAACTACGTGCCAGCAGCCGCGGTAATACGTAGGGGGCAAGCGTTATCC

GGATTCACTGGGTGTAAAGGGAGCGTAGACGGCGAAGCAAGTCTGAAGTGAAAACCCAGGGCTCAACCCTGGGACTG

-continued

CTTTGGAAACTGTTTTGCTAGAGTGTCGGAGAGGTAAGTGGAATTCCTAGTGTAGCGGTGAAATGCGTAGATATTAG

GAGGAACACCAGTGGCGAAGGCGGCTTACTGGACGATAACTGACGTTGAGGCTCGAAAGCGTGGGGAGCAAACAGGA

TTAGATACCCTGGTAGTCCACGCCGTAAACGATGAATGCTAGGTGTTGGGGGGCAAAGCCCTTCGGTGCCGTCGCAA

ACGCAGTAAGCATTCCACCTGGGGAGTACGTTCGCAAGAATGAAACTCAAAGGAATTGACGGGGACCCGCACAAGCG

GTGGAGCATGTGGTTTAATTCGAAGCAACGCGAAGAACCTTACCAAGTCTTGACATCCTCTTGACCGGCGTGTAACG

GCGCCTTCCCTTCGGGGCAAGAGAGACAGGTGGTGCATGGTTGTCGTCAGCTCGTGTCGTGAGATGTTGGGTTAAGT

CCCGCAACGAGCGCAACCCTTATCCTTAGTAGCCAGCAGGTAGAGCTGGGCACTCTAGGGAGACTGCCAGGGATAAC

CTGGAGGAAGGTGGGGATGACGTCAAATCATCATGCCCCTTATGATTTGGGCTACACACGTGCTACAATGGCGTAAA

CAAAGGGAAGCAAGACAGTGATGTGGAGCAAATCCCAAAAATAACGTCCCAGTTCGGACTGTAGTCTGCAACCCGAC

TACACGAAGCTGGAATCGCTAGTAATCGCGAATCAGAATGTCGCGGTGAATACGTTCCCGGGTCTTGTACACACCGC

CCGTCACACCATGGGAGTCAGCAACGCCCGAAGTCAGTGACCCAACTCGCAAGAGAGGGAGCTGCCGAAGGCGGGGC

AGGTAACTGGGGTGAAGTCGTAACAAGGTAGCCGTATCGGAAGGTGCGGCTGGATCACCTCCTTT

>SEQ ID NO: 125 |PROKKA_00709 16S ribosomal RNA gene | VE202-7
ATGAGAGTTTGATCCTGGCTCAGGATGAACGCTGGCGGCGTGCCTAACACATGCAAGTCGAACGAAGCAATTAAAAT

GAAGTTTTCGGATGGATTTTTGATTGACTGAGTGGCGGACGGGTGAGTAACGCGTGGATAACCTGCCTCACACTGGG

GGATAACAGTTAGAAATGACTGCTAATACCGCATAAGCGCACAGTACCGCATGGTACGGTGTGAAAAACTCCGGTGG

TGTGGGATGGATCCGCGTCTGATTAGCCAGTTGGCGGGGTAACGGCCCACCAAAGCGACGATCAGTAGCCGACCTGA

GAGGGTGACCGGCCACATTGGGACTGAGACACGGCCCAAACTCCTACGGGAGGCAGCAGTGGGGAATATTGCACAAT

GGGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGCGAAGCAAGTCTGAAGTGAAAACCCAGGGCTCAACCCTGGGAC

TGCTTTGGAAACTGTTTTGCTAGAGTGTCGGAGAGGTAAGTGGAATTCCTAGTGTAGCGGTGAAATGCGTAGATATT

AGGAGGAACACCAGTGGCGAAGGCGGCTTACTGGACGATAACTGACGTTGAGGCTCGAAAGCGTGGGGAGCAAACAG

GATTAGATACCCTGGTAGTCCACGCCGTAAACGATGAATGCTAGGTGTTGGGGGGCAAAGCCCTTCGGTGCCGTCGC

AAACGCAGTAAGCATTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCAAGTCTTGACATCCTCTTGACCGGCGTGTAA

CGGCGCCTTCCCTTCGGGGCAAGAGAGACAGGTGGTGCATGGTTGTCGTCAGCTCGTGTCGTGAGATGTTGGGTTAA

GTCCCGCAACGAGCGCAACCCTTATCCTTAGTAGCCAGCAGGTAAAGCTGGGCACTCTAGGGAGACTGCCAGGGATA

ACCTGGAGGAAGGTGGGGATGACGTCAAATCATCATGCCCCTTATGATTTGGGCTACACACGTGCTACAATGGCGTA

AACAAAGGGAAGCAAGACAGTGATGTGGAGCAAATCCCAAAAATAACGTCCCAGTTCGGACTGTAGTCTGCAACCCG

ACTACACGAAGCTGGAATCGCTAGTAATCGCGAATCAGAATGTCGCGGTGAATACGTTCCCGGGTCTTGTACACACC

GCCCGTCACACCATGGGAGTCAGCAACGCCCGAAGTCAGTGACCCAACTCGCAAGAGAGGGAGCTGCCGAAGGCGGG

GCAGGTAACTGGGGTGAAGTCGTAACAAGGTAGCCGTATCGGAAGGTGCGGCTGGATCACCTCCTTT

>SEQ ID NO: 126 |PROKKA_01766 16S ribosomal RNA gene | VE202-7
ATGAGAGTTTGATCCTGGCTCAGGATGAACGCTGGCGGCGTGCCTAACACATGCAAGTCGAACGAAGCAATTAAAAT

GAAGTTTTCGGATGGATTTTTGATTGACTGAGTGGCGGACGGGTGAGTAACGCGTGGATAACCTGCCTCACACTGGG

GGATAACAGTTAGAAATGACTGCTAATACCGCATAAGCGCACAGTACCGCATGGTACGGTGTGAAAAACTCCGGTGG

TGTGAGATGGATCCGCGTCTGATTAGCCAGTTGGCGGGGTAACGGCCCACCAAAGCGACGATCAGTAGCCGACCTGA

GAGGGTGACCGGCCACATTGGGACTGAGACACGGCCCAAACTCCTACGGGAGGCAGCAGTGGGGAATATTGCACAAT

GGGCGAAAGCCTGATGCAGCGACGCCGCGTGAGTGAAGAAGTATTTCGGTATGTAAAGCTCTATCAGCAGGGAAGAA

ATGACGGTACCTGACTAAGAAGCCCCGGCTAACTACGTGCCAGCAGCCGCGGTAATACGTAGGGGGCAAGCGTTATC

CGGATTTACTGGGTGTAAAGGGAGCGTAGACGGCGAAGCAAGTCTGAAGTGAAAACCCAGGGCTCAACCCTGGGACT

-continued

GCTTTGGAAACTGTTTTGCTAGAGTGTCGGAGAGGTAAGTGGAATTCCTAGTGTAGCGGTGAAATGCGTAGATATTA

GGAGGAACACCAGTGGCGAAGGCGGCTTACTGGACGATAACTGACGTTGAGGCTCGAAAGCGTGGGGAGCAAACAGG

ATTAGATACCCTGGTAGTCCACGCCGTAAACGATGAATGCTAGGTGTTGGGGGCAAAGCCCTTCGGTGCCGTCGCAA

ACGCAGTAAGCATTCCACCTGGGGAGTACGTTCGCAAGAATGAAACTCAAAGGAATTGACGGGGACCCGCACAAGCG

GTGGAGCATGTGGTTTAATTCGAAGCAACGCGAAGAACCTTACCAAGTCTTGACATCCTCTTGACCGGCGTGTAACG

GCGCCTTCCCTTCGGGGCAAGAGAGACAGGTGGTGCATGGTTGTCGTCAGCTCGTGTCGTGAGATGTTGGGTTAAGT

CCCGCAACGAGCGCAACCCTTATCCTTAGTAGCCAGCAGGTAAAGCTGGGCACTCTAGGGAGACTGCCAGGGATAAC

CTGGAGGAAGGTGGGGATGACGTCAAATCATCATGCCCCTTATGATTTGGGCTACACACGTGCTACAATGGCGTAAA

CAAAGGGAAGCAAGACAGTGATGTGGAGCAAATCCCAAAAATAACGTCCCAGTTCGGACTGTAGTCTGCAACCCGAC

TACACGAAGCTGGAATCGCTAGTAATCGCGAATCAGAATGTCGCGGTGAATACGTTCCCGGGTCTTGTACACACCGC

CCGTCACACCATGGGAGTCAGCAACGCCCGAAGTCAGTGACCCAACTCGCAAGAGAGGGAGCTGCCGAAGGCGGGGC

AGGTAACTGGGGTGAAGTCGTAACAAGGTAGCCGTATCGGAAGGTGCGGCTGGATCACCTCCTTT

>SEQ ID NO: 127 |PROKKA_01779 16S ribosomal RNA gene | VE202-7
ATGAGAGTTTGATCCTGGCTCAGGATGAACGCTGGCGGCGTGCCTAACACATGCAAGTCGAACGAAGCAATTAAAAT

GAAGTTTTCGGATGGATTTTTGATTGACTGAGTGGCGGACGGGTGAGTAACGCGTGGATAACCTGCCTCACACTGGG

GGATAACAGTTAGAAATGACTGCTAATACCGCATAAGCGCACAGTACCGCATGGTACGGTGTGAAAAACTCCGGTGG

TGTGAGATGGATCCGCGTCTGATTAGCCAGTTGGCGGGGTAACGGCCCACCAAAGCGACGATCAGTAGCCGACCTGA

GAGGGTGACCGGCCACATTGGGACTGAGACACGGCCCAAACTCCTACGGGAGGCAGCAGTGGGGAATATTGCACAAT

GGGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGCGAAGCAAGTCTGAAGTGAAAACCCAGGGCTCAACCCTGGGAC

TGCTTTGGAAACTGTTTTGCTAGAGTGTCGGAGAGGTAAGTGGAATTCCTAGTGTAGCGGTGAAATGCGTAGATATT

AGGAGGAACACCAGTGGCGAAGGCGGCTTACTGGACGATAACTGACGTTGAGGCTCGAAAGCGTGGGGAGCAAACAG

GATTAGATACCCTGGTAGTCCACGCCGTAAACGATGAATGCTAGGTGTTGGGGGCAAAGCCCTTCGGTGCCGTCGCA

AACGCAGTAAGCATTCCACCTGGGGAGTACGTTCGCAAGAATGAAACTCAAAGGAATTGACGGGGACCCGCACAAGC

GGTGGAGCATGTGGTTTAATTCGAAGCAACGCGAAGAACCTTACCAAGTCTTGACATCCTCTTGACCGGCGTGTAAC

GGCGCCTTCCCTTCGGGGCAGGAGAGACAGGTGGTGCATGGTTGTCGTCAGCTCGTGTCGTGAGATGTTGGGTTAAG

TCCCGCAACGAGCGCAACCCTTATCCTTAGTAGCCAGCAGGTAGAGCTGGGCACTCTAGGGAGACTGCCAGGGATAA

CCTGGAGGAAGGTGGGGATGACGTCAAATCATCATGCCCCTTATGATTTGGGCTACACACGTGCTACAATGGCGTAA

ACAAAGGGAAGCAAGACAGTGATGTGGAGCAAATCCCAAAATAACGTCCCAGTTCGGACTGTAGTCTGCAACCCGAC

TACACGAAGCTGGAATCGCTAGTAATCGCGAATCAGAATGTCGCGGTGAATACGTTCCCGGGTCTTGTACACACCGC

CCGTCACACCATGGGAGTCAGCAACGCCCGAAGTCAGTGACCCAACTCGCAAGAGAGGGAGCTGCCGAAGGCGGGGC

AGGTAACTGGGGTGAAGTCGTAACAAGGTAGCCGTATCGGAAGGTGCGGCTGGATCACCTCCTTT

>SEQ ID NO: 128 |PROKKA_05926 16S ribosomal RNA gene | VE202-7
ATGAGAGTTTGATCCTGGCTCAGGATGAACGCTGGCGGCGTGCCTAACACATGCAAGTCGAACGAAGCAATTAAAAT

GAAGTTTTCGGATGGATTTTAATTGACTGAGTGGCGGACGGGTGAGTAACGCGTGGATAACCTGCCTCACACTGGGG

GATAACAGTTAGAAATGACTGCTAATACCGCATAAGCGCACAGTACCGCATGGTACGGTGTGAAAAACTCCGGTGGT

GTGAGATGGATCCGCGTCTGATTAGCCAGTTGGCGGGGTAACGGCCCACCAAAGCGACGATCAGTAGCCGACCTGAG

AGGGTGACCGGCCACATTGGGACTGAGACACGGCCCAAACTCCTACGGGAGGCAGCAGTGGGGAATATTGCACAATG

GGCGAAAGCCTGATGCAGCGACGCCGCGTGAGTGAAGAAGTATTTCGGTATGTAAAGCTCTATCAGCAGGGAAGAAA

ATGACGGTACCTGACTAAGAAGCCCCGGCTAACTACGTGCCAGCAGCCGCGGTAATACGTAGGGGGCAAGCGTTATC

-continued

CGGATTTACTGGGTGTAAAGGGAGCGTAGACGGCGAAGCAAGTCTGAAGTGAAAACCCAGGGCTCAACCCTGGGACT

GCTTTGGAAACTGTTTTGCTAGAGTGTCGGAGAGGTAAGTGGAATTCCTAGTGTAGCGGTGAAATGCGTAGATATTA

GGAGGAACACCAGTGGCGAAGGCGGCTTACTGGACGATAACTGACGTTGAGGCTCGAAAGCGTGGGGAGCAAACAGG

ATTAGATACCCTGGTAGTCCACGCCGTAAACGATGAATGCTAGGTGTTGGGGGGCAAAGCCCTTCGGTGCCGTCGCA

AACGCAGTAAGCATTCCACCTGGGGAGTACGTTCGCAAGAATGAAACTCAAAGGAATTGACGGGGACCCGCACAAGC

GGTGGAGCATGTGGTTTAATTCGAAGCAACGCGAAGAACCTTACCAAGTCTTGACATCCTCTTGACCGGCGTGTAAC

GGCGCCTTCCCTTCGGGGCAAGAGAGACAGGTGGTGCATGGTTGTCGTCAGCTCGTGTCGTGAGATGTTGGGTTAAG

TCCCGCAACGAGCGCAACCCTTATCCTTAGTAGCCAGCAGGTAAAGCTGGGCACTCTAGGGAGACTGCCAGGGATAA

CCTGGAGGAAGGTGGGGATGACGTCAAATCATCATGCCCCTTATGATTTGGGCTACACACGTGCTACAATGGCGTAA

ACAAAGGGAAGCAAGACAGTGATGTGGAGCAAATCCCAAAATAACGTCCCAGTTCGGACTGTAGTCTGCAACCCGAC

TACACGAAGCTGGAATCGCTAGTAATCGCGAATCAGAATGTCGCGGTGAATACGTTCCCGGGTCTTGTACACACCGC

CCGTCACACCATGGGAGTCAGCAACGCCCGAAGTCAGTGACCCAACTCGCAAGAGAGGGAGCTGCCGAAGGCGGGGC

AGGTAACTGGGGTGAAGTCGTAACAAGGTAGCCGTATCGGAAGGTGCGGCTGGATCACCTCCTTT

>SEQ ID NO: 129 | PROKKA_01784 16S ribosomal RNA gene
TCAAAGAGTTTGATCCTGGCTCAGGACGAACGCTGGCGGCGCGCCTAACACATGCAAGTCGAACGGAGCTTACGTTT

TGAAGTTTTCGGATGGATGAATGTAAGCTTAGTGGCGGACGGGTGAGTAACACGTGAGCAACCTGCCTTTCAGAGGG

GGATAACAGCCGGAAACGGCTGCTAATACCGCATGATGTTGCGGGGGCACATGCCCCTGCAACCAAAGGAGCAATCC

GCTGAAAGATGGGCTCGCGTCCGATTAGCCAGTTGGCGGGGTAACGGCCCACCAAAGCGACGATCGGTAGCCGGACT

GAGAGGTTGAACGGCCACATTGGGACTGAGACACGGCCCAGACTCCTACGGGAGGCAGCAGTGGGGGATATTGCACA

ATGGGCGAAAGCCTGATGCAGCGACGCCGCGTGAGGGAAGACGGTCTTCGGATTGTAAACCTCTGTCTTTGGGGAAG

AAAATGACGGTACCCAAAGAGGAAGCTCCGGCTAACTACGTGCCAGCAGCCGCGGTAATACGTAGGGAGCAAGCGTT

GTCCGGAATTACTGGGTGTAAAGGGAGCGTAGGCGGGATGGCAAGTAGAATGTTAAATCCATCGGCTCAACCGGTGG

CTGCGTTCTAAACTGCCGTTCTTGAGTGAAGTAGAGGCAGGCGGAATTCCTAGTGTAGCGGTGAAATGCGTAGATAT

TAGGAGGAACACCAGTGGCGAAGGCGGCCTGCTGGGCTTTAACTGACGCTGAGGCTCGAAAGCGTGGGGAGCAAACA

GGATTAGATACCCTGGTAGTCCACGCCGTAAACGATGATTACTAGGTGTGGGGGGACTGACCCCTTCCGTGCCGCAG

TTAACACAATAAGTAATCCACCTGGGGAGTACGGCCGCAAGGTTGAAACTCAAAGGAATTGACGGGGGCCCGCACAA

GCAGTGGAGTATGTGGTTTAATTCGAAGCAACGCGAAGAACCTTACCAGGTCTTGACATCGGATGCATAGCCTAGAG

ATAGGTGAAGCCCTTCGGGGCATCCAGACAGGTGGTGCATGGTTGTCGTCAGCTCGTGTCGTGAGATGTTGGGTTAA

GTCCCGCAACGAGCGCAACCCTTATTATTAGTTGCTACGCAAGAGCACTCTAATGAGACTGCCGTTGACAAAACGGA

GGAAGGTGGGGATGACGTCAAATCATCATGCCCCTTATGACCTGGGCTACACACGTACTACAATGGCACTAAAACAG

AGGGCGGCGACACCGCGAGGTGAAGCGAATCCCGAAAAAGTGTCTCAGTTCAGATTGCAGGCTGCAACCCGCCTGCA

TGAAGTCGGAATTGCTAGTAATCGCGGATCAGCATGCCGCGGTGAATACGTTCCCGGGCCTTGTACACACCGCCCGT

CACACCATGGGAGTCGGTAACACCCGAAGCCAGTAGCCTAACCGCAAGGGGGGCGCTGTCGAAGGTGGGATTGATGA

CTGGGGTGAAGTCGTAACAAGGTAGCCGTATCGGAAGGTGCGGCTGGATCACCTCCTTT

>SEQ ID NO: 130 | PROKKA_01864 16S ribosomal RNA gene
TCAAAGAGTTTGATCCTGGCTCAGGACGAACGCTGGCGGCGCGCCTAACACATGCAAGTCGAACGGAGCTTACGTTT

TGAAGTTTTCGGATGGACGAATGTAAGCTTAGTGGCGGACGGGTGAGTAACACGTGAGCAACCTGCCTTTCAGAGGG

GATAACAGCCGGAAACGGCTGCTAATACCGCATGATGTTGCGGGGGCACATGCCCCTGCAACCAAAGGAGCAATCCG

CTGAAAGATGGGCTCGCGTCCGATTAGCCAGTTGGCGGGGTAACGGCCCACCAAAGCGACGATCGGTAGCCGGACTG

AGAGGTTGAACGGCCACATTGGGACTGAGACACGGCCCAGACTCCTACGGGAGGCAGCAGTGGGGGATATTGCACAA

TGGGCGAAAGCCTGATGCAGCGACGCCGCGTGAGGGAAGACGGTCTTCGGATTGTAAACCTCTGTCTTTGGGGAAGA

AAATGACGGTACCCAAAGAGGAAGCTCCGGCTAACTACGTGCCAGCAGCCGCGGTAATACGTAGGGAGCAAGCGTTG

-continued

TCCGGAATTACTGGGTGTAAAGGGAGCGTAGGCGGGATGGCAAGTAGAATGTTAAATCCATCGGCTCAACCGGTGGC

TGCGTTCTAAACTGCCGTTCTTGAGTGAAGTAGAGGCAGGCGGAATTCCTAGTGTAGCGGTGAAATGCGTAGATATT

AGGAGGAACACCAGTGGCGAAGGCGGCCTGCTGGGCTTTAACTGACGCTGAGGCTCGAAAGCGTGGGGAGCAAACAG

GATTAGATACCCTGGTAGTCCACGCCGTAAACGATGATTACTAGGTGTGGGGGGACTGACCCCTTCCGTGCCGCAGT

TAACACAATAAGTAATCCACCTGGGGAGTACGGCCGCAAGGTTGAAACTCAAAGGAATTGACGGGGGCCCGCACAAG

CAGTGGAGTATGTGGTTTAATTCGAAGCAACGCGAAGAACCTTACCAGGTCTTGACATCGGATGCATAGCCTAGAGA

TAGGTGAAGCCCTTCGGGGCATCCAGACAGGTGGTGCATGGTTGTCGTCAGCTCGTGTCGTGAGATGTTGGGTTAAG

TCCCGCAACGAGCGCAACCCTTATTATTAGTTGCTACGCAAGAGCACTCTAATGAGACTGCCGTTGACAAAACGGAG

GAAGGTGGGGATGACGTCAAATCATCATGCCCCTTATGACCTGGGCTACACACGTACTACAATGGCACTAAAACAGA

GGGCGGCGACACCGCGAGGTGAAGCGAATCCCGAAAAAGTGTCTCAGTTCAGATTGCAGGCTGCAACCCGCCTGCAT

GAAGTCGGAATTGCTAGTAATCGCGGATCAGCATGCCGCGGTGAATACGTTCCCGGGCCTTGTACACACCGCCCGTC

ACACCATGGGAGTCGGTAACACCCGAAGCCAGTAGCCTAACCGCAAGGGGGGCGCTGTCGAAGGTGGGATTGATGAC

TGGGGTGAAGTCGTAACAAGGTAGCCGTATCGGAAGGTGCGGCTGGATCACCTCCTTT

>SEQ ID NO: 131 | PROKKA_02671 16S ribosomal RNA gene
TCAAAGAGTTTGATCCTGGCTCAGGACGAACGCTGGCGGCGCGCCTAACACATGCAAGTCGAACGGAGCTTACGTTT

TGAAGTTTTCGGATGGATGAATGTAAGCTTAGTGGCGGACGGGTGAGTAACACGTGAGCAACCTGCCTTTCAGAGGG

GGATAACAGCCGGAAACGGCTGCTAATACCGCATGATGTTGCGGGGGCACATGCCCCTGCAACCAAAGGAGCAATCC

GCTGAAAGATGGGCTCGCGTCCGATTAGCCAGTTGGCGGGGTAACGGCCCACCAAAGCGACGATCGGTAGCCGGACT

GAGAGGTTGAACGGCCACATTGGGACTGAGACACGGCCCAGACTCCTACGGGAGGCAGCAGTGGGGGATATTGCACA

ATGGGCGAAAGCCTGATGCAGCGACGCCGCGTGAGGGAAGACGGTCTTCGGATTGTAAACCTCTGTCTTTGGGGAAG

AAAATGACGGTACCCAAAGAGGAAGCTCCGGCTAACTACGTGCCAGCAGCCGCGGTAATACGTAGGGAGCAAGCGTT

GTCCGGAATTACTGGGTGTAAAGGGAGCGTAGGCGGGATGGCAAGTAGAATGTTAAATCCATCGGCTCAACCGGTGG

CTGCGTTCTAAACTGCCGTTCTTGAGTGAAGTAGAGGCAGGCGGAATTCCTAGTGTAGCGGTGAAATGCGTAGATAT

TAGGAGGAACACCAGTGGCGAAGGCGGCCTGCTGGGCTTTAACTGACGCTGAGGCTCGAAAGCGTGGGGAGCAAACA

GGATTAGATACCCTGGTAGTCCACGCCGTAAACGATGATTACTAGGTGTGGGGGGACTGACCCCTTCCGTGCCGCAG

TTAACACAATAAGTAATCCACCTGGGGAGTACGGCCGCAAGGTTGAAACTCAAAGGAATTGACGGGGGCCCGCACAA

GCAGTGGAGTATGTGGTTTAATTCGAAGCAACGCGAAGAACCTTACCAGGTCTTGACATCGGATGCATAGCCTAGAG

ATAGGTGAAGCCCTTCGGGGCATCCAGACAGGTGGTGCATGGTTGTCGTCAGCTCGTGTCGTGAGATGTTGGGTTAA

GTCCCGCAACGAGCGCAACCCTTATTATTAGTTGCTACGCAAGAGCACTCTAATGAGACTGCCGTTGACAAAACGGA

GGAAGGTGGGGATGACGTCAAATCATCATGCCCCTTATGACCTGGGCTACACACGTACTACAATGGCACTAAAACAG

AGGGCGGCGACACCGCGAGGTGAAGCGAATCCCGAAAAAGTGTCTCAGTTCAGATTGCAGGCTGCAACCCGCCTGCA

TGAAGTCGGAATTGCTAGTAATCGCGGATCAGCATGCCGCGGTGAATACGTTCCCGGGCCTTGTACACACCGCCCGT

CACACCATGGGAGTCGGTAACACCCGAAGCCAGTAGCCTAACCGCAAGGGGGGCGCTGTCGAAGGTGGGATTGATGA

CTGGGGTGAAGTCGTAACAAGGTAGCCGTATCGGAAGGTGCGGCTGGATCACCTCCTTT

>SEQ ID NO: 132 | PROKKA_00690 16S ribosomal RNA gene
TACGAGAGTTTGATCCTGGCTCAGGATGAACGCTGGCGGCGTGCCTAACACATGCAAGTCGAGCGAAGCGCTGTTTT

CAGAATCTTCGGAGGAAGAGGACAGTGACTGAGCGGCGGACGGGTGAGTAACGCGTGGGCAACCTGCCTCATACAGG

GGGATAACAGTTAGAAATGACTGCTAATACCGCATAAGCGCACAGGACCGCATGGTGTAGTGTGAAAAACTCCGGTG

GTATGAGATGGACCCGCGTCTGATTAGGTAGTTGGTGGGGTAAAGGCCTACCAAGCCGACGATCAGTAGCCGACCTG

AGAGGGTGACCGGCCACATTGGGACTGAGACACGGCCCAAACTCCTACGGGAGGCAGCAGTGGGGAATATTGCACAA

TGGGGGAAACCCTGATGCAGCGACGCCGCGTGAAGGAAGAAGTATTTCGGTATGTAAACTTCTATCAGCAGGGAAGA

-continued

AAATGACGGTACCTGAGTAAGAAGCACCGGCTAAATACGTGCCAGCAGCCGCGGTAATACGTATGGTGCAAGCGTTA

TCCGGATTTACTGGGTGTAAAGGGAGCGTAGACGGATAGGCAAGTCTGGAGTGAAAACCCAGGGCTCAACCCTGGGA

CTGCTTTGGAAACTGCAGATCTGGAGTGCCGGAGAGGTAAGCGGAATTCCTAGTGTAGCGGTGAAATGCGTAGATAT

TAGGAGGAACACCAGTGGCGAAGGCGGCTTACTGGACGGTGACTGACGTTGAGGCTCGAAAGCGTGGGGAGCAAACA

GGATTAGATACCCTGGTAGTCCACGCCGTAAACGATGACTACTAGGTGTCGGTGTGCAAAGCACATCGGTGCCGCAG

CAAACGCAATAAGTAGTCCACCTGGGGAGTACGTTCGCAAGAATGAAACTCAAAGGAATTGACGGGGACCCGCACAA

GCGGTGGAGCATGTGGTTTAATTCGAAGCAACGCGAAGAACCTTACCTGGTCTTGACATCCGGATGACGGGCGAGTA

ATGTCGCCGTCCCTTCGGGGCGTCCGAGACAGGTGGTGCATGGTTGTCGTCAGCTCGTGTCGTGAGATGTTGGGTTA

AGTCCCGCAACGAGCGCAACCCTTATCTTCAGTAGCCAGCATATAAGGTGGGCACTCTGGAGAGACTGCCAGGGAGA

ACCTGGAGGAAGGTGGGGATGACGTCAAATCATCATGCCCCTTATGGCCAGGGCTACACACGTGCTACAATGGCGTA

AACAAAGGGAAGCGAGAGGGTGACCTGGAGCGAATCCCAAAAATAACGTCTCAGTTCGGATTGTAGTCTGCAACTCG

ACTACATGAAGCTGGAATCGCTAGTAATCGCGGATCAGCATGCCGCGGTGAATACGTTCCCGGGTCTTGTACACACC

GCCCGTCACACCATGGGAGTCAGTAACGCCCGAAGCCAGTGACCCAACCTTAGAGGAGGGAGCTGTCGAAGGCGGGA

CGGATAACTGGGGTGAAGTCGTAACAAGGTAGCCGTATCGGAAGGTGCGGCTGGATCACCTCCTTT

>SEQ ID NO: 133 | PROKKA_00991 16S ribosomal RNA gene
TACGAGAGTTTGATCCTGGCTCAGGATGAACGCTGGCGGCGTGCCTAACACATGCAAGTCGAGCGAAGCGCTGTTTT

CAGAATCTTCGGAGGAAGAGGACAGTGACTGAGCGGCGGACGGGTGAGTAACGCGTGGGCAACCTGCCTCATACAGG

GGGATAACAGTTAGAAATGACTGCTAATACCGCATAAGCGCACAGGACCGCATGGTGTAGTGTGAAAAACTCCGGTG

GTATGAGATGGACCCGCGTCTGATTAGGTAGTTGGTGGGGTAAAGGCCTACCAAGCCGACGATCAGTAGCCGACCTG

AGAGGGTGACCGGCCACATTGGGACTGAGACACGGCCCAAACTCCTACGGGAGGCAGCAGTGGGGAATATTGCACAA

TGGGGGAAACCCTGATGCAGCGACGCCGCGTGAAGGAAGAAGTATTTCGGTATGTAAACTTCTATCAGCAGGGAAGA

AGATGACGGTACCTGAGTAAGAAGCACCGGCTAAATACGTGCCAGCAGCCGCGGTAATACGTATGGTGCAAGCGTTA

TCCGGATTTACTGGGTGTAAAGGGAGCGTAGACGGATAGGCAAGTCTGGAGTGAAAACCCAGGGCTCAACCCTGGGA

CTGCTTTGGAAACTGCAGATCTGGAGTGCCGGAGAGGTAAGCGGAATTCCTAGTGTAGCGGTGAAATGCGTAGATAT

TAGGAGGAACACCAGTGGCGAAGGCGGCTTACTGGACGGTGACTGACGTTGAGGCTCGAAAGCGTGGGGAGCAAACA

GGATTAGATACCCTGGTAGTCCACGCCGTAAACGATGACTACTAGGTGTCGGTGTGCAAAGCACATCGGTGCCGCAG

CAAACGCAATAAGTAGTCCACCTGGGGAGTACGTTCGCAAGAATGAAACTCAAAGGAATTGACGGGGACCCGCACAA

GCGGTGGAGCATGTGGTTTAATTCGAAGCAACGCGAAGAACCTTACCTGGTCTTGACATCCGGATGACGGGCGAGTA

ATGTCGCCGTCCCTTCGGGGCATCCGAGACAGGTGGTGCATGGTTGTCGTCAGCTCGTGTCGTGAGATGTTGGGTTA

AGTCCCGCAACGAGCGCAACCCTTATCTTCAGTAGCCAGCATATAAGGTGGGCACTCTGGAGAGACTGCCAGGGAGA

ACCTGGAGGAAGGTGGGGATGACGTCAAATCATCATGCCCCTTATGGCCAGGGCTACACACGTGCTACAATGGCGTA

AACAAAGGGAAGCGAGAGGGTGACCTGAAGCGAATCCCAAAAATAACGTCTCAGTTCGGATTGTAGTCTGCAACTCG

ACTACATGAAGCTGGAATCGCTAGTAATCGCGGATCAGCATGCCGCGGTGAATACGTTCCCGGGTCTTGTACACACC

GCCCGTCACACCATGGGAGTCAGTAACGCCCGAAGCCAGTGACCCAACCTTAGAGGAGGGAGCTGTCGAAGGCGGGA

CGGATAACTGGGGTGAAGTCGTAACAAGGTAGCCGTATCGGAAGGTGCGGCTGGATCACCTCCTTT

>SEQ ID NO: 134 | PROKKA_01948 16S ribosomal RNA gene
TACGAGAGTTTGATCCTGGCTCAGGATGAACGCTGGCGGCGTGCCTAACACATGCAAGTCGAGCGAAGCGCTGTTTT

CAGAATCTTCGGAGGAAGAGGACAGTGACTGAGCGGCGGACGGGTGAGTAACGCGTGGGCAACCTGCCTCATACAGG

GGGATAACAGTTAGAAATGACTGCTAATACCGCATAAGCGCACAGGACCGCATGGTGTAGTGTGAAAAACTCCGGTG

GTATGAGATGGACCCGCGTCTGATTAGGTAGTTGGTGGGGTAAAGGCCTACCAAGCCGACGATCAGTAGCCGACCTG

AGAGGGTGACCGGCCACATTGGGACTGAGACACGGCCCAAACTCCTACGGGAGGCAGCAGTGGGGAATATTGCACAA

TGGGGGAAACCCTGATGCAGCGACGCCGCGTGAAGGAAGAAGTATTTCGGTATGTAAACTTCTATCAGCAGGGAAGA

-continued

AGATGACGGTACCTGAGTAAGAAGCACCGGCTAAATACGTGCCAGCAGCCGCGGTAATACGTATGGTGCAAGCGTTA

TCCGGATTTACTGGGTGTAAAGGGAGCGTAGACGGATAGGCAAGTCTGGAGTGAAAACCCAGGGCTCAACCCTGGGA

CTGCTTTGGAAACTGCAGATCTGGAGTGCCGGAGAGGTAAGCGGAATTCCTAGTGTAGCGGTGAAATGCGTAGATAT

TAGGAGGAACACCAGTGGCGAAGGCGGCTTACTGGACGGTGACTGACGTTGAGGCTCGAAAGCGTGGGGAGCAAACA

GGATTAGATACCCTGGTAGTCCACGCCGTAAACGATGACTACTAGGTGTCGGTGTGCAAAGCACATCGGTGCCGCAG

CAAACGCAATAAGTAGTCCACCTGGGGAGTACGTTCGCAAGAATGAAACTCAAAGGAATTGACGGGGACCCGCACAA

GCGGTGGAGCATGTGGTTTAATTCGAAGCAACGCGAAGAACCTTACCTGGTCTTGACATCCGGATGACGGGCGAGTA

ATGTCGCCGTCCCTTCGGGGCATCCGAGACAGGTGGTGCATGGTTGTCGTCAGCTCGTGTCGTGAGATGTTGGGTTA

AGTCCCGCAACGAGCGCAACCCTTATCTTCAGTAGCCAGCATATAAGGTGGGCACTCTGGAGAGACTGCCAGGGAGA

ACCTGGAGGAAGGTGGGGATGACGTCAAATCATCATGCCCCTTATGGCCAGGGCTACACACGTGCTACAATGGCGTA

AACAAAGGGAAGCGAGAGGGTGACCTGGAGCGAATCCCAAAAATAACGTCTCAGTTCGGATTGTAGTCTGCAACTCG

ACTACATGAAGCTGGAATCGCTAGTAATCGCGGATCAGCATGCCGCGGTGAATACGTTCCCGGGTCTTGTACACACC

GCCCGTCACACCATGGGAGTCAGTAACGCCCGAAGCCAGTGACCCAACCTTAGAGGAGGGAGCTGTCGAAGGCGGGA

CGGATAACTGGGGTGAAGTCGTAACAAGGTAGCCGTATCGGAAGGTGCGGCTGGATCACCTCCTTT

>SEQ ID NO: 135 | PROKKA_02310 16S ribosomal RNA gene
TACGAGAGTTTGATCCTGGCTCAGGATGAACGCTGGCGGCGTGCCTAACACATGCAAGTCGAGCGAAGCGCTGTTTT

CAGAATCTTCGGAGGAAGAGGACAGTGACTGAGCGGCGGACGGGTGAGTAACGCGTGGGCAACCTGCCTCATACAGG

GGGATAACAGTTAGAAATGACTGCTAATACCGCATAAGCGCACAGGACCGCATGGTGTAGTGTGAAAAACTCCGGTG

GTATGAGATGGACCCGCGTCTGATTAGGTAGTTGGTGGGGTAAAGGCCTACCAAGCCGACGATCAGTAGCCGACCTG

AGAGGGTGACCGGCCACATTGGGACTGAGACACGGCCCAAACTCCTACGGGAGGCAGCAGTGGGGAATATTGCACAA

TGGGGGAAACCCTGATGCAGCGACGCCGCGTGAAGGAAGAAGTATTTCGGTATGTAAACTTCTATCAGCAGGGAAGA

AGATGACGGTACCTGAGTAAGAAGCACCGGCTAAATACGTGCCAGCAGCCGCGGTAATACGTATGGTGCAAGCGTTA

TCCGGATTTACTGGGTGTAAAGGGAGCGTAGACGGATAGGCAAGTCTGGAGTGAAAACCCAGGGCTCAACCCTGGGA

CTGCTTTGGAAACTGCAGATCTGGAGTGCCGGAGAGGTAAGCGGAATTCCTAGTGTAGCGGTGAAATGCGTAGATAT

TAGGAGGAACACCAGTGGCGAAGGCGGCTTACTGGACGGTGACTGACGTTGAGGCTCGAAAGCGTGGGGAGCAAACA

GGATTAGATACCCTGGTAGTCCACGCCGTAAACGATGACTACTAGGTGTCGGTGTGCAAAGCACATCGGTGCCGCAG

CAAACGCAATAAGTAGTCCACCTGGGGAGTACGTTCGCAAGAATGAAACTCAAAGGAATTGACGGGGACCCGCACAA

GCGGTGGAGCATGTGGTTTAATTCGAAGCAACGCGAAGAACCTTACCTGGTCTTGACATCCGGATGACGGGCGAGTA

ATGTCGCCGTCCCTTCGGGGCATCCGAGACAGGTGGTGCATGGTTGTCGTCAGCTCGTGTCGTGAGATGTTGGGTTA

AGTCCCGCAACGAGCGCAACCCTTATCTTCAGTAGCCAGCATATAAGGTGGGCACTCTGGAGAGACTGCCAGGGAGA

ACCTGGAGGAAGGTGGGGATGACGTCAAATCATCATGCCCCTTATGGCCAGGGCTACACACGTGCTACAATGGCGTA

AACAAAGGGAAGCGAGAGGGTGACCTGAAGCGAATCCCAAAAATAACGTCTCAGTTCGGATTGTAGTCTGCAACTCG

ACTACATGAAGCTGGAATCGCTAGTAATCGCGGATCAGCATGCCGCGGTGAATACGTTCCCGGGTCTTGTACACACC

GCCCGTCACACCATGGGAGTCAGTAACGCCCGAAGCCAGTGACCCAACCTTAGAGGAGGGAGCTGTCGAAGGCGGGA

CGGATAACTGGGGTGAAGTCGTAACAAGGTAGCCGTATCGGAAGGTGCGGCTGGATCACCTCCTTT

>SEQ ID NO: 136 | PROKKA_02993 16S ribosomal RNA gene
TACGAGAGTTTGATCCTGGCTCAGGATGAACGCTGGCGGCGTGCCTAACACATGCAAGTCGAGCGAAGCGCTGTTTT

CAGAATCTTCGGAGGAAGAGGACAGTGACTGAGCGGCGGACGGGTGAGTAACGCGTGGGCAACCTGCCTCATACAGG

GGGATAACAGTTAGAAATGACTGCTAATACCGCATAAGCGCACAGGACCGCATGGTGTAGTGTGAAAAACTCCGGTG

GTATGAGATGGACCCGCGTCTGATTAGGTAGTTGGTGGGGTAAAGGCCTACCAAGCCGACGATCAGTAGCCGACCTG

AGAGGGTGACCGGCCACATTGGGACTGAGACACGGCCCAAACTCCTACGGGAGGCAGCAGTGGGGAATATTGCACAA

-continued

TGGGGGAAACCCTGATGCAGCGACGCCGCGTGAAGGAAGAAGTATTTCGGTATGTAAACTTCTATCAGCAGGGAAGA

AGATGACGGTACCTGAGTAAGAAGCACCGGCTAAATACGTGCCAGCAGCCGCGGTAATACGTATGGTGCAAGCGTTA

TCCGGATTTACTGGGTGTAAAGGGAGCGTAGACGGATAGGCAAGTCTGGAGTGAAAACCCAGGGCTCAACCCTGGGA

CTGCTTTGGAAACTGCAGATCTGGAGTGCCGGAGAGGTAAGCGGAATTCCTAGTGTAGCGGTGAAATGCGTAGATAT

TAGGAGGAACACCAGTGGCGAAGGCGGCTTACTGGACGGTGACTGACGTTGAGGCTCGAAAGCGTGGGGAGCAAACA

GGATTAGATACCCTGGTAGTCCACGCCGTAAACGATGACTACTAGGTGTCGGTGTGCAAAGCACATCGGTGCCGCAG

CAAACGCAATAAGTAGTCCACCTGGGGAGTACGTTCGCAAGAATGAAACTCAAAGGAATTGACGGGGACCCGCACAA

GCGGTGGAGCATGTGGTTTAATTCGAAGCAACGCGAAGAACCTTACCTGGTCTTGACATCCGGATGACGGGCGAGTA

ATGTCGCCGTCCCTTCGGGGCATCCGAGACAGGTGGTGCATGGTTGTCGTCAGCTCGTGTCGTGAGATGTTGGGTTA

AGTCCCGCAACGAGCGCAACCCTTATCTTCAGTAGCCAGCATATAAGGTGGGCACTCTGGAGAGACTGCCAGGGAGA

ACCTGGAGGAAGGTGGGGATGACGTCAAATCATCATGCCCCTTATGGCCAGGGCTACACACGTGCTACAATGGCGTA

AACAAAGGGAAGCGAGAGGGTGACCTGGAGCGAATCCCAAAAATAACGTCTCAGTTCGGATTGTAGTCTGCAACTCG

ACTACATGAAGCTGGAATCGCTAGTAATCGCGGATCAGCATGCCGCGGTGAATACGTTCCCGGGTCTTGTACACACC

GCCCGTCACACCATGGGAGTCAGTAACGCCCGAAGCCAGTGACCCAACCTTAGAGGAGGGAGCTGTCGAAGGCGGGA

CGGATAACTGGGGTGAAGTCGTAACAAGGTAGCCGTATCGGAAGGTGCGGCTGGATCACCTCCTTT

>SEQ ID NO: 137 | PROKKA_00436 16S ribosomal RNA gene
ATGAGAGTTTGATCCTAGCTCAGGATGAACGCTGGCGGCGTGCCTAACACATGCAAGTCGAACGAAGCAATTTAACG

GAAGTTTTCGGATGGAAGTTGAATTGACTGAGTGGCGGACGGGTGAGTAACGCGTGGGTAACCTGCCTTGTACTGGG

GGACAACAGTTAGAAATGACTGCTAATACCGCATAAGCGCACAGTATCGCATGATACAGTGTGAAAAACTCCGGTGG

TACAAGATGGACCCGCGTCTGATTAGCTAGTTGGTAAGGTAACGGCTTACCAAGGCGACGATCAGTAGCCGACCTGA

GAGGGTGACCGGCCACATTGGGACTGAGACACGGCCCAAACTCCTACGGGAGGCAGCAGTGGGGAATATTGCACAAT

GGGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGTAAAGCAAGTCTGAAGTGAAAGCCCGCGGCTCAACTGCGGGAC

TGCTTTGGAAACTGTTTAACTGGAGTGTCGGAGAGGTAAGTGGAATTCCTAGTGTAGCGGTGAAATGCGTAGATATT

AGGAGGAACACCAGTGGCGAAGGCGACTTACTGGACGATAACTGACGTTGAGGCTCGAAAGCGTGGGGAGCAAACAG

GATTAGATACCCTGGTAGTCCACGCCGTAAACGATGAATACTAGGTGTTGGGGAGCAAAGCTCTTCGGTGCCGTCGC

AAACGCAGTAAGTATTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCAGGTCTTGACATCGATCCGACGGGGGAGTAA

CGTCCCCTTCCCTTCGGGGCGGAGAAGACAGGTGGTGCATGGTTGTCGTCAGCTCGTGTCGTGAGATGTTGGGTTAA

GTCCCGCAACGAGCGCAACCCTTATTCTAAGTAGCCAGCGGTTCGGCCGGGAACTCTTGGGAGACTGCCAGGGATAA

CCTGGAGGAAGGTGGGGATGACGTCAAATCATCATGCCCCTTATGATCTGGGCTACACACGTGCTACAATGGCGTAA

ACAAAGAGAAGCAAGACCGCGAGGTGGAGCAAATCTCAAAAATAACGTCTCAGTTCGGACTGCAGGCTGCAACTCGC

CTGCACGAAGCTGGAATCGCTAGTAATCGCGAATCAGAATGTCGCGGTGAATACGTTCCCGGGTCTTGTACACACCG

CCCGTCACACCATGGGAGTCAGTAACGCCCGAAGTCAGTGACCCAACCGCAAGGAGGGAGCTGCCGAAGGCGGGACC

GATAACTGGGGTGAAGTCGTAACAAGGTAGCCGTATCGGAAGGTGCGGCTGGATCACCTCCTTT

>SEQ ID NO: 138 | PROKKA_00685 16S ribosomal RNA gene
ATGAGAGTTTGATCCTGGCTCAGGATGAACGCTGGCGGCGTGCCTAACACATGCAAGTCGAACGAAGCGATTTAACG

GAAATTTTCGGATGGAAGTTGAATTGACTGAGTGGCGGACGGGTGAGTAACGCGTGGGTAACCTGCCTTGTACTGGG

GGACAACAGTTAGAAATGACTGCTAATACCGCATAAGCGCACAGTATCGCATGATACAGTGTGAAAAACTCCGGTGG

TACAAGATGGACCCGCGTCTGATTAGCTAGTTGGTAAGGTAACGGCTTACCAAGGCGACGATCAGTAGCCGACCTGA

GAGGGTGACCGGCCACATTGGGACTGAGACACGGCCCAAACTCCTACGGGAGGCAGCAGTGGGGAATATTGCACAAT

-continued

GGGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGTAAAGCAAGTCTGAAGTGAAAGCCCGCGGCTCAACTGCGGGAC

TGCTTTGGAAACTGTTTAACTGGAGTGTCGGAGAGGTAAGTGGAATTCCTAGTGTAGCGGTGAAATGCGTAGATATT

AGGAGGAACACCAGTGGCGAAGGCGACTTACTGGACGATAACTGACGTTGAGGCTCGAAAGCGTGGGGAGCAAACAG

GATTAGATACCCTGGTAGTCCACGCCGTAAACGATGAATACTAGGTGTTGGGGAGCAAAGCTCTTCGGTGCCGTCGC

AAACGCAGTAAGTATTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCAGGTCTTGACATCGATCCGACGGGGGAGTAA

CGTCCCCTTCCCTTCGGGGCGGAGAAGACAGGTGGTGCATGGTTGTCGTCAGCTCGTGTCGTGAGATGTTGGGTTAA

GTCCCGCAACGAGCGCAACCCTTATTCTAAGTAGCCAGCGGTTCGGCCGGGAACTCTTGGGAGACTGCCAGGGATAA

CCTGGAGGAAGGTGGGGATGACGTCAAATCATCATGCCCCTTATGATCTGGGCTACACACGTGCTACAATGGCGTAA

ACAAAGAGAAGCAAGACCGCGAGGTGGAGCAAATCTCAAAAATAACGTCTCAGTTCGGACTGCAGGCTGCAACTCGC

CTGCACGAAGCTGGAATCGCTAGTAATCGCGAATCAGAATGTCGCGGTGAATACGTTCCCGGGTCTTGTACACACCG

CCCGTCACACCATGGGAGTCAGTAACGCCCGAAGTCAGTGACCCAACCGCAAGGAGGGAGCTGCCGAAGGCGGGACC

GATAACTGGGGTGAAGTCGTAACAAGGTAGCCGTATCGGAAGGTGCGGCTGGATCACCTCCTTT

>SEQ ID NO: 139 | PROKKA_01171 16S ribosomal RNA gene
ATGAGAGTTTGATCCTGGCTCAGGATGAACGCTGGCGGCGTGCCTAACACATGCAAGTCGAACGAAGCGATTTAACG

GAAGTTTTCGGATGGAAGTTGAATTGACTGAGTGGCGGACGGGTGAGTAACGCGTGGGTAACCTGCCTTGTACTGGG

GGACAACAGTTAGAAATGACTGCTAATACCGCATAAGCGCACAGTATCGCATGATACAGTGTGAAAAACTCCGGTGG

TACAAGATGGACCCGCGTCTGATTAGCTAGTTGGTAAGGTAACGGCTTACCAAGGCGACGATCAGTAGCCGACCTGA

GAGGGTGACCGGCCACATTGGGACTGAGACACGGCCCAAACTCCTACGGGAGGCAGCAGTGGGGAATATTGCACAAT

GGGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGTAAAGCAAGTCTGAAGTGAAAGCCCGCGGCTCAACTGCGGGAC

TGCTTTGGAAACTGTTTAACTGGAGTGTCGGAGAGGTAAGTGGAATTCCTAGTGTAGCGGTGAAATGCGTAGATATT

AGGAGGAACACCAGTGGCGAAGGCGACTTACTGGACGATAACTGACGTTGAGGCTCGAAAGCGTGGGGAGCAAACAG

GATTAGATACCCTGGTAGTCCACGCCGTAAACGATGAATACTAGGTGTTGGGGAGCAAAGCTCTTCGGTGCCGTCGC

AAACGCAGTAAGTATTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCAGGTCTTGACATCGATCCGACGGGGGAGTAA

CGTCCCCTTCCCTTCGGGGCGGAGAAGACAGGTGGTGCATGGTTGTCGTCAGCTCGTGTCGTGAGATGTTGGGTTAA

GTCCCGCAACGAGCGCAACCCTTATTCTAAGTAGCCAGCGGTTCGGCCGGGAACTCTTGGGAGACTGCCAGGGATAA

CCTGGAGGAAGGTGGGGATGACGTCAAATCATCATGCCCCTTATGATCTGGGCTACACACGTGCTACAATGGCGTAA

ACAAAGAGAAGCAAGACCGCGAGGTGGAGCAAATCTCAAAAATAACGTCTCAGTTCGGACTGCAGGCTGCAACTCGC

CTGCACGAAGCTGGAATCGCTAGTAATCGCGAATCAGAATGTCGCGGTGAATACGTTCCCGGGTCTTGTACACACCG

CCCGTCACACCATGGGAGTCAGTAACGCCCGAAGTCAGTGACCCAACCGCAAGGAGGGAGCTGCCGAAGGCGGGACC

GATAACTGGGGTGAAGTCGTAACAAGGTAGCCGTATCGGAAGGTGCGGCTGGATCACCTCCTTT

>SEQ ID NO: 140 | PROKKA_05969 16S ribosomal RNA gene
ATGAGAGTTTGATCCTGGCTCAGGATGAACGCTGGCGGCGTGCCTAACACATGCAAGTCGAACGAAGCGATTTAACG

GAAGTTTTCGGATGGAAGTTGGATTGACTGAGTGGCGGACGGGTGAGTAACGCGTGGGTAACCTGCCTTGTACTGGG

GGACAACAGTTAGAAATGACTGCTAATACCGCATAAGCGCACAGTATCGCATGATACAGTGTGAAAAACTCCGGTGG

TACAAGATGGACCCGCGTCTGATTAGCTAGTTGGTAAGGTAACGGCTTACCAAGGCGACGATCAGTAGCCGACCTGA

-continued

GAGGGTGACCGGCCACATTGGGACTGAGACACGGCCCAAACTCCTACGGGAGGCAGCAGTGGGGAATATTGCACAAT

GGGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGTAAAGCAAGTCTGAAGTGAAAGCCCGCGGCTCAACTGCGGGAC

TGCTTTGGAAACTGTTTAACTGGAGTGTCGGAGAGGTAAGTGGAATTCCTAGTGTAGCGGTGAAATGCGTAGATATT

AGGAGGAACACCAGTGGCGAAGGCGACTTACTGGACGATAACTGACGTTGAGGCTCGAAAGCGTGGGGAGCAAACAG

GATTAGATACCCTGGTAGTCCACGCCGTAAACGATGAATACTAGGTGTTGGGGAGCAAAGCTCTTCGGTGCCGTCGC

AAACGCAGTAAGTATTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCAGGTCTTGACATCGATCCGACGGGGGAGTAA

CGTCCCCTTCCCTTCGGGGCGGAGAAGACAGGTGGTGCATGGTTGTCGTCAGCTCGTGTCGTGAGATGTTGGGTTAA

GTCCCGCAACGAGCGCAACCCTTATTCTAAGTAGCCAGCGGTTCGGCCGGGAACTCTTGGGAGACTGCCAGGGATAA

CCTGGAGGAAGGTGGGGATGACGTCAAATCATCATGCCCCTTATGATCTGGGCTACACACGTGCTACAATGGCGTAA

ACAAAGAGAAGCAAGACCGCGAGGTGGAGCAAATCTCAAAAATAACGTCTCAGTTCGGACTGCAGGCTGCAACTCGC

CTGCACGAAGCTGGAATCGCTAGTAATCGCGAATCAGAATGTCGCGGTGAATACGTTCCCGGGTCTTGTACACACCG

CCCGTCACACCATGGGAGTCAGTAACGCCCGAAGTCAGTGACCCAACCGCAAGGAGGGAGCTGCCGAAGGCGGGACC

GATAACTGGGGTGAAGTCGTAACAAGGTAGCCGTATCGGAAGGTGCGGCTGGATCACCTCCTTT

>SEQ ID NO: 141 | PROKKA_00279 16S ribosomal RNA gene
ATCAGAGAGTTTGATCCTGGCTCAGGATGAACGCTGGCGGCGTGCTTAACACATGCAAGTCGAGCGAAGCACTTAAG

TGGATCTCTTCGGATTGAAACTTATTTGACTGAGCGGCGGACGGGTGAGTAACGCGTGGGTAACCTGCCTCATACAG

GGGGATAACAGTTAGAAATGGCTGCTAATACCGCATAAGCGCACAGGACCGCATGGTCTGGTGTGAAAAACTCCGGT

GGTATGAGATGGACCCGCGTCTGATTAGCTAGTTGGAGGGGTAACGGCCCACCAAGGCGACGATCAGTAGCCGGCCT

GAGAGGGTGAACGGCCACATTGGGACTGAGACACGGCCCAGACTCCTACGGGAGGCAGCAGTGGGGAATATTGCACA

ATGGGGGAAACCCTGATGCAGCGACGCCGCGTGAAGGAAGAAGTATCTCGGTATGTAAACTTCTATCAGCAGGGAAG

AAAATGACGGTACCTGACTAAGAAGCCCCGGCTAACTACGTGCCAGCAGCCGCGGTAATACGTAGGGGGCAAGCGTT

ATCCGGATTTACTGGGTGTAAAGGGAGCGTAGACGGAAGAGCAAGTCTGATGTGAAAGGCTGGGGCTTAACCCCAGG

ACTGCATTGGAAACTGTTTTTCTAGAGTGCCGGAGAGGTAAGCGGAATTCCTAGTGTAGCGGTGAAATGCGTAGATA

TTAGGAGGAACACCAGTGGCGAAGGCGGCTTACTGGACGGTAACTGACGTTGAGGCTCGAAAGCGTGGGGAGCAAAC

AGGATTAGATACCCTGGTAGTCCACGCCGTAAACGATGAATACTAGGTGTCGGGTGGCAAAGCCATTCGGTGCCGCA

GCAAACGCAATAAGTATTCCACCTGGGGAGTACGTTCGCAAGAATGAAACTCAAAGGAATTGACGGGGACCCGCACA

AGCGGTGGAGCATGTGGTTTAATTCGAAGCAACGCGAAGAACCTTACCAAGTCTTGACATCCCTCTGACCGGCCCGT

AACGGGGCCTTCCCTTCGGGGCAGAGGAGACAGGTGGTGCATGGTTGTCGTCAGCTCGTGTCGTGAGATGTTGGGTT

AAGTCCCGCAACGAGCGCAACCCCTATCCTTAGTAGCCAGCAGGTGAAGCTGGGCACTCTAGGGAGACTGCCGGGGA

TAACCCGGAGGAAGGCGGGGACGACGTCAAATCATCATGCCCCTTATGATTTGGGCTACACACGTGCTACAATGGCG

TAAACAAAGGGAAGCGAGACAGCGATGTTGAGCAAATCCCAAAAATAACGTCCCAGTTCGGACTGCAGTCTGCAACT

CGACTGCACGAAGCTGGAATCGCTAGTAATCGCGAATCAGAATGTCGCGGTGAATACGTTCCCGGGTCTTGTACACA

CCGCCCGTCACACCATGGGAGTCAGTAACGCCCGAAGTCAGTGACCCAACCTTTTAGGAGGGAGCTGCCGAAGGCGG

GACCGATAACTGGGGTGAAGTCGTAACAAGGTAGCCGTATCGGAAGGTGCGGCTGGATCACCTCCTTT

>SEQ ID NO: 142 | PROKKA_01221 16S ribosomal RNA gene
ATCAGAGAGTTTGATCCTGGCTCAGGATGAACGCTGGCGGCGTGCTTAACACATGCAAGTCGAGCGAAGCACTTAAG

TGGATCTCTTCGGATTGAAACTTATTTGACTGAGCGGCGGACGGGTGAGTAACGCGTGGGTAACCTGCCTCATACAG

GGGGATAACAGTTAGAAATGGCTGCTAATACCGCATAAGCGCACAGGACCGCATGGTCTGGTGTGAAAAACTCCGGT

GGTATGAGATGGACCCGCGTCTGATTAGCTAGTTGGAGGGGTAACGGCCCACCAAGGCGACGATCAGTAGCCGGCCT

-continued

GAGAGGGTGAACGGCCACATTGGGACTGAGACACGGCCCAGACTCCTACGGGAGGCAGCAGTGGGGAATATTGCACA

ATGGGGGAAACCCTGATGCAGCGACGCCGCGTGAAGGAAGAAGTATCTCGGTATGTAAACTTCTATCAGCAGGGAAG

AAAATGACGGTACCTGACTAAGAAGCCCCGGCTAACTACGTGCCAGCAGCCGCGGTAATACGTAGGGGGCAAGCGTT

ATCCGGATTTACTGGGTGTAAAGGGAGCGTAGACGGAAGAGCAAGTCTGATGTGAAAGGCTGGGGCTTAACCCCAGG

ACTGCATTGGAAACTGTTTTTCTAGAGTGCCGGAGAGGTAAGTGGAATTCCTAGTGTAGCGGTGAAATGCGTAGATA

TTAGGAGGAACACCAGTGGCGAAGGCGGCTTACTGGACGGTAACTGACGTTGAGGCTCGAAAGCGTGGGGAGCAAAC

AGGATTAGATACCCTGGTAGTCCACGCCGTAAACGATGAATACTAGGTGTCGGGTGGCAAAGCCATTCGGTGCCGCA

GCAAACGCAATAAGTATTCCACCTGGGGAGTACGTTCGCAAGAATGAAACTCAAAGGAATTGACGGGGACCCGCACA

AGCGGTGGAGCATGTGGTTTAATTCGAAGCAACGCGAAGAACCTTACCAAGTCTTGACATCCCTCTGACCGGCCCGT

AACGGGGCCTTCCCTTCGGGGCAGAGGAGACAGGTGGTGCATGGTTGTCGTCAGCTCGTGTCGTGAGATGTTGGGTT

AAGTCCCGCAACGAGCGCAACCCCTATCCTTAGTAGCCAGCAGGTGAAGCTGGGCACTCTAGGGAGACTGCCGGGGA

TAACCCGGAGGAAGGCGGGGACGACGTCAAATCATCATGCCCCTTATGATTTGGGCTACACACGTGCTACAATGGCG

TAAACAAAGGGAAGCGGGACAGCGATGTTGAGCAAATCCCAAAAATAACGTCCCAGTTCGGACTGCAGTCTGCAACT

CGACTGCACGAAGCTGGAATCGCTAGTAATCGCGAATCAGAATGTCGCGGTGAATACGTTCCCGGGTCTTGTACACA

CCGCCCGTCACACCATGGGAGTCAGTAACGCCCGAAGTCAGTGACCCAACCTTACAGGAGGGAGCTGCCGAAGGCGG

GACCGATAACTGGGGTGAAGTCGTAACAAGGTAGCCGTATCGGAAGGTGCGGCTGGATCACCTCCTTT

>SEQ ID NO: 143 | PROKKA_02318 16S ribosomal RNA gene
ATCAGAGAGTTTGATCCTGGCTCAGGATGAACGCTGGCGGCGTGCTTAACACATGCAAGTCGAGCGAAGCACTTAAG

TGGATCTCTTCGGATTGAAGCTTATTTGACTGAGCGGCGGACGGGTGAGTAACGCGTGGGTAACCTGCCTCATACAG

GGGGATAACAGTTAGAAATGGCTGCTAATACCGCATAAGCGCACAGGACCGCATGGTCTGGTGTGAAAAACTCCGGT

GGTATGAGATGGACCCGCGTCTGATTAGCTAGTTGGAGGGGTAACGGCCCACCAAGGCGACGATCAGTAGCCGGCCT

GAGAGGGTGAACGGCCACATTGGGACTGAGACACGGCCCAGACTCCTACGGGAGGCAGCAGTGGGGAATATTGCACA

ATGGGGGAAACCCTGATGCAGCGACGCCGCGTGAAGGAAGAAGTATCTCGGTATGTAAACTTCTATCAGCAGGGAAG

AAAATGACGGTACCTGACTAAGAAGCCCCGGCTAACTACGTGCCAGCAGCCGCGGTAATACGTAGGGGGCAAGCGTT

ATCCGGATTTACTGGGTGTAAAGGGAGCGTAGACGGAAGAGCAAGTCTGATGTGAAAGGCTGGGGCTTAACCCCAGG

ACTGCATTGGAAACTGTTTTTCTAGAGTGCCGGAGAGGTAAGCGGAATTCCTAGTGTAGCGGTGAAATGCGTAGATA

TTAGGAGGAACACCAGTGGCGAAGGCGGCTTACTGGACGGTAACTGACGTTGAGGCTCGAAAGCGTGGGGAGCAAAC

AGGATTAGATACCCTGGTAGTCCACGCCGTAAACGATGAATACTAGGTGTCGGGTGGCAAAGCCATTCGGTGCCGCA

GCAAACGCAATAAGTATTCCACCTGGGGAGTACGTTCGCAAGAATGAAACTCAAAGGAATTGACGGGGACCCGCACA

AGCGGTGGAGCATGTGGTTTAATTCGAAGCAACGCGAAGAACCTTACCAAGTCTTGACATCCCTCTGACCGGCCCGT

AACGGGGCCTTCCCTTCGGGGCAGAGGAGACAGGTGGTGCATGGTTGTCGTCAGCTCGTGTCGTGAGATGTTGGGTT

AAGTCCCGCAACGAGCGCAACCCCTATCCTTAGTAGCCAGCAGGTGAAGCTGGGCACTCTAGGGAGACTGCCGGGGA

TAACCCGGAGGAAGGCGGGGACGACGTCAAATCATCATGCCCCTTATGATTTGGGCTACACACGTGCTACAATGGCG

TAAACAAAGGGAAGCGAGACAGCGATGTTGAGCAAATCCCAAAAATAACGTCCCAGTTCGGACTGCAGTCTGCAACT

CGACTGCACGAAGCTGGAATCGCTAGTAATCGCGAATCAGAATGTCGCGGTGAATACGTTCCCGGGTCTTGTACACA

CCGCCCGTCACACCATGGGAGTCAGTAACGCCCGAAGTCAGTGACCCAACCTTACAGGAGGGAGCTGCCGAAGGCGG

GACCGATAACTGGGGTGAAGTCGTAACAAGGTAGCCGTATCGGAAGGTGCGGCTGGATCACCTCCTTT

>SEQ ID NO: 144 | PROKKA_02336 16S ribosomal RNA gene
ATCAGAGAGTTTGATCCTGGCTCAGGATGAACGCTGGCGGCGTGCTTAACACATGCAAGTCGAGCGAAGCACTTAAG

CGGATCTCTTCGGATTGAAACTTATTTGACTGAGCGGCGGACGGGTGAGTAACGCGTGGGTAACCTGCCTCATACAG

GGGGATAACAGTTAGAAATGGCTGCTAATACCGCATAAGCGCACAGGACCGCATGGTCTGGTGTGAAAAACTCCGGT

-continued

GGTATGAGATGGACCCGCGTCTGATTAGCTAGTTGGAGGGGTAACGGCCCACCAAGGCGACGATCAGTAGCCGGCCT

GAGAGGGTGAACGGCCACATTGGGACTGAGACACGGCCCAGACTCCTACGGGAGGCAGCAGTGGGGAATATTGCACA

ATGGGGGAAACCCTGATGCAGCGACGCCGCGTGAAGGAAGAAGTATCTCGGTATGTAAACTTCTATCAGCAGGGAAG

AAAATGACGGTACCTGACTAAGAAGCCCCGGCTAACTACGTGCCAGCAGCCGCGGTAATACGTAGGGGGCAAGCGTT

ATCCGGATTTACTGGGTGTAAAGGGAGCGTAGACGGAAGAGCAAGTCTGATGTGAAAGGCTGGGGCTTAACCCCAGG

ACTGCATTGGAAACTGTTTTTCTAGAGTGCCGGAGAGGTAAGCGGAATTCCTAGTGTAGCGGTGAAATGCGTAGATA

TTAGGAGGAACACCAGTGGCGAAGGCGGCTTACTGGACGGTAACTGACGTTGAGGCTCGAAAGCGTGGGGAGCAAAC

AGGATTAGATACCCTGGTAGTCCACGCCGTAAACGATGAATACTAGGTGTCGGGTGGCAAAGCCATTCGGTGCCGCA

GCAAACGCAATAAGTATTCCACCTGGGGAGTACGTTCGCAAGAATGAAACTCAAAGGAATTGACGGGGACCCGCACA

AGCGGTGGAGCATGTGGTTTAATTCGAAGCAACGCGAAGAACCTTACCAAGTCTTGACATCCCTCTGACCGGCCCGT

AACGGGGCCTTCCCTTCGGGGCAGAGGAGACAGGTGGTGCATGGTTGTCGTCAGCTCGTGTCGTGAGATGTTGGGTT

AAGTCCCGCAACGAGCGCAACCCCTATCCTTAGTAGCCAGCAGGTGAAGCTGGGCACTCTAGGGAGACTGCCGGGGA

TAACCCGGAGGAAGGCGGGGACGACGTCAAATCATCATGCCCCTTATGATTTGGGCTACACACGTGCTACAATGGCG

TAAACAAAGGGAAGCGAGACAGCGATGTTGAGCAAATCCCAAAAATAACGTCCCAGTTCGGACTGCAGTCTGCAACT

CGACTGCACGAAGCTGGAATCGCTAGTAATCGCGAATCAGAATGTCGCGGTGAATACGTTCCCGGGTCTTGTACACA

CCGCCCGTCACACCATGGGAGTCAGTAACGCCCGAAGTCAGTGACCCAACCTTACAGGAGGGAGCTGCCGAAGGCGG

GACCGATAACTGGGGTGAAGTCGTAACAAGGTAGCCGTATCGGAAGGTGCGGCTGGATCACCTCCTTT

>SEQ ID NO: 145 | PROKKA_04947 16S ribosomal RNA gene
ATCAGAGAGTTTGATCCTGGCTCAGGATGAACGCTGGCGGCGTGCTTAACACATGCAAGTCGAGCGAAGCACTTAAG

TGGATCTCTTCGGATTGAAACTTATTTGACTGAGCGGCGGACGGGTGAGTAACGCGTGGGTAACCTGCCTCATACAG

GGGGATAACAGTTAGAAATGGCTGCTAATACCGCATAAGCGCACAGGACCGCATGGTCTGGTGTGAAAAACTCCGGT

GGTATGAGATGGACCCGCGTCTGATTAGCTAGTTGGAGGGGTAACGGCCCACCAAGGCGACGATCAGTAGCCGGCCT

GAGAGGGTGAACGGCCACATTGGGACTGAGACACGGCCCAGACTCCTACGGGAGGCAGCAGTGGGGAATATTGCACA

ATGGGGGAAACCCTGATGCAGCGACGCCGCGTGAAGGAAGAAGTATCTCGGTATGTAAACTTCTATCAGCAGGGAAG

AAAATGACGGTACCTGACTAAGAAGCCCCGGCTAACTACGTGCCAGCAGCCGCGGTAATACGTAGGGGGCAAGCGTT

ATCCGGATTTACTGGGTGTAAAGGGAGCGTAGACGGAAGAGCAAGTCTGATGTGAAAGGCTGGGGCTTAACCCCAGG

ACTGCATTGGAAACTGTTTTTCTAGAGTGCCGGAGAGGTAAGCGGAATTCCTAGTGTAGCGGTGAAATGCGTAGATA

TTAGGAGGAACATCAGTGGCGAAGGCGGCTTACTGGACGGTAACTGACGTTGAGGCTCGAAAGCGTGGGGAGCAAAC

AGGATTAGATACCCTGGTAGTCCACGCCGTAAACGATGAATACTAGGTGTCGGGTGGCAAAGCCATTCGGTGCCGCA

GCAAACGCAATAAGTATTCCACCTGGGGAGTACGTTCGCAAGAATGAAACTCAAAGGAATTGACGGGGACCCGCACA

AGCGGTGGAGCATGTGGTTTAATTCGAAGCAACGCGAAGAACCTTACCAAGTCTTGACATCCCTCTGACCGGCCCGT

AACGGGGCCTTCCCTTCGGGGCAGAGGAGACAGGTGGTGCATGGTTGTCGTCAGCTCGTGTCGTGAGATGTTGGGTT

AAGTCCCGCAACGAGCGCAACCCCTATCCTTAGTAGCCAGCAGGTGAAGCTGGGCACTCTAGGGAGACTGCCGGGGA

TAACCCGGAGGAAGGCGGGGACGACGTCAAATCATCATGCCCCTTATGATTTGGGCTACACACGTGCTACAATGGCG

TAAACAAAGGGAAGCGAGACAGCGATGTTGAGCAAATCCCAAAAATAACGTCCTAGTTCGGACTGCAGTCTGCAACT

CGACTGCACGAAGCTGGAATCGCTAGTAATCGCGAATCAGAATGTCGCGGTGAATACGTTCCCGGGTCTTGTACACA

CCGCCCGTCACACCATGGGAGTCAGTAACGCCCGAAGTCAGTGACCCAACCTTACAGGAGGGAGCTGCCGAAGGCGG

GACCGATAACTGGGGTGAAGTCGTAACAAGGTAGCCGTATCGGAAGGTGCGGCTGGATCACCTCCTTT

>SEQ ID NO: 146 | PROKKA_00208 16S ribosomal RNA gene
AACGAGAGTTTGATCCTGGCTCAGGATGAACGCTGGCGGCGTGCTTAACACATGCAAGTCGAGCGAAGCACTTAAGT

TTGATTCTTCGGATGAAGACTTTTGTGACTGAGCGGCGGACGGGTGAGTAACGCGTGGGTAACCTGCCTCATACAGG

GGGATAACAGTTAGAAATGACTGCTAATACCGCATAAGACCACGGTACCGCATGGTACAGTGGTAAAAACTCCGGTG

-continued

GTATGAGATGGACCCGCGTCTGATTAGGTAGTTGGTGGGGTAACGGCCTACCAAGCCGACGATCAGTAGCCGACCTG

AGAGGGTGACCGGCCACATTGGGACTGAGACACGGCCCAGACTCCTACGGGAGGCAGCAGTGGGGAATATTGCACAA

TGGAGGAAACTCTGATGCAGCGACGCCGCGTGAAGGATGAAGTATTTCGGTATGTAAACTTCTATCAGCAGGGAAGA

AAATGACGGTACCTGACTAAGAAGCCCCGGCTAACTACGTGCCAGCAGCCGCGGTAATACGTAGGGGGCAAGCGTTA

TCCGGATTTACTGGGTGTAAAGGGAGCGTAGACGGCACGGCAAGCCAGATGTGAAAGCCCGGGGCTCAACCCCGGGA

CTGCATTTGGAACTGCTGAGCTAGAGTGTCGGAGAGGCAAGTGGAATTCCTAGTGTAGCGGTGAAATGCGTAGATAT

TAGGAGGAACACCAGTGGCGAAGGCGGCTTGCTGGACGATGACTGACGTTGAGGCTCGAAAGCGTGGGGAGCAAACA

GGATTAGATACCCTGGTAGTCCACGCCGTAAACGATGACTGCTAGGTGTCGGGTGGCAAAGCCATTCGGTGCCGCAG

CTAACGCAATAAGCAGTCCACCTGGGGAGTACGTTCGCAAGAATGAAACTCAAAGGAATTGACGGGGACCCGCACAA

GCGGTGGAGCATGTGGTTTAATTCGAAGCAACGCGAAGAACCTTACCTGATCTTGACATCCCGATGACCGCTTCGTA

ATGGAAGTTTTTCTTCGGAACATCGGTGACAGGTGGTGCATGGTTGTCGTCAGCTCGTGTCGTGAGATGTTGGGTTA

AGTCCCGCAACGAGCGCAACCCCTATCTTCAGTAGCCAGCAGGTTAAGCTGGGCACTCTGGAGAGACTGCCAGGGAT

AACCTGGAGGAAGGTGGGGATGACGTCAAATCATCATGCCCCTTATGACCAGGGCTACACACGTGCTACAATGGCGT

AAACAAAGAGAAGCGAACTCGCGAGGGTAAGCAAATCTCAAAAATAACGTCTCAGTTCGGATTGTAGTCTGCAACTC

GACTACATGAAGCTGGAATCGCTAGTAATCGCAGATCAGAATGCTGCGGTGAATACGTTCCCGGGTCTTGTACACAC

CGCCCGTCACACCATGGGAGTCAGTAACGCCCGAAGTCAGTGACCCAACCGTAAGGAGGGAGCTGCCGAAGGTGGGA

CCGATAACTGGGGTGAAGTCGTAACAAGGTAGCCGTATCGGAAGGTGCGGCTGGATCACCTCCTTT

>SEQ ID NO: 147 | PROKKA_00340 16S ribosomal RNA gene
AACGAGAGTTTGATCCTGGCTCAGGATGAACGCTGGCGGCGTGCTTAACACATGCAAGTCGAGCGAAGCACTTTGGA

AAGATTCTTCGGATGATTTCCTTTGTGACTGAGCGGCGGACGGGTGAGTAACGCGTGGGTAACCTGCCTCATACAGG

GGGATAACAGTTAGAAATGACTGCTAATACCGCATAAGACCACGGTACCGCATGGTACAGTGGTAAAAACTCCGGTG

GTATGAGATGGACCCGCGTCTGATTAGGTAGTTGGTGGGGTAACGGCCTACCAAGCCGACGATCAGTAGCCGACCTG

AGAGGGTGACCGGCCACATTGGGACTGAGACACGGCCCAGACTCCTACGGGAGGCAGCAGTGGGGAATATTGCACAA

TGGAGGAAACTCTGATGCAGCGACGCCGCGTGAAGGATGAAGTATTTCGGTATGTAAACTTCTATCAGCAGGGAAGA

AAATGACGGTACCTGACTAAGAAGCCCCGGCTAACTACGTGCCAGCAGCCGCGGTAATACGTAGGGGGCAAGCGTTA

TCCGGATTTACTGGGTGTAAAGGGAGCGTAGACGGCACGGCAAGCCAGATGTGAAAGCCCGGGGCTCAACCCCGGAC

TGCATTTGGAACTGCTGAGCTAGAGTGTCGGAGAGGCAAGTGGAATTCCTAGTGTAGCGGTGAAATGCGTAGATATT

AGGAGGAACACCAGTGGCGAAGGCGGCTTGCTGGACGATGACTGACGTTGAGGCTCGAAAGCGTGGGGAGCAAACAG

GATTAGATACCCTGGTAGTCCACGCCGTAAACGATGACTGCTAGGTGTCGGGTGGCAAAGCCATTCGGTGCCGCAGC

TAACGCAATAAGCAGTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCTGATCTTGACATCCCGATGACCGCTTCGTAA

TGGAAGCTTTTCTTCGGAACATCGGTGACAGGTGGTGCATGGTTGTCGTCAGCTCGTGTCGTGAGATGTTGGGTTAA

GTCCCGCAACGAGCGCAACCCCTATCTTCAGTAGCCAGCAGGTTAAGCTGGGCACTCTGGAGAGACTGCCAGGGATA

ACCTGGAGGAAGGTGGGGATGACGTCAAATCATCATGCCCCTTATGACCAGGGCTACACACGTGCTACAATGGCGTA

AACAAAGAGAAGCGAACTCGCGAGGGTAAGCAAATCTCAAAAATAACGTCTCAGTTCGGATTGTAGTCTGCAACTCG

ACTACATGAAGCTGGAATCGCTAGTAATCGCAGATCAGAATGCTGCGGTGAATACGTTCCCGGGTCTTGTACACACC

GCCCGTCACACCATGGGAGTCAGTAACGCCCGAAGTCAGTGACCCAACCGTAAGGAGGGAGCTGCCGAAGGTGGGAC

CGATAACTGGGGTGAAGTCGTAACAAGGTAGCCGTATCGGAAGGTGCGGCTGGATCACCTCCTTT

>SEQ ID NO: 148 | PROKKA_01031 16S ribosomal RNA gene
AACGAGAGTTTGATCCTGGCTCAGGATGAACGCTGGCGGCGTGCTTAACACATGCAAGTCGAGCGAAGCACTTAAGT

TTGATTCTTCGGATGAAGACTTTTGTGACTGAGCGGCGGACGGGTGAGTAACGCGTGGGTAACCTGCCTCATACAGG

-continued

GGGATAACAGTTAGAAATGACTGCTAATACCGCATAAGACCACGGTACCGCATGGTACAGTGGTAAAAACTCCGGTG

GTATGAGATGGACCCGCGTCTGATTAGGTAGTTGGTGGGGTAACGGCCTACCAAGCCGACGATCAGTAGCCGACCTG

AGAGGGTGACCGGCCACATTGGGACTGAGACACGGCCCAGACTCCTACGGGAGGCAGCAGTGGGGAATATTGCACAA

TGGAGGAAACTCTGATGCAGCGACGCCGCGTGAAGGATGAAGTATTTCGGTATGTAAACTTCTATCAGCAGGGAAGA

AAATGACGGTACCTGACTAAGAAGCCCCGGCTAACTACGTGCCAGCAGCCGCGGTAATACGTAGGGGGCAAGCGTTA

TCCGGATTTACTGGGTGTAAAGGGAGCGTAGACGGCACGGCAAGCCAGATGTGAAAGCCCGGGGCTCAACCCCGGGA

CTGCATTTGGAACTGCTGAGCTAGAGTGTCGGAGAGGCAAGTGGAATTCCTAGTGTAGCGGTGAAATGCGTAGATAT

TAGGAGGAACACCAGTGGCGAAGGCGGCTTGCTGGACGATGACTGACGTTGAGGCTCGAAAGCGTGGGGAGCAAACA

GGATTAGATACCCTGGTAGTCCACGCCGTAAACGATGACTGCTAGGTGTCGGGTGGCAAAGCCATTCGGTGCCGCAG

CTAACGCAATAAGCAGTCCACCTGGGGAGTACGTTCGCAAGAATGAAACTCAAAGGAATTGACGGGGACCCGCACAA

GCGGTGGAGCATGTGGTTTAATTCGAAGCAACGCGAAGAACCTTACCTGATCTTGACATCCCGATGACCGCTTCGTA

ATGGAAGCTTTTCTTCGGAACATCGGTGACAGGTGGTGCATGGTTGTCGTCAGCTCGTGTCGTGAGATGTTGGGTTA

AGTCCCGCAACGAGCGCAACCCCTATCTTCAGTAGCCAGCAGGTTAAGCTGGGCACTCTGGAGAGACTGCCAGGGAT

AACCTGGAGGAAGGTGGGGATGACGTCAAATCATCATGCCCCTTATGACCAGGGCTACACACGTGCTACAATGGCGT

AAACAAAGAGAAGCGAACTCGCGAGGGTAAGCAAATCTCAAAAATAACGTCTCAGTTCGGATTGTAGTCTGCAACTC

GACTACATGAAGCTGGAATCGCTAGTAATCGCAGATCAGAATGCTGCGGTGAATACGTTCCCGGGTCTTGTACACAC

CGCCCGTCACACCATGGGAGTCAGTAACGCCCGAAGTCAGTGACCCAACCGTAAGGAGGGAGCTGCCGAAGGTGGGA

CCGATAACTGGGGTGAAGTCGTAACAAGGTAGCCGTATCGGAAGGTGCGGCTGGATCACCTCCTTT

>SEQ ID NO: 149 | PROKKA_01840 16S ribosomal RNA gene
AACGAGAGTTTGATCCTGGCTCAGGATGAACGCTGGCGGCGTGCTTAACACATGCAAGTCGAGCGAAGCACTTTGGA

AAGATTCTTCGGATGATTTCCTTTGTGACTGAGCGGCGGACGGGTGAGTAACGCGTGGGTAACCTGCCTCATACAGG

GGGATAACAGTTAGAAATGACTGCTAATACCGCATAAGACCACGGTACCGCATGGTACAGTGGTAAAAACTCCGGTG

GTATGAGATGGACCCGCGTCTGATTAGGTAGTTGGTGGGGTAACGGCCTACCAAGCCGACGATCAGTAGCCGACCTG

AGAGGGTGACCGGCCACATTGGGACTGAGACACGGCCCAGACTCCTACGGGAGGCAGCAGTGGGGAATATTGCACAA

TGGAGGAAACTCTGATGCAGCGACGCCGCGTGAAGGATGAAGTATTTCGGTATGTAAACTTCTATCAGCAGGGAAGA

AAATGACGGTACCTGACTAAGAAGCCCCGGCTAACTACGTGCCAGCAGCCGCGGTAATACGTAGGGGGCAAGCGTTA

TCCGGATTTACTGGGTGTAAAGGGAGCGTAGACGGCACGGCAAGCCAGATGTGAAAGCCCGGGGCTCAACCCCGGGA

CTGCATTTGGAACTGCTGAGCTAGAGTGTCGGAGAGGCAAGTGGAATTCCTAGTGTAGCGGTGAAATGCGTAGATAT

TAGGAGGAACACCAGTGGCGAAGGCGGCTTGCTGGACGATGACTGACGTTGAGGCTCGAAAGCGTGGGGAGCAAACA

GGATTAGATACCCTGGTAGTCCACGCCGTAAACGATGACTGCTAGGTGTCGGGTGGCAAAGCCATTCGGTGCCGCAG

CTAACGCAATAAGCAGTCCACCTGGGGAGTACGTTCGCAAGAATGAAACTCAAAGGAATTGACGGGGACCCGCACAA

GCGGTGGAGCATGTGGTTTAATTCGAAGCAACGCGAAGAACCTTACCTGATCTTGACATCCCGATGACCGCTTCGTA

ATGGAAGCTTTTCTTCGGAACATCGGTGACAGGTGGTGCATGGTTGTCGTCAGCTCGTGTCGTGAGATGTTGGGTTA

AGTCCCGCAACGAGCGCAACCCCTATCTTCAGTAGCCAGCAGGTTAAGCTGGGCACTCTGGAGAGACTGCCAGGGAT

AACCTGGAGGAAGGTGGGGATGACGTCAAATCATCATGCCCCTTATGACCAGGGCTACACACGTGCTACAATGGCGT

AAACAAAGAGAAGCGAACTCGCGAGGGTAAGCAAATCTCAAAAATAACGTCTCAGTTCGGATTGTAGTCTGCAACTC

GACTACATGAAGCTGGAATCGCTAGTAATCGCAGATCAGAATGCTGCGGTGAATACGTTCCCGGGTCTTGTACACAC

CGCCCGTCACACCATGGGAGTCAGTAACGCCCGAAGTCAGTGACCCAACCGTAAGGAGGGAGCTGCCGAAGGTGGGA

CCGATAACTGGGGTGAAGTCGTAACAAGGTAGCCGTATCGGAAGGTGCGGCTGGATCACCTCCTTT

>SEQ ID NO: 150 | PROKKA_02944 16S ribosomal RNA gene
AACGAGAGTTTGATCCTGGCTCAGGATGAACGCTGGCGGCGTGCTTAACACATGCAAGTCGAGCGAAGCGCTTAAGT

TTGATTCTTCGGATGAAGACTTTTGTGACTGAGCGGCGGACGGGTGAGTAACGCGTGGGTAACCTGCCTCATACAGG

-continued

GGGATAACAGTTAGAAATGACTGCTAATACCGCATAAGACCACGGTACCGCATGGTACAGTGGTAAAAACTCCGGTG

GTATGAGATGGACCCGCGTCTGATTAGGTAGTTGGTGGGGTAACGGCCTACCAAGCCGACGATCAGTAGCCGACCTG

AGAGGGTGACCGGCCACATTGGGACTGAGACACGGCCCAGACTCCTACGGGAGGCAGCAGTGGGGAATATTGCACAA

TGGAGGAAACTCTGATGCAGCGACGCCGCGTGAAGGATGAAGTATTTCGGTATGTAAACTTCTATCAGCAGGGAAGA

AAATGACGGTACCTGACTAAGAAGCCCCGGCTAACTACGTGCCAGCAGCCGCGGTAATACGTAGGGGGCAAGCGTTA

TCCGGATTTACTGGGTGTAAAGGGAGCGTAGACGGCACGGCAAGCCAGATGTGAAAGCCCGGGCTCAACCCCGGGAC

TGCATTTGGAACTGCTGAGCTAGAGTGTCGGAGAGGCAAGTGGAATTCCTAGTGTAGCGGTGAAATGCGTAGATATT

AGGAGGAACACCAGTGGCGAAGGCGGCTTGCTGGACGATGACTGACGTTGAGGCTCGAAAGCGTGGGGAGCAAACAG

GATTAGATACCCTGGTAGTCCACGCCGTAAACGATGACTGCTAGGTGTCGGGTGGCAAAGCCATTCGGTGCCGCAGC

TAACGCAATAAGCAGTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCTGATCTTGACATCCCGATGACCGCTTCGTAA

TGGAAGTTTTTCTTCGGAACATCGGTGACAGGTGGTGCATGGTTGTCGTCAGCTCGTGTCGTGAGATGTTGGGTTAA

GTCCCGCAACGAGCGCAACCCCTATCTTCAGTAGCCAGCAGGTTAAGCTGGGCACTCTGGAGAGACTGCCAGGGATA

ACCTGGAGGAAGGTGGGGATGACGTCAAATCATCATGCCCCTTATGACCAGGGCTACACACGTGCTACAATGGCGTA

AACAAAGAGAGGCAAACTCGCGAGGGTAAGCAAATCTCAAAAATAACGTCTCAGTTCGGATTGTAGTCTGCAACTCG

ACTACATGAAGCTGGAATCGCTAGTAATCGCAGATCAGAATGCTGCGGTGAATACGTTCCCGGGTCTTGTACACACC

GCCCGTCACACCATGGGAGTCAGTAACGCCCGAAGTCAGTGACCCAACCGTAAGGAGGGAGCTGCCGAAGGTGGGAC

CGATAACTGGGGTGAAGTCGTAACAAGGTAGCCGTATCGGAAGGTGCGGCTGGATCACCTCCTTT

>SEQ ID NO: 151 | PROKKA_04036 16S ribosomal RNA gene
AACGAGAGTTTGATCCTGGCTCAGGATGAACGCTGGCGGCGTGCTTAACACATGCAAGTCGAGCGAAGCGCTTTGGG

AAGATTCTTCGGATGATTTCCTTTGTGACTGAGCGGCGGACGGGTGAGTAACGCGTGGGTAACCTGCCTCATACAGG

GGGATAACAGTTAGAAATGACTGCTAATACCGCATAAGACCACGGTACCGCATGGTACAGTGGTAAAAACTCCGGTG

GTATGAGATGGACCCGCGTTTGATTAGGTAGTTGGTGGGGTAACGGCCTACCAAGCCGACGATCAGTAGCCGACCTG

AGAGGGTGACCGGCCACATTGGGACTGAGACACGGCCCAGACTCCTACGGGAGGCAGCAGTGGGGAATATTGCACAA

TGGAGGAAACTCTGATGCAGCGACGCCGCGTGAAGGATGAAGTATTTCGGTATGTAAACTTCTATCAGCAGGGAAGA

AAATGACGGTACCTGACTAAGAAGCCCCGGCTAACTACGTGCCAGCAGCCGCGGTAATACGTAGGGGGCAAGCGTTA

TCCGGATTTACTGGGTGTAAAGGGAGCGTAGACGGCACGGCAAGCCAGATGTGAAAGCCCGGGGCTCAACCCCGGGA

CTGCATTTGGAACTGCTGAGCTAGAGTGTCGGAGAGGCAAGTGGAATTCCTAGTGTAGCGGTGAAATGCGTAGATAT

TAGGAGGAACACCAGTGGCGAAGGCGGCTTGCTGGACGATGACTGACGTTGAGGCTCGAAAGCGTGGGGAGCAAACA

GGATTAGATACCCTGGTAGTCCACGCCGTAAACGATGACTGCTAGGTGTCGGGTGGCAAAGCCATTCGGTGCCGCAG

CTAACGCAATAAGCAGTCCACCTGGGGAGTACGTTCGCAAGAATGAAACTCAAAGGAATTGACGGGGACCCGCACAA

GCGGTGGAGCATGTGGTTTAATTCGAAGCAACGCGAAGAACCTTACCTGATCTTGACATCCCGATGACTGCTTCGTA

ATGGAAGTTTTTCTTCGGAACATCGGTGACAGGTGGTGCATGGTTGTCGTCAGCTCGTGTCGTGAGATGTTGGGTTA

AGTCCCGCAACGAGCGCAACCCCTATCTTCAGTAGCCAGCAGGTTAAGCTGGGCACTCTGGAGAGACTGCCAGGGAT

AACCTGGAGGAAGGTGGGGATGACGTCAAATCATCATGCCCCTTATGACCAGGGCTACACACGTGCTACAATGGCGT

AAACAAAGAGAAGCGAACTCGCGAGGGTAAGCAAATCTCAAAAATAACGTCTCAGTTCGGATTGTAGTCTGCAACTC

GACTACATGAAGCTGGAATCGCTAGTAATCGCAGATCAGAATGCTGCGGTGAATACGTTCCCGGGTCTTGTACACAC

CGCCCGTCACACCATGGGAGTCAGTAACGCCCGAAGTCAGTGACCCAACCGTAAGGAGGGAGCTGCCGAAGGTGGGA

CCGATAACTGGGGTGAAGTCGTAACAAGGTAGCCGTATCGGAAGGTGCGGCTGGATCACCTCCTTT

-continued

>SEQ ID NO: 152 | PROKKA_00437 16S ribosomal RNA gene
ATGGAGAGTTTGATCCTGGCTCAGGATGAACGCTGGCGGCATGCCTAATACATGCAAGTCGAACGAAGTTTCGAGGA

AGCTTGCTTCCAAAGAGACTTAGTGGCGAACGGGTGAGTAACACGTAGGTAACCTGCCCATGTGTCCGGGATAACTG

CTGGAAACGGTAGCTAAAACCGGATAGGTATACAGAGCGCATGCTCAGTATATTAAAGCGCCCATCAAGGCGTGAAC

ATGGATGGACCTGCGGCGCATTAGCTAGTTGGTGAGGTAACGGCTCACCAAGGCGATGATGCGTAGCCGGCCTGAGA

GGGTAAACGGCCACATTGGGACTGAGACACGGCCCAAACTCCTACGGGAGGCAGCAGTAGGGAATTTTCGTCAATGG

GGGAAACCCTGAACGAGCAATGCCGCGTGAGTGAAGAAGGTCTTCGGATCGTAAAGCTCTGTTGTAAGTGAAGAACG

GCTCATAGAGGAAATGCTATGGGAGTGACGGTAGCTTACCAGAAAGCCACGGCTAACTACGTGCCAGCAGCCGCGGT

AATACGTAGGTGGCAAGCGTTATCCGGAATCATTGGGCGTAAAGGGTGCGTAGGTGGCGTACTAAGTCTGTAGTAAA

AGGCAATGGCTCAACCATTGTAAGCTATGGAAACTGGTATGCTGGAGTGCAGAAGAGGGCGATGGAATTCCATGTGT

AGCGGTAAAATGCGTAGATATATGGAGGAACACCAGTGGCGAAGGCGGTCGCCTGGTCTGTAACTGACACTGAGGCA

CGAAAGCGTGGGGAGCAAATAGGATTAGATACCCTAGTAGTCCACGCCGTAAACGATGAGAACTAAGTGTTGGAGGA

ATTCAGTGCTGCAGTTAACGCAATAAGTTCTCCGCCTGGGGAGTATGCACGCAAGTGTGAAACTCAAAGGAATTGAC

GGGGGCCCGCACAAGCGGTGGAGTATGTGGTTTAATTCGAAGCAACGCGAAGAACCTTACCAGGCCTTGACATGGAA

ACAAATACCCTAGAGATAGGGGGATAATTATGGATCACACAGGTGGTGCATGGTTGTCGTCAGCTCGTGTCGTGAGA

TGTTGGGTTAAGTCCCGCAACGAGCGCAACCCTTGTCGCATGTTACCAGCATCAAGTTGGGGACTCATGCGAGACTG

CCGGTGACAAACCGGAGGAAGGTGGGGATGACGTCAAATCATCATGCCCCTTATGGCCTGGGCTACACACGTACTAC

AATGGCGGCCACAAAGAGCAGCGACACAGTGATGTGAAGCGAATCTCATAAAGGTCGTCTCAGTTCGGATTGAAGTC

TGCAACTCGACTTCATGAAGTCGGAATCGCTAGTAATCGCAGATCAGCATGCTGCGGTGAATACGTTCTCGGGCCTT

GTACACACCGCCCGTCAAACCATGGGAGTCAGTAATACCCGAAGCCGGTGGCATAACCGTAAGGAGTGAGCCGTCGA

AGGTAGGACCGATGACTGGGGTTAAGTCGTAACAAGGTATCCCTACGGGAACGTGGGGATGGATCACCTCCTTT

>SEQ ID NO: 153 | PROKKA_00896 16S ribosomal RNA gene
ATGGAGAGTTTGATCCTGGCTCAGGATGAACGCTGGCGGCATGCCTAATACATGCAAGTCGAACGAAGTTTCGAGGA

AGCTTGCTTCCAAAGAGACTTAGTGGCGAACGGGTGAGTAACACGTAGGTAACCTGCCCATGTGTCCGGGATAACTG

CTGGAAACGGTAGCTAAAACCGGATAGGTATACAGAGCGCATGCTCAGTATATTAAAGCGCCCATCAAGGCGTGAAC

ATGGATGGACCTGCGGCGCATTAGCTAGTTGGTGAGGTAACGGCCCACCAAGGCGATGATGCGTAGCCGGCCTGAGA

GGGTAAACGGCCACATTGGGACTGAGACACGGCCCAAACTCCTACGGGAGGCAGCAGTAGGGAATTTTCGTCAATGG

GGGAAACCCTGAACGAGCAATGCCGCGTGAGTGAAGAAGGTCTTCGGATCGTAAAGCTCTGTTGTAAGTGAAGAACG

GCTCATAGAGGAAATGCTATGGGAGTGACGGTAGCTTACCAGAAAGCCACGGCTAACTACGTGCCAGCAGCCGCGGT

AATACGTAGGTGGCAAGCGTTATCCGGAATCATTGGGCGTAAAGGGTGCGTAGGTGGCGTACTAAGTCTGTAGTAAA

AGGCAATGGCTCAACCATTGTAAGCTATGGAAACTGGTATGCTGGAGTGCAGAAGAGGGCGATGGAATTCCATGTGT

AGCGGTAAAATGCGTAGATATATGGAGGAACACCAGTGGCGAAGGCGGTCGCCTGGTCTGTAACTGACACTGAGGCA

CGAAAGCGTGGGGAGCAAATAGGATTAGATACCCTAGTAGTCCACGCCGTAAACGATGAGAACTAAGTGTTGGAGGA

ATTCAGTGCTGCAGTTAACGCAATAAGTTCTCCGCCTGGGGAGTATGCACGCAAGTGTGAAACTCAAAGGAATTGAC

GGGGGCCCGCACAAGCGGTGGAGTATGTGGTTTAATTCGAAGCAACGCGAAGAACCTTACCAGGCCTTGACATGGAA

ACAAATACCCTAGAGATAGGGGGATAATTATGGATCACACAGGTGGTGCATGGTTGTCGTCAGCTCGTGTCGTGAGA

TGTTGGGTTAAGTCCCGCAACGAGCGCAACCCTTGTCGCATGTTACCAGCATCAAGTTGGGGACTCATGCGAGACTG

CCGGTGACAAACCGGAGGAAGGTGGGGATGACGTCAAATCATCATGCCCCTTATGGCCTGGGCTACACACGTACTAC

AATGGCGGCCACAAAGAGCAGCGACACAGTGATGTGAAGCGAATCTCATAAAGGTCGTCTCAGTTCGGATTGAAGTC

TGCAACTCGACTTCATGAAGTCGGAATCGCTAGTAATCGCAGATCAGCATGCTGCGGTGAATACGTTCTCGGGCCTT

-continued

GTACACACCGCCCGTCAAACCATGGGAGTCAGTAATACCCGAAGCCGGTGGCATAACCGTAAGGAGTGAGCCGTCGA

AGGTAGGACCGATGACTGGGGTTAAGTCGTAACAAGGTATCCCTACGGGAACGTGGGGATGGATCACCTCCTTT

>SEQ ID NO: 154 | PROKKA_02845 16S ribosomal RNA gene
ATGGAGAGTTTGATCCTGGCTCAGGATGAACGCTGGCGGCATGCCTAATACATGCAAGTCGAACGAAGTTTCGAGGA

AGCTTGCTTCCAAAGAGACTTAGTGGCGAACGGGTGAGTAACACGTAGGTAACCTGCCCATGTGTCCGGGATAACTG

CTGGAAACGGTAGCTAAAACCGGATAGGTATACAGAGCGCATGCTCAGTATATTAAAGCGCCCATCAAGGCGTGAAC

ATGGATGGACCTGCGGCGCATTAGCTAGTTGGTGAGGTAACGGCTCACCAAGGCGATGATGCGTAGCCGGCCTGAGA

GGGTAAACGGCCACATTGGGACTGAGACACGGCCCAAACTCCTACGGGAGGCAGCAGTAGGGAATTTTCGTCAATGG

GGGAAACCCTGAACGAGCAATGCCGCGTGAGTGAAGAAGGTCTTCGGATCGTAAAGCTCTGTTGTAAGTGAAGAACG

GCTCATAGAGGAAATGCTATGGGAGTGACGGTAGCTTACCAGAAAGCCACGGCTAACTACGTGCCAGCAGCCGCGGT

AATACGTAGGTGGCAAGCGTTATCCGGAATCATTGGGCGTAAAGGGTGCGTAGGTGGCGTACTAAGTCTGTAGTAAA

AGGCAATGGCTCAACCATTGTAAGCTATGGAAACTGGTATGCTGGAGTGCAGAAGAGGGCGATGGAATTCCATGTGT

AGCGGTAAAATGCGTAGATATATGGAGGAACACCAGTGGCGAAGGCGGTCGCCTGGTCTGTAACTGACACTGAGGCA

CGAAAGCGTGGGGAGCAAATAGGATTAGATACCCTAGTAGTCCACGCCGTAAACGATGAGAACTAAGTGTTGGAGGA

ATTCAGTGCTGCAGTTAACGCAATAAGTTCTCCGCCTGGGGAGTATGCACGCAAGTGTGAAACTCAAAGGAATTGAC

GGGGGCCCGCACAAGCGGTGGAGTATGTGGTTTAATTCGAAGCAACGCGAAGAACCTTACCAGGCCTTGACATGGAA

ACAAATACCCTAGAGATAGGGGGATAATTATGGATCACACAGGTGGTGCATGGTTGTCGTCAGCTCGTGTCGTGAGA

TGTTGGGTTAAGTCCCGCAACGAGCGCAACCCTTGTCGCATGTTACCAGCATCAAGTTGGGGACTCATGCGAGACTG

CCGGTGACAAACCGGAGGAAGGTGGGGATGACGTCAAATCATCATGCCCCTTATGGCCTGGGCTACACACGTACTAC

AATGGCGGCCACAAAGAGCAGCGACACAGTGATGTGAAGCGAATCTCATAAAGGTCGTCTCAGTTCGGATTGAAGTC

TGCAACTCGACTTCATGAAGTCGGAATCGCTAGTAATCGCAGATCAGCATGCTGCGGTGAATACGTTCTCGGGCCTT

GTACACACCGCCCGTCAAACCATGGGAGTCAGTAATACCCGAAGCCGGTGGCATAACCGTAAGGAGTGAGCCGTCGA

AGGTAGGACCGATGACTGGGGTTAAGTCGTAACAAGGTATCCCTACGGGAACGTGGGGATGGATCACCTCCTTT

>SEQ ID NO: 155 | PROKKA_04164 16S ribosomal RNA gene
ATGGAGAGTTTGATCCTGGCTCAGGATGAACGCTGGCGGCATGCCTAATACATGCAAGTCGAACGAAGTTTCGAGGA

AGCTTGCTTCCAAAGAGACTTAGTGGCGAACGGGTGAGTAACACGTAGGTAACCTGCCCATGTGTCCGGGATAACTG

CTGGAAACGGTAGCTAAAACCGGATAGGTATACAGAGCGCATGCTCAGTATATTAAAGCGCCCATCAAGGCGTGAAC

ATGGATGGACCTGCGGCGCATTAGCTAGTTGGTGAGGTAACGGCCCACCAAGGCGATGATGCGTAGCCGGCCTGAGA

GGGTAAACGGCCACATTGGGACTGAGACACGGCCCAAACTCCTACGGGAGGCAGCAGTAGGGAATTTTCGTCAATGG

GGGAAACCCTGAACGAGCAATGCCGCGTGAGTGAAGAAGGTCTTCGGATCGTAAAGCTCTGTTGTAAGTGAAGAACG

GCTCATAGAGGAAATGCTATGGGAGTGACGGTAGCTTACCAGAAAGCCACGGCTAACTACGTGCCAGCAGCCGCGGT

AATACGTAGGTGGCAAGCGTTATCCGGAATCATTGGGCGTAAAGGGTGCGTAGGTGGCGTACTAAGTCTGTAGTAAA

AGGCAATGGCTCAACCATTGTAAGCTATGGAAACTGGTATGCTGGAGTGCAGAAGAGGGCGATGGAATTCCATGTGT

AGCGGTAAAATGCGTAGATATATGGAGGAACACCAGTGGCGAAGGCGGTCGCCTGGTCTGTAACTGACACTGAGGCA

CGAAAGCGTGGGGAGCAAATAGGATTAGATACCCTAGTAGTCCACGCCGTAAACGATGAGAACTAAGTGTTGGAGGA

ATTCAGTGCTGCAGTTAACGCAATAAGTTCTCCGCCTGGGGAGTATGCACGCAAGTGTGAAACTCAAAGGAATTGAC

GGGGGCCCGCACAAGCGGTGGAGTATGTGGTTTAATTCGAAGCAACGCGAAGAACCTTACCAGGCCTTGACATGGAA

ACAAATACCCTAGAGATAGGGGGATAATTATGGATCACACAGGTGGTGCATGGTTGTCGTCAGCTCGTGTCGTGAGA

TGTTGGGTTAAGTCCCGCAACGAGCGCAACCCTTGTCGCATGTTACCAGCATCAAGTTGGGGACTCATGCGAGACTG

CCGGTGACAAACCGGAGGAAGGTGGGGATGACGTCAAATCATCATGCCCCTTATGGCCTGGGCTACACACGTACTAC

AATGGCGACCACAAAGAGCAGCGACACAGTGATGTGAAGCGAATCTCATAAAGGTCGTCTCAGTTCGGATTGAAGTC

-continued

TGCAACTCGACTTCATGAAGTCGGAATCGCTAGTAATCGCAGATCAGCATGCTGCGGTGAATACGTTCTCGGGCCTT
GTACACACCGCCCGTCAAACCATGGGAGTCAGTAATACCCGAAGCCGGTGGCATAACCGCAAGGAGTGAGCCGTCGA
AGGTAGGACCGATGACTGGGGTTAAGTCGTAACAAGGTATCCCTACGGGAACGTGGGGATGGATCACCTCCTTT

>SEQ ID NO: 156 | PROKKA_04921 16S ribosomal RNA gene
ATGGAGAGTTTGATCCTGGCTCAGGATGAACGCTGGCGGCATGCCTAATACATGCAAGTCGAACGAAGTTTCGAGGA
AGCTTGCTTCCAAAGAGACTTAGTGGCGAACGGGTGAGTAACACGTAGGTAACCTGCCCATGTGTCCGGGATAACTG
CTGGAAACGGTAGCTAAAACCGGATAGGTATACAGAGCGCATGCTCAGTATATTAAAGCGCCCATCAAGGCGTGAAC
ATGGATGGACCTGCGGCGCATTAGCTAGTTGGTGAGGTAACGGCCCACCAAGGCGATGATGCGTAGCCGGCCTGAGA
GGGTAAACGGCCACATTGGGACTGAGACACGGCCCAAACTCCTACGGGAGGCAGCAGTAGGGAATTTTCGTCAATGG
GGGAAACCCTGAACGAGCAATGCCGCGTGAGTGAAGAAGGTCTTCGGATCGTAAAGCTCTGTTGTAAGTGAAGAACG
GCTCATAGAGGAAATGCTATGGGAGTGACGGTAGCTTACCAGAAAGCCACGGCTAACTACGTGCCAGCAGCCGCGGT
AATACGTAGGTGGCAAGCGTTATCCGGAATCATTGGGCGTAAAGGGTGCGTAGGTGGCGTACTAAGTCTGTAGTAAA
AGGCAATGGCTCAACCATTGTAAGCTATGGAAACTGGTATGCTGGAGTGCAGAAGAGGGCGATGGAATTCCATGTGT
AGCGGTAAAATGCGTAGATATATGGAGGAACACCAGTGGCGAAGGCGGTCGCCTGGTCTGTAACTGACACTGAGGCA
CGAAAGCGTGGGGAGCAAATAGGATTAGATACCCTAGTAGTCCACGCCGTAAACGATGAGAACTAAGTGTTGGAGGA
ATTCAGTGCTGCAGTTAACGCAATAAGTTCTCCGCCTGGGGAGTATGCACGCAAGTGTGAAACTCAAAGGAATTGAC
GGGGGCCCGCACAAGCGGTGGAGTATGTGGTTTAATTCGAAGCAACGCGAAGAACCTTACCAGGCCTTGACATGGAA
ACAAATACCCTAGAGATAGGGGGATAATTATGGATCACACAGGTGGTGCATGGTTGTCGTCAGCTCGTGTCGTGAGA
TGTTGGGTTAAGTCCCGCAACGAGCGCAACCCTTGTCGCATGTTACCAGCATCAAGTTGGGGACTCATGCGAGACTG
CCGGTGACAAACCGGAGGAAGGTGGGGATGACGTCAAATCATCATGCCCCTTATGGCCTGGGCTACACACGTACTAC
AATGGCGGCCACAAAGAGCAGCGACACAGTGATGTGAAGCGAATCTCATAAAGGTCGTCTCAGTTCGGATTGAAGTC
TGCAACTCGACTTCATGAAGTCGGAATCGCTAGTAATCGCAGATCAGCATGCTGCGGTGAATACGTTCTCGGGCCTT
GTACACACCGCCCGTCAAACCATGGGAGTCAGTAATACCCGAAGCCGGTGGCATAACCGTAAGGAGTGAGCCGTCGA
AGGTAGGACCGATGACTGGGGTTAAGTCGTAACAAGGTATCCCTACGGGAACGTGGGGATGGATCACCTCCTTT >SEQ ID NO: 157 | PROKKA_00199 16S ribosomal RNA gene
TATTGAGAGTTTGATCCTGGCTCAGGATGAACGCTGGCGGCGTGCTTAACACATGCAAGTCGAACGGGGTGCTCATG
ACGGAGGATTCGTCCAACGGATTGAGTTACCTAGTGGCGGACGGGTGAGTAACGCGTGAGGAACCTGCCTTGGAGAG
GGGAATAACACTCCGAAAGGAGTGCTAATACCGCATGATGCAGTTGGGTCGCATGGCTCTGACTGCCAAAGATTTAT
CGCTCTGAGATGGCCTCGCGTCTGATTAGCTAGTAGGCGGGGTAACGGCCCACCTAGGCGACGATCAGTAGCCGGAC
TGAGAGGTTGACCGGCCACATTGGGACTGAGACACGGCCCAGACTCCTACGGGAGGCAGCAGTGGGGAATATTGGGC
AATGGGCGCAAGCCTGACCCAGCAACGCCGCGTGAAGGAAGAAGGCTTTCGGGTTGTAAACTTCTTTTGTCGGGGAC
GAAACAAATGACGGTACCCGACGAATAAGCCACGGCTAACTACGTGCCAGCAGCCGCGGTAATACGTAGGTGGCAAG
CGTTATCCGGATTTACTGGGTGTAAAGGGCGTGTAGGCGGGATTGCAAGTCAGATGTGAAAACTGGGGGCTCAACCT
CCAGCCTGCATTTGAAACTGTAGTTCTTGAGTGCTGGAGAGGCAATCGGAATTCCGTGTGTAGCGGTGAAATGCGTA
GATATACGGAGGAACACCAGTGGCGAAGGCGGATTGCTGGACAGTAACTGACGCTGAGGCGCGAAAGCGTGGGGAGC
AAACAGGATTAGATACCCTGGTAGTCCACGCCGTAAACGATGGATACTAGGTGTGGGGGTCTGACCCCCTCCGTGCC
GCAGTTAACACAATAAGTATCCCACCTGGGGAGTACGATCGCAAGGTTGAAACTCAAAGGAATTGACGGGGGCCCGC
ACAAGCGGTGGAGTATGTGGTTTAATTCGAAGCAACGCGAAGAACCTTACCAGGGCTTGACATCCCACTAACGAAGC
AGAGATGCATTAGGTGCCCTTCGGGGAAAGTGGAGACAGGTGGTGCATGGTTGTCGTCAGCTCGTGTCGTGAGATGT
TGGGTTAAGTCCCGCAACGAGCGCAACCCTTATTGTTAGTTGCTACGCAAGAGCACTCTAGCGAGACTGCCGTTGAC
AAAACGGAGGAAGGTGGGGACGACGTCAAATCATCATGCCCCTTATGTCCTGGGCCACACACGTACTACAATGGTGG
TTAACAGAGGGAGGCAATACCGCGAGGTGGAGCAAATCCCTAAAAGCCATCCCAGTTCGGATTGCAGGCTGAAACCC -continued

GCCTGTATGAAGTTGGAATCGCTAGTAATCGCGGATCAGCATGCCGCGGTGAATACGTTCCCGGGCCTTGTACACAC

CGCCCGTCACACCATGAGAGTCGGGAACACCCGAAGTCCGTAGCCTAACCGCAAGGAGGGCGCGGCCGAAGGTGGGT

TCGATAATTGGGGTGAAGTCGTAACAAGGTAGCCGTATCGGAAGGTGCGGCTGGATCACCTCCTTT

>SEQ ID NO: 158 | PROKKA_00208 16S ribosomal RNA gene
TATTGAGAGTTTGATCCTGGCTCAGGATGAACGCTGGCGGCGTGCTTAACACATGCAAGTCGAACGGGGTGCTCATG

ACGGAGGATTCGTCCAACGGATTGAGTTACCTAGTGGCGGACGGGTGAGTAACGCGTGAGGAACCTGCCTTGGAGAG

GGGAATAACACTCCGAAAGGAGTGCTAATACCGCATGATGCAGTTGGGTCGCATGGCTCTGACTGCCAAAGATTTAT

CGCTCTGAGATGGCCTCGCGTCTGATTAGCTAGTAGGCGGGGTAACGGCCCACCTAGGCGACGATCAGTAGCCGGAC

TGAGAGGTTGACCGGCCACATTGGGACTGAGACACGGCCCAGACTCCTACGGGAGGCAGCAGTGGGGAATATTGGGC

AATGGGCGCAAGCCTGACCCAGCAACGCCGCGTGAAGGAAGAAGGCTTTCGGGTTGTAAACTTCTTTTGTCGGGGAC

GAAACAAATGACGGTACCCGACGAATAAGCCACGGCTAACTACGTGCCAGCAGCCGCGGTAATACGTAGGTGGCAAG

CGTTATCCGGATTTACTGGGTGTAAAGGGCGTGTAGGCGGGATTGCAAGTCAGATGTGAAAACTGGGGGCTCAACCT

CCAGCCTGCATTTGAAACTGTAGTTCTTGAGTGCTGGAGAGGCAATCGGAATTCCGTGTGTAGCGGTGAAATGCGTA

GATATACGGAGGAACACCAGTGGCGAAGGCGGATTGCTGGACAGTAACTGACGCTGAGGCGCGAAAGCGTGGGGAGC

AAACAGGATTAGATACCCTGGTAGTCCACGCCGTAAACGATGGATACTAGGTGTGGGGGGTCTGACCCCCTCCGTGC

CGCAGTTAACACAATAAGTATCCCACCTGGGGAGTACGATCGCAAGGTTGAAACTCAAAGGAATTGACGGGGGCCCG

CACAAGCGGTGGAGTATGTGGTTTAATTCGAAGCAACGCGAAGAACCTTACCAGGGCTTGACATCCCACTAACGAAG

CAGAGATGCATTAGGTGCCCTTCGGGGAAAGTGGAGACAGGTGGTGCATGGTTGTCGTCAGCTCGTGTCGTGAGATG

TTGGGTTAAGTCCCGCAACGAGCGCAACCCTTATTGTTAGTTGCTACGCAAGAGCACTCTAGCGAGACTGCCGTTGA

CAAAACGGAGGAAGGTGGGGACGACGTCAAATCATCATGCCCCTTATGTCCTGGGCCACACACGTACTACAATGGTG

GTTAACAGAGGGAGGCAATACCGCGAGGTGGAGCAAATCCCTAAAAGCCATCCCAGTTCGGATTGCAGGCTGAAACC

CGCCTGTATGAAGTTGGAATCGCTAGTAATCGCGGATCAGCATGCCGCGGTGAATACGTTCCCGGGCCTTGTACACA

CCGCCCGTCACACCATGAGAGTCGGGAACACCCGAAGTCCGTAGCCTAACCGCAAGGAGGGCGCGGCCGAAGGTGGG

TTCGATAATTGGGGTGAAGTCGTAACAAGGTAGCCGTATCGGAAGGTGCGGCTGGATCACCTCCTTT

>SEQ ID NO: 159 | PROKKA_04460 16S ribosomal RNA gene
TATTGAGAGTTTGATCCTGGCTCAGGATGAACGCTGGCGGCGTGCTTAACACATGCAAGTCGAACGGGGTGCTCATG

ACGGAGGATTCGTCCAACGGATTGAGTTACCTAGTGGCGGACGGGTGAGTAACGCGTGAGGAACCTGCCTTGGAGAG

GGGAATAACACTCCGAAAGGAGTGCTAATACCGCATAATGCAGTTGGGTCGCATGGCTCTGACTGCCAAAGATTTAT

CGCTCTGAGATGGCCTCGCGTCTGATTAGCTAGTAGGCGGGGTAACGGCCCACCTAGGCGACGATCAGTAGCCGGAC

TGAGAGGTTGACCGGCCACATTGGGACTGAGACACGGCCCAGACTCCTACGGGAGGCAGCAGTGGGGAATATTGGGC

AATGGGCGCAAGCCTGACCCAGCAACGCCGCGTGAAGGAAGAAGGCTTTCGGGTTGTAAACTTCTTTTGTCAGGGAC

GAAACAAATGACGGTACCTGACGAATAAGCCACGGCTAACTACGTGCCAGCAGCCGCGGTAATACGTAGGTGGCAAG

CGTTATCCGGATTTACTGGGTGTAAAGGGCGTGTAGGCGGGATTGCAAGTCAGATGTGAAAACTGGGGGCTCAACCT

CCAGCCTGCATTTGAAACTGTAGTTCTTGAGTGCTGGAGAGGCAATCGGAATTCCGTGTGTAGCGGTGAAATGCGTA

GATATACGGAGGAACACCAGTGGCGAAGGCGGATTGCTGGACAGTAACTGACGCTGAGGCGCGAAAGCGTGGGGAGC

AAACAGGATTAGATACCCTGGTAGTCCACGCCGTAAACGATGGATACTAGGTGTGGGGGGTCTGACCCCTCCGTGCC

GCAGTTAACACAATAAGTATCCCACCTGGGGAGTACGATCGCAAGGTTGAAACTCAAAGGAATTGACGGGGGCCCGC

ACAAGCGGTGGAGTATGTGGTTTAATTCGAAGCAACGCGAAGAACCTTACCAGGGCTTGACATCCCACTAACGAAGC

AGAGATGCATTAGGTGCCCTTCGGGGAAAGTGGAGACAGGTGGTGCATGGTTGTCGTCAGCTCGTGTCGTGAGATGT

TGGGTTAAGTCCCGCAACGAGCGCAACCCTTATTGTTAGTTGCTACGCAAGAGCACTCTAGCGAGACTGCCGTTGAC

AAAACGGAGGAAGGTGGGGACGACGTCAAATCATCATGCCCCTTATGTCCTGGGCCACACACGTACTACAATGGTGG

-continued

TTAACAGAGGGAGGCAATACCGCGAGGTGGAGCAAATCCCTAAAAGCCATCCCAGTTCGGATTGCAGGCTGAAACCC

GCCTGTATGAAGTTGGAATCGCTAGTAATCGCGGATCAGCATGCCGCGGTGAATACGTTCCCGGGCCTTGTACACAC

CGCCCGTCACACCATGAGAGTCGGGAACACCCGAAGTCCGTAGCCTAACCGCAAGGAGGGCGCGGCCGAAGGTGGGT

TCGATAATTGGGGTGAAGTCGTAACAAGGTAGCCGTATCGGAAGGTGCGGCTGGATCACCTCCTTT

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Unless otherwise defined herein, scientific and technical terms used in connection with the present disclosure shall have the meanings that are commonly understood by those of ordinary skill in the art. Further, unless otherwise required by context, singular terms shall include pluralities and plural terms hall include the singular. The methods and techniques of the present disclosure are generally performed according to conventional methods well-known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

EXAMPLES

Example 1: Mouse Model of *C. difficile* Infection

Mouse Husbandry

Experiments were performed using C57BL/6J female mice purchased from Jackson Laboratories (Bar Harbor, Me.) and housed in ventilated sterile cages. All animals were maintained in a specific-pathogen-free facility. Animals were acclimated to the vivarium for at least 3 days prior to study (i.e., commencing antibiotic courses). For experiments involving *C. difficile* infection, mice were administered 10-$10^4$ *C. difficile* VPI 10463 spores in 200 µl PBS by oral gavage. Experiments were performed in compliance with institutional guidelines and approved by the institution's Institutional Animal Care and Use Committee. Sterile food and drinking water were provided to the animals Live Biotherapeutic Product (LBP) Preparation Individual bacterial strains were isolated from fecal material obtained from healthy donors. The individual strains were struck out from 15% glycerol freezer stocks onto EG (Eggerth Gagnon) agar plates containing 5% horse blood in an anaerobic chamber and incubated for 24-48 hours at 37° C. Colonies were inoculated into pre-reduced liquid Peptone Yeast Glucose (PYG) media and grown for 24-48 hours until dense (static in the anaerobic chamber). Optical density ($OD_{600}$) of the cultures was assessed and live biotherapeutic product (LBP) cocktails were prepared inside an anaerobic chamber adjusting inputs based upon $OD_{600}$ for equal CFU ratio cocktails in PBS (sterile, pre-treated).

*C. difficile* Colony Forming Unit (CFU) Determination

Fecal pellets were collected, transported to an anaerobic chamber (<2 hours), and manually homogenized in 500 µL of pre-reduced PBS using a pipette tip and through repeated pipetting. Serial dilutions of fecal homogenates were prepared in pre-reduced PBS, 100 µL of which was spread onto cycloserine-cefoxitin-fructose agar with sodium taurocholate (TCCFA) plates, and incubated anaerobically at 37° C. *C. difficile* CFUs were enumerated at 48 hours.

Murine Susceptibility to *C. difficile* Infection

Groups of mice were evaluated for susceptibility to *C. difficile* using three antibiotic regimen protocols: (1) an antibiotic cocktail, (2) clindamycin administration, or (3) cefoperazone administration (FIGS. 2 and 3). The antibiotic cocktail consisted of kanamycin (0.4 mg/ml), gentamicin (0.035 mg/ml), colistin (0.056 mg/ml), metronidazole (0.215 mg/ml), *vancomycin* (0.045 mg/ml) in the drinking water from day −10 to day −3, followed by a single intraperitoneal clindamycin injection (200 m/mouse). The clindamycin administration involved a single intraperitoneal injection of clindamycin (200 µg/mouse) on day −1. The notation of days is relative to day 0, the day of *C. difficile* infection.

Figures 4A, 4B, 4C, 4D:
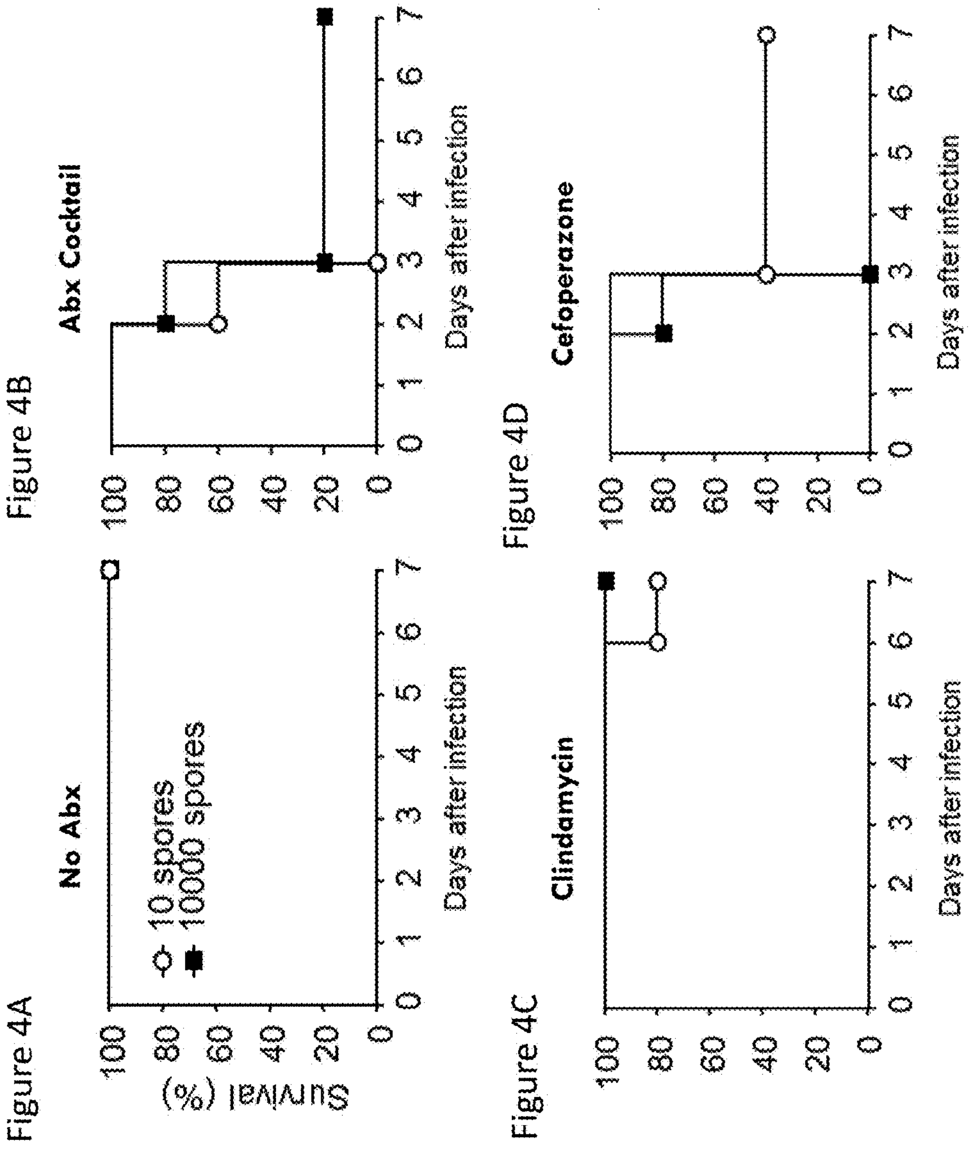
FIGS. 4A-4L show data obtained in Example 1.
Figures 4E, 4F, 4G, 4H:
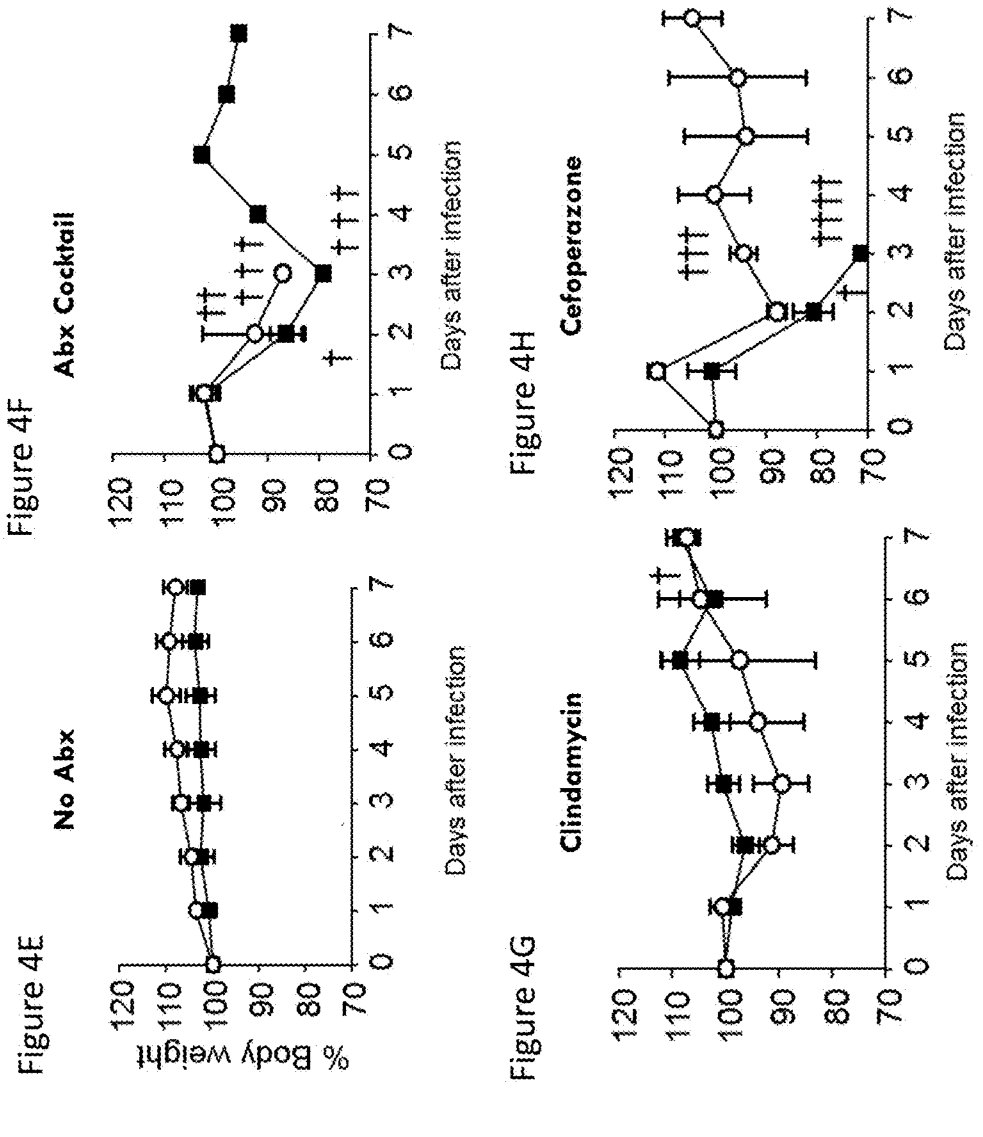
Figure 4I:
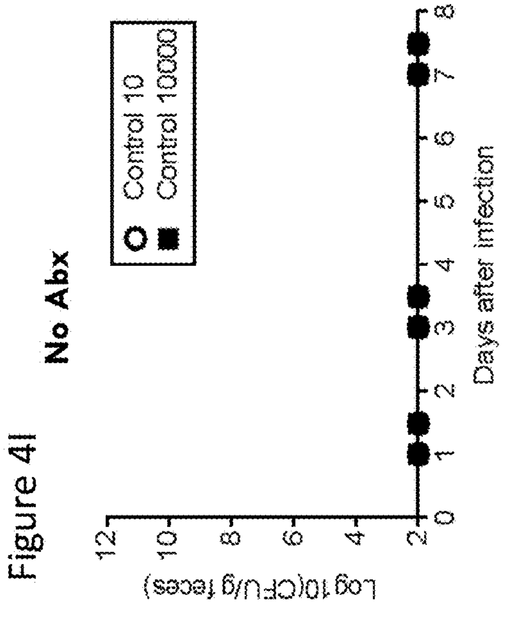
Figure 4J:
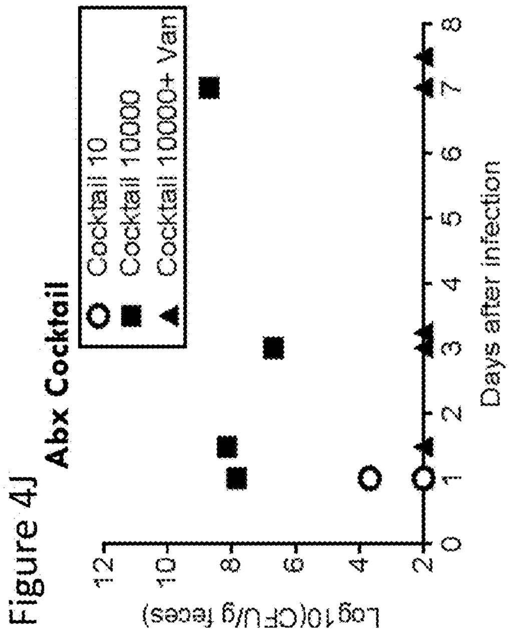
Figure 4K:
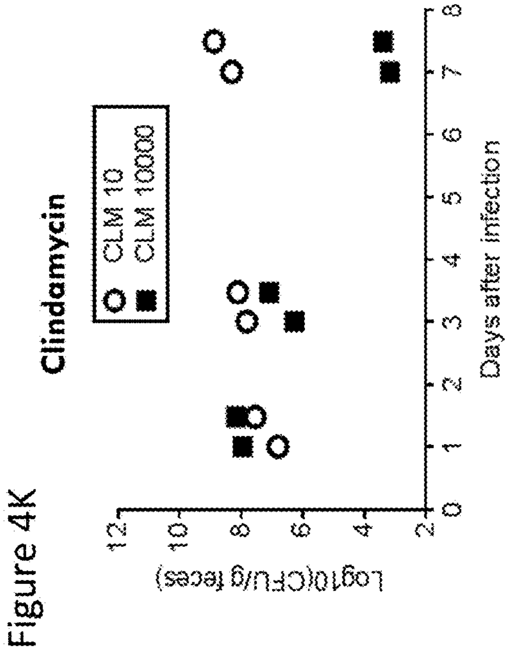
Figure 4L:
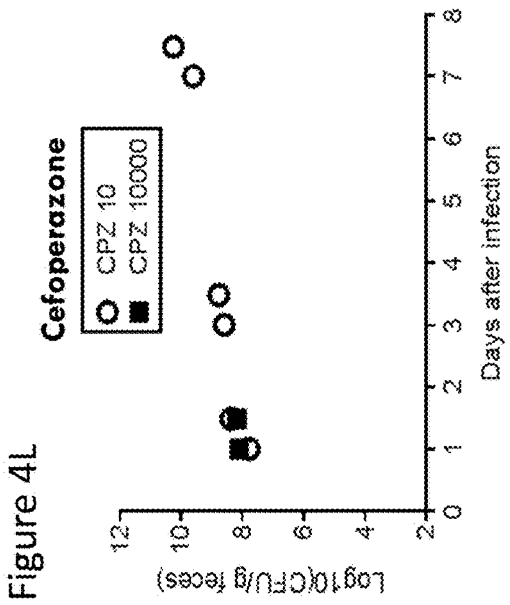

Mice were treated with the indicated antibiotic regimen as described above and then infected with either 10 or $10^4$ *C. difficile* spores by oral gavage on day 0 (FIGS. 2 and 3). An additional experimental arm was added to the antibiotic treatment model in which mice were treated with *vancomycin after C. difficile* infection (FIG. 4J; black triangles).

Mice were monitored daily following infection for mortality/survival (FIGS. 4A-4D) and weight (FIGS. 4E-4H). Fecal pellets were also collected daily and used for *C. difficile* CFU enumeration, presented as CFU/gram feces (FIGS. 4I-4L).

The groups of mice that received cefoperazone treatment had a significant change in weight (FIG. 4H) and substantial *C. difficile* bacterial load in the fecal pellets (FIG. 4L), even following administration with 10 *C. difficile* spores. These results indicated that the cefoperazone pre-treatment regimen provided a good model for *C. difficile* infection and for evaluating protection and/or treatment of *C. difficile* infection. In the absence of antibiotic treatment prior to infection, *C. difficile* infection was not established (FIG. 4I) and all mice survived (FIG. 4A) without significant change in body weight (FIG. 4E).

Example 2: Live Biotherapeutic Product (LBP) Preparations Protect Against *C. difficile* Infection The following LBP compositions were evaluated for their capacity to protect and/or treat *C. difficile* infection:

Composition A,

Composition B,

Composition C,

Composition D,

Composition E (See e.g., Narushima et al., Gut Microbes (2014) 5(3) 333-339), and Composition I: a mixture of *Clostridium scindens, Pseudoflavonifractor capillosus* and *Blautia hansenii* (FIG. 5).

In general, LBP cocktails were mixed in PYG media, and each mouse was administered a dose by oral gavage in 250 μL pre-reduced PBS (media-free). For composition E, bacteria were mixed in equal volumes (not equal ratios/CFUs) and administered in a 250 μL dose. Each LBP of Compositions A-D contained $10^8$ CFUs total in a 250 μL dose, comprised of $10^7$ CFU of each of the bacterial strains (FIG. 1), for a total of $10^8$ CFU administered to each animal. Composition I contained a total of $10^6$ CFUs in a 250 μL dose (approximately 333,000 of each of the 3 bacteria mixed).

Figure 6:
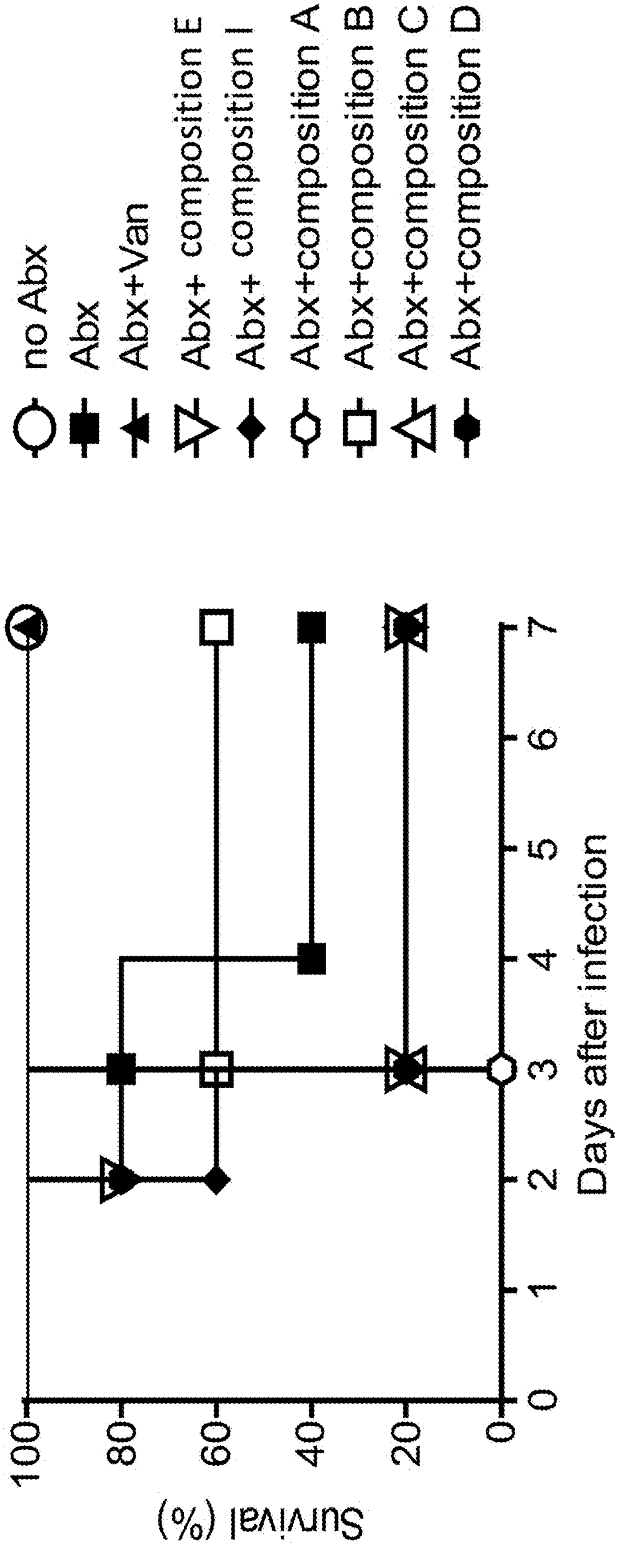
FIG. 6 shows survival of mice over time post infection with *C. difficile* spores, according to the experimental conditions shown in FIG. 5. Mice losing >20% body weight of baseline were included in mortality numbers in survival curves.
Figure 7B:
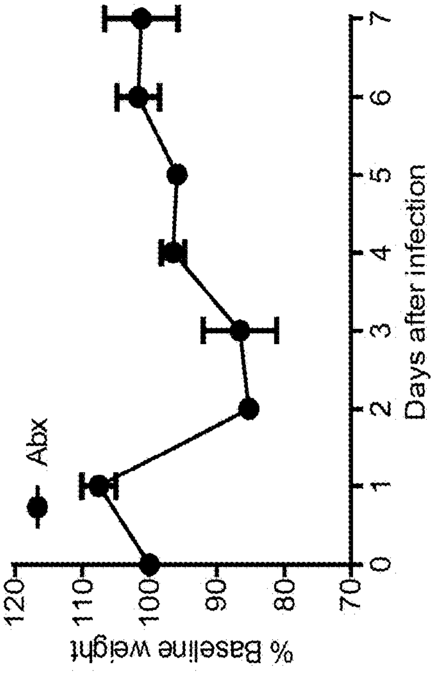
FIGS. 7A-7I show weight of the mice at various times post infection with *C. difficile* spores. Groups of mice received cefoperazone (Abx) treatment followed by the indicated composition, or no cefoperazone (no Abx), then were administered *C. difficile* spores.
Figure 7A:
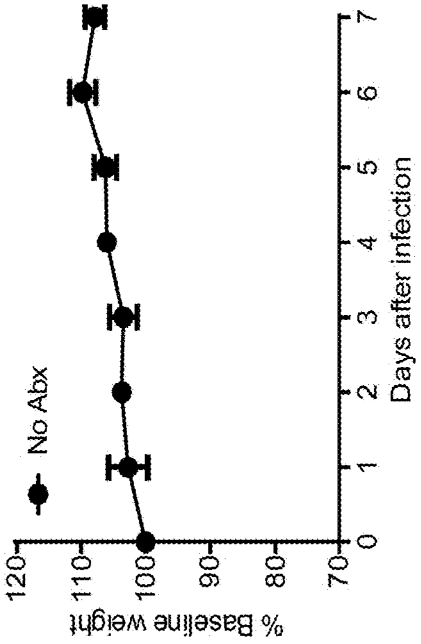
Figure 7C:
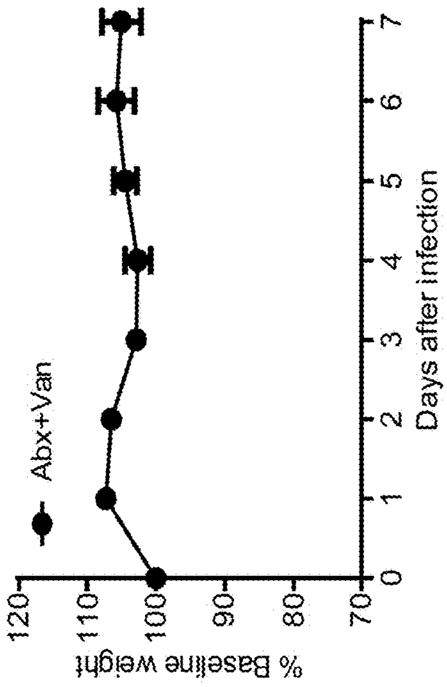
Figure 7E:
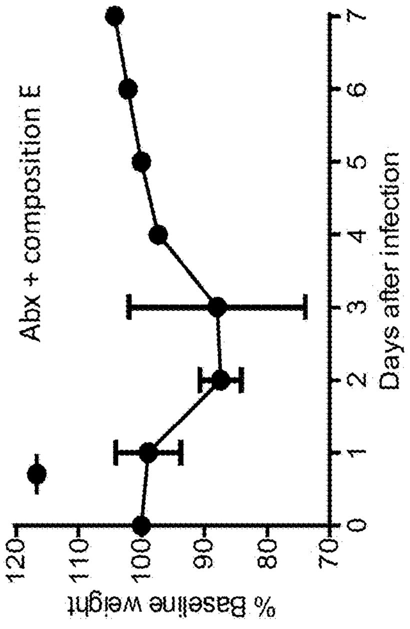
Figure 7D:
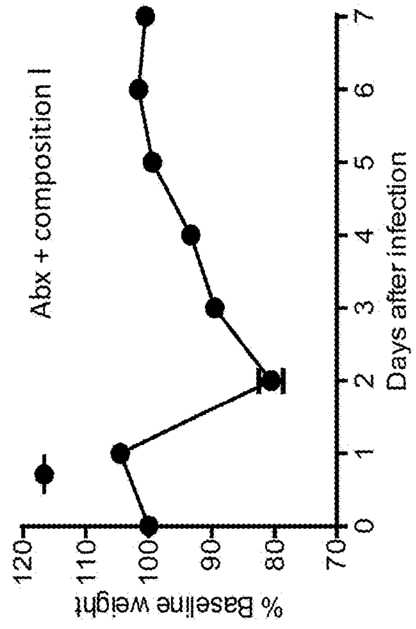
Figure 7F:
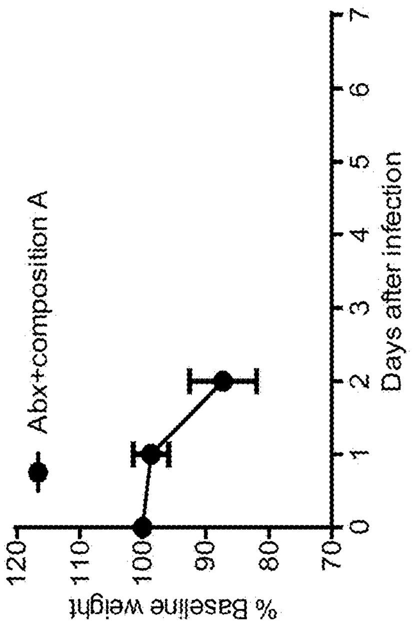
Figure 7H:
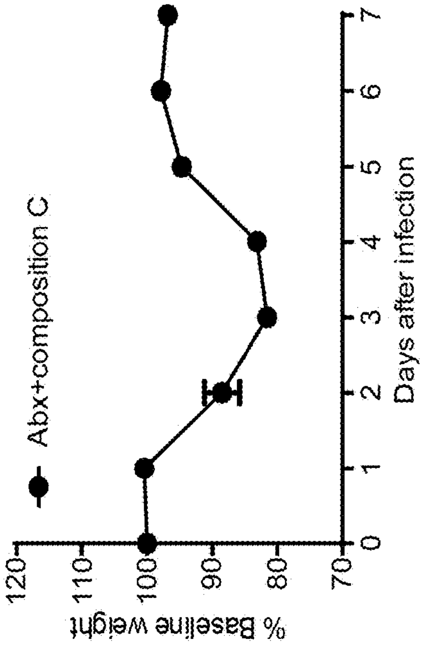
Figure 7G:
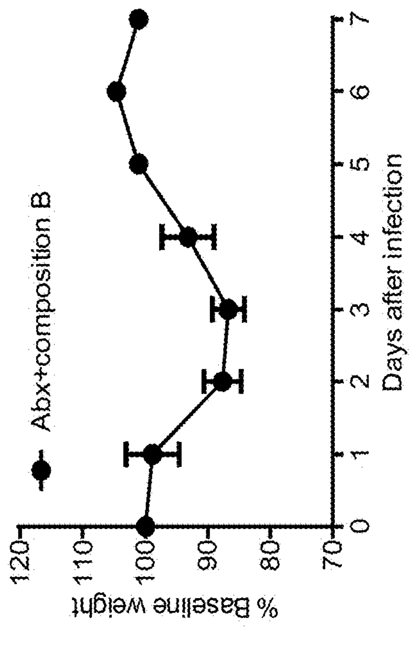
Figure 7I:
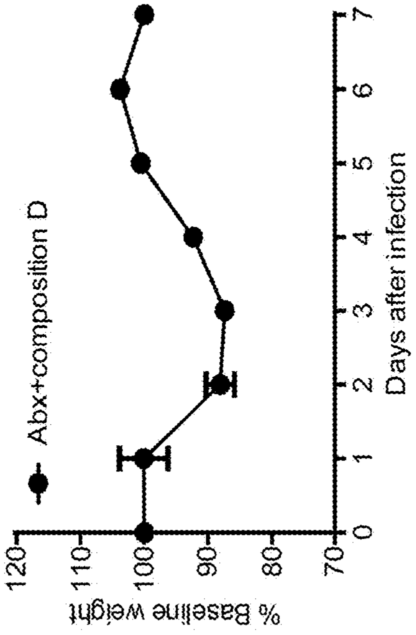
Figure 8B:
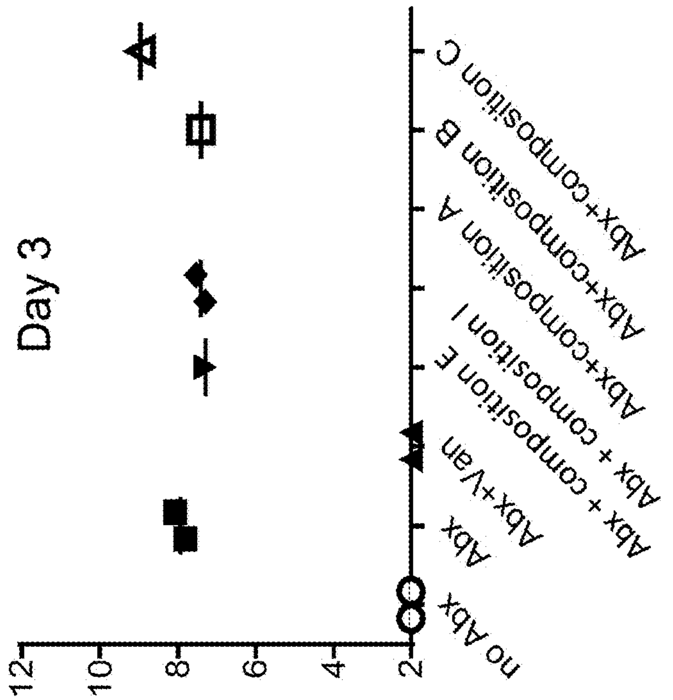
FIGS. 8A-8C show the load of *C. difficile* in colony forming units (CFUs) in fecal pellets at various times post infection with *C. difficile*.
Figure 8A:
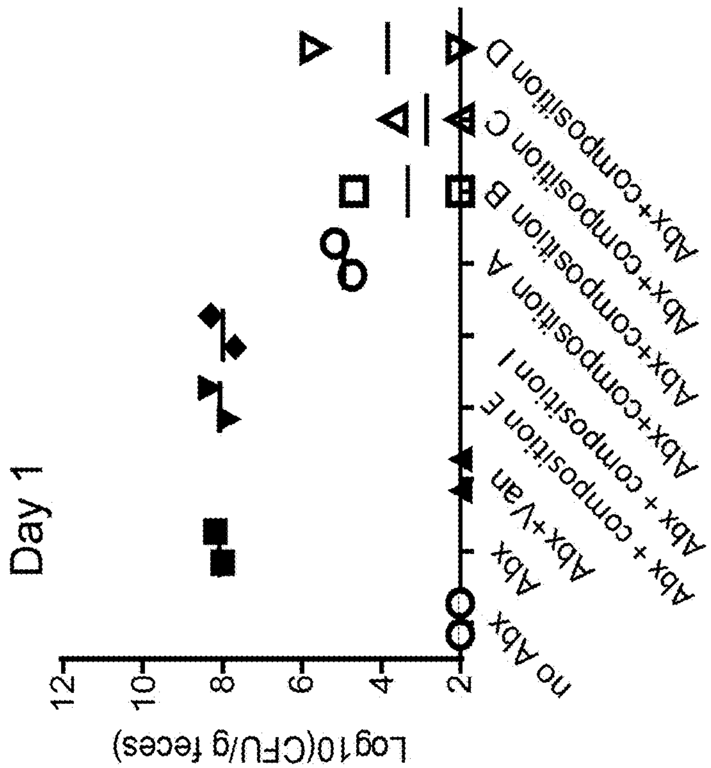
Figure 8C:
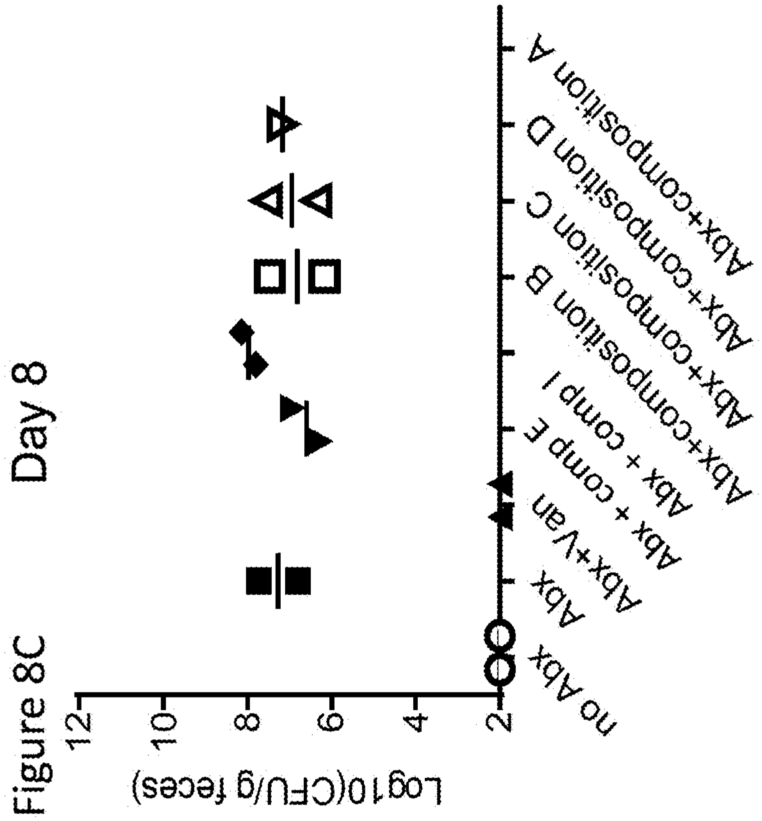

Groups of mice were subjected to cefoperazone treatment, as described in Example 1, and were administered the indicated composition by oral gavage 2 days after the cessation of cefoperazone treatment. Twenty-four hours later, the mice were subjected to infection with $10^4$ *C. difficile* spores (FIG. 5). Mice evaluated for survival/mortality (FIG. 6), weight (FIGS. 7A-7I, and *C. difficile* CFUs (FIGS. 8A-8C). The results show that administration of Composition B prior to *C. difficile* infection is an effective protection and/or treatment against *C. difficile infection.*

Figure 10:
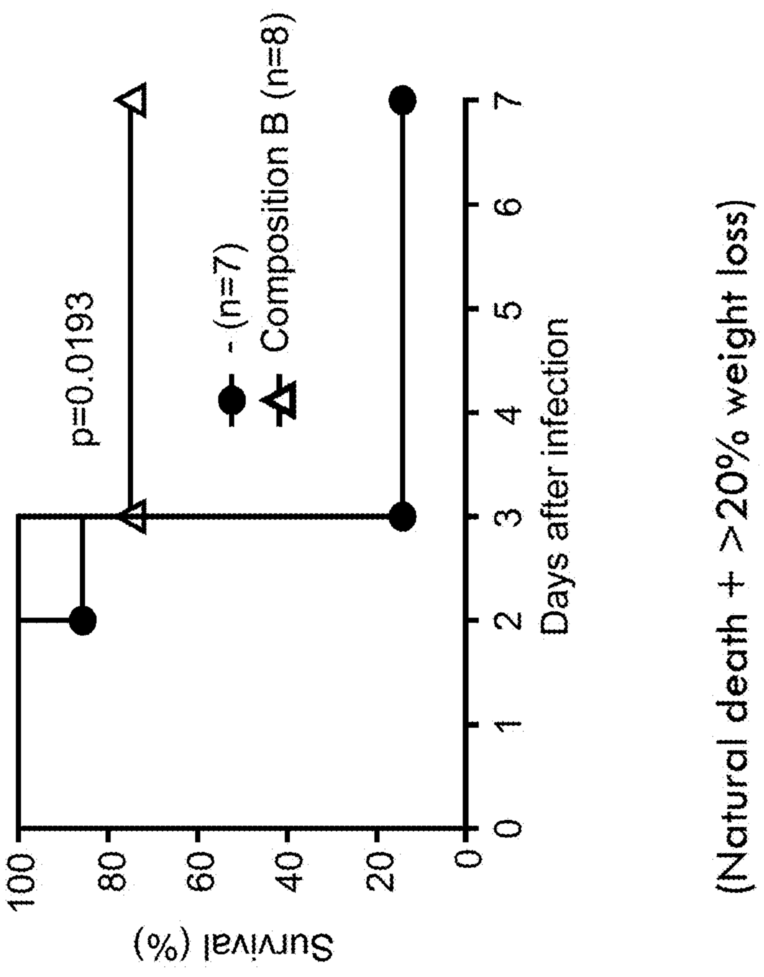
FIG. 10 shows survival of the mice over time post infection with *C. difficile* spores, according to the experimental conditions shown in FIG. 9. Mice losing >20% body weight of baseline were included in mortality numbers in survival curves.
Figure 11:
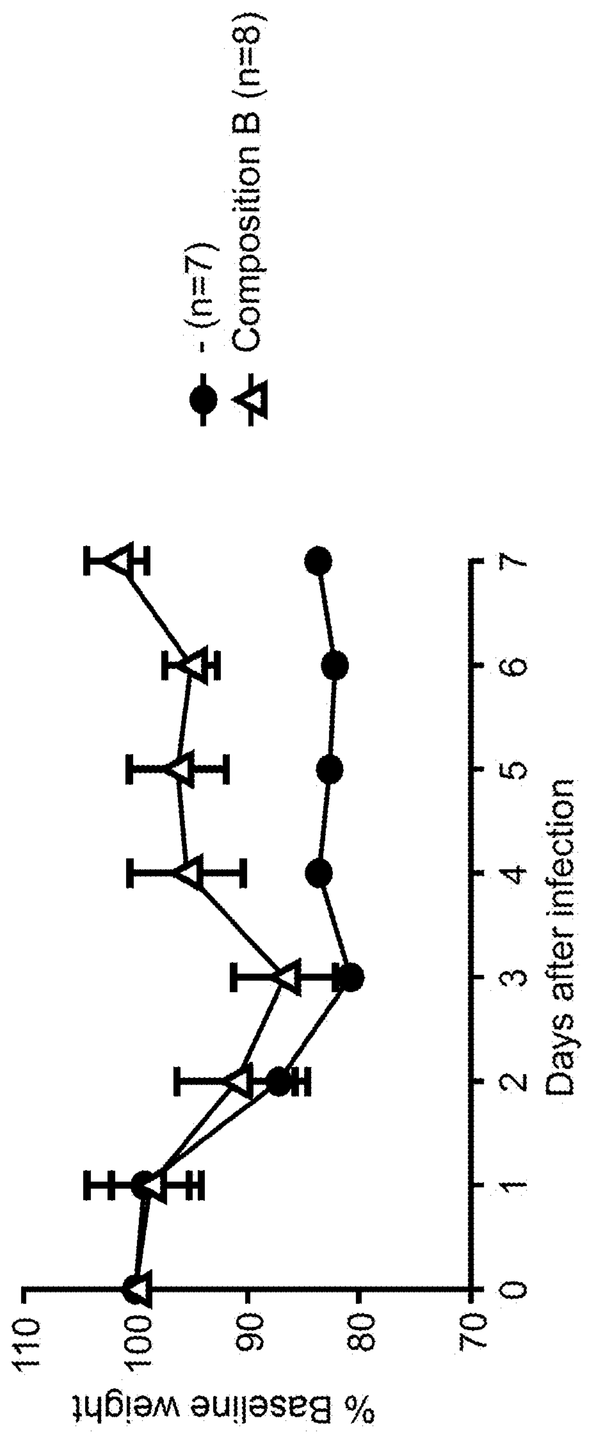
FIG. 11 shows weight of the mice at various times post infection with *C. difficile* spores.
Figure 12:
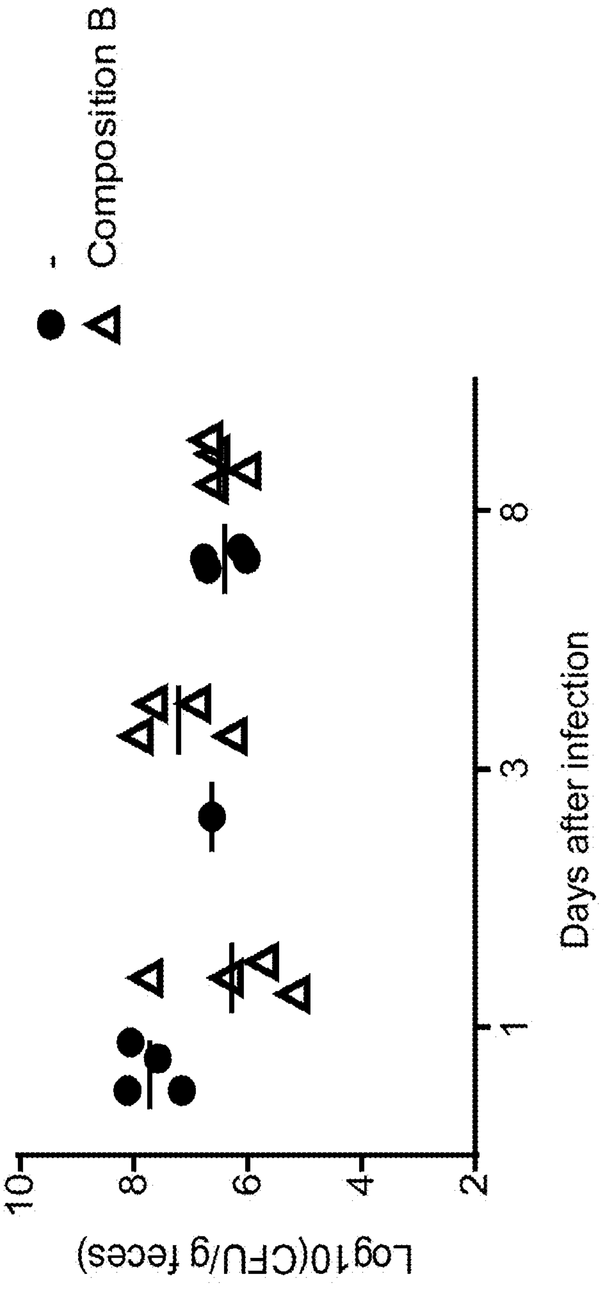
FIG. 12 shows the *C. difficile* burden in colony forming units (CFUs) in fecal pellets collected from mice 1, 3, and 8 days post infection with *C. difficile.*

Example 3: Composition B Protects Against and/or Treats *C. difficile* Infection Groups of 10-12 week old mice were used in the *C. difficile* mouse model (FIG. 9). Mice were subjected to cefoperazone treatment as described in Example 1. One group of mice was then administered Composition B ($10^8$ CFU per mouse) administered by oral gavage, as described in Examples 1 and 2, 2 days after the cessation of cefoperazone treatment. The other group of mice did not receive a live biotherapeutic product after cefoperazone treatment (control). Twenty-four hours later, the mice were subjected to *C. difficile* infection ($10^4$ *C. difficile* spores) and then evaluated for survival/mortality (FIG. 10), weight (FIG. 11), and *C. difficile* burden (CFUs per gram feces; FIG. 12). These results confirm the results of Example 2 that demonstrate treatment with Composition B prior to *C. difficile* infection is an effective protection and/or treatment against *C. difficile* infection.

Example 4: LBP Composition F Protects Against and/or Treat *C. difficile* Infection FIG. 13 shows the strains of live biotherapeutic product (LBP) Composition F. The genus-species classification indicates the closest species based on the sequence of the isolated strain. FIG. 14 shows the classification by *Clostridium* cluster of the strains in Composition F.

Figure 16:
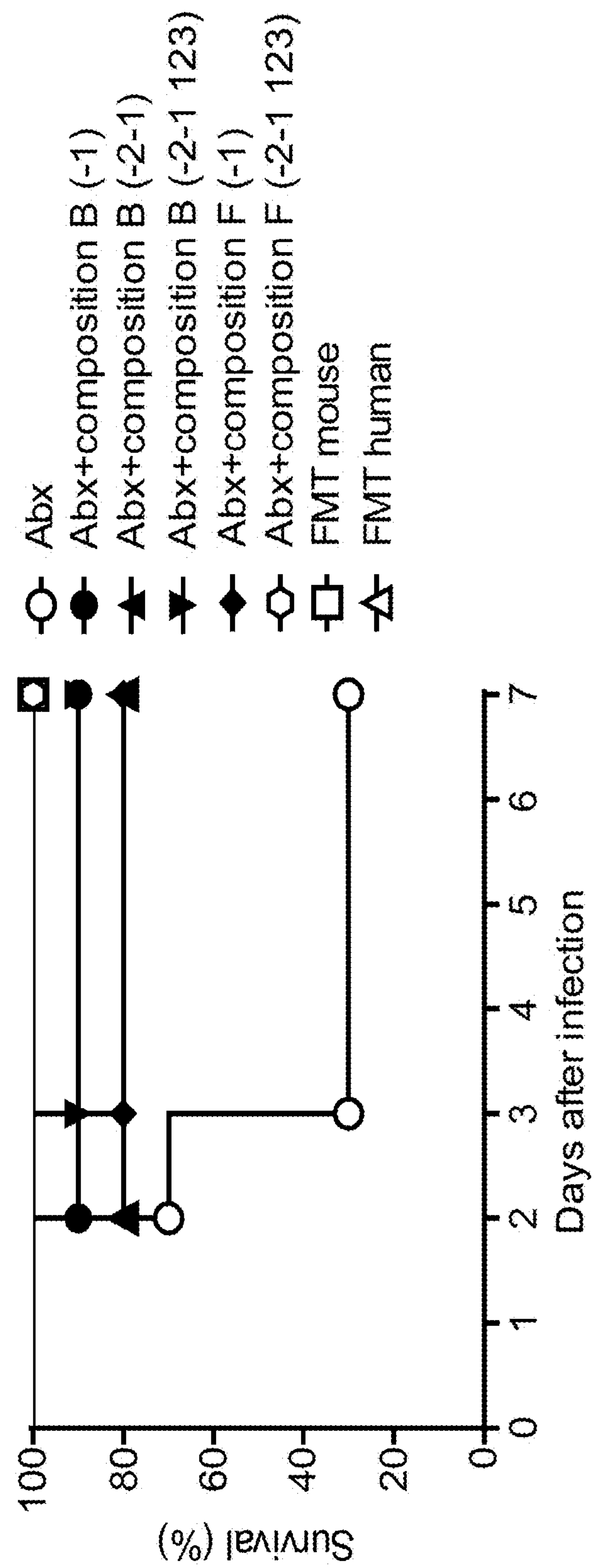
FIG. 16 shows survival of the mice over time post infection with *C. difficile* spores, according to the experimental conditions shown in FIG. 15. Mice losing >20% body weight of baseline were included in mortality numbers in survival curves.
Figure 17A:
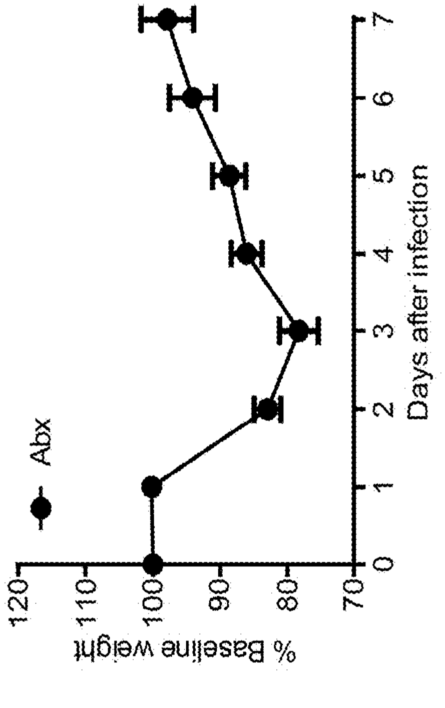
FIGS. 17A-17H show weight of the mice at various times post infection with *C. difficile* spores. Groups of mice received cefoperazone (Abx) treatment followed by the indicated composition, then were administered *C. difficile* spores.
Figure 17B:
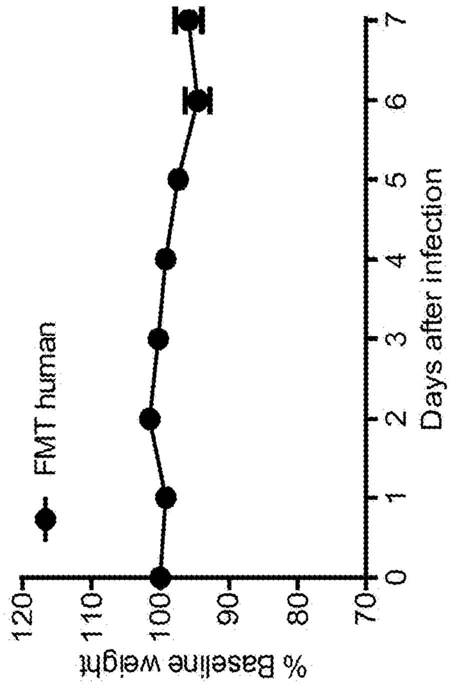
Figure 17C:
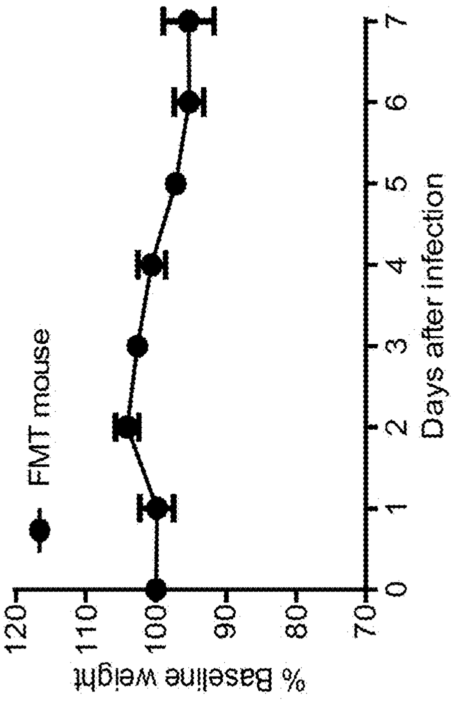
Figure 17E:
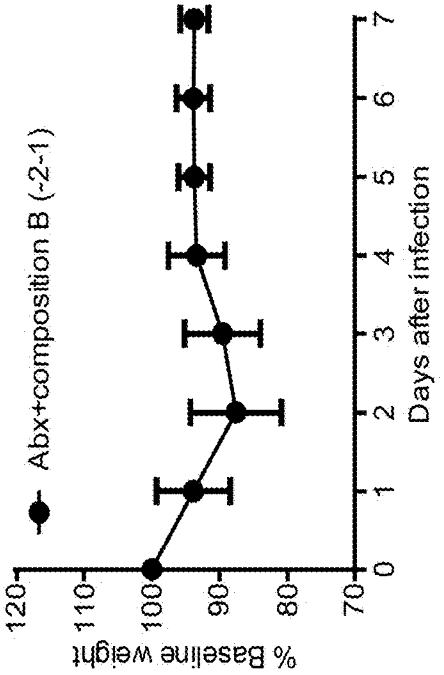
Figure 17D:
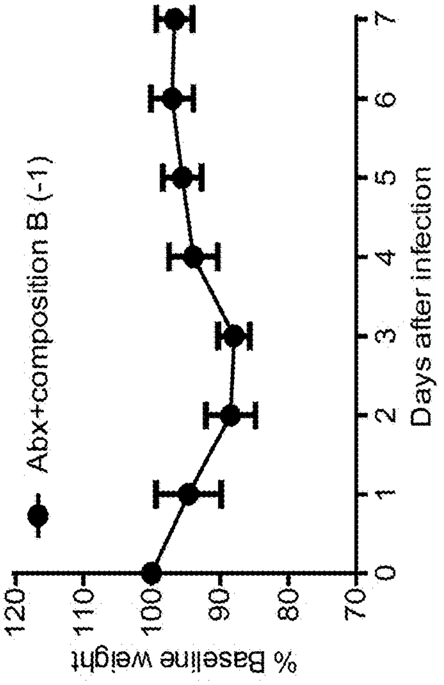
Figure 17F:
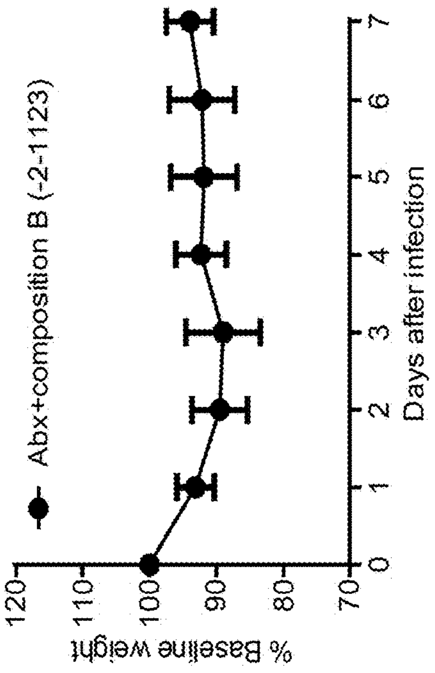
Figure 17G:
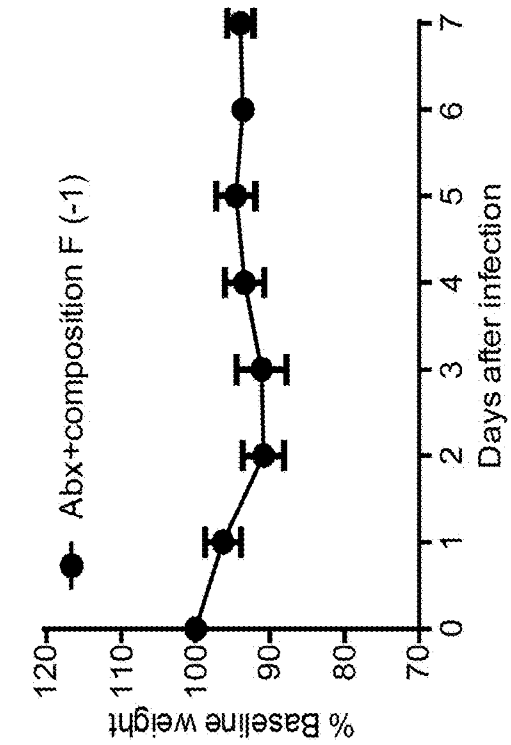
Figure 17H:
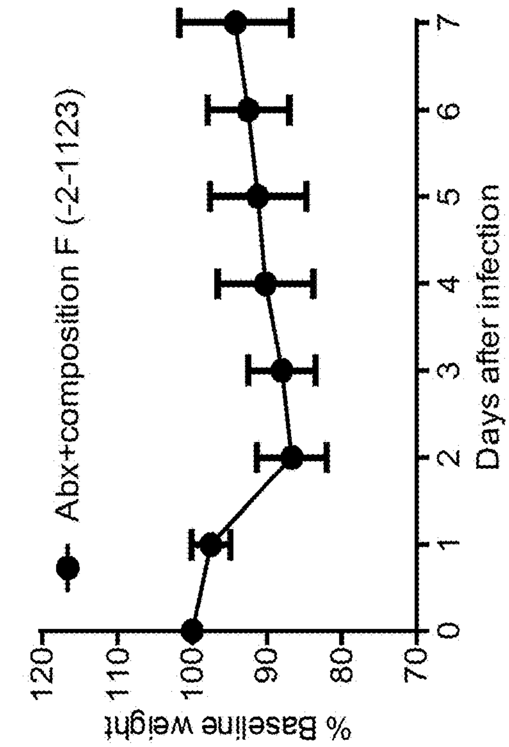
Figure 18B:
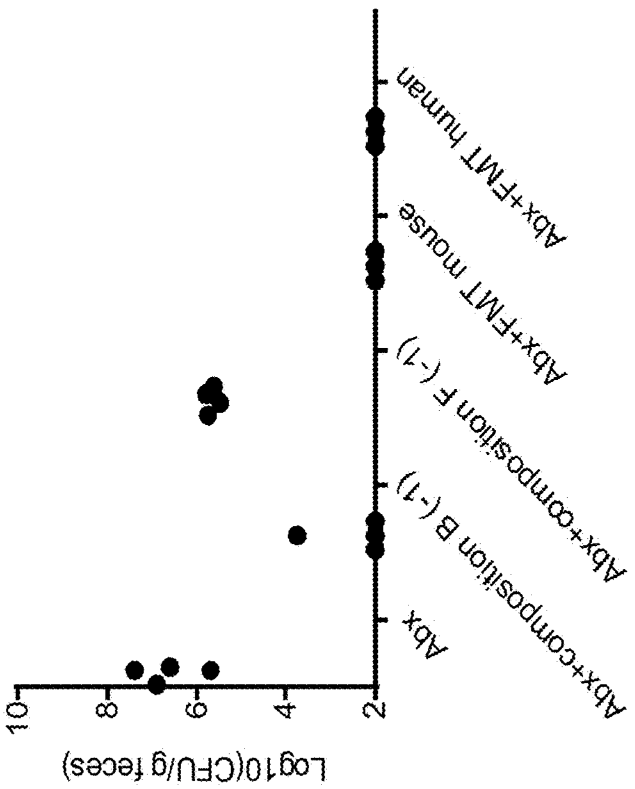
FIGS. 18A-18B show the load of *C. difficile* in colony forming units (CFUs) in fecal pellets at various times post infection with *C. difficile*.
Figure 18A:
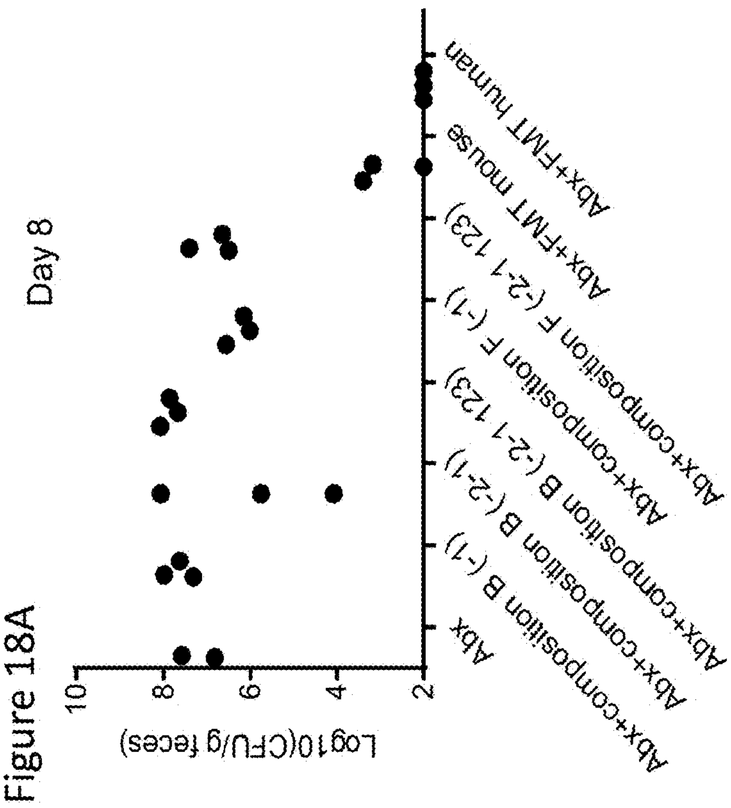

Groups of mice were administered cefoperazone, as described in the Examples above, then administered LBPs or fecal matter transplant (FMT) from mice or human (FIG. 15). Composition B was administered to the indicated groups on day −1; days −2 and −1; or on days −2, −1, 1, 2, and 3, relative to infection with $10^4$ *C. difficile* spores. Composition F was administered to the indicated groups on day −1 or on days −2, −1, 1, 2, and 3, relative to administration of *C. difficile* spores. Additional groups received FMT from mice or from humans (200 μL of a 10% fecal sample s per mouse). Mice were then evaluated for survival/mortality (FIG. 16), weight (FIGS. 17A-17H), and *C. difficile* burden (CFU/gram feces) on days 1, 3, 8 and 17 after infection (FIGS. 18A and 18B). The data demonstrate that Composition B, Composition F, and FMT protect against and/or treat *C. difficile* infection.

Example 5: LBP Compositions Protect Against and/or Treat *C. difficile* Infection FIG. 19 shows the strains of LBP Composition G. The genus-species notation indicates the closest species based on the sequence of the isolated strain. Composition G includes a subset of the strains of Composition F. Groups of mice were administered cefoperazone, as described in the Examples above, then administered the LBP:

Composition B;

Composition B-1 (Composition B with *Bacteroides* added);

Composition B-2 (Composition B from which *Flavonifractor plautii* was removed and *Bacteroides* added);

Composition F;

Composition G;

Human fecal samples subjected to ethanol treatment;

Composition B subjected to ethanol treatment;

Composition B that had been frozen; or

Composition J: *Clostridium innocuum, Clostridium bolteae* and *Clostridium symbiosum* subjected to ethanol treatment; (See also FIG. 20).

The *Bacteroides* strain used in Composition B-1 and B-2 was *Bacteroides ovatus* (strain identifier 211-B; SEQ ID NO: 83).

Figure 21:
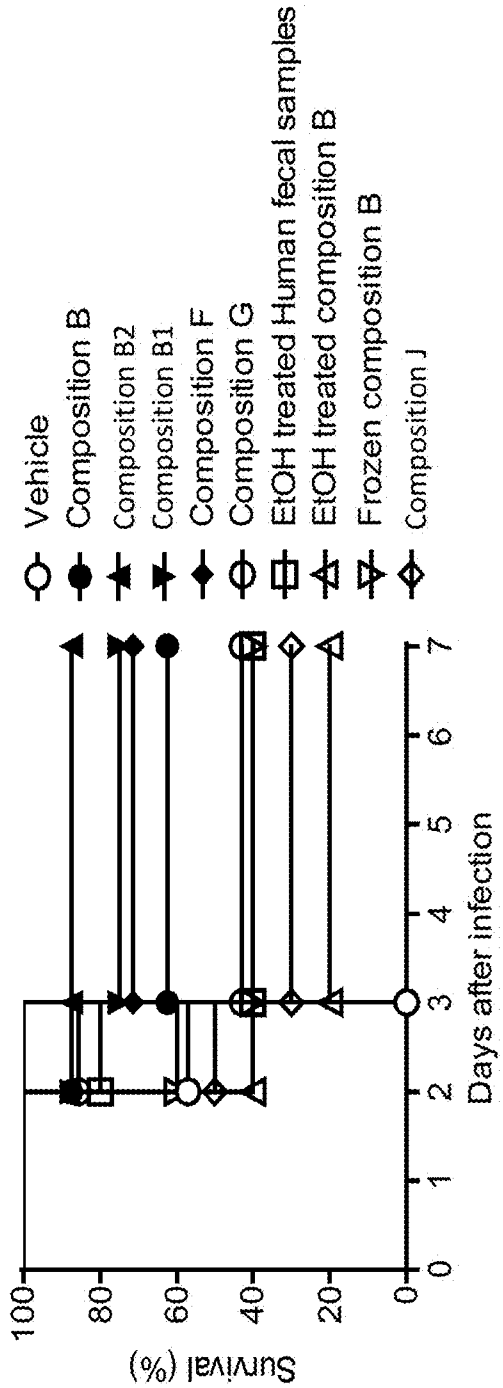
FIG. 21 shows survival of the mice over time post infection with *C. difficile* spores, according to the experimental conditions shown in FIG. 20. Mice losing >20% body weight of baseline were included in mortality numbers in survival curves.
Figure 22A:
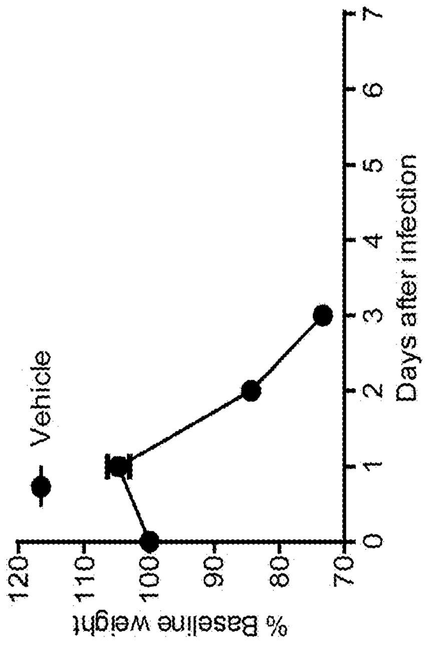
FIGS. 22A-22J show weight of the mice at various times post infection with *C. difficile* spores.
Figure 22B:
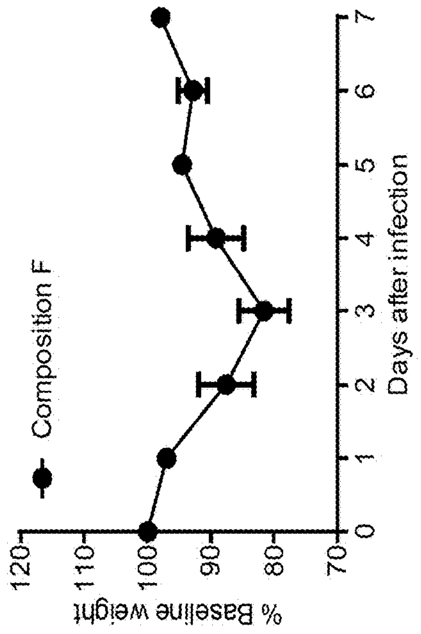
Figure 22C:
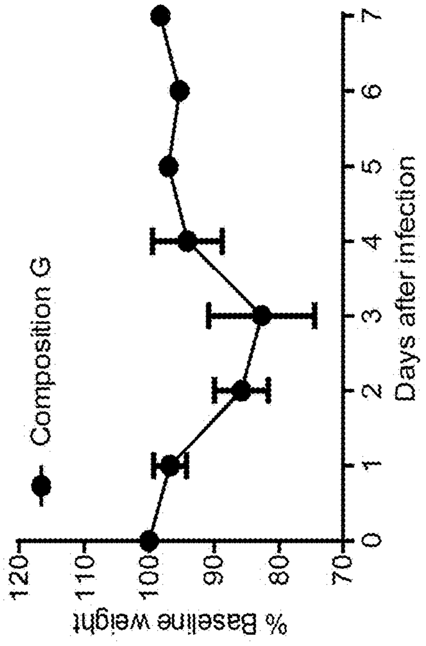
Figure 22D:
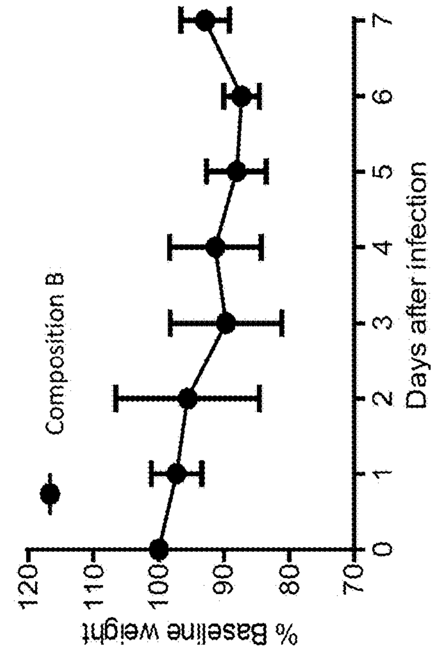
Figure 22E:
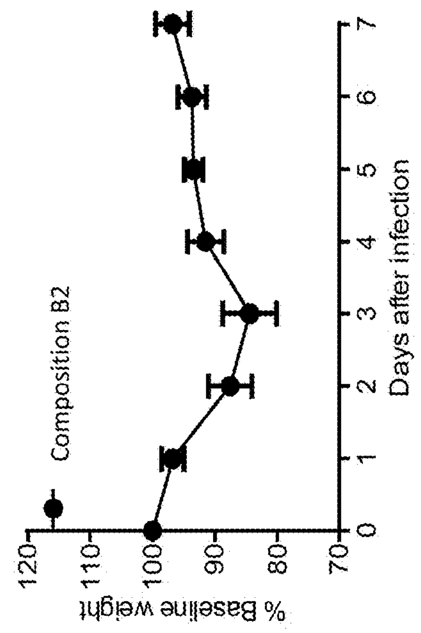
Figure 22F:
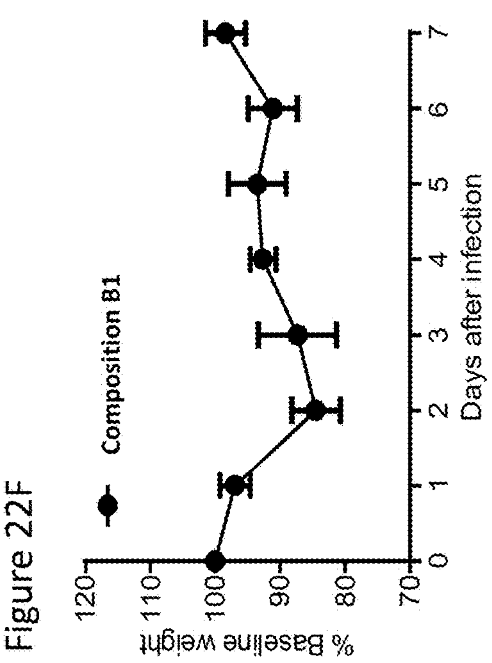
Figure 22G:
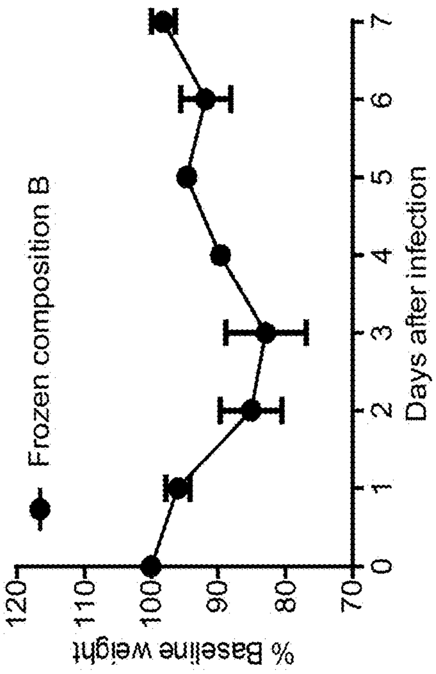
Figure 22I:
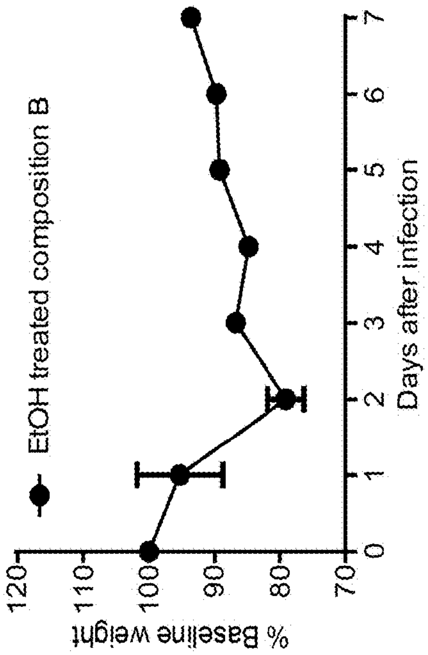
Figure 22H:
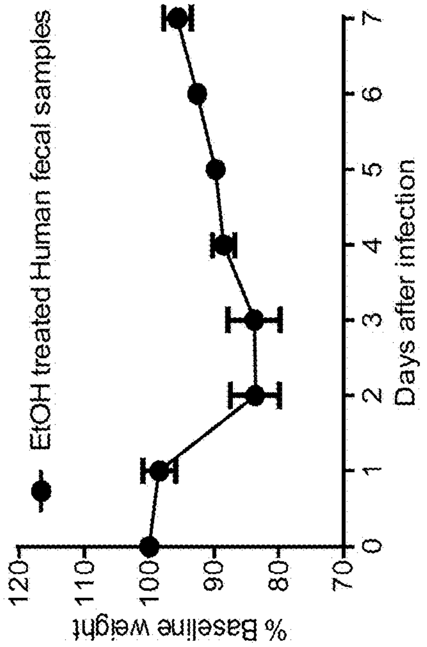
Figure 22J:
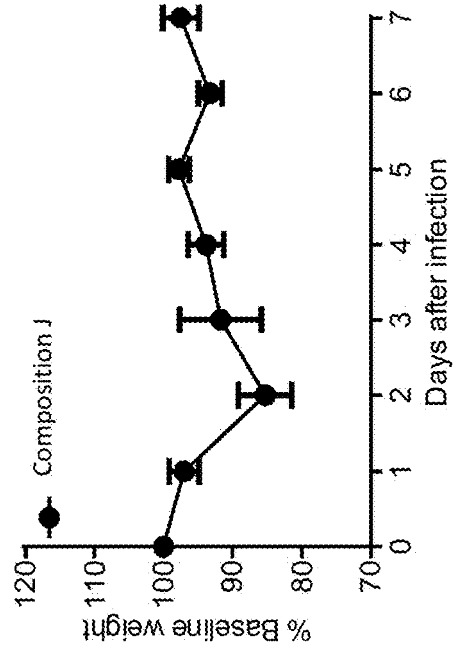
Figure 23:
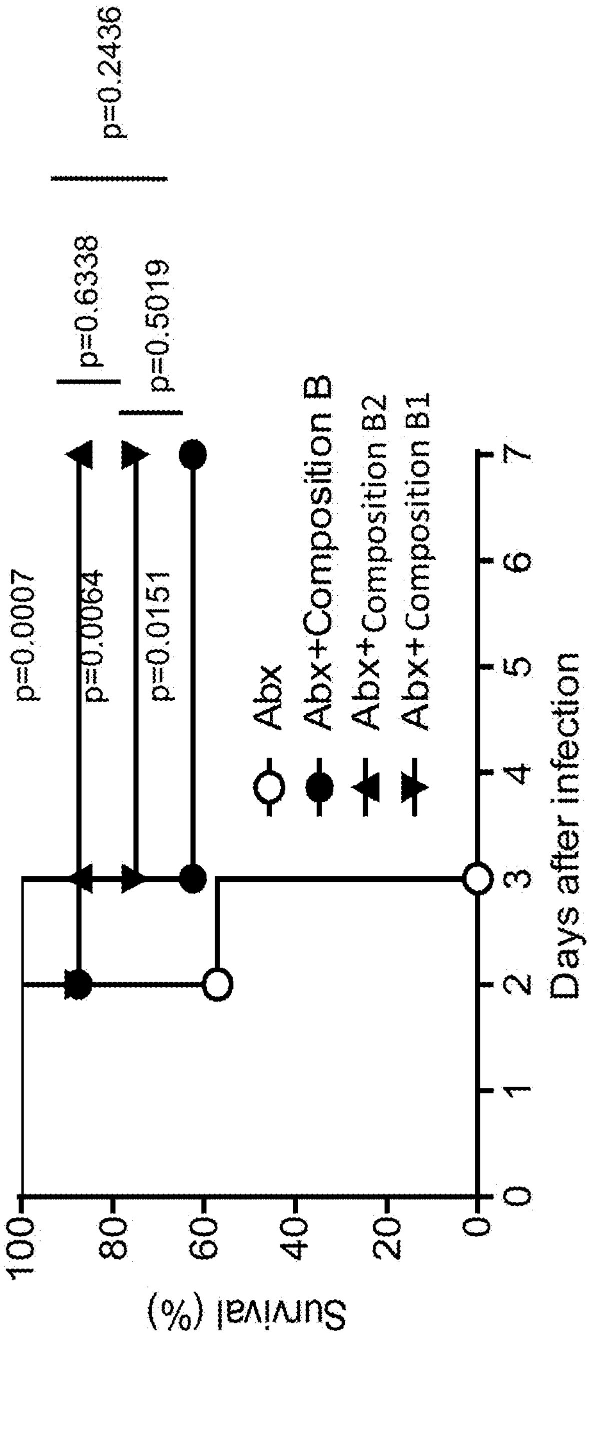
FIG. 23 shows the load of *C. difficile* in colony forming units (CFUs) in fecal pellets at various times post infection with *C. difficile*.
Figure 24:
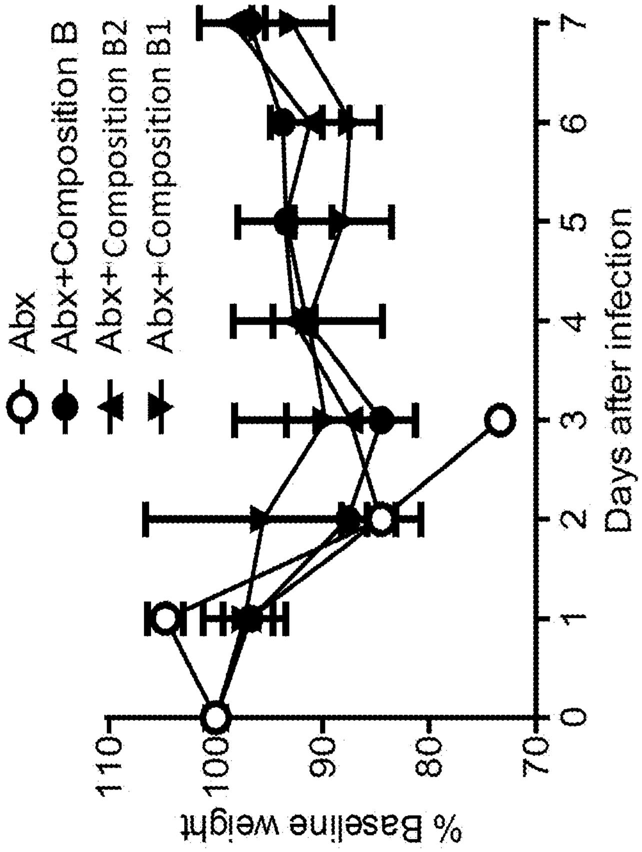
FIG. 24 shows weight of the indicated groups of mice at various times post infection with *C. difficile* spores.

Mice were challenged with *C. difficile* VPI 10463 spores ($10^4$) and monitored daily (Day 0 to Day 7 post *C. difficile* infection) for survival/mortality (FIGS. 21 and 23) and change in weight (FIGS. 22A-22J and 24I). These data show that the compositions protect against and/or treat *C. difficile* infection.

Example 6: LBP Compositions Protect Against and/or Treat *C. difficile* Infection Groups of mice were subjected to cefoperazone treatment, as described above, then administered human fecal matter transplant, Composition B, Composition B+4 spores, or Composition H (FIG. 25). "Composition B+4 spores" refers to Composition B plus the following four strains in spore form: *Clostridium bolteae, Anaerotruncus colihominis, Clostridium symbiosum* and *Clostridium innocuum*. Composition H contains the following six strains in spore form: *Clostridium bolteae, Anaerotruncus colihominis, Clostridium symbiosum, Clostridium innocuum, Clostridium* disporicum and *Erysipelatoclostridium ramosum* (FIG. 26).

Figure 27A:
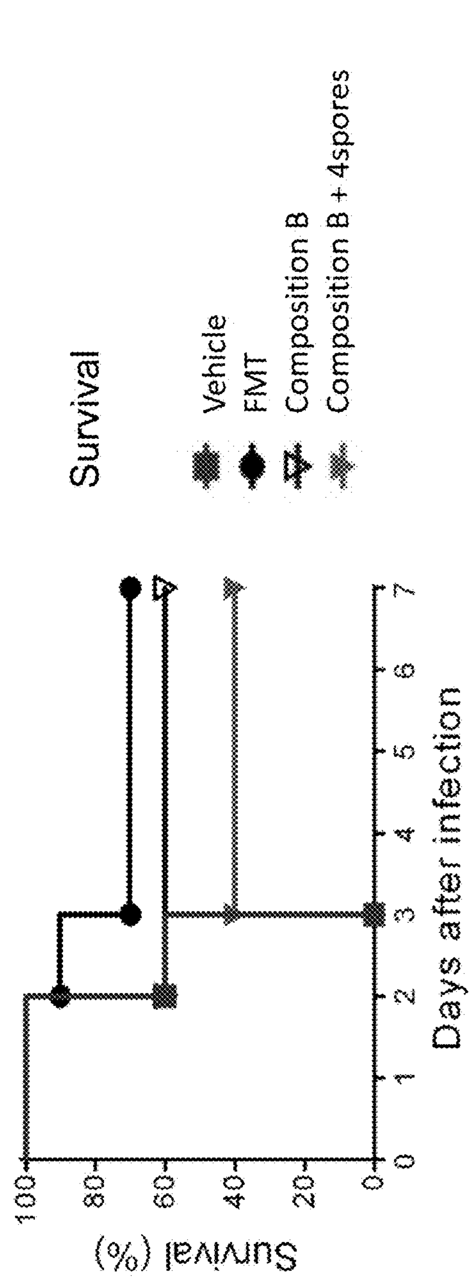
FIGS. 27A and 27B shows survival and weight loss of the mice over time post infection with *C. difficile* spores, according to the experimental conditions shown in FIG. 25. Mice losing >20% body weight of baseline were included in mortality numbers in survival curves.
Figure 27B:
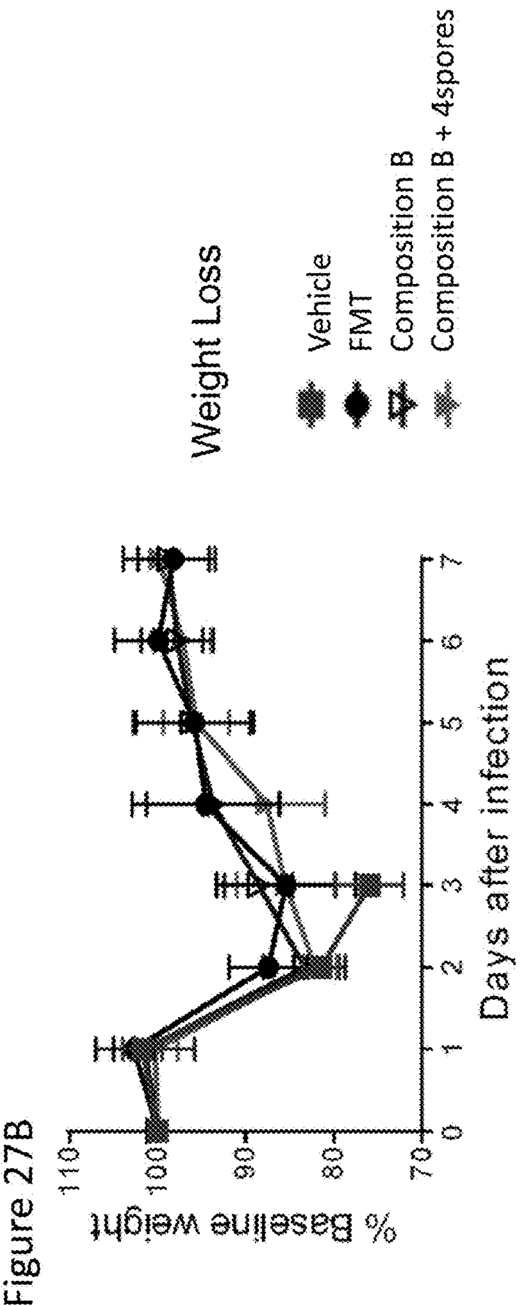
Figure 28A:
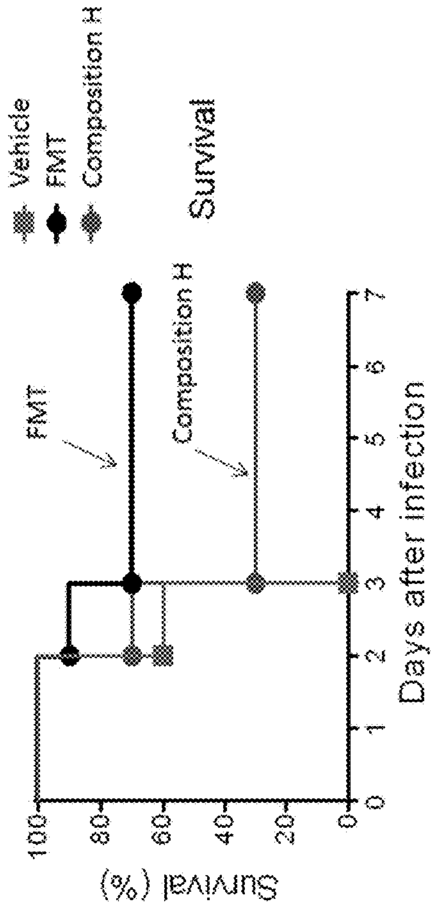
FIGS. 28A and 28B show results from the experimental conditions shown in FIG. 25.
Figure 28B:
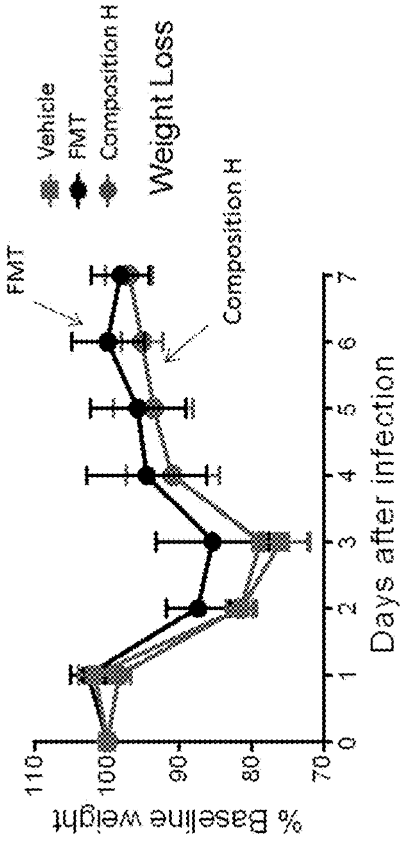
Figure 29A:
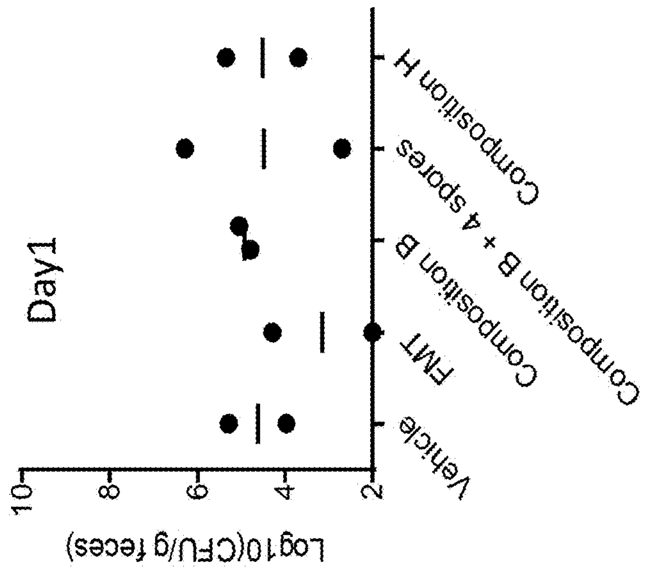
FIG. 29A shows survival/mortality of mice that received the indicated treatment prior to *C. difficile* infection.
Figure 29B:
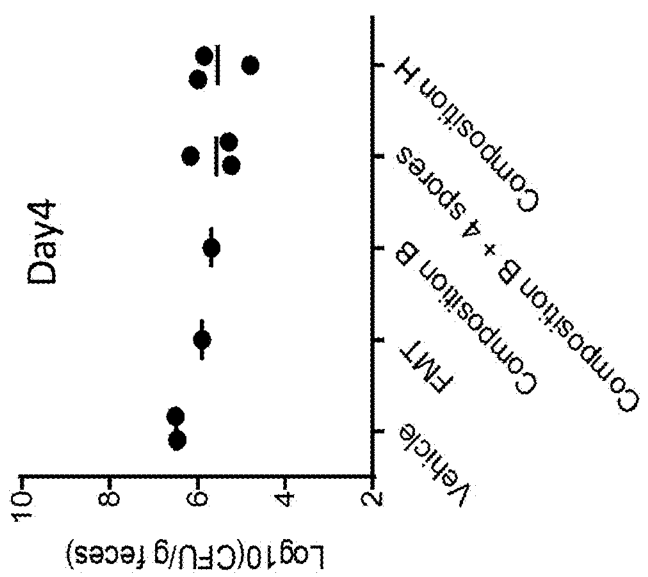
FIG. 29B shows the weight over time of mice that received the indicated treatment prior to *C. difficile* infection.
Figure 29C:
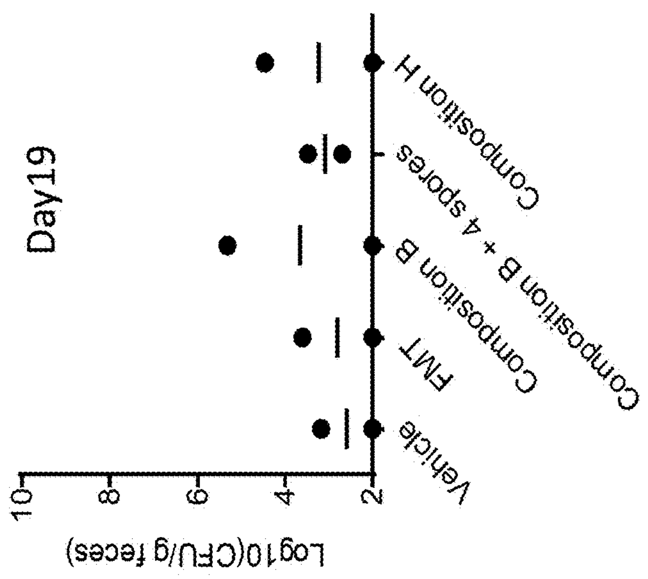
FIG. 29C shows *C. difficile* burden at 19 days post *C. difficile* infection.

Mice were then challenged with *C. difficile* infection with $10^4$ *C. difficile* VPI 10463 spores and monitored for survival/mortality (FIGS. 27A and 28A), weight (FIGS. 27B and 28B). Mice that lost more than 20% body weight relative to baseline were included in mortality numbers in survival curves. The *C. difficile* burden was assessed by CFU in fecal pellets on days 1, 4 and 19 after infection (FIGS. 29A-29C).

These data indicate that Composition B as well as other compositions can improve survival in the cefoperazone-induced *C. difficile* mouse model and protect against and/or treat *C. difficile* infection.

Example 7: *C. difficile* Toxin Experiment

Vero cells, epithelial cells derived from African Green Monkey kidney epithelium, are sensitive to a variety of bacterial toxins, including *C. difficile* Toxin B. Exposure of cells to *C. difficile* Toxin B results in inhibition of the function of Rho, Rac, and Cdc42 leading to a decline in F-actin, a change in cell morphology (e.g., cell rounding), and eventually apoptosis.

To determine whether administration of bacterial compositions described herein has an effect on the production or activity of *C. difficile* Toxin B, a cellular assay was performed. Briefly, groups of mice were treated with cefoperazone, as described above, and administered human fecal matter transplant (FMT) ("4-3"); Composition B ("5-3"); Composition B plus four strains in spore form: *Clostridium bolteae, Anaerotruncus colihominis, Clostridium symbiosum* and *Clostridium innocuum* ("7-4"), or no treatment. Each of the groups of mice were then exposed to *C. difficile* infection with $10^4$ *C. difficile* spores. The groups of mice that did not receive a treatment after cefoperazone administration and prior to *C. difficile* infection are referred to as "2-1 (Cdiff)" and "2-4 (Cdiff)." An additional group of mice was not exposed to *C. difficile* as indicated by "N3 (Healthy)".

Figure 30:
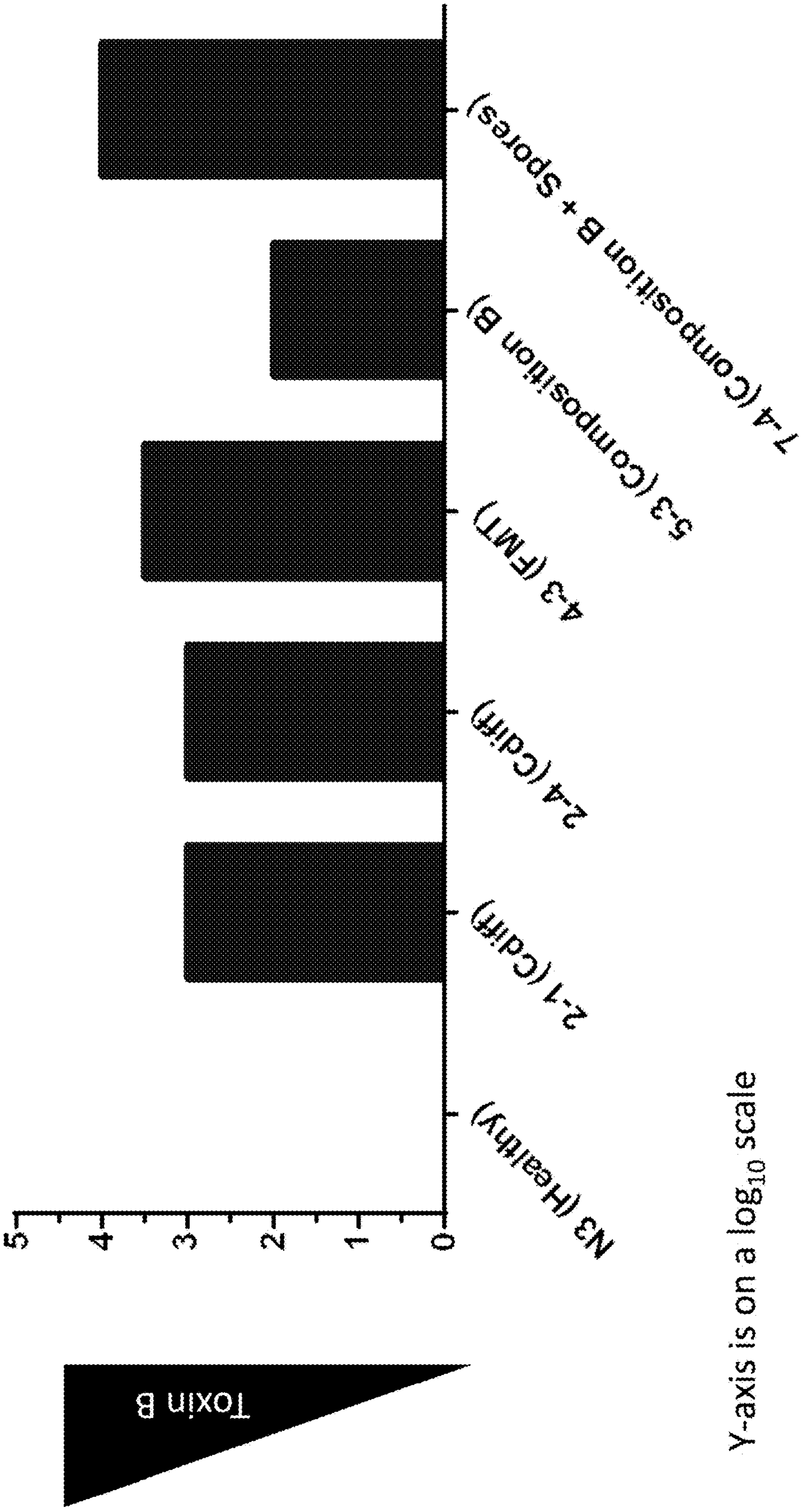
FIG. 30 shows that Composition B reduced the amount of *C. difficile* Toxin B compared to no treatment controls: "2-1 (Cdiff)" and "2-4 (Cdiff)" and FMT. In addition, Composition B reduced the amount of *C. difficile* Toxin B compared to Composition B with additional spores.

Fecal pellets were collected from each of the groups of mice, weighed, and homogenized in PBS and normalized to a fixed concentration (~25 mg/mL). The samples were centrifuged to prepare a clarified supernatant, which was then diluted in 10-fold serial dilutions to produce a range from 1:10 to 1:$10^{-6}$ dilutions of clarified pellet supernatant. Vero cell cultures were exposed to the diluted samples for approximately 18 hours, then visualized by phase contract microscopy to assess morphological changes (i.e., cell rounding) associated with *C. difficile* toxin exposure. The cells were scored based on the highest concentration of supernatant that did not yield a change in morphology (FIG. 30). The samples from mice that had been treated with Composition B prior to *C. difficile* infection had reduced amounts of *C. difficile* Toxin B, as compared to samples from control mice that did not receive a treatment after cefoperazone administration and prior to *C. difficile* infection ("2-1 (Cdiff)" and "2-4 (Cdiff)") as well as compared to samples from mice that received FMT. Notably, the samples from mice that had been treated with Composition B also had reduced amounts of *C. difficile* Toxin B, as compared to samples from mice that had been treated with Composition B with additional spores.

Example 8: In Vitro Competition Between Compositions B and *C. difficile*

Composition B was assessed for its ability to suppress *Clostridium difficile* growth by an in vitro mixed culture competition assay. From glycerol freezer stocks, individual strains of Composition B, *C. difficile* (Cdiff), *Clostridium bifermentans*, and *Bacteroides thetaiotaomicron* were struck out onto Eggerth-Gagnon agar plates with horse blood (EG+HB). Single colonies of each of the strains were subsequently inoculated into brain heart infusion (BHI) liquid media and allowed to grow in pure culture for 24-48 hours. Turbid cultures were sub-cultured then grown to exponential phase and finally diluted and combined to prepare a mixed culture with an optical density ($OD_{600}$) of 0.1. Exponential phase Cdiff culture was added to the mixed culture at a final concentration with an OD of 0.1. After the cultures were combined and incubated for 2-3 hours, samples were collected, serially diluted, and plated on Taurocholate-Cycloserine-Cefoxitin-Fructose Agar (TCCFA) plates to select for Cdiff growth. After 48-72 hours, the colony forming units (CFUs) of Cdiff in each competition experiment were determined by manual colony counting.

EG+HB agar plates were prepared according to standard procedures and reduced in an anaerobic environment for at least 6-8 hours prior to use. Liquid BHI medium was obtained from BD Biosciences (Catalog # 211059, San Jose, Calif.), prepared according to the manufacturer's instructions, and reduced in an anaerobic environment for at least 18-24 hours prior to use. TCCFA plates were prepared according to standard procedures and reduced in an anaerobic environment for at least 6-8 hours prior to use. *Clostridium difficile* strain used in the experiments: American Type Culture Collection (ATCC) 43255.

TABLE 4

| Composition B strains<br>Composition B |
|---|
| VE202-7 |
| VE202-13 |
| VE202-14 |
| VE202-16 |
| Strain #16 |
| Strain #170 |
| Strain #189 |
| Strain #211 |

Strains were struck out onto EG+HB agar plates from frozen glycerol stocks inside an anaerobic chamber for 48-72 hours. Single colonies were inoculated into 10 mL of BHI media and grown 24-48 hours at 37° C. in the anaerobic chamber. Turbid cultures were then diluted to an OD of 0.1 and grown for 2-3 hours at 37° C. in the anaerobic chamber. Exponential phase cultures were diluted and combined at equivalent ODs. For the competition assay, each of the strains of Combination B (Table 4) were combined in equal parts, based on $OD_{600}$, to reach a final consortium $OD_{600}$ of 0.1. *C. bifermentans* and *B. thetaiotaomicron* were setup to compete with Cdiff individually at an OD of 0.1. The OD600 for Cdiff in each of the mixed culture competition experiments was 0.1. After combination, the cultures were incubated for 2-3 hours at 37° C. in the anaerobic chamber, then prepared for enumerations on Cdiff selective plates.

TCCFA plates are selective for Cdiff growth, and none of the Combination B strains, nor either of the control strains (*C. bifermentans* and *B. thetaiotaomicron*), grow on these plates. Inside an anaerobic chamber, a 100 μL sample of each competition culture was collected and serially diluted 1:10 to reach a final dilution of $1\times10^{-6}$. Plates for CFU enumeration were prepared by spreading 100 μL of each of the $1\times10^{-4}$ through $1\times10^{-6}$ dilutions on TCCFA plates using sterile spreading loops. CFU plates were incubated for 48-72 hours at 37° C. in the anaerobic chamber. CFU enumeration was completed by manually counting colonies.

Figure 31:
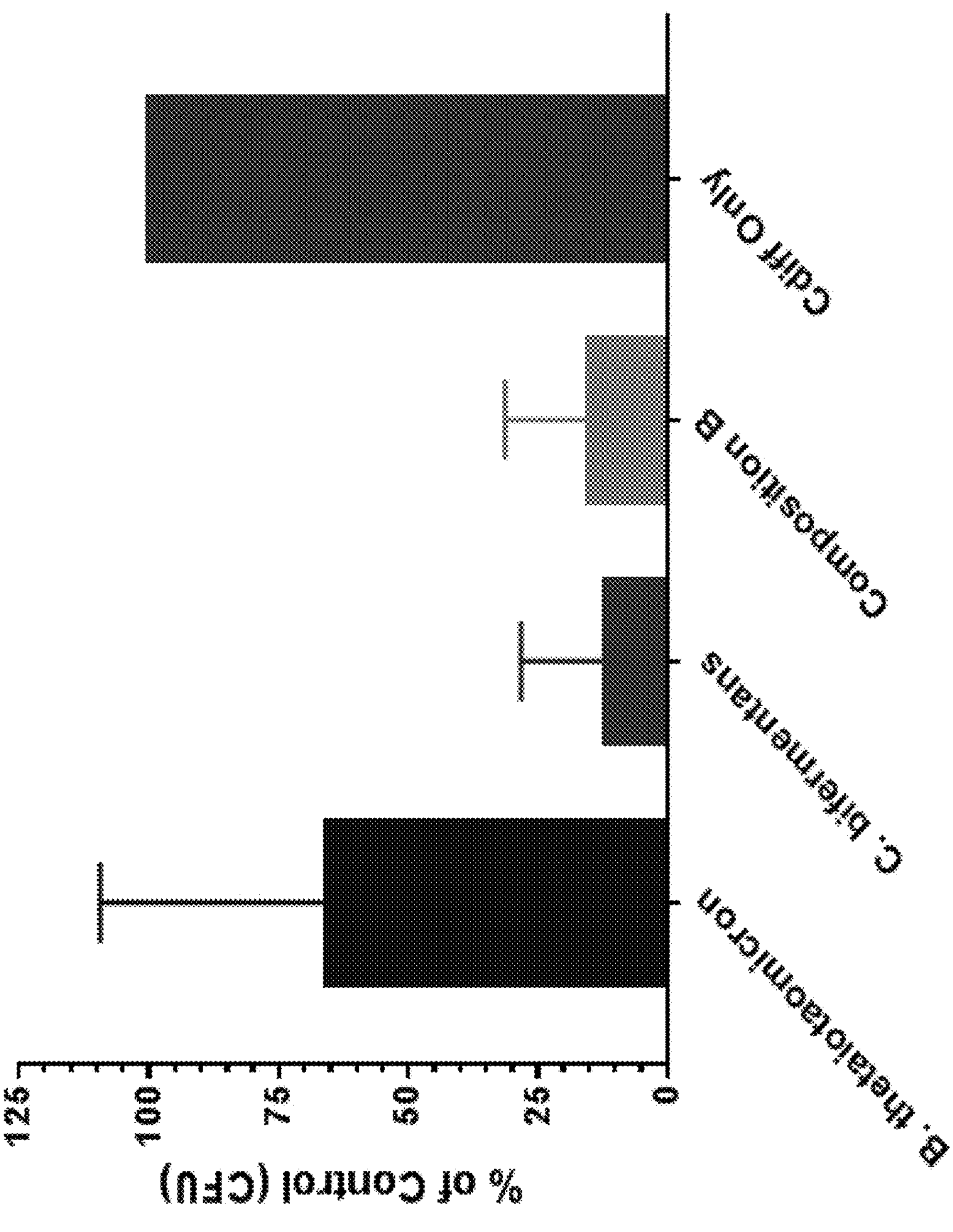
FIG. 31 shows Composition B reduced *C. difficile* growth in in vitro competition experiments. Cultures of *C. difficile* were incubated in the presence of *B. thetaiotaomicron, C. bifermentans*, or Composition B, or in the absence of a competing strain(s) (*C. diff* only). The quantity of *C. difficile* is presented as the percentage of the control (*C. diff* only).

To determine the effect of competition, the ratio of CFUs determined for the competition samples and Cdiff alone was calculated and expressed as a percentage. Inhibition of Cdiff growth by the Composition B cocktail was compared to the responses of *B. thetaiotaomicron* (negative control) and *C. bifermentans* (positive control). The results are shown in Table 5 and FIG. 31.

TABLE 5

Summary Results for In Vitro Competition

| Experiment Number | No Competing Strain(s) | Competition with *B. thetaiotaomicron* | Competition with *C. bifermentans* | Competition with Composition B |
|---|---|---|---|---|
| n = 1 | 100 | | | 33.8 |
| n = 2 | 100 | 9.90 | 0.1 | 0.5 |
| n = 3 | 100 | 115 | 39.5 | 33.1 |
| n = 4 | 100 | 41.3 | 0.7 | 0.7 |
| n = 5 | 100 | 105 | 14.1 | 20.9 |
| n = 6 | 100 | 57.4 | 4.1 | 1.6 |
| Mean | 100 | 65.6 | 11.7 | 15.1 |
| Std. Dev. | 0 | 43.8 | 16.5 | 16.2 |
| Total N | 6 | 5 | 5 | 6 |

Data is expressed as Cdiff CFU as a percentage of control. Each n is representative of a single biological replicate, independent of other measurements.

In in vitro competition, Composition B inhibited Cdiff growth to 15.1±16.2% of control (absence of competing strain(s)). This result is consistent with the inhibition observed by the positive control, *C. bifermentans*, of 11.7±16.5% of control. *B. thetaiotaomicron*, a negative control, yielded a negligible effect on Cdiff growth at 65.6±43.8% of control. Given the variability inherent in the assessment of CFU, inhibition of growth to <25% of control is considered to be significant inhibition and both the positive control and Composition B cocktail meet this threshold of activity. The Composition B consortium attenuated Cdiff growth in vitro comparable to the direct competition observed by *C. bifermentans*. Direct competition with *B. thetaiotaomicron* did not significantly inhibit Cdiff growth.

Example 9: Determination of in Vitro Short-Chain Fatty Acid Production

Each strain of Composition B was assessed for individual short-chain fatty acid (SCFA) production in vitro. Composition B strains were grown in pure cultures inside an anaerobic chamber. Spent supernatant from liquid media cultures was harvested by centrifugation, filter sterilized, and then stored at <−70° C. Frozen clarified supernatant specimens were analyzed for short-chain fatty acids (SCFAs).

EG+HB agar plates (Eggerth-Gagnon agar plates with horse blood) were prepared according to standard methods and reduced in an anaerobic environment for at least 6-8 hours prior to use. Liquid PYG medium (pre-formulated, pre-reduced) was obtained from Anaerobe Systems (Catalog#AS-822; Morgan Hill, Calif.).

Strains were struck out onto EG+HB agar plates from frozen 15% glycerol stocks inside an anaerobic chamber for 48-72 hours. Single colonies were inoculated into 7 mL PYG media and grown 24-48 hours at 37° C. in the anaerobic chamber. Unless otherwise noted, when the optical density (OD) was ≥0.2, samples were collected for CFU enumeration and filtration. Inside an anaerobic chamber, a 100 μL sample of turbid culture was collected and serially diluted 1:10 to reach a final dilution of $1\times10^{-6}$. Plates for CFU enumeration were prepared by spreading 100 μL/dilution for the $1\times10^{-4}$ through $1\times10^{-6}$ dilutions on EG+HB agar plates using sterile glass beads. CFU plates were incubated for 48-72 hours in the anaerobic chamber. CFU enumeration was completed using the EasyCount 2 (bioMérieux S A, Marcy-l'Étoile, France). Immediately after samples of turbid cultures were collected for CFU enumeration, the remaining turbid cultures were centrifuged at approximately 1000 RCF for 10 minutes to pellet cellular debris. The clarified supernatants were transferred to a 0.2 μm plate filter and vacuum filtered to remove any remaining particulates prior to bioanalysis. In the event of blockage in the filter plate, clarified supernatants were manually filtered using 0.2 μm syringe filters. Filtered supernatants were aliquoted and stored at <−70° C. prior to bioanalysis of SCFAs.

To facilitate easier comparisons between samples, raw SCFA data (μg/mL) was normalized by the $\log_{10}$ of corresponding determined/estimated CFU for the culture. The results are depicted in Table 6 and Table 7 below.

TABLE 6

Enumerated CFUs for Composition B Strains

| Sample ID | OD600 | Enumerated CFU (CFU/mL) |
|---|---|---|
| VE202-7 | >2 | 6.11E+08 |
| VE202-13 | 0.8 | 4.00E+08 |
| VE202-14 | >2 | 1.60E+09 |
| VE202-16 | 1.92 | 1.28E+09 |
| #16 | 1.97 | 1.69E+08 |
| # 170 | 1.8 | 1.08E+08 |
| # 189 | 1.03 | 1.74E+09 |
| # 211 | 0.35 | 3.71E+08 |

TABLE 7

SFCAs produced by individual Composition B strains

| Sample ID | Normalized (μg/Log(CFU/mL) * mL) | | | | | | | |
|---|---|---|---|---|---|---|---|---|
| | Acetate | Propionate | Iso-butyrate | Butyrate | 2-Methyl-butyrate | Iso-valerate | Valerate | Hexanoate |
| VE202-7 | 123.7 | 0.077 | 0.102 | 0.208 | 0.015 | 0.056 | BLOQ | 0.031 |
| VE202-13 | 30.1 | 0.545 | 0.116 | 34.452 | 0.288 | 0.188 | 0.097 | 0.034 |
| VE202-14 | 110.5 | 0.054 | 0.022 | 0.248 | 0.011 | 0.014 | BLOQ | 0.009 |
| VE202-16 | 313.2 | 0.000 | 0.000 | 0.280 | 0.004 | 0.000 | BLOQ | 0.009 |
| #16 | 104.0 | 0.005 | 0.000 | 50.988 | 0.014 | 0.033 | BLOQ | 0.009 |
| # 170 | 87.1 | 0.055 | 0.025 | 0.215 | 0.011 | 0.039 | BLOQ | 0.016 |

TABLE 7-continued

| SFCAs produced by individual Composition B strains | | | | | | | | |
|---|---|---|---|---|---|---|---|---|
| | Normalized (μg/Log(CFU/mL) * mL) | | | | | | | |
| Sample ID | Acetate | Propionate | Iso-butyrate | Butyrate | 2-Methyl-butyrate | Iso-valerate | Valerate | Hexanoate |
| # 189 | 0.0 | BLOQ | 0.000 | 35.751 | 0.005 | 0.019 | 0.359 | 0.587 |
| # 211 | 57.6 | 5.289 | 0.000 | 78.227 | 0.028 | 0.050 | 0.053 | 0.095 |

Seven strains of Composition B were found to produce significant quantities (>1 μg/Log(CFU/mL)*mL) of the 2-carbon SCFA, acetate. One strain, (#211), produced substantial quantities of the 3-carbon SCFA, propionate. Four strains of Composition B produced substantial quantities of the 4-carbon SCFA, butyrate. Trace quantities (<1 μg/Log (CFU/mL)*mL) of other SCFAs were also produced by the Composition B strains.

Example 10: Composition B Induces Regulatory T Cells (Tregs)

Each of the bacterial strains of Composition B were grown to log phase, combined to a total dose of ~$10^8$ cfu per mouse. Germ-free mice were inoculated with Composition B or a negative control by oral gavage and sacrificed following four weeks of colonization. Lamina propria leukocytes were isolated from colonic tissue of individual mice by standard procedures and assessed by flow cytometry. The regulatory T cell content was evaluated as the percentage of Foxp3-positive cells among CD4+ T cells.

Figure 32:
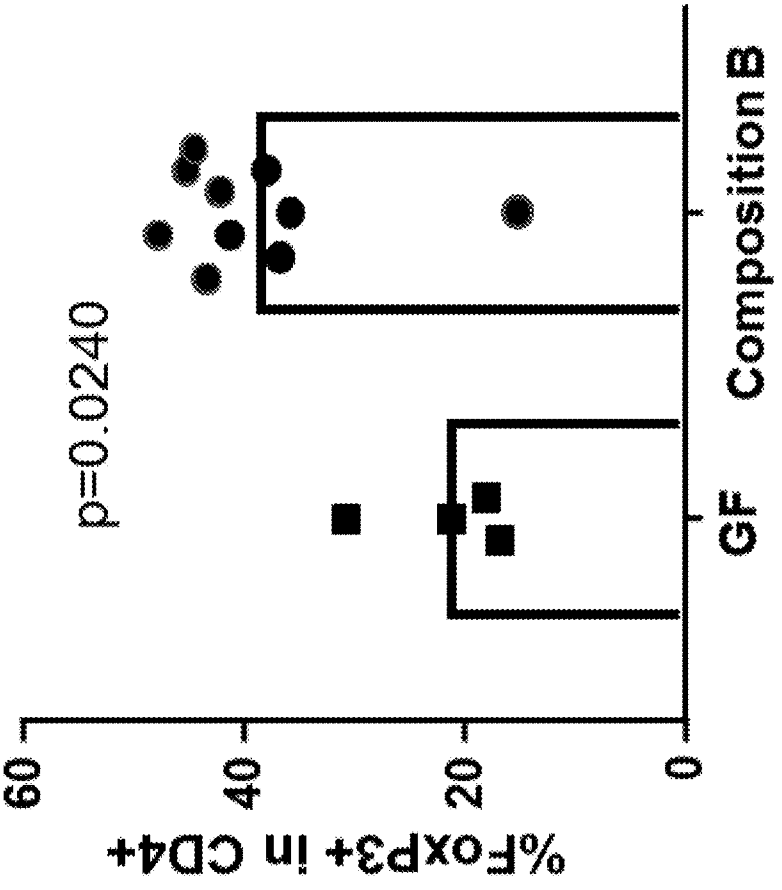
FIG. 32 shows that inoculation with Composition B induced the percentage of FoxP3+CD4+ cells (regulatory T cells) in the intestine of germ-free mice as compared to control mice ("GF").

As shown in FIG. 32, mice that were inoculated with Composition B were found to have significantly more regulatory T cells as compared to mice that were inoculated with the control.

What is claimed is:

1. A method of treating *Clostridium difficile* infection in a subject, the method comprising administering a pharmaceutical composition comprising a purified bacterial mixture consisting of bacterial strains comprising 16S rDNA sequences of at least 97% sequence identity to SEQ ID NO:10, SEQ ID NO:14, SEQ ID NO:15, SEQ ID NO:16, SEQ ID NO:17, SEQ ID NO:19, SEQ ID NO:20, and SEQ ID NO:21, to the subject in an amount sufficient to treat *Clostridium difficile* infection.

2. The method of claim 1, wherein the *Clostridium difficile* infection is a first occurrence of the *Clostridium difficile* infection.

3. The method of claim 1, wherein the *Clostridium difficile* infection is a recurrent *Clostridium difficile* infection.

4. The method of claim 3, wherein the subject has been treated with an antibiotic prior to recurrence of the *Clostridium difficile* infection.

5. The method of claim 1, further comprising administering an antibiotic.

6. The method of claim 1, wherein one or more of the bacterial strains are spore-formers.

7. The method of claim 1, wherein the bacterial strains originate from more than one human donor.

8. The method of claim 1, wherein the pharmaceutical composition further comprises a pharmaceutically acceptable excipient.

9. The method of claim 1, wherein the pharmaceutical composition is formulated for oral administration.

10. The method of claim 1, wherein the pharmaceutical composition wherein the pharmaceutical composition is in the form of a capsule.

11. The method of claim 1, wherein the pharmaceutical composition is formulated for delivery to the colon.

12. The method of claim 1, wherein the pharmaceutical composition further comprises one or more enteric polymers.

* * * * *

SEQUENCE LISTING

```
<160> NUMBER OF SEQ ID NOS: 159

<210> SEQ ID NO 1
<211> LENGTH: 210
<212> TYPE: DNA
<213> ORGANISM: Artificial Sequence
<220> FEATURE:
<223> OTHER INFORMATION: Synthetic Polynucleotide

<400> SEQUENCE: 1

gcccggagca gttgatgtga aggatgggtc acctgtggac tgcattggaa ctgtcatact      60

tgagtgccgg agggtaagcg gaattcctag tgtagcggtg aaatgcgtag atattaggag     120

gaacaccagt ggcgaaggcg gcttactgga cggtaactga cgttgaggct cgaaagcgtg     180

gggagcaaac aggattagat accctggtaa                                      210


<210> SEQ ID NO 2
<211> LENGTH: 184
<212> TYPE: DNA
<213> ORGANISM: Artificial Sequence
<220> FEATURE:
<223> OTHER INFORMATION: Synthetic Polynucleotide

<400> SEQUENCE: 2

ctaaccgtgg aggtcattgg aaactggtca acttgagtgc agaagaggga agtggaattc      60

catgtgtagc ggtgaaatgc gtagagatat ggaggaacac cagtggcgaa ggcggcttcc     120

tggtctgtaa ctgacactga ggcgcgaaag cgtgggggc aaacaggatt agatcccccg      180

gtaa                                                                  184


<210> SEQ ID NO 3
<211> LENGTH: 196
<212> TYPE: DNA
<213> ORGANISM: Artificial Sequence
<220> FEATURE:
<223> OTHER INFORMATION: Synthetic Polynucleotide
```

<400> SEQUENCE: 3
atgaaagccg gggctcaacc ccggtactgc tttggaaact gtttgacttg agtgcttgag 60
aggtaagtgg aattcctagt gtagcgggaa atgtttagat attaggagga caccagtggc 120
gaaggcggct tactggactg taactgacgt tgtggctcga tttgtgggga gcaaacagga 180
ttatatcccc tggtaa 196

<210> SEQ ID NO 4
<211> LENGTH: 211
<212> TYPE: DNA
<213> ORGANISM: Artificial Sequence
<220> FEATURE:
<223> OTHER INFORMATION: Synthetic Polynucleotide

<400> SEQUENCE: 4
cggaaggtct gatgtgaagg ttggggctta ccccggactg cattggaaac tgtttttcta 60
gagtgcccga gaggtaagcg gaattcctag tgtagcggtg aaatgcttta gatattagga 120
ggaacaccag tggcgaaggc ggcttactgg acggtaactg acgttgaggc tcgaaagcgt 180
ggggagcaaa caggattaga taccctggta a 211

<210> SEQ ID NO 5
<211> LENGTH: 207
<212> TYPE: DNA
<213> ORGANISM: Artificial Sequence
<220> FEATURE:
<223> OTHER INFORMATION: Synthetic Polynucleotide

<400> SEQUENCE: 5
cgatgtctga gtgaaggctg gggcttaccc caggactgca ttggaactgt ttttctagag 60
tgccggagag gtaagcggaa ttcctagtgt agcggtgaaa tgcgtagata ttaggaggaa 120
caccagtggc gaaggcggct tactggacgg taactgacgt tgaggctcga aagcgtgggg 180
agcaaacagg attagatacc ctggtaa 207

<210> SEQ ID NO 6
<211> LENGTH: 179
<212> TYPE: DNA
<213> ORGANISM: Artificial Sequence
<220> FEATURE:
<223> OTHER INFORMATION: Synthetic Polynucleotide

<400> SEQUENCE: 6
ttaaccaaga agtgcattgg aactgtcaga cttgggggaa aaaaagacag tgcaactcca 60
tgtgtagcgg tggaatgctc catatatatg gaagaacacc agtggcgaag gcggctgtct 120
ggtctgcaac tgacgctgag gctcgaattc atgggtaaga aagtattagt cccttgtaa 179

<210> SEQ ID NO 7
<211> LENGTH: 214
<212> TYPE: DNA
<213> ORGANISM: Artificial Sequence
<220> FEATURE:
<223> OTHER INFORMATION: Synthetic Polynucleotide

<400> SEQUENCE: 7
acccgcttgg tctgaggtga ggctggggct taaccccagg actgcattgg aaactgttgt 60
tctagagtgc cggagaggta agcggaattc ctagtgtagc ggtgaaatgc gtagatatta 120
ggaggaacac cagtggcgaa ggcggcttac tggacggtaa ctgacgttga ggctcgaaag 180
cgtggggagc aaacaggatt agataccctg gtaa 214

<210> SEQ ID NO 8
<211> LENGTH: 196
<212> TYPE: DNA
<213> ORGANISM: Artificial Sequence
<220> FEATURE:
<223> OTHER INFORMATION: Synthetic Polynucleotide

<400> SEQUENCE: 8
taggctgggg cttaacccca ggactgcatt ggaaactgtt tttctagagt gccggagagg 60
taagcggaat tcctagtgta gcggtgaaat gcgtagatat taggaggaac accagtggcg 120
aaggcggctt actggacggt aactgacgtt gaggctcgaa agcgtgggga gcaaacagga 180
ttagataccc tggtaa 196

<210> SEQ ID NO 9
<211> LENGTH: 297
<212> TYPE: DNA
<213> ORGANISM: Artificial Sequence
<220> FEATURE:
<223> OTHER INFORMATION: Synthetic Polynucleotide

<400> SEQUENCE: 9
ttgcattgga cactatgtca gctgagtgtc ggagaggtaa gtggaattcc tagtgtagcg 60
gtgaaatgcg tagatattag gaggaacacc agtggcgaag gcggcttact gcacgttttc 120
tgacgttgag gctcgaaatc gtggggagca aacaaaaata gataccctgg tagtccacgc 180
cgtaaacgat gcatactagg tgtcgggtgg caaagccatt cggtgccgca gcaaacgcaa 240
taagtatgcc acctggggag tacgttcgca agaatgaaac tcaaataaat tgacgga 297

<210> SEQ ID NO 10
<211> LENGTH: 209
<212> TYPE: DNA
<213> ORGANISM: Artificial Sequence
<220> FEATURE:
<223> OTHER INFORMATION: Synthetic Polynucleotide

<400> SEQUENCE: 10
cccgtcgtag atgtgaactg gggctcacc tccagcctgc atttgaaact gtagttcttg 60
agtgctggag aggcaatcgg aattccgtgt gtagcggtga aatgcgtaga tatacggagg 120
aacaccagtg gcgaaggcgg attgctggac agtaactgac gctgaggcgc gaaagcgtgg 180
ggagcaaaca ggattagata ccctcataa 209

<210> SEQ ID NO 11
<211> LENGTH: 401
<212> TYPE: DNA
<213> ORGANISM: Artificial Sequence
<220> FEATURE:
<223> OTHER INFORMATION: Synthetic Polynucleotide

<400> SEQUENCE: 11
acctgatgca gcgacgccgc gtgagtgaag aagtatttcg gtatgtaaag ctctatcagc 60
agggaagaaa aaagacggta cctgactaag aagccccggc taactacgtg ccagcagccg 120
cggtaatacg tagggggcaa gcgttatccg gaattactgg gtgtaaaggg tgcgtaggtg 180
gcatggtaag tcagaagtga aagcccgggg cttaaccccg ggactgcttt tgaaactgtc 240
atgctggagt gcaggagagg taagcggaat tcctagtgta gcggtgaaat gcgtagatat 300
taggaggaac accagtggcg aaggcggctt actggactgt cactgacact gatgcacgaa 360
agcgtgggga gcaaacagga ttagataccc tggaagtcca t 401

<210> SEQ ID NO 12
<211> LENGTH: 355
<212> TYPE: DNA
<213> ORGANISM: Artificial Sequence
<220> FEATURE:
<223> OTHER INFORMATION: Synthetic Polynucleotide

<400> SEQUENCE: 12
atgggagcgt agatggcgac tgggccatat gtgacagccc tggtctcaac cccttaactg 60
catttggaac tgagtggctg gagtgtcgga gaggcaggcg gaattcctag tgtagcggtg 120
aaatgcgtag atattaggag gaacaccagt ggcgaaggcg gcctgctgga cgatgactga 180
cgttgaggct cgaaagcgtg gggagcaaac aggattagat accctggtag tccacgccgt 240
aaacgatgac tactaggtgt cgggtggcaa ggacattcgg tgccgcagca aacgcaataa 300
gtagtccacc tggggagtac gttcgcaaga atgaaactca aaggaaattg acgga 355

<210> SEQ ID NO 13
<211> LENGTH: 197
<212> TYPE: DNA
<213> ORGANISM: Artificial Sequence
<220> FEATURE:
<223> OTHER INFORMATION: Synthetic Polynucleotide

<400> SEQUENCE: 13
cgcagcggag tgtatcctag gctcacctgg ctgctttcga actggttttc tagatcgtgt 60
agagggggag attcctggtg tagcgtgaaa tgcgtagata tctggaggaa caccagtggc 120
gaaggcggcc tcctggacgg caactgacgt tgaggctcga aagtgtgggg agcaaacagg 180
attagatacc ctggtaa 197

<210> SEQ ID NO 14
<211> LENGTH: 1522
<212> TYPE: DNA
<213> ORGANISM: Artificial Sequence
<220> FEATURE:
<223> OTHER INFORMATION: Synthetic Polynucleotide

<400> SEQUENCE: 14
tcaaagagtt tgatcctggc tcaggacgaa cgctggcggc gcgcctaaca catgcaagtc 60
gaacggagct tacgttttga agttttcgga tggacgaatg taagcttagt ggcggacggg 120
tgagtaacac gtgagcaacc tgcctttcag agggggataa cagccggaaa cggctgctaa 180
taccgcatga tgttgcgggg gcacatgccc ctgcaaccaa aggagcaatc cgctgaaaga 240
tgggctcgcg tccgattagc cagttggcgg ggtaacggcc caccaaagcg acgatcggta 300
gccggactga gaggttgaac ggccacattg ggactgagac acggcccaga ctcctacggg 360
aggcagcagt gggggatatt gcacaatggg cgaaagcctg atgcagcgac gccgcgtgag 420
ggaagacggt cttcggattg taaacctctg tctttgggga agaaaatgac ggtacccaaa 480
gaggaagctc cggctaacta cgtgccagca gccgcggtaa tacgtaggga gcaagcgttg 540
tccggaatta ctgggtgtaa agggagcgta ggcgggatgg caagtagaat gttaaatcca 600
tcggctcaac cggtggctgc gttctaaact gccgttcttg agtgaagtag aggcaggcgg 660
aattcctagt gtagcggtga aatgcgtaga tattaggagg aacaccagtg gcgaaggcgg 720
cctgctgggc tttaactgac gctgaggctc gaaagcgtgg ggagcaaaca ggattagata 780
ccctggtagt ccacgccgta aacgatgatt actaggtgtg gggggactga ccccttccgt 840
gccgcagtta acacaataag taatccacct ggggagtacg gccgcaaggt tgaaactcaa 900
aggaattgac gggggcccgc acaagcagtg gagtatgtgg tttaattcga agcaacgcga 960
agaaccttac caggtcttga catcggatgc atagcctaga gataggtgaa gcccttcggg 1020
gcatccagac aggtggtgca tggttgtcgt cagctcgtgt cgtgagatgt tgggttaagt 1080
cccgcaacga gcgcaaccct tattattagt tgctacgcaa gagcactcta atgagactgc 1140
cgttgacaaa acggaggaag gtggggatga cgtcaaatca tcatgcccct tatgacctgg 1200
gctacacacg tactacaatg gcactaaaac agagggcggc gacaccgcga ggtgaagcga 1260
atcccgaaaa agtgtctcag ttcagattgc aggctgcaac ccgcctgcat gaagtcggaa 1320
ttgctagtaa tcgcggatca gcatgccgcg gtgaatacgt tcccgggcct tgtacacacc 1380
gcccgtcaca ccatgggagt cggtaacacc cgaagccagt agcctaaccg caaggggggc 1440
gctgtcgaag gtgggattga tgactggggt gaagtcgtaa caaggtagcc gtatcggaag 1500
gtgcggctgg atcacctcct tt 1522

<210> SEQ ID NO 15
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 15
tacgagagtt tgatcctggc tcaggatgaa cgctggcggc gtgcctaaca catgcaagtc 60
gagcgaagcg ctgttttcag aatcttcgga ggaagaggac agtgactgag cggcggacgg 120
gtgagtaacg cgtgggcaac ctgcctcata caggggggata acagttagaa atgactgcta 180
ataccgcata agcgcacagg accgcatggt gtagtgtgaa aaactccggt ggtatgagat 240
ggacccgcgt ctgattaggt agttggtggg gtaaaggcct accaagccga cgatcagtag 300
ccgacctgag agggtgaccg gccacattgg gactgagaca cggcccaaac tcctacggga 360
ggcagcagtg gggaatattg cacaatgggg gaaaccctga tgcagcgacg ccgcgtgaag 420
gaagaagtat ttcggtatgt aaacttctat cagcagggaa gaagatgacg gtacctgagt 480
aagaagcacc ggctaaatac gtgccagcag ccgcggtaat acgtatggtg caagcgttat 540
ccggatttac tgggtgtaaa gggagcgtag acggataggc aagtctggag tgaaaaccca 600
gggctcaacc ctgggactgc tttggaaact gcagatctgg agtgccggag aggtaagcgg 660
aattcctagt gtagcggtga aatgcgtaga tattaggagg aacaccagtg gcgaaggcgg 720
cttactggac ggtgactgac gttgaggctc gaaagcgtgg ggagcaaaca ggattagata 780
ccctggtagt ccacgccgta aacgatgact actaggtgtc ggtgtgcaaa gcacatcggt 840
gccgcagcaa acgcaataag tagtccacct ggggagtacg ttcgcaagaa tgaaactcaa 900
aggaattgac ggggacccgc acaagcggtg gagcatgtgg tttaattcga agcaacgcga 960
agaaccttac ctggtcttga catccggatg acgggcgagt aatgtcgccg tcccttcggg 1020
gcatccgaga caggtggtgc atggttgtcg tcagctcgtg tcgtgagatg ttgggttaag 1080
tcccgcaacg agcgcaaccc ttatcttcag tagccagcat ataaggtggg cactctggag 1140
agactgccag ggagaacctg gaggaaggtg gggatgacgt caaatcatca tgccccttat 1200
ggccagggct acacacgtgc tacaatggcg taaacaaagg gaagcgagag ggtgacctgg 1260
agcgaatccc aaaaataacg tctcagttcg gattgtagtc tgcaactcga ctacatgaag 1320
ctggaatcgc tagtaatcgc ggatcagcat gccgcggtga atacgttccc gggtcttgta 1380
cacaccgccc gtcacaccat gggagtcagt aacgcccgaa gccagtgacc caaccttaga 1440
ggagggagct gtcgaaggcg ggacggataa ctggggtgaa gtcgtaacaa ggtagccgta 1500
tcggaaggtg cggctggatc acctcctttt 1529

<210> SEQ ID NO 16
<211> LENGTH: 1527
<212> TYPE: DNA
<213> ORGANISM: Artificial Sequence
<220> FEATURE:
<223> OTHER INFORMATION: Synthetic Polynucleotide

<400> SEQUENCE: 16
atgagagttt gatcctggct caggatgaac gctggcggcg tgcctaacac atgcaagtcg 60
aacgaagcga tttaacggaa gttttcggat ggaagttgaa ttgactgagt ggcggacggg 120
tgagtaacgc gtgggtaacc tgccttgtac tgggggacaa cagttagaaa tgactgctaa 180
taccgcataa gcgcacagta tcgcatgata cagtgtgaaa aactccggtg gtacaagatg 240
gacccgcgtc tgattagcta gttggtaagg taacggctta ccaaggcgac gatcagtagc 300
cgacctgaga gggtgaccgg ccacattggg actgagacac ggcccaaact cctacgggag 360
gcagcagtgg ggaatattgc acaatgggcg aaagcctgat gcagcgacgc cgcgtgagtg 420
aagaagtatt tcggtatgta aagctctatc agcagggaag aaaatgacgg tacctgacta 480
agaagccccg gctaactacg tgccagcagc cgcggtaata cgtagggggc aagcgttatc 540
cggatttact gggtgtaaag ggagcgtaga cggtaaagca agtctgaagt gaaagcccgc 600
ggctcaactg cgggactgct ttggaaactg tttaactgga gtgtcggaga ggtaagtgga 660
attcctagtg tagcggtgaa atgcgtagat attaggagga acaccagtgg cgaaggcgac 720
ttactggacg ataactgacg ttgaggctcg aaagcgtggg gagcaaacag gattagatac 780
cctggtagtc cacgccgtaa acgatgaata ctaggtgttg gggagcaaag ctcttcggtg 840
ccgtcgcaaa cgcagtaagt attccacctg gggagtacgt tcgcaagaat gaaactcaaa 900
ggaattgacg gggacccgca caagcggtgg agcatgtggt ttaattcgaa gcaacgcgaa 960
gaaccttacc aggtcttgac atcgatccga cgggggagta acgtcccctt cccttcgggg 1020
cggagaagac aggtggtgca tggttgtcgt cagctcgtgt cgtgagatgt tgggttaagt 1080
cccgcaacga gcgcaaccct tattctaagt agccagcggt tcggccggga actcttggga 1140
gactgccagg gataacctgg aggaaggtgg ggatgacgtc aaatcatcat gccccttatg 1200
atctgggcta cacacgtgct acaatggcgt aaacaaagag aagcaagacc gcgaggtgga 1260
gcaaatctca aaaataacgt ctcagttcgg actgcaggct gcaactcgcc tgcacgaagc 1320
tggaatcgct agtaatcgcg aatcagaatg tcgcggtgaa tacgttcccg ggtcttgtac 1380
acaccgcccg tcacaccatg ggagtcagta acgcccgaag tcagtgaccc aaccgcaagg 1440
agggagctgc cgaaggcggg accgataact ggggtgaagt cgtaacaagg tagccgtatc 1500
ggaaggtgcg gctggatcac ctcctttt 1527

<210> SEQ ID NO 17
<211> LENGTH: 1530
<212> TYPE: DNA
<213> ORGANISM: Artificial Sequence
<220> FEATURE:
<223> OTHER INFORMATION: Synthetic Polynucleotide

<400> SEQUENCE: 17
atgagagttt gatcctggct caggatgaac gctggcggcg tgcctaacac atgcaagtcg 60
aacgaagcaa ttaaaatgaa gttttcggat ggatttttga ttgactgagt ggcggacggg 120
tgagtaacgc gtggataacc tgcctcacac tgggggataa cagttagaaa tgactgctaa 180
taccgcataa gcgcacagta ccgcatggta cggtgtgaaa aactccggtg gtgtgagatg 240
gatccgcgtc tgattagcca gttggcgggg taacggccca ccaaagcgac gatcagtagc 300
cgacctgaga gggtgaccgg ccacattggg actgagacac ggcccaaact cctacgggag 360
gcagcagtgg ggaatattgc acaatgggcg aaagcctgat gcagcgacgc cgcgtgagtg 420
aagaagtatt tcggtatgta aagctctatc agcagggaag aaaatgacgg tacctgacta 480
agaagccccg gctaactacg tgccagcagc cgcggtaata cgtagggggc aagcgttatc 540
cggatttact gggtgtaaag ggagcgtaga cggcgaagca agtctgaagt gaaaacccag 600
ggctcaaccc tgggactgct ttggaaactg ttttgctaga gtgtcggaga ggtaagtgga 660
attcctagtg tagcggtgaa atgcgtagat attaggagga acaccagtgg cgaaggcggc 720
ttactggacg ataactgacg ttgaggctcg aaagcgtggg gagcaaacag gattagatac 780
cctggtagtc cacgccgtaa acgatgaatg ctaggtgttg gggggcaaag cccttcggtg 840
ccgtcgcaaa cgcagtaagc attccacctg gggagtacgt tcgcaagaat gaaactcaaa 900
ggaattgacg gggacccgca caagcggtgg agcatgtggt ttaattcgaa gcaacgcgaa 960
gaaccttacc aagtcttgac atcctcttga ccggcgtgta acggcgcctt cccttcgggg 1020
caagagagac aggtggtgca tggttgtcgt cagctcgtgt cgtgagatgt tgggttaagt 1080
cccgcaacga gcgcaaccct tatccttagt agccagcagg taaagctggg cactctaggg 1140
agactgccag ggataacctg gaggaaggtg gggatgacgt caaatcatca tgccccttat 1200
gatttgggct acacacgtgc tacaatggcg taaacaaagg gaagcaagac agtgatgtgg 1260
agcaaatccc aaaaataacg tcccagttcg gactgtagtc tgcaacccga ctacacgaag 1320
ctggaatcgc tagtaatcgc gaatcagaat gtcgcggtga atacgttccc gggtcttgta 1380
cacaccgccc gtcacaccat gggagtcagc aacgcccgaa gtcagtgacc caactcgcaa 1440
gagagggagc tgccgaaggc ggggcaggta actggggtga agtcgtaaca aggtagccgt 1500
atcggaaggt gcggctggat cacctccttt 1530

<210> SEQ ID NO 18
<211> LENGTH: 1528
<212> TYPE: DNA
<213> ORGANISM: Artificial Sequence
<220> FEATURE:
<223> OTHER INFORMATION: Synthetic Polynucleotide

<400> SEQUENCE: 18
aacgagagtt tgatcctggc tcaggatgaa cgctggcggc gtgcttaaca catgcaagtc 60
gagcgaagca ctttggaaga ttcttcggat gaagactttt gtgactgagc ggcggacggg 120
tgagtaacgc gtgggtaacc tgcctcatac agggggataa cagttagaaa tgactgctaa 180
taccgcataa gaccacggta ccgcatggta cagtggtaaa aactccggtg gtatgagatg 240
gacccgcgtc tgattaggta gttggtgggg taacggccta ccaagccgac gatcagtagc 300
cgacctgaga gggtgaccgg ccacattggg actgagacac ggcccagact cctacgggag 360
gcagcagtgg ggaatattgc acaatggagg aaactctgat gcagcgacgc cgcgtgaagg 420
atgaagtatt tcggtatgta aacttctatc agcagggaag aaaatgacgg tacctgacta 480
agaagccccg gctaactacg tgccagcagc cgcggtaata cgtagggggc aagcgttatc 540
cggatttact gggtgtaaag ggagcgtaga cggcacggca agccagatgt gaaagcccgg 600
ggctcaaccc cgggactgca tttggaactg ctgagctaga gtgtcggaga ggcaagtgga 660
attcctagtg tagcggtgaa atgcgtagat attaggagga acaccagtgg cgaaggcggc 720
ttgctggacg atgactgacg ttgaggctcg aaagcgtggg gagcaaacag gattagatac 780
cctggtagtc cacgccgtaa acgatgactg ctaggtgtcg ggtggcaaag ccattcggtg 840
ccgcagctaa cgcaataagc agtccacctg gggagtacgt tcgcaagaat gaaactcaaa 900
ggaattgacg gggacccgca caagcggtgg agcatgtggt ttaattcgaa gcaacgcgaa 960
gaaccttacc tgatcttgac atcccgatga ccgcttcgta atggaagctt ttcttcggaa 1020
catcggtgac aggtggtgca tggttgtcgt cagctcgtgt cgtgagatgt tgggttaagt 1080
cccgcaacga gcgcaacccc tatcttcagt agccagcagg ttaagctggg cactctggag 1140
agactgccag ggataacctg gaggaaggtg gggatgacgt caaatcatca tgccccttat 1200
gaccagggct acacacgtgc tacaatggcg taaacaaaga gaagcgaact cgcgagggta 1260
agcaaatctc aaaaataacg tctcagttcg gattgtagtc tgcaactcga ctacatgaag 1320
ctggaatcgc tagtaatcgc agatcagaat gctgcggtga atacgttccc gggtcttgta 1380
cacaccgccc gtcacaccat gggagtcagt aacgcccgaa gtcagtgacc caaccgtaag 1440
gagggagctg ccgaaggtgg gaccgataac tggggtgaag tcgtaacaag gtagccgtat 1500
cggaaggtgc ggctggatca cctccttt 1528

<210> SEQ ID NO 19
<211> LENGTH: 1531
<212> TYPE: DNA
<213> ORGANISM: Artificial Sequence
<220> FEATURE:
<223> OTHER INFORMATION: Synthetic Polynucleotide

<400> SEQUENCE: 19
atcagagagt ttgatcctgg ctcaggatga acgctggcgg cgtgcttaac acatgcaagt 60
cgagcgaagc acttaagtgg atctcttcgg attgaaactt atttgactga gcggcggacg 120
ggtgagtaac gcgtgggtaa cctgcctcat acagggggat aacagttaga aatggctgct 180
aataccgcat aagcgcacag gaccgcatgg tctggtgtga aaaactccgg tggtatgaga 240
tggacccgcg tctgattagc tagttggagg ggtaacggcc caccaaggcg acgatcagta 300
gccggcctga gagggtgaac ggccacattg ggactgagac acggcccaga ctcctacggg 360
aggcagcagt ggggaatatt gcacaatggg ggaaaccctg atgcagcgac gccgcgtgaa 420
ggaagaagta tctcggtatg taaacttcta tcagcaggga agaaaatgac ggtacctgac 480
taagaagccc cggctaacta cgtgccagca gccgcggtaa tacgtagggg gcaagcgtta 540
tccggattta ctgggtgtaa agggagcgta gacggaagag caagtctgat gtgaaaggct 600
ggggcttaac cccaggactg cattggaaac tgtttttcta gagtgccgga gaggtaagcg 660
gaattcctag tgtagcggtg aaatgcgtag atattaggag gaacaccagt ggcgaaggcg 720
gcttactgga cggtaactga cgttgaggct cgaaagcgtg gggagcaaac aggattagat 780
accctggtag tccacgccgt aaacgatgaa tactaggtgt cgggtggcaa agccattcgg 840
tgccgcagca aacgcaataa gtattccacc tggggagtac gttcgcaaga atgaaactca 900
aaggaattga cggggacccg cacaagcggt ggagcatgtg gtttaattcg aagcaacgcg 960
aagaacctta ccaagtcttg acatccctct gaccggcccg taacggggcc ttcccttcgg 1020

```
ggcagaggag acaggtggtg catggttgtc gtcagctcgt gtcgtgagat gttgggttaa   1080

gtcccgcaac gagcgcaacc cctatcctta gtagccagca ggtgaagctg ggcactctag   1140

ggagactgcc ggggataacc cggaggaagg cggggacgac gtcaaatcat catgcccctt   1200

atgatttggg ctacacacgt gctacaatgg cgtaaacaaa gggaagcgag acagcgatgt   1260

tgagcaaatc ccaaaaataa cgtcccagtt cggactgcag tctgcaactc gactgcacga   1320

agctggaatc gctagtaatc gcgaatcaga atgtcgcggt gaatacgttc ccgggtcttg   1380

tacacaccgc ccgtcacacc atgggagtca gtaacgcccg aagtcagtga cccaacctta   1440

caggagggag ctgccgaagg cgggaccgat aactggggtg aagtcgtaac aaggtagccg   1500

tatcggaagg tgcggctgga tcacctcctt t                                  1531


<210> SEQ ID NO 20
<211> LENGTH: 1528
<212> TYPE: DNA
<213> ORGANISM: Artificial Sequence
<220> FEATURE:
<223> OTHER INFORMATION: Synthetic Polynucleotide

<400> SEQUENCE: 20

aacgagagtt tgatcctggc tcaggatgaa cgctggcggc gtgcttaaca catgcaagtc     60

gagcgaagca ctttggaaga ttcttcggat gatttccttt gtgactgagc ggcggacggg    120

tgagtaacgc gtgggtaacc tgcctcatac aggggggataa cagttagaaa tgactgctaa    180

taccgcataa gaccacggta ccgcatggta cagtggtaaa aactccggtg gtatgagatg    240

gacccgcgtc tgattaggta gttggtgggg taacggccta ccaagccgac gatcagtagc    300

cgacctgaga gggtgaccgg ccacattggg actgagacac ggcccagact cctacgggag    360

gcagcagtgg ggaatattgc acaatggagg aaactctgat gcagcgacgc cgcgtgaagg    420

atgaagtatt tcggtatgta aacttctatc agcagggaag aaaatgacgg tacctgacta    480

agaagccccg gctaactacg tgccagcagc cgcggtaata cgtagggggc aagcgttatc    540

cggatttact gggtgtaaag ggagcgtaga cggcacggca agccagatgt gaaagcccgg    600

ggctcaaccc cgggactgca tttggaactg ctgagctaga gtgtcggaga ggcaagtgga    660

attcctagtg tagcggtgaa atgcgtagat attaggagga acaccagtgg cgaaggcggc    720

ttgctggacg atgactgacg ttgaggctcg aaagcgtggg gagcaaacag gattagatac    780

cctggtagtc cacgccgtaa acgatgactg ctaggtgtcg ggtggcaaag ccattcggtg    840

ccgcagctaa cgcaataagc agtccacctg gggagtacgt tcgcaagaat gaaactcaaa    900

ggaattgacg gggacccgca caagcggtgg agcatgtggt ttaattcgaa gcaacgcgaa    960

gaaccttacc tgatcttgac atcccgatga ccgcttcgta atggaagctt ttcttcggaa   1020

catcggtgac aggtggtgca tggttgtcgt cagctcgtgt cgtgagatgt tgggttaagt   1080

cccgcaacga gcgcaacccc tatcttcagt agccagcagg ttaagctggg cactctggag   1140

agactgccag ggataacctg gaggaaggtg gggatgacgt caaatcatca tgccccttat   1200

gaccagggct acacacgtgc tacaatggcg taaacaaaga gaagcgaact cgcgagggta   1260

agcaaatctc aaaaataacg tctcagttcg gattgtagtc tgcaactcga ctacatgaag   1320

ctggaatcgc tagtaatcgc agatcagaat gctgcggtga atacgttccc gggtcttgta   1380

cacaccgccc gtcacaccat gggagtcagt aacgcccgaa gtcagtgacc caaccgtaag   1440

gagggagctg ccgaaggtgg gaccgataac tggggtgaag tcgtaacaag gtagccgtat   1500
```

cggaaggtgc ggctggatca cctccttt 1528

<210> SEQ ID NO 21
<211> LENGTH: 1537
<212> TYPE: DNA
<213> ORGANISM: Artificial Sequence
<220> FEATURE:
<223> OTHER INFORMATION: Synthetic Polynucleotide

<400> SEQUENCE: 21
atggagagtt tgatcctggc tcaggatgaa cgctggcggc atgcctaata catgcaagtc 60
gaacgaagtt tcgaggaagc ttgcttccaa agagacttag tggcgaacgg gtgagtaaca 120
cgtaggtaac ctgcccatgt gtccgggata actgctggaa acggtagcta aaaccggata 180
ggtatacaga gcgcatgctc agtatattaa agcgcccatc aaggcgtgaa catggatgga 240
cctgcggcgc attagctagt tggtgaggta acggcccacc aaggcgatga tgcgtagccg 300
gcctgagagg gtaaacggcc acattgggac tgagacacgg cccaaactcc tacgggaggc 360
agcagtaggg aatttttcgtc aatgggggaa accctgaacg agcaatgccg cgtgagtgaa 420
gaaggtcttc ggatcgtaaa gctctgttgt aagtgaagaa cggctcatag aggaaatgct 480
atgggagtga cggtagctta ccagaaagcc acggctaact acgtgccagc agccgcggta 540
atacgtaggt ggcaagcgtt atccggaatc attgggcgta aagggtgcgt aggtggcgta 600
ctaagtctgt agtaaaaggc aatggctcaa ccattgtaag ctatggaaac tggtatgctg 660
gagtgcagaa gagggcgatg gaattccatg tgtagcggta aaatgcgtag atatatggag 720
gaacaccagt ggcgaaggcg gtcgcctggt ctgtaactga cactgaggca cgaaagcgtg 780
gggagcaaat aggattagat accctagtag tccacgccgt aaacgatgag aactaagtgt 840
tggaggaatt cagtgctgca gttaacgcaa taagttctcc gcctggggag tatgcacgca 900
agtgtgaaac tcaaaggaat tgacgggggc ccgcacaagc ggtggagtat gtggtttaat 960
tcgaagcaac gcgaagaacc ttaccaggcc ttgacatgga aacaaatacc ctagagatag 1020 gggataatt atggatcaca caggtggtgc atggttgtcg tcagctcgtg tcgtgagatg 1080
ttgggttaag tcccgcaacg agcgcaaccc ttgtcgcatg ttaccagcat caagttgggg 1140
actcatgcga gactgccggt gacaaaccgg aggaaggtgg ggatgacgtc aaatcatcat 1200
gccccttatg gcctgggcta cacacgtact acaatggcgg ccacaaagag cagcgacaca 1260
gtgatgtgaa gcgaatctca taaaggtcgt ctcagttcgg attgaagtct gcaactcgac 1320
ttcatgaagt cggaatcgct agtaatcgca gatcagcatg ctgcggtgaa tacgttctcg 1380
ggccttgtac acaccgcccg tcaaaccatg ggagtcagta atacccgaag ccggtggcat 1440
aaccgtaagg agtgagccgt cgaaggtagg accgatgact ggggttaagt cgtaacaagg 1500
tatccctacg ggaacgtggg gatggatcac ctccttt 1537

<210> SEQ ID NO 22
<211> LENGTH: 476
<212> TYPE: DNA
<213> ORGANISM: Artificial Sequence
<220> FEATURE:
<223> OTHER INFORMATION: Synthetic Polynucleotide

<400> SEQUENCE: 22
agtaacgcgt gggtaacctg cctcatacag gggataaca gttagaaatg actgctaata 60
ccgcataaga ccacggtacc gcatggtaca gtggtaaaaa ctccggtggt atgagatgga 120
cccgcgtctg attaggtagt tggtggggta acggcctacc aagccgacga tcagtagccg 180
acctgagagg gtgaccggcc acattgggac tgagacacgg cccagactcc tacgggaggc 240
agcagtgggg aatattgcac aatggaggaa actctgatgc agcgacgccg cgtgaaggat 300
gaagtatttc ggtatgtaaa cttctatcag cagggaagaa aatgacggta cctgactaag 360
aagccccggc taactacgtg ccagcagccg cggtaatacg tagggggcaa gcgttatccg 420
gatttactgg gtgtaaaggg agcgtagacg gcacggcaag ccagatgtga aagccc 476

<210> SEQ ID NO 23
<211> LENGTH: 354
<212> TYPE: DNA
<213> ORGANISM: Artificial Sequence
<220> FEATURE:
<223> OTHER INFORMATION: Synthetic Polynucleotide

<400> SEQUENCE: 23
caggctggag tgcaggagag gtaagcggaa ttcctagtgt agcggtgaaa tgcgtagata 60
ttaggaggaa caccagtggc gaaggcggct tactggactg taactgacgt tgaggctcga 120
aagcgtgggg agcaaacagg attagatacc ctggtagtcc acgcggtaaa cgatgattgc 180
taggtgtagg tgggtatgga cccatcggtg ccgcagctaa cgcaataagc aatccacctg 240
gggagtacgt tcgcaagaat gaaactcaaa ggaattgacg gggacccgca caagcggtgg 300
agcatgtggt ttaattcgaa gcaacgcgaa gaaccttacc aagtcttgac atcc 354

<210> SEQ ID NO 24
<211> LENGTH: 190
<212> TYPE: DNA
<213> ORGANISM: Artificial Sequence
<220> FEATURE:
<223> OTHER INFORMATION: Synthetic Polynucleotide

<400> SEQUENCE: 24
ccggggctca ccccgggact gcatttggaa ctgctgagct agagtgtcgg agaggcaagt 60
ggaattccta gtgtagcggt gaaatgcgta gatattagga ggaacaccag tggcgaaggc 120
ggcttgctgg acgatgactg acgttgaggc tcgaaagcgt ggggagcaaa caggattaga 180
taccctggta 190

<210> SEQ ID NO 25
<211> LENGTH: 190
<212> TYPE: DNA
<213> ORGANISM: Artificial Sequence
<220> FEATURE:
<223> OTHER INFORMATION: Synthetic Polynucleotide

<400> SEQUENCE: 25
agggtcaacc cctggactgc attggaaact gtcaggctgg agtgccggag aggtaagcgg 60
aattcctagt gtagcggtga aatgcgtaga tattaggagg aacaccagtg gcgaaggcgg 120
cttactggac ggtaactgac gttgatgctc gaaagcgtgg ggagcaaaca ggattagata 180
acctggtaaa 190

<210> SEQ ID NO 26
<211> LENGTH: 209
<212> TYPE: DNA
<213> ORGANISM: Artificial Sequence
<220> FEATURE:
<223> OTHER INFORMATION: Synthetic Polynucleotide

<400> SEQUENCE: 26
gggaagtcgg tcttaagtgc ggggcttaac cccgtgaggg gaccgaaact gtgaagctcg 60
agtgtcggag aggaaagcgg aattcctagt gtagcggtga aatgcgtaga tattaggagg 120
aacaccagtg gcgaaagcgg ctttctggac gacaactgac gctgaggcgc gaaagccagg 180
ggagcaaacg ggattagata ccccagtaa 209

<210> SEQ ID NO 27
<211> LENGTH: 203
<212> TYPE: DNA
<213> ORGANISM: Artificial Sequence
<220> FEATURE:
<223> OTHER INFORMATION: Synthetic Polynucleotide

<400> SEQUENCE: 27
tagtctgagt gatgcggggc ttaaccccgt atggcgttgg atactggaag tcttgagtgc 60
aggagaggaa aggggaattc ccagtgtagc ggtgaaatgc gtagatattg ggaggaacac 120
cagtggcgaa ggcgcctttc tggactgtgt ctgacgctga gatgcgaaag ccagggtagc 180
aaacgggatt agataccacg gta 203

<210> SEQ ID NO 28
<211> LENGTH: 207
<212> TYPE: DNA
<213> ORGANISM: Artificial Sequence
<220> FEATURE:
<223> OTHER INFORMATION: Synthetic Polynucleotide

<400> SEQUENCE: 28
gatagtcggt cttaagtgcg gggcttaccc cgtgagggga ccgaaactgt gaagctcgag 60
tgtcggagag gaaagcggaa ttcctagtgt agcggtgaaa tgcgtagata ttaggaggaa 120
caccagtggc gaaagcggct ttctggacga caactgacgc tgaggcgcga aagccagggg 180
agcaaacggg attagatacc acggtaa 207

<210> SEQ ID NO 29
<211> LENGTH: 424
<212> TYPE: DNA
<213> ORGANISM: Artificial Sequence
<220> FEATURE:
<223> OTHER INFORMATION: Synthetic Polynucleotide

<400> SEQUENCE: 29
cgtttgctcc acgctttcga gcctcacgtc agttaccgtc cagtaagccg ccttcgccac 60
tggtgttcct cctaatatct acgcatttca ccgctacact aggaattccg cttacctctc 120
cggtactcta gattgacagt ttccaatgca gtcccggggt tgagccccgg gttttcacat 180
cagacttgcc actccgtcta cgctcccttt acacccagta aatccggata acgcttgcac 240
catacgtatt accgcggctg ctggcacgta tttagccggt gcttcttagt caggtaccgt 300
cattttcttc cctgctgata gagctttaca taccgaaata cttcatcgct cacgcggcgt 360
cgctgcatca gggtttcccc cattgtgcaa tattccccac tgctgcctcc cgtaggagtt 420
tgga 424

<210> SEQ ID NO 30
<211> LENGTH: 441
<212> TYPE: DNA
<213> ORGANISM: Artificial Sequence
<220> FEATURE:
<223> OTHER INFORMATION: Synthetic Polynucleotide

<400> SEQUENCE: 30

```
tgtcacactt tcgagcatca gcgtcagtta cagtccagta agctgccttc gcaatcggag     60

ttcttcgtga tatctaagca tttcaccgct acaccacgaa ttccgcctac ctctactgca    120

ctcaagacga ccagtatcaa ctgcaatttt acggttgagc cgcaaacttt cacagctgac    180

ttaatagtcc gcctacgctc cctttaaacc caataaatcc ggataacgct tggatcctcc    240

gtattaccgc ggctgctggc acggagttag ccgatcctta ttcgtatggt acatacaaaa    300

agccacacgt ggctcacttt attcccatat aaaagaagtt tacaacccat agggcagtca    360

tccttcacgc tacttggctg gttcagactc tcgtccattg accaatattc ctcactgctg    420

cctcccgtag gtagtttgga a                                              441
```

```
<210> SEQ ID NO 31
<211> LENGTH: 422
<212> TYPE: DNA
<213> ORGANISM: Artificial Sequence
<220> FEATURE:
<223> OTHER INFORMATION: Synthetic Polynucleotide

<400> SEQUENCE: 31

ccgttgtcac gctttcgtgc tcagtgtcag tttcagtcca gtaagccgcc ttcgccactg     60

atgttcctcc taatatctac gcatttcacc gctacactag gaattccgct tacctctcct    120

gcactccagt ctgacagttt caaaagcagt cccagagtta agccctgggt tttcacttct    180

gacttgccat accacctacg caccctttac acccagtaat tccggataac gcttgccccc    240

tacgtattac cgcggctgct ggcacgtagt tagccggggc ttcttagtca ggtaccgtca    300

ttttcttccc tgctgataga gctttacata ccgaaatact tcttcactca cgcggcgtcg    360

ctgcatcagg gttcccccca ttgtgcaata ttccccactg ctgcctcccg tggaagtttg    420

ga                                                                   422
```

```
<210> SEQ ID NO 32
<211> LENGTH: 424
<212> TYPE: DNA
<213> ORGANISM: Artificial Sequence
<220> FEATURE:
<223> OTHER INFORMATION: Synthetic Polynucleotide

<400> SEQUENCE: 32

gcgaatgtca cgcattcgag cctcacgtca gttaccgtcc agtaagccgc cttcgccact     60

ggtgttcctc ctaatatcta cgcatttcac cgctacacta ggaattccgc ttacctctcc    120

ggcactcaag actaacagtt tccaatgcag tccaggggtt gagcccccgc ctttcacatc    180

agacttgcca gtccgtctac gctcccttta cacccagtaa atccggataa cgcttgcccc    240

ctacgtatta ccgcggctgc tggcacgtag ttagccgggg cttcttagtc aggtaccgtc    300

actatcttcc ctgctgatag aagtttacat accgagatac ttcttccttc acgcggcgtc    360

gctgcatcag ggtttccccc attgtgcaat attccccact gctgcctccc gtgggagttt    420

ggaa                                                                 424
```

```
<210> SEQ ID NO 33
<211> LENGTH: 422
<212> TYPE: DNA
<213> ORGANISM: Artificial Sequence
<220> FEATURE:
<223> OTHER INFORMATION: Synthetic Polynucleotide

<400> SEQUENCE: 33
```

-continued

```
tgctcacgct ttcgcgctca gcgtcagtta ctgtccagca atccgccttc gccactggtg     60

ttcctccgta tatctacgca tttcaccgct acacacggaa ttccgattgc ctctccagca    120

ctcaagaact acagtttcaa atgcaggctg gaggttgagc ccccagtttt cacatctgac    180

ttgcaatccc gcctacacgc cctttacacc cagtaaatcc ggataacgct tgccacctac    240

gtattaccgc ggctgctggc acgtagttag ccgtggctta ttcgtcaggt accgtcattt    300

gtttcgtccc tgacaaaaga agtttacaac ccgaaagcct tcttccttca cgcggcgttg    360

ctgggtcagg cttgcgccca ttgcccaata ttccccactg ctgcctcccg tggtagtttg    420

ga                                                                   422
```

<210> SEQ ID NO 34
<211> LENGTH: 419
<212> TYPE: DNA
<213> ORGANISM: Artificial Sequence
<220> FEATURE:
<223> OTHER INFORMATION: Synthetic Polynucleotide

<400> SEQUENCE: 34

```
tgtccacgct ttcgagctca gcgtcagtta tcgtccagta agccgccttc gccactggtg     60

ttcctcctaa tatctacgca tttcaccgct acactaggaa ttccgcttac ccctccgaca    120

ctctagtacg acagtttcca atgcagtacc ggggttgagc cccgggcttt cacatcagac    180

ttgccgcacc gcctgcgctc cctttacacc cagtaaatcc ggataacgct tgcaccatac    240

gtattaccgc ggctgctggc acgtatttag ccggtgcttc ttagtcaggt accgtcatta    300

tcttccctgc tgatagagct ttacataccg aaatacttct tcgctcacgc ggcgtcgctg    360

catcaggctt tcgcccattg tgcaatattc cccactgctg actcccgtag gagtttgga     419
```

<210> SEQ ID NO 35
<211> LENGTH: 424
<212> TYPE: DNA
<213> ORGANISM: Artificial Sequence
<220> FEATURE:
<223> OTHER INFORMATION: Synthetic Polynucleotide

<400> SEQUENCE: 35

```
cgtttctcca cgcttcgcgc tcagcgtcag ttactgtcca gcaatccgcc ttcgccactg     60

gtgttcctcc gtatatctac gcatttcacc gctacacacg gaattccgat tgcctctcca    120

gcactcaaga actacagttt caaatgcagg ctggaggttg agcccccagt tttcacatct    180

gacttgcaat cccgcctaca cgccctttac acccagtaaa tccggataac gcttgccacc    240

tacgtattac cgcggctgct ggcacgtagt tagccgtggc ttattcgtca ggtaccgtca    300

tttgtttcgt ccccgacaaa agaagtttac aacccgaaag ccttcttcct tcacgcggcg    360

ttgctgggtc aggcttgcgc ccattgccca atattcccca ctgctgcctc cctgggaagt    420

ttgg                                                                 424
```

<210> SEQ ID NO 36
<211> LENGTH: 445
<212> TYPE: DNA
<213> ORGANISM: Artificial Sequence
<220> FEATURE:
<223> OTHER INFORMATION: Synthetic Polynucleotide

<400> SEQUENCE: 36

```
atgtcctgac ttcgcgcctc agcgtcagtt gtcgtccaga aagccgcttt cgccactggt     60

gttcctccta atatctacgc atttcaccgc tacactagga attccgcttt cctctccgac    120
```

actcgagctt cacagtttcg gtcccctcac ggggttaagc cccgcacttt taagaccgac 180
ttgcgatgcc gcctgcgcgc cctttacgcc caataattcc ggacaacgct tgccacctac 240
gtattaccgc ggctgctggc acgtagttag ccgtggcttt ctcttacggt accgtcaggg 300
ataacgggta ttgaccgcta tcctgttcgt cccatataac agaactttac aacccgaagg 360
ccgtcatcgt tcacgcggcg ttgctccgtc agactttcgt ccattgcgga agattcccca 420
ctgctgcctc cctgggaagt ttgga 445

<210> SEQ ID NO 37
<211> LENGTH: 421
<212> TYPE: DNA
<213> ORGANISM: Artificial Sequence
<220> FEATURE:
<223> OTHER INFORMATION: Synthetic Polynucleotide

<400> SEQUENCE: 37
gtttgctcac gctttcgagc tcagcgtcag ttatcgtcca gtaagccgcc ttcgccactg 60
gtgttcctcc taatatctac gcatttcacc gctacactag gaattccgct tacccctccg 120
acactctagt acgacagttt ccaatgcagt accggggttg agccccgggc tttcacatca 180
gacttgccgc accgcctgcg ctccctttac acccagtaaa tccggataac gcttgcacca 240
tacgtattac cgcggctgct ggcacgtatt tagccggtgc ttcttagtca ggtaccgtca 300
ttatcttccc tgctgataga gctttacata ccgaaatact tcttcgctca cgcggcgtcg 360
ctgcatcagg ctttcgccca ttgtgcaata ttccccactg ctgcctcccg taggagtttg 420
g 421

<210> SEQ ID NO 38
<211> LENGTH: 424
<212> TYPE: DNA
<213> ORGANISM: Artificial Sequence
<220> FEATURE:
<223> OTHER INFORMATION: Synthetic Polynucleotide

<400> SEQUENCE: 38
cgttgctcac gcattcgagc ctcagcgtca gttaagccca gtaagccgcc ttcgccactg 60
atgttcctcc taatatctac gcatttcacc gctacactag gaattccgct tacctctact 120
tcactcaaga accacagttt caaatgcagt ttatgggtta agcccatagt tttcacatct 180
gacttgcgat cccgcctacg ctccctttac acccagtaat tccggacaac gctcgctccc 240
tacgtattac cgcggctgct ggcacgtagt tagccggagc ttcctcctca ggtaccgtct 300
tttttcgtcc ctgaagacag aggtttacaa tcctaaaacc ttcttccctc acgcggcatc 360
gctgcatcag agtttcctcc attgtgcaat attccccact gctgcctccc gtaggagttt 420
ggaa 424

<210> SEQ ID NO 39
<211> LENGTH: 189
<212> TYPE: DNA
<213> ORGANISM: Artificial Sequence
<220> FEATURE:
<223> OTHER INFORMATION: Synthetic Polynucleotide

<400> SEQUENCE: 39
tgggcttacc cataaactgc atttgaaact gtggttcttg agtgaagtag aggtaagcgg 60
aattcctagt gtagcggtga aatgcgtaga tattaggagg aacatcagtg gcgaaggcgg 120

-continued cttactgggc tttaactgac gctgaggctc gaaagcgtgg ggagcaaaca ggattagata 180
cccaagtaa 189

<210> SEQ ID NO 40
<211> LENGTH: 414
<212> TYPE: DNA
<213> ORGANISM: Artificial Sequence
<220> FEATURE:
<223> OTHER INFORMATION: Synthetic Polynucleotide

<400> SEQUENCE: 40
gtcagcatcg agctcacgtc agttaccgtc cagtaagccg ccttcgccac tggtgttcct 60
cctaatatct acgcatttca ccgctacact aggaattccg cttacctctc cggtactcta 120
gattgacagt ttccaatgca gtcccggggt tgagccccgg gttttcacat cagacttgcc 180
actccgtcta cgctcccttt acacccagta aatccggata acgcttgcac catacgtatt 240
accgcggctg ctggcacgta tttagccggt gcttcttagt caggtaccgt cattttcttc 300
cctgctgata gagctttaca taccgaaata cttcatcgct cacgcggcgt cgctgcatca 360
gggtttcccc cattgtgcaa tattccccac tgctgcctcc cgagggagtt tgga 414

<210> SEQ ID NO 41
<211> LENGTH: 191
<212> TYPE: DNA
<213> ORGANISM: Artificial Sequence
<220> FEATURE:
<223> OTHER INFORMATION: Synthetic Polynucleotide

<400> SEQUENCE: 41
tcatcgctta cggtggatct gcgccgggta cgggcgggct ggagtgcggt aggggagact 60
ggaattcccg gtgtaacggt ggaatgtgta gatatcggga agaacaccga tggcgaaggc 120
aggtctctgg gccgtcactg acgctgagga gcgaaagcgt ggggagcgaa caggattaga 180
tacaacggta a 191

<210> SEQ ID NO 42
<211> LENGTH: 196
<212> TYPE: DNA
<213> ORGANISM: Artificial Sequence
<220> FEATURE:
<223> OTHER INFORMATION: Synthetic Polynucleotide

<400> SEQUENCE: 42
tgaacccagg gcttaactct gggactgctt ttgaactgtc agactggagt gcaggagagg 60
taagcggaat tcctagtgta gcggtgaaat gcgtagatat taggaggaac atcagtggcg 120
aaggcggctt actggactga aactgacact gaggcacgaa agcgtgggga gcaaacagga 180
ttagatacca tggtaa 196

<210> SEQ ID NO 43
<211> LENGTH: 192
<212> TYPE: DNA
<213> ORGANISM: Artificial Sequence
<220> FEATURE:
<223> OTHER INFORMATION: Synthetic Polynucleotide

<400> SEQUENCE: 43
accagggctt aactctggga ctgcttttga actgtcagac tggagtgcag gagaggtaag 60
cggaattcct agtgtagcgg tgaaatgcgt agatattagg aggaacatca gtggcgaagg 120
cggcttactg gactgaaact gacactgagg cacgaaagcg tggggagcaa acaggattag 180 atacccctggt aa 192

<210> SEQ ID NO 44
<211> LENGTH: 195
<212> TYPE: DNA
<213> ORGANISM: Artificial Sequence
<220> FEATURE:
<223> OTHER INFORMATION: Synthetic Polynucleotide

<400> SEQUENCE: 44
gaacccaggg cttaactctg ggactgcttt tgaactgtca gactggagtg caggagaggt 60
aagcggaatt cctagtgtag cggtgaaatg cgtagatatt aggaggaaca tcagtggcga 120
aggcggctta ctggactgaa actgacactg aggcacgaaa gcgtggggag caaacaggat 180
tagatacccc ggtaa 195

<210> SEQ ID NO 45
<211> LENGTH: 418
<212> TYPE: DNA
<213> ORGANISM: Artificial Sequence
<220> FEATURE:
<223> OTHER INFORMATION: Synthetic Polynucleotide

<400> SEQUENCE: 45
gagtcagctt tcgagctcag cgtcagttat cgtccagtaa gccgccttcg ccactggtgt 60
tcctcctaat atctacgcat ttcaccgcta cactaggaat tccgcttacc cctccgacac 120
tctagtacga cagtttccaa tgcagtaccg gggttgagcc ccgggctttc acatcagact 180
tgccgcaccg cctgcgctcc ctttacaccc agtaaatccg gataacgctt gcaccatacg 240
tattaccgcg gctgctggca cgtatttagc cggtgcttct tagtcaggta ccgtcattat 300
cttccctgct gatagagctt tacataccga aatacttctt cgctcacgcg gcgtcgctgc 360
atcaggcttt cgcccattgt gcaatattcc ccactgctgc ctcccgaggg agtttgga 418

<210> SEQ ID NO 46
<211> LENGTH: 416
<212> TYPE: DNA
<213> ORGANISM: Artificial Sequence
<220> FEATURE:
<223> OTHER INFORMATION: Synthetic Polynucleotide

<400> SEQUENCE: 46
tgtcagcttt cgagctcacg tcagttaccg tccagtaagc cgccttcgcc actggtgttc 60
ctcctaatat ctacgcattt caccgctaca ctaggaattc cgcttacctc tccggtactc 120
tagattgaca gtttccaatg cagtcccggg gttgagcccc gggttttcac atcagacttg 180
ccactccgtc tacgctccct ttacacccag taaatccgga taacgcttgc accatacgta 240
ttaccgcggc tgctggcacg tatttagccg gtgcttctta gtcaggtacc gtcattttct 300
tccctgctga tagagcttta cataccgaaa tacttcatcg ctcacgcggc gtcgctgcat 360
cagggtttcc cccattgtgc aatattcccc actgctgcct cccgtaggag tttgga 416

<210> SEQ ID NO 47
<211> LENGTH: 400
<212> TYPE: DNA
<213> ORGANISM: Artificial Sequence
<220> FEATURE:
<223> OTHER INFORMATION: Synthetic Polynucleotide

<400> SEQUENCE: 47
cacgtcagtt accgtccagt aagccgcctt cgccactggt gttcctccta atatctacgc 60
atttcaccgc tacactagga attccgctta cctctccggc actcaagacg ggcagtttcc 120
aatgcagtcc cggggttgag ccccagcctt tcacatcaga cttgtccatc cgtctacgct 180
ccctttacac ccagtaaatc cggataacgc ttgcccccta cgtattaccg cggctgctgg 240
cacgtagtta gccggggctt cttagtcagg taccgtcatt ttcttccctg ctgatagaag 300
tttacatacc gagatacttc ttccttcacg cggcgtcgct gcatcagggt ttcccccatt 360
gtgcaatatt ccccactgct gcctcccgta ggagtttggg 400

<210> SEQ ID NO 48
<211> LENGTH: 416
<212> TYPE: DNA
<213> ORGANISM: Artificial Sequence
<220> FEATURE:
<223> OTHER INFORMATION: Synthetic Polynucleotide

<400> SEQUENCE: 48
gtcagctttc gagctcacgt cagttaccgt ccagtaagcc gccttcgcca ctggtgttcc 60
tcctaatatc tacgcatttc accgctacac taggaattcc gcttacctct ccggtactct 120
agattgacag tttccaatgc agtcccgggg ttgagccccg ggttttcaca tcagacttgc 180
cactccgtct acgctccctt tacacccagt aaatccggat aacgcttgca ccatacgtat 240
taccgcggct gctggcacgt atttagccgg tgcttcttag tcaggtaccg tcattttctt 300
ccctgctgat agagctttac ataccgaaat acttcatcgc tcacgcggcg tcgctgcatc 360
agggtttccc ccattgtgca atattcccca ctgctgcctc ccgtggggag tttgga 416

<210> SEQ ID NO 49
<211> LENGTH: 421
<212> TYPE: DNA
<213> ORGANISM: Artificial Sequence
<220> FEATURE:
<223> OTHER INFORMATION: Synthetic Polynucleotide

<400> SEQUENCE: 49
gatgctcagc tttcgtgctc agtgtcagtt tcagtccagt aagccgcctt cgccactgat 60
gttcctccta atatctacgc atttcaccgc tacactagga attccgctta cctctcctgc 120
actccagtct gacagtttca aaagcagtcc cagagttaag ccctgggttt tcacttctga 180
cttgccatac cacctacgca ccctttacac ccagtaattc cggataacgc ttgcccccta 240
cgtattaccg cggctgctgg cacgtagtta gccggggctt cttagtcagg taccgtcatt 300
ttcttccctg ctgatagagc tttacatacc gagatacttc ttcactcacg cggcgtcgct 360
gcatcagggt ttcccccatt gtgcaatatt ccccactgct gcctcccgaa ggaagtttgg 420
a 421

<210> SEQ ID NO 50
<211> LENGTH: 418
<212> TYPE: DNA
<213> ORGANISM: Artificial Sequence
<220> FEATURE:
<223> OTHER INFORMATION: Synthetic Polynucleotide

<400> SEQUENCE: 50
gtgtcagctt cgtgctcagt gtcagtttca gtccagtaag ccgccttcgc cactgatgtt 60
cctcctaata tctacgcatt tcaccgctac actaggaatt ccgcttacct ctcctgcact 120
ccagtctgac agtttcaaaa gcagtcccag agttaagccc tgggttttca cttctgactt 180
gccataccac ctacgcaccc tttacaccca gtaattccgg ataacgcttg ccccctacgt 240
attaccgcgg ctgctggcac gtagttagcc ggggcttctt agtcaggtac cgtcattttc 300
ttccctgctg atagagcttt acataccgag atacttcttc actcacgcgg cgtcgctgca 360
tcagggtttc ccccattgtg caatattccc cactgctgcc tcccgtaggg agtttgga 418

<210> SEQ ID NO 51
<211> LENGTH: 415
<212> TYPE: DNA
<213> ORGANISM: Artificial Sequence
<220> FEATURE:
<223> OTHER INFORMATION: Synthetic Polynucleotide

<400> SEQUENCE: 51
gtcagcttcg agcctcacgt cagttaccgt ccagtaagcc gccttcgcca ctggtgttcc 60
tcctaatatc tacgcatttc accgctacac taggaattcc gcttacctct ccggtactct 120
agattgacag tttccaatgc agtcccgggg ttgagccccg ggttttcaca tcagacttgc 180
cactccgtct acgctccctt tacacccagt aaatccggat aacgcttgca ccatacgtat 240
taccgcggct gctggcacgt atttagccgg tgcttcttag tcaggtaccg tcattttctt 300
ccctgctgat agagctttac ataccgaaat acttcatcgc tcacgcggcg tcgctgcatc 360
agggtttccc ccattgtgca atattcccca ctgctgcctc gcgtaggagt ttgga 415

<210> SEQ ID NO 52
<211> LENGTH: 418
<212> TYPE: DNA
<213> ORGANISM: Artificial Sequence
<220> FEATURE:
<223> OTHER INFORMATION: Synthetic Polynucleotide

<400> SEQUENCE: 52
tgtcagcttt cgagctcagc gtcagttatc gtccagtaag ccgccttcgc cactggtgtt 60
cctcctaata tctacgcatt tcaccgctac actaggaatt ccgcttaccc ctccgacact 120
ctagtacgac agtttccaat gcagtaccgg ggttgagccc cgggctttca catcagactt 180
gccgcaccgc ctgcgctccc tttacaccca gtaaatccgg ataacgcttg caccatacgt 240
attaccgcgg ctgctggcac gtatttagcc ggtgcttctt agtcaggtac cgtcattatc 300
ttccctgctg atagagcttt acataccgaa atacttcttc gctcacgcgg cgtcgctgca 360
tcaggctttc gcccattgtg caatattccc cactgctgcc tcccgaaggg agtttgga 418

<210> SEQ ID NO 53
<211> LENGTH: 416
<212> TYPE: DNA
<213> ORGANISM: Artificial Sequence
<220> FEATURE:
<223> OTHER INFORMATION: Synthetic Polynucleotide

<400> SEQUENCE: 53
ttcagctttc gagctcagcg tcagttatcg tccagtaagc cgccttcgcc actggtgttc 60
ctcctaatat ctacgcattt caccgctaca ctaggaattc cgcttacccc tccgacactc 120
tagtacgaca gtttccaatg cagtaccggg gttgagcccc gggctttcac atcagacttg 180
ccgcaccgcc tgcgctccct ttacacccag taaatccgga taacgcttgc accatacgta 240
ttaccgcggc tgctggcacg tatttagccg gtgcttctta gtcaggtacc gtcattatct 300
tccctgctga tagagcttta cataccgaaa tacttcttcg ctcacgcggc gtcgctgcat 360
caggctttcg cccattgtgc aatattcccc actgctgcct cccgagggga gtttgg 416

<210> SEQ ID NO 54
<211> LENGTH: 435
<212> TYPE: DNA
<213> ORGANISM: Artificial Sequence
<220> FEATURE:
<223> OTHER INFORMATION: Synthetic Polynucleotide

<400> SEQUENCE: 54
ttcggtctgc tttccccttc tcgcgcctca gtgtcagttt ctgtctagta agccgccttc 60
gccactgatg ttcctcctaa tatctacgca cttcaccgct ccacaatgaa ttccgcttac 120
ccctcccgcg ctctagtctg acagttttaa aaaaactccc cgagagaaac cctgggtttt 180
ttcttctgac atgcgatatc ccacccccac cctttataca cccaaaaatc ggataaaagg 240
tgcgacctac gtattatacc ggctgctggg gcgtagatag ccgggggttc ttatacaggg 300
accgtcattt tctttcccgc tgatacagct ttacataccg aaatacttct ttctcacgcg 360
gcgtcgctgc atcagggttt cccccattgt gcaatattcc ccactgctgc ctcccgaagg 420
ggaagttggg ggaaa 435

<210> SEQ ID NO 55
<211> LENGTH: 418
<212> TYPE: DNA
<213> ORGANISM: Artificial Sequence
<220> FEATURE:
<223> OTHER INFORMATION: Synthetic Polynucleotide

<400> SEQUENCE: 55
gttcagcttt cgagcctcac gtcagttacc gtccagtaag ccgccttcgc cactggtgtt 60
cctcctaata tctacgcatt tcaccgctac actaggaatt ccgcttacct ctccggtact 120
ctagattgac agtttccaat gcagtcccgg ggttgagccc cgggttttca catcagactt 180
gccactccgt ctacgctccc tttacaccca gtaaatccgg ataacgcttg caccatacgt 240
attaccgcgg ctgctggcac gtatttagcc ggtgcttctt agtcaggtac cgtcattttc 300
ttccctgctg atagagcttt acataccgaa atacttcatc gctcacgcgg cgtcgctgca 360
tcagggtttc ccccattgtg caatattccc cactgctgcc tcccgagggg agtttgga 418

<210> SEQ ID NO 56
<211> LENGTH: 416
<212> TYPE: DNA
<213> ORGANISM: Artificial Sequence
<220> FEATURE:
<223> OTHER INFORMATION: Synthetic Polynucleotide

<400> SEQUENCE: 56
gtcagctttc gagctcacgt cagttaccgt ccagtaagcc gccttcgcca ctggtgttcc 60
tcctaatatc tacgcatttc accgctacac taggaattcc gcttacctct ccggtactct 120
agattgacag tttccaatgc agtcccgggg ttgagccccg ggttttcaca tcagacttgc 180
cactccgtct acgctccctt tacacccagt aaatccggat aacgcttgca ccatacgtat 240
taccgcggct gctggcacgt atttagccgg tgcttcttag tcaggtaccg tcattttctt 300
ccctgctgat agagctttac ataccgaaat acttcatcgc tcacgcggcg tcgctgcatc 360
agggtttccc ccattgtgca atattcccca ctgctgcctc ccgaggggag tttgga 416

<210> SEQ ID NO 57
<211> LENGTH: 417

<212> TYPE: DNA
<213> ORGANISM: Artificial Sequence
<220> FEATURE:
<223> OTHER INFORMATION: Synthetic Polynucleotide

<400> SEQUENCE: 57
tctcacgctt tcgagctcac gtcagtcatc gtccagcaag ccgccttcgc cactggtgtt 60
cctcctaata tctacgcatt tcaccgctac actaggaatt ccacttgcct ctccgacact 120
ctagctcagc agttccaaat gcagtcccgg ggttgagccc cgggctttca catctggctt 180
gccgtgccgt ctacgctccc tttacaccca gtaaatccgg ataacgcttg ccccctacgt 240
attaccgcgg ctgctggcac gtagttagcc ggggcttctt agtcaggtac cgtcattttc 300
ttccctgctg atagaagttt acataccgaa atacttcatc cttcacgcgg cgtcgctgca 360
tcagagtttc ctccattgtg caatattccc cactgctgcc tcccgtaggg agtttgg 417

<210> SEQ ID NO 58
<211> LENGTH: 417
<212> TYPE: DNA
<213> ORGANISM: Artificial Sequence
<220> FEATURE:
<223> OTHER INFORMATION: Synthetic Polynucleotide

<400> SEQUENCE: 58
gtcagctttc gagctcagcg tcagttatcg tccagtaagc cgccttcgcc actggtgttc 60
ctcctaatat ctacgcattt caccgctaca ctaggaattc cacttacccc tccgacactc 120
tagtacgaca gtttccaatg cagtaccggg gttgagcccc gggctttcac atcagacttg 180
ccgcaccgcc tgcgctccct ttacacccag taaatccgga taacgcttgc accatacgta 240
ttaccgcggc tgctggcacg tatttagccg gtgcttctta gtcaggtacc gtcattcttc 300
ttccctgctg atagagcttt acataccgaa atacttcttc gctcacgcgg cgtcgctgca 360
tcagggtttc cccattgtg caatattccc cactgctgcc tcccgaggga gtttgga 417

<210> SEQ ID NO 59
<211> LENGTH: 419
<212> TYPE: DNA
<213> ORGANISM: Artificial Sequence
<220> FEATURE:
<223> OTHER INFORMATION: Synthetic Polynucleotide

<400> SEQUENCE: 59
agccccgctt tcgagcctca cgtcagttac cgtccagtaa gccgccttcg ccactggtgt 60
tcctcctaat atctacgcat ttcaccgcta cactaggaat tccgcttacc tctccggcac 120
tcaagacggg cagtttccaa tgcagtcccg gggttgagcc ccagcctttc acatcagact 180
tgtccatccg tctacgctcc ctttacaccc agtaaatccg gataacgctt gccccctacg 240
tattaccgcg gctgctggca cgtagttagc cggggcttct tagtcaggta ccgtcatttt 300
cttccctgct gatagaagtt tacataccga gatacttctt ccttcacgcg gcgtcgctgc 360
atcagggttt cccccattgt gcaatattcc ccactgctgc ctcccgaagg aagtttgga 419

<210> SEQ ID NO 60
<211> LENGTH: 419
<212> TYPE: DNA
<213> ORGANISM: Artificial Sequence
<220> FEATURE:
<223> OTHER INFORMATION: Synthetic Polynucleotide

<400> SEQUENCE: 60

```
tgctcagctt tcgagcctca cgtcagttac cgtccagtaa gccgccttcg ccactggtgt     60

tcttcctaat atctacgcat ttcaccgcta cactaggaat tccgcttacc tctccggcac    120

tcgagccaga cagtttccaa tgcagtccca gggttaagcc ctgggttttc acatcagact    180

tgccttgccg tctacgctcc ctttacaccc agtaaatccg gataacgctt gccccctacg    240

tattaccgcg gctgctggca cgtagttagc cggggcttct tagtcaggta ccgtcattat    300

cttccctgct gatagagctt tacataccga aatacttctt cgctcacgcg gcgtcgctgc    360

atcagggttt cccccattgt gcaatattcc ccactgctgc ctcccgaagg gagtttgga     419
```

<210> SEQ ID NO 61
<211> LENGTH: 421
<212> TYPE: DNA
<213> ORGANISM: Artificial Sequence
<220> FEATURE:
<223> OTHER INFORMATION: Synthetic Polynucleotide

<400> SEQUENCE: 61

```
gttgctcagc tttcgagctc acgtcagtta ccgtccagta agccgccttc gccactggtg     60

ttcttcctaa tatctacgca tttcaccgct acactaggaa ttccgcttac ctctccggca    120

ctcgagccag acagtttcca atgcagtccc agggttaagc cctgggtttt cacatcagac    180

ttgccttgcc gtctacgctc cctttacacc cagtaaatcc ggataacgct tgccccctac    240

gtattaccgc ggctgctggc acgtagttag ccggggcttc ttagtcaggt accgtcatta    300

tcttccctgc tgatagagct ttacataccg aaatacttct tcgctcacgc ggcgtcgctg    360

catcagggtt tcccccattg tgcaatattc cccactgctg cctcccgaag gaaagtttgg    420

a                                                                    421
```

<210> SEQ ID NO 62
<211> LENGTH: 420
<212> TYPE: DNA
<213> ORGANISM: Artificial Sequence
<220> FEATURE:
<223> OTHER INFORMATION: Synthetic Polynucleotide

<400> SEQUENCE: 62

```
tgctcagctt tcgagctcag cgtcagttat cgtccagtaa gccgccttcg ccactggtgt     60

tcctcctaat atctacgcat ttcaccgcta cactaggaat tccacttacc cctccgacac    120

tctagtacga cagtttccaa tgcagtaccg ggttgagcc ccgggctttc acatcagact     180

tgccgcaccg cctgcgctcc ctttacaccc agtaaatccg gataacgctt gcaccatacg    240

tattaccgcg gctgctggca cgtatttagc cggtgcttct tagtcaggta ccgtcattct    300

tcttccctgc tgatagagct ttacataccg aaatacttct tcgctcacgc ggcgtcgctg    360

catcagggtt tcccccattg tgcaatattc cccactgctg cctcccgaag ggagtttgga    420
```

<210> SEQ ID NO 63
<211> LENGTH: 446
<212> TYPE: DNA
<213> ORGANISM: Artificial Sequence
<220> FEATURE:
<223> OTHER INFORMATION: Synthetic Polynucleotide

<400> SEQUENCE: 63

```
gatgccctgg cttcgcgctc agcgtcagtt gtcgtccaga aagccgcttt cgccactggt     60

gttcctccta atatctacgc atttcaccgc tacactagga attccgcttt cctctccgac    120

actcgagctt cacagtttcg gtcccctcac ggggttaagc cccgcacttt taagaccgac    180
```

```
ttgcgatgcc gcctgcgcgc cctttacgcc caataattcc ggacaacgct tgccacctac    240

gtattaccgc ggctgctggc acgtagttag ccgtggcttt ctcttacggt accgtcaggg    300

ataacgggta ttgaccgcta tcctgttcgt cccatataac agaactttac aacccgaagg    360

ccgtcatcgt tcacgcggcg ttgctccgtc agactttcgt ccattgcgga agattcccca    420

ctgctgcctc ccgggggag tttgga                                          446
```

<210> SEQ ID NO 64
<211> LENGTH: 419
<212> TYPE: DNA
<213> ORGANISM: Artificial Sequence
<220> FEATURE:
<223> OTHER INFORMATION: Synthetic Polynucleotide

<400> SEQUENCE: 64

```
gtcccgcttt cgagcctcag cgtcagttat cgtccagtaa gccgccttcg ccactggtgt     60

tcctcctaat atctacgcat ttcaccgcta cactaggaat tccgcttacc cctccgacac    120

tctagtacga cagtttccaa tgcagtaccg gggttgagcc ccgggctttc acatcagact    180

tgccgcaccg cctgcgctcc ctttacaccc agtaaatccg gataacgctt gcaccatacg    240

tattaccgcg gctgctggca cgtatttagc cggtgcttct tagtcaggta ccgtcattat    300

cttccctgct gatagagctt tacataccga aatacttctt cgctcacgcg gcgtcgctgc    360

atcaggcttt cgcccattgt gcaatattcc ccactgctgc ctcccgaagg gaagtttgg     419
```

<210> SEQ ID NO 65
<211> LENGTH: 418
<212> TYPE: DNA
<213> ORGANISM: Artificial Sequence
<220> FEATURE:
<223> OTHER INFORMATION: Synthetic Polynucleotide

<400> SEQUENCE: 65

```
tgtcagcttt cgagctcagc gtcagttatc gtccagtaag ccgccttcgc cactggtgtt     60

cctcctaata tctacgcatt tcaccgctac actaggaatt ccgcttaccc ctccgacact    120

ctagtacgac agtttccaat gcagtaccgg ggttgagccc cgggctttca catcagactt    180

gccgcaccgc ctgcgctccc tttacaccca gtaaatccgg ataacgcttg caccatacgt    240

attaccgcgg ctgctggcac gtatttagcc ggtgcttctt agtcaggtac cgtcattatc    300

ttccctgctg atagagcttt acataccgaa atacttcttc gctcacgcgg cgtcgctgca    360

tcaggctttc gcccattgtg caatattccc cactgctgcc tcccgaaggg agtttgga      418
```

<210> SEQ ID NO 66
<211> LENGTH: 420
<212> TYPE: DNA
<213> ORGANISM: Artificial Sequence
<220> FEATURE:
<223> OTHER INFORMATION: Synthetic Polynucleotide

<400> SEQUENCE: 66

```
tgctcagctt tcgagctcag cgtcagttat cgtccagtaa gccgccttcg ccactggtgt     60

tcctcctaat atctacgcat ttcaccgcta cactaggaat tccacttacc cctccgacac    120

tctagtacga cagtttccaa tgcagtaccg gggttgagcc ccgggctttc acatcagact    180

tgccgcaccg cctgcgctcc ctttacaccc agtaaatccg gataacgctt gcaccatacg    240

tattaccgcg gctgctggca cgtatttagc cggtgcttct tagtcaggta ccgtcattct    300
```

-continued tcttccctgc tgatagagct ttacataccg aaatacttct tcgctcacgc ggcgtcgctg 360
catcagggtt tcccccattg tgcaatattc cccactgctg cctcccgaag ggagtttgga 420

<210> SEQ ID NO 67
<211> LENGTH: 417
<212> TYPE: DNA
<213> ORGANISM: Artificial Sequence
<220> FEATURE:
<223> OTHER INFORMATION: Synthetic Polynucleotide

<400> SEQUENCE: 67
attcagcttt cgagctcacg tcagttaccg tccagtaagc cgccttcgcc actggtgttc 60
ctcctaatat ctacgcattt caccgctaca ctaggaattc cgcttacccc tccggcactc 120
aagcatacca gtttccaatg cagtccaggg gttaagcccc tgcctttcac atcagacttg 180
atacgccgtc tacgctccct ttacacccag taaatccgga taacgctcgc cccctacgta 240
ttaccgcggc tgctggcacg tagttagccg gggcttctta gtcaggtacc gtcattatct 300
tccctgctga tagaagttta cataccgaga tacttcttcc ttcacgcggc gtcgctgcat 360
cagggtttcc cccattgtgc aatattcccc actgctgcct cccgagggaa gtttgga 417

<210> SEQ ID NO 68
<211> LENGTH: 416
<212> TYPE: DNA
<213> ORGANISM: Artificial Sequence
<220> FEATURE:
<223> OTHER INFORMATION: Synthetic Polynucleotide

<400> SEQUENCE: 68
gtgtcagctt tcgagctcac gtcagttacc gtccagtaag ccgccttcgc cactggtgtt 60
cttcctaata tctacgcatt tcaccgctac actaggaatt ccgcttacct ctccggcact 120
cgagccagac agtttccaat gcagtcccag ggttaagccc tgggttttca catcagactt 180
gccttgccgt ctacgctccc tttacaccca gtaaatccgg ataacgcttg ccccctacgt 240
attaccgcgg ctgctggcac gtagttagcc ggggcttctt agtcaggtac cgtcattatc 300
ttccctgctg atagagcttt acataccgaa atacttcttc gctcacgcgg cgtcgctgca 360
tcagggtttc ccccattgtg caatattccc cactgctgcc tcccgaggga gtttgg 416

<210> SEQ ID NO 69
<211> LENGTH: 416
<212> TYPE: DNA
<213> ORGANISM: Artificial Sequence
<220> FEATURE:
<223> OTHER INFORMATION: Synthetic Polynucleotide

<400> SEQUENCE: 69
gccagcttcg agcctcacgt cagtcatcgt ccagtaagcc gccttcgcca ctggtgttcc 60
tcctaatatc tacgcatttc accgctacac taggaattcc acttacctct ccgacactct 120
agctgcacag tttccaaagc agtccacagg ttgagcccat gcctttcact tcagacttgc 180
acagccgtct acgctccctt tacacccagt aaatccggat aacgcttgcc ccctacgtat 240
taccgcggct gctggcacgt agttagccgg ggcttcttag tcaggtaccg tcattttctt 300
ccctgctgat agaagtttac ataccgaaat acttcatcct tcacgcggcg tcgctgcatc 360
aggctttcgc ccattgtgca atattcccca ctgctgcctc ccgagggaag tttgga 416

<210> SEQ ID NO 70
<211> LENGTH: 418

<212> TYPE: DNA
<213> ORGANISM: Artificial Sequence
<220> FEATURE:
<223> OTHER INFORMATION: Synthetic Polynucleotide

<400> SEQUENCE: 70
tgatcagctt tcgagctcac gtcagttacc gtccagtaag ccgccttcgc cactggtgtt 60
cctcctaata tctacgcatt tcaccgctac actaggaatt ccgcttacct ctccggtact 120
ctagattgac agtttccaat gcagtcccgg ggttgagccc cgggttttca catcagactt 180
gccactccgt ctacgctccc tttacaccca gtaaatccgg ataacgcttg caccatacgt 240
attaccgcgg ctgctggcac gtatttagcc ggtgcttctt agtcaggtac cgtcattttc 300
ttccctgctg atagagcttt acataccgaa atacttcatc gctcacgcgg cgtcgctgca 360
tcagggtttc cccattgtg caatattccc cactgctgcc tcccgggggg agtttgga 418

<210> SEQ ID NO 71
<211> LENGTH: 420
<212> TYPE: DNA
<213> ORGANISM: Artificial Sequence
<220> FEATURE:
<223> OTHER INFORMATION: Synthetic Polynucleotide

<400> SEQUENCE: 71
gatgatcagc tttcgagctc acgtcagtta ccgtccagta agccgccttc gccactggtg 60
ttcctcctaa tatctacgca tttcaccgct acactaggaa ttccgcttac ctctccggca 120
ctctagaaaa acagtttcca atgcagtcct ggggttaagc cccagccttt cacatcagac 180
ttgctcttcc gtctacgctc cctttacacc cagtaaatcc ggataacgct tgccccctac 240
gtattaccgc ggctgctggc acgtagttag ccggggcttc ttagtcaggt accgtcattt 300
tcttccctgc tgatagaagt ttacataccg agatacttct tccttcacgc ggcgtcgctg 360
catcagggtt tcccccattg tgcaatattc cccactgctg cctcccgggg gaagtttgga 420

<210> SEQ ID NO 72
<211> LENGTH: 418
<212> TYPE: DNA
<213> ORGANISM: Artificial Sequence
<220> FEATURE:
<223> OTHER INFORMATION: Synthetic Polynucleotide

<400> SEQUENCE: 72
ttgatcagct ttcgagctca cgtcagttac cgtccagtaa gccgccttcg ccactggtgt 60
tcctcctaat atctacgcat ttcaccgcta cactaggaat tccgcttacc tctccggcac 120
tctagaaaaa cagtttccaa tgcagtcctg gggttaagcc ccagcctttc acatcagact 180
tgctcttccg tctacgctcc ctttacaccc agtaaatccg gataacgctt gccccctacg 240
tattaccgcg gctgctggca cgtagttagc cggggcttct tagtcaggta ccgtcatttt 300
cttccctgct gatagaagtt tacataccga gatacttctt ccttcacgcg gcgtcgctgc 360
atcagggttt cccccattgt gcaatattcc ccactgctgc ctcccgaagg gagtttgg 418

<210> SEQ ID NO 73
<211> LENGTH: 421
<212> TYPE: DNA
<213> ORGANISM: Artificial Sequence
<220> FEATURE:
<223> OTHER INFORMATION: Synthetic Polynucleotide

<400> SEQUENCE: 73
gtatttcagc tttcgagctc agcgtcagtt atcgtccagt aagccgcctt cgccactggt 60
gttcctccta atatctacgc atttcaccgc tacactagga attccgctta cccctccgac 120
actctagtac gacagtttcc aatgcagtac cggggttgag ccccgggctt tcacatcaga 180
cttgccgcac cgcctgcgct ccctttacac ccagtaaatc cggataacgc ttgcaccata 240
cgtattaccg cggctgctgg cacgtattta gccggtgctt cttagtcagg taccgtcatt 300
atcttccctg ctgatagagc tttacatacc gaaatacttc ttcgctcacg cggcgtcgct 360
gcatcaggct ttcgcccatt gtgcaatatt ccccactgct gcctcccgaa gggagtttgg 420
a 421

<210> SEQ ID NO 74
<211> LENGTH: 419
<212> TYPE: DNA
<213> ORGANISM: Artificial Sequence
<220> FEATURE:
<223> OTHER INFORMATION: Synthetic Polynucleotide

<400> SEQUENCE: 74
gctcagcttt cgagctcagc gtcagttatc gtccagtaag ccgccttcgc cactggtgtt 60
cctcctaata tctacgcatt tcaccgctac actaggaatt ccacttaccc ctccgacact 120
ctagtacgac agtttccaat gcagtaccgg ggttgagccc cgggctttca catcagactt 180
gccgcaccgc ctgcgctccc tttacaccca gtaaatccgg ataacgcttg caccatacgt 240
attaccgcgg ctgctggcac gtatttagcc ggtgcttctt agtcaggtac cgtcattctt 300
cttccctgct gatagagctt tacataccga aatacttctt cgctcacgcg gcgtcgctgc 360
atcagggttt cccccattgt gcaatattcc ccactgctgc ctcccgaggg gagtttgga 419

<210> SEQ ID NO 75
<211> LENGTH: 417
<212> TYPE: DNA
<213> ORGANISM: Artificial Sequence
<220> FEATURE:
<223> OTHER INFORMATION: Synthetic Polynucleotide

<400> SEQUENCE: 75
tttcagcttc gagcctcagc gtcagttatc gtccagtaag ccgccttcgc cactggtgtt 60
cctcctaata tctacgcatt tcaccgctac actaggaatt ccgcttaccc ctccgacact 120
ctagtacgac agtttccaat gcagtaccgg ggttgagccc cgggctttca catcagactt 180
gccgcaccgc ctgcgctccc tttacaccca gtaaatccgg ataacgcttg caccatacgt 240
attaccgcgg ctgctggcac gtatttagcc ggtgcttctt agtcaggtac cgtcattatc 300
ttccctgctg atagagcttt acataccgaa atacttcttc gctcacgcgg cgtcgctgca 360
tcaggctttc gcccattgtg caatattccc cactgctagc tcccgaagga gtttgga 417

<210> SEQ ID NO 76
<211> LENGTH: 419
<212> TYPE: DNA
<213> ORGANISM: Artificial Sequence
<220> FEATURE:
<223> OTHER INFORMATION: Synthetic Polynucleotide

<400> SEQUENCE: 76
agctcagctt tcgagctcag cgtcagttat cgtccagtaa gccgccttcg ccactggtgt 60
tcctcctaat atctacgcat ttcaccgcta cactaggaat tccgcttacc cctccgacac 120
tctagtacga cagtttccaa tgcagtaccg gggttgagcc ccgggctttc acatcagact 180
tgccgcaccg cctgcgctcc ctttacaccc agtaaatccg gataacgctt gcaccatacg 240
tattaccgcg gctgctggca cgtatttagc cggtgcttct tagtcaggta ccgtcattat 300
cttccctgct gatagagctt tacataccga aatacttctt cgctcacgcg gcgtcgctgc 360
atcaggcttt cgcccattgt gcaatattcc ccactgctgc ctcccgaagg gagtttgga 419

<210> SEQ ID NO 77
<211> LENGTH: 418
<212> TYPE: DNA
<213> ORGANISM: Artificial Sequence
<220> FEATURE:
<223> OTHER INFORMATION: Synthetic Polynucleotide

<400> SEQUENCE: 77
gtccagcttt cgagcctcag cgtcagttat cgtccagtaa gccgccttcg ccactggtgt 60
tcctcctaat atctacgcat ttcaccgcta cactaggaat tccgcttacc cctccgacac 120
tctagtacga cagtttccaa tgcagtaccg gggttgagcc ccgggctttc acatcagact 180
tgccgcaccg cctgcgctcc ctttacaccc agtaaatccg gataacgctt gcaccatacg 240
tattaccgcg gctgctggca cgtatttagc cggtgcttct tagtcaggta ccgtcattat 300
cttccctgct gatagagctt tacataccga aatacttctt cgctcacgcg gcgtcgctgc 360
atcaggcttt cgcccattgt gcaatattcc ccactgctgc ctcccgaggg agtttgga 418

<210> SEQ ID NO 78
<211> LENGTH: 193
<212> TYPE: DNA
<213> ORGANISM: Artificial Sequence
<220> FEATURE:
<223> OTHER INFORMATION: Synthetic Polynucleotide

<400> SEQUENCE: 78
tgagccgggc tcaccccggt actgcattgg aactgtcgta ctagagtgtc ggaggggtaa 60
gcggaattcc tagtgtagcg gtgaaatgcg tagatattag gaggaacacc agtggcgaag 120
gcggcttact ggacgataac tgacgctgag gctcgaaagc gtggggagca aacaggatta 180
gatacaccgg taa 193

<210> SEQ ID NO 79
<211> LENGTH: 424
<212> TYPE: DNA
<213> ORGANISM: Artificial Sequence
<220> FEATURE:
<223> OTHER INFORMATION: Synthetic Polynucleotide

<400> SEQUENCE: 79
cacgatgtca gctttcgagc tcagcgtcag ttatcgtcca gtaagccgcc ttcgccactg 60
gtgttcctcc taatatctac gcatttcacc gctacactag gaattccact tacccctccg 120
acactctagt acgacagttt ccaatgcagt accggggttg agccccgggc tttcacatca 180
gacttgccgc accgcctgcg ctccctttac acccagtaaa tccggataac gcttgcacca 240
tacgtattac cgcggctgct ggcacgtatt tagccggtgc ttcttagtca ggtaccgtca 300
ttcttcttcc ctgctgatag agctttacat accgaaatac ttcttcgctc acgcggcgtc 360
gctgcatcag ggtttccccc attgtgcaat attccccact gctgcctccc gaggggagtt 420
tgga 424

<210> SEQ ID NO 80

<211> LENGTH: 1524
<212> TYPE: DNA
<213> ORGANISM: Artificial Sequence
<220> FEATURE:
<223> OTHER INFORMATION: Synthetic Polynucleotide

<400> SEQUENCE: 80
atggagagtt tgatcctggc tcaggatgaa cgctggcggc gtgcctaata catgcaagtc 60
gaacgcgagc acttgtgctc gagtggcgaa cgggtgagta atacataagt aacctgccct 120
agacaggggg ataactattg gaaacgatag ctaagaccgc ataggtacgg acactgcatg 180
gtgaccgtat taaaagtgcc tcaaagcact ggtagaggat ggacttatgg cgcattagct 240
ggttggcggg gtaacggccc accaaggcga cgatgcgtag ccgacctgag agggtgaccg 300
gccacactgg gactgagaca cggcccagac tcctacggga ggcagcagta gggaattttc 360
ggcaatgggg gaaaccctga ccgagcaacg ccgcgtgaag gaagaaggtt ttcggattgt 420
aaacttctgt tataaaggaa gaacggcggc tacaggaaat ggtagccgag tgacggtact 480
ttattagaaa gccacggcta actacgtgcc agcagccgcg gtaatacgta ggtggcaagc 540
gttatccgga attattgggc gtaaagaggg agcaggcggc agcaagggtc tgtggtgaaa 600
gcctgaagct taacttcagt aagccataga aaccaggcag ctagagtgca ggagaggatc 660
gtggaattcc atgtgtagcg gtgaaatgcg tagatatatg gaggaacacc agtggcgaag 720
gcgacgatct ggcctgcaac tgacgctcag tcccgaaagc gtggggagca aataggatta 780
gataccctag tagtccacgc cgtaaacgat gagtactaag tgttggatgt caaagttcag 840
tgctgcagtt aacgcaataa gtactccgcc tgagtagtac gttcgcaaga atgaaactca 900
aaggaattga cgggggcccg cacaagcggt ggagcatgtg gtttaattcg aagcaacgcg 960
aagaacctta ccaggtcttg acatactcat aaaggctcca gagatggaga gatagctata 1020
tgagatacag gtggtgcatg gttgtcgtca gctcgtgtcg tgagatgttg ggttaagtcc 1080
cgcaacgagc gcaaccctta tcgttagtta ccatcattaa gttggggact ctagcgagac 1140
tgccagtgac aagctggagg aaggcgggga tgacgtcaaa tcatcatgcc ccttatgacc 1200
tgggctacac acgtgctaca atggatggtg cagagggaag cgaagccgcg aggtgaagca 1260
aaacccataa aaccattctc agttcggatt gtagtctgca actcgactac atgaagttgg 1320
aatcgctagt aatcgcgaat cagcatgtcg cggtgaatac gttctcgggc cttgtacaca 1380
ccgcccgtca caccacgaga gttgataaca cccgaagccg gtggcctaac cgcaaggaag 1440
gagctgtcta aggtgggatt gatgattggg gtgaagtcgt aacaaggtat ccctacggga 1500
acgtggggat ggatcacctc cttt 1524

<210> SEQ ID NO 81
<211> LENGTH: 1528
<212> TYPE: DNA
<213> ORGANISM: Artificial Sequence
<220> FEATURE:
<223> OTHER INFORMATION: Synthetic Polynucleotide

<400> SEQUENCE: 81
atgagagttt gatcctggct caggatgaac gctggcggcg tgcctaacac atgcaagtcg 60
aacgaagcaa ttgaaggaag ttttcggatg gaattcgatt gactgagtgg cggacgggtg 120
agtaacgcgt ggataacctg cctcacactg ggggataaca gttagaaatg actgctaata 180
ccgcataagc gcacagtacc gcatggtaca gtgtgaaaaa ctccggtggt gtgagatgga 240
tccgcgtctg attagccagt tggcggggta acggcccacc aaagcgacga tcagtagccg 300
acctgagagg gtgaccggcc acattgggac tgagacacgg cccaaactcc tacgggaggc 360
agcagtgggg aatattgcac aatgggcgaa agcctgatgc agcgacgccg cgtgagtgaa 420
gaagtatttc ggtatgtaaa gctctatcag cagggaagaa aatgacggta cctgactaag 480
aagccccggc taactacgtg ccagcagccg cggtaatacg taggggggcaa gcgttatccg 540 gatttactgg gtgtaaaggg agcgtagacg gcgaagcaag tctgaagtga aaacccaggg 600
ctcaaccctg ggactgcttt ggaaactgtt ttgctagagt gtcggagagg taagtggaat 660
tcctagtgta gcggtgaaat gcgtagatat taggaggaac accagtggcg aaggcggctt 720
actggacgat aactgacgtt gaggctcgaa agcgtgggga gcaaacagga ttagataccc 780
tggtagtcca cgccgtaaac gatgaatgct aggtgttggg gggcaaagcc cttcggtgcc 840
gtcgcaaacg cagtaagcat tccacctggg gagtacgttc gcaagaatga aactcaaagg 900
aattgacggg gacccgcaca agcggtggag catgtggttt aattcgaagc aacgcgaaga 960
accttaccaa gtcttgacat cctcttgacc ggcgtgtaac ggcgccttcc cttcggggca 1020
agagagacag gtggtgcatg gttgtcgtca gctcgtgtcg tgagatgttg ggttaagtcc 1080
cgcaacgagc gcaaccctta tccttagtag ccagcaggta aagctgggca ctctagggag 1140
actgccaggg ataacctgga ggaaggtggg gatgacgtca aatcatcatg ccccttatga 1200
tttgggctac acacgtgcta caatggcgta aacaaaggga agcaagacag tgatgtggag 1260
caaatcccaa aaataacgtc ccagttcgga ctgtagtctg caacccgact acacgaagct 1320
ggaatcgcta gtaatcgcga atcagaatgt cgcggtgaat acgttcccgg gtcttgtaca 1380
caccgcccgt cacaccatgg gagtcagcaa cgcccgaagt cagtgaccca actcgcaaga 1440
gagggagctg ccgaaggcgg ggcaggtaac tggggtgaag tcgtaacaag gtagccgtat 1500
cggaaggtgc ggctggatca cctccttt 1528

<210> SEQ ID NO 82
<211> LENGTH: 385
<212> TYPE: DNA
<213> ORGANISM: Artificial Sequence
<220> FEATURE:
<223> OTHER INFORMATION: Synthetic Polynucleotide

<400> SEQUENCE: 82
aattcgacgt tgtccggatt actgggcgta aagggagcgt aggcggactt ttaagtgaga 60
tgtgaaatac ccgggctcaa cttgggtgct gcatttcaaa ctggaagtct agagtgcagg 120
agaggagaat ggaattccta gtgtagcggt gaaatgcgta gagattagga agaacaccag 180
tggcgaaggc gattctctgg actgtaactg acgctgaggc tcgaaagcgt ggggagcaaa 240
caggattaga taccctggta gtccacgccg taaacgatga atactaggtg taggggttgt 300
catgacctct gtgccgccgc taacgcatta agtattccgc ctggggagta cggtcgcaag 360
attaaaactc aaagaaattg acgga 385

<210> SEQ ID NO 83
<211> LENGTH: 434
<212> TYPE: DNA
<213> ORGANISM: Artificial Sequence
<220> FEATURE:
<223> OTHER INFORMATION: Synthetic Polynucleotide

<400> SEQUENCE: 83
acgagcgtat cggattattg ggtttaaggg agcgtaggtg gattgttaag tcagttgtga 60
aagtttgcgg ctcaaccgta aaattgcagt tgaaactggc agtcttgagt acagtagagg 120
tgggcggaat tcgtggtgta gcggtgaaat gcttagatat cacgaagaac tccgattgcg 180
aaggcagctc actagactgt cactgacact gatgctcgaa agtgtgggta tcaaacagga 240
ttagataccc tggtagtcca cacagtaaac gatgaatact cgctgtttgc gatatacagt 300
aagcggccaa gcgaaagcat taagtattcc acctggggag tacgccggca acggtgaaac 360
tcaaagaaat tgacggaagc ccgcccaggg gggaaaaaca tggggtttag ttggatgata 420
cggggaggaa cctc 434

<210> SEQ ID NO 84
<211> LENGTH: 1457
<212> TYPE: DNA
<213> ORGANISM: Ruminococcus obeum
<220> FEATURE:
<221> NAME/KEY: misc_feature
<222> LOCATION: (65)..(66)
<223> OTHER INFORMATION: n is a, c, g, t or u
<220> FEATURE:
<221> NAME/KEY: misc_feature
<222> LOCATION: (960)..(960)
<223> OTHER INFORMATION: n is a, c, g, t or u

<400> SEQUENCE: 84
ggcggcgtgc ttaacacatg caagtcgaac gggaaacctt tcattgaagc ttcggcagat 60
ttggnntgtt tctagtggcg gacgggtgag taacgcgtgg gtaacctgcc ttatacaggg 120
ggataacaac cagaaatggt tgctaatacc gcataagcgc acaggaccgc atggtctggt 180
gtgaaaaact ccggtggtat aagatggacc cgcgttggat tagctagttg gcagggtaac 240
ggcctaccaa ggcgacgatc catagccggc ctgagagggt gaacggccac attgggactg 300
agacacggcc cagactccta cgggaggcag cagtggggaa tattgcacaa tgggggaaac 360
cctgatgcag cgacgccgcg tgaaggaaga agtatctcgg tatgtaaact tctatcagca 420
gggaagatag tgacggtacc tgactaagaa gccccggcta actacgtgcc agcagccgcg 480
gtaatacgta gggggcaagc gttatccgga tttactgggt gtaaagggag cgtagacgga 540
ctggcaagtc tgatgtgaaa ggcgggggct caacccctgg actgcattgg aaactgttag 600
tcttgagtgc cggagaggta agcggaattc ctagtgtagc ggtgaaatgc gtagatatta 660
ggaggaacac cagtggcgaa ggcggcttac tggacggtaa ctgacgttga ggctcgaaag 720
cgtggggagc aaacaggatt agataccctg gtagtccacg ccgtaaacga tgattactag 780
gtgttgggga gcaaagctct tcggtgccgc cgcaaacgca ttaagtattc cacctgggga 840
gtacgttcgc aagaatgaaa ctcaaaggaa ttgacgggga cccgcacaag cggtggagca 900
tgtggtttaa ttcgaagcaa cgcgaagaac cttaccaagt cttgacatcc ctctgaccgn 960
cccttaaccg gatctttcct tcgggacagg ggagacaggt ggtgcatggt tgtcgtcagc 1020
tcgtgtcgtg agatgttggg ttaagtcccg caacgagcgc aacccctatc cccagtagcc 1080
agcagtccgg ctgggcactc tgaggagact gccagggata acctggagga aggcggggat 1140
gacgtcaaat catcatgccc cttatgattt gggctacaca cgtgctacaa tggcgtaaac 1200
aaagggaagc aagcctgcga aggtaagcaa atcccaaaaa taacgtccca gttcggactg 1260
cagtctgcaa ctcgactgca cgaagctgga atcgctagta atcgcggatc agaatgccgc 1320
ggtgaatacg ttcccgggtc ttgtacacac cgcccgtcac accatgggag tcagtaacgc 1380
ccgaagtcag tgacctaact gcaaagaagg agctgccgaa ggcgggaccg atgactgggg 1440
tgaagtcgta acaaggt 1457

<210> SEQ ID NO 85
<211> LENGTH: 1398
<212> TYPE: DNA
<213> ORGANISM: Ruminococcus obeum
<220> FEATURE:
<221> NAME/KEY: misc_feature
<222> LOCATION: (1083)..(1083)
<223> OTHER INFORMATION: n is a, c, g, t or u
<220> FEATURE:
<221> NAME/KEY: misc_feature
<222> LOCATION: (1207)..(1207)
<223> OTHER INFORMATION: n is a, c, g, t or u
<220> FEATURE:
<221> NAME/KEY: misc_feature
<222> LOCATION: (1233)..(1233)
<223> OTHER INFORMATION: n is a, c, g, t or u

<400> SEQUENCE: 85
ggcgtgctta acacatgcaa gtcgaacggg aaacttttca ttgaagcttc ggcagatttg 60
gtctgtttct agtggcggac gggtgagtaa cgcgtgggta acctgcctta tacaggggga 120
taacaaccag aaatggttgc taataccgca taagcgcaca ggaccgcatg gtctggtgtg 180
aaaaactccg gtggtataag atggacccgc gttggattag ctagttggca gggtaacggc 240
ctaccaaggc gacgatccat agccggcctg agagggtgaa cggccacatt gggactgaga 300
cacgccccag actcctcggg aggcagcagt ggggaatatt gcacaatggg ggaaaccctg 360
atgcagcgac gccgcgtgaa ggaagaagta tctcggtatg taaacttcta tcagcaggga 420
agatagtgac ggtacctgac taagaagccc cgkctaacta cgtgccagca gccgcggtaa 480
tacgtagggg gcaagcgtta tccggattta ctgggtgtaa agggagcgta gacggactgg 540
caagtctgat gtgaaaggcg ggggctcaac ccctggactg cattggaaac tgttagtctt 600
gagtgccgga gaggtaagcg gaattcctag tgtagcggtg aaatgcgtag atattaggag 660
gaacaccagt ggcgaaggcg gcttactgga cggtaactga cgttgaggct cgaaagcgtg 720
gggagcaaac aggattagat accctggtag tccacgccgc aaacgatgaa tactaggtgt 780
tggggagcaa agctcttcgg tgccgccgca aacgcattaa gtattccacc tggggagtac 840
gttcgcaaga atgaaactca aaggaattga cggggacccg cacaagcggt ggagcatgtg 900
gtttaattcg aagcaacgcg aagaacctta ccaagtcttg acatccctct gaccgtccct 960
taaccggatc tttccttcgg gacaggggag acaggtggtg catggttgtc gtcagctcgt 1020
gtcgtgagat gttgggttaa gtcccgcaac gagcgcaacc cctatcccca gtagccagca 1080
gtncggctgg gcactctgag gagactgcca gggataacct ggaggaaggc ggggatgacg 1140
tcaaatcatc atgcccctta tgatttgggc tacacacgtg ctacaatggc gtaaacaaag 1200
ggaagcnagc ctkcgraggt aagcaaatcc canaaataac gtcccagttc ggactgcagt 1260
ctgcaactcg actgcacgaa gctggaatcg ctagtaatcg cggatcagaa tgccgcggtg 1320
aatacgttcc cgggtcttgt acacaccgcc cgtcacacca tgggagtcag taacgcccga 1380
agtcagtgac ctaactgc 1398

<210> SEQ ID NO 86
<211> LENGTH: 1472
<212> TYPE: DNA
<213> ORGANISM: Clostridium disporicum

<400> SEQUENCE: 86
gctcaggacg aacgctggcg gcgtgcctaa cacatgcaag tcgagcgagt tgattctctt 60

-continued

```
cggagatgaa gctagcggcg gacgggtgag taacacgtgg gcaacctgcc tcatagaggg    120
gaatagcctc ccgaaaggga gattaatacc gcataagatt gtagcttcgc atgaagtagc    180
aattaaagga gcaatccgct atgagatggg cccgcggcgc attagctagt tggtgaggta    240
acggctcacc aaggcgacga tgcgtagccg acctgagagg gtgatcggcc acattgggac    300
tgagacacgg cccagactcc tacgggaggc agcagtgggg aatattgcac aatgggggaa    360
accctgatgc agcaacgccg cgtgagtgat gacggccttc gggttgtaaa gctctgtctt    420
cagggacgat aatgacggta cctgaggagg aagccacggc taactacgtg ccagcagccg    480
cggtaatacg taggtggcga gcgttgtccg gatttactgg gcgtaaaggg agcgtaggcg    540
gacttttaag tgagatgtga aatacccggg ctcaacttgg gtgctgcatt tcaaactgga    600
agtctagagt gcaggagagg agaatggaat tcctagtgta gcggtgaaat gcgtagagat    660
taggaagaac accagtggcg aaggcgattc tctggactgt aactgacgct gaggctcgaa    720
agcgtgggga gcaaacagga ttagataccc tggtagtcca cgccgtaaac gatgaatact    780
aggtgtaggg gttgtcatga cctctgtgcc gccgctaacg cattaagtat tccgcctggg    840
gagtacggtc gcaagattaa aactcaaagg aattgacggg ggcccgcaca agcagcggag    900
catgtggttt aattcgaagc aacgcgaaga accttaccta gacttgacat ctcctgaatt    960
acccgtaact ggggaagcca cttcggtggc aggaagacag gtggtgcatg gttgtcgtca   1020
gctcgtgtcg tgagatgttg ggttaagtcc cgcaacgagc gcaaccctta ttgttagttg   1080
ctaccattta gttgagcact ctagcgagac tgcccgggtt aaccgggagg aaggtgggga   1140
tgacgtcaaa tcatcatgcc ccttatgtct agggctacac acgtgctaca atggcaagta   1200
caaagagaag caagaccgcg aggtggagca aaactcaaaa acttgtctca gttcggattg   1260
taggctgaaa ctcgcctaca tgaagctgga gttgctagta atcgcgaatc agcatgtcgc   1320
ggtgaatacg ttcccgggcc ttgtacacac cgcccgtcac accatgagag ttggcaatac   1380
ccaacgtacg tgatctaacc cgcaagggag gaagcgtcct aaggtagggt cagcgattgg   1440
ggtgaagtcg taacaaggta gccgtaggag aa                                 1472
```

<210> SEQ ID NO 87
<211> LENGTH: 1529
<212> TYPE: DNA
<213> ORGANISM: Clostridium scindens

<400> SEQUENCE: 87

```
gagagtttga tcctggctca ggatgaacgc tggcggcgtg cctaacacat gcaagtcgaa     60
cgaagcgcct ggccccgact tcttcggaac gaggagcctt gcgactgagt ggcggacggg    120
tgagtaacgc gtgggcaacc tgccttgcac tgggggataa cagccagaaa tggctgctaa    180
taccgcataa gaccgaagcg ccgcatggcg cggcggccaa agccccggcg gtgcaagatg    240
ggcccgcgtc tgattaggta gttggcgggg taacggccca ccaagccgac gatcagtagc    300
cgacctgaga gggtgaccgg ccacattggg actgagacac ggcccagact cctacgggag    360
gcagcagtgg ggaatattgc acaatggggg aaaccctgat gcagcgacgc cgcgtgaagg    420
atgaagtatt tcggtatgta aacttctatc agcagggaag aagatgacgg tacctgacta    480
agaagccccg gctaactacg tgccagcagc cgcggtaata cgtagggggc aagcgttatc    540
cggatttact gggtgtaaag ggagcgtaga cggcgatgca agccagatgt gaaagcccgg    600
ggctcaaccc cgggactgca tttggaactg cgtggctgga gtgtcggaga ggcaggcgga    660
attcctagtg tagcggtgaa atgcgtagat attaggagga acaccagtgg cgaaggcggc    720
```

ctgctggacg atgactgacg ttgaggctcg aaagcgtggg gagcaaacag gattagatac 780
cctggtagtc cacgccgtaa acgatgacta ctaggtgtcg ggtggcaagg ccattcggtg 840
ccgcagcaaa cgcaataagt agtccacctg gggagtacgt tcgcaagaat gaaactcaaa 900
ggaattgacg gggacccgca caagcggtgg agcatgtggt ttaattcgaa gcaacgcgaa 960
gaaccttacc tgatcttgac atcccgatgc caaagcgcgt aacgcgctct ttcttcggaa 1020
catcggtgac aggtggtgca tggttgtcgt cagctcgtgt cgtgagatgt tgggttaagt 1080
cccgcaacga gcgcaacccc tatcttcagt agccagcatt ttggatgggc actctggaga 1140
gactgccagg gagaacctgg aggaaggtgg ggatgacgtc aaatcatcat gccccttatg 1200
accagggcta cacacgtgct acaatggcgt aaacaaaggg aggcgaaccc gcgagggtgg 1260
gcaaatccca aaaataacgt ctcagttcgg attgtagtct gcaactcgac tacatgaagt 1320
tggaatcgct agtaatcgcg aatcagaatg tcgcggtgaa tacgttcccg ggtcttgtac 1380
acaccgcccg tcacaccatg ggagtcagta acgcccgaag ccggtgaccc aacccgtaag 1440
ggagggagcc gtcgaaggtg ggaccgataa ctggggtgaa gtcgtaacaa ggtagccgta 1500
tcggaaggtg cggctggatc acctccttc 1529

<210> SEQ ID NO 88
<211> LENGTH: 1456
<212> TYPE: DNA
<213> ORGANISM: Anaerostipes caccae

<400> SEQUENCE: 88
gcgcttaata catgtcaagt cgaacgaagc atttaggatt gaagttttcg gatggatttc 60
ctatatgact gagtggcgga cgggtgagta acgcgtgggg aacctgccct atacaggggg 120
ataacagctg gaaacggctg ctaataccgc ataagcgcac agaatcgcat gattcagtgt 180
gaaaagccct ggcagtatag gatggtcccg cgtctgatta gctggttggt gaggtaacgg 240
ctcaccaagg cgacgatcag tagccggctt gagagagtga acggccacat tgggactgag 300
acacggccca aactcctacg ggaggcagca gtggggaata ttgcacaatg gggtaaacc 360 ctgatgcagc gacgccgcgt gagtgaagaa gtatttcggt atgtaaagct ctatcagcag 420
ggaagaaaac agacggtacc tgactaagaa gccccggcta actacgtgcc agcagccgcg 480
gtaatacgta gggggcaagc gttatccgga attactgggt gtaaagggtg cgtaggtggc 540
atggtaagtc agaagtgaaa gcccggggct taaccccggg actgcttttg aaactgtcat 600
gctggagtgc aggagaggta agcggaattc ctagtgtagc ggtgaaatgc gtagatatta 660
ggaggaacac cagtggcgaa ggcggcttac tggactgtca ctgacactga tgcacgaaag 720
cgtggggagc aaacaggatt agataccctg gtagtccacg ccgtaaacga tgaatactag 780
gtgtcggggc cgtagaggct tcggtgccgc agcaaacgca gtaagtattc cacctgggga 840
gtacgttcgc aagaatgaaa ctcaaaggaa ttgacgggga cccgcacaag cggtggagca 900
tgtggtttaa ttcgaagcaa cgcgaagaac cttacctggt cttgacatcc caatgaccga 960
accttaaccg gtttttctt tcgagacatt ggagacaggt ggtgcatggt tgtcgtcagc 1020
tcgtgtcgtg agatgttggg ttaagtcccg caacgagcgc aacccctatc tttagtagcc 1080
agcatttaag gtgggcactc tagagagact gccagggata acctggagga aggtggggac 1140
gacgtcaaat catcatgccc cttatggcca gggctacaca cgtgctacaa tggcgtaaac 1200
aaagggaagc gaagtcgtga ggcgaagcaa atcccagaaa taacgtctca gttcggattg 1260
tagtctgcaa ctcgactaca tgaagctgga atcgctagta atcgtgaatc agaatgtcac 1320
ggtgaatacg ttcccgggtc ttgtacacac cgcccgtcac accatgggag tcagtaacgc 1380
ccgaagtcag tgacccaacc gcaaggaggg agctgccgaa ggtgggaccg ataactgggg 1440
tgaagtcgta acaagg 1456

<210> SEQ ID NO 89
<211> LENGTH: 1456
<212> TYPE: DNA
<213> ORGANISM: Marvinbryantia formatexigens

<400> SEQUENCE: 89
tggcggcgtg cttaacacat gcaagtcgag cgaagcattt taaatgaagt tttcggacgg 60
aatttaaaat gactgagcgg cggacgggtg agtaacgcgt ggataacctg ccttatacag 120
ggggataaca gccagaaatg gctgctaata ccgcataagc gcacggtacc gcatggtaca 180
gtgtgaaaaa ctccggtggt ataagatggg tccgcgttgg attaggcagt tggcggggta 240
aaggcccacc aaaccgacga tccatagccg gcctgagagg gtggacggcc acattgggac 300
tgagacacgg cccagactcc tacgggaggc agcagtgggg aatattgcac aatgggggaa 360
accctgatgc agcgacgccg cgtgggtgaa gaagtatttc ggtatgtaaa gccctatcag 420
cagggaagaa aatgacggta cctgaccaag aagccccggc taactacgtg ccagcagccg 480
cggtaatacg tagggggcaa gcgttatccg gatttactgg gtgtaaaggg agcgtagacg 540
gccatgcaag tctggtgtga aaggcggggg ctcaaccccc ggactgcatt ggaaactgta 600
tggcttgagt gccggagagg taagcggaat tcctggtgta gcggtgaaat gcgtagatat 660
caggaggaac accagtggcg aaggcggctt actggacggt aactgacgtt gaggctcgaa 720
agcgtgggga gcaaacagga ttagataccc tggtagtcca cgccgtaaac gatgaatacc 780
aggtgtcggg ggacacggtc cttcggtgcc gcagcaaacg cactaagtat tccacctggg 840
gagtacgttc gcaagaatga aactcaaagg aattgacggg gacccgcaca agcggtggag 900
catgtggttt aattcgaagc aacgcgaaga accttaccag gtcttgacat ccggacgacc 960
ggacagtaac gtgtccttcc cttcggggcg tccgagacag gtggtgcatg gttgtcgtca 1020
gctcgtgtcg tgagatgttg ggttaagtcc cgcaacgagc gcaacccctg ttcccagtag 1080
ccagcattca ggatgggcac tctggggaga ctgccaggga taacctggag gaaggcgggg 1140
atgacgtcaa atcatcatgc cccttatgat ctgggctaca cacgtgctac aatggcgtga 1200
acagagggaa gcgaacccgc gagggggagc aaatcccaga aataacgtcc cagttcggat 1260
tgtagtctgc aacccggcta catgaagctg gaatcgctag taatcgcgga tcagcatgcc 1320
gcggtgaata cgttcccggg tcttgtacac accgcccgtc acaccatggg agtcggaaat 1380
gcccgaagtc agtgacccaa ccggaaggag ggagctgccg aaggcggggc cggtaactgg 1440
ggtgaagtcg taacaa 1456

<210> SEQ ID NO 90
<211> LENGTH: 1568
<212> TYPE: DNA
<213> ORGANISM: Lactobacillus mucosae

<400> SEQUENCE: 90
agagtttgat cctggctcag gatgaacgcc ggcggtgtgc ctaatacatg caagtcgaac 60
gcgttggccc aactgattga acgtgcttgc acggacttga cgttggttta ccagcgagtg 120
gcggacgggt gagtaacacg taggtaacct gccccaaagc gggggataac atttggaaac 180

```
agatgctaat accgcataac aatttgaatc gcatgattca aatttaaaag atggcttcgg     240
ctatcacttt gggatggacc tgcggcgcat tagcttgttg gtagggtaac ggcctaccaa     300
ggctgtgatg cgtagccgag ttgagagact gatcggccac aatggaactg agacacggtc     360
catactccta cgggaggcag cagtagggaa tcttccacaa tgggcgcaag cctgatggag     420
caacaccgcg tgagtgaaga agggtttcgg ctcgtaaagc tctgttgtta gagaagaacg     480
tgcgtgagag caactgttca cgcagtgacg gtatctaacc agaaagtcac ggctaactac     540
gtgccagcag ccgcggtaat acgtaggtgg caagcgttat ccggatttat tgggcgtaaa     600
gcgagcgcag gcggtttgat aagtctgatg tgaaagcctt tggcttaacc aaagaagtgc     660
atcggaaact gtcagacttg agtgcagaag aggacagtgg aactccatgt gtagcggtgg     720
aatgcgtaga tatatggaag aacaccagtg gcgaaggcgg ctgtctggtc tgcaactgac     780
gctgaggctc gaaagcatgg gtagcgaaca ggattagata ccctggtagt ccatgccgta     840
aacgatgagt gctaggtgtt ggagggtttc cgcccttcag tgccgcagct aacgcattaa     900
gcactccgcc tggggagtac gaccgcaagg ttgaaactca aaggaattga cgggggcccg     960
cacaagcggt ggagcatgtg gtttaattcg aagctacgcg aagaacctta ccaggtcttg    1020
acatcttgcg ccaaccctag agatagggcg tttccttcgg gaacgcaatg acaggtggtg    1080
catggtcgtc gtcagctcgt gtcgtgagat gttgggttaa gtcccgcaac gagcgcaacc    1140
cttgttacta gttgccagca ttcagttggg cactctagtg agactgccgg tgacaaaccg    1200
gaggaaggtg gggacgacgt cagatcatca tgccccttat gacctgggct acacacgtgc    1260
tacaatggac ggtacaacga gtcgcgaact cgcgagggca agctaatctc ttaaaaccgt    1320
tctcagttcg gactgcaggc tgcaactcgc ctgcacgaag tcggaatcgc tagtaatcgc    1380
ggatcagcat gccgcggtga atacgttccc gggccttgta cacaccgccc gtcacaccat    1440
gagagtttgc aacacccaaa gtcggtgggg taacccttcg ggagctagc cgcctaaggt     1500
ggggcagatg attagggtga agtcgtaaca aggtagccgt aggagaacct gcggctggat    1560
cacctcct                                                             1568
```

<210> SEQ ID NO 91
<211> LENGTH: 1508
<212> TYPE: DNA
<213> ORGANISM: Turicibacter sanguinis

<400> SEQUENCE: 91

```
agagtttgat catggctcag gatgaacgct ggcggcgtgc ctaatacatg caagtcgagc      60
gaaccacttc ggtggtgagc ggcgaacggg tgagtaacac gtaggttatc tgcccatcag     120
acggggacaa cgattggaaa cgatcgctaa taccggatag gacgaaagtt taaaggtgct     180
tcggcaccac tgatggatga gcctgcggcg cattagctag ttggtagggt aaaggcctac     240
caaggcgacg atgcgtagcc gacctgagag ggtgaacggc cacactggga ctgagacacg     300
gcccagactc ctacgggagg cagcagtagg gaatcttcgg caatgggcga aagcctgacc     360
gagcaacgcc gcgtgaatga tgaaggcctt cgggttgtaa aattctgtta taagggaaga     420
atggctctag taggaaatgg ctagagtgtg acggtacctt atgagaaagc cacggctaac     480
tacgtgccag cagccgcggt aatacgtagg tggcgagcgt tatccggaat tattgggcgt     540
aaagagcgcg caggtggttg attaagtctg atgtgaaagc ccacggctta accgtggagg     600
gtcattggaa actggtcaac ttgagtgcag aagagggaag tggaattcca tgtgtagcgg     660
```

-continued

```
tgaaatgcgt agagatatgg aggaacacca gtggcgaagg cggcttcctg gtctgtaact    720

gacactgagg cgcgaaagcg tggggagcaa acaggattag ataccctggt agtccacgcc    780

gtaaacgatg agtgctaagt gttgggggtc gaacctcagt gctgaagtta acgcattaag    840

cactccgcct ggggagtacg gtcgcaagac tgaaactcaa aggaattgac ggggacccgc    900

acaagcggtg gagcatgtgg tttaattcga agcaacgcga agaaccttac caggtcttga    960

cataccagtg accgtcctag agataggatt ttcccttcgg ggacaatgga tacaggtggt   1020

gcatggttgt cgtcagctcg tgtcgtgaga tgttgggtta agtcccgcaa cgagcgcaac   1080

ccctgtcgtt agttgccagc attcagttgg ggactctaac gagactgcca gtgacaaact   1140

ggaggaaggt ggggatgacg tcaaatcatc atgcccctta tgacctgggc tacacacgtg   1200

ctacaatggt tggtacaaag agaagcgaag cggtgacgtg gagcaaacct cataaagcca   1260

atctcagttc ggattgtagg ctgcaactcg cctacatgaa gttggaatcg ctagtaatcg   1320

cgaatcagca tgtcgcggtg aatacgttcc cgggtcttgt acacaccgcc cgtcacacca   1380

cgagagttta caacacccga agtcagtggc ctaaccgcaa ggagggagct gcctaaggtg   1440

gggtagatga ttggggtgaa gtcgtaacaa ggtatcccta ccggaaggtg gggttggatc   1500

acctcctt                                                            1508
```

```
<210> SEQ ID NO 92
<211> LENGTH: 1456
<212> TYPE: DNA
<213> ORGANISM: Roseburia faecis

<400> SEQUENCE: 92
```

```
gatgaacgct ggcggcgtgc ttaacacatg caagtcgaac gaagcactct atttgatttt     60

cttcggaaat gaagattttg tgactgagtg gcggacgggt gagtaacgcg tgggtaacct    120

gcctcataca gggggataac agttggaaac gactgctaat accgcataag cgcacaggat    180

cgcatgatcc ggtgtgaaaa actccggtgg tatgagatgg acccgcgtct gattagccag    240

ttggcagggt aacggcctac caaagcgacg atcagtagcc gacctgagag ggtgaccggc    300

cacattggga ctgagacacg gcccaaactc ctacgggagg cagcagtggg gaatattgca    360

caatggggga aaccctgatg cagcgacgcc gcgtgagcga agaagtattt cggtatgtaa    420

agctctatca gcagggaaga agaatgacgg tacctgacta agaagcaccg gctaaatacg    480

tgccagcagc cgcggtaata cgtatggtgc aagcgttatc cggatttact gggtgtaaag    540

ggagcgcagg cggtgcggca agtctgatgt gaaagcccgg ggctcaaccc cggtactgca    600

ttggaaactg tcgtactaga gtgtcggagg ggtaagtgga attcctagtg tagcggtgaa    660

atgcgtagat attaggagga acaccagtgg cgaaggcggc ttactggacg ataactgacg    720

ctgaggctcg aaagcgtggg gagcaaacag gattagatac cctggtagtc cacgccgtaa    780

acgatgaata ctaggtgtcg ggagcattg ctcttcggtg ccgcagcaaa cgcaataagt    840

attccacctg gggagtacgt tcgcaagaat gaaactcaaa ggaattgacg gggacccgca    900

caagcggtgg agcatgtggt ttaattcgaa gcaacgcgaa gaaccttacc aagtcttgac    960

atcccgatga cagagtatgt aatgtacytt ctcttcggag catcggtgac aggtggtgca   1020

tggttgtcgt cagctcgtgt cgtgagatgt tgggttaagt cccgcaacga gcgcaacccc   1080

tgtccttagt agccagcggt tcggccgggc actctaggga gactgccagg gataacctgg   1140

aggaaggcgg ggatgacgtc aaatcatcat gccccttatg acttgggcta cacacgtgct   1200

acaatggcgt aaacaaaggg aagcggagcc gtgaggccga gcaaatctca aaaataacgt   1260
```

ctcagttcgg actgtagtct gcaacccgac tacacgaagc tggaatcgct agtaatcgca 1320
gatcagaatg ctgcggtgaa tacgttcccg ggtcttgtac acaccgcccg tcacaccatg 1380
ggagttggaa atgcccgaag tcagtgaccc aaccgcaagg agggagctgc cgaaggcagg 1440
ttcgataact ggggtg 1456

<210> SEQ ID NO 93
<211> LENGTH: 1465
<212> TYPE: DNA
<213> ORGANISM: Flavonifractor plautii

<400> SEQUENCE: 93
cgctggcggc gtgcttaaca catgcaagtc gaacggggtg ctcatgacgg aggattcgtc 60
caatggattg agttacctag tggcggacgg gtgagtaacg cgtgaggaac ctgccttgga 120
gaggggaata acactccgaa aggagtgcta ataccgcatg aagcagttgg gtcgcatggc 180
tctgactgcc aaagatttat cgctctgaga tggcctcgcg tctgattagc tagtaggcgg 240
ggtaacggcc cacctaggcg acgatcagta gccggactga gaggttgacc ggccacattg 300
ggactgagac acggcccaga ctcctacggg aggcagcagt ggggaatatt gggcaatggg 360
cgcaagcctg acccagcaac gccgcgtgaa ggaagaaggc tttcgggttg taaacttctt 420
ttgtcgggga cgaaacaaat gacggtaccc gacgaataag ccacggctaa ctacgtgcca 480
gcagccgcgg taatacgtag gtggcaagcg ttatccggat ttactgggtg taaagggcgt 540
gtaggcggga ttgcaagtca gatgtgaaaa ctgggggctc aacctccagc ctgcatttga 600
aactgtagtt cttgagtgct ggagaggcaa tcggaattcc gtgtgtagcg gtgaaatgcg 660
tagatatacg gaggaacacc agtggcgaag gcggattgct ggacagtaac tgacgctgag 720
gcgcgaaagc gtggggagca aacaggatta gataccctgg tagtccacgc cgtaaacgat 780
ggatactagg tgtggggggt ctgaccccct ccgtgccgca gttaacacaa taagtatccc 840
acctggggag tacgatcgca aggttgaaac tcaaaggaat tgacgggggc ccgcacaagc 900
ggtggagtat gtggtttaat tcgaagcaac gcgaagaacc ttaccagggc ttgacatccc 960
actaacgagg cagagatgcg ttaggtgccc ttcggggaaa gtggagacag gtggtgcatg 1020
gttgtcgtca gctcgtgtcg tgagatgttg ggttaagtcc cgcaacgagc gcaaccctta 1080
ttgttagttg ctacgcaaga gcactctagc gagactgccg ttgacaaaac ggaggaaggt 1140
ggggacgacg tcaaatcatc atgcccctta tgtcctgggc cacacacgta ctacaatggt 1200
ggttaacaga gggaggcaat accgcgaggt ggagcaaatc cctaaaagcc atcccagttc 1260
ggattgcagg ctgaaacccg cctgtatgaa gttggaatcg ctagtaatcg cggatcagca 1320
tgccgcggtg aatacgttcc cgggccttgt acacaccgcc cgtcacacca tgagagtcgg 1380
gaacacccga agtccgtagc ctaaccgcaa ggagggcgcg gccgaaggtg ggttcgataa 1440
ttggggtgaa gtcgtaacaa ggtag 1465

<210> SEQ ID NO 94
<211> LENGTH: 1438
<212> TYPE: DNA
<213> ORGANISM: Blautia wexlerae
<220> FEATURE:
<221> NAME/KEY: misc_feature
<222> LOCATION: (19)..(19)
<223> OTHER INFORMATION: n is a, c, g, t or u

<400> SEQUENCE: 94

-continued

```
caagtcgaac gggaattant ttattgaaac ttcggtcgat ttaatttaat tctagtggcg     60
gacgggtgag taacgcgtgg gtaacctgcc ttatacaggg ggataacagt cagaaatggc    120
tgctaatacc gcataagcgc acagagctgc atggctcagt gtgaaaaact ccggtggtat    180
aagatggacc cgcgttggat tagcttgttg gtggggtaac ggcccaccaa ggcgacgatc    240
catagccggc ctgagagggt gaacggccac attgggactg agacacggcc cagactccta    300
cgggaggcag cagtggggaa tattgcacaa tgggggaaac cctgatgcag cgacgccgcg    360
tgaaggaaga agtatctcgg tatgtaaact tctatcagca gggaagatag tgacggtacc    420
tgactaagaa gccccggcta actacgtgcc agcagccgcg gtaatacgta gggggcaagc    480
gttatccgga tttactgggt gtaaagggag cgtagacggt gtggcaagtc tgatgtgaaa    540
ggcatgggct caacctgtgg actgcattgg aaactgtcat acttgagtgc cggaggggta    600
agcggaattc ctagtgtagc ggtgaaatgc gtagatatta ggaggaacac cagtggcgaa    660
ggcggcttac tggacggtaa ctgacgttga ggctcgaaag cgtggggagc aaacaggatt    720
agataccctg gtagtccacg ccgtaaacga tgaataacta ggtgtcgggt ggcaaagcca    780
ttcggtgccg tcgcaaacgc agtaagtatt ccacctgggg agtacgttcg caagaatgaa    840
actcaaagga attgacgggg acccgcacaa gcggtggagc atgtggttta attcgaagca    900
acgcgaagaa ccttaccaag tcttgacatc cgcctgaccg atccttaacc ggatctttcc    960
ttcgggacag gcgagacagg tggtgcatgg ttgtcgtcag ctcgtgtcgt gagatgttgg   1020
gttaagtccc gcaacgagcg caacccctat cctcagtagc cagcatttaa ggtgggcact   1080
ctggggagac tgccagggat aacctggagg aaggcgggga tgacgtcaaa tcatcatgcc   1140
ccttatgatt tgggctacac acgtgctaca atggcgtaaa caaagggaag cgagattgtg   1200
agatggagca aatcccaaaa ataacgtccc agttcggact gtagtctgca acccgactac   1260
acgaagctgg aatcgctagt aatcgcggat cagaatgccg cggtgaatac gttcccgggt   1320
cttgtacaca ccgcccgtca caccatggga gtcagtaacg cccgaagtca gtgacctaac   1380
tgcaaagaag gagctgccga aggcgggacc gatgactggg gtgaagtcgt aacaaggt     1438
```

<210> SEQ ID NO 95
<211> LENGTH: 1365
<212> TYPE: DNA
<213> ORGANISM: Anaerotruncus colihominis

<400> SEQUENCE: 95

```
aacggagctt acgttttgaa gttttcggat ggatgaatgt aagcttagtg gcggacgggt     60
gagtaacacg tgagcaacct gcctttcaga gggggataac agccggaaac ggctgctaat    120
accgcatgat gttgcggggg cacatgcccc tgcaaccaaa ggagcaatcc gctgaaagat    180
gggctcgcgt ccgattagcc agttggcggg gtaacggccc accaaagcga cgatcggtag    240
ccggactgag aggttgaacg gccacattgg gactgagaca cggcccagac tcctacggga    300
ggcagcagtg gggatattg cacaatgggc gaaagcctga tgcagcgacg ccgcgtgagg    360
gaagacggtc ttcggattgt aaacctctgt ctttggggaa gaaaatgacg gtacccaaag    420
aggaagctcc ggctaactac gtgccagcag ccgcggtaat acgtagggag caagcgttgt    480
ccggaattac tgggtgtaaa gggagcgtag gcgggatggc aagtagaatg ttaaatccat    540
cggctcaacc ggtggctgcg ttctaaactg ccgttcttga gtgaagtaga ggcaggcgga    600
attcctagtg tagcggtgaa atgcgtagat attaggagga acaccagtgg cgaaggcggc    660
ctgctgggct ttaactgacg ctgaggctcg aaagcgtggg gagcaaacag gattagatac    720
```

```
cctggtagtc cacgccgtaa acgatgatta ctaggtgtgg ggggactgac cccttccgtg      780

ccgcagttaa cacaataagt aatccacctg gggagtacgg ccgcaaggtt gaaactcaaa      840

ggaattgacg ggggcccgca caagcagtgg agtatgtggt ttaattcgaa gcaacgcgaa      900

gaaccttacc aggtcttgac atcggcgtaa tagcctagag agtaggtgaa gcccttcggg      960

gcatccagac aggtggtgca tggttgtcgt cagctcgtgt cgtgagatgt tgggttaagt     1020

cccgcaacga gcgcaaccct tattattagt tgctacgcaa gagcactcta atgagactgc     1080

cgttgacaaa acggaggaag gtggggatga cgtcaaatca tcatgcccct tatgacctgg     1140

gctacacacg tactacaatg gcactaaaac agagggcggc gacaccgcga ggtgaagcga     1200

atcccagaaa aagtgtctca gttcagattg caggctgcaa cccgcctgca tgaagtcgga     1260

attgctagta atcgcggatc agcatgccgc ggtgaatacg ttcccgggcc ttgtacacac     1320

cgcccgtcac accatgggag tccgggtaac acccgaagcc agtag                     1365

<210> SEQ ID NO 96
<211> LENGTH: 1404
<212> TYPE: DNA
<213> ORGANISM: Ruminococcus faecis

<400> SEQUENCE: 96

atgcaagtcg aacgaagcac cttgatttga ttcttcggat gaagatcttg gtgactgagt       60

ggcggacggg tgagtaacgc gtgggtaacc tgcctcatac agggggataa cagttagaaa      120

tgactgctaa taccgcataa gaccacagca ccgcatggtg caggggtaaa aactccggtg      180

gtatgagatg gacccgcgtc tgattaggta gttggtgggg taacggccta ccaagccgac      240

gatcagtagc cgacctgaga gggtgaccgg ccacattggg actgagacac ggcccaaact      300

cctacgggag gcagcagtgg ggaatattgc acaatggggg aaaccctgat gcagcgacgc      360

cgcgtgagcg atgaagtatt tcggtatgta aagctctatc agcagggaag aaaatgacgg      420

tacctgacta agaagcaccg gctaaatacg tgccagcagc cgcggtaata cgtatggtgc      480

aagcgttatc cggatttact gggtgtaaag ggagcgtaga cggagtggca agtctgatgt      540

gaaaacccgg ggctcaaccc cgggactgca ttggaaactg tcaatctaga gtaccggaga      600

ggtaagcgga attcctagtg tagcggtgaa atgcgtagat attaggagga acaccagtgg      660

cgaaggcggc ttactggacg gtaactgacg ttgaggctcg aaagcgtggg gagcaaacag      720

gattagatac cctggtagtc cacgccgtaa acgatgacta ctaggtgtcg ggcagcaaag      780

ctgttcggtg ccgcagcaaa cgcaataagt agtccacctg gggagtacgt cgcaagaat      840

gaaactcaaa ggaattgacg gggacccgca caagcggtgg agcatgtggt ttaattcgaa      900

gcaacgcgaa gaaccttacc tgctcttgac atctccctga ccggcaagta atgttgcctt      960

tccttcggga cagggatgac aggtggtgca tggttgtcgt cagctcgtgt cgtgagatgt     1020

tgggttaagt cccgcaacga gcgcaacccc tatctttagt agccagcggt ttggccgggc     1080

actctagaga gactgccagg gataacctgg aggaaggtgg ggatgacgtc aaatcatcat     1140

gccccttatg agcagggcta cacacgtgct acaatggcgt aaacaaaggg aggcagaacc     1200

gcgaggtcga gcaaatccca aaaataacgt ctcagttcgg attgtagtct gcaactcgac     1260

tacatgaagc tggaatcgct agtaatcgcg aatcagaatg tcgcggtgaa tacgttcccg     1320

ggtcttgtac acaccgcccg tcacaccatg ggagtcagta acgcccgaag tcagtgaccc     1380

aaccgtaagg aggagctgcc gaag                                           1404
```

<210> SEQ ID NO 97
<211> LENGTH: 1316
<212> TYPE: DNA
<213> ORGANISM: Dorea longicatena

<400> SEQUENCE: 97
taacgcgtgg gtaacctgcc tcatacaggg ggataacagt tagaaatgac tgctaatacc 60
gcataagacc acgtaccgca tggtacagtg gtaaaaactc cggtggtatg agatggaccc 120
gcgtctgatt aggtagttgg tggggtaacg gcctaccaag ccgacgatca gtagccgacc 180
tgagagggtg accggccaca ttgggactga gacacggccc agactcctac gggaggcagc 240
agtggggaat attgcacaat ggaggaaact ctgatgcagc gacgccgcgt gaaggatgaa 300
gtatttcggt atgtaaactt ctatcagcag ggaagaaaat gacggtacct gactaagaag 360
ccccggctaa ctacgtgcca gcagccgcgg taatacgtag ggggcaagcg ttatccggat 420
ttactgggtg taaagggagc gtagacggca cggcaagcca gatgtgaaaa gcccggggct 480
caaccccggg actgcatttg gaactgctga gctagagtgt cggagaggca agtggaattc 540
ctagtgtagc ggtgaaatgc gtagatatta ggaggaacac cagtggcgaa ggcggcttgc 600
tggacgatga ctgacgttga ggctcgaaag cgtggggagc aaacaggatt agataccctg 660
gtagtccacg ccgtaaacga tgactgctag gtgtcgggtg gcaaagccat tcggtgccgc 720
agctaacgca ataagcagtc cacctgggga gtacgttcgc aagaatgaaa ctcaaaggaa 780
ttgacgggga cccgcacaag cggtggagca tgtggtttaa ttcgaagcaa cgcgaagaac 840
cttacctgat cttgacatcc cgatgaccgc ttcgtaatgg aagtttttct tcggaacatc 900
ggtgacaggt ggtgcatggt tgtcgtcagc tcgtgtcgtg agatgttggg ttaagtcccg 960
caacgagcgc aacccctatc ttcagtagcc agcaggttaa gctgggcact ctggagagac 1020
tgccagggat aacctggagg aaggtgggga tgacgtcaaa tcatcatgcc ccttatgacc 1080
agggctacac acgtgctaca atggcgtaaa caaagagaag cgaactcgcg agggtaagca 1140
aatctcaaaa ataacgtctc agttcggatt gtagtctgca actcgactac atgaagctgg 1200
aatcgctagt aatcgcagat cagaatgctg cggtgaatac gttcccgggt cttgtacaca 1260
ccgcccgtca caccatggga gtcataacgc ccgaagtcag tgacccaacc gtaagg 1316

<210> SEQ ID NO 98
<211> LENGTH: 1475
<212> TYPE: DNA
<213> ORGANISM: Clostridium innocuum
<220> FEATURE:
<221> NAME/KEY: misc_feature
<222> LOCATION: (905)..(905)
<223> OTHER INFORMATION: n is a, c, g, t or u
<220> FEATURE:
<221> NAME/KEY: misc_feature
<222> LOCATION: (942)..(942)
<223> OTHER INFORMATION: n is a, c, g, t or u

<400> SEQUENCE: 98
atggagagtt tgatcctggc tcaggatgaa cgctggcggc atgcctaata catgcaagtc 60
gaacgaagtc ttcaggaagc ttgcttccaa aaagacttag tggcgaacgg gtgagtaaca 120
cgtaggtaac ctgcccatgt gtccgggata actgctggaa acggtagcta aaaccggata 180
ggtatacgga gcgcatgctc tgtatattaa agcgcccttc aaggcgtgaa catggatgga 240
cctgcgacgc attagctagt tggtgaggta acggcccacc aaggcgatga tgcgtagccg 300
gcctgagagg gtaaacggcc acattgggac tgagacacgg cccaaactcc tacgggaggc 360
agcagtaggg aattttcgtc aatgggggaa accctgaacg agcaatgccg cgtgagtgaa 420
gaaggtcttc ggatcgtaaa gctctgttgt aagtgaagaa cggctcatag aggaaatgct 480
atgggagtga cggtagctta ccagaaagcc acggctaact acgtgccagy agccgcggta 540
atacgtaggt ggcaagcgtt atccggaatc attgggcgta aagggtgcgt aggtggcgta 600
ctaagtctgt agtaaaaggc aatggctcaa ccattgtaag ctatggaaac tggtatgctg 660
gagtgcagaa gagggcgatg gaattccatg tgtagcggta aaatgcgtag atatatggag 720
gaacaccagt ggcgaaggcg gtcgcctggt ctgtaactga cactgaggca cgaaagcgtg 780
gggagcaaat aggattagat accctagtag tccacgccgt aaacgatgag aactaagtgt 840
tggagaaatt cagtgctgca gttaacgcaa taagttctcc gcctggggag tatgcacgca 900
agttngaaac tcaaaggaat tgacgggggc ccgcacaagc gntggagtat gtggtttaat 960
tcgaagcaac gcgaagaacc ttaccaggcc ttgacatgga aacaaatacc ctagagatag 1020
ggggataatt atggatcaca caggtggtgc atggttgtcg tcagctcgtg tcgtgagatg 1080
ttgggttaag tcccgcaacg agcgcaaccc ttgtcgcatg ttaccagcat caagttgggg 1140
actcatgcga gactgccggt gacaaaccgg aggaaggtgg ggatgacgtc aaatcatcat 1200
gccccttatg gcctgggcta cacacgtact acaatggcga ccacaaagag cagcgacttg 1260
gtgacaagaa gcgaatctca taaagatcgt ctcagttcgg attgaagtct gcaactcgac 1320
ttcatgaagt cggaatcgct agtaatcgca gatcagcatg ctgcggtgaa tacgttctcg 1380
ggccttgtac acaccgcccg tcaaaccatg ggagtcagta atacccgaag ccggtggcat 1440
aaccgtaagg agtgagccgt cgaaggtagg accga 1475

<210> SEQ ID NO 99
<211> LENGTH: 1492
<212> TYPE: DNA
<213> ORGANISM: Blautia hansenii

<400> SEQUENCE: 99
agagtttgat cctggctcag gatgaacgct ggcggcgtgc ttaacacatg caagtcgagc 60
gaagcactta tcattgactc ttcggaagat ttgatatttg actgagcggc ggacgggtga 120
gtaacgcgtg ggtaacctgc ctcatacagg ggaataacag ttagaaatgg ctgctaatgc 180
cgcataagcg cacaggaccg catggtctgg tgtgaaaaac tgaggtggta tgagatggac 240
ccgcgtctga ttaggtagtt ggtggggtaa cggcctacca agccgacgat cagtagccgg 300
cctgagaggg tgaacggcca cattgggact gagacacggc ccagactcct acgggaggca 360
gcagtgggga atattgcaca atgggggaaa ccctgatgca gcgacgccgc gtgaaggaag 420
aagtatctcg gtatgtaaac ttctatcagc agggaagaaa atgacggtac ctgactaaga 480
agccccggct aactacgtgc cagcagccgc ggtaatacgt agggggcaag cgttatccgg 540
atttactggg tgtaaaggga gcgtagacgg aagagcaagt ctgatgtgaa aggctggggc 600
ttaaccccag gactgcattg gaaactgttt ttctagagtg ccggagaggt aagcggaatt 660
cctagtgtag cggtgaaatg cgtagatatt aggaggaaca ccagtggcga aggcggctta 720
ctggacggta actgacgttg aggctcgaaa gcgtggggag caaacaggat tagataccct 780
ggtagtccac gccgtaaacg atgaatacta ggtgtcgggg tgcaaagcag ttcggtgccg 840
cagcaaacgc aataagtatt ccacctgggg agtacgttcg caagaatgaa actcaaagga 900
attgacgggg acccgcacaa gcggtggagc atgtggttta attcgaagca acgcgaagaa 960

-continued

```
ccttaccaag tcttgacatc tgcctgaccg ttccttaacc ggagctttcc ttcgggacag   1020

gcaagacagg tggtgcatgg ttgtcgtcag ctcgtgtcgt gagatgttgg gttaagtccc   1080

gcaacgagcg caacccctat ccttagtagc cagcagtccg gctgggcact ctagggagac   1140

tgccggggat aacccggagg aaggcgggga cgacgtcaaa tcatcatgcc ccttatgatt   1200

tgggctacac acgtgctaca atggcgtaaa caaagggaag cgaagcggtg acgcttagca   1260

aatctcaaaa ataacgtccc agttcggact gcagtctgca actcgactgc acgaagctgg   1320

aatcgctagt aatcgcgaat cagaatgtcg cggtgaatac gttcccgggt cttgtacaca   1380

ccgcccgtca caccatggga gtcagtaacg cccgaagtca gtgacccaac cttatggagg   1440

gagctgccga aggcgggacc gataactggg gtgaagtcgt aacaaggtaa cc           1492
```

<210> SEQ ID NO 100
<211> LENGTH: 1473
<212> TYPE: DNA
<213> ORGANISM: Bacteroides cellulosilyticus

<400> SEQUENCE: 100

```
agagtttgat cctggctcag gatgaacgct agctacaggc ttaacacatg caagtcgagg     60

ggcagcatga cctagcaata ggttgatggc gaccggcgca cgggtgagta acacgtatcc    120

aacctaccgg ttattccggg atagcctttc gaaagaaaga ttaataccgg atagtataac    180

gagaaggcat ctttttgtta ttaaagaatt tcgataaccg atggggatgc gttccattag    240

tttgttggcg gggtaacggc ccaccaagac atcgatggat aggggttctg agaggaaggt    300

cccccacatt ggaactgaga cacggtccaa actcctacgg gaggcagcag tgaggaatat    360

tggtcaatgg acgagagtct gaaccagcca agtagcgtga aggatgactg ccctatgggt    420

tgtaaacttc ttttatatgg gaataaagtg agccacgtgt ggctttttgt atgtaccata    480

cgaataagga tcggctaact ccgtgccagc agccgcggta atacggagga tccgagcgtt    540

atccggattt attgggttta aagggagcgt aggcggacta ttaagtcagc tgtgaaagtt    600

tgcggctcaa ccgtaaaatt gcagttgata ctggtcgtct tgagtgcagt agaggtaggc    660

ggaattcgtg gtgtagcggt gaaatgctta gatatcacga agaactccga ttgcgaaggc    720

agcttactgg actgtaactg acgctgatgc tcgaaagtgt gggtatcaaa caggattaga    780

taccctggta gtccacacag taaacgatga atactcgctg tttgcgatat acagcaagcg    840

gccaagcgaa agcattaagt attccacctg gggagtacgc cggcaacggt gaaactcaaa    900

ggaattgacg gggcccgca caagcggagg aacatgtggt ttaattcgat gatacgcgag    960

gaaccttacc cgggcttaaa ttgcatctga ataatttgga aacagattag ccgcaaggca   1020

gatgtgaagg tgctgcatgg ttgtcgtcag ctcgtgccgt gaggtgtcgg cttaagtgcc   1080

ataacgagcg caacccttat ctttagttac taacaggtca tgctgaggac tctagagaga   1140

ctgccgtcgt aagatgtgag gaaggtgggg atgacgtcaa atcagcacgg cccttacgtc   1200

cggggctaca cacgtgttac aatggggggt acagaaggca gctacacagc gatgtgatgc   1260

taatcccaaa agcctctctc agttcggatt ggagtctgca acccgactcc atgaagctgg   1320

attcgctagt aatcgcgcat cagccacggc gcggtgaata cgttcccggg ccttgtacac   1380

accgcccgtc aagccatgaa agccgggggt acctgaagtc cgtaaccgca aggagcggcc   1440

tagggtaaaa ctggtaattg gggctaagtc gta                                1473
```

<210> SEQ ID NO 101
<211> LENGTH: 1459

<212> TYPE: DNA
<213> ORGANISM: Bacteroides ovatus

<400> SEQUENCE: 101

```
ggctcaggat gaacgctagc tacaggctta acacatgcaa gtcgaggggc agcattttag      60
tttgcttgca aactgaagat ggcgaccggc gcacgggtga gtaacacgta tccaacctgc     120
cgataactcc ggaatagcct ttcgaaagaa agattaatac cggatagcat acgaatatcg     180
catgatattt ttattaaaga atttcggtta tcgatgggga tgcgttccat tagtttgttg     240
gcggggtaac ggcccaccaa gactacgatg gataggggtt ctgagaggaa ggtcccccac     300
attggaactg agacacggtc caaactccta cgggaggcag cagtgaggaa tattggtcaa     360
tgggcgagag cctgaaccag ccaagtagcg tgaaggatga aggctctatg ggtcgtaaac     420
ttcttttata tgggaataaa gttttccacg tgtggaattt tgtatgtacc atatgaataa     480
ggatcggcta actccgtgcc agcagccgcg gtaatacgga ggatccgagc gttatccgga     540
tttattgggt ttaaagggag cgtaggtgga ttgttaagtc agttgtgaaa gtttgcggct     600
caaccgtaaa attgcagttg aaactggcag tcttgagtac agtagaggtg ggcggaattc     660
gtggtgtagc ggtgaaatgc ttagatatca cgaagaactc cgattgcgaa ggcagctcac     720
tagactgtta ctgacactga tgctcgaaag tgtgggtatc aaacaggatt agataccctg     780
gtagtccaca cagtaaacga tgaatactcg ctgtttgcga tatacagtaa gcggccaagc     840
gaaagcatta agtattccac ctggggagta cgccggcaac ggtgaaactc aaaggaattg     900
acgggggccc gcacaagcgg aggaacatgt ggtttaattc gatgatacgc gaggaacctt     960
acccgggctt aaattgcaac agaatatatt ggaaacagta tagccgtaag gctgttgtga    1020
aggtgctgca tggttgtcgt cagctcgtgc cgtgaggtgt cggcttaagt gccataacga    1080
gcgcaaccct tatctttagt tactaacagg ttatgctgag gactctagag agactgccgt    1140
cgtaagatgt gaggaaggtg gggatgacgt caaatcagca cggcccttac gtccggggct    1200
acacacgtgt tacaatgggg ggtacagaag gcagctacct ggcgacagga tgctaatccc    1260
aaaaacctct ctcagttcgg atcgaagtct gcaacccgac ttcgtgaagc tggattcgct    1320
agtaatcgcg catcagccat ggcgcggtga atacgttccc gggccttgta cacaccgccc    1380
gtcaagccat gaaagccggg ggtacctgaa gtacgtaacc gcaaggagcg tcctagggta    1440
aaactggtaa ttggggcta                                                 1459
```

<210> SEQ ID NO 102
<211> LENGTH: 1526
<212> TYPE: DNA
<213> ORGANISM: Eubacterium fissicatena

<400> SEQUENCE: 102

```
tagagtttga tcctggctca ggatgaacgc tggcggcgtg cttaacacat gcaagtcgag      60
cgaagcgctt tacttagatt tcttcggatt gaagagtttt gcgactgagc ggcggacggg     120
tgagtaacgc gtgggtaacc tgcctcatac agggggataa cagttagaaa tgactgctaa     180
taccgcataa gaccacagta ccgcatggta cagtgggaaa aactccggtg gtatgagatg     240
gacccgcgtc tgattagcta gttggtaagg taacggctta ccaaggcgac gatcagtagc     300
cgacctgaga gggtgaccgg ccacattggg actgagacac ggcccaaact cctacgggag     360
gcagcagtgg ggaatattgc acaatggggg aaaccctgat gcagcgacgc cgcgtgaagg     420
atgaagtatt tcggtatgta aacttctatc agcagggaag aaaatgacgg tacctgacta     480
```

agaagccccg gctaactacg tgccagcagc cgcggtaata cgtagggggc aagcgttatc 540
cggatttact gggtgtaaag ggagcgtaga cggttatgta agtctgatgt gaaaacccgg 600
ggctcaaccc cgggactgca ttggaaacta tgtaactaga gtgtcggaga ggtaagtgga 660
attcctagtg tagcggtgaa atgcgtagat attaggagga acaccagtgg cgaaggcggc 720
ttactggacg atcactgacg ttgaggctcg aaagcgtggg gagcaaacag gattagatac 780
cctggtagtc cacgccgtaa acgatgaata ctaggtgtcg ggtggcaaag ccattcggtg 840
ccgcagcaaa cgcaataagt attccacctg gggagtacgt tcgcaagaat gaaactcaaa 900
ggaattgacg gggacccgca caagcggtgg agcatgtggt ttaattcgaa gcaacgcgaa 960
gaaccttacc tgctcttgac atcccactga ccggcgtgta atggcgcctt cccttcgggg 1020
cagtggagac aggtggtgca tggttgtcgt cagctcgtgt cgtgagatgt tgggttaagt 1080
cccgcaacga gcgcaaccct tatctttagt agccagcggt ttggccgggc actctagaga 1140
gactgccagg gataacctgg aggaaggtgg ggatgacgtc aaatcatcat gccccttatg 1200
agcagggcta cacacgtgct acaatggcgt aaacaaaggg aggcaatacc gcgaggttga 1260
gcaaatccca aaaataacgt ctcagttcgg attgtagtct gcaactcgac tacatgaagc 1320
tggaatcgct agtaatcgcg aatcagaatg tcgcggtgaa tacgttcccg ggtcttgtac 1380
acaccgcccg tcacaccatg ggagttggta acgcccgaag tcagtgaccc aaccgtaagg 1440
agggagctgc cgaaggcggg atcgataact ggggtgaagt cgtaacaagg tagccgtatc 1500
ggaaggtgcg gctggatcac ctcctt 1526

<210> SEQ ID NO 103
<211> LENGTH: 1493
<212> TYPE: DNA
<213> ORGANISM: Blautia coccoides

<400> SEQUENCE: 103
agagtttgat cctggctcag gatgaacgct ggcggcgtgc ttaacacatg caagtcgagc 60
gaagcgctaa gacagatttc ttcggattga agtctttgtg actgagcggc ggacgggtga 120
gtaacgcgtg ggtaacctgc ctcatacagg gggataacag ttagaaatga ctgctaatac 180
cgcataagcg cacaggaccg catggtctgg tgtgaaaaac tccggtggta tgagatggac 240
ccgcgtctga ttagctagtt ggaggggtaa cggcccacca aggcgacgat cagtagccgg 300
cctgagaggg tgaacggcca cattgggact gagacacggc ccagactcct acgggaggca 360
gcagtgggga atattgcaca atgggggaaa ccctgatgca gcgacgccgc gtgaaggaag 420
aagtatctcg gtatgtaaac ttctatcagc agggaagaaa atgacggtac ctgactaaga 480
agccccggct aactacgtgc cagcagccgc ggtaatacgt agggggcaag cgttatccgg 540
atttactggg tgtaaaggga gcgtagacgg aagagcaagt ctgatgtgaa aggctggggc 600
ttaaccccag gactgcattg gaaactgttg ttctagagtg ccggagaggt aagcggaatt 660
cctagtgtag cggtgaaatg cgtagatatt aggaggaaca ccagtggcga aggcggctta 720
ctggacggta actgacgttg aggctcgaaa gcgtggggag caaacaggat tagataccct 780
ggtagtccac gccgtaaacg atgaatacta ggtgtcgggt ggcaaagcca ttcggtgccg 840
cagcaaacgc aataagtatt ccacctgggg agtacgttcg caagaatgaa actcaaagga 900
attgacgggg acccgcacaa gcggtggagc atgtggttta attcgaagca acgcgaagaa 960
ccttaccaag tcttgacatc cctctgaccg tcccgtaacg gggcttccc ttcggggcag 1020 aggagacagg tggtgcatgg ttgtcgtcag ctcgtgtcgt gagatgttgg gttaagtccc 1080
gcaacgagcg caacccttat ccttagtagc cagcacatga tggtgggcac tctagggaga 1140
ctgccgggga taacccggag gaaggcgggg acgacgtcaa atcatcatgc cccttatgat 1200
ttgggctaca cacgtgctac aatggcgtaa acaaagggaa gcgagacagc gatgttgagc 1260
gaatcccaaa aataacgtcc cagttcggac tgcagtctgc aactcgactg cacgaagctg 1320
gaatcgctag taatcgcgga tcagaatgcc gcggtgaata cgttcccggg tcttgtacac 1380
accgcccgtc acaccatggg agtcagtaac gcccgaagtc agtgacctaa ccgaaaggaa 1440
ggagctgccg aaggcgggac cgataactgg ggtgaagtcg taacaaggta acc 1493

<210> SEQ ID NO 104
<211> LENGTH: 1262
<212> TYPE: DNA
<213> ORGANISM: Blautia faecis

<400> SEQUENCE: 104
ataacagcca gaaatgactg ctaataccgc ataagcgcac agaaccgcat ggttcggtgt 60
gaaaaactcc ggtggtataa gatggacccg cgttggatta gctagttggc agggcagcgg 120
cctaccaagg cgacgatcca tagccggcct gagagggtga acggccacat tgggactgag 180
acacggccca gactcctacg ggaggcagca gtggggaata ttgcacaatg gggaaaccc 240 tgatgcagcg acgccgcgtg aaggaagaag tatctcggta tgtaaacttc tatcagcagg 300
gaagataatg acggtacctg actaagaagc cccggctaac tacgtgccag cagccgcggt 360
aatacgtagg gggcaagcgt tatccggatt tactgggtgt aaagggagcg tagacggcgc 420
agcaagtctg atgtgaaagg caggggctta acccctggac tgcattggaa actgctgtgc 480
ttgagtgccg gaggggtaag cggaattcct agtgtagcgg tgaaatgcgt agatattagg 540
aggaacacca gtggcgaagg cggcttactg gacggtaact gacgttgagg ctcgaaagcg 600
tggggagcaa acaggattag ataccctggt agtccacgcc gtaaacgatg aatactaggt 660
gtcagggagc acagctcttt ggtgccgccg caaacgcatt aagtattcca cctggggagt 720
acgttcgcaa gaatgaaact caaaggaatt gacggggacc cgcacaagcg gtggagcatg 780
tggtttaatt cgaagcaacg cgaagaacct taccaaatct tgacatccct ctgaccggga 840
cttaaccgtc cctttccttc gggacagggg agacaggtgg tgcatggttg tcgtcagctc 900
gtgtcgtgag atgttgggtt aagtcccgca acgagcgcaa cccctatcct tagtagccag 960
cacgcartgg tgggcactct gaggagactg ccagggataa cctggaggaa ggcggggatg 1020
acgtcaaatc atcatgcccc ttatgatttg ggctacacac gtgctacaat ggcgtaaaca 1080
aagggaagcg aacccgcgag ggtgggcaaa tctcaaaaat aacgtcccag ttcggactgc 1140
agtctgcaac tcgactgcac gaagctggaa tcgctagtaa tcgcggatca gaatgccgcg 1200
gtgaatacgt tcccgggtct tgtacacacc gcccgtcaca ccatgggagt cagtaacgcc 1260
cg 1262

<210> SEQ ID NO 105
<211> LENGTH: 1431
<212> TYPE: DNA
<213> ORGANISM: Clostridium hathewayi
<220> FEATURE:
<221> NAME/KEY: misc_feature
<222> LOCATION: (191)..(191)
<223> OTHER INFORMATION: n is a, c, g, t or u
<220> FEATURE:
<221> NAME/KEY: misc_feature
<222> LOCATION: (211)..(211)

<223> OTHER INFORMATION: n is a, c, g, t or u
<220> FEATURE:
<221> NAME/KEY: misc_feature
<222> LOCATION: (248)..(248)
<223> OTHER INFORMATION: n is a, c, g, t or u
<220> FEATURE:
<221> NAME/KEY: misc_feature
<222> LOCATION: (979)..(979)
<223> OTHER INFORMATION: n is a, c, g, t or u

<400> SEQUENCE: 105
ctcaggatga acgctggcgg cgtgcttaac acatgcaagt cgagcgaagc ggtttcaatg 60
aagttttcgg atggatttga aattgactta gcggcggacg ggtgagtaac gcgtgggtaa 120
cctgccttac actgggggat aacagttaga aatgactgct aataccgcat aagcgcacag 180
ggccgcatgg nctggtgtga aaaactccgg nggtgtaaga tggacccgcg tctgattagg 240
tagttggngg ggtaacggcc caccaagccg acgatcagta gccgacctga gagggtgacc 300
ggccacattg ggactgagac acggcccaaa ctcctacggg aggcagcagt ggggaatatt 360
ggacaatggg cgaaagcctg atccagcgac gccgcgtgag tgaagaagta tttcggtatg 420
taaagctcta tcagcaggga agaaaatgac ggtacctgac taagaagccc cggctaacta 480
cgtgccagca gccgcggtaa tacgtagggg gcaagcgtta tccggattta ctgggtgtaa 540
agggagcgta gacggtttag caagtctgaa gtgaaagccc ggggctcaac cccggtactg 600
ctttggaaac tgttagactt gagtgcagga gaggtaagtg gaattcctag tgtagcggtg 660
aaatgcgtag atattaggag gaacaccagt ggcgaaggcg gcttactgga ctgtaactga 720
cgttgaggct cgaaagcgtg gggagcaaac aggattagat accctggtag tccacgccgt 780
aaacgatgaa tactaggtgt cgggggcaa agcccttcgg tgccgccgca aacgcaataa 840
gtattccacc tggggagtac gttcgcaaga atgaaactca aaggaattga cggggacccg 900
cacaagcggt ggagcatgtg gtttaattcg aagcaacgcg aagaacctta ccaagtcttg 960
acatcccact gaaaacacnt taaccgtgat ccctcttcgg agcagtggag acaggtggtg 1020
catggttgtc gtcagctcgt gtcgtgagat gttgggttaa gtcccgcaac gagcgcaacc 1080
cttatcctta gtagccagcg agtagagtcg ggcactctgg ggagactgcc agggataacc 1140
tggaggaagg tggggatgac gtcaaatcat catgcccctt atgatttggg ctacacacgt 1200
gctacaatgg cgtaaacaaa gggaggcaaa ggagcgatct ggagcaaacc ccaaaaataa 1260
cgtctcagtt cggattgcag gctgcaactc gcctgcatga agctggaatc gctagtaatc 1320
gcgaatcaga atgtcgcggt gaatacgttc ccgggtcttg tacacaccgc ccgtcacacc 1380
atgggagttg gtaacgcccg aagtcagtga cccaaccgaa aggagggagc t 1431

<210> SEQ ID NO 106
<211> LENGTH: 1493
<212> TYPE: DNA
<213> ORGANISM: Blautia producta

<400> SEQUENCE: 106
agagtttgat cctggctcag gatgaacgct ggcggcgtgc ttaacacatg caagtcgagc 60
gaagcactaa gacggatttc ttcggattga agtctttgtg actgagcggc ggacgggtga 120
gtaacgcgtg ggtaacctgc ctcatacagg gggataacag ttagaaatga ctgctaatac 180
cgcataagcg cacaggaccg catggtctgg tgtgaaaaac tccggtggta tgagatggac 240
ccgcgtctga ttagctagtt ggaggggtaa cggcccacca aggcgacgat cagtagccgg 300
cctgagaggg tgaacggcca cattgggact gagacacggc ccagactcct acgggaggca 360
gcagtgggga atattgcaca atgggggaaa ccctgatgca gcgacgccgc gtgaaggaag 420
aagtatctcg gtatgtaaac ttctatcagc agggaagaaa atgacggtac ctgactaaga 480
agccccggct aactacgtgc cagcagccgc ggtaatacgt agggggcaag cgttatccgg 540
atttactggg tgtaaaggga gcgtagacgg aagagcaagt ctgatgtgaa aggctggggc 600
ttaaccccag gactgcattg gaaactgttg ttctagagtg ccggagaggt aagcggaatt 660
cctagtgtag cggtgaaatg cgtagatatt aggaggaaca ccagtggcga aggcggctta 720
ctggacggta actgacgttg aggctcgaaa gcgtggggag caaacaggat tagataccct 780
ggtagtccac gccgtaaacg atgaatacta ggtgtcgggt ggcaaagcca ttcggtgccg 840
cagcaaacgc aataagtatt ccacctgggg agtacgttcg caagaatgaa actcaaagga 900
attgacgggg acccgcacaa gcggtggagc atgtggttta attcgaagca acgcgaagaa 960
ccttaccaag tcttgacatc cctctgaccg tcccgtaacg gggacttccc ttcggggcag 1020
aggagacagg tggtgcatgg ttgtcgtcag ctcgtgtcgt gagatgttgg gttaagtccc 1080
gcaacgagcg caacccttat ccttagtagc cagcacatga tggtgggcac tctagggaga 1140
ctgccgggga taacccggag gaaggcgggg acgacgtcaa atcatcatgc cccttatgat 1200
ttgggctaca cacgtgctac aatggcgtaa acaaagggaa gcgagacagc gatgttgagc 1260
gaatcccaaa aataacgtcc cagttcggac tgcagtctgc aactcgactg cacgaagctg 1320
gaatcgctag taatcgcgga tcagaatgcc gcggtgaata cgttcccggg tcttgtacac 1380
accgcccgtc acaccatggg agtcagtaac gcccgaagtc agtgacctaa ccgaaaggaa 1440
ggagctgccg aaggcgggac cgataactgg ggtgaagtcg taacaaggta acc 1493

<210> SEQ ID NO 107
<211> LENGTH: 1515
<212> TYPE: DNA
<213> ORGANISM: Anaerostipes hadrus

<400> SEQUENCE: 107
tggctcagga tgaacgctgg cggcgtgctt aacacatgca agtcgaacga agctgcttaa 60
ctgatcttct tcggaattga cgttttgtag actgagtggc ggacgggtga gtaacgcgtg 120
ggcaacctgc cctgtacagg gggataacag tcagaaatga ctgctaatac cgcataagac 180
cacagcaccg catggtgcag gggtaaaaac tccggtggta caggatggac ccgcgtctga 240
ttagctggtt ggtgaggtaa cggctcacca aggcgacgat cagtagccgg cttgagagag 300
tgaacggcca cattgggact gagacacggc ccaaactcct acgggaggca gcagtgggga 360
atattgcaca atgggggaaa ccctgatgca gcgacgccgc gtgagtgaag aagtatctcg 420
gtatgtaaag ctctatcagc agggaagaaa atgacggtac ctgactaaga agccccggct 480
aactacgtgc cagcagccgc ggtaatacgt agggggcaag cgttatccgg aattactggg 540
tgtaaagggt gcgtaggtgg tatggcaagt cagaagtgaa aacccagggc ttaactctgg 600
gactgctttt gaaactgtca gactggagtg caggagaggt aagcggaatt cctagtgtag 660
cggtgaaatg cgtagatatt aggaggaaca tcagtggcga aggcggctta ctggactgaa 720
actgacactg aggcacgaaa gcgtggggag caaacaggat tagataccct ggtagtccac 780
gccgtaaacg atgaatacta ggtgtcgggg ccgtagaggc ttcggtgccg cagccaacgc 840
agtaagtatt ccacctgggg agtacgttcg caagaatgaa actcaaagga attgacgggg 900
acccgcacaa gcggtggagc atgtggttta attcgaagca acgcgaagaa ccttacctgg 960

-continued

```
tcttgacatc cttctgaccg gtccttaacc ggacctttcc ttcgggacag gagagacagg   1020

tggtgcatgg ttgtcgtcag ctcgtgtcgt gagatgttgg gttaagtccc gcaacgagcg   1080

caacccctat ctttagtagc cagcatttca ggtgggcact ctagagagac tgccagggat   1140

aacctggagg aaggtgggga cgacgtcaaa tcatcatgcc ccttatgacc agggctacac   1200

acgtgctaca atggcgtaaa cagagggaag cagcctcgtg agagtgagca aatcccaaaa   1260

ataacgtctc agttcggatt gtagtctgca actcgactac atgaagctgg aatcgctagt   1320

aatcgcgaat cagaatgtcg cggtgaatac gttcccgggt cttgtacaca ccgcccgtca   1380

caccatggga gtcagtaacg cccgaagtca gtgacccaac cgtaaggagg gagctgccga   1440

aggcgggacc gataactggg gtgaagtcgt aacaaggtag ccgtatcgga aggtgcggct   1500

ggatcacctc ctttc                                                    1515
```

<210> SEQ ID NO 108
<211> LENGTH: 1523
<212> TYPE: DNA
<213> ORGANISM: Eubacterium fissicatena

<400> SEQUENCE: 108

```
gtttgatcct ggctcaggat gaacgctggc ggcgtgctta acacatgcaa gtcgagcgaa     60

gcgctttact tagatttctt cggattgaag agttttgcga ctgagcggcg gacgggtgag    120

taacgcgtgg gtaacctgcc tcatacaggg ggataacagt tagaaatgac tgctaatacc    180

gcataagacc acagtaccgc atggtacagt gggaaaaact ccggtggtat gagatggacc    240

cgcgtctgat tagctagttg gtaaggtaac ggcttaccaa ggcaacgatc agtagccgac    300

ctgagagggt gaccggccac attgggactg agacacggcc caaactccta cgggaggcag    360

cagtggggaa tattgcacaa tgggggaaac cctgatgcag cgacgccgcg tgaaggatga    420

agtatttcgg tatgtaaact tctatcagca gggaagaaaa tgacggtacc tgactaagaa    480

gccccggcta actacgtgcc agcagccgcg gtaatacgta gggggcaagc gttatccgga    540

tttactgggt gtaaagggag cgtagacggt tatgtaagtc tgatgtgaaa acccggggct    600

caaccccggg actgcattgg aaactatgta actagagtgt cggagaggta agtggaattc    660

ctagtgtagc ggtgaaatgc gtagatatta ggaggaacac cagtggcgaa ggcggcttac    720

tggacgatca ctgacgttga ggctcgaaag cgtggggagc aaacaggatt agataccctg    780

gtagtccacg ccgtaaacga tgaatactag gtgtcgggtg gcaaagccat tcggtgccgc    840

agcaaacgca ataagtattc cacctgggga gtacgttcgc aagaatgaaa ctcaaaggaa    900

ttgacgggga cccgcacaag cggtggagca tgtggtttaa ttcgaagcaa cgcgaagaac    960

cttacctgct cttgacatcc cactgaccgg cgtgtaatgg cgccttccct tcggggcagt   1020

ggagacaggt ggtgcatggt tgtcgtcagc tcgtgtcgtg agatgttggg ttaagtcccg   1080

caacgagcgc aacccttatc tttagtagcc agcggtttgg ccgggcactc tagagagact   1140

gccagggata acctggagga aggtggggat gacgtcaaat catcatgccc cttatgagca   1200

gggctacaca cgtgctacaa tggcgtaaac aaagggaggc aataccgcga ggttgagcaa   1260

atcccaaaaa taacgtctca gttcggattg tagtctgcaa ctcgactaca tgaagctgga   1320

atcgctagta atcgcgaatc agaatgtcgc ggtgaatacg ttcccgggtc ttgtacacac   1380

cgcccgtcac accatgggag ttggtaacgc ccgaagtcag tgacccaacc gtaaggaggg   1440

agctgccgaa ggcgggatcg ataactgggg tgaagtcgta acaaggtagc cgtatcggaa   1500

ggtgcggctg gatcacctcc ttt                                           1523
```

<210> SEQ ID NO 109
<211> LENGTH: 1524
<212> TYPE: DNA
<213> ORGANISM: Eubacterium contortum

<400> SEQUENCE: 109

```
tttgatcctg gctcaggatg aacgctggcg acgtgcttaa cacatgcaag tcgagcgaag      60
cactttactt tgatttcttc ggaatgaaag gttttgtgac tgagcggcgg acgggtgagt     120
aacgcgtggg taacctgcct catacagggg gataacagtt agaaatgact gctaataccg     180
cataagacca cagtaccgca tggtacagtg ggaaaaactc cggtggtatg agatggaccc     240
gcgtctgatt agctagttgg taaggtaacg gcttaccaag gcgacgatca gtagccgacc     300
tgagagggtg accggccaca ttgggactga gacacggccc aaactcctac gggaggcagc     360
agtggggaat attgcacaat gggggaaacc ctgatgcagc gacgccgcgt gaaggatgaa     420
gtatttcggt atgtaaactt ctatcagcag ggaagaaaat gacggtacct gactaagaag     480
ccccggctaa ctacgtgcca gcagccgcgg taatacgtag ggggcaagcg ttatccggat     540
ttactgggtg taaagggagc gtagacggtt atgtaagtct gatgtgaaaa cccggggctc     600
aaccccggga ctgcattgga aactatgtaa ctagagtgtc ggagaggtaa gtggaattcc     660
tagtgtagcg gtgaaatgcg tagatattag gaggaacacc agtggcgaag gcggcttact     720
ggacgatgac tgacgttgag gctcgaaagc gtggggagca aacaggatta gataccctgg     780
tagtccacgc cgtaaacgat gaatactagg tgtcgggtgg caaagccatt cggtgccgca     840
gcaaacgcaa taagtattcc acctggggag tacgttcgca agaatgaaac tcaaaggaat     900
tgacggggac ccgcacaagc ggtggagcat gtggtttaat tcgaagcaac gcgaagaacc     960
ttacctgctc ttgacatccc cctgaccggc gtgtaatggt gcctttcctt cgggacaggg    1020
gagacaggtg gtgcatggtt gtcgtcagct cgtgtcgtga gatgttgggt taagtcccgc    1080
aacgagcgca acccttatct ttagtagcca gcggtttggc cgggcactct agagagactg    1140
ccagggataa cctggaggaa ggtggggatg acgtcaaatc atcatgcccc ttatgagcag    1200
ggctacacac gtgctacaat ggcgtaaaca aagggaggcg aagccgtgag gtggagcaaa    1260
tcccaaaaat aacgtctcag ttcggattgt agtctgcaac tcgactacat gaagctggaa    1320
tcgctagtaa tcgcgaatca gaatgtcgcg gtgaatacgt tcccgggtct tgtacacacc    1380
gcccgtcaca ccatgggagt tggtaacgcc cgaagtcagt gacccaaccg caaggaggga    1440
gctgccgagg gtgggaccga taactggggt gaagtcgtaa caaggtagcc gtatcggaag    1500
gtgcggctgg atcacctcct ttct                                           1524
```

<210> SEQ ID NO 110
<211> LENGTH: 1390
<212> TYPE: DNA
<213> ORGANISM: Clostridium bolteae

<400> SEQUENCE: 110

```
ttttaattga ctgagtggcg gacgggtgag taacgcgtgg ataacctgcc tcacactggg      60
ggataacagt tagaaatgac tgctaatacc gcataagcgc acagtaccgc atggtacagt     120
gtgaaaaact ccggtggtgt gagatggatc cgcgtctgat tagccagttg gcggggtaac     180
ggcccaccaa agcgacgatc agtagccgac ctgagagggt gaccggccac attgggactg     240
agacacggcc caaactccta cgggaggcag cagtggggaa tattgcacaa tgggcgaaag     300
```

-continued

```
cctgatgcag cgacgccgcg tgagtgaaga agtatttcgg tatgtaaagc tctatcagca    360
gggaagaaaa tgacggtacc tgactaagaa gccccggcta actacgtgcc agcagccgcg    420
gtaatacgta gggggcaagc gttatccgga tttactgggt gtaaagggag cgtagacggc    480
gaagcaagtc tgaagtgaaa acccagggct caaccctggg actgctttgg aaactgtttt    540
gctagagtgt cggagaggta agtggaattc ctagtgtagc ggtgaaatgc gtagatatta    600
ggaggaacac cagtggcgaa ggcggcttac tggacgataa ctgacgttga ggctcgaaag    660
cgtggggagc aaacaggatt agataccctg gtagtccacg ccgtaaacga tgaatgctag    720
gtgttggggg gcaaagccct tcggtgccgt cgcaaacgca gtaagcattc cacctgggga    780
gtacgttcgc aagaatgaaa ctcaaaggaa ttgacgggga cccgcacaag cggtggagca    840
tgtggtttaa ttcgaagcaa cgcgaagaac cttaccaagt cttgacatcc tcttgaccgg    900
cgtgtaacgg cgccttccct tcggggcaag agagacaggt ggtgcatggt tgtcgtcagc    960
tcgtgtcgtg agatgttggg ttaagtcccg caacgagcgc aacccttatc cttagtagcc   1020
agcaggtaaa gctgggcact ctagggagac tgccagggat aacctggagg aaggtgggga   1080
tgacgtcaaa tcatcatgcc ccttatgatt tgggctacac acgtgctaca atggcgtaaa   1140
caaagggaag caagacagtg atgtggagca aatcccaaaa ataacgtccc agttcggact   1200
gtagtctgca acccgactac acgaagctgg aatcgctagt aatcgcgaat cagaatgtcg   1260
cggtgaatac gttcccgggt cttgtacaca ccgcccgtca caccatggga gtcagcaacg   1320
cccgaagtca gtgacccaac tcgcaagaga gggagctgcc gaaggcgggg caggtaactg   1380
gggtgaagtc                                                          1390

<210> SEQ ID NO 111
<211> LENGTH: 1308
<212> TYPE: DNA
<213> ORGANISM: Blautia luti
<220> FEATURE:
<221> NAME/KEY: misc_feature
<222> LOCATION: (702)..(705)
<223> OTHER INFORMATION: n is a, c, g, t or u

<400> SEQUENCE: 111

gtgggtaacc tgccttatac agggggataa cagtcagaaa tgactgctaa taccgcataa     60
gcgcacagag ctgcatggct ccggtgtgaa aaactccggt ggtataagat ggacccgcgt    120
tggattagct agttggtgag gtaacggccc accaaggcga cgatccatag ccggcctgag    180
agggtgaacg gccacattgg gactgagaca cggcccagac tcctacggga ggcagcagtg    240
gggaatattg cacaatgggg gaaaccctga tgcagcgacg ccgcgtgaag gaagaagtat    300
ctcggtatgt aaacttctat cagcagggaa gaaaatgacg gtacctgact aagaagcccc    360
ggctaactac gtgccagcag ccgcggtaat acgtaggggg caagcgttat ccggatttac    420
tgggtgtaaa gggagcgtag acggcatgga caagtctgat gtgaaaggct ggggctcaac    480
cccgggactg cattggaaac tgcccgtctt gagtgccgga gaggtaagcg gaattcctag    540
tgtagcggtg aaatgcgtag atattaggag gaacaccagt ggcgaaggcg gcttactgga    600
cggtaactga cgttgaggct cgaaagcgtg gggagcaaac aggattagat accctggtag    660
tccacgcggt aaacgatgaa tcctaggtgt cggggagcaa annnnttcgg tgccgccgca    720
aacgcattaa gcattccacc tggggagtac gttcgcaaga atgaaactca aaggaattga    780
cggggacccg cacaagcggt ggagcatgtg gtttaattcg aagcaacgcg aagaacctta    840
ccaagtcttg acatccctct gaccgagtat gtatggtact tttccttcgg gagagagagg    900
```

agacaggtgg tgcatggttg tcgtcagctc gtgtcgtgag atgttgggtt aagtcccgca 960
acgagcgcaa cccctatccc cagtagccag cggttcggcc gggcactctg aggagactgc 1020
cagggataac ctggaggaag gcggggatga cgtcaaatca tcatgcccct tatgatttgg 1080
gctacacacg tgctacaatg gcgtaaacaa agggaagcaa gcctgcgagg gtgggcaaat 1140
cccaaaaata acgtcccagt tcggactgta gtctgcaacc cgactacacg aagctggaat 1200
cgctagtaat cgcggatcag aatgccgcgg tgaatacgtt cccgggtctt gtacacaccg 1260
cccgtcacac catgggagtc agtaacgccc gaagtcagtg acctaact 1308

<210> SEQ ID NO 112
<211> LENGTH: 1489
<212> TYPE: DNA
<213> ORGANISM: Acidaminococcus intestini

<400> SEQUENCE: 112
ctggcggcgt gcttaacaca tgcaagtcga acggagaact tatttcggta agttcttagt 60
ggcgaacggg tgagtaacgc gtgggcaacc tgccctccag ttggggacaa cattccgaaa 120
gggatgctaa taccgaatgt cctccctcct ccgcatggag gagggaggaa agatggcctc 180
tgcttgcaag ctatcgctgg aagatgggcc cgcgtctgat tagctagttg gtggggtaac 240
ggctcaccaa ggcgatgatc agtagccggt ctgagaggat gaacggccac attgggactg 300
agacacggcc caaactccta cgggaggcag cagtggggaa tcttccgcaa tggacgaaag 360
tctgacggag caacgccgcg tgagtgatga aggtcttcgg attgtaaaac tctgttgtta 420
gggacgaaag caccgtgttc gaacaggtca tggtgttgac ggtacctaac gaggaagcca 480
cggctaacta cgtgccagca gccgcggtaa tacgtaggtg gcaagcgttg tccggaatta 540
ttgggcgtaa agagcatgta ggcgggcttt taagtctgac gtgaaaatgc ggggcttaac 600
cccgtatggc gttggatact ggaagtcttg agtgcaggag aggaaagggg aattcccagt 660
gtagcggtga aatgcgtaga tattgggagg aacaccagtg gcgaaggcgc ctttctggac 720
tgtgtctgac gctgagatgc gaaagccagg gtagcaaacg ggattagata ccccggtagt 780
cctggccgta aacgatggat actaggtgta ggaggtatcg accccttctg tgccggagtt 840
aacgcaataa gtatcccgcc tggggactac gatcgcaaga ttgaaactca aaggaattga 900
cgggggcccg cacaagcggt ggagtatgtg gtttaattcg acgcaacgcg aagaacctta 960
ccaaggcttg acattgagtg aaagacctag agataggtcc ctcccttcgg ggacacgaaa 1020
acaggtggtg catggctgtc gtcagctcgt gtcgtgagat gttgggttaa gtcccgcaac 1080
gagcgcaacc cctatcctat gttaccagcg cgtaaaggcg gggactcata ggagactgcc 1140
agggataact tggaggaagg cggggatgac gtcaagtcat catgcccctt atgtcttggg 1200
ctacacacgt actacaatgg tcggcaacaa agggcagcga aaccgcgagg tggagcaaat 1260
cccagaaacc cgaccccagt tcggatcgta ggctgcaacc cgcctacgtg aagttggaat 1320
cgctagtaat cgcaggtcag catactgcgg tgaatacgtt cccgggcctt gtacacaccg 1380
cccgtcacac cacgaaagtt ggtaacaccc gaagccggtg agataacctt ttaggagtca 1440
gctgtctaag gtggggccga tgattggggt gaagtcgtaa caaggtagc 1489

<210> SEQ ID NO 113
<211> LENGTH: 1500
<212> TYPE: DNA
<213> ORGANISM: Ruminococcus albus

<400> SEQUENCE: 113

```
agagtttgat cctggctcag gacgaacgct ggcggcacgc ttaacacatg caagtcgaac     60
gagcgaaaga gtgcttgcac tctctagcta gtggcggacg ggtgagtaac acgtgagcaa    120
tctgcctttc ggagagggat accaattgga aacgattgtt aatacctcat aacataacga    180
agccgcatga ctttgttatc aaatgaattt cgccgaaaga tgagctcgcg tctgattagg    240
tagttggtga ggtaacggcc caccaagccg acgatcagta gccggactga gaggttgaac    300
ggccacattg ggactgagac acggcccaga ctcctacggg aggcagcagt ggggaatatt    360
gcacaatggg cgaaagcctg atgcagcgat gccgcgtgag ggaagaaggt tttaggattg    420
taaacctctg tctttgggga cgataatgac ggtacccaag gaggaagctc cggctaacta    480
cgtgccagca gccgcggtaa tacgtaggga gcgagcgttg tccggaatta ctgggtgtaa    540
agggagcgta ggcgggattg caagtcaggt gtgaaattta ggggcttaac ccctgaactg    600
cacttgaaac tgtagttctt gagtgaagta gaggtaagcg gaattcctag tgtagcggtg    660
aaatgcgtag atattaggag gaacatcagt ggcgaaggcg gcttactggg ctttaactga    720
cgctgaggct cgaaagcgtg gggagcaaac aggattagat accctggtag tccacgccgt    780
aaacgatgat tactaggtgt ggggggactg accccttccg tgccgcagtt aacacaataa    840
gtaatccacc tggggagtac ggccgcaagg ctgaaactca aaggaattga cggggacccg    900
cacaagcagt ggagtatgtg gtttaattcg aagcaacgcg aagaacctta ccaggtcttg    960
acatcgtacg catagcatag agatatgtga aatcccttcg ggacgtata gacaggtggt    1020
gcatggttgt cgtcagctcg tgtcgtgaga tgttggggtt aagtcccgca acgagcgcaa   1080
cccttactgt tagttgctac gcaagagcac tctagcagga ctgccgttga caaaacggag   1140
gaaggtgggg atgacgtcaa atcatcatgc cccttatgac ctgggctaca cacgtactac   1200
aatggctgtt aacagaggga agcaaaacag tgatgtggag caaaacccta aaagcagtct   1260
tagttcggat tgtaggctgc aacccgccta catgaagtcg gaattgctag taatcgcgga   1320
tcagcatgcc gcggtgaata cgttcccggg ccttgtacac accgcccgtc acgccatggg   1380
agtcggtaac acccgaagcc tgtgttctaa ccgcaaggag gaagcagtcg aaggtgggat   1440
tgatgactgg ggtgaagtcg taacaaggta gccgtatcgg aaggtgcggc tggatcacct   1500
```

<210> SEQ ID NO 114
<211> LENGTH: 1521
<212> TYPE: DNA
<213> ORGANISM: Eubacterium rectale

<400> SEQUENCE: 114

```
agagtttgat cctggctcag gatgaacgct ggcggcgtgc ttaacacatg caagtcgaac     60
gaagcacttt atttgatttc cttcgggact gattattttg tgactgagtg gcggacgggt    120
gagtaacgcg tgggtaacct gccttgtaca gggggataac agttggaaac ggctgctaat    180
accgcataag cgcacggcat cgcatgatgc agtgtgaaaa actccggtgg tataagatgg    240
acccgcgttg gattagctag ttggtgaggt aacggcccac caaggcgacg atccatagcc    300
gacctgagag ggtgaccggc cacattggga ctgagacacg gcccaaactc ctacgggagg    360
cagcagtggg gaatattgca caatgggcga aagcctgatg cagcgacgcc gcgtgagcga    420
agaagtattt cggtatgtaa agctctatca gcagggaaga taatgacggt acctgactaa    480
gaagcaccgg ctaaatacgt gccagcagcc gcggtaatac gtatggtgca agcgttatcc    540
ggatttactg ggtgtaaagg gagcgcaggc ggtgcggcaa gtctgatgtg aaagcccggg    600
```

```
gctcaacccc ggtactgcat tggaaactgt cgtactagag tgtcggaggg gtaagcggaa    660

ttcctagtgt agcggtgaaa tgcgtagata ttaggaggaa caccagtggc gaaggcggct    720

tactggacga taactgacgc tgaggctcga aagcgtgggg agcaaacagg attagatacc    780

ctggtagtcc acgccgtaaa cgatgaatac taggtgttgg gaagcattgc ttctcggtgc    840

cgtcgcaaac gcagtaagta ttccacctgg ggagtacgtt cgcaagaatg aaactcaaag    900

gaattgacgg ggacccgcac aagcggtgga gcatgtggtt taattcgaag caacgcgaag    960

aaccttacca agtcttgaca tccttctgac cggtacttaa ccgtaccttc tcttcggagc   1020

aggagtgaca ggtggtgcat ggttgtcgtc agctcgtgtc gtgagatgtt gggttaagtc   1080

ccgcaacgag cgcaaccctt atctttagta gccagcggtt cggccgggca ctctagagag   1140

actgccaggg ataacctgga ggaaggcggg gatgacgtca aatcatcatg ccccttatga   1200

cttgggctac acacgtgcta caatggcgta aacaaaggga agcaaagctg tgaagccgag   1260

caaatctcaa aaataacgtc tcagttcgga ctgtagtctg caacccgact acacgaagct   1320

ggaatcgcta gtaatcgcag atcagaatgc tgcggtgaat acgttcccgg gtcttgtaca   1380

caccgcccgt cacaccatgg gagttgggaa tgcccgaagc cagtgaccta accgaaagga   1440

aggagctgtc gaaggcaggc tcgataactg gggtgaagtc gtaacaaggt agccgtatcg   1500

gaaggtgcgg ctggatcacc t                                             1521
```

<210> SEQ ID NO 115
<211> LENGTH: 1545
<212> TYPE: DNA
<213> ORGANISM: Acidaminococcus fermentans

<400> SEQUENCE: 115

```
agagtttgat cctggctcag gacgaacgct ggcggcgtgc ttaacacatg caagtcgaac     60

ggagaacttt cttcggaatg ttcttagtgg cgaacgggtg agtaacgcgt aggcaacctg    120

ccctctggtt ggggacaaca ttccgaaagg gatgctaata ccgaatgaga tcctctttcc    180

gcatggagag aggatgaaag atggcctcta cttgtaagct atcgccagaa gatgggcctg    240

cgtctgatta gctagtaggt gaggtaacgg ctcacctagg cgatgatcag tagccggtct    300

gagaggatga acggccacat tgggactgag acacggccca aactcctacg ggaggcagca    360

gtggggaatc ttccgcaatg gacgaaagtc tgacggagca acgccgcgtg agtgatgaag    420

gccttcgggt tgtaaaactc tgttgtcagg gacgaaagca ccgatctata atacattttg    480

gtgttgacgg tacctgacga ggaagccacg gctaactacg tgccagcagc cgcggtaata    540

cgtaggtggc aagcgttgtc cggaattatt gggcgtaaag agcatgtagg cgggctttta    600

agtccgacgt gaaaatgcgg ggcttaaccc cgtatggcgt tggatactgg aagtcttgag    660

tgcaggagag gaaaggggaa ttcccagtgt agcggtgaaa tgcgtagata ttgggaggaa    720

caccagtggc gaaggcgcct ttctggactg tgtctgacgc tgagatgcga aagccagggt    780

agcaaacggg attagatacc ccggtagtcc tggccgtaaa cgatgggtac taggtgtagg    840

aggtatcgac cccttctgtg ccggagttaa cgcaataagt accccgcctg gggactacga    900

tcgcaagatt gaaactcaaa ggaattgacg gggggcccgca caagcggtgg agtatgtggt    960

ttaattcgac gcaacgcgaa gaaccttacc aaggcttgac attgagtgaa agacccagag   1020

atgggtcccc ttcttcggaa gcacgaaaac aggtggtgca tggctgtcgt cagctcgtgt   1080

cgtgagatgt tgggttaagt cccgcaacga gcgcaaccct tatcctatgt taccagcacg   1140
```

-continued

```
taatggtggg gactcatagg agactgccag ggataacctg gaggaaggcg gggatgacgt   1200

caagtcatca tgccccttat gtcttgggct acacacgtac tacaatggtc ggcaacaaag   1260

ggcagcgaag ccgcgaggcg gagccaatcc cagaaacccg accccagttc ggatcgcagg   1320

ctgcaacccg cctgcgtgaa gttggaatcg ctagtaatcg caggtcagca tactgcggtg   1380

aatacgttcc cgggccttgt acacaccgcc cgtcacacca cgaaagttgg taacacccga   1440

agccggtgag ataacctttt aggagtcagc tgtctaaggt ggggccgatg attggggtga   1500

agtcgtaaca aggtagccgt tcgagaacga gcggctggat cacct                   1545
```

```
<210> SEQ ID NO 116
<211> LENGTH: 1423
<212> TYPE: DNA
<213> ORGANISM: Fusicatenibacter saccharivorans

<400> SEQUENCE: 116

tggctcagga tgaacgctgg cggcgtgctt aacacatgca agtcgagcga agcagttaag     60

aagattyttc ggatgattct tgactgactg agcggcggac gggtgagtaa cgcgtgggtg    120

acctgcccca taccgggggga taacagctgg aaacggctgc taataccgca taagcgcaca    180

gagctgcatg gctcggtgtg aaaaactccg gtggtatggg atgggcccgc gtctgattag    240

gcagttggcg gggtaacggc ccaccaaacc gacgatcagt agccggcctg agagggcgac    300

cggccacatt gggactgaga cacggcccaa actcctacgg gaggcagcag tggggaatat    360

tgcacaatgg gggaaaccct gatgcagcga cgccgcgtga gcgaagaagt atttcggtat    420

gtaaagctct atcagcaggg aagataatga cggtacctga ctaagaagcc ccggctaact    480

acgtgccagc agccgcggta atacgtaggg ggcaagcgtt atccggattt actgggtgta    540

aagggagcgt agacggcaag gcaagtctga tgtgaaaacc cagggcttaa ccctgggact    600

gcattggaaa ctgtctggct cgagtgccgg agaggtaagc ggaattccta gtgtagcggt    660

gaaatgcgta gatattagga agaacaccag tggcgaaggc ggcttactgg acggtaactg    720

acgttgaggc tcgaaagcgt ggggagcaaa caggattaga taccctggta gtccacgccg    780

taaacgatga atgctaggtg ttggggagca aagctcttcg gtgccgccgc aaacgcatta    840

agcattccac ctggggagta cgttcgcaag aatgaaactc aaaggaattg acggggaccc    900

gcacaagcgg tggagcatgt ggtttaattc gaagcaacgc gaagaacctt accaggtctt    960

gacatcccga tgaccggccc gtaacggggc cttctcttcg gagcattgga gacaggtggt   1020

gcatggttgt cgtcagctcg tgtcgtgaga tgttgggtta agtcccgcaa cgagcgcaac   1080

ccttatcctc agtagccagc aggtaaagct gggcactctg tggagactgc cagggataac   1140

ctggaggaag gtggggatga cgtcaaatca tcatgcccct tatgatctgg gctacacacg   1200

tgctacaatg gcgtaaacaa agggaggcaa agccgcgagg tggagcaaat cccaaaaata   1260

acgtctcagt tcggactgca gtctgcaact cgactgcacg aagctggaat cgctagtaat   1320

cgcgaatcag aatgtcgcgg tgaatacgtt cccgggtctt gtacacaccg cccgtcacac   1380

catgggagtt ggtaacgccc gaagtcagtg acccaacctt tta                      1423
```

```
<210> SEQ ID NO 117
<211> LENGTH: 1494
<212> TYPE: DNA
<213> ORGANISM: Ruminococcus champanellensis

<400> SEQUENCE: 117

agagtttgat cctggctcag gacgaacgct ggcggcacgc ctaacacatg caagtcgaac     60
```

```
ggagataaag acttcggttt ttatcttagt ggcggacggg tgagtaacac gtgagcaacc    120
tgcctctgag agagggatag cttctggaaa cggatggtaa tacctcataa catagcggta    180
ccgcatgata ctgctatcaa agatttatcg ctcagagatg ggctcgcgtc tgattagcta    240
gatggtgagg taacggctca ccatggcgac gatcagtagc cggactgaga ggttgaacgg    300
ccacattggg actgagacac ggcccagact cctacgggag gcagcagtgg ggaatattgc    360
acaatgggcg caagcctgat gcagcgatgc cgcgtggagg aagaaggttt tcggattgta    420
aactcctgtc ttaagggacg ataatgacgg taccttagga ggaagctccg gctaactacg    480
tgccagcagc cgcggtaata cgtagggagc gagcgttgtc cggaattact gggtgtaaag    540
ggagcgtagg cgggattgca agtcagatgt gaaaactatg ggcttaaccc atagactgca    600
tttgaaactg tagttcttga gtgaagtaga ggtaagcgga attcctagtg tagcggtgaa    660
atgcgtagat attaggagga acatcggtgg cgaaggcggc ttactgggct tttactgacg    720
ctgaggctcg aaagcgtggg gagcaaacag gattagatac cctggtagtc cacgctgtaa    780
acgatgatta ctaggtgtgg ggggactgac cccttccgtg ccgcagttaa cacaataagt    840
aatccacctg gggagtacgg ccgcaaggtt gaaactcaaa ggaattgacg gggcccgca    900
caagcagtgg agtatgtggt ttaattcgaa gcaacgcgaa aaaccttacc aggtcttgac    960
atcgagtgaa tgatctagag atagatcagt ccttcgggac acaaagacag gtggtgcatg   1020
gttgtcgtca gctcgtgtcg tgagatgttg ggttaagtcc cgcaacgagc gcaaccctta   1080
cctttagttg ctacgcaaga gcactctaga gggactgccg ttgacaaaac ggaggaaggt   1140
ggggatgacg tcaaatcatc atgcccctta tgacctgggc tacacacgta ctacaatggc   1200
aatgaacaga gggaagcaat acagtgatgt ggagcaaatc cccaaaaatt gtcccagttc   1260
agattgtagg ctgcaactcg cctacatgaa gtcggaattg ctagtaatcg cagatcagca   1320
tgctgcggtg aatacgttcc cgggccttgt acacaccgcc cgtcacacca tgggagtcgg   1380
taacacccga agccagtagc ctaaccgcaa ggagggcgct gtcgaaggtg ggattgatga   1440
ctggggtgaa gtcgtaacaa ggtagccgta tcggaaggtg cggctggatc acct         1494

<210> SEQ ID NO 118
<211> LENGTH: 1533
<212> TYPE: DNA
<213> ORGANISM: Bifidobacterium bifidum

<400> SEQUENCE: 118

tttttgtgga gggttcgatt ctggctcagg atgaacgctg gcggcgtgct taacacatgc     60
aagtcgaacg ggatccatcg ggctttgctt ggtggtgaga gtggcgaacg ggtgagtaat    120
gcgtgaccga cctgccccat gctccggaat agctcctgga aacgggtggt aatgccggat    180
gttccacatg atcgcatgtg attgtgggaa agattctatc ggcgtgggat ggggtcgcgt    240
cctatcagct tgttggtgag gtaacggctc accaaggctt cgacgggtag ccggcctgag    300
agggcgaccg gccacattgg gactgagata cggcccagac tcctacggga ggcagcagtg    360
gggaatattg cacaatgggc gcaagcctga tgcagcgacg ccgcgtgagg gatggaggcc    420
ttcgggttgt aaacctcttt tgtttgggag caagccttcg ggtgagtgta cctttcgaat    480
aagcgccggc taactacgtg ccagcagccg cggtaatacg tagggcgcaa gcgttatccg    540
gatttattgg gcgtaaaggg ctcgtaggcg gctcgtcgcg tccggtgtga aagtccatcg    600
cttaacggtg gatctgcgcc gggtacgggc gggctggagt gcggtagggg agactggaat    660
```

tcccggtgta acggtggaat gtgtagatat cgggaagaac accgatggcg aaggcaggtc 720
tctgggccgt cactgacgct gaggagcgaa agcgtgggga gcgaacagga ttagataccc 780
tggtagtcca cgccgtaaac ggtggacgct ggatgtgggg cacgttccac gtgttccgtg 840
tcggagctaa cgcgttaagc gtcccgcctg gggagtacgg ccgcaaggct aaaactcaaa 900
gaaattgacg gggggcccgca caagcggcgg agcatgcgga ttaattcgat gcaacgcgaa 960
gaaccttacc tgggcttgac atgttcccga cgacgccaga gatggcgttt cccttcgggg 1020
cgggttcaca ggtggtgcat ggtcgtcgtc agctcgtgtc gtgagatgtt gggttaagtc 1080
ccgcaacgag cgcaaccctc gccccgtgtt gccagcacgt tatggtggga actcacgggg 1140
gaccgccggg gttaactcgg aggaaggtgg ggatgacgtc agatcatcat gccccttacg 1200
tccagggctt cacgcatgct acaatggccg gtacagcggg atgcgacatg gcgacatgga 1260
gcggatccct gaaaaccggt ctcagttcgg atcggagcct gcaacccggc tccgtgaagg 1320
cggagtcgct agtaatcgcg gatcagcaac gccgcggtga atgcgttccc gggccttgta 1380
cacaccgccc gtcaagtcat gaaagtgggc agcacccgaa gccggtggcc taaccccttg 1440
tgggatggag ccgtctaagg tgaggctcgt gattgggact aagtcgtaac aaggtagccg 1500
taccggaagg tgcggctgga tcacctcctt tct 1533

<210> SEQ ID NO 119
<211> LENGTH: 1552
<212> TYPE: DNA
<213> ORGANISM: Megasphaera elsdenii

<400> SEQUENCE: 119
agagtttgat cctggctcag gacgaacgct ggcggcgtgc ttaacacatg caagtcgaac 60
gagaagagat gagaagcttg cttcttatca attcgagtgg caaacgggtg agtaacgcgt 120
aagcaacctg cccttcagat ggggacaaca gctggaaacg gctgctaata ccgaatacgt 180
tctttttgtc gcatggcaga gggaagaaag ggaggctctt cggagctttc gctgaaggag 240
gggcttgcgt ctgattagct agttggaggg gtaacggccc accaaggcga cgatcagtag 300
ccggtctgag aggatgaacg gccacattgg gactgagaca cggcccagac tcctacggga 360
ggcagcagtg gggaatcttc cgcaatggac gaaagtctga cggagcaacg ccgcgtgaac 420
gatgacggcc ttcgggttgt aaagttctgt tatacgggac gaatggcgta gcggtcaata 480
cccgttacga gtgacggtac cgtaagagaa agccacggct aactacgtgc cagcagccgc 540
ggtaatacgt aggtggcaag cgttgtccgg aattattggg cgtaaagggc gcgcaggcgg 600
cgtcgtaagt cggtcttaaa agtgcggggc ttaaccccgt gaggggaccg aaactgcgat 660
gctagagtat cggagaggaa agcggaattc ctagtgtagc ggtgaaatgc gtagatatta 720
ggaggaacac cagtggcgaa agcggctttc tggacgacaa ctgacgctga ggcgcgaaag 780
ccaggggagc aaacgggatt agataccccg gtagtcctgg ccgtaaacga tggatactag 840
gtgtaggagg tatcgacccc ttctgtgccg gagttaacgc aataagtatc ccgcctgggg 900
agtacggccg caaggctgaa actcaaagga attgacgggg gcccgcacaa gcggtggagt 960
atgtggttta attcgacgca acgcgaagaa ccttaccaag ccttgacatt gattgctatg 1020
gatagagata tccagttcct cttcggagga caagaaaaca ggtggtgcac ggctgtcgtc 1080
agctcgtgtc gtgagatgtt gggttaagtc ccgcaacgag cgcaacccct atcttctgtt 1140
accagcggtt cggccgggga ctcaggagag actgccgcag acaatgcgga ggaaggcggg 1200
gatgacgtca agtcatcatg ccccttatgg cttgggctac acacgtacta caatggctct 1260

```
taatagaggg aagcgaagga gcgatccgga gcaaacccca aaaacagagt cccagttcgg   1320

attgcaggct gcaactcgcc tgcatgaagc aggaatcgct agtaatcgca ggtcagcata   1380

ctgcggtgaa tacgttcccg ggccttgtac acaccgcccg tcacaccacg aaagtcattc   1440

acacccgaag ccggtgaggt aaccttttgg agccagccgt cgaaggtggg ggcgatgatt   1500

ggggtgaagt cgtaacaagg tagccgtatc ggaaggtgcg gctggatcac ct            1552
```

```
<210> SEQ ID NO 120
<211> LENGTH: 1479
<212> TYPE: DNA
<213> ORGANISM: Dorea formicigenerans
<220> FEATURE:
<221> NAME/KEY: misc_feature
<222> LOCATION: (123)..(125)
<223> OTHER INFORMATION: n is a, c, g, t or u
<220> FEATURE:
<221> NAME/KEY: misc_feature
<222> LOCATION: (220)..(222)
<223> OTHER INFORMATION: n is a, c, g, t or u
<220> FEATURE:
<221> NAME/KEY: misc_feature
<222> LOCATION: (287)..(287)
<223> OTHER INFORMATION: n is a, c, g, t or u
<220> FEATURE:
<221> NAME/KEY: misc_feature
<222> LOCATION: (349)..(350)
<223> OTHER INFORMATION: n is a, c, g, t or u
<220> FEATURE:
<221> NAME/KEY: misc_feature
<222> LOCATION: (517)..(517)
<223> OTHER INFORMATION: n is a, c, g, t or u
<220> FEATURE:
<221> NAME/KEY: misc_feature
<222> LOCATION: (534)..(535)
<223> OTHER INFORMATION: n is a, c, g, t or u
<220> FEATURE:
<221> NAME/KEY: misc_feature
<222> LOCATION: (725)..(725)
<223> OTHER INFORMATION: n is a, c, g, t or u
<220> FEATURE:
<221> NAME/KEY: misc_feature
<222> LOCATION: (918)..(918)
<223> OTHER INFORMATION: n is a, c, g, t or u
<220> FEATURE:
<221> NAME/KEY: misc_feature
<222> LOCATION: (921)..(921)
<223> OTHER INFORMATION: n is a, c, g, t or u
<220> FEATURE:
<221> NAME/KEY: misc_feature
<222> LOCATION: (955)..(956)
<223> OTHER INFORMATION: n is a, c, g, t or u
<220> FEATURE:
<221> NAME/KEY: misc_feature
<222> LOCATION: (1184)..(1185)
<223> OTHER INFORMATION: n is a, c, g, t or u

<400> SEQUENCE: 120

ttaaacgaga gtttgatcct ggctcaggat gaacgctggc ggcgtgctta acacatgcaa     60

gtcgagcgaa gcacataagt ttgattcttc ggatgaagac ttttgtgact gagcggcgga    120

cgnnngagta acgcgtgggt aacctgcctc atacaggggg ataacagyta gaaatggctg    180

ctaataccgc ataagaccac agtactgcat ggtacagtgn nnaaaactcc ggtggtatga    240

gatggacccg cgtctgatta ggtagttggt gaggtaacgg cccaccnagc cgacgatcag    300

tagccgacct gagagggtga ccggccacat tgggactgag acacggccnn gactcctacg    360

ggaggcagca gtggggaata ttgcacaatg ggcgaaagcc tgatgcagcg acgccgcgtg    420

aaggatgaag tatttcggta tgtaaacttc tatcagcagg gaagaaaatg acggtacctg    480
```

-continued

```
actaagaagc cccggctaac tacgtgccag cagccgnggt aatacgtagg gggnnagcgt    540
tatccggatt tactgggtgt aaagggagcg tagacggctg tgcaagtctg aagtgaaagg    600
catgggctca acctgtggac tgctttggaa actgtgcagc tagagtgtcg gagaggtaag    660
tggaattcct agtgtagcgg tgaaatgcgt agatattagg aggaacacca gtggcgaagg    720
cggcntactg gacgatgact gacgttgagg ctcgaaagcg tggggagcaa acaggattag    780
ataccctggt agtccacgcc gtaaacgatg actgctaggt gtcgggtagc aaagctattc    840
ggtgccgcag ctaacgcaat aagcagtcca cctggggagt acgttcgcaa gaatgaaact    900
caaaggaatt gacggggncc ngcacaagcg gtggagcatg tggtttaatt cgaannaacg    960
cgaagaacct tacctgatct tgacatcccg atgaccgctt cgtaatggaa gyttttcttc   1020
ggaacatcgg tgacaggtgg tgcatggttg tcgtcagctc gtgtcgtgag atgttgggtt   1080
aagtcccgca acgagcgcaa cccttatctt cagtagccag catttaggat gggcactctg   1140
gagagactgc cagggataac ctggaggaag gtggggatga cgtnnaatca tcatgcccct   1200
tatgaccagg gctacacacg tgctacaatg gcgtaaacag agggaggcag agccgcgagg   1260
ccgagcaaat ctcaaaaata acgtctcagt tcggattgta gtctgcaact cgactacatg   1320
aagctggaat cgctagtaat cgcagatcag aatgctgcgg tgaatacgtt cccgggtctt   1380
gtacacaccg cccgtcacac catgggagtc agtaacgccc gaagtcagtg acccaaccga   1440
aaggagggag ctgccgaagg tgggaccgat aactggggt                          1479
```

<210> SEQ ID NO 121
<211> LENGTH: 1390
<212> TYPE: DNA
<213> ORGANISM: Eisenbergiella tayi

<400> SEQUENCE: 121

```
ggtataactt agtggcggac gggtgagtaa cgcgtgggaa acctgccctg taccgggga      60
taacacttag aaataggtgc taataccgca taagcgcacg gaaccgcatg gttccgtgtg    120
aaaaactccg gtggtacagg atggtcccgc gtctgattag ccagttggca gggtaacggc    180
ctaccaaagc gacgatcagt agccggcctg agagggtgaa cggccacatt gggactgaga    240
cacggcccaa actcctacgg gaggcagcag tggggaatat tgcacaatgg gggaaaccct    300
gatgcagcga cgccgcgtga gtgaagaagt atttcggtat gtaaagctct atcagcaggg    360
aagaaaatga cggtacctga ctaagaagcc ccggctaact acgtgccagc agccgcggta    420
atacgtaggg ggcaagcgtt atccggattt actgggtgta aagggagcgt agacggcatg    480
gcaagccaga tgtgaaaacc cagggctcaa ccttgggatt gcatttggaa ctgccaggct    540
ggagtgcagg agaggtaagc ggaattccta gtgtagcggt gaaatgcgta gatattagga    600
ggaacaccag tggcgaaggc ggcttactgg actgtaactg acgttgaggc tcgaaagcgt    660
ggggagcaaa caggattaga taccctggta gtccacgcgg taaacgatga ttgctaggtg    720
taggtgggta tggacccatc ggtgccgcag ctaacgcaat aagcaatcca cctggggagt    780
acgttcgcaa gaatgaaact caaaggaatt gacggggacc cgcacaagcg gtggagcatg    840
tggtttaatt cgaagcaacg cgaagaacct taccaagtct tgacatccca atgacgcacc    900
tgtaaagagg tgttcccttc ggggcattgg agacaggtgg tgcatggttg tcgtcagctc    960
gtgtcgtgag atgttgggtt aagtcccgca acgagcgcaa cccttattct tagtagccag   1020
caggtaaagc tgggcactct aaggagactg ccggggataa cccggaggaa ggcggggatg   1080
acgtcaaatc atcatgcccc ttatgatttg ggctacacac gtgctacaat ggcgtaaaca   1140
```

aagggaagcg agacagtgat gtggagcaaa tcycagaaat aacgtctcag ttcggattgt 1200
agtctgcaac tcgactacat gaagctggaa tcgctagtaa tcgcgaatca gcatgtcgcg 1260
gtgaatacgt tcccgggtct tgtacacacc gcccgtcaca ccatgggagt tggaaatgcc 1320
cgaagtctgt gacctaaccg aaagggagga gcagccgaag gcaggtctga taactggggt 1380
gaagtcgtaa 1390

<210> SEQ ID NO 122
<211> LENGTH: 1478
<212> TYPE: DNA
<213> ORGANISM: Clostridium symbiosum
<220> FEATURE:
<221> NAME/KEY: misc_feature
<222> LOCATION: (349)..(350)
<223> OTHER INFORMATION: n is a, c, g, t or u
<220> FEATURE:
<221> NAME/KEY: misc_feature
<222> LOCATION: (534)..(535)
<223> OTHER INFORMATION: n is a, c, g, t or u
<220> FEATURE:
<221> NAME/KEY: misc_feature
<222> LOCATION: (606)..(606)
<223> OTHER INFORMATION: n is a, c, g, t or u
<220> FEATURE:
<221> NAME/KEY: misc_feature
<222> LOCATION: (618)..(619)
<223> OTHER INFORMATION: n is a, c, g, t or u
<220> FEATURE:
<221> NAME/KEY: misc_feature
<222> LOCATION: (709)..(709)
<223> OTHER INFORMATION: n is a, c, g, t or u
<220> FEATURE:
<221> NAME/KEY: misc_feature
<222> LOCATION: (921)..(921)
<223> OTHER INFORMATION: n is a, c, g, t or u
<220> FEATURE:
<221> NAME/KEY: misc_feature
<222> LOCATION: (955)..(956)
<223> OTHER INFORMATION: n is a, c, g, t or u
<220> FEATURE:
<221> NAME/KEY: misc_feature
<222> LOCATION: (1012)..(1013)
<223> OTHER INFORMATION: n is a, c, g, t or u
<220> FEATURE:
<221> NAME/KEY: misc_feature
<222> LOCATION: (1015)..(1015)
<223> OTHER INFORMATION: n is a, c, g, t or u
<220> FEATURE:
<221> NAME/KEY: misc_feature
<222> LOCATION: (1081)..(1081)
<223> OTHER INFORMATION: n is a, c, g, t or u
<220> FEATURE:
<221> NAME/KEY: misc_feature
<222> LOCATION: (1185)..(1185)
<223> OTHER INFORMATION: n is a, c, g, t or u
<220> FEATURE:
<221> NAME/KEY: misc_feature
<222> LOCATION: (1240)..(1240)
<223> OTHER INFORMATION: n is a, c, g, t or u
<220> FEATURE:
<221> NAME/KEY: misc_feature
<222> LOCATION: (1391)..(1392)
<223> OTHER INFORMATION: n is a, c, g, t or u
<220> FEATURE:
<221> NAME/KEY: misc_feature
<222> LOCATION: (1470)..(1470)
<223> OTHER INFORMATION: n is a, c, g, t or u
<220> FEATURE:
<221> NAME/KEY: misc_feature
<222> LOCATION: (1474)..(1475)
<223> OTHER INFORMATION: n is a, c, g, t or u

<400> SEQUENCE: 122

```
aaacatgaga gtttgatcct ggctcaggat gaacgctggc ggcgtgccta acacatgcaa      60
gtcgaacgaa gcgatttaac ggaagttttc ggatggaagt tgaattgact gagtggcgga     120
cgggtgagta acgcgtgggt aacctgcctt gtactggggg acaacagtta gaaatgactg     180
ctaataccgc ataagcgcac agtattgcat gatacagtgt gaaaaactcc ggtggtacaa     240
gatggacccg cgtctgatta gctagttggt aaggtaacgg cttaccaagg cgacgatcag     300
tagccgacct gagagggtga ccggccacat tgggactgag acacggccnn aactcctacg     360
ggaggcagca gtggggaata ttgcacaatg ggcgaaagcc tgatgcagcg acgccgcgtg     420
agtgaagaag tatttcggta tgtaaagctc tatcagcagg gaagaaaatg acggtacctg     480
actaagaagc cccggctaac tacgtgccag cagccgcggt aatacgtagg gggnnagcgt     540
tatccggatt tactgggtgt aaagggagcg tagacggtaa agcaagtctg aagtgaaagc     600
ccgcgnctca actgcggnnc tgctttggaa actgtttaac tggagtgtcg gagaggtaag     660
tggaattcct agtgtagcgg tgaaatgcgt agatattagg aggaacacna gtggcgaagg     720
cgacttactg gacgataact gacgttgagg ctcgaaagcg tggggagcaa acaggattag     780
ataccctggt agtccacgcc gtaaacgatg aatactaggt gttggggagc aaagctcttc     840
ggtgccgtcg caaacgcagt aagtattcca cctggggagt acgttcgcaa gaatgaaact     900
caaaggaatt gacggggacc ngcacaagcg gtggagcatg tggtttaatt cgaannaacg     960
cgaagaacct taccaggtct tgacatcgac tcgacggggg agtaacgtcc cnntnccttc    1020
ggggcggaga agacaggtgg tgcatggttg tcgtcagctc gtgtcgtgag atgttgggtt    1080
nagtcccgca acgagcgcaa cccttattct aagtagccag cggttcggcc gggaactctt    1140
gggagactgc cagggataac ctggaggaag gtggggatga cgtcnaatca tcatgcccct    1200
tatgatctgg gctacacacg tgctacaatg gcgtaaacan agagaagcaa gaccgcgagg    1260
tggagcaaat ctcaaaaata acgtctcagt tcggactgca ggctgcaact cgcctgcacg    1320
aagctggaat cgctagtaat cgcgaatcag aatgtcgcgg tgaatacgtt cccgggtctt    1380
gtacacaccg nncgtcacac catgggagtc agtaacgccc gaagtcagtg acccaaccgc    1440
aaggagggag ctgccgaagg cgggaccgan aacnnggg                            1478
```

<210> SEQ ID NO 123
<211> LENGTH: 1488
<212> TYPE: DNA
<213> ORGANISM: Erysipelatoclostridium ramosum

<400> SEQUENCE: 123

```
agagtttgat cctggctcag gatgaacgct ggcggcgtgc ctaatacatg caagtcgaac      60
gcgagcactt gtgctcgagt ggcgaacggg tgagtaatac ataagtaacc tgccctagac     120
agggggataa ctattggaaa cgatagctaa gaccgcatag gtacggacac tgcatggtga     180
ccgtattaaa agtgcctcaa agcactggta gaggatggac ttatggcgca ttagctggtt     240
ggcggggtaa cggcccacca aggcgacgat gcgtagccga cctgagaggg tgaccggcca     300
cactgggact gagacacggc ccagactcct acgggaggca gcagtaggga attttcggca     360
atgggggaaa ccctgaccga gcaacgccgc gtgaaggaag aaggttttcg gattgtaaac     420
ttctgttata aaggaagaac ggcggctaca ggaaatggta gccgagtgac ggtactttat     480
tagaaagcca cggctaacta cgtgccagca gccgcggtaa tacgtaggtg gcaagcgtta     540
tccggaatta ttgggcgtaa agagggagca ggcggcagca agggtctgtg gtgaaagcct     600
gaagcttaac ttcagtaagc catagaaacc aggcagctag agtgcaggag aggatcgtgg     660
```

```
aattccatgt gtagcggtga aatgcgtaga tatatggagg aacaccagtg gcgaaggcga    720

cgatctggcc tgcaactgac gctcagtccc gaaagcgtgg ggagcaaata ggattagata    780

ccctagtagt ccacgccgta aacgatgagt actaagtgtt ggatgtcaaa gttcagtgct    840

gcagttaacg caataagtac tccgcctgag tagtacgttc gcaagaatga aactcaaagg    900

aattgacggg ggcccgcaca agcggtggag catgtggttt aattcgaagc aacgcgaaga    960

accttaccag gtcttgacat actcataaag gctccagaga tggagagata gctatatgag   1020

atacaggtgg tgcatggttg tcgtcagctc gtgtcgtgag atgttgggtt aagtcccgca   1080

acgagcgcaa cccttatcgt tagttaccat cattaagttg ggactctag cgagactgcc   1140

agtgacaagc tggaggaagg cggggatgac gtcaaatcat catgcccctt atgacctggg   1200

ctacacacgt gctacaatgg atggtgcaga gggaagcgaa gccgcgaggt gaagcaaaac   1260

ccataaaacc attctcagtt cggattgtag tctgcaactc gactacatga agttggaatc   1320

gctagtaatc gcgaatcagc atgtcgcggt gaatacgttc tcgggccttg tacacaccgc   1380

ccgtcacacc acgagagttg ataacacccg aagccggtgg cctaaccgca aggaaggagc   1440

tgtctaaggt gggattgatg attggggtga agtcgtaaca aggtaacc                1488
```

<210> SEQ ID NO 124
<211> LENGTH: 1528
<212> TYPE: DNA
<213> ORGANISM: Artificial Sequence
<220> FEATURE:
<223> OTHER INFORMATION: Synthetic Polynucleotide

<400> SEQUENCE: 124

```
atgagagttt gatcctggct caggatgaac gctggcggcg tgcctaacac atgcaagtcg     60

aacgaagcaa ttaaaggaag ttttcggatg gaatttgatt gactgagtgg cggacgggtg    120

agtaacgcgt ggataacctg cctcacactg ggggataaca gttagaaatg actgctaata    180

ccgcataagc gcacagtacc gcatggtacg gtgtgaaaaa ctccggtggt gtgagatgga    240

tccgcgtctg attagccagt tggcggggta acggcccacc aaagcgacga tcagtagccg    300

acctgagagg gtgaccggcc acattgggac tgagacacgg cccaaactcc tacgggaggc    360

agcagtgggg aatattgcac aatgggcgaa agcctgatgc agcgacgccg cgtgagtgaa    420

gaagtatttc ggtatgtaaa gctctatcag cagggaagaa aatgacggta cctgactaag    480

aagccccggc taactacgtg ccagcagccg cggtaatacg taggggggcaa gcgttatccg   540

gattcactgg gtgtaaaggg agcgtagacg gcgaagcaag tctgaagtga aaacccaggg    600

ctcaaccctg ggactgcttt ggaaactgtt ttgctagagt gtcggagagg taagtggaat    660

tcctagtgta gcggtgaaat gcgtagatat taggaggaac accagtggcg aaggcggctt    720

actggacgat aactgacgtt gaggctcgaa agcgtgggga gcaaacagga ttagataccc    780

tggtagtcca cgccgtaaac gatgaatgct aggtgttggg gggcaaagcc cttcggtgcc    840

gtcgcaaacg cagtaagcat tccacctggg gagtacgttc gcaagaatga aactcaaagg    900

aattgacggg gacccgcaca agcggtggag catgtggttt aattcgaagc aacgcgaaga    960

accttaccaa gtcttgacat cctcttgacc ggcgtgtaac ggcgccttcc cttcggggca   1020

agagagacag gtggtgcatg gttgtcgtca gctcgtgtcg tgagatgttg ggttaagtcc   1080

cgcaacgagc gcaaccctta tccttagtag ccagcaggta gagctgggca ctctagggag   1140

actgccaggg ataacctgga ggaaggtggg gatgacgtca aatcatcatg ccccttatga   1200
```

```
tttgggctac acacgtgcta caatggcgta aacaaaggga agcaagacag tgatgtggag   1260

caaatcccaa aaataacgtc ccagttcgga ctgtagtctg caacccgact acacgaagct   1320

ggaatcgcta gtaatcgcga atcagaatgt cgcggtgaat acgttcccgg gtcttgtaca   1380

caccgcccgt cacaccatgg gagtcagcaa cgcccgaagt cagtgaccca actcgcaaga   1440

gagggagctg ccgaaggcgg ggcaggtaac tggggtgaag tcgtaacaag gtagccgtat   1500

cggaaggtgc ggctggatca cctccttt                                      1528
```

<210> SEQ ID NO 125
<211> LENGTH: 1530
<212> TYPE: DNA
<213> ORGANISM: Artificial Sequence
<220> FEATURE:
<223> OTHER INFORMATION: Synthetic Polynucleotide

<400> SEQUENCE: 125

```
atgagagttt gatcctggct caggatgaac gctggcggcg tgcctaacac atgcaagtcg     60

aacgaagcaa ttaaaatgaa gttttcggat ggatttttga ttgactgagt ggcggacggg    120

tgagtaacgc gtggataacc tgcctcacac tgggggataa cagttagaaa tgactgctaa    180

taccgcataa gcgcacagta ccgcatggta cggtgtgaaa aactccggtg gtgtgggatg    240

gatccgcgtc tgattagcca gttggcgggg taacggccca ccaaagcgac gatcagtagc    300

cgacctgaga gggtgaccgg ccacattggg actgagacac ggcccaaact cctacgggag    360

gcagcagtgg ggaatattgc acaatgggcg aaagcctgat gcagcgacgc cgcgtgagtg    420

aagaagtatt tcggtatgta aagctctatc agcagggaag aaaatgacgg tacctgacta    480

agaagccccg gctaactacg tgccagcagc cgcggtaata cgtagggggc aagcgttatc    540

cggatttact gggtgtaaag ggagcgtaga cggcgaagca agtctgaagt gaaaacccag    600

ggctcaaccc tgggactgct ttggaaactg ttttgctaga gtgtcggaga ggtaagtgga    660

attcctagtg tagcggtgaa atgcgtagat attaggagga acaccagtgg cgaaggcggc    720

ttactggacg ataactgacg ttgaggctcg aaagcgtggg gagcaaacag gattagatac    780

cctggtagtc cacgccgtaa acgatgaatg ctaggtgttg gggggcaaag cccttcggtg    840

ccgtcgcaaa cgcagtaagc attccacctg gggagtacgt tcgcaagaat gaaactcaaa    900

ggaattgacg gggacccgca caagcggtgg agcatgtggt ttaattcgaa gcaacgcgaa    960

gaaccttacc aagtcttgac atcctcttga ccggcgtgta acggcgcctt cccttcgggg   1020

caagagagac aggtggtgca tggttgtcgt cagctcgtgt cgtgagatgt tgggttaagt   1080

cccgcaacga gcgcaaccct tatccttagt agccagcagg taaagctggg cactctaggg   1140

agactgccag ggataacctg gaggaaggtg gggatgacgt caaatcatca tgccccttat   1200

gatttgggct acacacgtgc tacaatggcg taaacaaagg gaagcaagac agtgatgtgg   1260

agcaaatccc aaaaataacg tcccagttcg gactgtagtc tgcaacccga ctacacgaag   1320

ctggaatcgc tagtaatcgc gaatcagaat gtcgcggtga atacgttccc gggtcttgta   1380

cacaccgccc gtcacaccat gggagtcagc aacgcccgaa gtcagtgacc caactcgcaa   1440

gagagggagc tgccgaaggc ggggcaggta actggggtga agtcgtaaca aggtagccgt   1500

atcggaaggt gcggctggat cacctccttt                                    1530
```

<210> SEQ ID NO 126
<211> LENGTH: 1528
<212> TYPE: DNA
<213> ORGANISM: Artificial Sequence
<220> FEATURE:
<223> OTHER INFORMATION: Synthetic Polynucleotide

<400> SEQUENCE: 126
atgagagttt gatcctggct caggatgaac gctggcggcg tgcctaacac atgcaagtcg 60
aacgaagcaa ttaaaatgaa gttttcggat ggatttttga ttgactgagt ggcggacggg 120
tgagtaacgc gtggataacc tgcctcacac tgggggataa cagttagaaa tgactgctaa 180
taccgcataa gcgcacagta ccgcatggta cggtgtgaaa aactccggtg gtgtgagatg 240
gatccgcgtc tgattagcca gttggcgggg taacggccca ccaaagcgac gatcagtagc 300
cgacctgaga gggtgaccgg ccacattggg actgagacac ggcccaaact cctacgggag 360
gcagcagtgg ggaatattgc acaatgggcg aaagcctgat gcagcgacgc cgcgtgagtg 420
aagaagtatt tcggtatgta aagctctatc agcagggaag aaatgacggt acctgactaa 480
gaagccccgg ctaactacgt gccagcagcc gcggtaatac gtagggggca agcgttatcc 540
ggatttactg ggtgtaaagg gagcgtagac ggcgaagcaa gtctgaagtg aaaacccagg 600
gctcaaccct gggactgctt tggaaactgt tttgctagag tgtcggagag gtaagtggaa 660
ttcctagtgt agcggtgaaa tgcgtagata ttaggaggaa caccagtggc gaaggcggct 720
tactggacga taactgacgt tgaggctcga aagcgtgggg agcaaacagg attagatacc 780
ctggtagtcc acgccgtaaa cgatgaatgc taggtgttgg gggcaaagcc cttcggtgcc 840
gtcgcaaacg cagtaagcat tccacctggg gagtacgttc gcaagaatga aactcaaagg 900
aattgacggg gacccgcaca agcggtggag catgtggttt aattcgaagc aacgcgaaga 960
accttaccaa gtcttgacat cctcttgacc ggcgtgtaac ggcgccttcc cttcggggca 1020
agagagacag gtggtgcatg gttgtcgtca gctcgtgtcg tgagatgttg ggttaagtcc 1080
cgcaacgagc gcaaccctta tccttagtag ccagcaggta aagctgggca ctctagggag 1140
actgccaggg ataacctgga ggaaggtggg gatgacgtca aatcatcatg ccccttatga 1200
tttgggctac acacgtgcta caatggcgta aacaaaggga agcaagacag tgatgtggag 1260
caaatcccaa aaataacgtc ccagttcgga ctgtagtctg caacccgact acacgaagct 1320
ggaatcgcta gtaatcgcga atcagaatgt cgcggtgaat acgttcccgg gtcttgtaca 1380
caccgcccgt cacaccatgg gagtcagcaa cgcccgaagt cagtgaccca actcgcaaga 1440
gagggagctg ccgaaggcgg ggcaggtaac tggggtgaag tcgtaacaag gtagccgtat 1500
cggaaggtgc ggctggatca cctccttt 1528

<210> SEQ ID NO 127
<211> LENGTH: 1528
<212> TYPE: DNA
<213> ORGANISM: Artificial Sequence
<220> FEATURE:
<223> OTHER INFORMATION: Synthetic Polynucleotide

<400> SEQUENCE: 127
atgagagttt gatcctggct caggatgaac gctggcggcg tgcctaacac atgcaagtcg 60
aacgaagcaa ttaaaatgaa gttttcggat ggatttttga ttgactgagt ggcggacggg 120
tgagtaacgc gtggataacc tgcctcacac tgggggataa cagttagaaa tgactgctaa 180
taccgcataa gcgcacagta ccgcatggta cggtgtgaaa aactccggtg gtgtgagatg 240
gatccgcgtc tgattagcca gttggcgggg taacggccca ccaaagcgac gatcagtagc 300
cgacctgaga gggtgaccgg ccacattggg actgagacac ggcccaaact cctacgggag 360

```
gcagcagtgg ggaatattgc acaatgggcg aaagcctgat gcagcgacgc cgcgtgagtg    420
aagaagtatt tcggtatgta aagctctatc agcagggaag aaaatgacgg tacctgacta    480
agaagccccg gctaactacg tgccagcagc cgcggtaata cgtagggggc aagcgttatc    540
cggatttact gggtgtaaag ggagcgtaga cggcgaagca agtctgaagt gaaaacccag    600
ggctcaaccc tgggactgct ttggaaactg ttttgctaga gtgtcggaga ggtaagtgga    660
attcctagtg tagcggtgaa atgcgtagat attaggagga acaccagtgg cgaaggcggc    720
ttactggacg ataactgacg ttgaggctcg aaagcgtggg gagcaaacag gattagatac    780
cctggtagtc cacgccgtaa acgatgaatg ctaggtgttg ggggcaaagc ccttcggtgc    840
cgtcgcaaac gcagtaagca ttccacctgg ggagtacgtt cgcaagaatg aaactcaaag    900
gaattgacgg ggacccgcac aagcggtgga gcatgtggtt taattcgaag caacgcgaag    960
aaccttacca agtcttgaca tcctcttgac cggcgtgtaa cggcgccttc ccttcggggc   1020
aggagagaca ggtggtgcat ggttgtcgtc agctcgtgtc gtgagatgtt gggttaagtc   1080
ccgcaacgag cgcaaccctt atccttagta gccagcaggt agagctgggc actctaggga   1140
gactgccagg gataacctgg aggaaggtgg ggatgacgtc aaatcatcat gccccttatg   1200
atttgggcta cacacgtgct acaatggcgt aaacaaaggg aagcaagaca gtgatgtgga   1260
gcaaatccca aaataacgtc ccagttcgga ctgtagtctg caacccgact acacgaagct   1320
ggaatcgcta gtaatcgcga atcagaatgt cgcggtgaat acgttcccgg gtcttgtaca   1380
caccgcccgt cacaccatgg gagtcagcaa cgcccgaagt cagtgaccca actcgcaaga   1440
gagggagctg ccgaaggcgg ggcaggtaac tggggtgaag tcgtaacaag gtagccgtat   1500
cggaaggtgc ggctggatca cctccttt                                      1528
```

```
<210> SEQ ID NO 128
<211> LENGTH: 1528
<212> TYPE: DNA
<213> ORGANISM: Artificial Sequence
<220> FEATURE:
<223> OTHER INFORMATION: Synthetic Polynucleotide

<400> SEQUENCE: 128
```

```
atgagagttt gatcctggct caggatgaac gctggcggcg tgcctaacac atgcaagtcg     60
aacgaagcaa ttaaaatgaa gttttcggat ggattttaat tgactgagtg gcggacgggt    120
gagtaacgcg tggataacct gcctcacact gggggataac agttagaaat gactgctaat    180
accgcataag cgcacagtac cgcatggtac ggtgtgaaaa actccggtgg tgtgagatgg    240
atccgcgtct gattagccag ttggcggggt aacggcccac caaagcgacg atcagtagcc    300
gacctgagag ggtgaccggc cacattggga ctgagacacg gcccaaactc ctacgggagg    360
cagcagtggg gaatattgca caatgggcga aagcctgatg cagcgacgcc gcgtgagtga    420
agaagtattt cggtatgtaa agctctatca gcagggaaga aaatgacggt acctgactaa    480
gaagccccgg ctaactacgt gccagcagcc gcggtaatac gtagggggca agcgttatcc    540
ggatttactg ggtgtaaagg gagcgtagac ggcgaagcaa gtctgaagtg aaaacccagg    600
gctcaaccct gggactgctt tggaaactgt tttgctagag tgtcggagag gtaagtggaa    660
ttcctagtgt agcggtgaaa tgcgtagata ttaggaggaa caccagtggc gaaggcggct    720
tactggacga taactgacgt tgaggctcga aagcgtgggg agcaaacagg attagatacc    780
ctggtagtcc acgccgtaaa cgatgaatgc taggtgttgg ggggcaaagc ccttcggtgc    840
cgtcgcaaac gcagtaagca ttccacctgg ggagtacgtt cgcaagaatg aaactcaaag    900
```

gaattgacgg ggacccgcac aagcggtgga gcatgtggtt taattcgaag caacgcgaag 960
aaccttacca agtcttgaca tcctcttgac cggcgtgtaa cggcgccttc ccttcggggc 1020
aagagagaca ggtggtgcat ggttgtcgtc agctcgtgtc gtgagatgtt gggttaagtc 1080
ccgcaacgag cgcaaccctt atccttagta gccagcaggt aaagctgggc actctaggga 1140
gactgccagg gataacctgg aggaaggtgg ggatgacgtc aaatcatcat gccccttatg 1200
atttgggcta cacacgtgct acaatggcgt aaacaaaggg aagcaagaca gtgatgtgga 1260
gcaaatccca aaataacgtc ccagttcgga ctgtagtctg caacccgact acacgaagct 1320
ggaatcgcta gtaatcgcga atcagaatgt cgcggtgaat acgttcccgg gtcttgtaca 1380
caccgcccgt cacaccatgg gagtcagcaa cgcccgaagt cagtgaccca actcgcaaga 1440
gagggagctg ccgaaggcgg ggcaggtaac tggggtgaag tcgtaacaag gtagccgtat 1500
cggaaggtgc ggctggatca cctccttt 1528

<210> SEQ ID NO 129
<211> LENGTH: 1522
<212> TYPE: DNA
<213> ORGANISM: Artificial Sequence
<220> FEATURE:
<223> OTHER INFORMATION: Synthetic Polynucleotide

<400> SEQUENCE: 129
tcaaagagtt tgatcctggc tcaggacgaa cgctggcggc gcgcctaaca catgcaagtc 60
gaacggagct tacgttttga agttttcgga tggatgaatg taagcttagt ggcggacggg 120
tgagtaacac gtgagcaacc tgcctttcag agggggataa cagccggaaa cggctgctaa 180
taccgcatga tgttgcgggg gcacatgccc ctgcaaccaa aggagcaatc cgctgaaaga 240
tgggctcgcg tccgattagc cagttggcgg ggtaacggcc caccaaagcg acgatcggta 300
gccggactga gaggttgaac ggccacattg ggactgagac acggcccaga ctcctacggg 360
aggcagcagt gggggatatt gcacaatggg cgaaagcctg atgcagcgac gccgcgtgag 420
ggaagacggt cttcggattg taaacctctg tctttgggga agaaaatgac ggtacccaaa 480
gaggaagctc cggctaacta cgtgccagca gccgcggtaa tacgtaggga gcaagcgttg 540
tccggaatta ctgggtgtaa agggagcgta ggcgggatgg caagtagaat gttaaatcca 600
tcggctcaac cggtggctgc gttctaaact gccgttcttg agtgaagtag aggcaggcgg 660
aattcctagt gtagcggtga aatgcgtaga tattaggagg aacaccagtg gcgaaggcgg 720
cctgctgggc tttaactgac gctgaggctc gaaagcgtgg ggagcaaaca ggattagata 780
ccctggtagt ccacgccgta aacgatgatt actaggtgtg gggggactga ccccttccgt 840
gccgcagtta acacaataag taatccacct ggggagtacg gccgcaaggt tgaaactcaa 900
aggaattgac gggggcccgc acaagcagtg gagtatgtgg tttaattcga agcaacgcga 960
agaaccttac caggtcttga catcggatgc atagcctaga gataggtgaa gcccttcggg 1020
gcatccagac aggtggtgca tggttgtcgt cagctcgtgt cgtgagatgt tgggttaagt 1080
cccgcaacga gcgcaaccct tattattagt tgctacgcaa gagcactcta atgagactgc 1140
cgttgacaaa acggaggaag gtggggatga cgtcaaatca tcatgcccct tatgacctgg 1200
gctacacacg tactacaatg gcactaaaac agagggcggc gacaccgcga ggtgaagcga 1260
atcccgaaaa agtgtctcag ttcagattgc aggctgcaac ccgcctgcat gaagtcggaa 1320
ttgctagtaa tcgcggatca gcatgccgcg gtgaatacgt tcccgggcct tgtacacacc 1380
gcccgtcaca ccatgggagt cggtaacacc cgaagccagt agcctaaccg caagggggc 1440 gctgtcgaag gtgggattga tgactggggt gaagtcgtaa caaggtagcc gtatcggaag 1500
gtgcggctgg atcacctcct tt 1522

<210> SEQ ID NO 130
<211> LENGTH: 1521
<212> TYPE: DNA
<213> ORGANISM: Artificial Sequence
<220> FEATURE:
<223> OTHER INFORMATION: Synthetic Polynucleotide

<400> SEQUENCE: 130
tcaaagagtt tgatcctggc tcaggacgaa cgctggcggc gcgcctaaca catgcaagtc 60
gaacggagct tacgttttga agttttcgga tggacgaatg taagcttagt ggcggacggg 120
tgagtaacac gtgagcaacc tgcctttcag aggggataac agccggaaac ggctgctaat 180
accgcatgat gttgcggggg cacatgcccc tgcaaccaaa ggagcaatcc gctgaaagat 240
gggctcgcgt ccgattagcc agttggcggg gtaacggccc accaaagcga cgatcggtag 300
ccggactgag aggttgaacg gccacattgg gactgagaca cggcccagac tcctacggga 360
ggcagcagtg gggatattg cacaatgggc gaaagcctga tgcagcgacg ccgcgtgagg 420
gaagacggtc ttcggattgt aaacctctgt ctttggggaa gaaaatgacg gtacccaaag 480
aggaagctcc ggctaactac gtgccagcag ccgcggtaat acgtagggag caagcgttgt 540
ccggaattac tgggtgtaaa gggagcgtag gcgggatggc aagtagaatg ttaaatccat 600
cggctcaacc ggtggctgcg ttctaaactg ccgttcttga gtgaagtaga ggcaggcgga 660
attcctagtg tagcggtgaa atgcgtagat attaggagga acaccagtgg cgaaggcggc 720
ctgctgggct ttaactgacg ctgaggctcg aaagcgtggg gagcaaacag gattagatac 780
cctggtagtc cacgccgtaa acgatgatta ctaggtgtgg ggggactgac cccttccgtg 840
ccgcagttaa cacaataagt aatccacctg gggagtacgg ccgcaaggtt gaaactcaaa 900
ggaattgacg gggcccgca caagcagtgg agtatgtggt ttaattcgaa gcaacgcgaa 960
gaaccttacc aggtcttgac atcggatgca tagcctagag ataggtgaag cccttcgggg 1020
catccagaca ggtggtgcat ggttgtcgtc agctcgtgtc gtgagatgtt gggttaagtc 1080
ccgcaacgag cgcaaccctt attattagtt gctacgcaag agcactctaa tgagactgcc 1140
gttgacaaaa cggaggaagg tggggatgac gtcaaatcat catgcccctt atgacctggg 1200
ctacacacgt actacaatgg cactaaaaca gagggcggcg acaccgcgag gtgaagcgaa 1260
tcccgaaaaa gtgtctcagt tcagattgca ggctgcaacc cgcctgcatg aagtcggaat 1320
tgctagtaat cgcggatcag catgccgcgg tgaatacgtt cccgggcctt gtacacaccg 1380
cccgtcacac catgggagtc ggtaacaccc gaagccagta gcctaaccgc aaggggggcg 1440
ctgtcgaagg tgggattgat gactggggtg aagtcgtaac aaggtagccg tatcggaagg 1500
tgcggctgga tcacctcctt t 1521

<210> SEQ ID NO 131
<211> LENGTH: 1522
<212> TYPE: DNA
<213> ORGANISM: Artificial Sequence
<220> FEATURE:
<223> OTHER INFORMATION: Synthetic Polynucleotide

<400> SEQUENCE: 131
tcaaagagtt tgatcctggc tcaggacgaa cgctggcggc gcgcctaaca catgcaagtc 60
gaacggagct tacgttttga agttttcgga tggatgaatg taagcttagt ggcggacggg 120
tgagtaacac gtgagcaacc tgcctttcag agggggataa cagccggaaa cggctgctaa 180
taccgcatga tgttgcgggg gcacatgccc ctgcaaccaa aggagcaatc cgctgaaaga 240
tgggctcgcg tccgattagc cagttggcgg ggtaacggcc caccaaagcg acgatcggta 300
gccggactga gaggttgaac ggccacattg ggactgagac acggcccaga ctcctacggg 360
aggcagcagt gggggatatt gcacaatggg cgaaagcctg atgcagcgac gccgcgtgag 420
ggaagacggt cttcggattg taaacctctg tctttgggga agaaaatgac ggtacccaaa 480
gaggaagctc cggctaacta cgtgccagca gccgcggtaa tacgtaggga gcaagcgttg 540
tccggaatta ctgggtgtaa agggagcgta ggcgggatgg caagtagaat gttaaatcca 600
tcggctcaac cggtggctgc gttctaaact gccgttcttg agtgaagtag aggcaggcgg 660
aattcctagt gtagcggtga aatgcgtaga tattaggagg aacaccagtg gcgaaggcgg 720
cctgctgggc tttaactgac gctgaggctc gaaagcgtgg ggagcaaaca ggattagata 780
ccctggtagt ccacgccgta aacgatgatt actaggtgtg gggggactga ccccttccgt 840
gccgcagtta acacaataag taatccacct ggggagtacg gccgcaaggt tgaaactcaa 900
aggaattgac gggggcccgc acaagcagtg gagtatgtgg tttaattcga agcaacgcga 960
agaaccttac caggtcttga catcggatgc atagcctaga gataggtgaa gcccttcggg 1020
gcatccagac aggtggtgca tggttgtcgt cagctcgtgt cgtgagatgt tgggttaagt 1080
cccgcaacga gcgcaaccct tattattagt tgctacgcaa gagcactcta atgagactgc 1140
cgttgacaaa acggaggaag gtggggatga cgtcaaatca tcatgcccct tatgacctgg 1200
gctacacacg tactacaatg gcactaaaac agagggcggc gacaccgcga ggtgaagcga 1260
atcccgaaaa agtgtctcag ttcagattgc aggctgcaac ccgcctgcat gaagtcggaa 1320
ttgctagtaa tcgcggatca gcatgccgcg gtgaatacgt tcccgggcct tgtacacacc 1380
gcccgtcaca ccatgggagt cggtaacacc cgaagccagt agcctaaccg caaggggggc 1440
gctgtcgaag gtgggattga tgactggggt gaagtcgtaa caaggtagcc gtatcggaag 1500
gtgcggctgg atcacctcct tt 1522

<210> SEQ ID NO 132
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 132
tacgagagtt tgatcctggc tcaggatgaa cgctggcggc gtgcctaaca catgcaagtc 60
gagcgaagcg ctgttttcag aatcttcgga ggaagaggac agtgactgag cggcggacgg 120
gtgagtaacg cgtgggcaac ctgcctcata caggggggata acagttagaa atgactgcta 180
ataccgcata agcgcacagg accgcatggt gtagtgtgaa aaactccggt ggtatgagat 240
ggacccgcgt ctgattaggt agttggtggg gtaaaggcct accaagccga cgatcagtag 300
ccgacctgag agggtgaccg gccacattgg gactgagaca cggcccaaac tcctacggga 360
ggcagcagtg gggaatattg cacaatgggg gaaaccctga tgcagcgacg ccgcgtgaag 420
gaagaagtat ttcggtatgt aaacttctat cagcagggaa gaaaatgacg gtacctgagt 480
aagaagcacc ggctaaatac gtgccagcag ccgcggtaat acgtatggtg caagcgttat 540

```
ccggatttac tgggtgtaaa gggagcgtag acggataggc aagtctggag tgaaaaccca    600
gggctcaacc ctgggactgc tttggaaact gcagatctgg agtgccggag aggtaagcgg    660
aattcctagt gtagcggtga aatgcgtaga tattaggagg aacaccagtg gcgaaggcgg    720
cttactggac ggtgactgac gttgaggctc gaaagcgtgg ggagcaaaca ggattagata    780
ccctggtagt ccacgccgta aacgatgact actaggtgtc ggtgtgcaaa gcacatcggt    840
gccgcagcaa acgcaataag tagtccacct ggggagtacg ttcgcaagaa tgaaactcaa    900
aggaattgac ggggacccgc acaagcggtg gagcatgtgg tttaattcga agcaacgcga    960
agaaccttac ctggtcttga catccggatg acgggcgagt aatgtcgccg tcccttcggg   1020
gcgtccgaga caggtggtgc atggttgtcg tcagctcgtg tcgtgagatg ttgggttaag   1080
tcccgcaacg agcgcaaccc ttatcttcag tagccagcat ataaggtggg cactctggag   1140
agactgccag ggagaacctg gaggaaggtg gggatgacgt caaatcatca tgccccttat   1200
ggccagggct acacacgtgc tacaatggcg taaacaaagg gaagcgagag ggtgacctgg   1260
agcgaatccc aaaaataacg tctcagttcg gattgtagtc tgcaactcga ctacatgaag   1320
ctggaatcgc tagtaatcgc ggatcagcat gccgcggtga atacgttccc gggtcttgta   1380
cacaccgccc gtcacaccat gggagtcagt aacgcccgaa gccagtgacc caaccttaga   1440
ggagggagct gtcgaaggcg ggacggataa ctggggtgaa gtcgtaacaa ggtagccgta   1500
tcggaaggtg cggctggatc acctccttt                                     1529
```

<210> SEQ ID NO 133
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 133

```
tacgagagtt tgatcctggc tcaggatgaa cgctggcggc gtgcctaaca catgcaagtc     60
gagcgaagcg ctgttttcag aatcttcgga ggaagaggac agtgactgag cggcggacgg    120
gtgagtaacg cgtgggcaac ctgcctcata caggggggata acagttagaa atgactgcta   180
ataccgcata agcgcacagg accgcatggt gtagtgtgaa aaactccggt ggtatgagat    240
ggacccgcgt ctgattaggt agttggtggg gtaaaggcct accaagccga cgatcagtag    300
ccgacctgag agggtgaccg gccacattgg gactgagaca cggcccaaac tcctacggga    360
ggcagcagtg gggaatattg cacaatgggg gaaaccctga tgcagcgacg ccgcgtgaag    420
gaagaagtat ttcggtatgt aaacttctat cagcagggaa gaagatgacg gtacctgagt    480
aagaagcacc ggctaaatac gtgccagcag ccgcggtaat acgtatggtg caagcgttat    540
ccggatttac tgggtgtaaa gggagcgtag acggataggc aagtctggag tgaaaaccca    600
gggctcaacc ctgggactgc tttggaaact gcagatctgg agtgccggag aggtaagcgg    660
aattcctagt gtagcggtga aatgcgtaga tattaggagg aacaccagtg gcgaaggcgg    720
cttactggac ggtgactgac gttgaggctc gaaagcgtgg ggagcaaaca ggattagata    780
ccctggtagt ccacgccgta aacgatgact actaggtgtc ggtgtgcaaa gcacatcggt    840
gccgcagcaa acgcaataag tagtccacct ggggagtacg ttcgcaagaa tgaaactcaa    900
aggaattgac ggggacccgc acaagcggtg gagcatgtgg tttaattcga agcaacgcga    960
agaaccttac ctggtcttga catccggatg acgggcgagt aatgtcgccg tcccttcggg   1020
gcatccgaga caggtggtgc atggttgtcg tcagctcgtg tcgtgagatg ttgggttaag   1080
```

tcccgcaacg agcgcaaccc ttatcttcag tagccagcat ataaggtggg cactctggag 1140
agactgccag ggagaacctg gaggaaggtg gggatgacgt caaatcatca tgccccttat 1200
ggccagggct acacacgtgc tacaatggcg taaacaaagg gaagcgagag ggtgacctga 1260
agcgaatccc aaaaataacg tctcagttcg gattgtagtc tgcaactcga ctacatgaag 1320
ctggaatcgc tagtaatcgc ggatcagcat gccgcggtga atacgttccc gggtcttgta 1380
cacaccgccc gtcacaccat gggagtcagt aacgcccgaa gccagtgacc caaccttaga 1440
ggagggagct gtcgaaggcg ggacggataa ctggggtgaa gtcgtaacaa ggtagccgta 1500
tcggaaggtg cggctggatc acctccttt 1529

<210> SEQ ID NO 134
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 134
tacgagagtt tgatcctggc tcaggatgaa cgctggcggc gtgcctaaca catgcaagtc 60
gagcgaagcg ctgttttcag aatcttcgga ggaagaggac agtgactgag cggcggacgg 120
gtgagtaacg cgtgggcaac ctgcctcata caggggggata acagttagaa atgactgcta 180
ataccgcata agcgcacagg accgcatggt gtagtgtgaa aaactccggt ggtatgagat 240
ggacccgcgt ctgattaggt agttggtggg gtaaaggcct accaagccga cgatcagtag 300
ccgacctgag agggtgaccg gccacattgg gactgagaca cggcccaaac tcctacggga 360
ggcagcagtg gggaatattg cacaatgggg gaaaccctga tgcagcgacg ccgcgtgaag 420
gaagaagtat ttcggtatgt aaacttctat cagcagggaa gaagatgacg gtacctgagt 480
aagaagcacc ggctaaatac gtgccagcag ccgcggtaat acgtatggtg caagcgttat 540
ccggatttac tgggtgtaaa gggagcgtag acggataggc aagtctggag tgaaaaccca 600
gggctcaacc ctgggactgc tttggaaact gcagatctgg agtgccggag aggtaagcgg 660
aattcctagt gtagcggtga aatgcgtaga tattaggagg aacaccagtg gcgaaggcgg 720
cttactggac ggtgactgac gttgaggctc gaaagcgtgg ggagcaaaca ggattagata 780
ccctggtagt ccacgccgta aacgatgact actaggtgtc ggtgtgcaaa gcacatcggt 840
gccgcagcaa acgcaataag tagtccacct ggggagtacg ttcgcaagaa tgaaactcaa 900
aggaattgac ggggacccgc acaagcggtg gagcatgtgg tttaattcga agcaacgcga 960
agaaccttac ctggtcttga catccggatg acgggcgagt aatgtcgccg tcccttcggg 1020
gcatccgaga caggtggtgc atggttgtcg tcagctcgtg tcgtgagatg ttgggttaag 1080
tcccgcaacg agcgcaaccc ttatcttcag tagccagcat ataaggtggg cactctggag 1140
agactgccag ggagaacctg gaggaaggtg gggatgacgt caaatcatca tgccccttat 1200
ggccagggct acacacgtgc tacaatggcg taaacaaagg gaagcgagag ggtgacctgg 1260
agcgaatccc aaaaataacg tctcagttcg gattgtagtc tgcaactcga ctacatgaag 1320
ctggaatcgc tagtaatcgc ggatcagcat gccgcggtga atacgttccc gggtcttgta 1380
cacaccgccc gtcacaccat gggagtcagt aacgcccgaa gccagtgacc caaccttaga 1440
ggagggagct gtcgaaggcg ggacggataa ctggggtgaa gtcgtaacaa ggtagccgta 1500
tcggaaggtg cggctggatc acctccttt 1529

<210> SEQ ID NO 135
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 135
tacgagagtt tgatcctggc tcaggatgaa cgctggcggc gtgcctaaca catgcaagtc 60
gagcgaagcg ctgttttcag aatcttcgga ggaagaggac agtgactgag cggcggacgg 120
gtgagtaacg cgtgggcaac ctgcctcata caggggggata acagttagaa atgactgcta 180
ataccgcata agcgcacagg accgcatggt gtagtgtgaa aaactccggt ggtatgagat 240
ggacccgcgt ctgattaggt agttggtggg gtaaaggcct accaagccga cgatcagtag 300
ccgacctgag agggtgaccg gccacattgg gactgagaca cggcccaaac tcctacggga 360
ggcagcagtg gggaatattg cacaatgggg gaaaccctga tgcagcgacg ccgcgtgaag 420
gaagaagtat ttcggtatgt aaacttctat cagcagggaa gaagatgacg gtacctgagt 480
aagaagcacc ggctaaatac gtgccagcag ccgcggtaat acgtatggtg caagcgttat 540
ccggatttac tgggtgtaaa gggagcgtag acggataggc aagtctggag tgaaaaccca 600
gggctcaacc ctgggactgc tttggaaact gcagatctgg agtgccggag aggtaagcgg 660
aattcctagt gtagcggtga aatgcgtaga tattaggagg aacaccagtg gcgaaggcgg 720
cttactggac ggtgactgac gttgaggctc gaaagcgtgg ggagcaaaca ggattagata 780
ccctggtagt ccacgccgta aacgatgact actaggtgtc ggtgtgcaaa gcacatcggt 840
gccgcagcaa acgcaataag tagtccacct ggggagtacg ttcgcaagaa tgaaactcaa 900
aggaattgac ggggacccgc acaagcggtg gagcatgtgg tttaattcga agcaacgcga 960
agaaccttac ctggtcttga catccggatg acgggcgagt aatgtcgccg tcccttcggg 1020
gcatccgaga caggtggtgc atggttgtcg tcagctcgtg tcgtgagatg ttgggttaag 1080
tcccgcaacg agcgcaaccc ttatcttcag tagccagcat ataaggtggg cactctggag 1140
agactgccag ggagaacctg gaggaaggtg gggatgacgt caaatcatca tgccccttat 1200
ggccagggct acacacgtgc tacaatggcg taaacaaagg gaagcgagag ggtgacctga 1260
agcgaatccc aaaaataacg tctcagttcg gattgtagtc tgcaactcga ctacatgaag 1320
ctggaatcgc tagtaatcgc ggatcagcat gccgcggtga atacgttccc gggtcttgta 1380
cacaccgccc gtcacaccat gggagtcagt aacgcccgaa gccagtgacc caaccttaga 1440
ggagggagct gtcgaaggcg ggacggataa ctggggtgaa gtcgtaacaa ggtagccgta 1500
tcggaaggtg cggctggatc acctccttt 1529

<210> SEQ ID NO 136
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 136
tacgagagtt tgatcctggc tcaggatgaa cgctggcggc gtgcctaaca catgcaagtc 60
gagcgaagcg ctgttttcag aatcttcgga ggaagaggac agtgactgag cggcggacgg 120
gtgagtaacg cgtgggcaac ctgcctcata caggggggata acagttagaa atgactgcta 180
ataccgcata agcgcacagg accgcatggt gtagtgtgaa aaactccggt ggtatgagat 240
ggacccgcgt ctgattaggt agttggtggg gtaaaggcct accaagccga cgatcagtag 300
ccgacctgag agggtgaccg gccacattgg gactgagaca cggcccaaac tcctacggga 360
ggcagcagtg gggaatattg cacaatgggg gaaaccctga tgcagcgacg ccgcgtgaag 420
gaagaagtat ttcggtatgt aaacttctat cagcagggaa gaagatgacg gtacctgagt 480
aagaagcacc ggctaaatac gtgccagcag ccgcggtaat acgtatggtg caagcgttat 540
ccggatttac tgggtgtaaa gggagcgtag acggataggc aagtctggag tgaaaaccca 600
gggctcaacc ctgggactgc tttggaaact gcagatctgg agtgccggag aggtaagcgg 660
aattcctagt gtagcggtga aatgcgtaga tattaggagg aacaccagtg gcgaaggcgg 720
cttactggac ggtgactgac gttgaggctc gaaagcgtgg ggagcaaaca ggattagata 780
ccctggtagt ccacgccgta aacgatgact actaggtgtc ggtgtgcaaa gcacatcggt 840
gccgcagcaa acgcaataag tagtccacct ggggagtacg ttcgcaagaa tgaaactcaa 900
aggaattgac ggggacccgc acaagcggtg gagcatgtgg tttaattcga agcaacgcga 960
agaaccttac ctggtcttga catccggatg acgggcgagt aatgtcgccg tcccttcggg 1020
gcatccgaga caggtggtgc atggttgtcg tcagctcgtg tcgtgagatg ttgggttaag 1080
tcccgcaacg agcgcaaccc ttatcttcag tagccagcat ataaggtggg cactctggag 1140
agactgccag ggagaacctg gaggaaggtg gggatgacgt caaatcatca tgccccttat 1200
ggccagggct acacacgtgc tacaatggcg taaacaaagg gaagcgagag ggtgacctgg 1260
agcgaatccc aaaaataacg tctcagttcg gattgtagtc tgcaactcga ctacatgaag 1320
ctggaatcgc tagtaatcgc ggatcagcat gccgcggtga atacgttccc gggtcttgta 1380
cacaccgccc gtcacaccat gggagtcagt aacgcccgaa gccagtgacc caaccttaga 1440
ggagggagct gtcgaaggcg ggacggataa ctggggtgaa gtcgtaacaa ggtagccgta 1500
tcggaaggtg cggctggatc acctcctt 1529

<210> SEQ ID NO 137
<211> LENGTH: 1527
<212> TYPE: DNA
<213> ORGANISM: Artificial Sequence
<220> FEATURE:
<223> OTHER INFORMATION: Synthetic Polynucleotide

<400> SEQUENCE: 137
atgagagttt gatcctagct caggatgaac gctggcggcg tgcctaacac atgcaagtcg 60
aacgaagcaa tttaacggaa gttttcggat ggaagttgaa ttgactgagt ggcggacggg 120
tgagtaacgc gtgggtaacc tgccttgtac tgggggacaa cagttagaaa tgactgctaa 180
taccgcataa gcgcacagta tcgcatgata cagtgtgaaa aactccggtg gtacaagatg 240
gacccgcgtc tgattagcta gttggtaagg taacggctta ccaaggcgac gatcagtagc 300
cgacctgaga gggtgaccgg ccacattggg actgagacac ggcccaaact cctacgggag 360
gcagcagtgg ggaatattgc acaatgggcg aaagcctgat gcagcgacgc cgcgtgagtg 420
aagaagtatt tcggtatgta aagctctatc agcagggaag aaaatgacgg tacctgacta 480
agaagccccg gctaactacg tgccagcagc cgcggtaata cgtagggggc aagcgttatc 540
cggatttact gggtgtaaag ggagcgtaga cggtaaagca agtctgaagt gaaagcccgc 600
ggctcaactg cgggactgct ttggaaactg tttaactgga gtgtcggaga ggtaagtgga 660
attcctagtg tagcggtgaa atgcgtagat attaggagga acaccagtgg cgaaggcgac 720

```
ttactggacg ataactgacg ttgaggctcg aaagcgtggg gagcaaacag gattagatac    780

cctggtagtc cacgccgtaa acgatgaata ctaggtgttg gggagcaaag ctcttcggtg    840

ccgtcgcaaa cgcagtaagt attccacctg gggagtacgt tcgcaagaat gaaactcaaa    900

ggaattgacg gggacccgca caagcggtgg agcatgtggt ttaattcgaa gcaacgcgaa    960

gaaccttacc aggtcttgac atcgatccga cgggggagta acgtcccctt cccttcgggg   1020

cggagaagac aggtggtgca tggttgtcgt cagctcgtgt cgtgagatgt tgggttaagt   1080

cccgcaacga gcgcaaccct tattctaagt agccagcggt tcggccggga actcttggga   1140

gactgccagg gataacctgg aggaaggtgg ggatgacgtc aaatcatcat gccccttatg   1200

atctgggcta cacacgtgct acaatggcgt aaacaaagag aagcaagacc gcgaggtgga   1260

gcaaatctca aaaataacgt ctcagttcgg actgcaggct gcaactcgcc tgcacgaagc   1320

tggaatcgct agtaatcgcg aatcagaatg tcgcggtgaa tacgttcccg ggtcttgtac   1380

acaccgcccg tcacaccatg ggagtcagta acgcccgaag tcagtgaccc aaccgcaagg   1440

agggagctgc cgaaggcggg accgataact ggggtgaagt cgtaacaagg tagccgtatc   1500

ggaaggtgcg gctggatcac ctccttt                                       1527
```

<210> SEQ ID NO 138
<211> LENGTH: 1527
<212> TYPE: DNA
<213> ORGANISM: Artificial Sequence
<220> FEATURE:
<223> OTHER INFORMATION: Synthetic Polynucleotide

<400> SEQUENCE: 138

```
atgagagttt gatcctggct caggatgaac gctggcggcg tgcctaacac atgcaagtcg     60

aacgaagcga tttaacggaa attttcggat ggaagttgaa ttgactgagt ggcggacggg    120

tgagtaacgc gtgggtaacc tgccttgtac tgggggacaa cagttagaaa tgactgctaa    180

taccgcataa gcgcacagta tcgcatgata cagtgtgaaa aactccggtg gtacaagatg    240

gacccgcgtc tgattagcta gttggtaagg taacggctta ccaaggcgac gatcagtagc    300

cgacctgaga gggtgaccgg ccacattggg actgagacac ggcccaaact cctacgggag    360

gcagcagtgg ggaatattgc acaatgggcg aaagcctgat gcagcgacgc cgcgtgagtg    420

aagaagtatt tcggtatgta aagctctatc agcagggaag aaaatgacgg tacctgacta    480

agaagccccg gctaactacg tgccagcagc cgcggtaata cgtagggggc aagcgttatc    540

cggatttact gggtgtaaag ggagcgtaga cggtaaagca agtctgaagt gaaagcccgc    600

ggctcaactg cgggactgct ttggaaactg tttaactgga gtgtcggaga ggtaagtgga    660

attcctagtg tagcggtgaa atgcgtagat attaggagga acaccagtgg cgaaggcgac    720

ttactggacg ataactgacg ttgaggctcg aaagcgtggg gagcaaacag gattagatac    780

cctggtagtc cacgccgtaa acgatgaata ctaggtgttg gggagcaaag ctcttcggtg    840

ccgtcgcaaa cgcagtaagt attccacctg gggagtacgt tcgcaagaat gaaactcaaa    900

ggaattgacg gggacccgca caagcggtgg agcatgtggt ttaattcgaa gcaacgcgaa    960

gaaccttacc aggtcttgac atcgatccga cgggggagta acgtcccctt cccttcgggg   1020

cggagaagac aggtggtgca tggttgtcgt cagctcgtgt cgtgagatgt tgggttaagt   1080

cccgcaacga gcgcaaccct tattctaagt agccagcggt tcggccggga actcttggga   1140

gactgccagg gataacctgg aggaaggtgg ggatgacgtc aaatcatcat gccccttatg   1200

atctgggcta cacacgtgct acaatggcgt aaacaaagag aagcaagacc gcgaggtgga   1260
```

gcaaatctca aaaataacgt ctcagttcgg actgcaggct gcaactcgcc tgcacgaagc 1320
tggaatcgct agtaatcgcg aatcagaatg tcgcggtgaa tacgttcccg ggtcttgtac 1380
acaccgcccg tcacaccatg ggagtcagta acgcccgaag tcagtgaccc aaccgcaagg 1440
agggagctgc cgaaggcggg accgataact ggggtgaagt cgtaacaagg tagccgtatc 1500
ggaaggtgcg gctggatcac ctccttt 1527

<210> SEQ ID NO 139
<211> LENGTH: 1527
<212> TYPE: DNA
<213> ORGANISM: Artificial Sequence
<220> FEATURE:
<223> OTHER INFORMATION: Synthetic Polynucleotide

<400> SEQUENCE: 139
atgagagttt gatcctggct caggatgaac gctggcggcg tgcctaacac atgcaagtcg 60
aacgaagcga tttaacggaa gttttcggat ggaagttgaa ttgactgagt ggcggacggg 120
tgagtaacgc gtgggtaacc tgccttgtac tgggggacaa cagttagaaa tgactgctaa 180
taccgcataa gcgcacagta tcgcatgata cagtgtgaaa aactccggtg gtacaagatg 240
gacccgcgtc tgattagcta gttggtaagg taacggctta ccaaggcgac gatcagtagc 300
cgacctgaga gggtgaccgg ccacattggg actgagacac ggcccaaact cctacgggag 360
gcagcagtgg ggaatattgc acaatgggcg aaagcctgat gcagcgacgc cgcgtgagtg 420
aagaagtatt tcggtatgta aagctctatc agcagggaag aaaatgacgg tacctgacta 480
agaagccccg gctaactacg tgccagcagc cgcggtaata cgtagggggc aagcgttatc 540
cggatttact gggtgtaaag ggagcgtaga cggtaaagca agtctgaagt gaaagcccgc 600
ggctcaactg cgggactgct ttggaaactg tttaactgga gtgtcggaga ggtaagtgga 660
attcctagtg tagcggtgaa atgcgtagat attaggagga acaccagtgg cgaaggcgac 720
ttactggacg ataactgacg ttgaggctcg aaagcgtggg gagcaaacag gattagatac 780
cctggtagtc cacgccgtaa acgatgaata ctaggtgttg gggagcaaag ctcttcggtg 840
ccgtcgcaaa cgcagtaagt attccacctg gggagtacgt tcgcaagaat gaaactcaaa 900
ggaattgacg gggacccgca caagcggtgg agcatgtggt ttaattcgaa gcaacgcgaa 960
gaaccttacc aggtcttgac atcgatccga cgggggagta acgtcccctt cccttcgggg 1020
cggagaagac aggtggtgca tggttgtcgt cagctcgtgt cgtgagatgt tgggttaagt 1080
cccgcaacga gcgcaaccct tattctaagt agccagcggt tcggccggga actcttggga 1140
gactgccagg gataacctgg aggaaggtgg ggatgacgtc aaatcatcat gccccttatg 1200
atctgggcta cacacgtgct acaatggcgt aaacaaagag aagcaagacc gcgaggtgga 1260
gcaaatctca aaaataacgt ctcagttcgg actgcaggct gcaactcgcc tgcacgaagc 1320
tggaatcgct agtaatcgcg aatcagaatg tcgcggtgaa tacgttcccg ggtcttgtac 1380
acaccgcccg tcacaccatg ggagtcagta acgcccgaag tcagtgaccc aaccgcaagg 1440
agggagctgc cgaaggcggg accgataact ggggtgaagt cgtaacaagg tagccgtatc 1500
ggaaggtgcg gctggatcac ctccttt 1527

<210> SEQ ID NO 140
<211> LENGTH: 1527
<212> TYPE: DNA
<213> ORGANISM: Artificial Sequence
<220> FEATURE:

<223> OTHER INFORMATION: Synthetic Polynucleotide

<400> SEQUENCE: 140
atgagagttt gatcctggct caggatgaac gctggcggcg tgcctaacac atgcaagtcg 60
aacgaagcga tttaacggaa gttttcggat ggaagttgga ttgactgagt ggcggacggg 120
tgagtaacgc gtgggtaacc tgccttgtac tgggggacaa cagttagaaa tgactgctaa 180
taccgcataa gcgcacagta tcgcatgata cagtgtgaaa aactccggtg gtacaagatg 240
gacccgcgtc tgattagcta gttggtaagg taacggctta ccaaggcgac gatcagtagc 300
cgacctgaga gggtgaccgg ccacattggg actgagacac ggcccaaact cctacgggag 360
gcagcagtgg ggaatattgc acaatgggcg aaagcctgat gcagcgacgc cgcgtgagtg 420
aagaagtatt tcggtatgta aagctctatc agcagggaag aaaatgacgg tacctgacta 480
agaagccccg gctaactacg tgccagcagc cgcggtaata cgtagggggc aagcgttatc 540
cggatttact gggtgtaaag ggagcgtaga cggtaaagca agtctgaagt gaaagcccgc 600
ggctcaactg cgggactgct ttggaaactg tttaactgga gtgtcggaga ggtaagtgga 660
attcctagtg tagcggtgaa atgcgtagat attaggagga acaccagtgg cgaaggcgac 720
ttactggacg ataactgacg ttgaggctcg aaagcgtggg gagcaaacag gattagatac 780
cctggtagtc cacgccgtaa acgatgaata ctaggtgttg gggagcaaag ctcttcggtg 840
ccgtcgcaaa cgcagtaagt attccacctg gggagtacgt tcgcaagaat gaaactcaaa 900
ggaattgacg gggacccgca caagcggtgg agcatgtggt ttaattcgaa gcaacgcgaa 960
gaaccttacc aggtcttgac atcgatccga cgggggagta acgtcccctt cccttcgggg 1020
cggagaagac aggtggtgca tggttgtcgt cagctcgtgt cgtgagatgt tgggttaagt 1080
cccgcaacga gcgcaaccct tattctaagt agccagcggt tcggccggga actcttggga 1140
gactgccagg gataacctgg aggaaggtgg ggatgacgtc aaatcatcat gccccttatg 1200
atctgggcta cacacgtgct acaatggcgt aaacaaagag aagcaagacc gcgaggtgga 1260
gcaaatctca aaaataacgt ctcagttcgg actgcaggct gcaactcgcc tgcacgaagc 1320
tggaatcgct agtaatcgcg aatcagaatg tcgcggtgaa tacgttcccg ggtcttgtac 1380
acaccgcccg tcacaccatg ggagtcagta acgcccgaag tcagtgaccc aaccgcaagg 1440
agggagctgc cgaaggcggg accgataact ggggtgaagt cgtaacaagg tagccgtatc 1500
ggaaggtgcg gctggatcac ctccttt 1527

<210> SEQ ID NO 141
<211> LENGTH: 1531
<212> TYPE: DNA
<213> ORGANISM: Artificial Sequence
<220> FEATURE:
<223> OTHER INFORMATION: Synthetic Polynucleotide

<400> SEQUENCE: 141
atcagagagt ttgatcctgg ctcaggatga acgctggcgg cgtgcttaac acatgcaagt 60
cgagcgaagc acttaagtgg atctcttcgg attgaaactt atttgactga gcggcggacg 120
ggtgagtaac gcgtgggtaa cctgcctcat acagggggat aacagttaga aatggctgct 180
aataccgcat aagcgcacag gaccgcatgg tctggtgtga aaaactccgg tggtatgaga 240
tggacccgcg tctgattagc tagttggagg ggtaacggcc caccaaggcg acgatcagta 300
gccggcctga gagggtgaac ggccacattg ggactgagac acggcccaga ctcctacggg 360
aggcagcagt ggggaatatt gcacaatggg ggaaaccctg atgcagcgac gccgcgtgaa 420
ggaagaagta tctcggtatg taaacttcta tcagcaggga agaaaatgac ggtacctgac 480
taagaagccc cggctaacta cgtgccagca gccgcggtaa tacgtagggg gcaagcgtta 540
tccggattta ctgggtgtaa agggagcgta gacggaagag caagtctgat gtgaaaggct 600
ggggcttaac cccaggactg cattggaaac tgtttttcta gagtgccgga gaggtaagcg 660
gaattcctag tgtagcggtg aaatgcgtag atattaggag gaacaccagt ggcgaaggcg 720
gcttactgga cggtaactga cgttgaggct cgaaagcgtg ggagcaaac aggattagat 780 accctggtag tccacgccgt aaacgatgaa tactaggtgt cgggtggcaa agccattcgg 840
tgccgcagca aacgcaataa gtattccacc tggggagtac gttcgcaaga atgaaactca 900
aaggaattga cggggacccg cacaagcggt ggagcatgtg gtttaattcg aagcaacgcg 960
aagaacctta ccaagtcttg acatccctct gaccggcccg taacggggcc ttcccttcgg 1020
ggcagaggag acaggtggtg catggttgtc gtcagctcgt gtcgtgagat gttgggttaa 1080
gtcccgcaac gagcgcaacc cctatcctta gtagccagca ggtgaagctg ggcactctag 1140
ggagactgcc ggggataacc cggaggaagg cggggacgac gtcaaatcat catgcccctt 1200
atgatttggg ctacacacgt gctacaatgg cgtaaacaaa gggaagcgag acagcgatgt 1260
tgagcaaatc ccaaaaataa cgtcccagtt cggactgcag tctgcaactc gactgcacga 1320
agctggaatc gctagtaatc gcgaatcaga atgtcgcggt gaatacgttc ccgggtcttg 1380
tacacaccgc ccgtcacacc atgggagtca gtaacgcccg aagtcagtga cccaaccttt 1440
taggagggag ctgccgaagg cgggaccgat aactggggtg aagtcgtaac aaggtagccg 1500
tatcggaagg tgcggctgga tcacctcctt t 1531

<210> SEQ ID NO 142
<211> LENGTH: 1531
<212> TYPE: DNA
<213> ORGANISM: Artificial Sequence
<220> FEATURE:
<223> OTHER INFORMATION: Synthetic Polynucleotide

<400> SEQUENCE: 142
atcagagagt ttgatcctgg ctcaggatga acgctggcgg cgtgcttaac acatgcaagt 60
cgagcgaagc acttaagtgg atctcttcgg attgaaactt atttgactga gcggcggacg 120
ggtgagtaac gcgtgggtaa cctgcctcat acagggggat aacagttaga aatggctgct 180
aataccgcat aagcgcacag gaccgcatgg tctggtgtga aaaactccgg tggtatgaga 240
tggacccgcg tctgattagc tagttggagg ggtaacggcc caccaaggcg acgatcagta 300
gccggcctga gagggtgaac ggccacattg ggactgagac acggcccaga ctcctacggg 360
aggcagcagt ggggaatatt gcacaatggg ggaaaccctg atgcagcgac gccgcgtgaa 420
ggaagaagta tctcggtatg taaacttcta tcagcaggga agaaaatgac ggtacctgac 480
taagaagccc cggctaacta cgtgccagca gccgcggtaa tacgtagggg gcaagcgtta 540
tccggattta ctgggtgtaa agggagcgta gacggaagag caagtctgat gtgaaaggct 600
ggggcttaac cccaggactg cattggaaac tgtttttcta gagtgccgga gaggtaagtg 660
gaattcctag tgtagcggtg aaatgcgtag atattaggag gaacaccagt ggcgaaggcg 720
gcttactgga cggtaactga cgttgaggct cgaaagcgtg ggagcaaac aggattagat 780 accctggtag tccacgccgt aaacgatgaa tactaggtgt cgggtggcaa agccattcgg 840
tgccgcagca aacgcaataa gtattccacc tggggagtac gttcgcaaga atgaaactca 900

```
aaggaattga cggggacccg cacaagcggt ggagcatgtg gtttaattcg aagcaacgcg    960

aagaacctta ccaagtcttg acatccctct gaccggcccg taacggggcc ttcccttcgg   1020

ggcagaggag acaggtggtg catggttgtc gtcagctcgt gtcgtgagat gttgggttaa   1080

gtcccgcaac gagcgcaacc cctatcctta gtagccagca ggtgaagctg ggcactctag   1140

ggagactgcc ggggataacc cggaggaagg cggggacgac gtcaaatcat catgcccctt   1200

atgatttggg ctacacacgt gctacaatgg cgtaaacaaa gggaagcggg acagcgatgt   1260

tgagcaaatc ccaaaaataa cgtcccagtt cggactgcag tctgcaactc gactgcacga   1320

agctggaatc gctagtaatc gcgaatcaga atgtcgcggt gaatacgttc ccgggtcttg   1380

tacacaccgc ccgtcacacc atgggagtca gtaacgcccg aagtcagtga cccaacctta   1440

caggagggag ctgccgaagg cgggaccgat aactggggtg aagtcgtaac aaggtagccg   1500

tatcggaagg tgcggctgga tcacctcctt t                                  1531
```

<210> SEQ ID NO 143
<211> LENGTH: 1531
<212> TYPE: DNA
<213> ORGANISM: Artificial Sequence
<220> FEATURE:
<223> OTHER INFORMATION: Synthetic Polynucleotide

<400> SEQUENCE: 143

```
atcagagagt ttgatcctgg ctcaggatga acgctggcgg cgtgcttaac acatgcaagt     60

cgagcgaagc acttaagtgg atctcttcgg attgaagctt atttgactga gcggcggacg    120

ggtgagtaac gcgtgggtaa cctgcctcat acagggggat aacagttaga aatggctgct    180

aataccgcat aagcgcacag gaccgcatgg tctggtgtga aaaactccgg tggtatgaga    240

tggacccgcg tctgattagc tagttggagg ggtaacggcc caccaaggcg acgatcagta    300

gccggcctga gagggtgaac ggccacattg ggactgagac acggcccaga ctcctacggg    360

aggcagcagt ggggaatatt gcacaatggg ggaaaccctg atgcagcgac gccgcgtgaa    420

ggaagaagta tctcggtatg taaacttcta tcagcaggga agaaaatgac ggtacctgac    480

taagaagccc cggctaacta cgtgccagca gccgcggtaa tacgtagggg gcaagcgtta    540

tccggattta ctgggtgtaa agggagcgta gacggaagag caagtctgat gtgaaaggct    600

ggggcttaac cccaggactg cattggaaac tgtttttcta gagtgccgga gaggtaagcg    660

gaattcctag tgtagcggtg aaatgcgtag atattaggag gaacaccagt ggcgaaggcg    720

gcttactgga cggtaactga cgttgaggct cgaaagcgtg ggagcaaac aggattagat    780

accctggtag tccacgccgt aaacgatgaa tactaggtgt cgggtggcaa agccattcgg    840

tgccgcagca aacgcaataa gtattccacc tggggagtac gttcgcaaga atgaaactca    900

aaggaattga cggggacccg cacaagcggt ggagcatgtg gtttaattcg aagcaacgcg    960

aagaacctta ccaagtcttg acatccctct gaccggcccg taacggggcc ttcccttcgg   1020

ggcagaggag acaggtggtg catggttgtc gtcagctcgt gtcgtgagat gttgggttaa   1080

gtcccgcaac gagcgcaacc cctatcctta gtagccagca ggtgaagctg ggcactctag   1140

ggagactgcc ggggataacc cggaggaagg cggggacgac gtcaaatcat catgcccctt   1200

atgatttggg ctacacacgt gctacaatgg cgtaaacaaa gggaagcgag acagcgatgt   1260

tgagcaaatc ccaaaaataa cgtcccagtt cggactgcag tctgcaactc gactgcacga   1320

agctggaatc gctagtaatc gcgaatcaga atgtcgcggt gaatacgttc ccgggtcttg   1380

tacacaccgc ccgtcacacc atgggagtca gtaacgcccg aagtcagtga cccaacctta   1440
```

caggagggag ctgccgaagg cgggaccgat aactggggtg aagtcgtaac aaggtagccg 1500
tatcggaagg tgcggctgga tcacctcctt t 1531

<210> SEQ ID NO 144
<211> LENGTH: 1531
<212> TYPE: DNA
<213> ORGANISM: Artificial Sequence
<220> FEATURE:
<223> OTHER INFORMATION: Synthetic Polynucleotide

<400> SEQUENCE: 144
atcagagagt ttgatcctgg ctcaggatga acgctggcgg cgtgcttaac acatgcaagt 60
cgagcgaagc acttaagcgg atctcttcgg attgaaactt atttgactga gcggcggacg 120
ggtgagtaac gcgtgggtaa cctgcctcat acagggggat aacagttaga aatggctgct 180
aataccgcat aagcgcacag gaccgcatgg tctggtgtga aaaactccgg tggtatgaga 240
tggacccgcg tctgattagc tagttggagg ggtaacggcc caccaaggcg acgatcagta 300
gccggcctga gagggtgaac ggccacattg ggactgagac acggcccaga ctcctacggg 360
aggcagcagt ggggaatatt gcacaatggg ggaaaccctg atgcagcgac gccgcgtgaa 420
ggaagaagta tctcggtatg taaacttcta tcagcaggga agaaaatgac ggtacctgac 480
taagaagccc cggctaacta cgtgccagca gccgcggtaa tacgtagggg gcaagcgtta 540
tccggattta ctgggtgtaa agggagcgta gacggaagag caagtctgat gtgaaaggct 600
ggggcttaac cccaggactg cattggaaac tgtttttcta gagtgccgga gaggtaagcg 660
gaattcctag tgtagcggtg aaatgcgtag atattaggag gaacaccagt ggcgaaggcg 720
gcttactgga cggtaactga cgttgaggct cgaaagcgtg gggagcaaac aggattagat 780
accctggtag tccacgccgt aaacgatgaa tactaggtgt cgggtggcaa agccattcgg 840
tgccgcagca aacgcaataa gtattccacc tggggagtac gttcgcaaga atgaaactca 900
aaggaattga cggggacccg cacaagcggt ggagcatgtg gtttaattcg aagcaacgcg 960
aagaacctta ccaagtcttg acatccctct gaccggcccg taacggggcc ttcccttcgg 1020
ggcagaggag acaggtggtg catggttgtc gtcagctcgt gtcgtgagat gttgggttaa 1080
gtcccgcaac gagcgcaacc cctatcctta gtagccagca ggtgaagctg ggcactctag 1140
ggagactgcc ggggataacc cggaggaagg cggggacgac gtcaaatcat catgcccctt 1200
atgatttggg ctacacacgt gctacaatgg cgtaaacaaa gggaagcgag acagcgatgt 1260
tgagcaaatc ccaaaaataa cgtcccagtt cggactgcag tctgcaactc gactgcacga 1320
agctggaatc gctagtaatc gcgaatcaga atgtcgcggt gaatacgttc ccgggtcttg 1380
tacacaccgc ccgtcacacc atgggagtca gtaacgcccg aagtcagtga cccaacctta 1440
caggagggag ctgccgaagg cgggaccgat aactggggtg aagtcgtaac aaggtagccg 1500
tatcggaagg tgcggctgga tcacctcctt t 1531

<210> SEQ ID NO 145
<211> LENGTH: 1531
<212> TYPE: DNA
<213> ORGANISM: Artificial Sequence
<220> FEATURE:
<223> OTHER INFORMATION: Synthetic Polynucleotide

<400> SEQUENCE: 145
atcagagagt ttgatcctgg ctcaggatga acgctggcgg cgtgcttaac acatgcaagt 60
cgagcgaagc acttaagtgg atctcttcgg attgaaactt atttgactga gcggcggacg 120
ggtgagtaac gcgtgggtaa cctgcctcat acagggggat aacagttaga aatggctgct 180
aataccgcat aagcgcacag gaccgcatgg tctggtgtga aaaactccgg tggtatgaga 240
tggacccgcg tctgattagc tagttggagg ggtaacggcc caccaaggcg acgatcagta 300
gccggcctga gagggtgaac ggccacattg ggactgagac acggcccaga ctcctacggg 360
aggcagcagt ggggaatatt gcacaatggg ggaaaccctg atgcagcgac gccgcgtgaa 420
ggaagaagta tctcggtatg taaacttcta tcagcaggga agaaaatgac ggtacctgac 480
taagaagccc cggctaacta cgtgccagca gccgcggtaa tacgtagggg gcaagcgtta 540
tccggattta ctgggtgtaa agggagcgta gacggaagag caagtctgat gtgaaaggct 600
ggggcttaac cccaggactg cattggaaac tgtttttcta gagtgccgga gaggtaagcg 660
gaattcctag tgtagcggtg aaatgcgtag atattaggag gaacatcagt ggcgaaggcg 720
gcttactgga cggtaactga cgttgaggct cgaaagcgtg gggagcaaac aggattagat 780
accctggtag tccacgccgt aaacgatgaa tactaggtgt cgggtggcaa agccattcgg 840
tgccgcagca aacgcaataa gtattccacc tggggagtac gttcgcaaga atgaaactca 900
aaggaattga cggggacccg cacaagcggt ggagcatgtg gtttaattcg aagcaacgcg 960
aagaacctta ccaagtcttg acatccctct gaccggcccg taacggggcc ttcccttcgg 1020
ggcagaggag acaggtggtg catggttgtc gtcagctcgt gtcgtgagat gttgggttaa 1080
gtcccgcaac gagcgcaacc cctatcctta gtagccagca ggtgaagctg ggcactctag 1140
ggagactgcc ggggataacc cggaggaagg cggggacgac gtcaaatcat catgcccctt 1200
atgatttggg ctacacacgt gctacaatgg cgtaaacaaa gggaagcgag acagcgatgt 1260
tgagcaaatc ccaaaaataa cgtcctagtt cggactgcag tctgcaactc gactgcacga 1320
agctggaatc gctagtaatc gcgaatcaga atgtcgcggt gaatacgttc ccgggtcttg 1380
tacacaccgc ccgtcacacc atgggagtca gtaacgcccg aagtcagtga cccaacctta 1440
caggagggag ctgccgaagg cgggaccgat aactggggtg aagtcgtaac aaggtagccg 1500
tatcggaagg tgcggctgga tcacctcctt t 1531

<210> SEQ ID NO 146
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 146
aacgagagtt tgatcctggc tcaggatgaa cgctggcggc gtgcttaaca catgcaagtc 60
gagcgaagca cttaagtttg attcttcgga tgaagacttt tgtgactgag cggcggacgg 120
gtgagtaacg cgtgggtaac ctgcctcata caggggggata acagttagaa atgactgcta 180
ataccgcata agaccacggt accgcatggt acagtggtaa aaactccggt ggtatgagat 240
ggacccgcgt ctgattaggt agttggtggg gtaacggcct accaagccga cgatcagtag 300
ccgacctgag agggtgaccg gccacattgg gactgagaca cggcccagac tcctacggga 360
ggcagcagtg gggaatattg cacaatggag gaaactctga tgcagcgacg ccgcgtgaag 420
gatgaagtat ttcggtatgt aaacttctat cagcagggaa gaaaatgacg gtacctgact 480
aagaagcccc ggctaactac gtgccagcag ccgcggtaat acgtaggggg caagcgttat 540
ccggatttac tgggtgtaaa gggagcgtag acggcacggc aagccagatg tgaaagcccg 600
gggctcaacc ccgggactgc atttggaact gctgagctag agtgtcggag aggcaagtgg 660
aattcctagt gtagcggtga aatgcgtaga tattaggagg aacaccagtg gcgaaggcgg 720
cttgctggac gatgactgac gttgaggctc gaaagcgtgg ggagcaaaca ggattagata 780
ccctggtagt ccacgccgta aacgatgact gctaggtgtc gggtggcaaa gccattcggt 840
gccgcagcta acgcaataag cagtccacct ggggagtacg ttcgcaagaa tgaaactcaa 900
aggaattgac ggggacccgc acaagcggtg gagcatgtgg tttaattcga agcaacgcga 960
agaaccttac ctgatcttga catcccgatg accgcttcgt aatggaagtt tttcttcgga 1020
acatcggtga caggtggtgc atggttgtcg tcagctcgtg tcgtgagatg ttgggttaag 1080
tcccgcaacg agcgcaaccc ctatcttcag tagccagcag gttaagctgg gcactctgga 1140
gagactgcca gggataacct ggaggaaggt ggggatgacg tcaaatcatc atgcccctta 1200
tgaccagggc tacacacgtg ctacaatggc gtaaacaaag agaagcgaac tcgcgagggt 1260
aagcaaatct caaaaataac gtctcagttc ggattgtagt ctgcaactcg actacatgaa 1320
gctggaatcg ctagtaatcg cagatcagaa tgctgcggtg aatacgttcc cgggtcttgt 1380
acacaccgcc cgtcacacca tgggagtcag taacgcccga agtcagtgac ccaaccgtaa 1440
ggagggagct gccgaaggtg ggaccgataa ctggggtgaa gtcgtaacaa ggtagccgta 1500
tcggaaggtg cggctggatc acctccttt 1529

<210> SEQ ID NO 147
<211> LENGTH: 1528
<212> TYPE: DNA
<213> ORGANISM: Artificial Sequence
<220> FEATURE:
<223> OTHER INFORMATION: Synthetic Polynucleotide

<400> SEQUENCE: 147
aacgagagtt tgatcctggc tcaggatgaa cgctggcggc gtgcttaaca catgcaagtc 60
gagcgaagca ctttggaaag attcttcgga tgatttcctt tgtgactgag cggcggacgg 120
gtgagtaacg cgtgggtaac ctgcctcata caggggggata acagttagaa atgactgcta 180
ataccgcata agaccacggt accgcatggt acagtggtaa aaactccggt ggtatgagat 240
ggacccgcgt ctgattaggt agttggtggg gtaacggcct accaagccga cgatcagtag 300
ccgacctgag agggtgaccg gccacattgg gactgagaca cggcccagac tcctacggga 360
ggcagcagtg gggaatattg cacaatggag gaaactctga tgcagcgacg ccgcgtgaag 420
gatgaagtat ttcggtatgt aaacttctat cagcagggaa gaaaatgacg gtacctgact 480
aagaagcccc ggctaactac gtgccagcag ccgcggtaat acgtaggggg caagcgttat 540
ccggatttac tgggtgtaaa gggagcgtag acggcacggc aagccagatg tgaaagcccg 600
gggctcaacc ccggactgca tttggaactg ctgagctaga gtgtcggaga ggcaagtgga 660
attcctagtg tagcggtgaa atgcgtagat attaggagga acaccagtgg cgaaggcggc 720
ttgctggacg atgactgacg ttgaggctcg aaagcgtggg gagcaaacag gattagatac 780
cctggtagtc cacgccgtaa acgatgactg ctaggtgtcg ggtggcaaag ccattcggtg 840
ccgcagctaa cgcaataagc agtccacctg gggagtacgt tcgcaagaat gaaactcaaa 900
ggaattgacg gggacccgca caagcggtgg agcatgtggt ttaattcgaa gcaacgcgaa 960
gaaccttacc tgatcttgac atcccgatga ccgcttcgta atggaagctt ttcttcggaa 1020
catcggtgac aggtggtgca tggttgtcgt cagctcgtgt cgtgagatgt tgggttaagt 1080

```
cccgcaacga gcgcaacccc tatcttcagt agccagcagg ttaagctggg cactctggag   1140
agactgccag ggataacctg gaggaaggtg gggatgacgt caaatcatca tgccccttat   1200
gaccagggct acacacgtgc tacaatggcg taaacaaaga gaagcgaact cgcgagggta   1260
agcaaatctc aaaaataacg tctcagttcg gattgtagtc tgcaactcga ctacatgaag   1320
ctggaatcgc tagtaatcgc agatcagaat gctgcggtga atacgttccc gggtcttgta   1380
cacaccgccc gtcacaccat gggagtcagt aacgcccgaa gtcagtgacc caaccgtaag   1440
gagggagctg ccgaaggtgg gaccgataac tggggtgaag tcgtaacaag gtagccgtat   1500
cggaaggtgc ggctggatca cctccttt                                      1528
```

```
<210> SEQ ID NO 148
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 148
```

```
aacgagagtt tgatcctggc tcaggatgaa cgctggcggc gtgcttaaca catgcaagtc     60
gagcgaagca cttaagtttg attcttcgga tgaagacttt tgtgactgag cggcggacgg    120
gtgagtaacg cgtgggtaac ctgcctcata caggggggata acagttagaa atgactgcta   180
ataccgcata agaccacggt accgcatggt acagtggtaa aaactccggt ggtatgagat    240
ggacccgcgt ctgattaggt agttggtggg gtaacggcct accaagccga cgatcagtag    300
ccgacctgag agggtgaccg gccacattgg gactgagaca cggcccagac tcctacggga    360
ggcagcagtg gggaatattg cacaatggag gaaactctga tgcagcgacg ccgcgtgaag    420
gatgaagtat ttcggtatgt aaacttctat cagcagggaa gaaaatgacg gtacctgact    480
aagaagcccc ggctaactac gtgccagcag ccgcggtaat acgtaggggg caagcgttat    540
ccggatttac tgggtgtaaa gggagcgtag acggcacggc aagccagatg tgaaagcccg    600
gggctcaacc ccgggactgc atttggaact gctgagctag agtgtcggag aggcaagtgg    660
aattcctagt gtagcggtga aatgcgtaga tattaggagg aacaccagtg gcgaaggcgg    720
cttgctggac gatgactgac gttgaggctc gaaagcgtgg ggagcaaaca ggattagata    780
ccctggtagt ccacgccgta aacgatgact gctaggtgtc gggtggcaaa gccattcggt    840
gccgcagcta acgcaataag cagtccacct ggggagtacg ttcgcaagaa tgaaactcaa    900
aggaattgac ggggacccgc acaagcggtg gagcatgtgg tttaattcga agcaacgcga    960
agaaccttac ctgatcttga catcccgatg accgcttcgt aatggaagct tttcttcgga   1020
acatcggtga caggtggtgc atggttgtcg tcagctcgtg tcgtgagatg ttgggttaag   1080
tcccgcaacg agcgcaaccc ctatcttcag tagccagcag gttaagctgg gcactctgga   1140
gagactgcca gggataacct ggaggaaggt ggggatgacg tcaaatcatc atgcccctta   1200
tgaccagggc tacacacgtg ctacaatggc gtaaacaaag agaagcgaac tcgcgagggt   1260
aagcaaatct caaaaataac gtctcagttc ggattgtagt ctgcaactcg actacatgaa   1320
gctggaatcg ctagtaatcg cagatcagaa tgctgcggtg aatacgttcc cgggtcttgt   1380
acacaccgcc cgtcacacca tgggagtcag taacgcccga agtcagtgac ccaaccgtaa   1440
ggagggagct gccgaaggtg ggaccgataa ctggggtgaa gtcgtaacaa ggtagccgta   1500
tcggaaggtg cggctggatc acctccttt                                     1529
```

```
<210> SEQ ID NO 149
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 149

aacgagagtt tgatcctggc tcaggatgaa cgctggcggc gtgcttaaca catgcaagtc     60

gagcgaagca ctttggaaag attcttcgga tgatttcctt tgtgactgag cggcggacgg    120

gtgagtaacg cgtgggtaac ctgcctcata caggggggata acagttagaa atgactgcta    180

ataccgcata agaccacggt accgcatggt acagtggtaa aaactccggt ggtatgagat    240

ggacccgcgt ctgattaggt agttggtggg gtaacggcct accaagccga cgatcagtag    300

ccgacctgag agggtgaccg gccacattgg gactgagaca cggcccagac tcctacggga    360

ggcagcagtg gggaatattg cacaatggag gaaactctga tgcagcgacg ccgcgtgaag    420

gatgaagtat ttcggtatgt aaacttctat cagcagggaa gaaaatgacg gtacctgact    480

aagaagcccc ggctaactac gtgccagcag ccgcggtaat acgtaggggg caagcgttat    540

ccggatttac tgggtgtaaa gggagcgtag acggcacggc aagccagatg tgaaagcccg    600

gggctcaacc ccgggactgc atttggaact gctgagctag agtgtcggag aggcaagtgg    660

aattcctagt gtagcggtga aatgcgtaga tattaggagg aacaccagtg gcgaaggcgg    720

cttgctggac gatgactgac gttgaggctc gaaagcgtgg ggagcaaaca ggattagata    780

ccctggtagt ccacgccgta aacgatgact gctaggtgtc gggtggcaaa gccattcggt    840

gccgcagcta acgcaataag cagtccacct ggggagtacg ttcgcaagaa tgaaactcaa    900

aggaattgac ggggacccgc acaagcggtg gagcatgtgg tttaattcga agcaacgcga    960

agaaccttac ctgatcttga catcccgatg accgcttcgt aatggaagct tttcttcgga   1020

acatcggtga caggtggtgc atggttgtcg tcagctcgtg tcgtgagatg ttgggttaag   1080

tcccgcaacg agcgcaaccc ctatcttcag tagccagcag gttaagctgg gcactctgga   1140

gagactgcca gggataacct ggaggaaggt ggggatgacg tcaaatcatc atgcccctta   1200

tgaccagggc tacacacgtg ctacaatggc gtaaacaaag agaagcgaac tcgcgagggt   1260

aagcaaatct caaaaataac gtctcagttc ggattgtagt ctgcaactcg actacatgaa   1320

gctggaatcg ctagtaatcg cagatcagaa tgctgcggtg aatacgttcc cgggtcttgt   1380

acacaccgcc cgtcacacca tgggagtcag taacgcccga agtcagtgac ccaaccgtaa   1440

ggagggagct gccgaaggtg ggaccgataa ctggggtgaa gtcgtaacaa ggtagccgta   1500

tcggaaggtg cggctggatc acctccttt                                     1529


<210> SEQ ID NO 150
<211> LENGTH: 1528
<212> TYPE: DNA
<213> ORGANISM: Artificial Sequence
<220> FEATURE:
<223> OTHER INFORMATION: Synthetic Polynucleotide

<400> SEQUENCE: 150

aacgagagtt tgatcctggc tcaggatgaa cgctggcggc gtgcttaaca catgcaagtc     60

gagcgaagcg cttaagtttg attcttcgga tgaagacttt tgtgactgag cggcggacgg    120

gtgagtaacg cgtgggtaac ctgcctcata caggggggata acagttagaa atgactgcta    180

ataccgcata agaccacggt accgcatggt acagtggtaa aaactccggt ggtatgagat    240
```

ggacccgcgt ctgattaggt agttggtggg gtaacggcct accaagccga cgatcagtag 300
ccgacctgag agggtgaccg gccacattgg gactgagaca cggcccagac tcctacggga 360
ggcagcagtg gggaatattg cacaatggag gaaactctga tgcagcgacg ccgcgtgaag 420
gatgaagtat ttcggtatgt aaacttctat cagcagggaa gaaaatgacg gtacctgact 480
aagaagcccc ggctaactac gtgccagcag ccgcggtaat acgtaggggg caagcgttat 540
ccggatttac tgggtgtaaa gggagcgtag acggcacggc aagccagatg tgaaagcccg 600
ggctcaaccc cgggactgca tttggaactg ctgagctaga gtgtcggaga ggcaagtgga 660
attcctagtg tagcggtgaa atgcgtagat attaggagga acaccagtgg cgaaggcggc 720
ttgctggacg atgactgacg ttgaggctcg aaagcgtggg gagcaaacag gattagatac 780
cctggtagtc cacgccgtaa acgatgactg ctaggtgtcg ggtggcaaag ccattcggtg 840
ccgcagctaa cgcaataagc agtccacctg gggagtacgt tcgcaagaat gaaactcaaa 900
ggaattgacg gggacccgca caagcggtgg agcatgtggt ttaattcgaa gcaacgcgaa 960
gaaccttacc tgatcttgac atcccgatga ccgcttcgta atggaagttt ttcttcggaa 1020
catcggtgac aggtggtgca tggttgtcgt cagctcgtgt cgtgagatgt tgggttaagt 1080
cccgcaacga gcgcaacccc tatcttcagt agccagcagg ttaagctggg cactctggag 1140
agactgccag ggataacctg gaggaaggtg gggatgacgt caaatcatca tgccccttat 1200
gaccagggct acacacgtgc tacaatggcg taaacaaaga gaggcaaact cgcgagggta 1260
agcaaatctc aaaaataacg tctcagttcg gattgtagtc tgcaactcga ctacatgaag 1320
ctggaatcgc tagtaatcgc agatcagaat gctgcggtga atacgttccc gggtcttgta 1380
cacaccgccc gtcacaccat gggagtcagt aacgcccgaa gtcagtgacc caaccgtaag 1440
gagggagctg ccgaaggtgg gaccgataac tggggtgaag tcgtaacaag gtagccgtat 1500
cggaaggtgc ggctggatca cctccttt 1528

<210> SEQ ID NO 151
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 151
aacgagagtt tgatcctggc tcaggatgaa cgctggcggc gtgcttaaca catgcaagtc 60
gagcgaagcg ctttgggaag attcttcgga tgatttcctt tgtgactgag cggcggacgg 120
gtgagtaacg cgtgggtaac ctgcctcata cagggggata acagttagaa atgactgcta 180
ataccgcata agaccacggt accgcatggt acagtggtaa aaactccggt ggtatgagat 240
ggacccgcgt ttgattaggt agttggtggg gtaacggcct accaagccga cgatcagtag 300
ccgacctgag agggtgaccg gccacattgg gactgagaca cggcccagac tcctacggga 360
ggcagcagtg gggaatattg cacaatggag gaaactctga tgcagcgacg ccgcgtgaag 420
gatgaagtat ttcggtatgt aaacttctat cagcagggaa gaaaatgacg gtacctgact 480
aagaagcccc ggctaactac gtgccagcag ccgcggtaat acgtaggggg caagcgttat 540
ccggatttac tgggtgtaaa gggagcgtag acggcacggc aagccagatg tgaaagcccg 600
gggctcaacc ccgggactgc atttggaact gctgagctag agtgtcggag aggcaagtgg 660
aattcctagt gtagcggtga aatgcgtaga tattaggagg aacaccagtg gcgaaggcgg 720
cttgctggac gatgactgac gttgaggctc gaaagcgtgg ggagcaaaca ggattagata 780

```
ccctggtagt ccacgccgta aacgatgact gctaggtgtc gggtggcaaa gccattcggt    840

gccgcagcta acgcaataag cagtccacct ggggagtacg ttcgcaagaa tgaaactcaa    900

aggaattgac ggggacccgc acaagcggtg gagcatgtgg tttaattcga agcaacgcga    960

agaaccttac ctgatcttga catcccgatg actgcttcgt aatggaagtt tttcttcgga   1020

acatcggtga caggtggtgc atggttgtcg tcagctcgtg tcgtgagatg ttgggttaag   1080

tcccgcaacg agcgcaaccc ctatcttcag tagccagcag gttaagctgg gcactctgga   1140

gagactgcca gggataacct ggaggaaggt ggggatgacg tcaaatcatc atgcccctta   1200

tgaccagggc tacacacgtg ctacaatggc gtaaacaaag agaagcgaac tcgcgagggt   1260

aagcaaatct caaaaataac gtctcagttc ggattgtagt ctgcaactcg actacatgaa   1320

gctggaatcg ctagtaatcg cagatcagaa tgctgcggtg aatacgttcc cgggtcttgt   1380

acacaccgcc cgtcacacca tgggagtcag taacgcccga agtcagtgac ccaaccgtaa   1440

ggagggagct gccgaaggtg ggaccgataa ctggggtgaa gtcgtaacaa ggtagccgta   1500

tcggaaggtg cggctggatc acctcctttt                                    1529
```

<210> SEQ ID NO 152
<211> LENGTH: 1537
<212> TYPE: DNA
<213> ORGANISM: Artificial Sequence
<220> FEATURE:
<223> OTHER INFORMATION: Synthetic Polynucleotide

<400> SEQUENCE: 152

```
atggagagtt tgatcctggc tcaggatgaa cgctggcggc atgcctaata catgcaagtc     60

gaacgaagtt tcgaggaagc ttgcttccaa agagacttag tggcgaacgg gtgagtaaca    120

cgtaggtaac ctgcccatgt gtccgggata actgctggaa acggtagcta aaaccggata    180

ggtatacaga gcgcatgctc agtatattaa agcgcccatc aaggcgtgaa catggatgga    240

cctgcggcgc attagctagt tggtgaggta acggctcacc aaggcgatga tgcgtagccg    300

gcctgagagg gtaaacggcc acattgggac tgagacacgg cccaaactcc tacgggaggc    360

agcagtaggg aattttcgtc aatgggggaa accctgaacg agcaatgccg cgtgagtgaa    420

gaaggtcttc ggatcgtaaa gctctgttgt aagtgaagaa cggctcatag aggaaatgct    480

atgggagtga cggtagctta ccagaaagcc acggctaact acgtgccagc agccgcggta    540

atacgtaggt ggcaagcgtt atccggaatc attgggcgta aagggtgcgt aggtggcgta    600

ctaagtctgt agtaaaaggc aatggctcaa ccattgtaag ctatggaaac tggtatgctg    660

gagtgcagaa gagggcgatg gaattccatg tgtagcggta aaatgcgtag atatatggag    720

gaacaccagt ggcgaaggcg gtcgcctggt ctgtaactga cactgaggca cgaaagcgtg    780

gggagcaaat aggattagat accctagtag tccacgccgt aaacgatgag aactaagtgt    840

tggaggaatt cagtgctgca gttaacgcaa taagttctcc gcctggggag tatgcacgca    900

agtgtgaaac tcaaaggaat tgacgggggc ccgcacaagc ggtggagtat gtggtttaat    960

tcgaagcaac gcgaagaacc ttaccaggcc ttgacatgga aacaaatacc ctagagatag   1020

ggggataatt atggatcaca caggtggtgc atggttgtcg tcagctcgtg tcgtgagatg   1080

ttgggttaag tcccgcaacg agcgcaaccc ttgtcgcatg ttaccagcat caagttgggg   1140

actcatgcga gactgccggt gacaaaccgg aggaaggtgg ggatgacgtc aaatcatcat   1200

gccccttatg gcctgggcta cacacgtact acaatggcgg ccacaaagag cagcgacaca   1260
```

gtgatgtgaa gcgaatctca taaaggtcgt ctcagttcgg attgaagtct gcaactcgac 1320
ttcatgaagt cggaatcgct agtaatcgca gatcagcatg ctgcggtgaa tacgttctcg 1380
ggccttgtac acaccgcccg tcaaaccatg ggagtcagta atacccgaag ccggtggcat 1440
aaccgtaagg agtgagccgt cgaaggtagg accgatgact ggggttaagt cgtaacaagg 1500
tatccctacg ggaacgtggg gatggatcac ctccttt 1537

<210> SEQ ID NO 153
<211> LENGTH: 1537
<212> TYPE: DNA
<213> ORGANISM: Artificial Sequence
<220> FEATURE:
<223> OTHER INFORMATION: Synthetic Polynucleotide

<400> SEQUENCE: 153
atggagagtt tgatcctggc tcaggatgaa cgctggcggc atgcctaata catgcaagtc 60
gaacgaagtt tcgaggaagc ttgcttccaa agagacttag tggcgaacgg gtgagtaaca 120
cgtaggtaac ctgcccatgt gtccgggata actgctggaa acggtagcta aaaccggata 180
ggtatacaga gcgcatgctc agtatattaa agcgcccatc aaggcgtgaa catggatgga 240
cctgcggcgc attagctagt tggtgaggta acggcccacc aaggcgatga tgcgtagccg 300
gcctgagagg gtaaacggcc acattgggac tgagacacgg cccaaactcc tacgggaggc 360
agcagtaggg aattttcgtc aatggggggaa accctgaacg agcaatgccg cgtgagtgaa 420
gaaggtcttc ggatcgtaaa gctctgttgt aagtgaagaa cggctcatag aggaaatgct 480
atgggagtga cggtagctta ccagaaagcc acggctaact acgtgccagc agccgcggta 540
atacgtaggt ggcaagcgtt atccggaatc attgggcgta aagggtgcgt aggtggcgta 600
ctaagtctgt agtaaaaggc aatggctcaa ccattgtaag ctatggaaac tggtatgctg 660
gagtgcagaa gagggcgatg gaattccatg tgtagcggta aaatgcgtag atatatggag 720
gaacaccagt ggcgaaggcg gtcgcctggt ctgtaactga cactgaggca cgaaagcgtg 780
gggagcaaat aggattagat accctagtag tccacgccgt aaacgatgag aactaagtgt 840
tggaggaatt cagtgctgca gttaacgcaa taagttctcc gcctggggag tatgcacgca 900
agtgtgaaac tcaaaggaat tgacgggggc ccgcacaagc ggtggagtat gtggtttaat 960
tcgaagcaac gcgaagaacc ttaccaggcc ttgacatgga aacaaatacc ctagagatag 1020
ggggataatt atggatcaca caggtggtgc atggttgtcg tcagctcgtg tcgtgagatg 1080
ttgggttaag tcccgcaacg agcgcaaccc ttgtcgcatg ttaccagcat caagttgggg 1140
actcatgcga gactgccggt gacaaaccgg aggaaggtgg ggatgacgtc aaatcatcat 1200
gccccttatg gcctgggcta cacacgtact acaatggcgg ccacaaagag cagcgacaca 1260
gtgatgtgaa gcgaatctca taaaggtcgt ctcagttcgg attgaagtct gcaactcgac 1320
ttcatgaagt cggaatcgct agtaatcgca gatcagcatg ctgcggtgaa tacgttctcg 1380
ggccttgtac acaccgcccg tcaaaccatg ggagtcagta atacccgaag ccggtggcat 1440
aaccgtaagg agtgagccgt cgaaggtagg accgatgact ggggttaagt cgtaacaagg 1500
tatccctacg ggaacgtggg gatggatcac ctccttt 1537

<210> SEQ ID NO 154
<211> LENGTH: 1537
<212> TYPE: DNA
<213> ORGANISM: Artificial Sequence
<220> FEATURE:
<223> OTHER INFORMATION: Synthetic Polynucleotide

<400> SEQUENCE: 154
atggagagtt tgatcctggc tcaggatgaa cgctggcggc atgcctaata catgcaagtc 60
gaacgaagtt tcgaggaagc ttgcttccaa agagacttag tggcgaacgg gtgagtaaca 120
cgtaggtaac ctgcccatgt gtccgggata actgctggaa acggtagcta aaaccggata 180
ggtatacaga gcgcatgctc agtatattaa agcgcccatc aaggcgtgaa catggatgga 240
cctgcggcgc attagctagt tggtgaggta acggctcacc aaggcgatga tgcgtagccg 300
gcctgagagg gtaaacggcc acattgggac tgagacacgg cccaaactcc tacgggaggc 360
agcagtaggg aattttcgtc aatgggggaa accctgaacg agcaatgccg cgtgagtgaa 420
gaaggtcttc ggatcgtaaa gctctgttgt aagtgaagaa cggctcatag aggaaatgct 480
atgggagtga cggtagctta ccagaaagcc acggctaact acgtgccagc agccgcggta 540
atacgtaggt ggcaagcgtt atccggaatc attgggcgta aagggtgcgt aggtggcgta 600
ctaagtctgt agtaaaaggc aatggctcaa ccattgtaag ctatggaaac tggtatgctg 660
gagtgcagaa gagggcgatg gaattccatg tgtagcggta aaatgcgtag atatatggag 720
gaacaccagt ggcgaaggcg gtcgcctggt ctgtaactga cactgaggca cgaaagcgtg 780
gggagcaaat aggattagat accctagtag tccacgccgt aaacgatgag aactaagtgt 840
tggaggaatt cagtgctgca gttaacgcaa taagttctcc gcctggggag tatgcacgca 900
agtgtgaaac tcaaaggaat tgacgggggc ccgcacaagc ggtggagtat gtggtttaat 960
tcgaagcaac gcgaagaacc ttaccaggcc ttgacatgga aacaaatacc ctagagatag 1020
ggggataatt atggatcaca caggtggtgc atggttgtcg tcagctcgtg tcgtgagatg 1080
ttgggttaag tcccgcaacg agcgcaaccc ttgtcgcatg ttaccagcat caagttgggg 1140
actcatgcga gactgccggt gacaaaccgg aggaaggtgg ggatgacgtc aaatcatcat 1200
gccccttatg gcctgggcta cacacgtact acaatggcgg ccacaaagag cagcgacaca 1260
gtgatgtgaa gcgaatctca taaaggtcgt ctcagttcgg attgaagtct gcaactcgac 1320
ttcatgaagt cggaatcgct agtaatcgca gatcagcatg ctgcggtgaa tacgttctcg 1380
ggccttgtac acaccgcccg tcaaaccatg ggagtcagta atacccgaag ccggtggcat 1440
aaccgtaagg agtgagccgt cgaaggtagg accgatgact ggggttaagt cgtaacaagg 1500
tatccctacg ggaacgtggg gatggatcac ctccttt 1537

<210> SEQ ID NO 155
<211> LENGTH: 1537
<212> TYPE: DNA
<213> ORGANISM: Artificial Sequence
<220> FEATURE:
<223> OTHER INFORMATION: Synthetic Polynucleotide

<400> SEQUENCE: 155
atggagagtt tgatcctggc tcaggatgaa cgctggcggc atgcctaata catgcaagtc 60
gaacgaagtt tcgaggaagc ttgcttccaa agagacttag tggcgaacgg gtgagtaaca 120
cgtaggtaac ctgcccatgt gtccgggata actgctggaa acggtagcta aaaccggata 180
ggtatacaga gcgcatgctc agtatattaa agcgcccatc aaggcgtgaa catggatgga 240
cctgcggcgc attagctagt tggtgaggta acggcccacc aaggcgatga tgcgtagccg 300
gcctgagagg gtaaacggcc acattgggac tgagacacgg cccaaactcc tacgggaggc 360
agcagtaggg aattttcgtc aatgggggaa accctgaacg agcaatgccg cgtgagtgaa 420

```
gaaggtcttc ggatcgtaaa gctctgttgt aagtgaagaa cggctcatag aggaaatgct    480

atgggagtga cggtagctta ccagaaagcc acggctaact acgtgccagc agccgcggta    540

atacgtaggt ggcaagcgtt atccggaatc attgggcgta aagggtgcgt aggtggcgta    600

ctaagtctgt agtaaaaggc aatggctcaa ccattgtaag ctatggaaac tggtatgctg    660

gagtgcagaa gagggcgatg gaattccatg tgtagcggta aaatgcgtag atatatggag    720

gaacaccagt ggcgaaggcg gtcgcctggt ctgtaactga cactgaggca cgaaagcgtg    780

gggagcaaat aggattagat accctagtag tccacgccgt aaacgatgag aactaagtgt    840

tggaggaatt cagtgctgca gttaacgcaa taagttctcc gcctggggag tatgcacgca    900

agtgtgaaac tcaaaggaat tgacgggggc ccgcacaagc ggtggagtat gtggtttaat    960

tcgaagcaac gcgaagaacc ttaccaggcc ttgacatgga aacaaatacc ctagagatag   1020

ggggataatt atggatcaca caggtggtgc atggttgtcg tcagctcgtg tcgtgagatg   1080

ttgggttaag tcccgcaacg agcgcaaccc ttgtcgcatg ttaccagcat caagttgggg   1140

actcatgcga gactgccggt gacaaaccgg aggaaggtgg ggatgacgtc aaatcatcat   1200

gccccttatg gcctgggcta cacacgtact acaatggcga ccacaaagag cagcgacaca   1260

gtgatgtgaa gcgaatctca taaaggtcgt ctcagttcgg attgaagtct gcaactcgac   1320

ttcatgaagt cggaatcgct agtaatcgca gatcagcatg ctgcggtgaa tacgttctcg   1380

ggccttgtac acaccgcccg tcaaaccatg ggagtcagta atacccgaag ccggtggcat   1440

aaccgcaagg agtgagccgt cgaaggtagg accgatgact ggggttaagt cgtaacaagg   1500

tatccctacg ggaacgtggg gatggatcac ctccttt                             1537
```

<210> SEQ ID NO 156
<211> LENGTH: 1537
<212> TYPE: DNA
<213> ORGANISM: Artificial Sequence
<220> FEATURE:
<223> OTHER INFORMATION: Synthetic Polynucleotide

<400> SEQUENCE: 156

```
atggagagtt tgatcctggc tcaggatgaa cgctggcggc atgcctaata catgcaagtc     60

gaacgaagtt tcgaggaagc ttgcttccaa agagacttag tggcgaacgg gtgagtaaca    120

cgtaggtaac ctgcccatgt gtccgggata actgctggaa acggtagcta aaaccggata    180

ggtatacaga gcgcatgctc agtatattaa agcgcccatc aaggcgtgaa catggatgga    240

cctgcggcgc attagctagt tggtgaggta acggcccacc aaggcgatga tgcgtagccg    300

gcctgagagg gtaaacggcc acattgggac tgagacacgg cccaaactcc tacgggaggc    360

agcagtaggg aattttcgtc aatgggggaa accctgaacg agcaatgccg cgtgagtgaa    420

gaaggtcttc ggatcgtaaa gctctgttgt aagtgaagaa cggctcatag aggaaatgct    480

atgggagtga cggtagctta ccagaaagcc acggctaact acgtgccagc agccgcggta    540

atacgtaggt ggcaagcgtt atccggaatc attgggcgta aagggtgcgt aggtggcgta    600

ctaagtctgt agtaaaaggc aatggctcaa ccattgtaag ctatggaaac tggtatgctg    660

gagtgcagaa gagggcgatg gaattccatg tgtagcggta aaatgcgtag atatatggag    720

gaacaccagt ggcgaaggcg gtcgcctggt ctgtaactga cactgaggca cgaaagcgtg    780

gggagcaaat aggattagat accctagtag tccacgccgt aaacgatgag aactaagtgt    840

tggaggaatt cagtgctgca gttaacgcaa taagttctcc gcctggggag tatgcacgca    900

agtgtgaaac tcaaaggaat tgacgggggc ccgcacaagc ggtggagtat gtggtttaat    960
```

tcgaagcaac gcgaagaacc ttaccaggcc ttgacatgga aacaaatacc ctagagatag 1020
ggggataatt atggatcaca caggtggtgc atggttgtcg tcagctcgtg tcgtgagatg 1080
ttgggttaag tcccgcaacg agcgcaaccc ttgtcgcatg ttaccagcat caagttgggg 1140
actcatgcga gactgccggt gacaaaccgg aggaaggtgg ggatgacgtc aaatcatcat 1200
gccccttatg gcctgggcta cacacgtact acaatggcgg ccacaaagag cagcgacaca 1260
gtgatgtgaa gcgaatctca taaaggtcgt ctcagttcgg attgaagtct gcaactcgac 1320
ttcatgaagt cggaatcgct agtaatcgca gatcagcatg ctgcggtgaa tacgttctcg 1380
ggccttgtac acaccgcccg tcaaaccatg ggagtcagta atacccgaag ccggtggcat 1440
aaccgtaagg agtgagccgt cgaaggtagg accgatgact ggggttaagt cgtaacaagg 1500
tatccctacg ggaacgtggg gatggatcac ctccttt 1537

<210> SEQ ID NO 157
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 157
tattgagagt ttgatcctgg ctcaggatga acgctggcgg cgtgcttaac acatgcaagt 60
cgaacggggt gctcatgacg gaggattcgt ccaacggatt gagttaccta gtggcggacg 120
ggtgagtaac gcgtgaggaa cctgccttgg agaggggaat aacactccga aaggagtgct 180
aataccgcat gatgcagttg ggtcgcatgg ctctgactgc caaagattta tcgctctgag 240
atggcctcgc gtctgattag ctagtaggcg gggtaacggc ccacctaggc gacgatcagt 300
agccggactg agaggttgac cggccacatt gggactgaga cacggcccag actcctacgg 360
gaggcagcag tggggaatat tgggcaatgg gcgcaagcct gacccagcaa cgccgcgtga 420
aggaagaagg ctttcgggtt gtaaacttct tttgtcgggg acgaaacaaa tgacggtacc 480
cgacgaataa gccacggcta actacgtgcc agcagccgcg gtaatacgta ggtggcaagc 540
gttatccgga tttactgggt gtaaagggcg tgtaggcggg attgcaagtc agatgtgaaa 600
actgggggct caacctccag cctgcatttg aaactgtagt tcttgagtgc tggagaggca 660
atcggaattc cgtgtgtagc ggtgaaatgc gtagatatac ggaggaacac cagtggcgaa 720
ggcggattgc tggacagtaa ctgacgctga ggcgcgaaag cgtggggagc aaacaggatt 780
agataccctg gtagtccacg ccgtaaacga tggatactag gtgtgggggt ctgacccccct 840 ccgtgccgca gttaacacaa taagtatccc acctggggag tacgatcgca aggttgaaac 900
tcaaaggaat tgacgggggc ccgcacaagc ggtggagtat gtggtttaat tcgaagcaac 960
gcgaagaacc ttaccagggc ttgacatccc actaacgaag cagagatgca ttaggtgccc 1020
ttcggggaaa gtggagacag gtggtgcatg gttgtcgtca gctcgtgtcg tgagatgttg 1080
ggttaagtcc cgcaacgagc gcaaccctta ttgttagttg ctacgcaaga gcactctagc 1140
gagactgccg ttgacaaaac ggaggaaggt ggggacgacg tcaaatcatc atgcccctta 1200
tgtcctgggc cacacacgta ctacaatggt ggttaacaga gggaggcaat accgcgaggt 1260
ggagcaaatc cctaaaagcc atcccagttc ggattgcagg ctgaaacccg cctgtatgaa 1320
gttggaatcg ctagtaatcg cggatcagca tgccgcggtg aatacgttcc cgggccttgt 1380
acacaccgcc cgtcacacca tgagagtcgg gaacacccga agtccgtagc ctaaccgcaa 1440

-continued ggagggcgcg gccgaaggtg ggttcgataa ttggggtgaa gtcgtaacaa ggtagccgta 1500
tcggaaggtg cggctggatc acctccttt 1529

<210> SEQ ID NO 158
<211> LENGTH: 1530
<212> TYPE: DNA
<213> ORGANISM: Artificial Sequence
<220> FEATURE:
<223> OTHER INFORMATION: Synthetic Polynucleotide

<400> SEQUENCE: 158
tattgagagt ttgatcctgg ctcaggatga acgctggcgg cgtgcttaac acatgcaagt 60
cgaacggggt gctcatgacg gaggattcgt ccaacggatt gagttaccta gtggcggacg 120
ggtgagtaac gcgtgaggaa cctgccttgg agaggggaat aacactccga aaggagtgct 180
aataccgcat gatgcagttg ggtcgcatgg ctctgactgc caaagattta tcgctctgag 240
atggcctcgc gtctgattag ctagtaggcg gggtaacggc ccacctaggc gacgatcagt 300
agccggactg agaggttgac cggccacatt gggactgaga cacggcccag actcctacgg 360
gaggcagcag tggggaatat tgggcaatgg gcgcaagcct gacccagcaa cgccgcgtga 420
aggaagaagg ctttcgggtt gtaaacttct tttgtcgggg acgaaacaaa tgacggtacc 480
cgacgaataa gccacggcta actacgtgcc agcagccgcg gtaatacgta ggtggcaagc 540
gttatccgga tttactgggt gtaaagggcg tgtaggcggg attgcaagtc agatgtgaaa 600
actgggggct caacctccag cctgcatttg aaactgtagt tcttgagtgc tggagaggca 660
atcggaattc cgtgtgtagc ggtgaaatgc gtagatatac ggaggaacac cagtggcgaa 720
ggcggattgc tggacagtaa ctgacgctga ggcgcgaaag cgtggggagc aaacaggatt 780
agataccctg gtagtccacg ccgtaaacga tggatactag gtgtgggggg tctgaccccc 840
tccgtgccgc agttaacaca ataagtatcc cacctgggga gtacgatcgc aaggttgaaa 900
ctcaaaggaa ttgacggggg cccgcacaag cggtggagta tgtggtttaa ttcgaagcaa 960
cgcgaagaac cttaccaggg cttgacatcc cactaacgaa gcagagatgc attaggtgcc 1020
cttcggggaa agtggagaca ggtggtgcat ggttgtcgtc agctcgtgtc gtgagatgtt 1080
gggttaagtc ccgcaacgag cgcaaccctt attgttagtt gctacgcaag agcactctag 1140
cgagactgcc gttgacaaaa cggaggaagg tggggacgac gtcaaatcat catgcccctt 1200
atgtcctggg ccacacacgt actacaatgg tggttaacag agggaggcaa taccgcgagg 1260
tggagcaaat ccctaaaagc catcccagtt cggattgcag gctgaaaccc gcctgtatga 1320
agttggaatc gctagtaatc gcggatcagc atgccgcggt gaatacgttc ccgggccttg 1380
tacacaccgc ccgtcacacc atgagagtcg ggaacacccg aagtccgtag cctaaccgca 1440
aggagggcgc ggccgaaggt gggttcgata attggggtga agtcgtaaca aggtagccgt 1500
atcggaaggt gcggctggat cacctccttt 1530

<210> SEQ ID NO 159
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 159
tattgagagt ttgatcctgg ctcaggatga acgctggcgg cgtgcttaac acatgcaagt 60
cgaacggggt gctcatgacg gaggattcgt ccaacggatt gagttaccta gtggcggacg 120

-continued

```
ggtgagtaac gcgtgaggaa cctgccttgg agaggggaat aacactccga aaggagtgct    180
aataccgcat aatgcagttg ggtcgcatgg ctctgactgc caaagattta tcgctctgag    240
atggcctcgc gtctgattag ctagtaggcg gggtaacggc ccacctaggc gacgatcagt    300
agccggactg agaggttgac cggccacatt gggactgaga cacggcccag actcctacgg    360
gaggcagcag tggggaatat tgggcaatgg gcgcaagcct gacccagcaa cgccgcgtga    420
aggaagaagg ctttcgggtt gtaaacttct tttgtcaggg acgaaacaaa tgacggtacc    480
tgacgaataa gccacggcta actacgtgcc agcagccgcg gtaatacgta ggtggcaagc    540
gttatccgga tttactgggt gtaaagggcg tgtaggcggg attgcaagtc agatgtgaaa    600
actgggggct caacctccag cctgcatttg aaactgtagt tcttgagtgc tggagaggca    660
atcggaattc cgtgtgtagc ggtgaaatgc gtagatatac ggaggaacac cagtggcgaa    720
ggcggattgc tggacagtaa ctgacgctga ggcgcgaaag cgtggggagc aaacaggatt    780
agataccctg gtagtccacg ccgtaaacga tggatactag gtgtgggggg tctgacccct    840
ccgtgccgca gttaacacaa taagtatccc acctggggag tacgatcgca aggttgaaac    900
tcaaaggaat tgacgggggc ccgcacaagc ggtggagtat gtggtttaat tcgaagcaac    960
gcgaagaacc ttaccagggc ttgacatccc actaacgaag cagagatgca ttaggtgccc   1020
ttcggggaaa gtggagacag gtggtgcatg gttgtcgtca gctcgtgtcg tgagatgttg   1080
ggttaagtcc cgcaacgagc gcaaccctta ttgttagttg ctacgcaaga gcactctagc   1140
gagactgccg ttgacaaaac ggaggaaggt ggggacgacg tcaaatcatc atgcccctta   1200
tgtcctgggc cacacacgta ctacaatggt ggttaacaga gggaggcaat accgcgaggt   1260
ggagcaaatc cctaaaagcc atcccagttc ggattgcagg ctgaaacccg cctgtatgaa   1320
gttggaatcg ctagtaatcg cggatcagca tgccgcggtg aatacgttcc cgggccttgt   1380
acacaccgcc cgtcacacca tgagagtcgg gaacacccga agtccgtagc ctaaccgcaa   1440
ggagggcgcg gccgaaggtg ggttcgataa ttggggtgaa gtcgtaacaa ggtagccgta   1500
tcggaaggtg cggctggatc acctccttt                                     1529
```